US012275938B2

(12) United States Patent
Matsuda et al.

(10) Patent No.: US 12,275,938 B2
(45) Date of Patent: Apr. 15, 2025

(54) MODIFIED RNA AGENTS WITH REDUCED OFF-TARGET EFFECT

(71) Applicant: Alnylam Pharmaceuticals, Inc., Cambridge, MA (US)

(72) Inventors: Shigeo Matsuda, Cambridge, MA (US); Mark K. Schlegel, Cambridge, MA (US); Maja Janas, Cambridge, MA (US); Vasant R. Jadhav, Cambridge, MA (US); Martin Maier, Cambridge, MA (US); Klaus Charisse, Cambridge, MA (US); Muthiah Manoharan, Cambridge, MA (US); Kallanthottathil Rajeev, Cambridge, MA (US); Jayaprakash K. Nair, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 17/743,663

(22) Filed: May 13, 2022

(65) Prior Publication Data

US 2022/0290145 A1 Sep. 15, 2022

Related U.S. Application Data

(63) Continuation of application No. 17/055,710, filed as application No. PCT/US2019/032633 on May 16, 2019.

(60) Provisional application No. 62/672,405, filed on May 16, 2018, provisional application No. 62/719,291, filed on Aug. 17, 2018.

(51) Int. Cl.
C07H 21/04 (2006.01)
C12N 15/113 (2010.01)

(52) U.S. Cl.
CPC ........ *C12N 15/113* (2013.01); *C12N 2310/14* (2013.01); *C12N 2310/318* (2013.01); *C12N 2310/323* (2013.01); *C12N 2310/33* (2013.01); *C12N 2310/344* (2013.01); *C12N 2310/53* (2013.01)

(58) Field of Classification Search
None
See application file for complete search history.

(56) References Cited

U.S. PATENT DOCUMENTS

2004/0171029 A1 9/2004 Prakash et al.
2011/0059187 A1 3/2011 Basu et al.

FOREIGN PATENT DOCUMENTS

| WO | 2004/044245 A1 | 5/2004 |
|---|---|---|
| WO | 2008137771 A2 | 11/2008 |
| WO | 2011/133876 A2 | 10/2011 |
| WO | 2011/133876 A3 | 10/2011 |
| WO | 2011/139710 A1 | 11/2011 |
| WO | 2015/106128 A2 | 7/2015 |
| WO | 2015/106128 A3 | 7/2015 |
| WO | 2016028649 A1 | 3/2016 |
| WO | 2016/100401 A1 | 6/2016 |
| WO | 2016/209862 A1 | 12/2016 |
| WO | 2016/209862 A8 | 12/2016 |
| WO | 2017/015175 A1 | 1/2017 |
| WO | 2018098328 A1 | 5/2018 |

OTHER PUBLICATIONS

Pubchem CID 126553604, Apr. 22, 2017.
Pubchem CID 129301917, Aug. 4, 2017.
International Search Report, PCT/US2019/032633, Aug. 29, 2019.
Alagia et al. "RNA modified with acyclic threoninol nucleic acids for RNA interference." RNA & Disease 3 (2016).
Betson et al. "A review of methods to synthesise 4'-substituted nucleosides." Organic & Biomolecular Chemistry 12.46 (2014): 9291-9306.
Boyer et al. "The nucleoside analogs 4' C-methyl thymidine and 4' C-ethyl thymidine block DNA synthesis by wild-type HIV-1 RT and excision proficient NRTI resistant RT variants." Journal of molecular biology 371.4 (2007): 873-882.
Bramsen et al. "Development of therapeutic-grade small interfering RNAs by chemical engineering." Frontiers in genetics 3 (2012): 154.
Huang et al. "Preclinical and clinical advances of GalNAc-decorated nucleic acid therapeutics." Molecular Therapy—Nucleic Acids 6 (2017): 116-132.
Ivanov et al. "Synthesis and biological properties of pyrimidine 4'-fluoronucleosides and 4'-fluorouridine 5'-O-triphosphate." Russian journal of bioorganic chemistry 36.4 (2010): 488-496.
Kel'In et al. "Structural basis of duplex thermodynamic stability and enhanced nuclease resistance of 5'-C-methyl byrimidine-modified oligonucleotides." The Journal of organic chemistry 81.6 (2016): 2261-2279.
Laursen et al. "Utilization of unlocked nucleic acid (UNA) to enhance siRNA performance in vitro and in vivo." Molecular BioSystems 6.5 (2010): 862-870.

(Continued)

*Primary Examiner* — Kimberly Chong
(74) *Attorney, Agent, or Firm* — Nixon Peabody LLP; David S. Resnick; Ravinderjit S. Braich

(57) ABSTRACT

One aspect of the present invention relates to double-stranded RNA (dsRNA) agent capable of inhibiting the expression of a target gene. The antisense strand of the dsRNA molecule comprises at least one thermally destabilizing nucleotide occurring at a seed region; the dsRNA comprises at least four 2'-fluoro modifications, and the sense strand of the dsRNA molecule comprises ligand, wherein the ligand is an ASGPR ligand. Other aspects of the invention relate to pharmaceutical compositions comprising these dsRNA molecules suitable for therapeutic use, and methods of inhibiting the expression of a target gene by administering these dsRNA molecules, e.g., for the treatment of various disease conditions.

38 Claims, 47 Drawing Sheets

Specification includes a Sequence Listing.

(56) References Cited

OTHER PUBLICATIONS

Malek-Adamian et al. "4'-C-Methoxy-2'-deoxy-2'-fluoro modified ribonucleotides improve metabolic stability and elicit efficient RNAi-mediated gene silencing." Journal of the American Chemical Society 139.41 (2017): 14542-14555.
Martinez-Montero et al. "Locked 2'-deoxy-2', 4'-difluororibo modified nucleic acids: thermal stability, structural studies, and siRNA activity." ACS chemical biology 10.9 (2015): 2016-2023.
Ogata et al. "Incorporation of an acyclic alkynyl nucleoside analog into siRNA improves silencing activity and nuclease resistance." Bioorganic & Medicinal Chemistry Letters 25.12 (2015): 2574-2578.
Owen et al. "4'-Substituted nucleosides. 3. Synthesis of some 4'-fluorouridine derivatives." The Journal of Organic Chemistry 41.18 (1976): 3010-3017.
Schlegel et al. "Chirality dependent potency enhancement and structural impact of glycol nucleic acid modification on siRNA." Journal of the American Chemical Society 139.25 (2017): 8537-8546.
Snead et al. "5' Unlocked nucleic acid modification improves siRNA targeting." Molecular Therapy—Nucleic Acids 2 (2013): e103.
Waga et al. "Synthesis and biological evaluation of 4'-C-methyl nucleosides." Nucleosides and Nucleotides 15.1-3 (1996): 287-304.
Werk et al. "Application of small interfering RNAs modified by unlocked nucleic acid (UNA) to inhibit the heart-pathogenic coxsackievirus B3." FEBS letters 584.3 (2010): 591-598.
Braasch et al. "RNA interference in mammalian cells by chemically-modified RNA." Biochemistry 42.26: 7967-7975 (2003).
Flur et al. "Chemical synthesis of RNA with site-specific methylphosphonate modifications." Methods 107: 79-88 (2016).
Manoharan et al. "Unique gene-silencing and structural properties of 2' fluoro-modified siRNAs." Angewandte Chemie 123.10: 2332-2336 (2011).
Parmar et al. "5'-(E)-Vinylphosphonate: A Stable Phosphate Mimic Can Improve the RNAi Activity of siRNA-GalNAc Conjugates." ChemBioChem 17.11: 985-989 (2016).
Parmar, Rubina, et al. "5'-(E)-Vinylphosphonate: A Stable Phosphate Mimic Can Improve the RNAi Activity of siRNA-GalNAc Conjugates." ChemBioChem 17.11, Supporting Information: 11 pages (2016).
Prakash et al. "RNA interference by 2', 5'-linked nucleic acid duplexes In mammalian cells." Bioorganic & medicinal chemistry letters 16.12: 3238-3240 (2006).
Watts et al. "Chemically modified siRNA: tools and applications." Drug discovery today 13.19-20: 842-855 (2008).

AM-156: GfafUf (6PS) AM-163: Q327GfafUf: 5'-3' 19 mers (4PS) AM-164: Q328GfafUf: 5'-5' 19 mers (6PS)
AM-165: Q327GfafUf: 5'-3' 21 mers (4PS) AM-166: Q324Q303Q303Q303Q303dA: 5'-3' 21mers (4PS)

AM-156: GfafUf (6PS) AM-163: Q327GfafUf: 5'-3' 19 mers (4PS) AM-164: Q328GfafUf: 5'-5' 19 mers (6PS)
AM-165: Q327GfafUf: 5'-3' 21 mers (4PS) AM-166: Q324Q303Q303Q303Q303dA: 5'-3' 21mers (4PS)

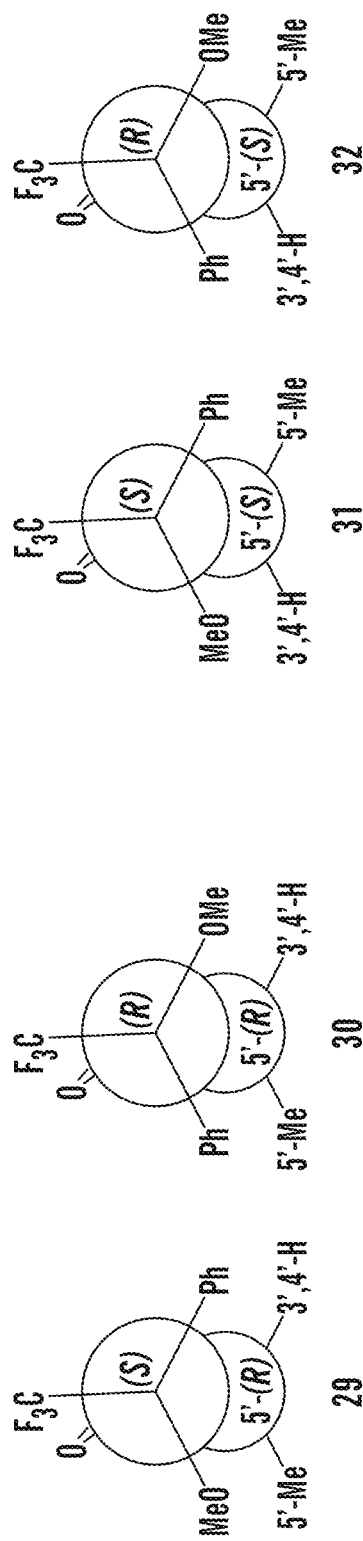
FIG. 27
FIG. 28
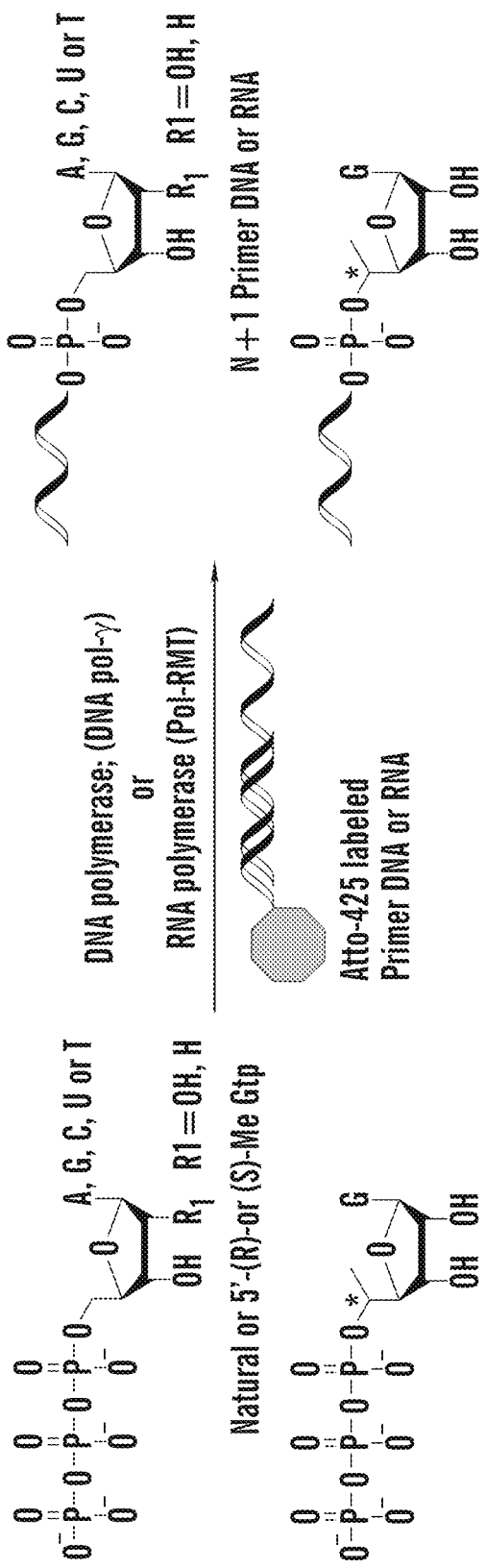
FIG. 29

5'-(R)-C-Me-Gtp

5'-(R)-C-Me-Gtp

SEQUENCE LISTING

<160> NUMBER OF SEQ ID NOS: 708

<210> SEQ ID NO 1

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tttttttttt tttttttttt                                                 20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttttttttt tttttttt                                                   18

<210> SEQ ID NO 3
<211> LENGTH: 16
<212> TYPE: PRT
<213> ORGANISM: Unknown
<220> FEATURE:
<223> OTHER INFORMATION: Description of Unknown:
      RFGF peptide

<400> SEQUENCE: 3

Ala Ala Val Ala Leu Leu Pro Ala Val Leu Leu Ala Leu Leu Ala Pro
1               5                   10                  15

<210> SEQ ID NO 4
<211> LENGTH: 11
<212> TYPE: PRT
<213> ORGANISM: Unknown
<220> FEATURE:
<223> OTHER INFORMATION: Description of Unknown:
      RFGF analogue peptide

<400> SEQUENCE: 4

Ala Ala Leu Leu Pro Val Leu Leu Ala Ala Pro
1               5                   10

<210> SEQ ID NO 5
<211> LENGTH: 13
<212> TYPE: PRT
<213> ORGANISM: Human immunodeficiency virus

<400> SEQUENCE: 5

Gly Arg Lys Lys Arg Arg Gln Arg Arg Arg Pro Pro Gln
1               5                   10

<210> SEQ ID NO 6
<211> LENGTH: 16
<212> TYPE: PRT
<213> ORGANISM: Drosophila sp.

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7 utututut ututututut u                                              21

<210> SEQ ID NO 8
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uuucgaauca auccaacagu agu                                          23

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tttttttttt tttttttt                                                19

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gaaugugaaa gucaucgaca a                                            21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
aacaguguuc uugcucuaua a                                            21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12 aguuucuug cucuauaaac a                                             21

<210> SEQ ID NO 13
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
uucuugcucu auaaaccgug u                                              21

<210> SEQ ID NO 14
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uugucgauga cuuucacauu cug                                            23

<210> SEQ ID NO 15
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
uuauagagca agaacacugu uuu                                            23

<210> SEQ ID NO 16
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uguuuauaga gcaagaacac ugu                                            23

<210> SEQ ID NO 17
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
acacgguuua uagagcaaga aca                                            23

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
aggaucuugc caaagcagua a                                              21

<210> SEQ ID NO 19
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 19
uuacugcuuu ggcaagaucc ugg                                                23

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
aggaucuugc caaagcagua a                                                  21

<210> SEQ ID NO 21
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
uuacugcuuu ggcaagaucc ugg                                                23

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gaccaggauc uugccaaagc a                                                  21

<210> SEQ ID NO 23
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ugcuuuggca agauccuggu ccu                                                23

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ugcuuugagc cucagcuucu a                                                  21

<210> SEQ ID NO 25
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 25
uagaagcuga ggcucaaagc acu                                          23

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ggagcccaag aaagugaaag a                                            21

<210> SEQ ID NO 27
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ucuuucacuu ucuugggcuc cac                                          23

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
caguguucuu gcucuauaa                                               19

<210> SEQ ID NO 29
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gauggaucau cucaagucuu aa                                           22

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uuauagagca agaacacugu u                                            21

<210> SEQ ID NO 31
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 31
uuaagacuug agaugauccu g                                                   21

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
caguguucuu gcucuauaa                                                      19

<210> SEQ ID NO 33
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
gauggaucau cucaagucuu aa                                                  22

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
uuauagagca agaacacugu u                                                   21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uuaagacuug agaugauccu g                                                   21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
aacaguguuc uugcucuaua a                                                   21

<210> SEQ ID NO 37
<211> LENGTH: 24
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 37
gaucaggauc aucucaaguc uuaa                                              24

<210> SEQ ID NO 38
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
uuauagagca agaacacugu uuu                                               23

<210> SEQ ID NO 39
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
uuaagacuug agaugauccu ggc                                               23

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
aacaguguuc uugcucuaua a                                                 21

<210> SEQ ID NO 41
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
acaggaucau cucaagucuu aa                                                22

<210> SEQ ID NO 42
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
uuauagagca agaacacugu uuu                                               23

<210> SEQ ID NO 43
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 43
uuaagacuug agaugauccu ggc                                           23

<210> SEQ ID NO 44
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
uuagaaauaa gugguaguca cuu                                           23

<210> SEQ ID NO 45
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
uuucuggcau ucuucauuug uua                                           23

<210> SEQ ID NO 46
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
uaaagcacuu uauugaguuu cug                                           23

<210> SEQ ID NO 47
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
ucguuuucaa agcacuuuau uga                                           23

<210> SEQ ID NO 48
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uauugaccca aaauucaaca aug                                           23

<210> SEQ ID NO 49
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
uacagucuau gu                                                              12

<210> SEQ ID NO 50
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
acauagacug ua                                                              12

<210> SEQ ID NO 51
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
uacagtcuau gu                                                              12

<210> SEQ ID NO 52
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
acauagacug ua                                                              12

<210> SEQ ID NO 53
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tacagtctat gt                                                              12

<210> SEQ ID NO 54
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
acatagactg ta                                                              12

<210> SEQ ID NO 55
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
tacagtctat gt                                                         12

<210> SEQ ID NO 56
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
acatagactg ta                                                         12

<210> SEQ ID NO 57
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
uacagucuau gu                                                         12

<210> SEQ ID NO 58
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
acauagacug ua                                                         12

<210> SEQ ID NO 59
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uacagucuau gu                                                         12

<210> SEQ ID NO 60
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
acauagacug ua                                                         12

<210> SEQ ID NO 61
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tacagcctat gt                                                              12

<210> SEQ ID NO 62
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
acataggctg ta                                                              12

<210> SEQ ID NO 63
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tacagcctat gt                                                              12

<210> SEQ ID NO 64
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
acataggctg ta                                                              12

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tttttttttt tttttttttt                                                      20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gttttttttt tttttttttt                                                      20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 67 gtttttttttt tttttttttt                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68 gtttttttttt tttttttttt                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69 gtttttttttt tttttttttt                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70 gtttttttttt tttttttttt                                              20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71 gtttttttttt tttttttttt                                              20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tttttttttt tttttttttt                                               20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
```
tttttttttt ttttttttg                                              20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tttttttttt ttttttttg                                              20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tttttttttt ttttttttg                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tttttttttt ttttttttg                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tttttttttt ttttttttg                                              20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tttttttttt ttttttttg                                              20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tttttttttt tttttttttgg                                     20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tttttttttt tttttttttgg                                     20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tttttttttt tttttttttgg                                     20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tttttttttt tttttttttgg                                     20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
tttttttttt tttttttttgg                                     20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tttttttttt tttttttttgg                                     20

<210> SEQ ID NO 85
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
uacagucuau gu                                              12

```
<210> SEQ ID NO 86
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tacagtctat gt                                                              12

<210> SEQ ID NO 87
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
tacaguctat gt                                                              12

<210> SEQ ID NO 88
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uacagucuau gu                                                              12

<210> SEQ ID NO 89
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 89
uacagncuau gu                                                              12

<210> SEQ ID NO 90
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 90
tacagnctat gt                                                              12

<210> SEQ ID NO 91
```

```
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 91
uacagncuau gu                                                            12

<210> SEQ ID NO 92
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 92
tacagnctat gt                                                            12

<210> SEQ ID NO 93
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 93
uacagncuau gu                                                            12

<210> SEQ ID NO 94
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 94
tacagnctat gt                                                            12

<210> SEQ ID NO 95
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid
```

```
<400> SEQUENCE: 95
uacagncuau gu                                                                12

<210> SEQ ID NO 96
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 96
tacagnctat gt                                                                12

<210> SEQ ID NO 97
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 97
uacagncuau gu                                                                12

<210> SEQ ID NO 98
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 98
tacagnctat gt                                                                12

<210> SEQ ID NO 99
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 99
uacagncuau gu                                                                12

<210> SEQ ID NO 100
<211> LENGTH: 12
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 100
tacagnctat gt                                                          12

<210> SEQ ID NO 101
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 101
uacagncuau gu                                                          12

<210> SEQ ID NO 102
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 102
tacagnctat gt                                                          12

<210> SEQ ID NO 103
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 103
uacagncuau gu                                                          12

<210> SEQ ID NO 104
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 104
tacagnctat gt                                                          12
```

```
<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 105
nttttttttt tttttttttt                                                     20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 106
nttttttttt tttttttttt                                                     20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 107
nttttttttt tttttttttt                                                     20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 108
nttttttttt tttttttttt                                                     20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid
```

```
<400> SEQUENCE: 109
nttttttttt tttttttttt                                              20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 110
nttttttttt tttttttttt                                              20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 111
nttttttttt tttttttttt                                              20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 112
nttttttttt tttttttttt                                              20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 113
nttttttttt tttttttttt                                              20

<210> SEQ ID NO 114
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 114
nttttttttt tttttttttt                                                   20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 115
nttttttttt tttttttttt                                                   20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 116
nttttttttt tttttttttt                                                   20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 117
nttttttttt tttttttttt                                                   20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 118
nttttttttt tttttttttt                                                   20
```

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 119
nttttttttt tttttttttt                                            20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Unlocked nucleic acid

<400> SEQUENCE: 120
nttttttttt tttttttttt                                            20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121 utttttttttt tttttttttt                                           20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122 utttttttttt tttttttttt                                           20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Unlocked nucleic acid

<400> SEQUENCE: 123
tttttttttt tttttttttn                                                              20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Unlocked nucleic acid

<400> SEQUENCE: 124
tttttttttt tttttttttn                                                              20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: Unlocked nucleic acid

<400> SEQUENCE: 125
tttttttttt ttttttttnn                                                              20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: Unlocked nucleic acid

<400> SEQUENCE: 126
tttttttttt ttttttttnn                                                              20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Unlocked nucleic acid

<400> SEQUENCE: 127
tttttttttt ttttttttnt                                                              20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic

```
        oligonucleotide
<220> FEATURE:
<221> NAME/KEY: modified_base
<222> LOCATION: (19)..(19)
<223> OTHER INFORMATION: Unlocked nucleic acid

<400> SEQUENCE: 128
tttttttttt tttttttnt                                                    20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (20)..(20)
<223> OTHER INFORMATION: Unlocked nucleic acid

<400> SEQUENCE: 129
tttttttttt ttttttttn                                                    20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (20)..(20)
<223> OTHER INFORMATION: Unlocked nucleic acid

<400> SEQUENCE: 130
tttttttttt ttttttttn                                                    20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (19)..(20)
<223> OTHER INFORMATION: Unlocked nucleic acid

<400> SEQUENCE: 131
tttttttttt tttttttnn                                                    20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (19)..(20)
<223> OTHER INFORMATION: Unlocked nucleic acid

<400> SEQUENCE: 132
tttttttttt tttttttnn                                                    20
```

```
<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Unlocked nucleic acid

<400> SEQUENCE: 133
tttttttttt tttttttnt                                              20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Unlocked nucleic acid

<400> SEQUENCE: 134
tttttttttt tttttttnt                                              20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Unlocked nucleic acid

<400> SEQUENCE: 135
tttttttttt ttttttttn                                              20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Unlocked nucleic acid

<400> SEQUENCE: 136
tttttttttt ttttttttn                                              20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: Unlocked nucleic acid
```

```
<400> SEQUENCE: 137
tttttttttt ttttttttnn                                              20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: Unlocked nucleic acid

<400> SEQUENCE: 138
tttttttttt ttttttttnn                                              20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Unlocked nucleic acid

<400> SEQUENCE: 139
tttttttttt tttttttnt                                               20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Unlocked nucleic acid

<400> SEQUENCE: 140
tttttttttt tttttttnt                                               20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Unlocked nucleic acid

<400> SEQUENCE: 141
tttttttttt tttttttttn                                              20

<210> SEQ ID NO 142
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Unlocked nucleic acid

<400> SEQUENCE: 142
tttttttttt tttttttttn                                              20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: Unlocked nucleic acid

<400> SEQUENCE: 143
tttttttttt ttttttttnn                                              20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: Unlocked nucleic acid

<400> SEQUENCE: 144
tttttttttt ttttttttnn                                              20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Unlocked nucleic acid

<400> SEQUENCE: 145
tttttttttt ttttttttnt                                              20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Unlocked nucleic acid

<400> SEQUENCE: 146
tttttttttt ttttttttnt                                              20
```

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Unlocked nucleic acid

<400> SEQUENCE: 147
tttttttttt tttttttttn                                              20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Unlocked nucleic acid

<400> SEQUENCE: 148
tttttttttt tttttttttn                                              20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: Unlocked nucleic acid

<400> SEQUENCE: 149
tttttttttt ttttttttnn                                              20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: Unlocked nucleic acid

<400> SEQUENCE: 150
tttttttttt ttttttttnn                                              20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)

<223> OTHER INFORMATION: Unlocked nucleic acid

<400> SEQUENCE: 151
tttttttttt tttttttnt                                          20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Unlocked nucleic acid

<400> SEQUENCE: 152
tttttttttt tttttttnt                                          20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Unlocked nucleic acid

<400> SEQUENCE: 153
tttttttttt ttttttttn                                          20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Unlocked nucleic acid

<400> SEQUENCE: 154
tttttttttt ttttttttn                                          20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: Unlocked nucleic acid

<400> SEQUENCE: 155
tttttttttt tttttttnn                                          20

<210> SEQ ID NO 156
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: Unlocked nucleic acid

<400> SEQUENCE: 156
tttttttttt ttttttttnn                                                    20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Unlocked nucleic acid

<400> SEQUENCE: 157
tttttttttt ttttttttnt                                                    20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Unlocked nucleic acid

<400> SEQUENCE: 158
tttttttttt ttttttttnt                                                    20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Unlocked nucleic acid

<400> SEQUENCE: 159
tttttttttt tttttttttn                                                    20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Unlocked nucleic acid

<400> SEQUENCE: 160
tttttttttt tttttttttn                                                    20
```

```
<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: Unlocked nucleic acid

<400> SEQUENCE: 161
tttttttttt ttttttttnn                                             20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: Unlocked nucleic acid

<400> SEQUENCE: 162
tttttttttt ttttttttnn                                             20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Unlocked nucleic acid

<400> SEQUENCE: 163
tttttttttt ttttttttnt                                             20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Unlocked nucleic acid

<400> SEQUENCE: 164
tttttttttt ttttttttnt                                             20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

-continued

```
<222> LOCATION: (20)..(20)
<223> OTHER INFORMATION: Unlocked nucleic acid

<400> SEQUENCE: 165
tttttttttt tttttttttn                                           20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Unlocked nucleic acid

<400> SEQUENCE: 166
tttttttttt tttttttttn                                           20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: Unlocked nucleic acid

<400> SEQUENCE: 167
tttttttttt ttttttttnn                                           20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: Unlocked nucleic acid

<400> SEQUENCE: 168
tttttttttt ttttttttnn                                           20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Unlocked nucleic acid

<400> SEQUENCE: 169
tttttttttt ttttttttnt                                           20

<210> SEQ ID NO 170
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Unlocked nucleic acid

<400> SEQUENCE: 170
tttttttttt tttttttttnt                                              20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 171
tttttttttt ttttttttttu                                              20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 172
tttttttttt ttttttttttu                                              20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 173
tttttttttt tttttttuu                                                20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 174
tttttttttt tttttttuu                                                20

<210> SEQ ID NO 175
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 175
tttttttttt ttttttttut                                              20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 176
tttttttttt ttttttttut                                              20

<210> SEQ ID NO 177
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 177
uguutauaga gcaagaacac ugu                                          23

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 178
uguuuataga gcaagaacac ugu                                          23

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 179
acacggtuua uagagcaaga aca                                          23
```

```
<210> SEQ ID NO 180
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
uguuuauaga gcaagaacac ugu                                              23

<210> SEQ ID NO 181
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
uguuuauaga gcaagaacac ugu                                              23

<210> SEQ ID NO 182
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
acacgguuua uagagcaaga aca                                              23

<210> SEQ ID NO 183
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 183
acacggnuua uagagcaaga aca                                              23

<210> SEQ ID NO 184
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 184
acacggnuua uagagcaaga aca                                              23

<210> SEQ ID NO 185
<211> LENGTH: 23
<212> TYPE: RNA
<213> ORGANISM: Artificial Sequence
<220> FEATURE:
<223> OTHER INFORMATION: Description of Artificial Sequence: Synthetic
```

```
            oligonucleotide
<220> FEATURE:
<221> NAME/KEY: modified_base
<222> LOCATION: (7)..(7)
<223> OTHER INFORMATION: Unlocked nucleic acid

<400> SEQUENCE: 185
acacggnuua uagagcaaga aca                                              23

<210> SEQ ID NO 186
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 186
acacggnuua uagagcaaga aca                                              23

<210> SEQ ID NO 187
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 187
acacggnuua uagagcaaga aca                                              23

<210> SEQ ID NO 188
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 188
acacggnuua uagagcaaga aca                                              23

<210> SEQ ID NO 189
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Unlocked nucleic acid

<400> SEQUENCE: 189
uguunauaga gcaagaacac ugu                                              23
```

```
<210> SEQ ID NO 190
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Unlocked nucleic acid

<400> SEQUENCE: 190
uguunauaga gcaagaacac ugu                                              23

<210> SEQ ID NO 191
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Unlocked nucleic acid

<400> SEQUENCE: 191
uguunauaga gcaagaacac ugu                                              23

<210> SEQ ID NO 192
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Unlocked nucleic acid

<400> SEQUENCE: 192
uguunauaga gcaagaacac ugu                                              23

<210> SEQ ID NO 193
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Unlocked nucleic acid

<400> SEQUENCE: 193
uguunauaga gcaagaacac ugu                                              23

<210> SEQ ID NO 194
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Unlocked nucleic acid
```

<400> SEQUENCE: 194
uguunauaga gcaagaacac ugu                                              23

<210> SEQ ID NO 195
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Unlocked nucleic acid

<400> SEQUENCE: 195
uguunauaga gcaagaacac ugu                                              23

<210> SEQ ID NO 196
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 196
uguuuanaga gcaagaacac ugu                                              23

<210> SEQ ID NO 197
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 197
uguuuanaga gcaagaacac ugu                                              23

<210> SEQ ID NO 198
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 198
uguuuanaga gcaagaacac ugu                                              23

<210> SEQ ID NO 199
<211> LENGTH: 23
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 199
uguuuanaga gcaagaacac ugu                                           23

<210> SEQ ID NO 200
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 200
uguuuanaga gcaagaacac ugu                                           23

<210> SEQ ID NO 201
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 201
uguuuanaga gcaagaacac ugu                                           23

<210> SEQ ID NO 202
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 202
uguuuanaga gcaagaacac ugu                                           23

<210> SEQ ID NO 203
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 203
uacagtcuau gu                                                       12
```

-continued

```
<210> SEQ ID NO 204
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tacagtctat gt                                                         12

<210> SEQ ID NO 205
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
uacagucuau gu                                                         12

<210> SEQ ID NO 206
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
acauagacug ua                                                         12

<210> SEQ ID NO 207
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
acauagacug ua                                                         12

<210> SEQ ID NO 208
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
acatagactg ta                                                         12

<210> SEQ ID NO 209
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
acatagactg ta                                                         12

<210> SEQ ID NO 210
```

```
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
tacagtctat gt                                                          12

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
tttttttttt tttttttttt                                                  20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tttttttttt tttttttttt                                                  20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
tttttttttt tttttttttt                                                  20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
tttttttttt tttttttttt                                                  20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
tttttttttt tttttttttt                                                  20

<210> SEQ ID NO 216
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
tttttttttt tttttttttt                                            20

<210> SEQ ID NO 217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
aacaguguuc uugcucuaua a                                          21

<210> SEQ ID NO 218
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
aacaguguuc uugcucuaua a                                          21

<210> SEQ ID NO 219
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
aacaguguuc uugcucuaua a                                          21

<210> SEQ ID NO 220
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
aacaguguuc uugcucuaua a                                          21

<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
aacaguguuc uugcucuaua a                                          21

<210> SEQ ID NO 222
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 222
aacagtguuc uugcucuaua a                                              21

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
aacaguguuc uugcucuaua a                                              21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 224
aacagugtuc uugcucuaua a                                              21

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 225
aacagugutc uugcucuaua a                                              21

<210> SEQ ID NO 226
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
aacaguguuc uugcucuaua a                                              21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 227
aacaguguuc tugcucuaua a                                              21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 228
aacaguguuc utgcucuaua a                                              21

<210> SEQ ID NO 229
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
aacaguguuc uugcucuaua a                                              21

<210> SEQ ID NO 230
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
aacaguguuc uugcucuaua a                                              21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 231
aacaguguuc uugctcuaua a                                              21

<210> SEQ ID NO 232
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
aacaguguuc uugcucuaua a                                              21
```

```
<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 233
aacaguguuc uugcuctaua a                                              21

<210> SEQ ID NO 234
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
aacaguguuc uugcucuaua a                                              21

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 235
aacaguguuc uugcucuata a                                              21

<210> SEQ ID NO 236
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
aacaguguuc uugcucuaua a                                              21

<210> SEQ ID NO 237
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
aacaguguuc uugcucuaua a                                              21

<210> SEQ ID NO 238
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 238
tuauagagca agaacacugu uuu                                              23

<210> SEQ ID NO 239
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 239
utauagagca agaacacugu uuu                                              23

<210> SEQ ID NO 240
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
uuauagagca agaacacugu uuu                                              23

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 241
uuatagagca agaacacugu uuu                                              23

<210> SEQ ID NO 242
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
uuauagagca agaacacugu uuu                                              23

<210> SEQ ID NO 243
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
uuauagagca agaacacugu uuu                                              23
```

```
<210> SEQ ID NO 244
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
uuauagagca agaacacugu uuu                                              23

<210> SEQ ID NO 245
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
uuauagagca agaacacugu uuu                                              23

<210> SEQ ID NO 246
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
uuauagagca agaacacugu uuu                                              23

<210> SEQ ID NO 247
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
uuauagagca agaacacugu uuu                                              23

<210> SEQ ID NO 248
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
uuauagagca agaacacugu uuu                                              23

<210> SEQ ID NO 249
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
uuauagagca agaacacugu uuu                                              23

<210> SEQ ID NO 250
```

<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
uuauagagca agaacacugu uuu                                              23

<210> SEQ ID NO 251
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
uuauagagca agaacacugu uuu                                              23

<210> SEQ ID NO 252
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
uuauagagca agaacacugu uuu                                              23

<210> SEQ ID NO 253
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
uuauagagca agaacacugu uuu                                              23

<210> SEQ ID NO 254
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
uuauagagca agaacacugu uuu                                              23

<210> SEQ ID NO 255
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 255
uuauagagca agaacactgu uuu                                              23

```
<210> SEQ ID NO 256
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
uuauagagca agaacacugu uuu                                             23

<210> SEQ ID NO 257
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 257
uuauagagca agaacacugt uuu                                             23

<210> SEQ ID NO 258
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 258
uuauagagca agaacacugu tuu                                             23

<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 259
uuauagagca agaacacugu utu                                             23

<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 260
uuauagagca agaacacugu uut                                             23

<210> SEQ ID NO 261
```

```
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
gaugacuuuc acauucug                                                       18

<210> SEQ ID NO 262
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
augacuuuca cauucug                                                        17

<210> SEQ ID NO 263
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
ugacuuucac auucug                                                         16

<210> SEQ ID NO 264
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
gacuuucaca uucug                                                          15

<210> SEQ ID NO 265
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
gagcaagaac acuguuuu                                                       18

<210> SEQ ID NO 266
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
agcaagaaca cuguuuu                                                        17

<210> SEQ ID NO 267
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
gcaagaacac uguuu                                                          16

<210> SEQ ID NO 268
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
caagaacacu guuuu                                                          15

<210> SEQ ID NO 269
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
auagagcaag aacacuguuu u                                                   21

<210> SEQ ID NO 270
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
uagagcaaga acacuguuuu                                                     20

<210> SEQ ID NO 271
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
agagcaagaa cacuguuuu                                                      19

<210> SEQ ID NO 272
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
agagcaagaa cacuguuuu                                                      19

<210> SEQ ID NO 273
<211> LENGTH: 18
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 273
gagcaagaac acuguuuu                                                 18

<210> SEQ ID NO 274
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
agcaagaaca cuguuuu                                                  17

<210> SEQ ID NO 275
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
gcaagaacac uguuuu                                                   16

<210> SEQ ID NO 276
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
caagaacacu guuuu                                                    15

<210> SEQ ID NO 277
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
aagaacacug uuuu                                                     14

<210> SEQ ID NO 278
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
aagaacacug uuuu                                                     14

<210> SEQ ID NO 279
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
ucgaugacuu ucacauucug                                                    20

<210> SEQ ID NO 280
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
ucgaugacuu ucacauucug                                                    20

<210> SEQ ID NO 281
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
cgaugacuuu cacauucug                                                     19

<210> SEQ ID NO 282
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
cgaugacuuu cacauucug                                                     19

<210> SEQ ID NO 283
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
gaugacuuuc acauucug                                                      18

<210> SEQ ID NO 284
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
augacuuuca cauucug                                                       17

<210> SEQ ID NO 285
<211> LENGTH: 16
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 285
ugacuuucac auucug                                                      16

<210> SEQ ID NO 286
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
gacuuucaca uucug                                                       15

<210> SEQ ID NO 287
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
acuuucacau ucug                                                        14

<210> SEQ ID NO 288
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
acuuucacau ucug                                                        14

<210> SEQ ID NO 289
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
uacagucuau gu                                                          12

<210> SEQ ID NO 290
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 290
uacagncuau gu                                                          12

<210> SEQ ID NO 291
<211> LENGTH: 12
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 291
uacagncuau gu                                                           12

<210> SEQ ID NO 292
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 292
uacagncuau gu                                                           12

<210> SEQ ID NO 293
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 293
uacagncuau gu                                                           12

<210> SEQ ID NO 294
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 294
uacagncuau gu                                                           12

<210> SEQ ID NO 295
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 295
```
uacagncuau gu                                                             12

<210> SEQ ID NO 296
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 296
uacagncuau gu                                                             12

<210> SEQ ID NO 297
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 297
uacagncuau gu                                                             12

<210> SEQ ID NO 298
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
uacagucuau gu                                                             12

<210> SEQ ID NO 299
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
tacagtctat gt                                                             12

<210> SEQ ID NO 300
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 300
tacagnctat gt                                                             12

<210> SEQ ID NO 301
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 301
tacagnctat gt                                                           12

<210> SEQ ID NO 302
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 302
tacagnctat gt                                                           12

<210> SEQ ID NO 303
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 303
tacagnctat gt                                                           12

<210> SEQ ID NO 304
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 304
tacagnctat gt                                                           12

<210> SEQ ID NO 305
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (6)..(6)
<223> OTHER INFORMATION: Unlocked nucleic acid

<400> SEQUENCE: 305
tacagnctat gt                                                          12

<210> SEQ ID NO 306
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 306
tacagnctat gt                                                          12

<210> SEQ ID NO 307
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 307
tacagnctat gt                                                          12

<210> SEQ ID NO 308
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 308
tacaguctat gt                                                          12

<210> SEQ ID NO 309
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
uacagucuau gu                                                          12

<210> SEQ ID NO 310
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

-continued

```
<221> NAME/KEY: modified_base
<222> LOCATION: (6)..(6)
<223> OTHER INFORMATION: Unlocked nucleic acid

<400> SEQUENCE: 310
uacagncuau gu                                                              12

<210> SEQ ID NO 311
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 311
uacagncuau gu                                                              12

<210> SEQ ID NO 312
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 312
uacagncuau gu                                                              12

<210> SEQ ID NO 313
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 313
uacagncuau gu                                                              12

<210> SEQ ID NO 314
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 314
uacagncuau gu                                                              12

<210> SEQ ID NO 315
<211> LENGTH: 12
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 315
uacagncuau gu                                                            12

<210> SEQ ID NO 316
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 316
uacagncuau gu                                                            12

<210> SEQ ID NO 317
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 317
uacagncuau gu                                                            12

<210> SEQ ID NO 318
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
uacagucuau gu                                                            12

<210> SEQ ID NO 319
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
tacagtctat gt                                                            12

<210> SEQ ID NO 320
<211> LENGTH: 12
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 320
tacagnctat gt                                                            12

<210> SEQ ID NO 321
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 321
tacagnctat gt                                                            12

<210> SEQ ID NO 322
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 322
tacagnctat gt                                                            12

<210> SEQ ID NO 323
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 323
tacagnctat gt                                                            12

<210> SEQ ID NO 324
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 324
tacagnctat gt                                                            12
```

```
<210> SEQ ID NO 325
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 325
tacagnctat gt                                                      12

<210> SEQ ID NO 326
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 326
tacagnctat gt                                                      12

<210> SEQ ID NO 327
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Unlocked nucleic acid

<400> SEQUENCE: 327
tacagnctat gt                                                      12

<210> SEQ ID NO 328
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 328
tacaguctat gt                                                      12

<210> SEQ ID NO 329
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
```
acauagacug ua                                                      12

<210> SEQ ID NO 330
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
acauagacug ua                                                      12

<210> SEQ ID NO 331
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
acauagacug ua                                                      12

<210> SEQ ID NO 332
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
acauagacug ua                                                      12

<210> SEQ ID NO 333
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
acauagacug ua                                                      12

<210> SEQ ID NO 334
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
acauagacug ua                                                      12

<210> SEQ ID NO 335
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
acauagacug ua                                                      12

```
<210> SEQ ID NO 336
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
acauagacug ua                                                          12

<210> SEQ ID NO 337
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
acauagacug ua                                                          12

<210> SEQ ID NO 338
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
acauagacug ua                                                          12

<210> SEQ ID NO 339
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
acatagactg ta                                                          12

<210> SEQ ID NO 340
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
acatagactg ta                                                          12

<210> SEQ ID NO 341
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
acatagactg ta                                                          12
```

<210> SEQ ID NO 342
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
acatagactg ta                                                              12

<210> SEQ ID NO 343
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
acatagactg ta                                                              12

<210> SEQ ID NO 344
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
acatagactg ta                                                              12

<210> SEQ ID NO 345
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
acatagactg ta                                                              12

<210> SEQ ID NO 346
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
acatagactg ta                                                              12

<210> SEQ ID NO 347
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
acatagactg ta                                                              12

```
-continued

<210> SEQ ID NO 348
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
acatagactg ta                                                              12

<210> SEQ ID NO 349
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
acatagactg ta                                                              12

<210> SEQ ID NO 350
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
acatagactg ta                                                              12

<210> SEQ ID NO 351
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
acatagactg ta                                                              12

<210> SEQ ID NO 352
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
acatagactg ta                                                              12

<210> SEQ ID NO 353
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
acatagactg ta                                                              12

<210> SEQ ID NO 354
```

```
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
acatagactg ta                                                            12

<210> SEQ ID NO 355
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
acatagactg ta                                                            12

<210> SEQ ID NO 356
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
acatagactg ta                                                            12

<210> SEQ ID NO 357
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
acatagactg ta                                                            12

<210> SEQ ID NO 358
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
acatagactg ta                                                            12

<210> SEQ ID NO 359
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
acauagacug ua                                                            12

<210> SEQ ID NO 360
<211> LENGTH: 12
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
acauagacug ua                                                              12

<210> SEQ ID NO 361
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
acauagacug ua                                                              12

<210> SEQ ID NO 362
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
acauagacug ua                                                              12

<210> SEQ ID NO 363
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
acauagacug ua                                                              12

<210> SEQ ID NO 364
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
acauagacug ua                                                              12

<210> SEQ ID NO 365
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
acauagacug ua                                                              12

<210> SEQ ID NO 366
<211> LENGTH: 12
<212> TYPE: RNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 366
acauagacug ua                                                              12

<210> SEQ ID NO 367
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
acauagacug ua                                                              12

<210> SEQ ID NO 368
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
acauagacug ua                                                              12

<210> SEQ ID NO 369
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
uucuugcucu auaaaccgug u                                                    21

<210> SEQ ID NO 370
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
uucuugcucu auaaaccgug u                                                    21

<210> SEQ ID NO 371
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
aguguucuug cucuauaaac a                                                    21

<210> SEQ ID NO 372
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 372
aguguucuug cucuauaaac a                                              21

<210> SEQ ID NO 373
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
uucuugcucu auaaaccgug u                                              21

<210> SEQ ID NO 374
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
aguguucuug cucuauaaac a                                              21

<210> SEQ ID NO 375
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
aguguucuug cucuauaaac a                                              21

<210> SEQ ID NO 376
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
uucuugcucu auaaaccgug u                                              21

<210> SEQ ID NO 377
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
aguguucuug cucuauaaac a                                              21

<210> SEQ ID NO 378
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 378
aguguucuug cucuauaaac a                                              21

<210> SEQ ID NO 379
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
aguguucuug cucuauaaac a                                              21

<210> SEQ ID NO 380
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
uucuugcucu auaaaccgug u                                              21

<210> SEQ ID NO 381
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
aguguucuug cucuauaaac a                                              21

<210> SEQ ID NO 382
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
aguguucuug cucuauaaac a                                              21

<210> SEQ ID NO 383
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
aguguucuug cucuauaaac a                                              21

<210> SEQ ID NO 384
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 384
uucuugcucu auaaaccgug u                                              21

<210> SEQ ID NO 385
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
aguguucuug cucuauaaac a                                              21

<210> SEQ ID NO 386
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
aguguucuug cucuauaaac a                                              21

<210> SEQ ID NO 387
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
aguguucuug cucuauaaac a                                              21

<210> SEQ ID NO 388
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
uucuugcucu auaaaccgug u                                              21

<210> SEQ ID NO 389
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
aguguucuug cucuauaaac a                                              21

<210> SEQ ID NO 390
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 390
aguguucuug cucuauaaac a                                      21

<210> SEQ ID NO 391
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
uucuugcucu auaaaccgug u                                      21

<210> SEQ ID NO 392
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
aguguucuug cucuauaaac a                                      21

<210> SEQ ID NO 393
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
aguguucuug cucuauaaac a                                      21

<210> SEQ ID NO 394
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
uucuugcucu auaaaccgug u                                      21

<210> SEQ ID NO 395
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
aguguucuug cucuauaaac a                                      21

<210> SEQ ID NO 396
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 396
aguguucuug cucuauaaac a                                                   21

<210> SEQ ID NO 397
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
acacgguuua uagagcaaga aca                                                 23

<210> SEQ ID NO 398
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 398
acacggnuua uagagcaaga aca                                                 23

<210> SEQ ID NO 399
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Unlocked nucleic acid

<400> SEQUENCE: 399
uguunauaga gcaagaacac ugu                                                 23

<210> SEQ ID NO 400
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 400
uguuuanaga gcaagaacac ugu                                                 23

<210> SEQ ID NO 401
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 401
acacggtuua uagagcaaga aca                                           23

<210> SEQ ID NO 402
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Unlocked nucleic acid

<400> SEQUENCE: 402
uguunauaga gcaagaacac ugu                                           23

<210> SEQ ID NO 403
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 403
uguuuanaga gcaagaacac ugu                                           23

<210> SEQ ID NO 404
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
acacgguuua uagagcaaga aca                                           23

<210> SEQ ID NO 405
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
uguuuauaga gcaagaacac ugu                                           23

<210> SEQ ID NO 406
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Unlocked nucleic acid

<400> SEQUENCE: 406
```
uguunauaga gcaagaacac ugu         23

<210> SEQ ID NO 407
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 407
uguuuanaga gcaagaacac ugu         23

<210> SEQ ID NO 408
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 408
acacggnuua uagagcaaga aca         23

<210> SEQ ID NO 409
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 409
uguutauaga gcaagaacac ugu         23

<210> SEQ ID NO 410
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Unlocked nucleic acid

<400> SEQUENCE: 410
uguunauaga gcaagaacac ugu         23

<210> SEQ ID NO 411
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (7)..(7)
<223> OTHER INFORMATION: Unlocked nucleic acid

<400> SEQUENCE: 411
uguuuanaga gcaagaacac ugu                                              23

<210> SEQ ID NO 412
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 412
acacggnuua uagagcaaga aca                                              23

<210> SEQ ID NO 413
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
uguuuauaga gcaagaacac ugu                                              23

<210> SEQ ID NO 414
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 414
uguuuataga gcaagaacac ugu                                              23

<210> SEQ ID NO 415
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 415
uguuuanaga gcaagaacac ugu                                              23

<210> SEQ ID NO 416
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (7)..(7)
<223> OTHER INFORMATION: Unlocked nucleic acid

<400> SEQUENCE: 416
acacggnuua uagagcaaga aca                                          23

<210> SEQ ID NO 417
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Unlocked nucleic acid

<400> SEQUENCE: 417
uguunauaga gcaagaacac ugu                                          23

<210> SEQ ID NO 418
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
uguuuauaga gcaagaacac ugu                                          23

<210> SEQ ID NO 419
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 419
acacggnuua uagagcaaga aca                                          23

<210> SEQ ID NO 420
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Unlocked nucleic acid

<400> SEQUENCE: 420
uguunauaga gcaagaacac ugu                                          23

<210> SEQ ID NO 421
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 421
uguuuanaga gcaagaacac ugu                                           23

<210> SEQ ID NO 422
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 422
acacggnuua uagagcaaga aca                                           23

<210> SEQ ID NO 423
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Unlocked nucleic acid

<400> SEQUENCE: 423
uguunauaga gcaagaacac ugu                                           23

<210> SEQ ID NO 424
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Unlocked nucleic acid

<400> SEQUENCE: 424
uguuuanaga gcaagaacac ugu                                           23

<210> SEQ ID NO 425
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
uacagucuau gu                                                       12

<210> SEQ ID NO 426
<211> LENGTH: 12
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 426
uacagucuau gu                                                          12

<210> SEQ ID NO 427
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
uacagucuau gu                                                          12

<210> SEQ ID NO 428
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
uacagucuau gu                                                          12

<210> SEQ ID NO 429
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 429
uacagtcuau gu                                                          12

<210> SEQ ID NO 430
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 430
uacagtcuau gu                                                          12

<210> SEQ ID NO 431
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
uacagucuau gu                                                          12
```

```
<210> SEQ ID NO 432
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
uacagucuau gu                                                            12

<210> SEQ ID NO 433
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
uacagucuau gu                                                            12

<210> SEQ ID NO 434
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
uacagucuau gu                                                            12

<210> SEQ ID NO 435
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
uacagucuau gu                                                            12

<210> SEQ ID NO 436
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
uacagucuau gu                                                            12

<210> SEQ ID NO 437
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
uacagucuau gu                                                            12
```

```
<210> SEQ ID NO 438
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
uacagucuau gu                                                              12

<210> SEQ ID NO 439
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
tacagtctat gt                                                              12

<210> SEQ ID NO 440
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
tacagtctat gt                                                              12

<210> SEQ ID NO 441
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
tacagtctat gt                                                              12

<210> SEQ ID NO 442
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
tacagtctat gt                                                              12

<210> SEQ ID NO 443
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
tacagtctat gt                                                              12
```

```
<210> SEQ ID NO 444
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
tacagtctat gt                                                         12

<210> SEQ ID NO 445
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
tacagtctat gt                                                         12

<210> SEQ ID NO 446
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
tacagtctat gt                                                         12

<210> SEQ ID NO 447
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
tacagtctat gt                                                         12

<210> SEQ ID NO 448
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
tacagtctat gt                                                         12

<210> SEQ ID NO 449
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
tacagtctat gt                                                         12

<210> SEQ ID NO 450
```

```
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 450
tacaguctat gt                                                         12

<210> SEQ ID NO 451
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 451
tacaguctat gt                                                         12

<210> SEQ ID NO 452
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
tacagtctat gt                                                         12

<210> SEQ ID NO 453
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
acauagacug ua                                                         12

<210> SEQ ID NO 454
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
acauagacug ua                                                         12

<210> SEQ ID NO 455
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
```
acauagacug ua                        12

<210> SEQ ID NO 456
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
acauagacug ua                        12

<210> SEQ ID NO 457
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
acauagacug ua                        12

<210> SEQ ID NO 458
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
acauagacug ua                        12

<210> SEQ ID NO 459
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
acauagacug ua                        12

<210> SEQ ID NO 460
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
acauagacug ua                        12

<210> SEQ ID NO 461
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
acauagacug ua                                              12

<210> SEQ ID NO 462
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
acauagacug ua                                              12

<210> SEQ ID NO 463
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
acauagacug ua                                              12

<210> SEQ ID NO 464
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
acauagacug ua                                              12

<210> SEQ ID NO 465
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
acauagacug ua                                              12

<210> SEQ ID NO 466
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
acauagacug ua                                              12

<210> SEQ ID NO 467
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
acatagactg ta                                              12

```
<210> SEQ ID NO 468
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
acatagactg ta                                                        12

<210> SEQ ID NO 469
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
acatagactg ta                                                        12

<210> SEQ ID NO 470
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
acatagactg ta                                                        12

<210> SEQ ID NO 471
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
acatagactg ta                                                        12

<210> SEQ ID NO 472
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
acatagactg ta                                                        12

<210> SEQ ID NO 473
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
acatagactg ta                                                        12
```

<210> SEQ ID NO 474
<211> LENGTH: 12
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 474
acatagactg ta                                                    12

<210> SEQ ID NO 475
<211> LENGTH: 12
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 475
acatagactg ta                                                    12

<210> SEQ ID NO 476
<211> LENGTH: 12
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 476
acatagactg ta                                                    12

<210> SEQ ID NO 477
<211> LENGTH: 12
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 477
acatagactg ta                                                    12

<210> SEQ ID NO 478
<211> LENGTH: 12
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 478
acatagactg ta                                                    12

<210> SEQ ID NO 479
<211> LENGTH: 12
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 479
acatagactg ta                                                    12

-continued

```
<210> SEQ ID NO 480
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
acatagactg ta                                                             12

<210> SEQ ID NO 481
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
aacaguguuc uugcucuaua a                                                   21

<210> SEQ ID NO 482
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
aacaguguuc uugcucuaua a                                                   21

<210> SEQ ID NO 483
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
aacaguguuc uugcucuaua a                                                   21

<210> SEQ ID NO 484
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
aacaguguuc uugcucuaua a                                                   21

<210> SEQ ID NO 485
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
aacaguguuc uugcucuaua a                                                   21

<210> SEQ ID NO 486
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
aacaguguuc uugcucuaua a                                              21

<210> SEQ ID NO 487
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 487
aacagtguuc uugcucuaua a                                              21

<210> SEQ ID NO 488
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
aacaguguuc uugcucuaua a                                              21

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 489
aacagugtuc uugcucuaua a                                              21

<210> SEQ ID NO 490
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 490
aacagugutc uugcucuaua a                                              21

<210> SEQ ID NO 491
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
      oligonucleotide

<400> SEQUENCE: 491
aacaguguuc uugcucuaua a                                             21

<210> SEQ ID NO 492
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 492
aacaguguuc tugcucuaua a                                             21

<210> SEQ ID NO 493
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 493
aacaguguuc utgcucuaua a                                             21

<210> SEQ ID NO 494
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
aacaguguuc uugcucuaua a                                             21

<210> SEQ ID NO 495
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
aacaguguuc uugcucuaua a                                             21

<210> SEQ ID NO 496
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 496
aacaguguuc uugctcuaua a                                             21
```

<210> SEQ ID NO 497
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 497
aacaguguuc uugcucuaua a                                              21

<210> SEQ ID NO 498
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 498
aacaguguuc uugcuctaua a                                              21

<210> SEQ ID NO 499
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 499
aacaguguuc uugcucuaua a                                              21

<210> SEQ ID NO 500
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 500
aacaguguuc uugcucuata a                                              21

<210> SEQ ID NO 501
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 501
aacaguguuc uugcucuaua a                                              21

<210> SEQ ID NO 502
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 502
aacaguguuc uugcucuaua a                                              21

<210> SEQ ID NO 503
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 503
aacaguguuc uugcucuaua a                                              21

<210> SEQ ID NO 504
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
aacaguguuc uugcucuaua a                                              21

<210> SEQ ID NO 505
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
aacaguguuc uugcucuaua a                                              21

<210> SEQ ID NO 506
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
aacaguguuc uugcucuaua a                                              21

<210> SEQ ID NO 507
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
aacaguguuc uugcucuaua a                                              21

<210> SEQ ID NO 508
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 508
aacaguguuc uugcucuaua a                                              21

<210> SEQ ID NO 509
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509
aacaguguuc uugcucuaua a                                              21

<210> SEQ ID NO 510
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
aacaguguuc uugcucuaua a                                              21

<210> SEQ ID NO 511
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
aacaguguuc uugcucuaua a                                              21

<210> SEQ ID NO 512
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
aacaguguuc uugcucuaua a                                              21

<210> SEQ ID NO 513
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
aacaguguuc uugcucuaua a                                              21

<210> SEQ ID NO 514
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 514
aacaguguuc uugcucuaua a                                              21

<210> SEQ ID NO 515
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
aacaguguuc uugcucuaua a                                              21

<210> SEQ ID NO 516
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
aacaguguuc uugcucuaua a                                              21

<210> SEQ ID NO 517
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
aacaguguuc uugcucuaua a                                              21

<210> SEQ ID NO 518
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
aacaguguuc uugcucuaua a                                              21

<210> SEQ ID NO 519
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
aacaguguuc uugcucuaua a                                              21

<210> SEQ ID NO 520
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
```
aacaguguuc uugcucuaua a                                    21

<210> SEQ ID NO 521
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 521
aacaguguuc uugcucuaua a                                    21

<210> SEQ ID NO 522
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
aacaguguuc uugcucuaua a                                    21

<210> SEQ ID NO 523
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
aacaguguuc uugcucuaua a                                    21

<210> SEQ ID NO 524
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
aacaguguuc uugcucuaua a                                    21

<210> SEQ ID NO 525
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
aacaguguuc uugcucuaua a                                    21

<210> SEQ ID NO 526
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526

-continued aacaguguuc uugcucuaua a   21

<210> SEQ ID NO 527
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
aacaguguuc uugcucuaua a   21

<210> SEQ ID NO 528
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
aacaguguuc uugcucuaua a   21

<210> SEQ ID NO 529
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
aacaguguuc uugcucuaua a   21

<210> SEQ ID NO 530
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
aacaguguuc uugcucuaua a   21

<210> SEQ ID NO 531
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
aacaguguuc uugcucuaua a   21

<210> SEQ ID NO 532
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 532
aacagtguuc uugcucuaua a                                              21

<210> SEQ ID NO 533
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533
aacaguguuc uugcucuaua a                                              21

<210> SEQ ID NO 534
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 534
aacagugtuc uugcucuaua a                                              21

<210> SEQ ID NO 535
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 535
aacagugutc uugcucuaua a                                              21

<210> SEQ ID NO 536
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536
aacaguguuc uugcucuaua a                                              21

<210> SEQ ID NO 537
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 537
aacaguguuc tugcucuaua a                                              21
```

```
<210> SEQ ID NO 538
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 538
aacaguguuc utgcucuaua a                                                    21

<210> SEQ ID NO 539
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 539
aacaguguuc uugcucuaua a                                                    21

<210> SEQ ID NO 540
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 540
aacaguguuc uugcucuaua a                                                    21

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541
aacaguguuc uugctcuaua a                                                    21

<210> SEQ ID NO 542
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 542
aacaguguuc uugcucuaua a                                                    21

<210> SEQ ID NO 543
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
      Synthetic oligonucleotide

<400> SEQUENCE: 543
aacaguguuc uugcuctaua a                                              21

<210> SEQ ID NO 544
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 544
aacaguguuc uugcucuaua a                                              21

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 545
aacaguguuc uugcucuata a                                              21

<210> SEQ ID NO 546
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
aacaguguuc uugcucuaua a                                              21

<210> SEQ ID NO 547
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 547
aacaguguuc uugcucuaua a                                              21

<210> SEQ ID NO 548
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
uuauagagca agaacacugu uuu                                            23

<210> SEQ ID NO 549
<211> LENGTH: 23
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 549
uuauagagca agaacacugu uuu                                            23

<210> SEQ ID NO 550
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
uuauagagca agaacacugu uuu                                            23

<210> SEQ ID NO 551
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
uuauagagca agaacacugu uuu                                            23

<210> SEQ ID NO 552
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552
uuauagagca agaacacugu uuu                                            23

<210> SEQ ID NO 553
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553
uuauagagca agaacacugu uuu                                            23

<210> SEQ ID NO 554
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 554
uuauagagca agaacacugu uuu                                            23

<210> SEQ ID NO 555
<211> LENGTH: 23
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 555
uuauagagca agaacacugu uuu                                              23

<210> SEQ ID NO 556
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556
uuauagagca agaacacugu uuu                                              23

<210> SEQ ID NO 557
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
uuauagagca agaacacugu uuu                                              23

<210> SEQ ID NO 558
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 558
uuauagagca agaacacugu uuu                                              23

<210> SEQ ID NO 559
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 559
uuauagagca agaacacugu uuu                                              23

<210> SEQ ID NO 560
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 560
uuauagagca agaacacugu uuu                                              23

<210> SEQ ID NO 561
<211> LENGTH: 23
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 561
uuauagagca agaacacugu uuu                                              23

<210> SEQ ID NO 562
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 562
uuauagagca agaacacugu uuu                                              23

<210> SEQ ID NO 563
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 563
uuauagagca agaacacugu uuu                                              23

<210> SEQ ID NO 564
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 564
uuauagagca agaacacugu uuu                                              23

<210> SEQ ID NO 565
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 565
uuauagagca agaacacugu uuu                                              23

<210> SEQ ID NO 566
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 566
uuauagagca agaacacugu uuu                                              23

<210> SEQ ID NO 567
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 567
uuauagagca agaacacugu uuu                                                 23

<210> SEQ ID NO 568
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 568
uuauagagca agaacacugu uuu                                                 23

<210> SEQ ID NO 569
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 569
uuauagagca agaacacugu uuu                                                 23

<210> SEQ ID NO 570
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 570
tuauagagca agaacacugu uuu                                                 23

<210> SEQ ID NO 571
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 571
utauagagca agaacacugu uuu                                                 23

<210> SEQ ID NO 572
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 572
uuauagagca agaacacugu uuu                                                 23

<210> SEQ ID NO 573

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 573
uuatagagca agaacacugu uuu                                             23

<210> SEQ ID NO 574
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 574
uuauagagca agaacacugu uuu                                             23

<210> SEQ ID NO 575
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 575
uuauagagca agaacacugu uuu                                             23

<210> SEQ ID NO 576
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 576
uuauagagca agaacacugu uuu                                             23

<210> SEQ ID NO 577
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
uuauagagca agaacacugu uuu                                             23

<210> SEQ ID NO 578
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 578
uuauagagca agaacacugu uuu                                             23
```

```
<210> SEQ ID NO 579
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579
uuauagagca agaacacugu uuu                                              23

<210> SEQ ID NO 580
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
uuauagagca agaacacugu uuu                                              23

<210> SEQ ID NO 581
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 581
uuauagagca agaacacugu uuu                                              23

<210> SEQ ID NO 582
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582
uuauagagca agaacacugu uuu                                              23

<210> SEQ ID NO 583
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583
uuauagagca agaacacugu uuu                                              23

<210> SEQ ID NO 584
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584
uuauagagca agaacacugu uuu                                              23
```

```
<210> SEQ ID NO 585
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 585
uuauagagca agaacacugu uuu                                              23

<210> SEQ ID NO 586
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 586
uuauagagca agaacacugu uuu                                              23

<210> SEQ ID NO 587
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 587
uuauagagca agaacactgu uuu                                              23

<210> SEQ ID NO 588
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 588
uuauagagca agaacacugu uuu                                              23

<210> SEQ ID NO 589
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 589
uuauagagca agaacacugt uuu                                              23

<210> SEQ ID NO 590
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 590
uuauagagca agaacacugu tuu                                              23

<210> SEQ ID NO 591
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 591
uuauagagca agaacacugu utu                                              23

<210> SEQ ID NO 592
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 592
uuauagagca agaacacugu uut                                              23

<210> SEQ ID NO 593
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 593
uuauagagca agaacacugu uuu                                              23

<210> SEQ ID NO 594
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 594
uuauagagca agaacacugu tuu                                              23

<210> SEQ ID NO 595
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 595
uuauagagca agaacacugt uuu					23

<210> SEQ ID NO 596
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 596
uuauagagca agaacacugu uuu					23

<210> SEQ ID NO 597
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 597
uuauagagca agaacactgu uuu					23

<210> SEQ ID NO 598
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598
uuauagagca agaacacugu uuu					23

<210> SEQ ID NO 599
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 599
uuauagagca agaacacugu uuu					23

<210> SEQ ID NO 600
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 600
uuauagagca agaacacugu uuu					23

<210> SEQ ID NO 601
<211> LENGTH: 23
<212> TYPE: RNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 601
uuauagagca agaacacugu uuu                                              23

<210> SEQ ID NO 602
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 602
uuauagagca agaacacugu uuu                                              23

<210> SEQ ID NO 603
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603
uuauagagca agaacacugu uuu                                              23

<210> SEQ ID NO 604
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604
uuauagagca agaacacugu uuu                                              23

<210> SEQ ID NO 605
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 605
uuauagagca agaacacugu uuu                                              23

<210> SEQ ID NO 606
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
uuauagagca agaacacugu uuu                                              23

<210> SEQ ID NO 607
<211> LENGTH: 23
<212> TYPE: RNA
<213> ORGANISM: Artificial Sequence
<220> FEATURE:
<223> OTHER INFORMATION: Description of Artificial Sequence: Synthetic
```

```
            oligonucleotide

<400> SEQUENCE: 607
uuauagagca agaacacugu uuu                                                 23

<210> SEQ ID NO 608
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 608
uuauagagca agaacacugu uuu                                                 23

<210> SEQ ID NO 609
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 609
uuauagagca agaacacugu uuu                                                 23

<210> SEQ ID NO 610
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 610
uuauagagca agaacacugu uuu                                                 23

<210> SEQ ID NO 611
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 611
uuatagagca agaacacugu uuu                                                 23

<210> SEQ ID NO 612
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 612
uuauagagca agaacacugu uuu                                                 23

<210> SEQ ID NO 613
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 613
utauagagca agaacacugu uuu                                           23

<210> SEQ ID NO 614
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 614
tuauagagca agaacacugu uuu                                           23

<210> SEQ ID NO 615
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 615
aacaguguuc uugcucuaua a                                             21

<210> SEQ ID NO 616
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 616
aacaguguuc uugcucuaua a                                             21

<210> SEQ ID NO 617
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 617
aacaguguuc uugcucuaua a                                             21

<210> SEQ ID NO 618
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
aacaguguuc uugcucuaua a                                             21
```

<210> SEQ ID NO 619
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 619
aacaguguuc uugcucuaua a                                           21

<210> SEQ ID NO 620
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 620
aacaguguuc uugcucuaua a                                           21

<210> SEQ ID NO 621
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 621
aacaguguuc uugcucuaua a                                           21

<210> SEQ ID NO 622
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 622
aacaguguuc uugcucuaua a                                           21

<210> SEQ ID NO 623
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 623
aacaguguuc uugcucuaua a                                           21

<210> SEQ ID NO 624
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 624
aacaguguuc uugcucuaua a                                           21

-continued

```
<210> SEQ ID NO 625
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 625
aacaguguuc uugcucuaua a                                                    21

<210> SEQ ID NO 626
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 626
uuauagagca agaacacugu uuu                                                  23

<210> SEQ ID NO 627
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 627
agagcaagaa cacuguuuu                                                       19

<210> SEQ ID NO 628
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 628
agagcaagaa cacuguuuu                                                       19

<210> SEQ ID NO 629
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 629
gagcaagaac acuguuuu                                                        18

<210> SEQ ID NO 630
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 630
gagcaagaac acuguuuu                                                        18

<210> SEQ ID NO 631
```

```
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 631
agcaagaaca cuguuuu                                                   17

<210> SEQ ID NO 632
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 632
agcaagaaca cuguuuu                                                   17

<210> SEQ ID NO 633
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 633
gcaagaacac uguuuu                                                    16

<210> SEQ ID NO 634
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 634
gcaagaacac uguuuu                                                    16

<210> SEQ ID NO 635
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 635
caagaacacu guuuu                                                     15

<210> SEQ ID NO 636
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 636
caagaacacu guuuu                                                     15

<210> SEQ ID NO 637
<211> LENGTH: 21
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 637
gaaugugaaa gucaucgaca a                                              21

<210> SEQ ID NO 638
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 638
gaaugugaaa gucaucgaca a                                              21

<210> SEQ ID NO 639
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 639
gaaugugaaa gucaucgaca a                                              21

<210> SEQ ID NO 640
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 640
gaaugugaaa gucaucgaca a                                              21

<210> SEQ ID NO 641
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 641
gaaugugaaa gucaucgaca a                                              21

<210> SEQ ID NO 642
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 642
gaaugugaaa gucaucgaca a                                              21

<210> SEQ ID NO 643
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 643
gaaugugaaa gucaucgaca a                                               21

<210> SEQ ID NO 644
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 644
gaaugugaaa gucaucgaca a                                               21

<210> SEQ ID NO 645
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 645
gaaugugaaa gucaucgaca a                                               21

<210> SEQ ID NO 646
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 646
gaaugugaaa gucaucgaca a                                               21

<210> SEQ ID NO 647
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 647
gaaugugaaa gucaucgaca a                                               21

<210> SEQ ID NO 648
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 648
gaaugugaaa gucaucgaca a                                               21

<210> SEQ ID NO 649
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 649
gaaugugaaa gucaucgaca a                                              21

<210> SEQ ID NO 650
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 650
gaaugugaaa gucaucgaca a                                              21

<210> SEQ ID NO 651
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 651
gaaugugaaa gucaucgaca a                                              21

<210> SEQ ID NO 652
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 652
uugucgauga cuuucacauu cug                                            23

<210> SEQ ID NO 653
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 653
ucgaugacuu ucacauucug                                                20

<210> SEQ ID NO 654
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 654
ucgaugacuu ucacauucug                                                20

<210> SEQ ID NO 655
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 655
cgaugacuuu cacauucug                                                      19

<210> SEQ ID NO 656
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 656
cgaugacuuu cacauucug                                                      19

<210> SEQ ID NO 657
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 657
gaugacuuuc acauucug                                                       18

<210> SEQ ID NO 658
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 658
gaugacuuuc acauucug                                                       18

<210> SEQ ID NO 659
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 659
augacuuuca cauucug                                                        17

<210> SEQ ID NO 660
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 660
augacuuuca cauucug                                                        17

<210> SEQ ID NO 661
<211> LENGTH: 16
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 661
ugacuuucac auucug                                                    16

<210> SEQ ID NO 662
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 662
ugacuuucac auucug                                                    16

<210> SEQ ID NO 663
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 663
gacuuucaca uucug                                                     15

<210> SEQ ID NO 664
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 664
gacuuucaca uucug                                                     15

<210> SEQ ID NO 665
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 665
acuuucacau ucug                                                      14

<210> SEQ ID NO 666
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 666
acuuucacau ucug                                                      14

<210> SEQ ID NO 667
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 667
tttttttttt tttttttttt                                        20

<210> SEQ ID NO 668
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 668
tttttttttt tttttttuu                                         20

<210> SEQ ID NO 669
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 669
tttttttttt tttttttuu                                         20

<210> SEQ ID NO 670
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
tttttttttt tttttttttt                                        20

<210> SEQ ID NO 671
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671
tttttttttt tttttttttt                                        20

<210> SEQ ID NO 672
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
tttttttttt tttttttttt                                        20

<210> SEQ ID NO 673
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 673
tttttttttt tttttttttt                                                  20

<210> SEQ ID NO 674
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 674
tttttttttt tttttttttt                                                  20

<210> SEQ ID NO 675
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 675
tttttttttt tttttttttt                                                  20

<210> SEQ ID NO 676
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 676
tttttttttt tttttttttt                                                  20

<210> SEQ ID NO 677
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 677
aacaguguuc uugcucuaua a                                                21

<210> SEQ ID NO 678
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 678
uuauagagca agaacacugu uuu                                              23

<210> SEQ ID NO 679
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 679
aacaguguuc uugcucuaua a                                              21

<210> SEQ ID NO 680
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 680
uuaagagcaa gaacacuguu uu                                             22

<210> SEQ ID NO 681
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 681
aacaguguuc uugcucuaua a                                              21

<210> SEQ ID NO 682
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 682
uuatagagca agaacacugu uuu                                            23

<210> SEQ ID NO 683
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 683
aacaguguuc uugcucuaua a                                              21

<210> SEQ ID NO 684
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 684
uuaugagcaa gaacacuguu uu                                             22

<210> SEQ ID NO 685
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 685
aacaguguuc uugcucuaua a                                              21

<210> SEQ ID NO 686
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 686
uuauagagca agaacacugu uuu                                            23

<210> SEQ ID NO 687
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 687
aacaguguuc uugcucuaua a                                              21

<210> SEQ ID NO 688
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 688
uuauagagca agaacacugu uuu                                            23

<210> SEQ ID NO 689
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 689
aacaguguuc uugcucuaua a                                              21

<210> SEQ ID NO 690
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 690
uuauagagca agaacacugu uuu                                            23

<210> SEQ ID NO 691
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 691
aacaguguuc uugcucuaua a                                              21

<210> SEQ ID NO 692
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 692
uuauagagca agaacacugu uuu                                            23

<210> SEQ ID NO 693
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 693
aacaguguuc uugcucuaua a                                              21

<210> SEQ ID NO 694
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 694
uuauagagca agaacacugu uuu                                            23

<210> SEQ ID NO 695
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 695
aacaguguuc uugcucuaua a                                              21

<210> SEQ ID NO 696
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 696
uuauaagcaa gaacacuguu uu                                             22

<210> SEQ ID NO 697
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 697
aacaguguuc uugcucuaua a                                                 21

<210> SEQ ID NO 698
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 698
uuauagagca agaacacugu uuu                                               23

<210> SEQ ID NO 699
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 699
aacaguguuc uugcucuaua a                                                 21

<210> SEQ ID NO 700
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 700
uuauaggcaa gaacacuguu uu                                                22

<210> SEQ ID NO 701
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 701
aacaguguuc uugcucuaua a                                                 21

<210> SEQ ID NO 702
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 702
uuauagagca agaacacugu uuu                                               23

<210> SEQ ID NO 703
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 703
tttttttttt tttttttttt                                              20

<210> SEQ ID NO 704
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 704
tttttttttt tttttttttt                                              20

<210> SEQ ID NO 705
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
tttttttttt tttttttttt                                              20

<210> SEQ ID NO 706
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
tttttttttt tttttttttt                                              20

<210> SEQ ID NO 707
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
tttttttttt tttttttttt                                              20

<210> SEQ ID NO 708
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708
tttttttttt tttttttttt                                              20
```

MODIFIED RNA AGENTS WITH REDUCED OFF-TARGET EFFECT

RELATED APPLICATIONS

This application is a continuation under 35 U.S.C. § 120 of U.S. Application Ser. No. 17/055,710 filed on Nov. 16, 2020, which is a 35 U.S.C. § 371 National Phase Entry Application of International Patent Application No. PCT/US2019/032633 filed on May 16, 2019, which claims benefit under 35 U.S.C. § 119 (e) of the U.S. Provisional Application No. 62/672,405, filed on May 16, 2018 and the U.S. Provisional Application No. 62/719,291, filed on Aug. 17, 2018, the contents of all of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jun. 28, 2019, is named 051058-092330WOPT_SL.txt and is 186301 bytes in size.

FIELD OF THE INVENTION

The invention relates to RNAi duplex agents having particular motifs that are advantageous for inhibition of target gene expression by reducing the undesired off-target effects, as well as RNAi compositions suitable for therapeutic use. Additionally, the invention provides methods of inhibiting the expression of a target gene by administering these RNAi duplex agents, e.g., for the treatment of various diseases.

BACKGROUND

RNA interference or "RNAi" is a term initially coined by Fire and co-workers to describe the observation that double-stranded RNAi (dsRNA) can block gene expression (Fire et al. (1998) *Nature* 391, 806-811; Elbashir et al. (2001) *Genes Dev.* 15, 188-200). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 22 nucleotides) derived from the double-stranded RNA trigger, but the protein components of this activity remained unknown.

One of the off-target effects of siRNA is the miRNA-like effect—the argonaute protein, the core effector in RNA interference, treats siRNA, which is artificially introduced in order to induce RNA interference, as a miRNA (microRNA). (Lam et al. (2015) Molecular Therapy Nucleic Acids (2015) 4, e252). The miRNA recognizes a target gene majorly through base-pairing between the seed region (positions 2-9 from the 5' end) and the target mRNA for gene suppression. The off-targets caused by siRNAs originate from base-complementarity of the seed regions of the RISC-loaded antisense strand of siRNA with one or more mRNA. The miRNA-like off-target effects in siRNAs have been reported in several studies, and affect expression of multitude of genes depending on sequences of the seed regions and are serious enough to cause up to 30% of the positive hits in siRNA based phenotype screening. Additionally, in the case of miRNAs, they are also reported to silence target genes through compensatory pairings within their 3' end regions (3'-compensatory pairing) when the interactions between seed region and targets become weak, implicating that the miRNA-like off-target effects are likely to be mediated by such mechanism.

There is thus an ongoing effort to eliminate or reduce miRNA-like off-target effects of siRNAs by modulating siRNA design by judicious application of chemical modifications without compromising the gene silencing efficacy of siRNA gene therapeutics. This invention is directed to that effort.

SUMMARY

This invention provides effective nucleotide or chemical motifs for dsRNA molecules, which are advantageous for inhibition of target gene expression, while having reduced off-target gene silencing effects, as well as RNAi compositions suitable for therapeutic use.

The inventors have discovered inter alia that dsRNA molecules where the antisense strand comprises at least one thermally destabilizing modification of the duplex within the seed region (i.e., at position 2-9 of the 5'-end of the antisense strand, counting from the 5'-end) and the dsRNA molecule has a melting temperature in the range of from about 40° C. to about 80° C. can be more effective in mediating RNA interference than the parent dsRNA molecule lacking the destabilizing modification. In some embodiments, the destabilizing modification is selected from the Modified Unlocked Nucleic Acid (mUNA) and Glycol Nucleic Acid (GNA) building blocks described in Examples 1-3 herein. In some embodiments, the destabilizing modification is selected from the group consisting of GNA-isoC, GNA-isoG, 5'-mUNA, 4'-mUNA, 3'-mUNA, 2'-mUNA, structures of which are as follows:

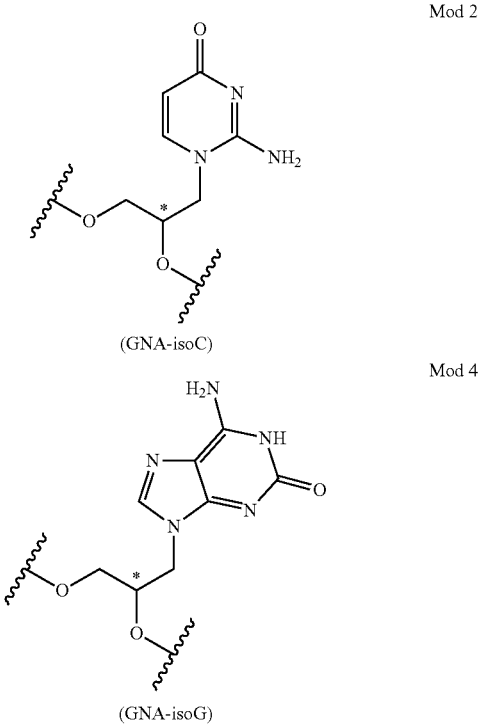

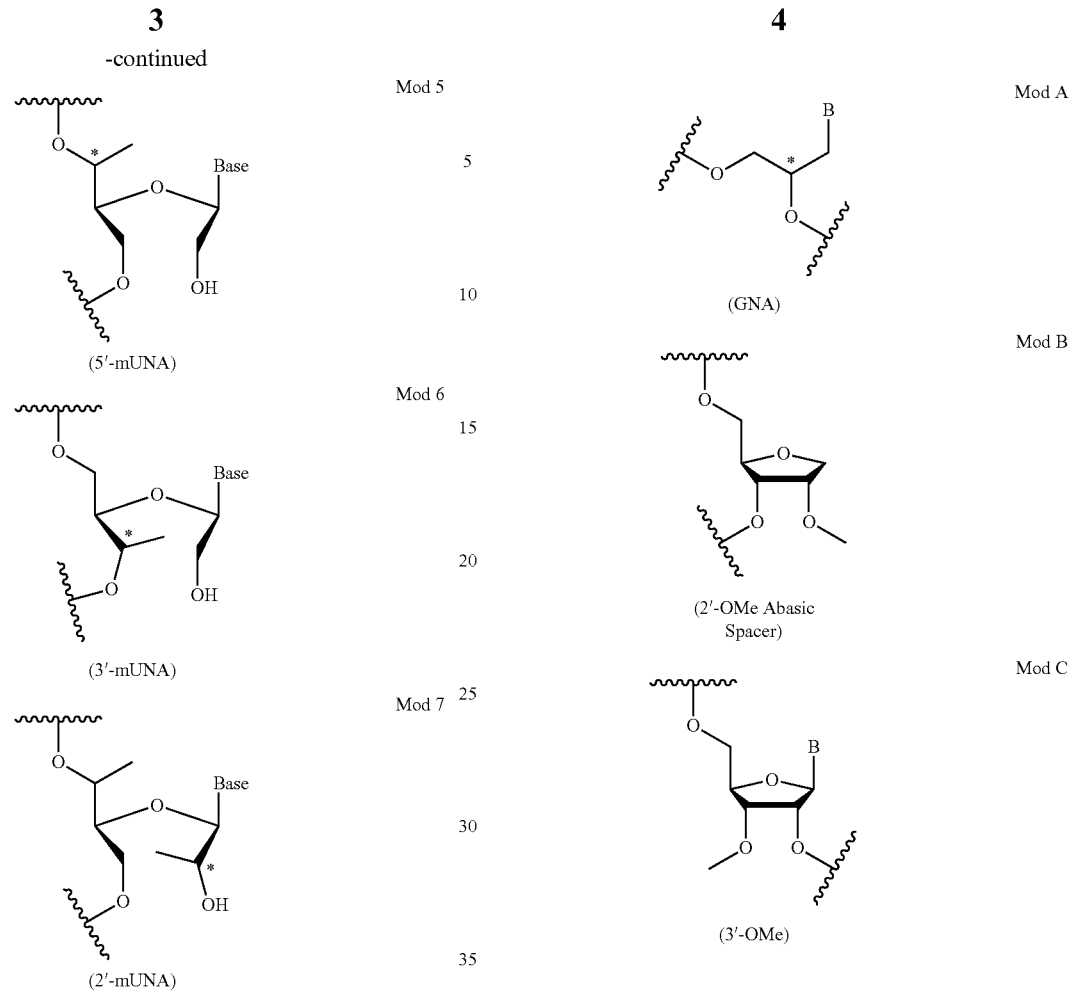

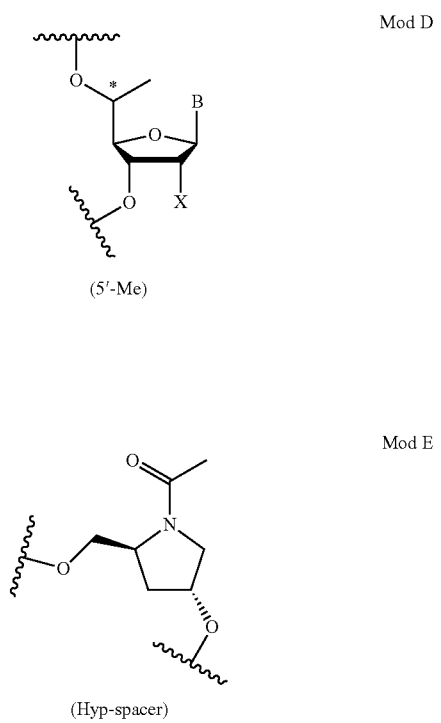

wherein Base is a modified or unmodified nucleobase and the asterisk on each structure represents either R, S or racemic.

In some embodiments of the various aspects disclosed herein, the destabilizing modification is 2'-5' RNA, i.e., Mod 8. In some preferred embodiments, the destabilizing modification is present at position 7 of the antisense strand (counting from the 5'-end) when the destabilizing modification is 2'-5' RNA.

In some embodiments of the various aspects disclosed herein, 5'-mUNA is 5'-(S)-Me-UNA (Y95) or 5'-(R)-Me-UNA (Y97), structures of which are shown in FIG. 32. In some embodiments of the various aspects disclosed herein, 2'-mUNA is 2'-(S)-Me-UNA (Y96) or 2'-(R)-Me-UNA (Y98), structures of which are shown in FIG. 32. In some embodiments of the various aspects disclosed herein, 3'-mUNA is 3'-(S)-Me-UNA (Y99), 3'-(R)-Me-UNA (Y100), or 3'-(R)-Me-4'-(S)-hydroxymethyl-UNA (Y102) structures of which are shown in FIG. 32. In some embodiments of the various aspects disclosed herein, 4'-(B)-OMe-UNA (Y101), structure of which is shown in FIG. 32.

In some embodiments, the dsRNA molecule further comprises at least one thermally destabilizing modification selected from the group consisting of GNA, 2'-OMe, 3'-OMe, 5'-Me, Hyp-spacer, SNA, hGNA, hhGNA, mGNA, TNA and h'GNA (Mod A-Mod K), structures of which are as follows:

-continued
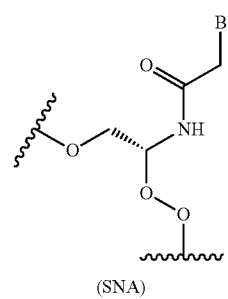
(SNA)
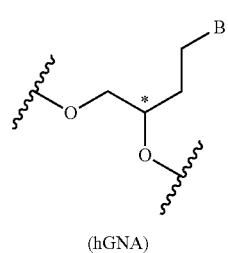
(hGNA)
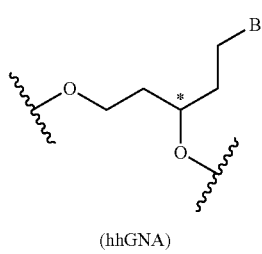
(hhGNA)
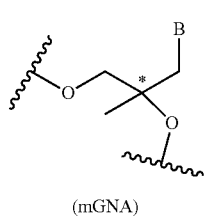
(mGNA)
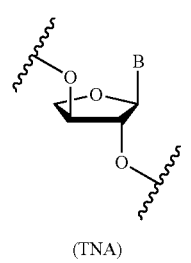
(TNA)
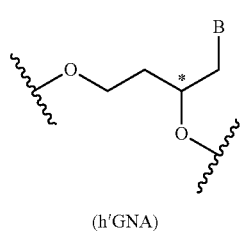
(h'GNA)
X = OMe, F
wherein B is a modified or unmodified nucleobase and the asterisk on each structure represents either R, S or racemic.
Exemplary Hyp-spacer nucleoisides include the following:
Mod F
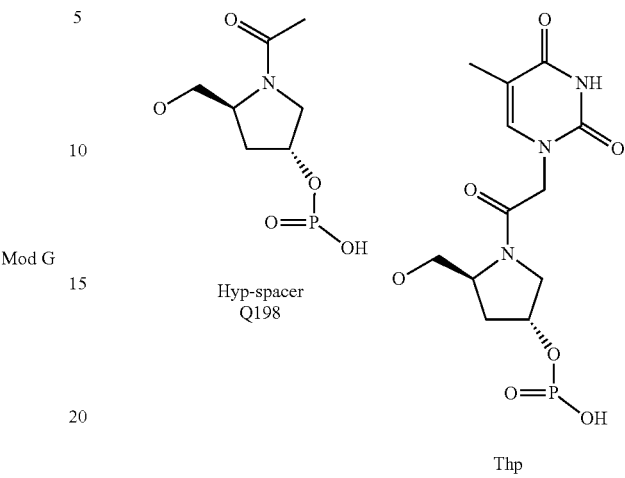
Hyp-spacer Q198
Thp
Mod G
Mod H
Mod I
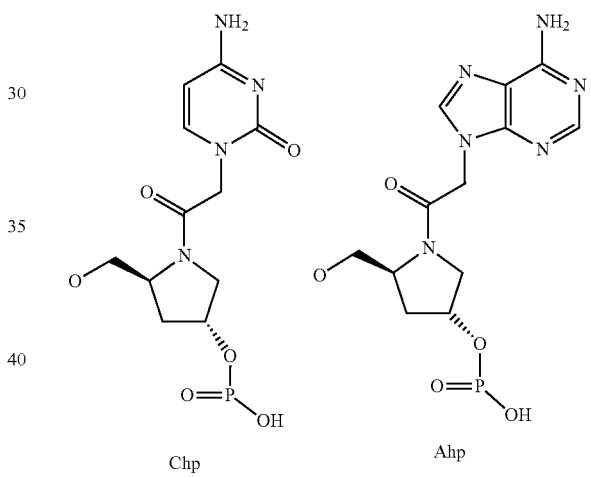
Chp
Ahp
Mod J
Mod K
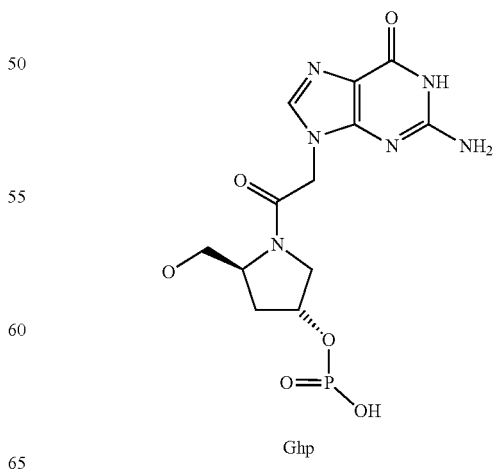
Ghp Examply TNA nucleosides include the following:

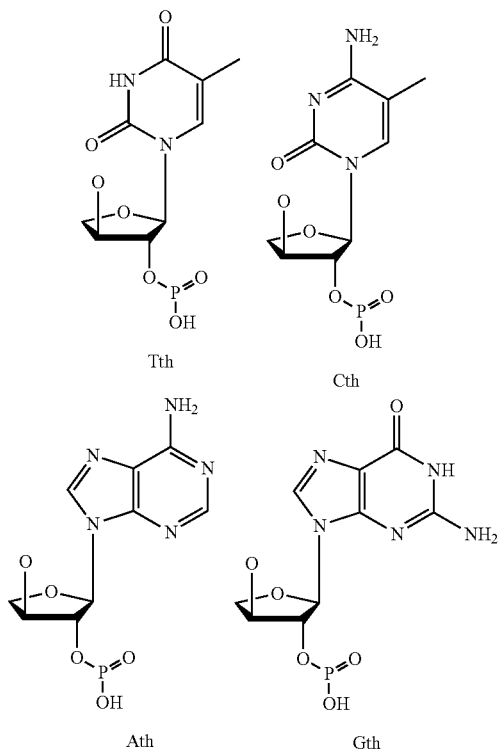

Also provided herein are monomers and phosphoramidites of the destabilizing modifications. For example, monomers and phosphoramidites can be selected from the Modified Unlocked Nucleic Acid (mUNA) and Glycol Nucleic Acid (GNA) building blocks described in Examples 1-3. In some embodiments, monomer or a phosphoramidite thereof is selected from the group consisting of GNA-isoC, GNA-isoG, 5'-mUNA, 4'-mUNA, 3'-mUNA, and 2'-mUNA. Also provided herein are nucleic acids comprising one or more of the mUNA and/or GNA monomers described herein. Without limitation, a nucleic acid comprising one or more of the mUNA and/or GNA monomers described herein can be single-stranded, double-stranded, partially double-stranded, hairpin or a circular nucleic acid.

In one aspect the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five, six seven, eight or all nine) of the following characteristics: (i) a melting temperature ($T_m$) of from about 40° C. to about 80° C.; (ii) the antisense comprises 2, 3, 4, 5 or 6 2'-fluoro modifications; (iii) the antisense comprises 1, 2, 3 or 4 phosphorothioate internucleotide linkages; (iv) the sense strand is conjugated with a ligand; (v) the sense strand comprises 2, 3, 4 or 5 2'-fluoro modifications; (vi) the sense strand comprises 1, 2, 3 or 4 phosphorothioate internucleotide linkages; (vii) the dsRNA comprises at least four 2'-fluoro modifications; (viii) the dsRNA comprises a duplex region of 12-40 nucleotide pairs in length; and (ix) a blunt end at 5'end of the antisense strand. In some embodiments, the destabilizing modification is selected from the mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA.

In some embodiments, the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9, preferably 3-8, of the 5'-end of the antisense strand, counting from the 5'-end), and the dsRNA further has at least one (e.g., one, two, three, four, five, six seven, eight or all nine) of the following characteristics: (i) a melting temperature ($T_m$) of from about 40° C. to about 80° C.; (ii) the antisense comprises 6, 7, 8, 9, 10, 11 or 12 2'-OMe modifications; (iii) the antisense comprises 1, 2, 3 or 4 phosphorothioate internucleotide linkages; (iv) the sense strand is conjugated with a ligand; (v) the sense strand comprises 6, 7, 8, 9, 10, 11 or 12 2'-OMe modifications; (vi) the sense strand comprises 1, 2, 3 or 4 phosphorothioate internucleotide linkages; (vii) the dsRNA comprises at least 1, 2, 3, 4 or 5 2'-deoxy modification(s); (viii) the dsRNA comprises a duplex region of 12-40 nucleotide pairs in length; (ix) a blunt end at 5'end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA has a melting temperature with a lower end of the range from about 40° C., 45° C., 50° C., 55° C., 60° C. or 65° C., and upper end of the range from about 70° C., 75° C. or 80° C. In some embodiments, the dsRNA has a melting temperature in the range from about 55° C. to about 70° C. In some embodiments, the dsRNA has a melting temperature in the range from about 57° C. to about 67° C. In some particular embodiments, the dsRNA has a melting temperature in the range from about 60° C. to about 67° C. In some additional embodiments, the dsRNA has a melting temperature in the range from about 62° C. to about 66° C.

The inventors have also discovered that dsRNA molecules having a melting temperature of at least 60° C. are more effective in vivo and in vitro. Thus, in some embodiments, the dsRNA has a melting temperature of at least 60° C.

The inventors also discovered that for the dsRNA molecules to be more effective in vivo, there must be at least 40-50% of the antisense strand present at day 7 in vivo, for example in the mouse liver, after administration.

In another aspect, the invention further provides a method for delivering the dsRNA molecule of the invention to a specific target in a subject by subcutaneous or intravenous administration. The invention further provides the dsRNA molecules of the invention for use in a method for delivering said agents to a specific target in a subject by subcutaneous or intravenous administration.

BRIEF DESCRIPTION OF THE DRAWINGS

FIG. 14 discloses SEQ ID NOS 667-669, 668, 670, 705, 671, 706, 667-669, 668, 670, 705, 671 and 706, respectively, in order from top to bottom, left to right.

FIG. 15 discloses SEQ ID NOS 672-673, 707, 672-673 and 707, respectively, in order of appearance.

FIG. 27 show conformations of some(S)- and (R)-MTPA esters.

FIG. 28 show conformations used for the analysis of some other(S)- and (R)-MTPA esters FIG. 29 schematically shows DNA Pol-γ and Pol-RMT protocols.

FIG. 34 discloses SEQ ID NOS 674-676, 703-704 and 706, respectively, in order of appearance.

FIG. 35 discloses SEQ ID NOS 673 and 707, respectively, in order of appearance.

FIG. 39 discloses SEQ ID NOS 677-686, respectively, in order of appearance.

FIG. 40 discloses SEQ ID NOS 687-692, respectively, in order of appearance. FIG. 41 discloses SEQ ID NOS 693-702, respectively, in order of appearance.

DETAILED DESCRIPTION

Figure 1:
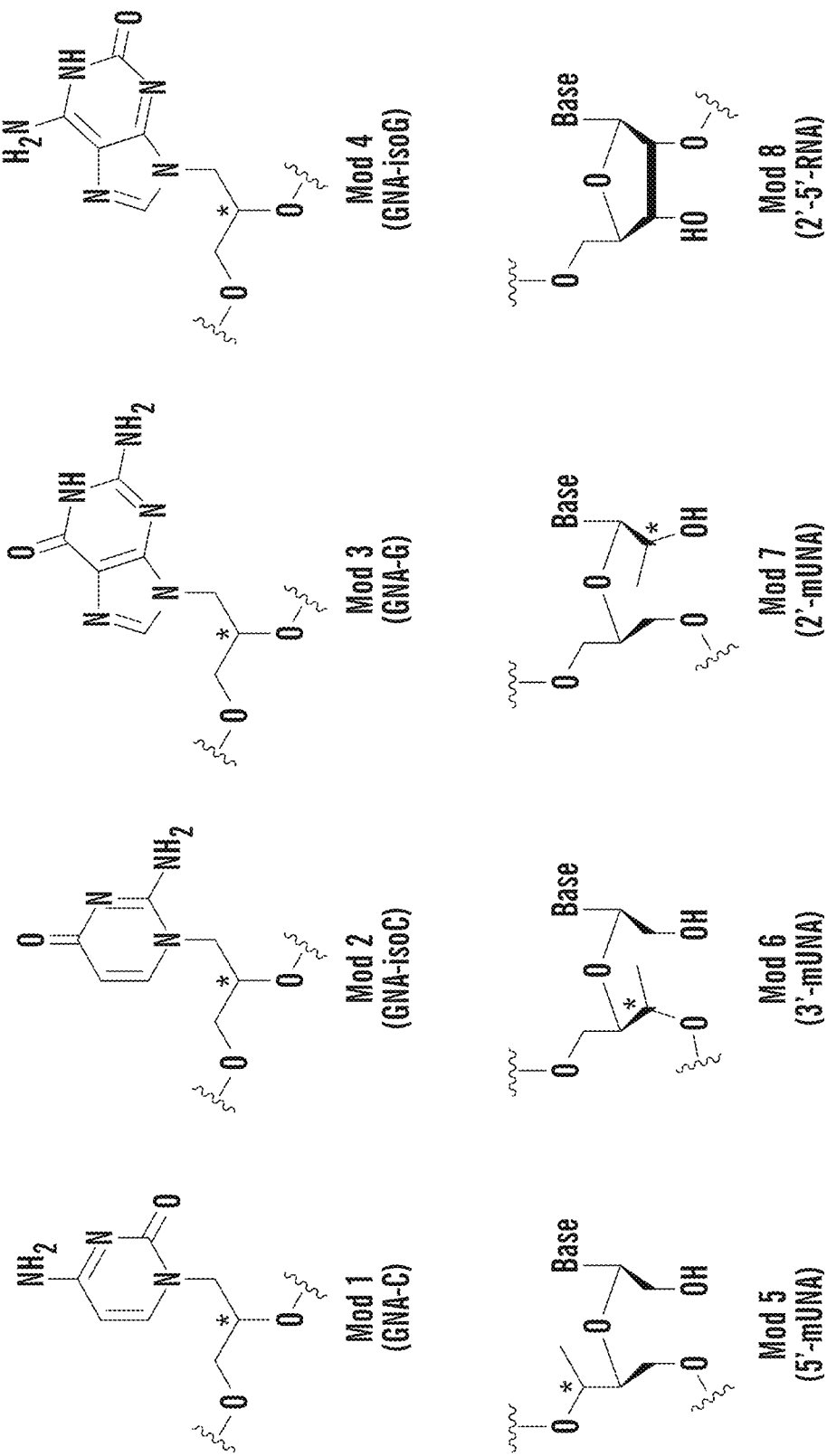
FIG. 1 shows some exemplary destabilizing modifications of the invention.
Figure 2:
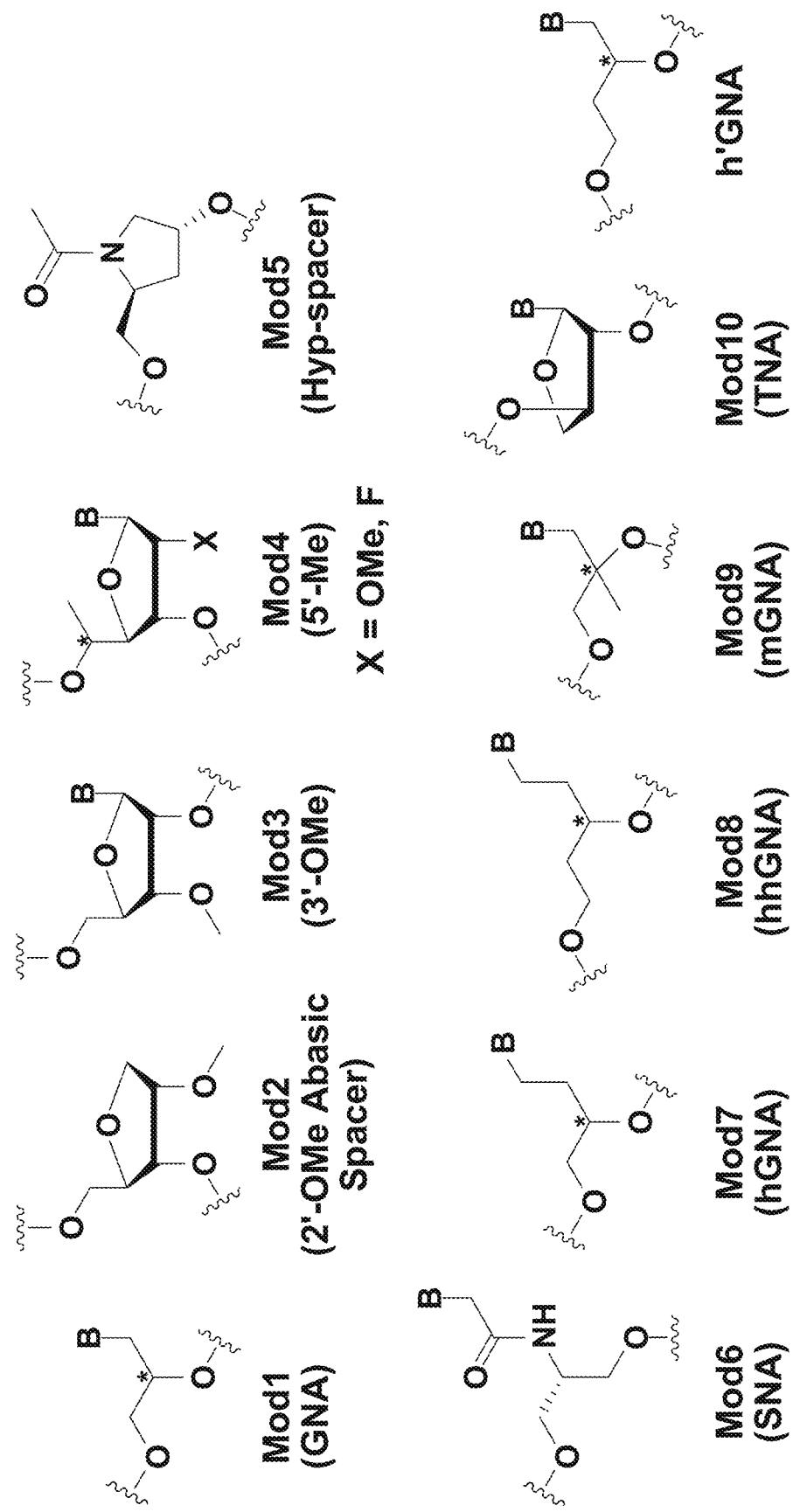
FIG. 2 shows other exemplary destabilizing modifications of the invention.
Figure 3:
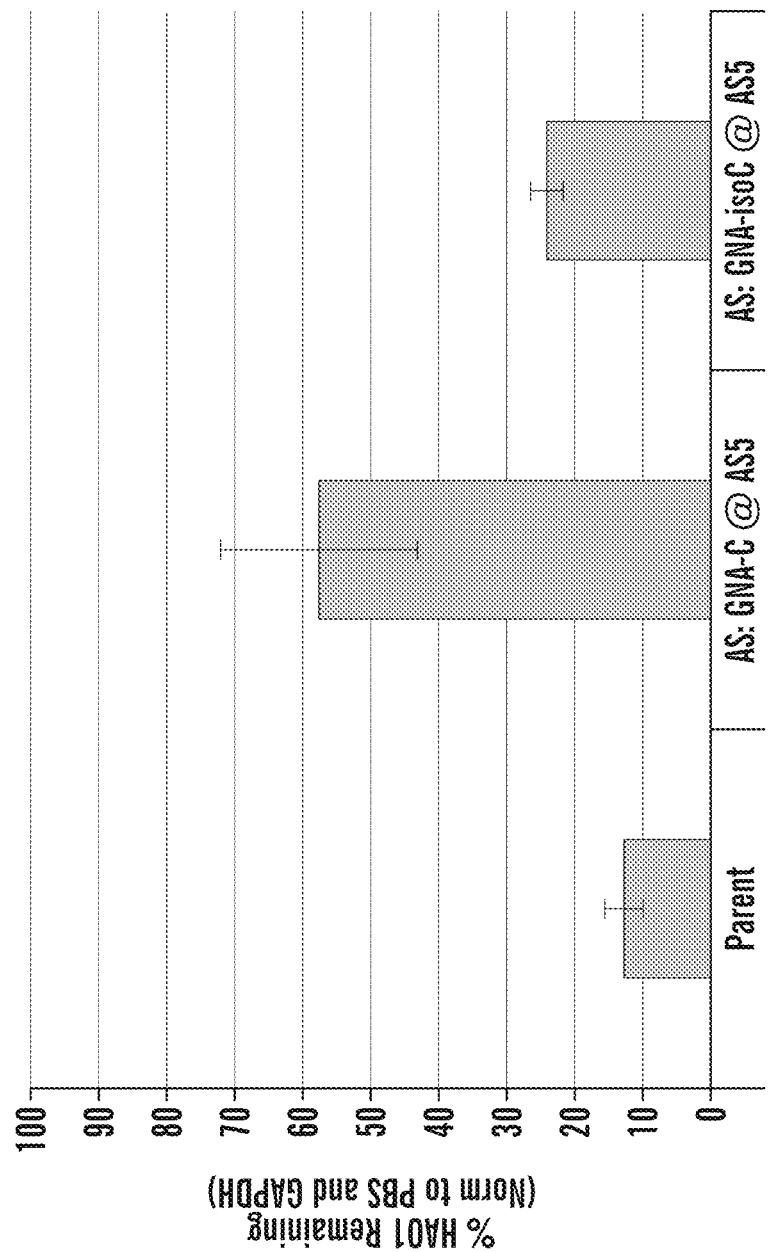
FIG. 3 is a bar graph showing that incorporation of GNA-isoC into seed region of antisense strand is better tolerated than GNA-C in HAO1 sequence.
Figure 4:
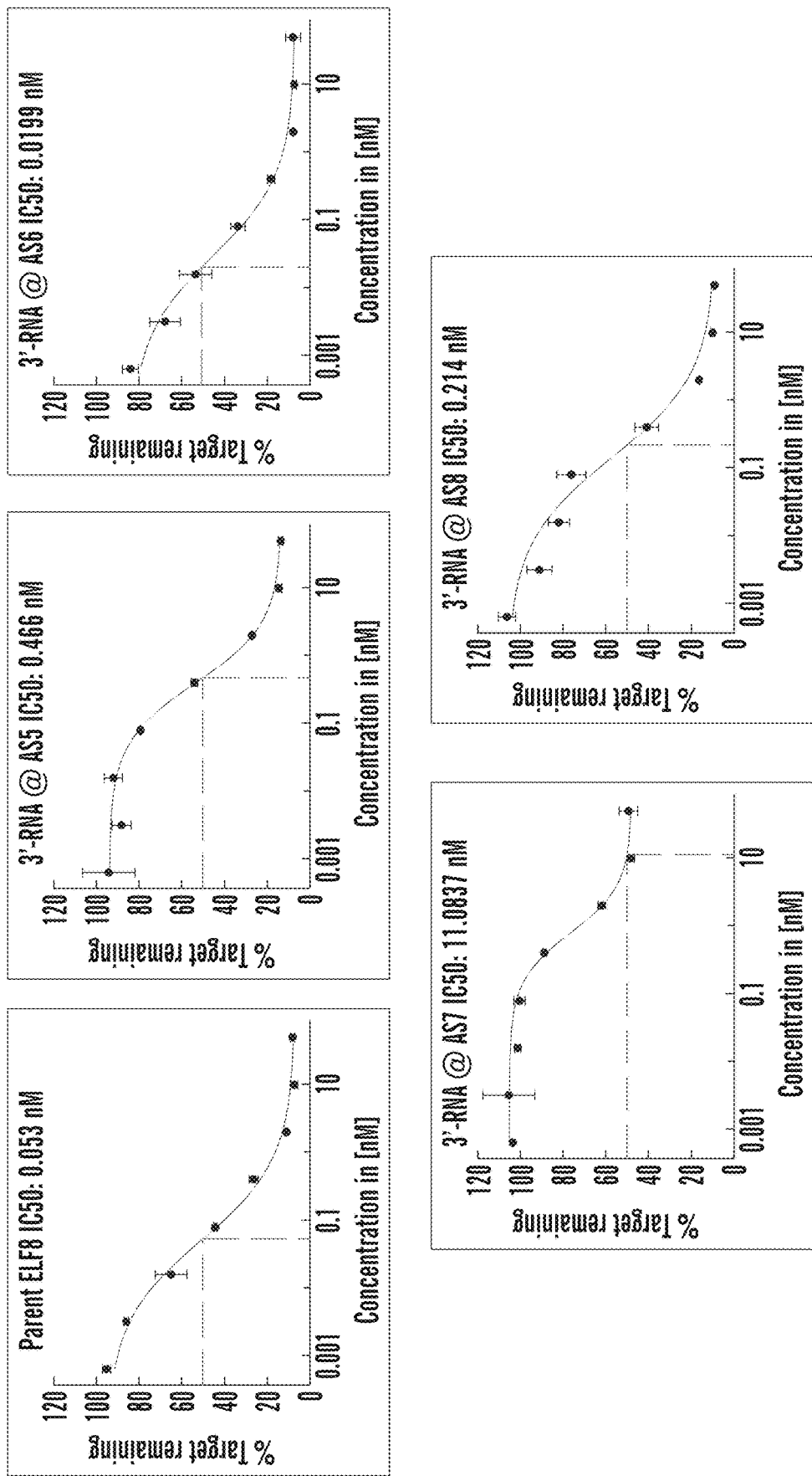
FIG. 4 are graphs showing that incorporation of 3'-RNA into antisense seed region leads to position specific reduction in off-targets in dual luciferase assay.
Figure 5:
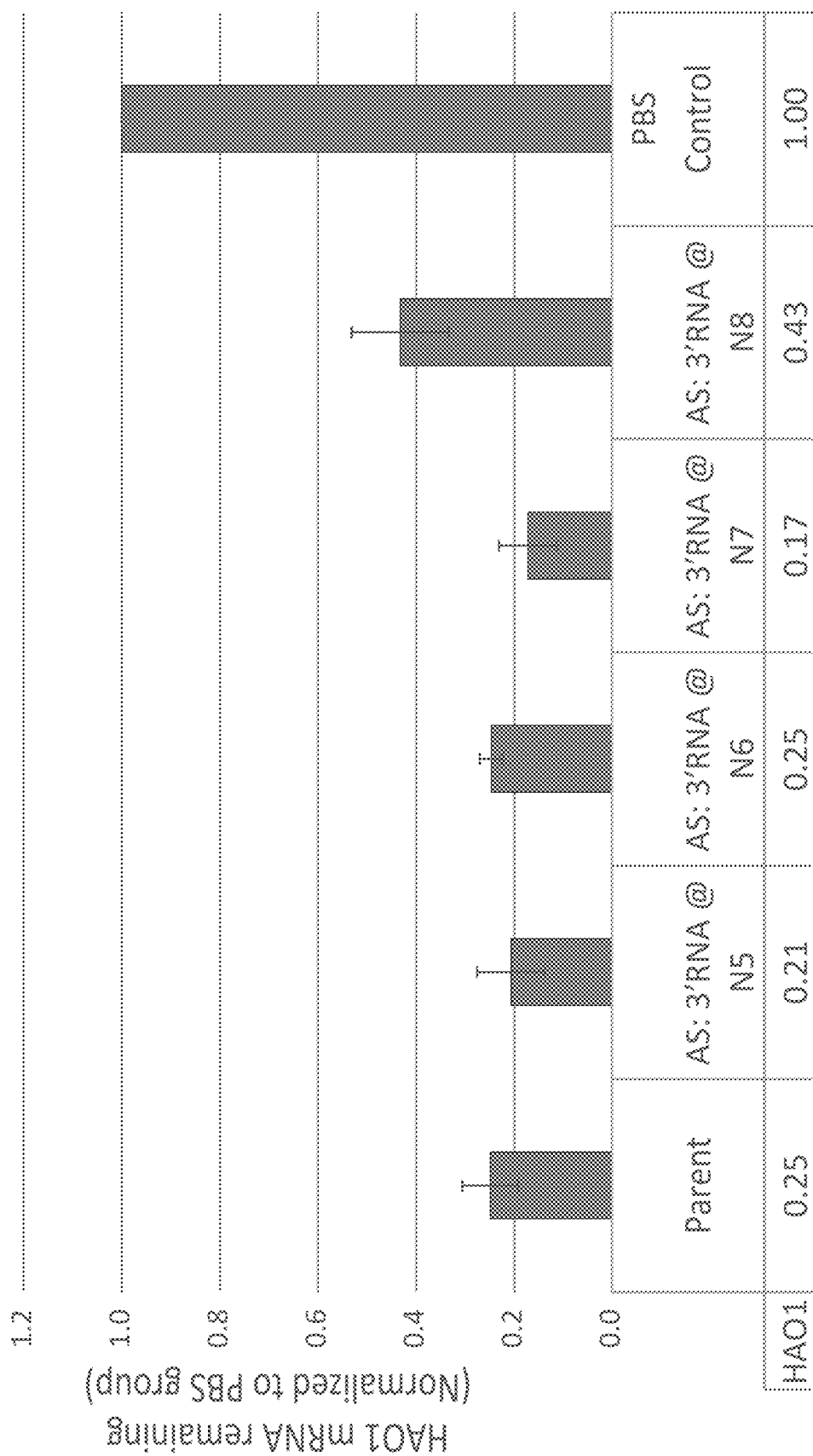
FIG. 5 is a bar graph showing that incorporation of 3'-RNA into antisense seed region is well tolerated in vivo (HAO1 sequence).
Figure 6:
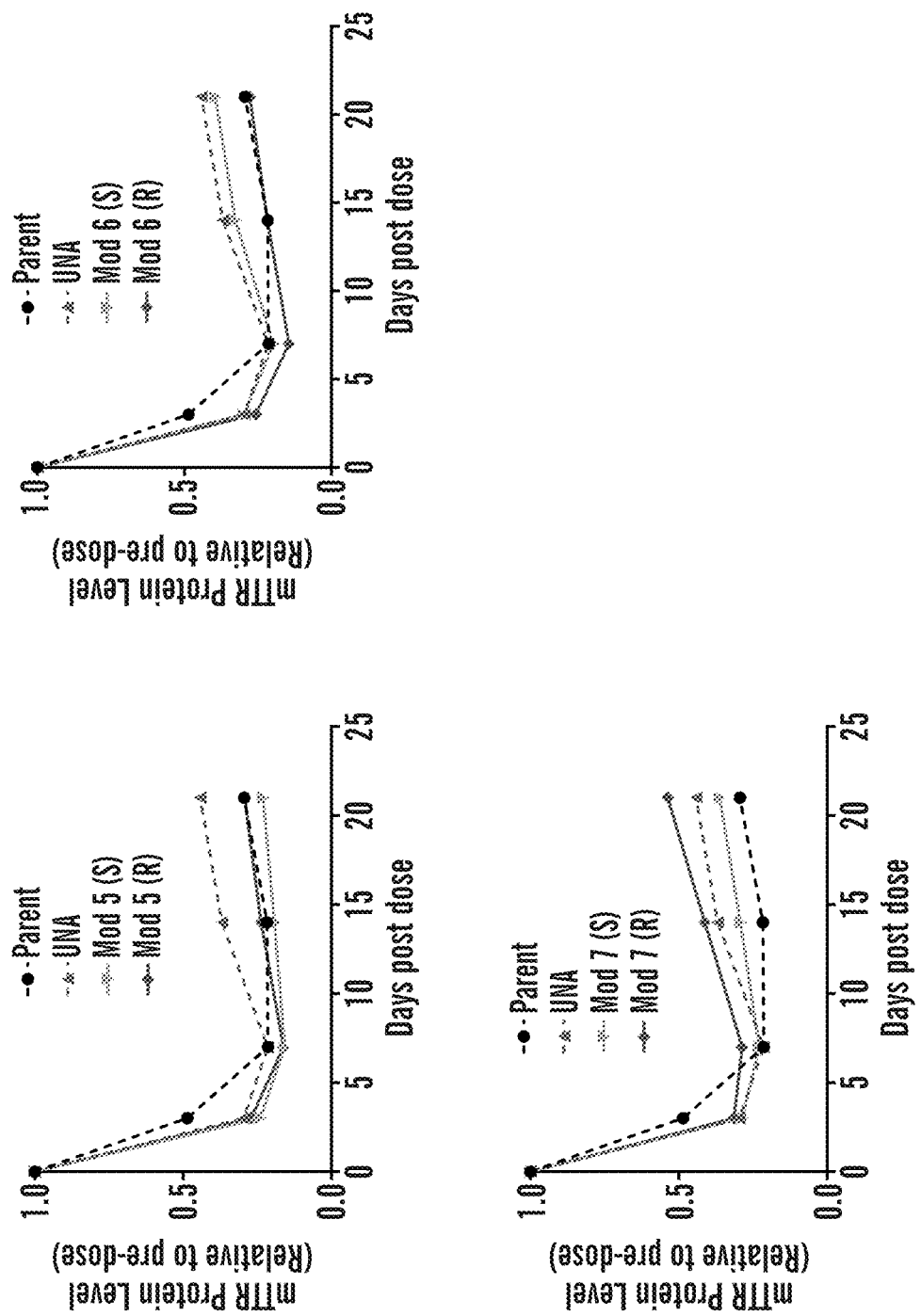
FIG. 6 are graphs showing that incorporation of Mods 5-7 into antisense seed region is well tolerated in vivo (TTR sequence 1).
Figure 7:
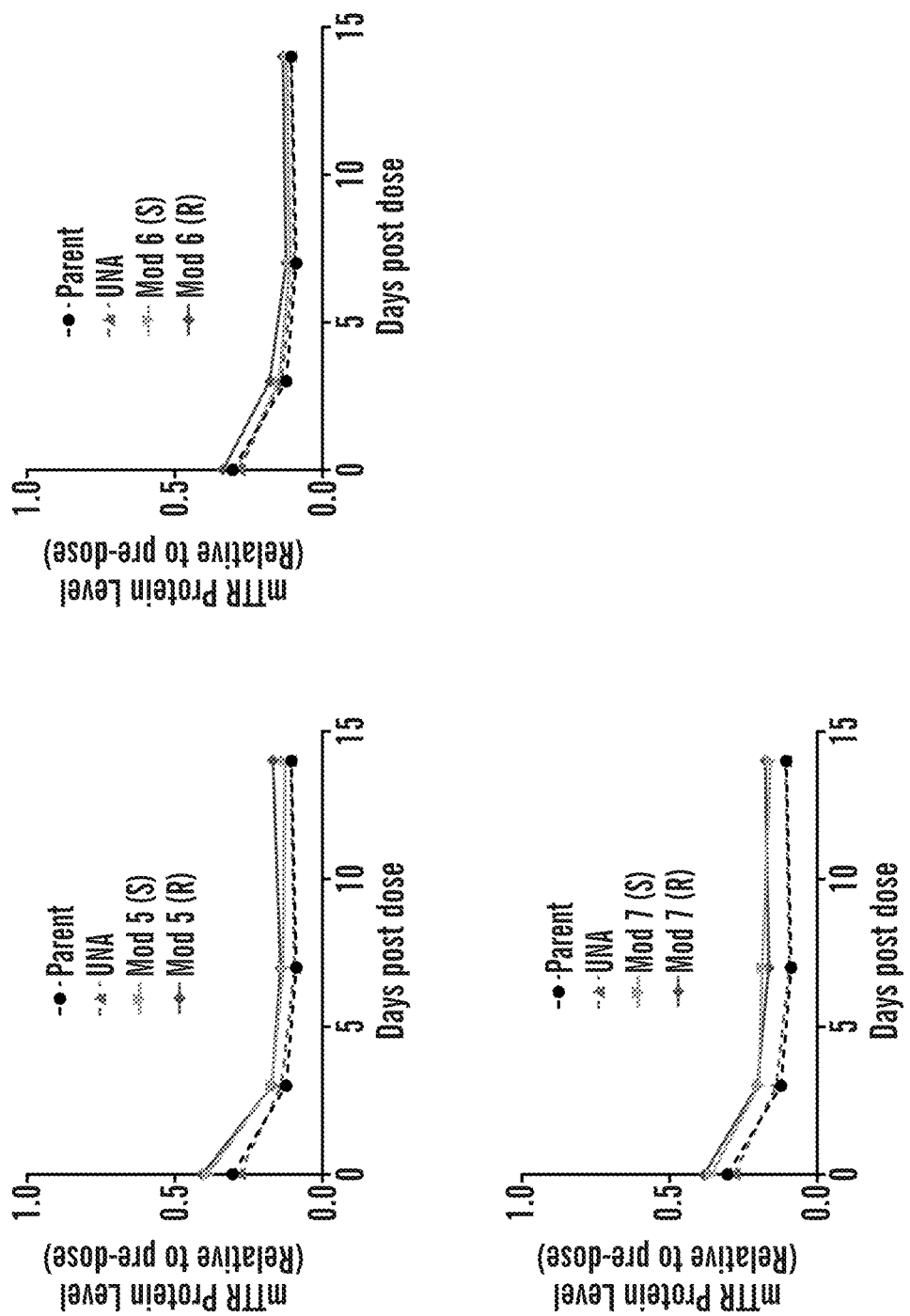
FIG. 7 are graphs showing that incorporation of Mods 5-7 into antisense seed region is well tolerated in vivo (TTR sequence 2).
Figure 8:
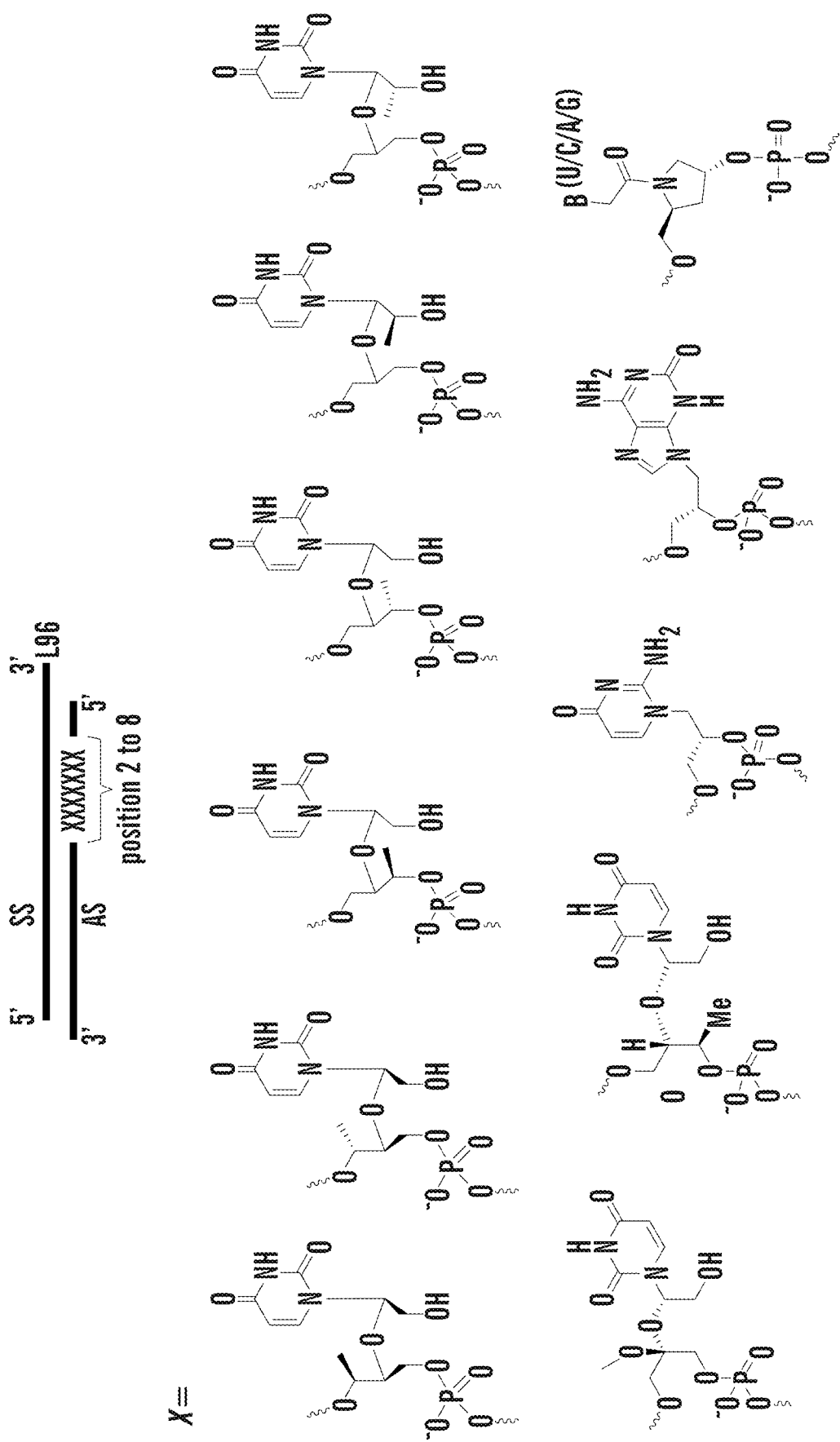
FIGS. 8 and 9 are schematic representations of exemplary siRNAs containing acyclic/non-natural nucleoside amidites (FIG. 8) and naturally-occurring base modified nucleosides (FIG. 9).
Figure 9:
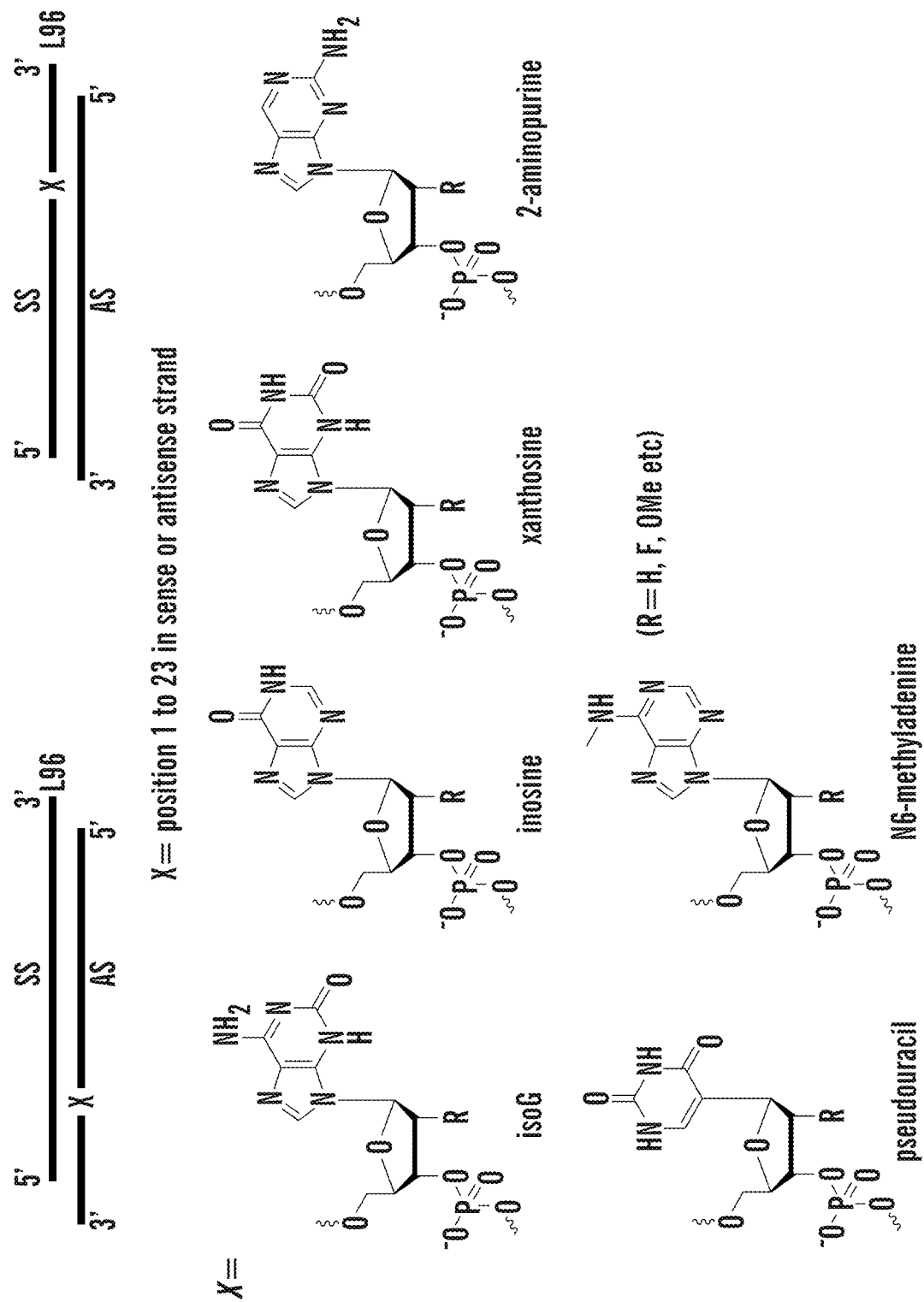

Inventors have discovered inter alia that off-target effects of dsRNA molecules can be reduced or inhibited by incorporating thermally destabilizing nucleotides at certain positions in the antisense strand of the dsRNA. With these thermally destabilizing modifications at certain positions in antisense strand, the dsRNA molecules were able to retain gene silencing activity similar to the parent dsRNA while having reduced off-target gene silencing. Further, the number of off-target genes that are down-regulated or up-regulated is also reduced by dsRNA molecules comprising these thermally destabilizing modifications when compared to the parent dsRNA.

As such, in one aspect, the invention provides a double-stranded RNAi (dsRNA) agent capable of inhibiting expression of a target gene. Generally, the dsRNA molecules of the invention show high on-target gene silencing while reducing or minimizing off-target gene silencing and/or toxicity. Without limitations, the dsRNA molecules of the invention can be substituted for the dsRNA molecules and can be used for in RNA interference based gene silencing techniques, including, but not limited to, in vitro or in vivo applications.

Generally, the dsRNA molecule comprises a sense strand (also referred to as passenger strand) and an antisense strand (also referred to as guide strand). Each strand of the dsRNA molecule can range from 12-40 nucleotides in length. For example, each strand can be between 14-40 nucleotides in length, 17-37 nucleotides in length, 25-37 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length. Without limitations, the sense and antisense strands can be equal length or unequal length.

In some embodiments, the antisense strand is of length 18 to 35 nucleotides. In some embodiments, the antisense strand is 21-25, 19-25, 19-21 or 21-23 nucleotides in length. In some particular embodiments, the antisense strand is 23 nucleotides in length. Similar to the antisense strand, the sense strand can be, in some embodiments, 18-35 nucleotides in length. In some embodiments, the sense strand is 21-25, 19-25, 19-21 or 21-23 nucleotides in length. In some particular embodiments, the antisense strand is 21 nucleotides in length.

The inventors also discovered that for the dsRNA molecules to be more effective in vivo, the antisense strand must have some metabolic stability. In other words, for the dsRNA molecules to be more effective in vivo, some amount of the antisense stand may need to be present in vivo after a period time after administration. Accordingly, in some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 5 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 6 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 7 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 8 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 9 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 10 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 11 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 12 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 13 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 14 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 15 after in vivo administration.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), the dsRNA has a melting temperature ($T_m$) of from about 40° C. to about 80° C., and the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; (vii) the dsRNA comprises a duplex region of 12-40 nucleotide pairs in length; (viii) a blunt end at 5'end of the antisense strand; and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the dsRNA molecule has a duplex region of 12-40 nucleotide pairs in length, wherein the antisense strand comprises at least one thermally destabilizing modification of the duplex within the seed region (i.e., at position 2-9 of the 5'-end of the antisense strand, counting from the 5'-end), and the dsRNA has a $T_m$ of from about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; vii) a blunt end at 5'end of the antisense strand; and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the Tx of from about 40° C. to about 80° C. is optional.

In some embodiments, the dsRNA molecule has a duplex region of 19, 20, 21, 22 or 23 nucleotide base pairs in length, wherein the antisense strand contains at least one thermally destabilizing modification of the duplex located in the seed region of the antisense strand (i.e., at position 2-9 of the 5'-end of the antisense strand), and wherein the dsRNA has a melting temperature of about 40° C. to about 80° C., wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the dsRNA molecule has a duplex region of 19, 20, 21, 22 or 23 nucleotide base pairs in length, wherein the antisense strand contains at least one thermally destabilizing modification of the duplex located in the seed region of the antisense strand (i.e., at position 2-9 of the 5'-end of the antisense strand), wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K), and wherein the dsRNA has a melting temperature of about 40° C. to about 80° C. (e.g., 40° C., 50° C., 60° C., 70° C. or 80° C.). In some embodiments, the $T_m$ of from about 40° C. to about 80° C. is optional.

In some particular embodiments, the thermally destabilizing modification of the duplex is at position 5, 6, 7, or 8 of the antisense strand, counting from 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, bGNA, bhGNA, mGNA, TNA and h'GNA (Mod A-Mod K).

In some particular embodiments, the thermally destabilizing modification of the duplex is at position 5 of the antisense strand, counting from 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some particular embodiments, the thermally destabilizing modification of the duplex is at position 6 of the antisense strand, counting from 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some particular embodiments, the thermally destabilizing modification of the duplex is at position 7 of the antisense strand, counting from 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some particular embodiments, the thermally destabilizing modification of the duplex is at position 8 of the antisense strand, counting from 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises one or both of the following characteristics:

(i) 2, 3, 4, 5 or 6 2'-fluoro modifications; and
(ii) 1, 2, 3 or 4 phosphorothioate internucleotide linkages; and the sense strand comprises one, two or three of the following characteristics:

(i) a ligand conjugated with the sense strand;
(ii) 2, 3, 4 or 5 2'-fluoro modifications; and
(iii) 1, 2, 3 or 4 phosphorothioate internucleotide linkages;

wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments of this, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, and a ligand is conjugated with the sense strand, wherein the dsRNA has a melting temperature of about 40° C. to about 80° C., and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, a ligand is conjugated with the sense strand, the dsRNA comprises at least four 2'-fluoro modifications, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, said sense strand comprises a ligand, wherein the dsRNA has a melting temperature of about 40° C. to about 80° C., and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, bGNA, hbGNA, mGNA, TNA and h'GNA (Mod A-Mod K). In some further embodiments of this, the ligand is an ASGPR ligand. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, wherein each of the sense and antisense strands comprise at least two 2'-fluoro modifications, wherein the dsRNA has a melting temperature of about 40° C. to about 80° C., and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some further embodiments of this, the ligand is an ASGPR ligand. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and wherein the antisense further comprises at least two of the following characteristics: (i) the thermally destabilizing modification of the duplex is located in position 4 to 8 of the antisense strand; (ii) at least two 2'-fluoro modifications; (iii) phosphorothioate internucleotide linkages between nucleotide positions 1 and 2 (counting from the 5' end); antisense strand has a length of 18 to 35 nucleotides, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some further embodiments the ligand is an ASGPR ligand. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and the sense strand has at least one of the following characteristics: (i) the ligand is attached to either end of the sense strand; (ii) sense strand comprises at least two 2'-fluoro modifications; and (iii) the sense strand and the antisense strand show sufficient complementarity to form a double stranded region spanning at least 19 nucleotide positions, wherein the thermally destabilizing modification of the duplex is located within said double-stranded region, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and wherein the thermally destabilizing modification of the duplex is selected from the group consisting of GNA-isoC, GNA-isoG, 5'm-UNA, 3'-mUNA and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, wherein the dsRNA has a melting temperature of about 400° C. to about 800° C., and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex located at position 7, counting from the 5'-end of the antisense strand, wherein said sense strand comprises a ligand, wherein the dsRNA has a melting temperature of about 40° C. to about 80° C. and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located at position 7, counting from the 5'-end, wherein said sense strand comprises a ligand, and wherein each of the sense and antisense strands comprise at least two 2'-fluoro modifications, wherein the dsRNA has a melting temperature of about 40° C. to about 80° C., and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, wherein said sense strand comprises a ligand, wherein the dsRNA has a melting temperature of about 40° C. to about 80° C., wherein the ligand comprises one or more GalNAc derivatives attached through a bivalent or trivalent branched linker, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA optionally has a melting temperature of about 40° C. to about 80° C., and wherein the ligand is an ASGPR ligand of structure:

comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the sense and antisense strands are independently 19, 20, 21, 22, 23, 24 or 25 nucleotides in length; the antisense strand contains at least one thermally

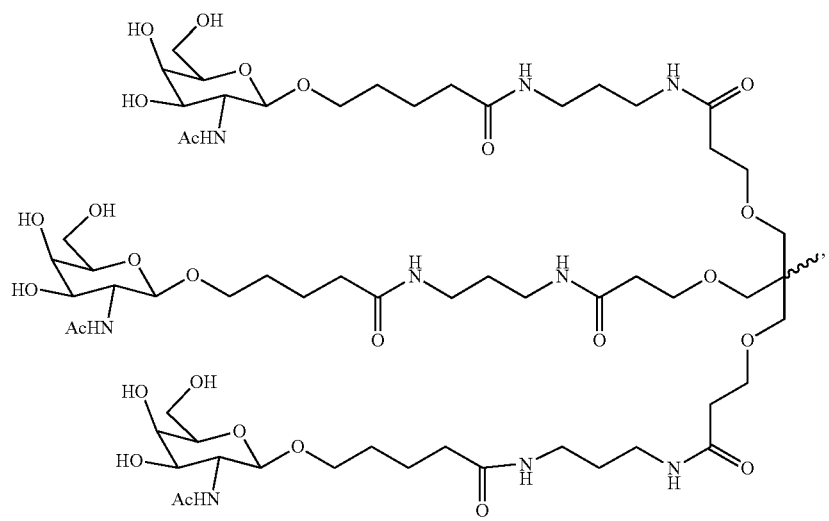 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the Tw of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 3, 4, 5 or 6 2'-fluoro modifications, and comprises 2, 3, 4 or 5 phosphorothioate internucleotide linkages; wherein the dsRNA has a melting temperature of about 40° C. to about 80° C.; and wherein the dsRNA optionally further has at least one (e.g., one, two or all three) of the following characteristics: (i) the dsRNA destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 3, 4, 5 or 6 2'-fluoro modifications, comprises 2, 3, 4 or 5 phosphorothioate internucleotide linkages; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, bGNA, bhGNA, mGNA, TNA and h'GNA (Mod A-Mod K). In some embodiments, the $T_m$ of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the Tw of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the sense and antisense strands are independently 19, 20, 21, 22, 23, 24 or 25 nucleotides in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 18, 19, 20, 21, 22, 23, 24 or 24 nucleotide pairs in length; and (viii) the dsRNA comprises a blunt end at 5'-end of the sense strand, and wherein the destabilizing modification is selected from mUNA and GNA building blocks described in Examples 1-3 herein. In some embodiments, the destabilizing modification is selected from the group consisting of GNA-isoC, GNA-isoG, S'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some particular embodiments, sense strand is 19, 20 or 21 or 22 nucleotides in length and the antisense strand is 20, 21 or 22 nucleotides in length. In some embodiments, the $T_m$ of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, one end of the dsRNA is a blunt end and the other end has an overhang, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) and the dsRNA comprises a duplex region of 12-40 nucleotide pairs in length, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the overhang is on the 3'-end of the antisense strand and the blunt end is at the 5'-end of the antisense strand. In some particular embodiments, the overhang is 2, 3 or 4-nucleotides in length. In some embodiments, the $T_m$ of from about 40° C. to about 80° C. is optional.

In some embodiments, the dsRNA molecule has a duplex region of 19, 20, 21, 22 or 23 nucleotide base pairs in length, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications, and optionally the 2 nucleotide overhang is on the 3'-end of the antisense strand and the blunt end is at the 5'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the overhang is on the 3'-end of the antisense strand and the blunt end is at the 5'-end of the antisense strand. In some embodiments, the $T_m$ of from about 40° C. to about 80° C. is optional.

In some embodiments, the dsRNA molecule of the invention may also have two blunt ends, at both ends of the dsRNA duplex.

In some embodiments, the dsRNA has a blunt end at both ends of the duplex, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a duplex region of 12-40 nucleotide pairs in length, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the dsRNA molecule has a duplex region of 19, 20, 21, 22 or 23 nucleotide base pairs in length and has a blunt end at both ends of the duplex, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the dsRNA molecule of the invention comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a blunt end at 5'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). Preferably, the 2 nt overhang is at the 3'-end of the antisense. In some embodiments, the Tw of from about 40° C. to about 80° C. is optional.

In some embodiments, the dsRNA molecule of the invention comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3 'terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand), and wherein the dsRNA has a melting temperature of about 40° C. to about 80° C., na wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). For example, the thermally destabilizing nucleotide occurs between positions opposite or complimentary to positions 14-17 of the 5'-end of the sense strand, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA comprises a duplex region of 12-30 nucleotide pairs in length. In some embodiments, the $T_m$ of from about 40° C. to about 80° C. is optional.

In some embodiments, the dsRNA molecule of the invention comprises a sense and antisense strands, wherein said dsRNA molecule comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5'end, wherein the 3' end of said sense strand and the 5' end of said antisense strand form a blunt end and said antisense strand is 1-4 nucleotides longer at its 3' end than the sense strand, wherein the duplex region which is at least 25 nucleotides in length, and said antisense strand is sufficiently complementary to a target mRNA along at least. 19 nt of said antisense strand length to reduce target gene expression when said dsRNA molecule is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA has a duplex region of 12-29 nucleotide pairs in length, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; and (viii) the dsRNA has a blunt end at 5'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 3, 4 or 5 phosphorothioate internucleotide linkages; (v) the dsRNA comprises at least four 2'-fluoro modifications; (vi) the dsRNA comprises a duplex region of 12-40 nucleotide pairs in length; and (vii) the dsRNA has a blunt end at 5'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the $T_m$ of from about 40° C. to about 80° C. is optional.

In one aspect the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five, six seven or all eight) of the following characteristics:
  (i) the antisense comprises 2, 3, 4, 5 or 6 2'-fluoro modifications;
  (ii) the antisense comprises 1, 2, 3, 4 or 5 phosphorothioate internucleotide linkages;
  (iii) the sense strand is conjugated with a ligand;
  (iv) the sense strand comprises 2, 3, 4 or 5 2'-fluoro modifications;
  (v) the sense strand comprises 1, 2, 3, 4 or 5 phosphorothioate internucleotide linkages;
  (vi) the dsRNA comprises at least four 2'-fluoro modifications;
  (vii) the dsRNA comprises a duplex region of 12-40 nucleotide pairs in length; and
  (viii) a blunt end at 5'end of the antisense strand.

In some particular embodiments, the thermally destabilizing modification of the duplex is at position 7 of the antisense strand, counting from 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the thermally destabilizing modification of the duplex is at position 2, 3, 4, 5, 6, 8 or 9 of the antisense strand, counting from 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the antisense strand further comprises one or both of the following characteristics:
  (i) 2, 3, 4, 5 or 6 2'-fluoro modifications; and
  (ii) 1, 2, 3, 4 or 5 phosphorothioate internucleotide linkages; and
the sense strand comprises one, two or three of the following characteristics:
  (i) a ligand conjugated with the sense strand;
  (ii) 2, 3, 4 or 5 2'-fluoro modifications; and
  (iii) 1, 2, 3, 4 or 5 phosphorothioate internucleotide linkages; and
wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, and a ligand is conjugated with the sense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, a ligand is conjugated with the sense strand, and the dsRNA comprises at least four 2'-fluoro modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand. In some further embodiments of this, the ligand is an ASGPR ligand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and b'GNA (Mod A-Mod K). In some further embodiments of this, the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein the antisense further comprises at least two of the following characteristics: (i) the thermally destabilizing modification of the duplex is located in position 4 to 8 of the antisense strand; (ii) at least two 2'-fluoro modifications; (iii) phosphorothioate internucleotide linkages between nucleotide positions 1 and 2 (counting from the 5' end); and antisense strand has a length of 18 to 35 nucleotides, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some further embodiments the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and the sense strand has at least one of the following characteristics: (i) the ligand is attached to either end of the sense strand; (ii) sense strand comprises at least two 2'-fluoro modifications; and (iii) the sense strand and the antisense strand show sufficient complementarity to form a double stranded region spanning at least 19 nucleotide positions and wherein the thermally destabilizing modification of the duplex is located within said double-stranded region, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex located at position 7, counting from the 5'-end of the antisense strand, and wherein said sense strand comprises a ligand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located at position 7, counting from the 5'-end, wherein said sense strand comprises a ligand, and wherein each of the sense and antisense strands comprise at least two 2'-fluoro modifications, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the ligand comprises one or more GalNAc derivatives attached through a bivalent or trivalent branched linker, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, bGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the ligand is an ASGPR ligand of structure:

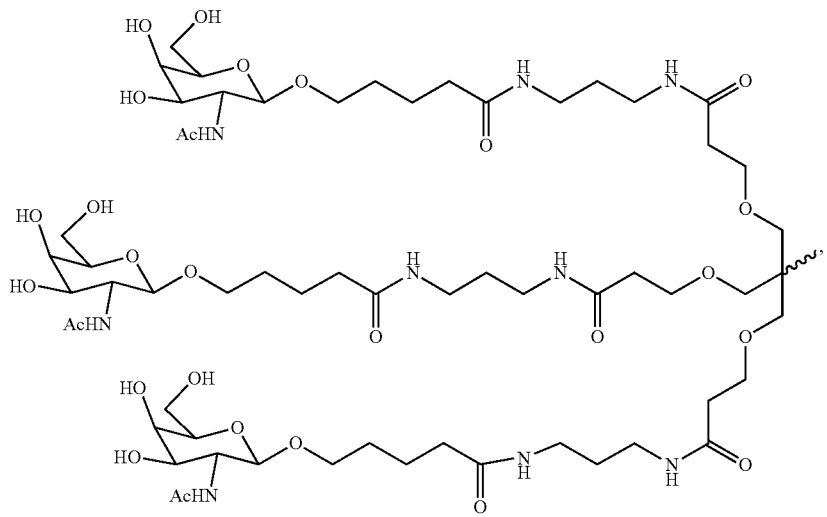 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 3, 4, 5 or 6 2'-fluoro modifications, comprises 2, 3, 4 or 5 phosphorothioate internucleotide linkages; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 3, 4, 5 or 6 2'-fluoro modifications, comprises 2, 3, 4 or 5 phosphorothioate internucleotide linkages; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the deRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hbGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In a particular embodiment, the dsRNA molecules of the present invention comprise:
(a) a sense strand having:
   (i) a length of 21 nucleotides;
   (ii) an ASGPR ligand attached to the 3'-end, wherein said ASGPR ligand comprises three GalNAc derivatives attached through a trivalent branched linker; and
   (iii) 2'-F modifications at positions 7, 10, and 11 (counting from the 5' end);
   and
(b) an antisense strand having:
   (i) a length of 23 nucleotides;
   (ii) 2'-F modifications at positions 2, 6 to 8, 9, 14, and 16 (counting from the 5' end);
   (iii) phosphorothioate internucleotide linkages between nucleotide positions 21 and 22, and between nucleotide positions 22 and 23 (counting from the 5' end); and
   (iv) a thermally destabilizing modification of the duplex at position 7 (counting from the 5' end);

wherein the dsRNA molecules have a two nucleotide overhang at the 3'-end of the antisense strand, and a blunt end at the 5'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and (iv) phosphorothioate internucleotide linkages between nucleotide positions 1 and 2, and between nucleotide positions 2 and 3 (counting from the 5' end);
  and
(b) an antisense strand having:
  (i) a length of 23 nucleotides;
  (ii) 2'-F modifications at positions 2, 6, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 7 (counting from the 5' end);
wherein the dsRNA molecules have a two nucleotide overhang at the 3'-end of the antisense strand, and a blunt end at the 5'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) phosphorothioate internucleotide linkages between nucleotide positions 1 and 2, and between nucleotide positions 2 and 3 (counting from the 5' end);
and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 6 or 7 (counting from the 5' end);
wherein the dsRNA molecules have a two nucleotide overhang at the 3'-end of the antisense strand, and a blunt end at the 5'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) phosphorothioate internucleotide linkages between nucleotide positions 1 and 2, and between nucleotide positions 2 and 3 (counting from the 5' end);
and
(b) an antisense strand having:
  (i) a length of 23 nucleotides;
  (ii) 2'-F modifications at positions 2, 6, 8, 9, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 7 (counting from the 5' end); wherein the dsRNA molecules have a two nucleotide overhang at the 3'-end of the antisense strand, and a blunt end at the 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In another particular embodiment, the dsRNA molecules of the present invention comprising an antisense strand having:
(i) 2'-F modifications at positions 2, 14, and 16 (counting from the 5' end); and
(ii) a thermally destabilizing modification of the duplex at position 6 or 7 (counting from the 5' end), wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In another particular embodiment, the dsRNA molecules of the present invention comprise:
(a) a sense strand having:
(i) an ASGPR ligand, wherein said ASGPR ligand comprises three GalNAc derivatives attached through a trivalent branched linker;
(ii) phosphorothioate internucleotide linkages between nucleotide positions 1 and 2, and between nucleotide positions 2 and 3 (counting from the 5' end); and
(b) an antisense strand having:
(i) 2'-F modifications at positions 2, 14, and 16 (counting from the 5' end);
(ii) a thermally destabilizing modification of the duplex at position 6 or 7 (counting from the 5' end), wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In another particular embodiment, the dsRNA molecules of the present invention comprise:
(a) a sense strand having:
(i) an ASGPR ligand attached to the 3'-end, wherein said ASGPR ligand comprises three GalNAc derivatives attached through a trivalent branched linker;
(ii) phosphorothioate internucleotide linkages between nucleotide positions 1 and 2, and between nucleotide positions 2 and 3 (counting from the 5' end); and
(b) an antisense strand having:
(ii) 2'-F modifications at positions 2, 14, and 16 (counting from the 5' end);
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
(iv) a thermally destabilizing modification of the duplex at position 6 or 7 (counting from the 5' end); wherein the dsRNA molecules have a two nucleotide overhang at the 3'-end of the antisense strand, and a blunt end at the 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule further comprises at least one ASGPR ligand. For example, the ASGPR ligand is one or more GalNAc derivatives attached through a bivalent or trivalent branched linker, such as:

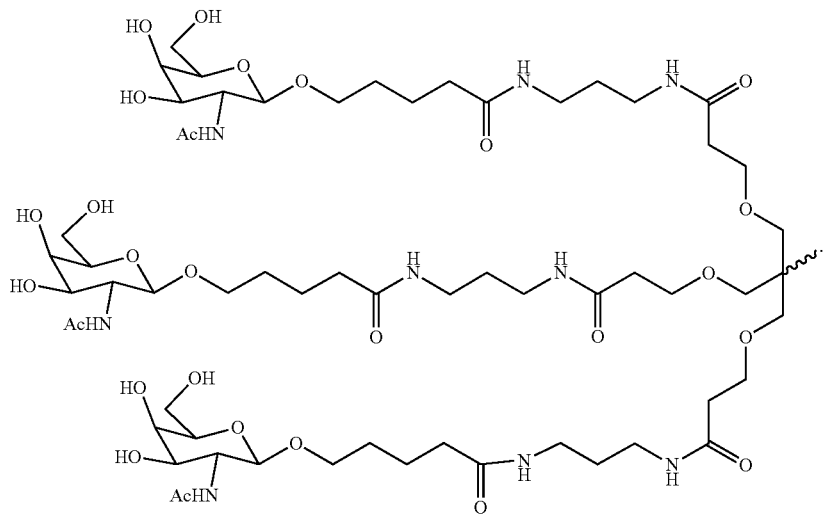 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one example, the ASGPR ligand is attached to the 3' end of the sense strand.

In some cases 2'-fluoro modifications in the seed region of the antisense strand, e.g., positions 2-9, particularly positions 3-9, can adversely affect the in vivo activity of the dsRNA while having minimal effect on in vitro potency of the dsRNA. Inventors have discovered inter alia that in vivo activity of such dsRNAs can be restored to comparable levels relative to the parent dsRNA by removing-some or all of 2'-fluoro modifications from the seed region of the antisense strand, i.e., position 2-9, particularly position 3-9 counting from the 5'-end.

Accordingly, in some embodiments, the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five, six seven, eight, nine or all ten) of the following characteristics: (i) a melting temperature ($T_m$) of from about 40° C. to about 80° C.; (ii) the antisense comprises 2, 3, 4, 5, 6, 7, 8, 9, or 10 2'-fluoro modifications; (iii) the antisense comprises 1, 2, 3, 4 or 5 phosphorothioate internucleotide linkages; (iv) the sense strand is conjugated with a ligand; (v) the sense strand comprises 2, 3, 4 or 5 2'-fluoro modifications; (vi) the sense strand comprises 1, 2, 3, 4 or 5 phosphorothioate internucleotide linkages; (vii) the dsRNA comprises at least four 2'-fluoro modifications; (viii) the dsRNA comprises a duplex region of 12-40 nucleotide pairs in length; (ix) a blunt end at 5'end of the antisense strand; (x) the sense strand comprises 1, 2, 3, 4, 5, 6, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five, six seven, eight, nine or all ten) of the following characteristics: (i) a melting temperature ($T_m$) of from about 40° C. to about 80° C.; (ii) the antisense comprises 2, 3, 4, 5, 6, 7, 8, 9, or 10 2'-fluoro modifications; (iii) the antisense comprises 1, 2, 3, 4 or 5 phosphorothioate internucleotide linkages; (iv) the sense strand is conjugated with a ligand; (v) the sense strand comprises 2, 3, 4 or 5 2'-fluoro modifications; (vi) the sense strand comprises 1, 2, 3, 4 or 5 phosphorothioate internucleotide linkages; (vii) the dsRNA comprises at least four 2'-fluoro modifications; (viii) the dsRNA comprises a duplex region of 12-40 nucleotide pairs in length; (ix) a blunt end at 5'end of the antisense strand; and (x) the sense strand comprises 1, 2, 3, 4, 5, 6, 7, 8, 9 or 10 LNA modifications, and wherein no 2'-fluoro modification is present at positions 3-9 (counting from 5'-end) of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises one or both of the following characteristics: (i) 2, 3, 4, 5, 6, 7, 8, 9 or 10 2'-fluoro modifications, wherein the antisense does not have a 2'-fluoro modification at positions 3-9 (counting from 5'-end); and (ii) 1, 2, 3, 4 or 5 phosphorothioate internucleotide linkages; and the sense strand comprises one, two, three of four of the following characteristics: (i) a ligand conjugated with the sense strand; (ii) 2, 3, 4 or 5 2'-fluoro modifications; (iii) 1, 2, 3, 4 or 5 phosphorothioate internucleotide linkages; and (iv) 1, 2, 3, 4, 5, 6, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises: (i) 2, 3, 4, 5, 6, 7, 8, 9 or 10 2'-fluoro modifications; and (ii) 1, 2, 3, 4 or 5 phosphorothioate internucleotide linkages; and the sense strand comprises: 1, 2, 3, 4, 5, 6, 7, 8, 9 or 10 LNA modifications, and wherein the sense strand optionally comprises one, two or three of the following characteristics: (i) a ligand conjugated with the sense strand; (ii) 2, 3, 4 or 5 2'-fluoro modifications; (iii) 1, 2, 3, 4 or 5 phosphorothioate internucleotide linkages; and (iv) 1, 2, 3, 4, 5, 6, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, S'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, bhGNA, mGNA, TNA and h'GNA (Mod A-Mod K). In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises 1, 2, 3 or 4 phosphorothioate internucleotide linkages, wherein the antisense strand optionally comprises 2, 3, 4, 5, 6, 7, 8, 9 or 10 2'-fluoro modifications; and the sense strand comprises 1, 2, 3, 4, 5, 6, 7, 8, 9 or 10 LNA modifications, and wherein the sense strand optionally comprises a ligand conjugated with the sense strand, 2, 3, 4 or 5 2'-fluoro modifications; and/or 1, 2, 3, 4 or 5 phosphorothioate internucleotide linkages, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises 1, 2, 3 or 4 phosphorothioate internucleotide linkages, wherein the antisense strand optionally comprises 2, 3, 4, 5, 6, 7, 8, 9 or 10 2'-fluoro modifications, provided that no 2'-fluoro modification is present at positions 3-9 (counting from 5'-end); and the sense strand comprises 1, 2, 3, 4, 5, 6, 7, 8, 9 or 10 LNA modifications, and wherein the sense strand optionally comprises a ligand conjugated with the sense strand, 2, 3, 4 or 5 2'-fluoro modifications; and/or 1, 2, 3, 4 or 5phosphorothioate internucleotide linkages, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, a ligand is conjugated with the sense strand, and the dsRNA comprises at least four 2'-fluoro modifications, and wherein no 2'-fluoro modification is present at positions 3-9 of the antisense strand (counting from 5'-end), wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, said sense strand comprises a ligand, wherein the dsRNA has a melting temperature of about 40° C. to about 80° C., and wherein no 2'-fluoro modification is present at positions 3-9 of the antisense strand (counting from 5'-end), wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some further embodiments of this, the ligand is an ASGPR ligand. In some embodiments, the melting temperature of about 40° C. to about 80° C. is optional In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, wherein each of the sense and antisense strands comprise at least two 2'-fluoro modifications, wherein the dsRNA has a melting temperature of about 40° C. to about 80° C., and wherein no 2'-fluoro modification is present at positions 3-9 of the antisense strand (counting from 5'-end), wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some further embodiments of this, the ligand is an ASGPR ligand. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and wherein the antisense further comprises at least two of the following characteristics: (i) the thermally destabilizing modification of the duplex is located in position 4 to 8 of the antisense strand; (ii) at least two 2'-fluoro modifications; (iii) phosphorothioate internucleotide linkages between nucleotide positions 1 and 2 (counting from the 5' end); and (iv) antisense strand has a length of 18 to 35 nucleotides, and wherein no 2'-fluoro modification is present at positions 3-9 of the antisense strand (counting from 5'-end), wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some further embodiments the ligand is an ASGPR ligand. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and the sense strand has at least one of the following characteristics: (i) the ligand is attached to either end of the sense strand; (ii) sense strand comprises at least two 2'-fluoro modifications; (iii) sense strand comprises 1, 2, 3, 4, 5, 6, 78, 9 or 10 LNA modifications; and (iv) the sense strand and the antisense strand show sufficient complementarity to form a double stranded region spanning at least 19 nucleotide positions, wherein the thermally destabilizing modification of the duplex is located within said double-stranded region, and wherein no 2'-fluoro modification is present at positions 3-9 of the antisense strand (counting from 5'-end), wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand and optionally at least one LNA modification, and wherein each of the sense and antisense strands comprise at least two 2'-fluoro modifications, wherein no 2'-fluoro modification is present at positions 3-9 of the antisense strand (counting from 5'-end), wherein the dsRNA has a melting temperature of about 40° C. to about 80° C., and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, bbGNA, mGNA, TNA and b'GNA (Mod A-Mod K). In some embodiments, the melting temperature of about 40° C. to about 80° C. is optional In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex located at position 5, 6 or 7, counting from the 5'-end of the antisense strand, wherein no 2'-fluoro modification is present at positions 3-9 of the antisense strand (counting from 5'-end), wherein said sense strand comprises a ligand and optionally at least one LNA modification, and wherein the dsRNA has a melting temperature of about 40° C. to about 80° C., wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located at position 5, 6 or 7, counting from the 5'-end, wherein said sense strand comprises a ligand and optionally at least one LNA modification, and wherein each of the sense and antisense strands comprise at least two 2'-fluoro modifications, wherein no 2'-fluoro modification is present at positions 3-9 of the antisense strand (counting from 5'-end), wherein the dsRNA has a melting temperature of about 40° C. to about 80° C., and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected 2'-fluoro modification is present at positions 3-9 of the antisense strand (counting from 5'-end), wherein the dsRNA has a melting temperature of about 40° C. to about 80° C., and wherein the ligand is an ASGPR ligand of structure:

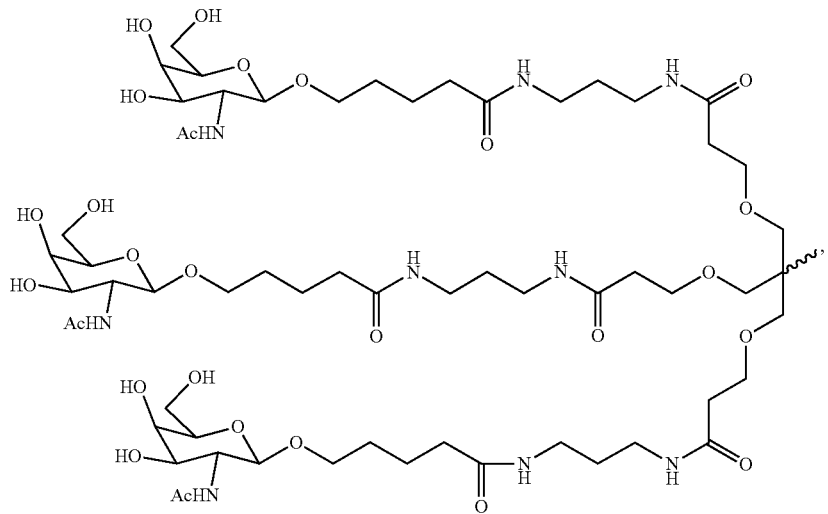 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, wherein said sense strand comprises a ligand and optionally at least one LNA modification, wherein no 2'-fluoro modification is present at positions 3-9 of the antisense strand (counting from 5'-end), wherein the dsRNA has a melting temperature of about 40° C. to about 80° C., and wherein the ligand comprises one or more GalNAc derivatives attached through a bivalent or trivalent branched linker, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand and optionally at least one LNA modification, wherein no wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand and optionally comprises at least one LNA modification, comprises 3 or 4 2'-fluoro modifications, and comprises 0, 1, 2 or 3 phosphorothioate internucleotide linkages; wherein the antisense strand comprises 3, 4, 5 or 6 2'-fluoro modifications, provided that no 2'-modification is present at positions 3-9 of the antisense strand (counting from 5'-end), comprises 2, 3, 4 or 5 phosphorothioate internucleotide linkages; wherein the dsRNA has a melting temperature of about 400° C. to about 800° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 400° C. to about 800° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3, and optionally comprises at least one LNA modification; wherein the antisense strand comprises 3, 4, 5 or 6 2'-fluoro modifications, provided that no 2'-modification is present at positions 3-9 of the antisense strand (counting from 5'-end), comprises 2, 3, 4 or 5 phosphorothioate internucleotide linkages; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, bGNA, hhGNA, mGNA, TNA and h'GNA (Mod A-Mod K). In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 0, 1, 2 or 3 phosphorothioate internucleotide linkages, and optionally comprises at least one LNA modification; wherein the antisense strand comprises 2'-fluoro modifications at positions 2, 14 or 16; and the antisense comprises phosphorothioate internucleotide linkages between nucleotide positions 21 and 22, and between nucleotide positions 22 and 23; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the deRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises at least one LNA modification, and optionally comprises 0, 1, 2 or 3 phosphorothioate internucleotide linkages; wherein the antisense strand comprises 2'-fluoro modifications at positions 2, 14 or 16; and the antisense comprises phosphorothioate internucleotide linkages between nucleotide positions 21 and 22, and between nucleotide positions 22 and 23; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2, or 3 phosphorothioate internucleotide linkages, and optionally comprises at least one LNA modification; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 0, 1, 2, or 3 phosphorothioate internucleotide linkages, and comprises at least one LNA modification; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises phosphorothioate internucleotide linkages between nucleotide positions 1 and 2, and between nucleotide positions 2 and 3, and optionally comprises at least one LNA modification; wherein the antisense strand comprises 2'-fluoro modifications at positions 2, 14 or 16; and the antisense comprises phosphorothioate internucleotide linkages between nucleotide positions 21 and 22, and between nucleotide positions 22 and 23; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises at least one LNA modification, and optionally comprises phosphorothioate internucleotide linkages between nucleotide positions 1 and 2, and between nucleotide positions 2 and 3; wherein the antisense strand comprises 2'-fluoro modifications at positions 2, 14 or 16; and the antisense comprises phosphorothioate internucleotide linkages between nucleotide positions 21 and 22, and between nucleotide positions 22 and 23; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the sense and antisense strands are independently 19, 20, 21, 22, 23, 24 or 25 nucleotides in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven, eight or all nine) of the following characteristics: (i) the antisense comprises 2, 3, 4, 5 or 6 2'-fluoro modifications, provided that no 2'-modification is present at positions 3-9 of the antisense strand (counting from 5'-end); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 18, 19, 20, 21, 22, 23, 24 or 24 nucleotide pairs in length; (viii) the dsRNA comprises a blunt end at 5'-end of the sense strand; and (ix) the sense strand comprises 1, 2, 3, 4, 5, 6, 7, 8, 9 1 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some particular embodiments, sense strand is 19, 20 or 21 or 22 nucleotides in length and the antisense strand is 20, 21 or 22 nucleotides in length. In some embodiments, the melting temperature of about 40° C. to about 80° C. is optional.

In some embodiments, the sense and antisense strands are independently 19, 20, 21, 22, 23, 24 or 25 nucleotides in length, wherein the antisense strand contains at least one thermally destabilizing nucleotide and 1, 2, 3 or 4 phosphorothioate internucleotide linkages, and where the at least one thermally destabilizing nucleotide is in the seed region of the antisense strand (i.e., at position 2-9 of the 5'-end of the antisense strand), the sense strand comprises 1, 2, 3, 4, 5, 6, 7, 8, 9 or 10 LNA modifications, wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications, provided that no 2'-modification is present at positions 3-9 of the antisense strand (counting from 5'-end); (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 18, 19, 20, 21, 22, 23, 24 or 24 nucleotide pairs in length; and (vii) the dsRNA comprises a blunt end at 5'-end of the sense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, bhGNA, mGNA, TNA and h'GNA (Mod A-Mod K). In some particular embodiments, sense strand is 19, 20 or 21 or 22 nucleotides in length and the antisense strand is 20, 21 or 22 nucleotides in length. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises 1, 2, 3, 4, 5, 6, 7, 8, 9 or 10 LNA modifications, and optionally comprises phosphorothioate internucleotide linkages between nucleotide positions 1 and 2, and between nucleotide positions 2 and 3; wherein the antisense strand comprises 2'-fluoro modifications at positions 2, 9, 14 or 16, or at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the deRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises 1, 2, 3, 4, 5, 6, 7, 8, 9 or 10 LAN modifications, and optionally comprises phosphorothioate internucleotide linkages between nucleotide positions 1 and 2, and between nucleotide positions 2 and 3; wherein the antisense strand comprises 2'-fluoro modifications at positions 2, 9, 14 or 16, or at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, one end of the dsRNA is a blunt end and the other end has an overhang, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present in positions 3-9 (counting from the 5'-end); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (vii) the sense strand comprises 1, 2, 3, 4, 5, 6, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the overhang is on the 3'-end of the antisense strand and the blunt end is at the 5'-end of the antisense strand. In some particular embodiments, the overhang is 2, 3 or 4-nucleotides in length. In some embodiments, the melting temperature of about 40° C. to about 80° C. is optional.

In some embodiments, the dsRNA molecule has a duplex region of 19, 20, 21, 22 or 23 nucleotide base pairs in length, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, five, six or all seven) of the following characteristics: (i) the antisense comprises 2, 3, 4, 5 or 6 2'-fluoro modifications, wherein no 2'-fluoro modification is present at positions 3-9 (counting from 5'-end of the antisense strand); (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the sense strand comprises 1, 2, 3, 4, 5, 6, 7, 8, 9 or 10 LNA modifications, and optionally the 2 nucleotide overhang is on the 3'-end of the antisense strand and the blunt end is at the 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the overhang is on the 3'-end of the antisense strand and the blunt end is at the 5'-end of the antisense strand. In some embodiments, the melting temperature of about 40° C. to about 80° C. is optional.

In some embodiments, the dsRNA molecule of the invention may also have two blunt ends, at both ends of the dsRNA duplex.

In some embodiments, the dsRNA has a blunt end at both ends of the duplex, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present at positions 3-9 (counting from the 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the sense strand comprises at least 1, 2, 3, 4, 5, 6, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the dsRNA molecule has a duplex region of 19, 20, 21, 22 or 23 nucleotide base pairs in length and has a blunt end at both ends of the duplex, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, five, six or all seven) of the following characteristics: (i) the antisense comprises 2, 3, 4, 5 or 6 2'-fluoro modifications, wherein no 2'-fluoro modification is present at positions 3-9 (counting from the 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the sense strand comprises at least 1, 2, 3, 4, 5, 6, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNAisoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the dsRNA molecule of the invention comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present at positions 3-9 (counting from the 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a blunt end at 5'-end of the antisense strand. Preferably, the 2 nt overhang is at the 3'-end of the antisense; and (viii) the sense strand comprises at least 1, 2, 3, 4, 5, 6, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the dsRNA molecule of the invention comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3 'terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand), and wherein the dsRNA has a melting temperature of about 40° C. to about 80° C., wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

For example, the thermally destabilizing nucleotide occurs between positions opposite or complimentary to positions 14-17 of the 5'-end of the sense strand, and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present at positions 3-9 (counting from 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; (vii) the dsRNA comprises a duplex region of 12-30 nucleotide pairs in length; and the sense strand comprises 1, 2, 3, 4, 5, 6, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the dsRNA molecule of the invention comprises a sense and antisense strands, wherein said deRNA molecule comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5'end, wherein the 3' end of said sense strand and the 5' end of said antisense strand form a blunt end and said antisense strand is 1~4 nucleotides longer at its 3' end than the sense strand, wherein the duplex region which is at least 25 nucleotides in length, and said antisense strand is sufficiently complementary to a target mRNA along at least 19 nt of said antisense strand length to reduce target gene expression when said dsRNA molecule is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present at positions 3-9 (counting from 5'-end of antisense strand); (ii) the antisense comprises 1, 2, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; (vii) the dsRNA has a duplex region of 12-29 nucleotide pairs in length; (viii) and the sense strand comprises 1, 2, 3, 4, 5, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven, eight or all nine) of the following characteristics: (i) the antisense comprises 2, 3, 4, 5 or 6 2'-fluoro modifications, wherein no 2'-fluoro modification is present at positions 3-9 (counting from 5'-end of antisense strand); (ii) the antisense comprises 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; (viii) the dsRNA has a blunt end at 5'-end of the antisense strand; (ix) and the sense strand comprises 1, 2, 3, 4, 5, 6, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven, eight or all nine) of the following characteristics: (i) the antisense comprises 2, 3, 4, 5 or 6 2'-fluoro modifications, wherein no 2'-fluoro modification is present at positions 3-9 (counting from 5'-end of the antisense strand); (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; (viii) the dsRNA has a blunt end at 5'-end of the antisense strand; and (ix) and the sense strand comprises 1, 2, 3, 4, 5, 6, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven, eight or all nine) of the following characteristics: (i) the antisense comprises 2, 3, 4, 5 or 6 2'-fluoro modifications, wherein no 2'-fluoro modification is present at positions 3-9 (counting from 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; (viii) the dsRNA has a blunt end at 5'-end of the antisense strand; and (ix) the sense strand comprises 1, 2, 3, 4, 5, 6, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications, wherein no 2'-fluoro modification is present at positions 3-9 (counting from 5'-end of the antisense strand); (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA has a blunt end at 5'-end of the antisense strand; and (viii) the sense strand comprises 1, 2, 3, 4, 5, 6, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In one aspect the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five, six seven, eight or all nine) of the following characteristics: (i) the antisense comprises 2, 3, 4, 5 or 6 2'-fluoro modifications, wherein no 2'-fluoro modification is present at positions 3-9 (counting from 5'-end); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; (viii) a blunt end at 5'end of the antisense strand; and (ix) the sense strand comprises 1, 2, 3, 4, 5, 6, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some particular embodiments, the thermally destabilizing modification of the duplex is at position 5, 6 or 7 of the antisense strand, counting from 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the thermally destabilizing modification of the duplex is at position 2, 3, 4, 8 or 9 of the antisense strand, counting from 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the antisense strand further comprises one or both of the following characteristics: (i) 2, 3, 4, 5 or 6 2'-fluoro modifications, wherein no 2'-modification is present at positions 3-9 (counting from 5'-end of the antisense strand); and (ii) 1, 2, 3, 4 or 5 phosphorothioate internucleotide linkages; and the sense strand comprises one, two, three or four of the following characteristics: (i) a ligand conjugated with the sense strand; (ii) 2, 3, 4 or 5 2'-fluoro modifications; (iii) 1, 2, 3, 4 or 5 phosphorothioate internucleotide linkages; and (iv) 1, 2, 3, 4, 5, 6, 7, 8, 9 or 10 LNA modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, a ligand is conjugated with the sense strand, and the dsRNA comprises at least four 2'-fluoro modifications, and wherein no 2'-modification is present at positions 3-9 of the antisense strand (counting from 5'-end of the antisense strand), wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein no 2'-modification is present at positions 3-9 of the antisense strand (counting from 5'-end of the antisense strand), wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and b'GNA (Mod A-Mod K). In some further embodiments of this, the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, and wherein no 2'-modification is present at positions 3-9 of the antisense strand (counting from 5'-end of the antisense strand), wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some further embodiments of this, the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein the antisense further comprises at least two of the following characteristics: (i) the thermally destabilizing modification of the duplex is located in position 4 to 8 of the antisense strand; (ii) at least two 2'-fluoro modifications, and wherein no 2'-modification is present at positions 3-9 of the antisense strand (counting from 5'-end of the antisense strand); (iii) phosphorothioate internucleotide linkages between nucleotide positions 1 and 2 (counting from the 5' end); and antisense strand has a length of 18 to 35 nucleotides, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some further embodiments the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and the sense strand has at least one of the following characteristics: (i) the ligand is attached to either end of the sense strand; (ii) sense strand comprises at least two 2'-fluoro modifications; (iii) the sense strand and the antisense strand show sufficient complementarity to form a double stranded region spanning at least 19 nucleotide positions; (iv) the sense strand comprises at least 1, 2, 3, 4, 5, 6, 7, 8, 9 or 10 LNA modifications, and wherein the thermally destabilizing modification of the duplex is located within said double-stranded region, and wherein no 2'-modification is present at positions 3-9 of the antisense strand (counting from 5'-end of the antisense strand), wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA, In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, where no 2'-modification is present at positions 3-9 of the antisense strand (counting from 5'-end of the antisense strand), wherein said antisense strand comprises at least one thermally destabilizing modification of the duplex within the first 9 nucleotide positions, counting from the 5'-end, and wherein said sense strand comprises a ligand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, wherein no 2'-modification is present at positions 3-9 of the antisense strand (counting from 5'-end of the antisense strand), and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein no 2'-modification is present at positions 3-9 of the antisense strand (counting from 5'-end of the antisense strand), wherein said antisense strand comprises at least one thermally destabilizing modification of the duplex located at position 5, 6 or 7, counting from the 5'-end of the antisense strand, and wherein said sense strand comprises a ligand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located at position 5, 6 or 7, counting from the 5'-end, wherein said sense strand comprises a ligand, and wherein each of the sense and antisense strands comprise at least two 2'-fluoro modifications, wherein no 2'-modification is present at positions 3-9 of the antisense strand (counting from 5'-end of the antisense strand) and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein no 2'-modification is present at positions 3-9 of the antisense strand (counting from 5'-end of the antisense strand), wherein said antisense strand comprises at least one thermally destabilizing modification of the duplex within the first 9 nucleotide positions, counting from the 5'-end, and wherein said sense strand comprises a ligand, wherein the ligand comprises one or more GalNAc derivatives attached through a bivalent or trivalent branched linker, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein no 2'-modification is present at positions 3-9 of the antisense strand (counting from 5'-end of the antisense strand), wherein said antisense strand comprises at least one thermally destabilizing modification of the duplex within the first 9 nucleotide positions, counting from the 5'-end, and wherein said sense strand comprises a ligand, wherein the ligand is an ASGPR ligand of structure:

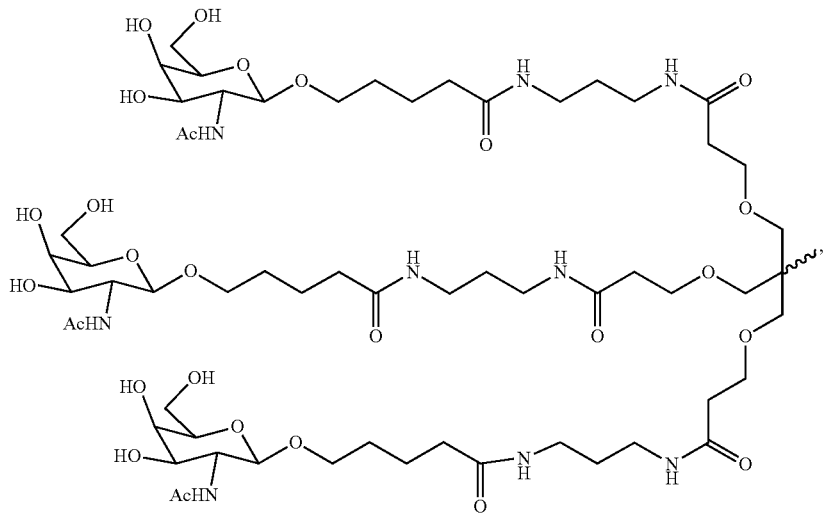 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 3, 4, 5 or 6 2'-fluoro modifications, comprises 2, 3, 4 or 5 phosphorothioate internucleotide linkages; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 3, 4, 5 or 6 2'-fluoro modifications, where no 2'-fluoo modification is present at positions 3-9 of the antisense strand, comprises 2, 3 or 4 phosphorothioate internucleotide linkages; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 0 or 2 phosphorothioate internucleotide linkages, and optionally comprises 1, 2, 3, 4, 5, 6, 7, 8, 9 or 10 LNA modifications; wherein the antisense strand comprises 2'-fluoro modifications at positions 2, 14 or 16, or at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 1, 2, 3, 4, 5, 6, 7, 8, 9 or 10 LNA modifications, and optionally comprises 0 or 2 phosphorothioate internucleotide linkages; wherein the antisense strand comprises 2'-fluoro modifications at positions 2, 14 or 16, or at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 1, 2, 3, 4, 5, 6, 7, 8, 9 or 10 LNA modifications, and comprises 0, 1, 2 or 3 phosphorothioate internucleotide linkages; wherein the antisense strand comprises 2'-fluoro modifications at positions 2, 14 or 16, or at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 0, 1, 2 or 3 phosphorothioate internucleotide linkages, and optionally comprises 1, 2, 3, 4, 5, 6, 7, 8, 9 or 10 LNA modifications; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 1, 2, 3, 4, 5, 6, 7, 8, 9 or 10 LNA modifications, and optionally comprises 0, 1, 2 or 3 phosphorothioate internucleotide linkages; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 1, 2, 3, 4, 5, 6, 7, 8, 9 or 10 LNA modifications, and comprises 0, 1, 2, or 3 phosphorothioate internucleotide linkages; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 2'-fluoro modifications at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 2'-fluoro modifications at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hbGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises 1, 2, 3, 4, 5, 6, 7, 8, 9 or 10 LNA modifications and optionally comprises phosphorothioate internucleotide linkages between nucleotide positions 1 and 2, and between nucleotide positions 2 and 3; wherein the antisense strand comprises 2'-fluoro modifications at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the deRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises 1, 2, 3, 4, 5, 6, 7, 8, 9 or 10 LNA modifications, and comprises phosphorothioate internucleotide linkages between nucleotide positions 1 and 2, and between nucleotide positions 2 and 3; wherein the antisense strand comprises 2'-fluoro modifications at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, S'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, bGNA, bhGNA, mGNA, TNA and h'GNA (Mod A-Mod K).

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises 1, 2, 3, 4, 5, 6, 7, 8, 9 or 10 LNA modifications, and optionally comprises phosphorothioate internucleotide linkages between nucleotide positions 1 and 2, and between nucleotide positions 2 and 3; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), the dsRNA has a melting temperature ($T_m$) of from about 40° C. to about 80° C., and the dsRNA optionally further has at least one (e.g., one, two, three, four, five, six, seven, eight or all nine) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; (viii) a blunt end at 5'end of the antisense strand; (ix) provided that no 2'-fluoro modification is present at positions 3-9 (counting from 5'-end) of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the dsRNA molecule has a duplex region of 12-40 nucleotide pairs in length, wherein the antisense strand comprises at least one thermally destabilizing modification of the duplex within the seed region (i.e., at position 2-9 of the 5'-end of the antisense strand, counting from the 5'-end), and the dsRNA has a $T_m$ of from about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and vii) a blunt end at 5'end of the antisense strand, provided that no 2'-fluoro modification is present at positions 3-9 (counting from 5'-end) of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In some embodiments, the dsRNA molecule has a duplex region of 19, 20, 21, 22 or 23 nucleotide base pairs in length, wherein the antisense strand contains at least one thermally destabilizing modification of the duplex located in the seed region of the antisense strand (i.e., at position 2-9 of the 5'-end of the antisense strand), and wherein the dsRNA has a melting temperature of about 40° C. to about 80° C., provided that no 2'-fluoro modification is present at positions 3-9 (counting from 5'-end) of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the melting temperature of about 40° C. to about 80° C. is optional.

In a particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker; and
  (iii) 2'-F modifications at positions 7, 10, and 11 (counting from the 5' end);
  and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 21 and 22, and between nucleotide positions 22 and 23 (counting from the 5' end); and
  (iv) a thermally destabilizing modification of the duplex at position 5, 6 or 7 (counting from the 5' end);
  wherein the dsRNA molecules have a two nucleotide overhang at the 3'-end of the antisense strand, and a blunt end at the 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hhGNA, mGNA, TNA and h'GNA (Mod A-Mod K).

In another particular embodiment, the dsRNA molecules of the present invention comprise:
- (a) a sense strand having:
  - (i) a length of 21 nucleotides;
  - (ii) an ASGPR ligand attached to the 3'-end, wherein said ASGPR ligand comprises three GalNAc derivatives attached through a trivalent branched linker;
  - (iii) 2'-F modifications at positions 7, 9, 10, and 11 (counting from the 5' end); and
  - (iv) phosphorothioate internucleotide linkages between nucleotide positions 1 and 2, and between nucleotide positions 2 and 3 (counting from the 5' end); and
- (b) an antisense strand having:
  - (i) a length of 23 nucleotides;
  - (ii) 2'-F modifications at positions 2, 14, and 16 (counting from the 5' end);
  - (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  - (iv) a thermally destabilizing modification of the duplex at position 5, 6 or 7 (counting from the 5' end);

wherein the dsRNA molecules have a two nucleotide overhang at the 3'-end of the antisense strand, and a blunt end at the 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In another particular embodiment, the dsRNA molecules of the present invention comprise:
- (a) a sense strand having:
  - (i) a length of 21 nucleotides;
  - (ii) an ASGPR ligand attached to the 3'-end, wherein said ASGPR ligand comprises three GalNAc derivatives attached through a trivalent branched linker;
  - (iii) 2'-F modifications at positions 7, 9, 10, and 11 (counting from the 5' end); and
  - (iv) phosphorothioate internucleotide linkages between nucleotide positions 1 and 2, and between nucleotide positions 2 and 3 (counting from the 5' end); and
- (b) an antisense strand having:
  - (i) a length of 23 nucleotides;
  - (ii) 2'-F modifications at positions 2, 14, and 16 (counting from the 5' end);
  - (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  - (iv) a thermally destabilizing modification of the duplex at position 5, 6 or 7 (counting from the 5' end);

wherein the dsRNA molecules have a two nucleotide overhang at the 3'-end of the antisense strand, and a blunt end at the 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In another particular embodiment, the dsRNA molecules of the present invention comprise:
- (a) a sense strand having:
  - (i) a length of 21 nucleotides;
  - (ii) an ASGPR ligand attached to the 3'-end, wherein said ASGPR ligand comprises three GalNAc derivatives attached through a trivalent branched linker;
  - (iii) 2'-F modifications at positions 7, 9, 10, and 11 (counting from the 5' end); and
  - (iv) at least one (e.g., one, two, three, four, five, six, seven, eight, nine, ten or more) LNA modification; and
- (b) an antisense strand having:
  - (i) a length of 23 nucleotides;
  - (ii) 2'-F modifications at positions 2, 14, and 16 (counting from the 5' end);
  - (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  - (iv) a thermally destabilizing modification of the duplex at position 5, 6 or 7 (counting from the 5' end);

wherein the dsRNA molecules have a two nucleotide overhang at the 3'-end of the antisense strand, and a blunt end at the 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In another particular embodiment, the dsRNA molecules of the present invention comprise:
- (a) a sense strand having:
  - (i) a length of 21 nucleotides;
  - (ii) an ASGPR ligand attached to the 3'-end, wherein said ASGPR ligand comprises three GalNAc derivatives attached through a trivalent branched linker;
  - (iii) 2'-F modifications at positions 7, 9, 10, and 11 (counting from the 5' end); and
  - (iv) at least one (e.g., one, two or three) LNA modifications at positions 1, 2 and 3 (counting from the 5' end); and
- (b) an antisense strand having:
  - (i) a length of 23 nucleotides;
  - (ii) 2'-F modifications at positions 2, 14, and 16 (counting from the 5' end);
  - (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and (iv) a thermally destabilizing modification of the duplex at position 5, 6 or 7 (counting from the 5' end);

wherein the dsRNA molecules have a two nucleotide overhang at the 3'-end of the antisense strand, and a blunt end at the 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In another particular embodiment, the dsRNA molecules of the present invention comprise:

(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-F modifications at positions 7, 9, 10, and 11 (counting from the 5' end);
(iv) at least one (e.g., one, two, three, four, five, six, seven, eight, nine, ten or more) LNA modification; and
(iv) phosphorothioate internucleotide linkages between nucleotide positions 1 and 2, and between nucleotide positions 2 and 3 (counting from the 5' end);

and (b) an antisense strand having:
(i) a length of 23 nucleotides;
(ii) 2'-F modifications at positions 2, 14, and 16 (counting from the 5' end);
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
(iv) a thermally destabilizing modification of the duplex at position 5, 6 or 7 (counting from the 5' end);

wherein the dsRNA molecules have a two nucleotide overhang at the 3'-end of the antisense strand, and a blunt end at the 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In another particular embodiment, the dsRNA molecules of the present invention comprise:

(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-F modifications at positions 7, 9, 10, and 11 (counting from the 5' end); and
(iv) at least one (e.g., one, two or three) LNA modifications at positions 1, 2 and 3 (counting from the 5' end);
and (b) an antisense strand having:
(i) a length of 23 nucleotides;
(ii) 2'-F modifications at positions 2, 14, and 16 (counting from the 5' end);
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
(iv) a thermally destabilizing modification of the duplex at position 5, 6 or 7 (counting from the 5' end);

wherein the dsRNA molecules have a two nucleotide overhang at the 3'-end of the antisense strand, and a blunt end at the 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In another particular embodiment, the dsRNA molecules of the present invention comprise:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-F modifications at positions 7, 9, 10, and 11 (counting from the 5' end);
(iv) at least one (e.g., one, two or three) LNA modifications at positions 1, 2 and 3 (counting from the 5' end);
and
(iv) phosphorothioate internucleotide linkages between nucleotide positions 1 and 2, and between nucleotide positions 2 and 3 (counting from the 5' end);
and
(b) an antisense strand having:
(i) a length of 23 nucleotides;
(ii) 2'-F modifications at positions 2, 14, and 16 (counting from the 5' end);
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
(iv) a thermally destabilizing modification of the duplex at position 5, 6 or 7 (counting from the 5' end);

wherein the dsRNA molecules have a two nucleotide overhang at the 3'-end of the antisense strand, and a blunt end at the 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense and antisense strands are independently 19, 20, 21, 22, 23, 24 or 25 nucleotides in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 18, 19, 20, 21, 22, 23, 24 or 24 nucleotide pairs in length; and (viii) the dsRNA comprises a blunt end at 5'-end of the sense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some particular embodiments, sense strand is 19, 20 or 21 or 22 nucleotides in length and the antisense strand is 20, 21 or 22 nucleotides in length.

The sense strand and antisense strand typically form a duplex dsRNA. The duplex region of a dsRNA molecule may be 12-40 nucleotide pairs in length. For example, the duplex region can be between 14-40 nucleotide pairs in length, 17-30 nucleotide pairs in length, 25-35 nucleotides in length, 27-35 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotide pairs in length.

In some embodiments, the dsRNA molecule of the invention has a duplex region of 12-40 nucleotides pairs in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA comprises a blunt end at 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some particular embodiments, the duplex region is 18, 19, 20, 21, 22 or 23 nucleotides pairs in length. In a particular embodiment, the duplex region is 21 nucleotide pairs in length.

In some embodiments, the dsRNA molecule of the invention comprises one or more overhang regions and/or capping groups of dsRNA molecule at the 3'-end, or 5'-end or both ends of a strand. The overhang can be 1-10 nucleotides in length, 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be other sequence. The first and second strands can also be joined, e.g., by additional bases to form a hairpin, or by other non-base linkers.

In some embodiments, the nucleotides in the overhang region of the dsRNA molecule of the invention can each independently be a modified or unmodified nucleotide including, but not limited to 2'-sugar modified, such as, 2'-Fluoro 2'-O-methyl, thymidine (T), 2'-O-methoxyethyl-5-methyluridine, 2'-O-methoxyethyladenosine, 2'-O-methoxyethyl-5-methylcytidine, GNA, SNA, hGNA, hhGNA, mGNA, TNA, h'GNA, and any combinations thereof. For example, TT can be an overhang sequence for either end on either strand. The overhang can form a mismatch with the target mRNA or it can be complementary to the gene sequences being targeted or can be other sequence.

The 5'- or 3'-overhangs at the sense strand, antisense strand or both strands of the dsRNA molecule of the invention may be phosphorylated. In some embodiments, the overhang region contains two nucleotides having a phosphorothioate between the two nucleotides, where the two nucleotides can be the same or different. In some embodiments, the overhang is present at the 3'-end of the sense strand, antisense strand or both strands. In some embodiments, this 3'-overhang is present in the antisense strand. In some embodiments, this 3'-overhang is present in the sense strand.

The dsRNA molecule of the invention may comprise only a single overhang, which can strengthen the interference activity of the dsRNA, without affecting its overall stability. For example, the single-stranded overhang is located at the 3'-terminal end of the sense strand or, alternatively, at the 3'-terminal end of the antisense strand. The dsRNA may also have a blunt end, located at the 5'-end of the antisense strand (or the 3'-end of the sense strand) or vice versa. Generally, the antisense strand of the dsRNA has a nucleotide overhang at the 3'-end, and the 5'-end is blunt. While not bound by theory, the asymmetric blunt end at the 5'-end of the antisense strand and 3'-end overhang of the antisense strand favor the guide strand loading into RISC process. For example the single overhang comprises at least two, three, four, five, six, seven, eight, nine, or ten nucleotides in length. In some embodiments, the dsRNA has a 2 nucleotide overhang on the 3'-end of the antisense strand and a blunt end at the 5'-end of the antisense strand.

In some embodiments, one end of the dsRNA is a blunt end and the other end has an overhang, wherein the antisense strand contains at least one thermally destabilizing nucleotide, and where the at least one thermally destabilizing nucleotide is in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) and the dsRNA comprises a duplex region of 12-40 nucleotide pairs in length, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the deRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the overhang is on the 3'-end of the antisense strand and the blunt end is at the 5'-end of the antisense strand. In some particular embodiments, the overhang is 2, 3 or 4-nucleotides in length.

In some embodiments, the dsRNA molecule has a duplex region of 19, 20, 21, 22 or 23 nucleotide base pairs in length, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications, and optionally the 2 nucleotide overhang is on the 3'-end of the antisense strand and the blunt end is at the 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). In some embodiments, the overhang is on the 3'-end of the antisense strand and the blunt end is at the 5'-end of the antisense strand.

In some embodiments, the dsRNA molecule of the invention may also have two blunt ends, at both ends of the dsRNA duplex.

In some embodiments, the dsRNA has a blunt end at both ends of the duplex, wherein the antisense strand contains at least one thermally destabilizing nucleotide, and where the at least one thermally destabilizing nucleotide is in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a duplex region of 12-40 nucleotide pairs in length, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule has a duplex region of 19, 20, 21, 22 or 23 nucleotide base pairs in length and has a blunt end at both ends of the duplex, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

Thermally Destabilizing Modifications.

As noted above, dsRNA molecule can be optimized for RNA interference by incorporating thermally destabilizing modifications in the seed region of the antisense strand (i.e., at positions 2-9 of the 5'-end of the antisense strand) to reduce or inhibit off-target gene silencing. Inventors have discovered that dsRNAs with an antisense strand comprising at least one thermally destabilizing modification of the duplex within the first 9 nucleotide positions, counting from the 5' end, of the antisense strand have reduced off-target gene silencing activity. Accordingly, in some embodiments, the antisense strand comprises at least one (e.g., one, two, three, four, five or more) thermally destabilizing modification of the duplex within the first 9 nucleotide positions of the 5' region of the antisense strand. In some embodiments, thermally destabilizing modification of the duplex is located in positions 2-9, or preferably positions 4-8, from the 5'-end of the antisense strand. In some further embodiments, the thermally destabilizing modification of the duplex is located at position 6, 7 or 8 from the 5'-end of the antisense strand.

In still some further embodiments, the thermally destabilizing modification of the duplex is located at position 7 from the 5'-end of the antisense strand. The term "thermally destabilizing modification(s)" includes modification(s) that would result with a dsRNA with a lower overall melting temperature (Tm) (preferably a Tm with one, two, three or four degrees lower than the Tm of the dsRNA without having such modification(s)). In some embodiments, the thermally destabilizing modification of the duplex is located at position 2, 3, 4, 5 or 9 from the 5'-end of the antisense strand.

The thermally destabilizing modifications can include, but are not limited to, abasic modification; mismatch with the opposing nucleotide in the opposing strand; and sugar modification such as 2'-deoxy modification or acyclic nucleotide, e.g., unlocked nucleic acids (UNA) or glycol nucleic acid (GNA). For example, the thermally destabilizing modifications can include, but are not limited to, mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA.

In some embodiments, the destabilizing modification mUNA is selected from the group consisting of

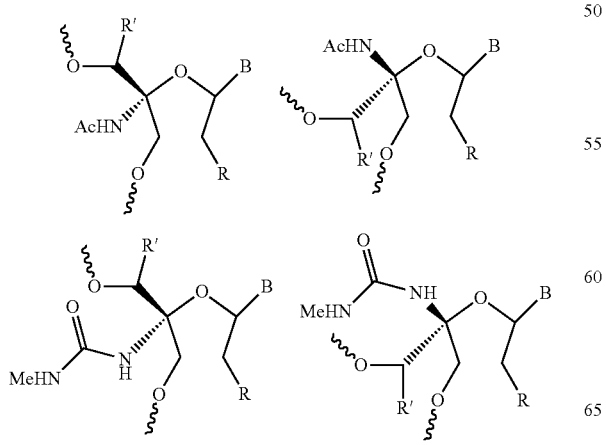

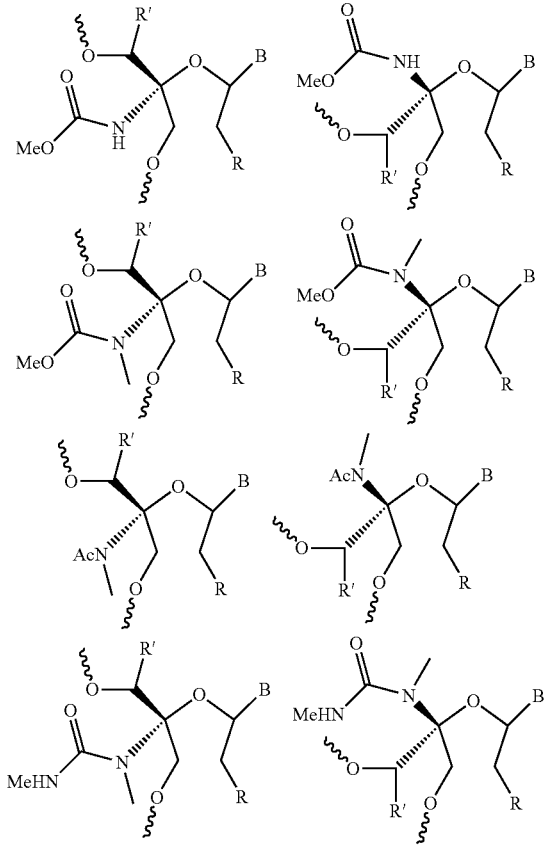

Wherein:

R is H, OH; OMe; Cl, F; OH; O—(CH$_2$)$_2$OMe; SMe, NMe$_2$; NH$_2$; Me; CCH (alkyne), O-nPr; O-alkyl; or O-alkylamino;

R' is H or Me;

B is A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; O6-alkyl-G; 2-thiouridine; 4-thiouridine; C5-modified pyrimidines; C2-modified purines; N8-modified purines; 7-deazapurines, phenoxazine; G-clamp; or non-canonical mono, bi and tricyclic heterocycles; and Stereochemistry is R or S and combination of R and S for the unspecified chiral centers.

In some embodiments, the destabilizing modification mUNA is selected from the group consisting of

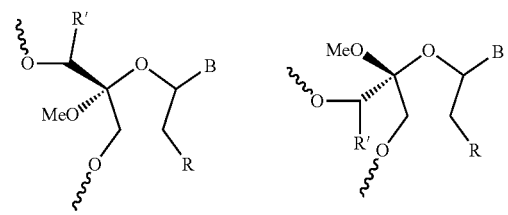

-continued

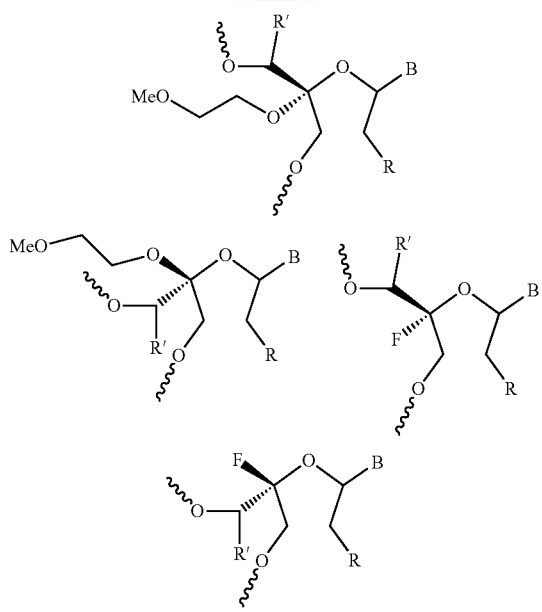

Wherein:

R is H, OH; OMe; Cl, F; OH; O—(CH$_2$)$_2$OMe; SMe, NMe$_2$; NH$_2$; Me; CCH (alkyne), O-nPr; O-alkyl; or O-alkylamino;

R' is H or Me;

B is A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; O6-alkyl-G; 2-thiouridine; 4-thiouridine; C5-modified pyrimidines; C2-modified purines; N8-modified purines; 7-deazapurines, phenoxazine; G-clamp; or non-canonical mono, bi and tricyclic heterocycles; and Stereochemistry is R or S and combination of R and S for the unspecified chiral centers.

In some embodiments, the destabilizing modification mUNA is selected from the group consisting of

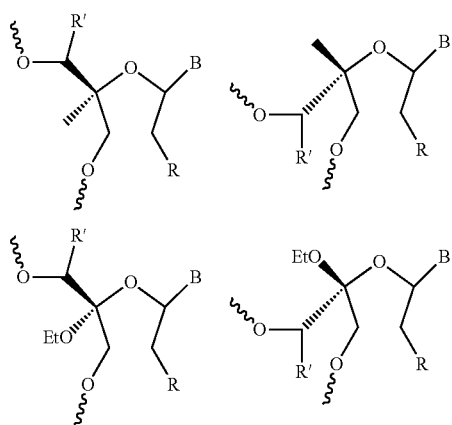

-continued

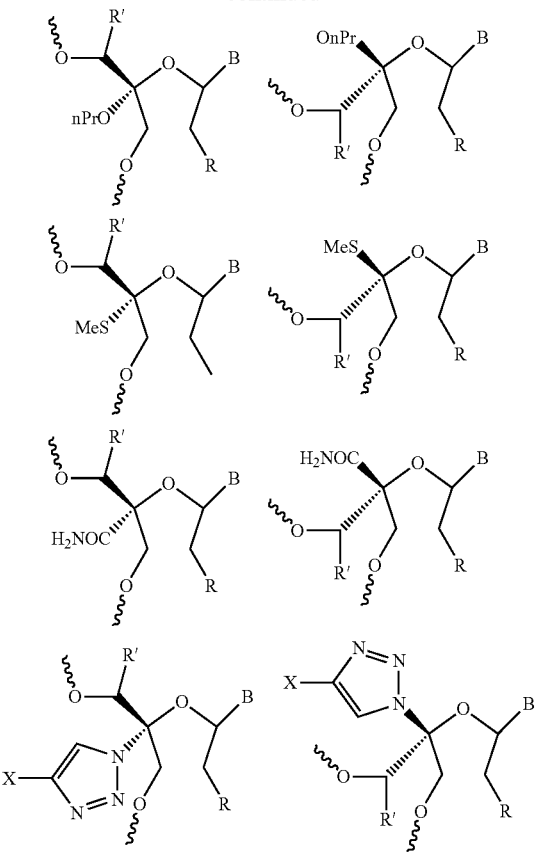

Wherein:

R is H, OMe; F; OH; O—(CH$_2$)$_2$OMe; SMe, NMe$_2$; NH$_2$; Me; O-nPr; O-alkyl; or O-alkylamino; R' is H or Me;

B is A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; O6-alkyl-G; or 7-deazapurines; and Stereochemistry is R or S and combination of R and S for the unspecified chiral centers.

In some embodiments, the destabilizing modification mUNA is selected from the group consisting of

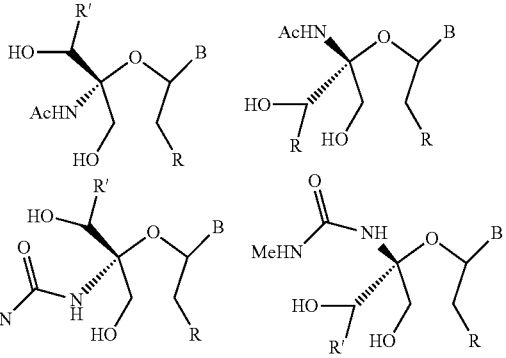

-continued

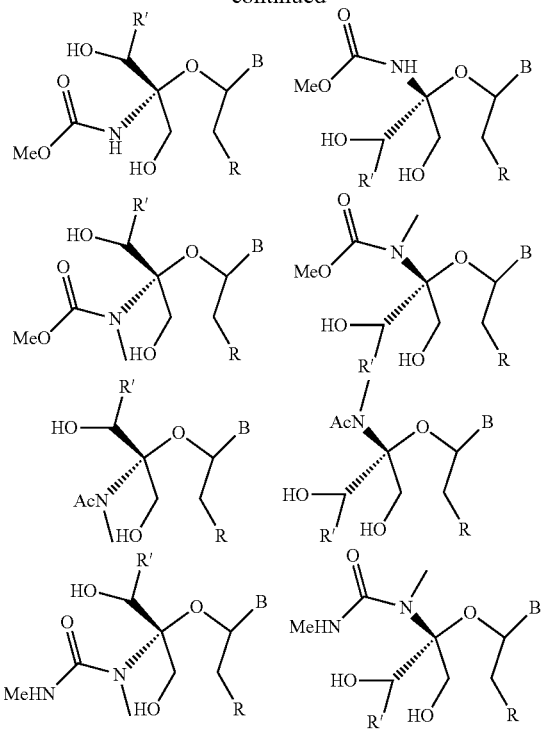

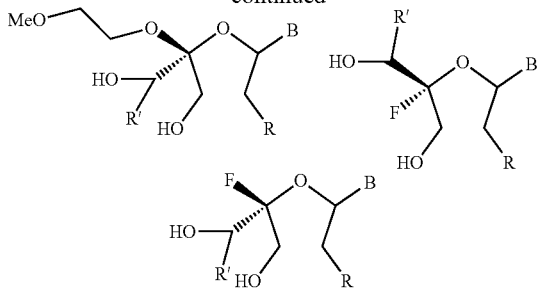

Wherein:
R is H, OH; OMe; Cl, F; OH; O—(CH$_2$)$_2$OMe; SMe, NMe$_2$; NH$_2$; Me; CCH (alkyne), O-nPr; O-alkyl; or O-alkylamino;

R' is H or Me;

B is A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; O6-alkyl-G; 2-thiouridine; 4-thiouridine; C5-modified pyrimidines; C2-modified purines; N8-modified purines; 7-deazapurines, phenoxazine; G-clamp; or non-canonical mono, bi and tricyclic heterocycles; and Stereochemistry is R or S and combination of R and S for the unspecified chiral centers In some embodiments, the destabilizing modification mUNA is selected from the group consisting of

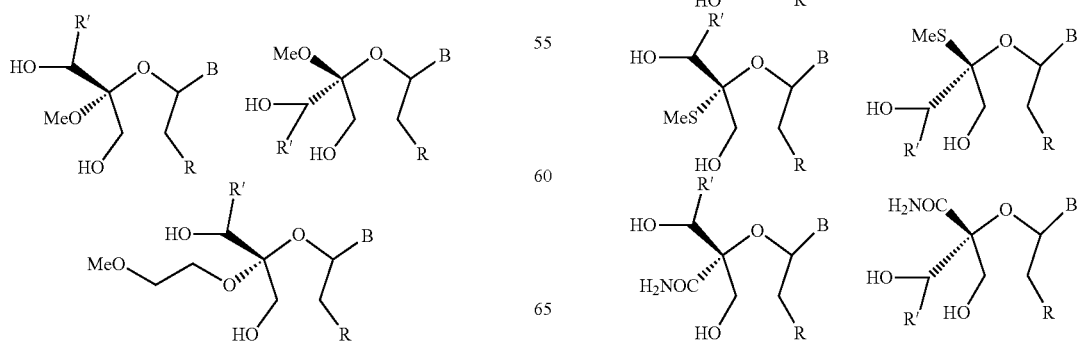

Wherein:
R is H, OH; OMe; Cl, F; OH; O—(CH$_2$)$_2$OMe; SMe, NMe$_2$; NH$_2$; Me; CCH (alkyne), O-nPr; O-alkyl; or O-alkylamino;

R' is H or Me;

B is A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; O6-alkyl-G; 2-thiouridine; 4-thiouridine; C5-modified pyrimidines; C2-modified purines; N8-modified purines; 7-deazapurines, phenoxazine; G-clamp; or non-canonical mono, bi and tricyclic heterocycles; and Stereochemistry is R or S and combination of R and S for the unspecified chiral centers In some embodiments, the modification mUNA is selected from the group consisting of

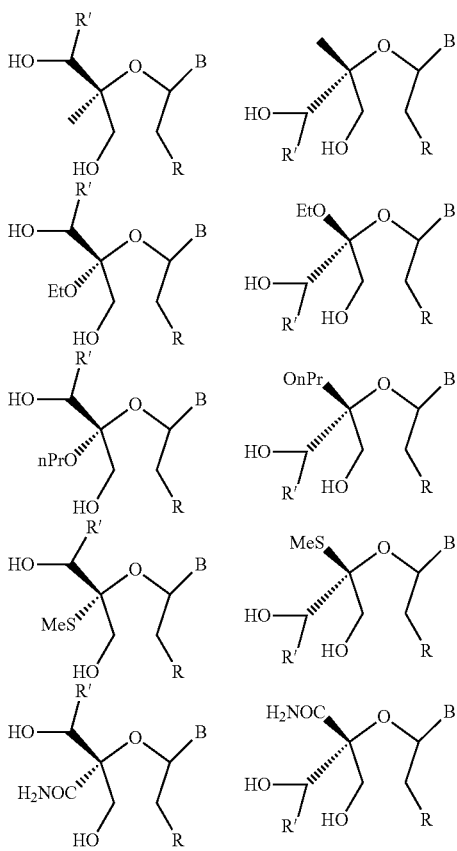

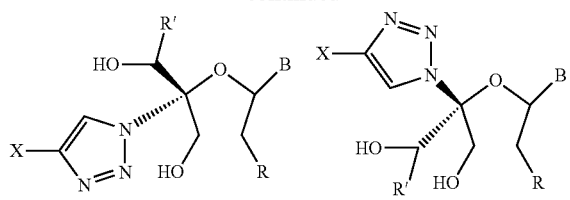

Wherein:

R is H, OMe; F; OH; O—(CH$_2$)$_2$OMe; SMe, NMe$_2$; NH$_2$; Me; O-nPr, O-alkyl; orO-alkylamino;

R' is H or Me;

B is A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; O6-alkyl-G; or 7-deazapurines; and Stereochemistry is R or S and combination of R and S for the unspecified chiral centers In some embodiments, the modification mUNA is selected from the group consisting of

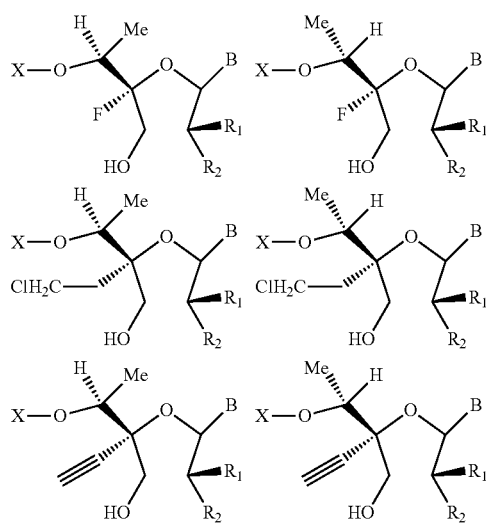

R$_1$, R$_2$ = OTBS; F, H, Me, Cl
B = A$^{Bz}$; C$^{Bz}$; 5-Me-C$^{Bz}$; G; I; U; T; Y; 2-thiouridine; 4- thiouridine; C5-modified pyrimidines; C2- modified purines; N8-modified purines; phenoxazine; G-clamp; non-canonical mono, bi and tricyclic heterocycles; pseudouracil isoC; isoG; 2,6-diamninopurine; pseudocytosine; 2-amnopurine; xanthosine; N6-alkyl-A; O6-alkyl-G; 7-deazapurines

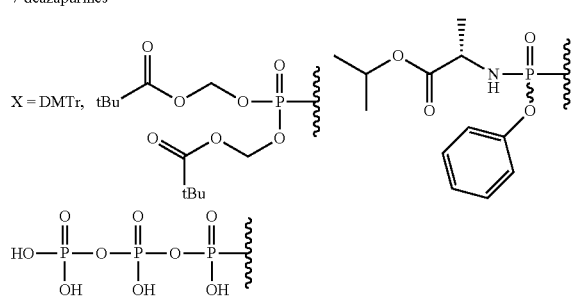

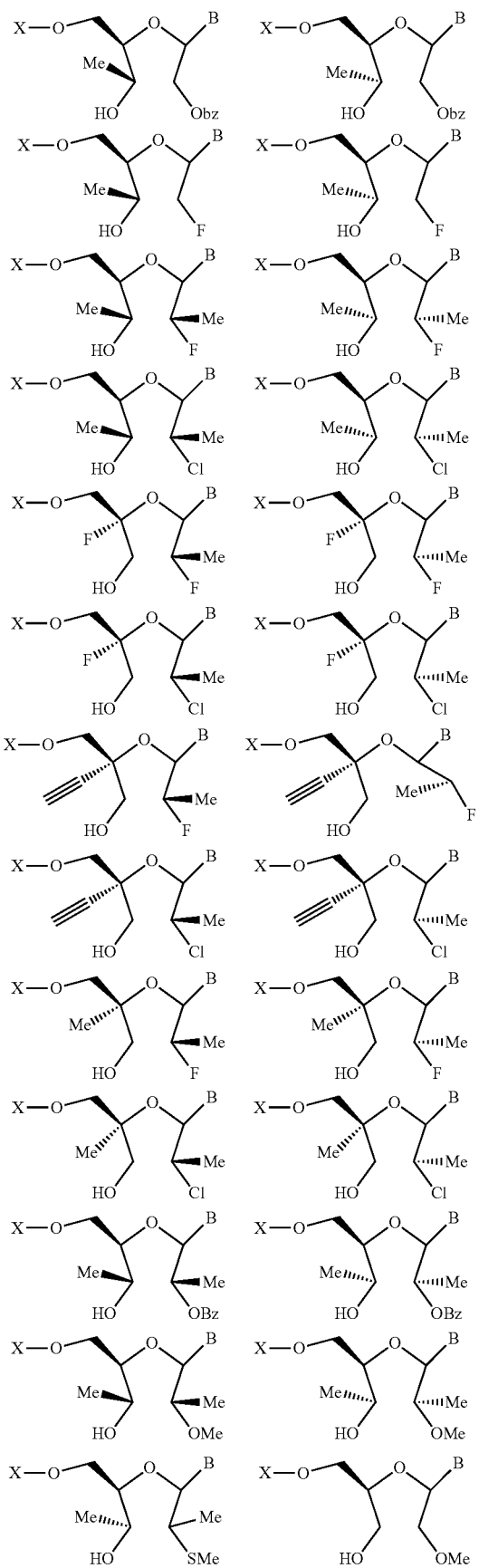

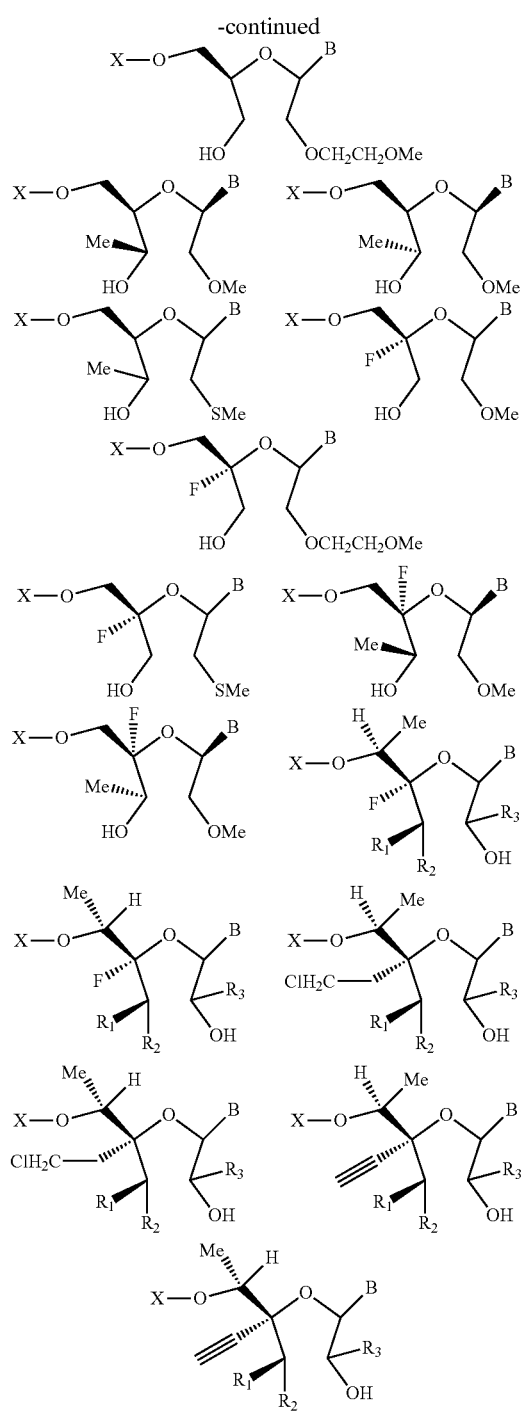
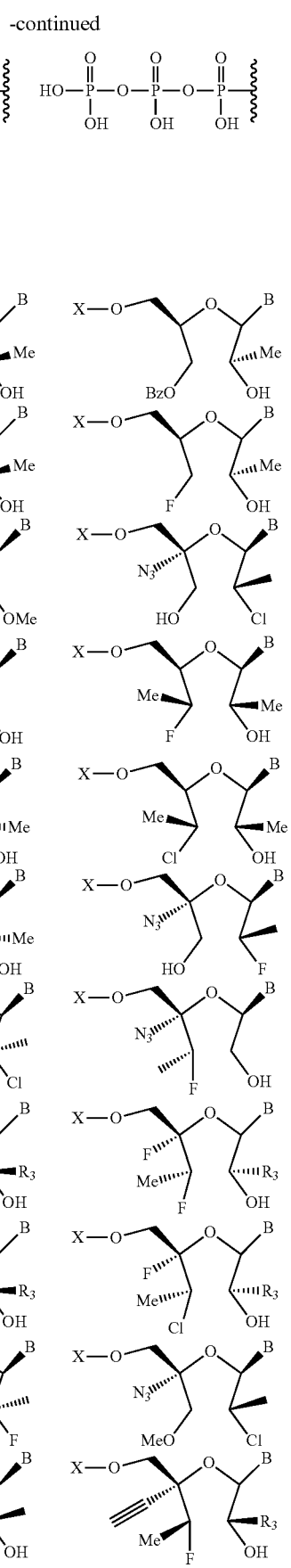
$R_1, R_2$ = OTBS; F, H, Me, Cl
$R_3$ = H, Me
B = $A^{Bz}$; $C^{Bz}$; 5-Me-$C^{Bz}$; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil isoC; isoG; 2,6-diamninopurine; pseudocytosine; 2-aminopurine; xanthosine; N6-alkyl-A; O6-alkyl-G; 7-deazapurines
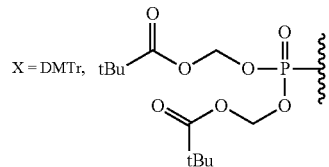

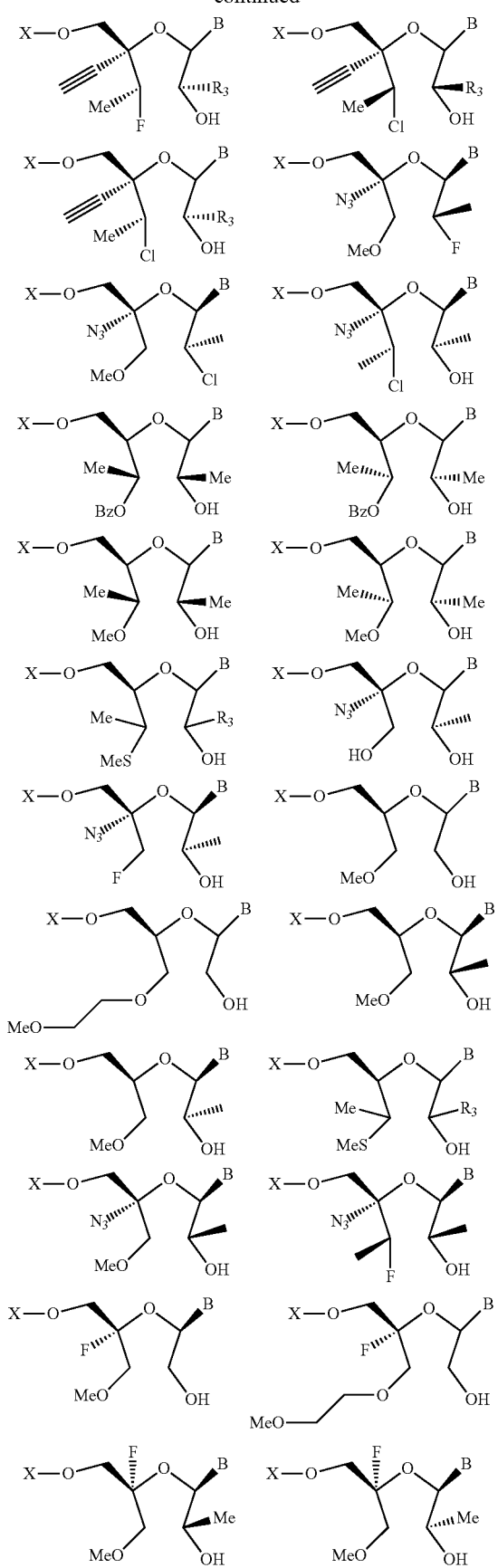
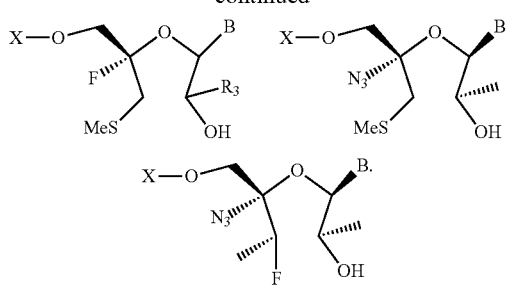
Exemplified abasic modifications include, but are not limited to the following:
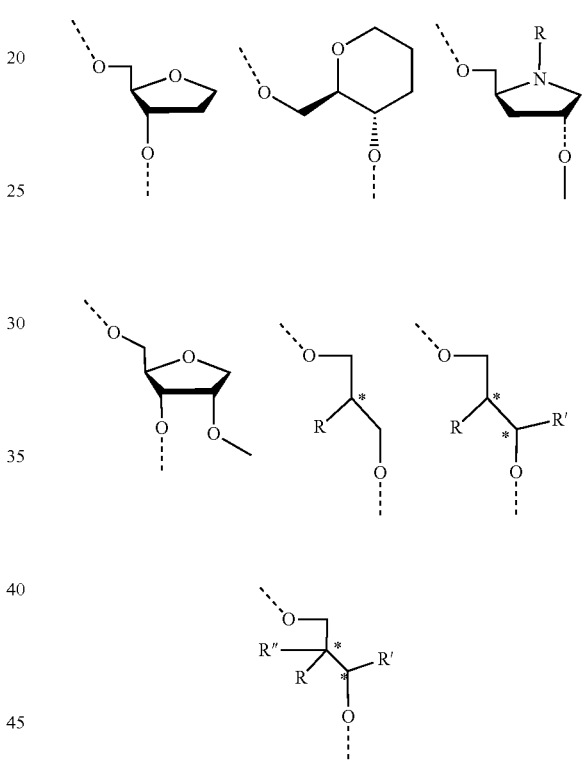
Wherein R is H, Me, Et or OMe; R' is H, Me, Et or OMe; and R" is H, Me, Et or OMe
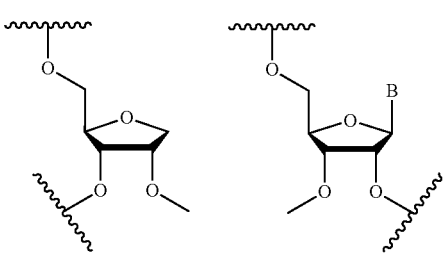
Mod2 (2'-OMe Abasic Spacer)
Mod3 (3'-OMe)

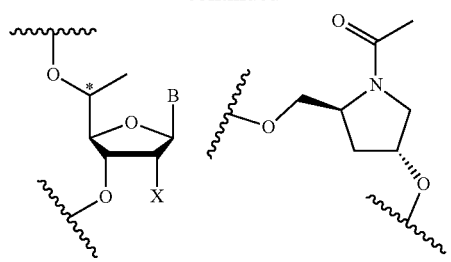
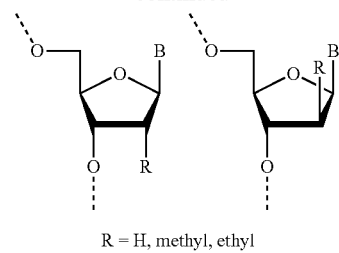

Mod4 (5'-Me) X = OMe, F
Mod5 (hyp-spacer)

wherein B is a modified or unmodified nucleobase and the asterisk on each structure represents either R, S or racemdic.

Exemplified sugar modifications include, but are not limited to the following:

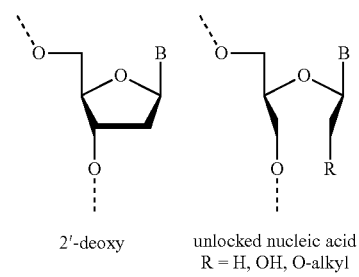

2'-deoxy
unlocked nucleic acid R = H, OH, O-alkyl

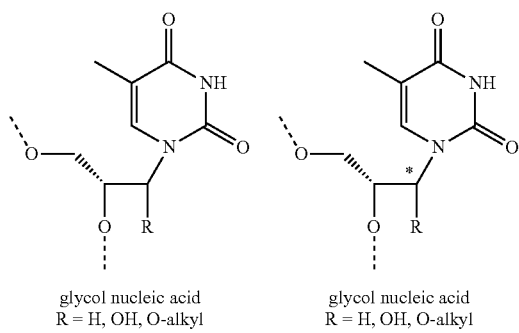

glycol nucleic acid R = H, OH, O-alkyl
glycol nucleic acid R = H, OH, O-alkyl

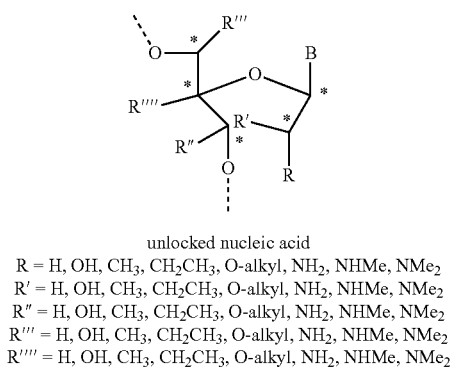

unlocked nucleic acid
R = H, OH, CH$_3$, CH$_2$CH$_3$, O-alkyl, NH$_2$, NHMe, NMe$_2$
R' = H, OH, CH$_3$, CH$_2$CH$_3$, O-alkyl, NH$_2$, NHMe, NMe$_2$
R'' = H, OH, CH$_3$, CH$_2$CH$_3$, O-alkyl, NH$_2$, NHMe, NMe$_2$
R''' = H, OH, CH$_3$, CH$_2$CH$_3$, O-alkyl, NH$_2$, NHMe, NMe$_2$
R'''' = H, OH, CH$_3$, CH$_2$CH$_3$, O-alkyl, NH$_2$, NHMe, NMe$_2$

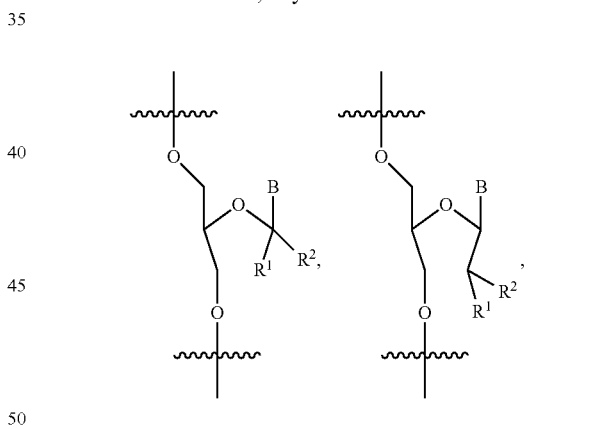

R = H, methyl, ethyl wherein B is a modified or unmodified nucleobase and the asterisk on each structure represents either R, S or racemic.

In some embodiments the thermally destabilizing modification of the duplex is selected from the mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

The term "acyclic nucleotide" refers to any nucleotide having an acyclic ribose sugar, for example, where any of bonds between the ribose carbons (e.g., C1'-C2', C2'-C3', C3'-C4', C4'-C4', or C1'-C4') is absent and/or at least one of ribose carbons or oxygen (e.g., C1', C2', C3', C4' or C4') are independently or in combination absent from the nucleotide. In some embodiments, acyclic nucleotide is

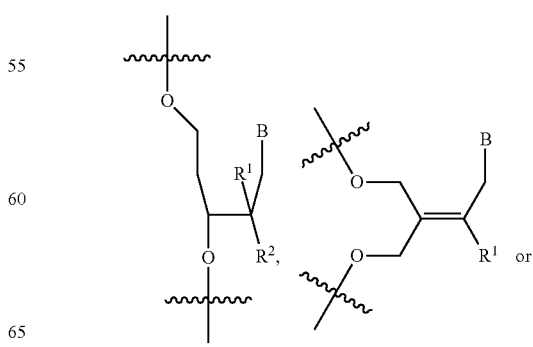

-continued

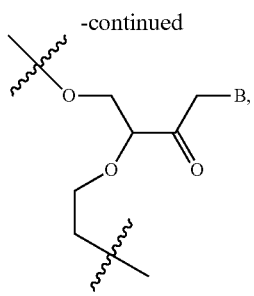

wherein B is a modified or unmodified nucleobase, R1 and R2 independently are H, halogen, OR3, or alkyl; and R3 is H, alkyl, cycloalkyl, aryl, aralkyl, heteroaryl or sugar). The term "UNA" refers to unlocked acyclic nucleic acid, wherein any of the bonds of the sugar has been removed, forming an unlocked "sugar" residue. In one example, UNA also encompasses monomers with bonds between C1'-C4' being removed (i.e. the covalent carbon-oxygen-carbon bond between the C1' and C4' carbons). In another example, the C2'-C3' bond (i.e. the covalent carbon-carbon bond between the C2' and C3' carbons) of the sugar is removed (see Mikhailov et. al., Tetrahedron Letters, 26 (17): 2059 (1985); and Fluiter et al., Mol. Biosyst., 10:1039 (2009), which are hereby incorporated by reference in their entirety). The acyclic derivative provides greater backbone flexibility without affecting the Watson-Crick pairings. The acyclic nucleotide can be linked via 2'-5' or 3'-5' linkage.

The term 'GNA' refers to glycol nucleic acid which is a polymer similar to DNA or RNA but differing in the composition of its "backbone" in that is composed of repeating glycerol units linked by phosphodiester bonds:

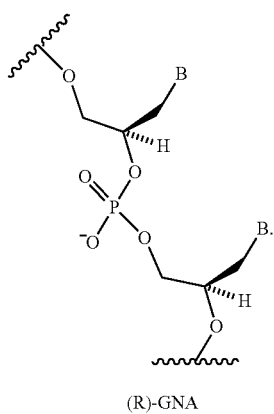

(R)-GNA

The thermally destabilizing modification of the duplex can be mismatches (i.e., noncomplementary base pairs) between the thermally destabilizing nucleotide and the opposing nucleotide in the opposite strand within the dsRNA duplex. Exemplary mismatch base pairs include G:G, G:A, G:U, G:T, A:A, A:C, C:C, C:U, C:T, U:U, T:T, U:T, or a combination thereof.

Other mismatch base pairings known in the art are also amenable to the present invention. A mismatch can occur between nucleotides that are either naturally occurring nucleotides or modified nucleotides, i.e., the mismatch base pairing can occur between the nucleobases from respective nucleotides independent of the modifications on the ribose sugars of the nucleotides. In certain embodiments, the dsRNA molecule contains at least one nucleobase in the mismatch pairing that is a 2'-deoxy nucleobase; e.g., the 2'-deoxy nucleobase is in the sense strand.

In some embodiments, the thermally destabilizing modification of the duplex in the seed region of the antisense strand includes nucleotides with impaired W-C H-bonding to complementary base on the target mRNA, such as:

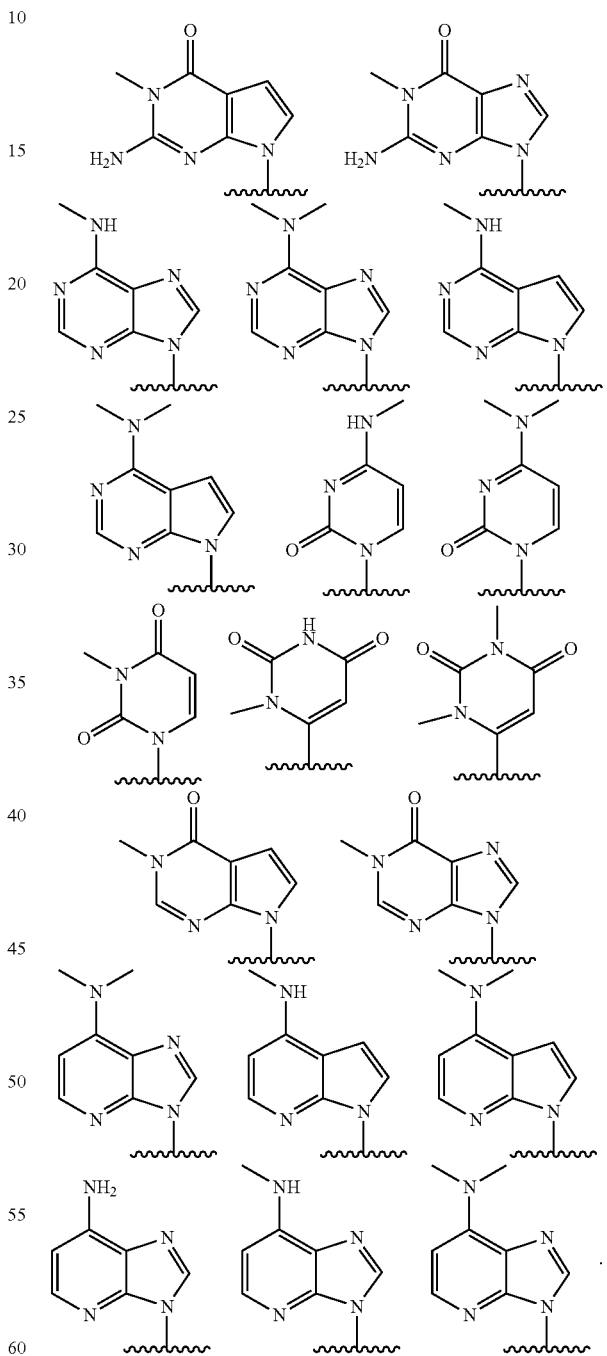

More examples of abasic nucleotide, acyclic nucleotide modifications (including UNA and GNA), and mismatch modifications have been described in detail in WO 2011/133876, which is herein incorporated by reference in its entirety.

The thermally destabilizing modifications may also include universal base with reduced or abolished capability to form hydrogen bonds with the opposing bases, and phosphate modifications.

In some embodiments, the thermally destabilizing modification of the duplex includes nucleotides with non-canonical bases such as, but not limited to, nucleobase modifications with impaired or completely abolished capability to form hydrogen bonds with bases in the opposite strand. These nucleobase modifications have been evaluated for destabilization of the central region of the dsRNA duplex as described in WO 2010/0011895, which is herein incorporated by reference in its entirety. Exemplary nucleobase modifications are:

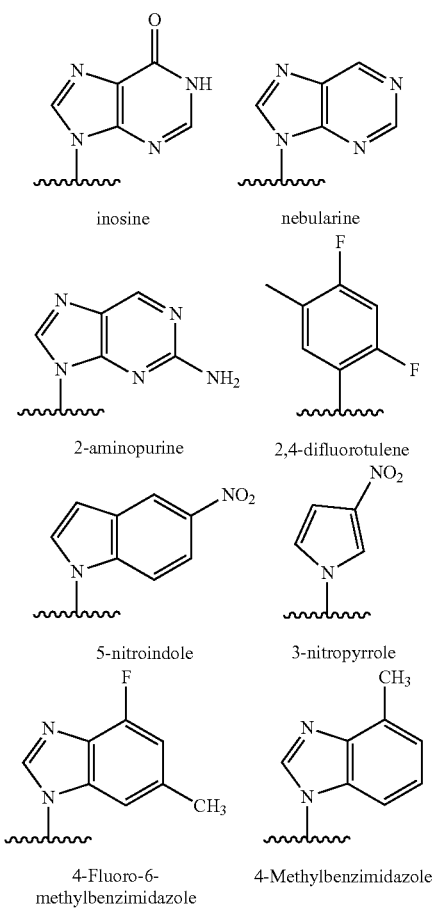

In some embodiments, the thermally destabilizing modification of the duplex in the seed region of the antisense strand includes one or more α-nucleotide complementary to the base on the target mRNA, such as:

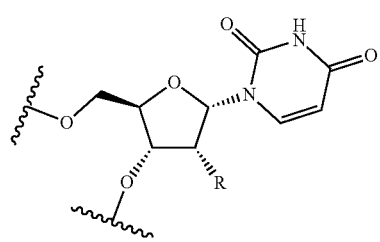

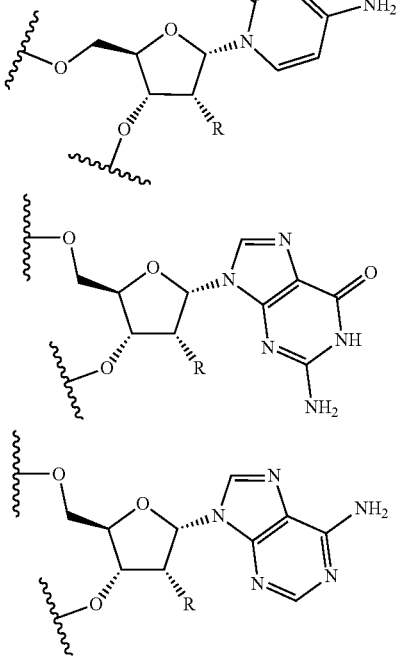

Wherein R is H, OH, OCH$_3$, F, NH$_2$, NHMe, NMe$_2$ or O-alkyl

Exemplary phosphate modifications known to decrease the thermal stability of dsRNA duplexes compared to natural phosphodiester linkages are:

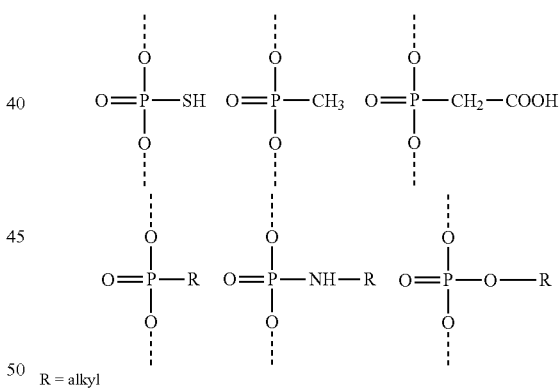

R = alkyl

The alkyl for the R group can be a $C_1$-$C_6$alkyl. Specific alkyls for the R group include, but are not limited to methyl, ethyl, propyl, isopropyl, butyl, pentyl and hexyl.

In some embodiments, exemplary destabilizing modifications shown in FIG. 1.

In addition to the antisense strand comprising a thermally destabilizing modification, the dsRNA can also comprise one or more stabilizing modifications. For example, the dsRNA can comprise at least two (e.g., two, three, four, five, six, seven, eight, nine, ten or more) stabilizing modifications. Without limitations, the stabilizing modifications all can be present in one strand. In some embodiments, both the sense and the antisense strands comprise at least two stabilizing modifications. The stabilizing modification can occur on any nucleotide of the sense strand or antisense strand. For instance, the stabilizing modification can occur on every nucleotide on the sense strand and/or antisense strand; each stabilizing modification can occur in an alternating pattern on the sense strand or antisense strand; or the sense strand or antisense strand comprises both stabilizing modification in an alternating pattern. The alternating pattern of the stabilizing modifications on the sense strand may be the same or different from the antisense strand, and the alternating pattern of the stabilizing modifications on the sense strand can have a shift relative to the alternating pattern of the stabilizing modifications on the antisense strand.

In some embodiments, the antisense strand comprises at least two (e.g., two, three, four, five, six, seven, eight, nine, ten or more) stabilizing modifications. Without limitations, a stabilizing modification in the antisense strand can be present at any positions. In some embodiments, the antisense comprises stabilizing modifications at positions 2, 6, 8, 9, 14 and 16 from the 5'-end. In some other embodiments, the antisense comprises stabilizing modifications at positions 2, 6, 14 and 16 from the 5'-end. In still some other embodiments, the antisense comprises stabilizing modifications at positions 2, 14 and 16 from the 5'-end.

In some embodiments, the antisense strand comprises at least one stabilizing modification adjacent to the destabilizing modification. For example, the stabilizing modification can be the nucleotide at the 5'-end or the 3'-end of the destabilizing modification, i.e., at position −1 or +1 from the position of the destabilizing modification. In some embodiments, the antisense strand comprises a stabilizing modification at each of the 5'-end and the 3'-end of the destabilizing modification, i.e., positions-1 and +1 from the position of the destabilizing modification.

In some embodiments, the antisense strand comprises at least two stabilizing modifications at the 3'-end of the destabilizing modification, i.e., at positions +1 and +2 from the position of the destabilizing modification. In some embodiments, the sense strand comprises at least two (e.g., two, three, four, five, six, seven, eight, nine, ten or more) stabilizing modifications. Without limitations, a stabilizing modification in the sense strand can be present at any positions. In some embodiments, the sense strand comprises stabilizing modifications at positions 7, 10 and 11 from the 5'-end. In some other embodiments, the sense strand comprises stabilizing modifications at positions 7, 9, 10 and 11 from the 5'-end. In some embodiments, the sense strand comprises stabilizing modifications at positions opposite or complimentary to positions 11, 12 and 15 of the antisense strand, counting from the 5'-end of the antisense strand. In some other embodiments, the sense strand comprises stabilizing modifications at positions opposite or complimentary to positions 11, 12, 13 and 15 of the antisense strand, counting from the 5'-end of the antisense strand. In some embodiments, the sense strand comprises a block of two, three or four stabilizing modifications.

In some embodiments, the sense strand does not comprise a stabilizing modification in position opposite or complimentary to the thermally destabilizing modification of the duplex in the antisense strand.

Exemplary thermally stabilizing modifications include, but are not limited to 2'-fluoro modifications. Other thermally stabilizing modifications include, but are not limited to LNA.

In some embodiments, the dsRNA of the invention comprises at least four (e.g., four, five, six, seven, eight, nine, ten or more) 2'-fluoro nucleotides. Without limitations, the 2'-fluoro nucleotides all can be present in one strand. In some embodiments, both the sense and the antisense strands comprise at least two 2'-fluoro nucleotides. The 2'-fluoro modification can occur on any nucleotide of the sense strand or antisense strand. For instance, the 2'-fluoro modification can occur on every nucleotide on the sense strand and/or antisense strand; each 2'-fluoro modification can occur in an alternating pattern on the sense strand or antisense strand; or the sense strand or antisense strand comprises both 2'-fluoro modifications in an alternating pattern. The alternating pattern of the 2'-fluoro modifications on the sense strand may be the same or different from the antisense strand, and the alternating pattern of the 2'-fluoro modifications on the sense strand can have a shift relative to the alternating pattern of the 2'-fluoro modifications on the antisense strand.

In some embodiments, the antisense strand comprises at least two (e.g., two, three, four, five, six, seven, eight, nine, ten or more) 2'-fluoro nucleotides. Without limitations, a 2'-fluoro modification in the antisense strand can be present at any positions. In some embodiments, the antisense comprises 2'-fluoro nucleotides at positions 2, 6, 8, 9, 14 and 16 from the 5'-end. In some other embodiments, the antisense comprises 2'-fluoro nucleotides at positions 2, 6, 14 and 16 from the 5'-end. In still some other embodiments, the antisense comprises 2'-fluoro nucleotides at positions 2, 14 and 16 from the 5'-end.

In some embodiments, the antisense strand comprises at least one 2'-fluoro nucleotide adjacent to the destabilizing modification. For example, the 2'-fluoro nucleotide can be the nucleotide at the 5'-end or the 3'-end of the destabilizing modification, i.e., at position-1 or +1 from the position of the destabilizing modification. In some embodiments, the antisense strand comprises a 2'-fluoro nucleotide at each of the 5'-end and the 3'-end of the destabilizing modification, i.e., positions −1 and +1 from the position of the destabilizing modification.

In some embodiments, the antisense strand comprises at least two 2'-fluoro nucleotides at the 3'-end of the destabilizing modification, i.e., at positions +1 and +2 from the position of the destabilizing modification.

In some embodiments, the sense strand comprises at least two (e.g., two, three, four, five, six, seven, eight, nine, ten or more) 2'-fluoro nucleotides. Without limitations, a 2'-fluoro modification in the sense strand can be present at any positions. In some embodiments, the antisense comprises 2'-fluoro nucleotides at positions 7, 10 and 11 from the 5'-end. In some other embodiments, the sense strand comprises 2'-fluoro nucleotides at positions 7, 9, 10 and 11 from the 5'-end. In some embodiments, the sense strand comprises 2'-fluoro nucleotides at positions opposite or complimentary to positions 11, 12 and 15 of the antisense strand, counting from the 5'-end of the antisense strand. In some other embodiments, the sense strand comprises 2'-fluoro nucleotides at positions opposite or complimentary to positions 11, 12, 13 and 15 of the antisense strand, counting from the 5'-end of the antisense strand. In some embodiments, the sense strand comprises a block of two, three or four 2'-fluoro nucleotides.

In some embodiments, the sense strand does not comprise a 2'-fluoro nucleotide in position opposite or complimentary to the thermally destabilizing modification of the duplex in the antisense strand.

In some embodiments, the dsRNA molecule of the invention comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a blunt end at 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). Preferably, the 2 nt overhang is at the 3'-end of the antisense.

In some embodiments, the dsRNA molecule of the invention comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3 'terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the deRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K). For example, the thermally destabilizing nucleotide occurs between positions opposite or complimentary to positions 14-17 of the 5'-end of the sense strand, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA comprises a duplex region of 12-30 nucleotide pairs in length.

In some embodiments, the dsRNA molecule of the invention comprises a sense and antisense strands, wherein said dsRNA molecule comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5'end, wherein the 3' end of said sense strand and the 5' end of said antisense strand form a blunt end and said antisense strand is 1~4 nucleotides longer at its 3' end than the sense strand, wherein the duplex region which is at least 25 nucleotides in length, and said antisense strand is sufficiently complementary to a target mRNA along at least 19 nt of said antisense strand length to reduce target gene expression when said dsRNA molecule is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA has a duplex region of 12-29 nucleotide pairs in length, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, every nucleotide in the sense strand and antisense strand of the dsRNA molecule may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar, wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a RNA or may only occur in a single strand region of a RNA. E.g., a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, HNA, CeNA, 2'-methoxyethyl, 2'-O-methyl, 2'-O-allyl, 2'-C-allyl, 2'-deoxy, or 2'-fluoro. The strands can contain more than one modification. In some embodiments, each residue of the sense strand and antisense strand is independently modified with 2'-O-methyl or 2'-fluoro. It is to be understood that these modifications are in addition to the at least one thermally destabilizing modification of the duplex present in the antisense strand.

At least two different modifications are typically present on the sense strand and antisense strand. Those two modifications may be the 2'-deoxy, 2'-O-methyl or 2'-fluoro modifications, acyclic nucleotides or others. In some embodiments, the sense strand and antisense strand each comprises two differently modified nucleotides selected from 2'-O-methyl or 2'-deoxy. In some embodiments, each residue of the sense strand and antisense strand is independently modified with 2'-O-methyl nucleotide, 2'-deoxy nucleotide, 2'-deoxy-2'-fluoro nucleotide, 2'-O-N-methylacetamido (2'-O-NMA) nucleotide, a 2'-O-dimethylaminoethoxyethyl (2'-O-DMAEOE) nucleotide, 2'-O-aminopropyl (2'-O-AP) nucleotide, or 2'-ara-F nucleotide. Again, it is to be understood that these modifications are in addition to the at least one thermally destabilizing modification of the duplex present in the antisense strand.

In some embodiments, the dsRNA molecule of the invention comprises modifications of an alternating pattern, particular in the B1, B2, B3, B1', B2', B3', B4' regions. The term "alternating motif" or "alternative pattern" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAAB-BAABB . . . ," "AABAABAABAAB . . . ," "AAABAAA-BAAAB . . . ," "AAABBBAAABBB . . . ," or "ABCAB-CABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABA-BAB . . . ," "ACACAC . . . ," "BDBDBD . . . ," or "CDCDCD . . . ," etc.

In some embodiments, the dsRNA molecule of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 3'-5' of the strand within the duplex region. As another example, the alternating motif in the sense strand may start with "AABBAABB" from 5'-3' of the strand and the alternating motif in the antisense strand may start with "BBAABBAA" from 3'-5' of the strand within the duplex region, so that there is a complete or partial shift of the modification patterns between the sense strand and the antisense strand.

The dsRNA molecule of the invention may further comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand and/or antisense strand; each internucleotide linkage modification may occur in an alternating pattern on the sense strand or antisense strand; or the sense strand or antisense strand comprises both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In some embodiments, the dsRNA molecule comprises the phosphorothioate or methylphosphonate internucleotide linkage modification in the overhang region. For example, the overhang region comprises two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. Preferably, these terminal three nucleotides may be at the 3'-end of the antisense strand.

In some embodiments, the sense strand of the dsRNA molecule comprises 1-10 blocks of two to ten phosphorothioate or methylphosphonate internucleotide linkages separated by 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said sense strand is paired with an antisense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of two phosphorothioate or methylphosphonate internucleotide linkages separated by 1, 2, 3, 4, 5, 6, 7, 8, 9, 10, 11, 12, 13, 14, 15, 16, 17, or 18 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of three phosphorothioate or methylphosphonate internucleotide linkages separated by 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of four phosphorothioate or methylphosphonate internucleotide linkages separated by 1, 2, 3, 4, 5, 6, 7, 8, 9, 10, 11, 12, 13 or 14 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of five phosphorothioate or methylphosphonate internucleotide linkages separated by 1, 2, 3, 4, 5, 6, 7, 8, 9, 10, 11 or 12 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of six phosphorothioate or methylphosphonate internucleotide linkages separated by 1, 2, 3, 4, 5, 6, 7, 8, 9 or 10 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of seven phosphorothioate or methylphosphonate internucleotide linkages separated by 1, 2, 3, 4, 5, 6, 7 or 8 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of eight phosphorothioate or methylphosphonate internucleotide linkages separated by 1, 2, 3, 4, 5 or 6 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of nine phosphorothioate or methylphosphonate internucleotide linkages separated by 1, 2, 3 or 4 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the dsRNA molecule of the invention further comprises one or more phosphorothioate or methylphosphonate internucleotide linkage modification within 1-10 of the termini position(s) of the sense and/or antisense strand. For example, at least 2, 3, 4, 5, 6, 7, 8, 9 or 10 nucleotides may be linked through phosphorothioate or methylphosphonate internucleotide linkage at one end or both ends of the sense and/or antisense strand.

In some embodiments, the dsRNA molecule of the invention further comprises one or more phosphorothioate or methylphosphonate internucleotide linkage modification within 1-10 of the internal region of the duplex of each of the sense and/or antisense strand. For example, at least 2, 3, 4, 5, 6, 7, 8, 9 or 10 nucleotides may be linked through phosphorothioate methylphosphonate internucleotide linkage at position 8-16 of the duplex region counting from the 5'-end of the sense strand; the dsRNA molecule can optionally further comprise one or more phosphorothioate or methylphosphonate internucleotide linkage modification within 1-10 of the termini position(s).

In some embodiments, the dsRNA molecule of the invention further comprises one to five phosphorothioate or methylphosphonate internucleotide linkage modification(s) within position 1-5 and one to five phosphorothioate or methylphosphonate internucleotide linkage modification(s) within position 18-23 of the sense strand (counting from the 5'-end), and one to five phosphorothioate or methylphosphonate internucleotide linkage modification at positions 1 and 2 and one to five within positions 18-23 of the antisense strand (counting from the 5'-end).

In some embodiments, the dsRNA molecule of the invention further comprises one phosphorothioate internucleotide linkage modification within position 1-5 and one phosphorothioate or methylphosphonate internucleotide linkage modification within position 18-23 of the sense strand (counting from the 5'-end), and one phosphorothioate internucleotide linkage modification at positions 1 and 2 and two phosphorothioate or methylphosphonate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the invention further comprises one phosphorothioate internucleotide linkage modification within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the invention further comprises one phosphorothioate internucleotide linkage modification within position 1-5 and one within position 18-23 of the sense strand (counting from the 5'-end), and two phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the invention further comprises one phosphorothioate internucleotide linkage modification within position 1-5 (counting from the 5'-end) of the sense strand, and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the invention further comprises two phosphorothioate internucleotide linkage modifications within position 1-5 (counting from the 5'-end) of the sense strand, and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and one within position 18-23 of the sense strand (counting from the 5'-end), and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the invention further comprises two phosphorothioate internucleotide linkage modifications within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications at position 1 and 2, and two phosphorothioate internucleotide linkage modifications at position 20 and 21 of the sense strand (counting from the 5'-end), and one phosphorothioate internucleotide linkage modification at positions 1 and one at position 21 of the antisense strand (counting from the 5'-end).

In some embodiments, the dsRNA molecule of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 20 and 21 the antisense strand (counting from the 5'-end).

In some embodiments, the dsRNA molecule of the invention further comprises two phosphorothioate internucleotide linkage modifications at position 1 and 2, and two phosphorothioate internucleotide linkage modifications at position 21 and 22 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA molecule of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 21 and 22 the antisense strand (counting from the 5'-end).

In some embodiments, the dsRNA molecule of the invention further comprises two phosphorothioate internucleotide linkage modifications at position 1 and 2, and two phosphorothioate internucleotide linkage modifications at position 22 and 23 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA molecule of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 23 and 23 the antisense strand (counting from the 5'-end).

In some embodiments, compound of the invention comprises a pattern of backbone chiral centers. In some embodiments, a common pattern of backbone chiral centers comprises at least 5 internucleotidic linkages in the Sp configuration. In some embodiments, a common pattern of backbone chiral centers comprises at least 6 internucleotidic linkages in the Sp configuration. In some embodiments, a common pattern of backbone chiral centers comprises at least 7 internucleotidic linkages in the Sp configuration. In some embodiments, a common pattern of backbone chiral centers comprises at least 8 internucleotidic linkages in the Sp configuration. In some embodiments, a common pattern of backbone chiral centers comprises at least 9 internucleotidic linkages in the Sp configuration. In some embodiments, a common pattern of backbone chiral centers comprises at least 10 internucleotidic linkages in the Sp configuration. In some embodiments, a common pattern of backbone chiral centers comprises at least 11 internucleotidic linkages in the Sp configuration. In some embodiments, a common pattern of backbone chiral centers comprises at least 12 internucleotidic linkages in the Sp configuration. In some embodiments, a common pattern of backbone chiral centers comprises at least 13 internucleotidic linkages in the Sp configuration. In some embodiments, a common pattern of backbone chiral centers comprises at least 14 internucleotidic linkages in the Sp configuration. In some embodiments, a common pattern of backbone chiral centers comprises at least 15 internucleotidic linkages in the Sp configuration. In some embodiments, a common pattern of backbone chiral centers comprises at least 16 internucleotidic linkages in the Sp configuration. In some embodiments, a common pattern of backbone chiral centers comprises at least 17 internucleotidic linkages in the Sp configuration. In some embodiments, a common pattern of backbone chiral centers comprises at least 18 internucleotidic linkages in the Sp configuration. In some embodiments, a common pattern of backbone chiral centers comprises at least 19 internucleotidic linkages in the Sp configuration. In some embodiments, a common pattern of backbone chiral centers comprises no more than 8 internucleotidic linkages in the Rp configuration. In some embodiments, a common pattern of backbone chiral centers comprises no more than? internucleotidic linkages in the Rp configuration. In some embodiments, a common pattern of backbone chiral centers comprises no more than 6 internucleotidic linkages in the Rp configuration. In some embodiments, a common pattern of backbone chiral centers comprises no more than 5 internucleotidic linkages in the Rp configuration. In some embodiments, a common pattern of backbone chiral centers comprises no more than 4 internucleotidic linkages in the Rp configuration. In some embodiments, a common pattern of backbone chiral centers comprises no more than 3 internucleotidic linkages in the Rp configuration. In some embodiments, a common pattern of backbone chiral centers comprises no more than 2 internucleotidic linkages in the Rp configuration. In some embodiments, a common pattern of backbone chiral centers comprises no more than 1 internucleotidic linkages in the Rp configuration. In some embodiments, a common pattern of backbone chiral centers comprises no more than 8 internucleotidic linkages which are not chiral (as a non-limiting example, a phosphodiester). In some embodiments, a common pattern of backbone chiral centers comprises no more than 7 internucleotidic linkages which are not chiral. In some embodiments, a common pattern of backbone chiral centers comprises no more than 6 internucleotidic linkages which are not chiral. In some embodiments, a common pattern of backbone chiral centers comprises no more than 5 internucleotidic linkages which are not chiral. In some embodiments, a common pattern of backbone chiral centers comprises no more than 4 internucleotidic linkages which are not chiral. In some embodiments, a common pattern of backbone chiral centers comprises no more than 3 internucleotidic linkages which are not chiral. In some embodiments, a common pattern of backbone chiral centers comprises no more than 2 internucleotidic linkages which are not chiral. In some embodiments, a common pattern of backbone chiral centers comprises no more than 1 internucleotidic linkages which are not chiral. In some embodiments, a common pattern of backbone chiral centers comprises at least 10 internucleotidic linkages in the Sp configuration, and no more than 8 internucleotidic linkages which are not chiral. In some embodiments, a common pattern of backbone chiral centers comprises at least 11 internucleotidic linkages in the Sp configuration, and no more than 7 internucleotidic linkages which are not chiral. In some embodiments, a common pattern of backbone chiral centers comprises at least 12 internucleotidic linkages in the Sp configuration, and no more than 6 internucleotidic linkages which are not chiral. In some embodiments, a common pattern of backbone chiral centers comprises at least 13 internucleotidic linkages in the Sp configuration, and no more than 6 internucleotidic linkages which are not chiral. In some embodiments, a common pattern of backbone chiral centers comprises at least 14 internucleotidic linkages in the Sp configuration, and no more than 5 internucleotidic linkages which are not chiral. In some embodiments, a common pattern of backbone chiral centers comprises at least 15 internucleotidic linkages in the Sp configuration, and no more than 4 internucleotidic linkages which are not chiral. In some embodiments, the internucleotidic linkages in the Sp configuration are optionally contiguous or not contiguous. In some embodiments, the internucleotidic linkages in the Rp configuration are optionally contiguous or not contiguous. In some embodiments, the internucleotidic linkages which are not chiral are optionally contiguous or not contiguous.

In some embodiments, compound of the invention comprises a block is a stereochemistry block. In some embodiments, a block is an Rp block in that each internucleotidic linkage of the block is Rp. In some embodiments, a 5'-block is an Rp block. In some embodiments, a 3'-block is an Rp block. In some embodiments, a block is an Sp block in that each internucleotidic linkage of the block is Sp. In some embodiments, a 5'-block is an Sp block. In some embodiments, a 3'-block is an Sp block. In some embodiments, provided oligonucleotides comprise both Rp and Sp blocks. In some embodiments, provided oligonucleotides comprise one or more Rp but no Sp blocks. In some embodiments, provided oligonucleotides comprise one or more Sp but no Rp blocks. In some embodiments, provided oligonucleotides comprise one or more PO blocks wherein each internucleotidic linkage in a natural phosphate linkage.

In some embodiments, compound of the invention comprises a 5'-block is an Sp block wherein each sugar moiety comprises a 2'-F modification. In some embodiments, a 5'-block is an Sp block wherein each of internucleotidic linkage is a modified internucleotidic linkage and each sugar moiety comprises a 2'-F modification. In some embodiments, a 5'-block is an Sp block wherein each of internucleotidic linkage is a phosphorothioate linkage and each sugar moiety comprises a 2'-F modification. In some embodiments, a 5'-block comprises 4 or more nucleoside units. In some embodiments, a 5'-block comprises 5 or more nucleoside units. In some embodiments, a 5'-block comprises 6 or more nucleoside units. In some embodiments, a 5'-block comprises 7 or more nucleoside units. In some embodiments, a 3'-block is an Sp block wherein each sugar moiety comprises a 2'-F modification. In some embodiments, a 3'-block is an Sp block wherein each of internucleotidic linkage is a modified internucleotidic linkage and each sugar moiety comprises a 2'-F modification. In some embodiments, a 3'-block is an Sp block wherein each of internucleotidic linkage is a phosphorothioate linkage and each sugar moiety comprises a 2'-F modification. In some embodiments, a 3'-block comprises 4 or more nucleoside units. In some embodiments, a 3'-block comprises 5 or more nucleoside units. In some embodiments, a 3'-block comprises 6 or more nucleoside units. In some embodiments, a 3'-block comprises 7 or more nucleoside units.

In some embodiments, compound of the invention comprises a type of nucleoside in a region or an oligonucleotide is followed by a specific type of internucleotidic linkage, e.g., natural phosphate linkage, modified internucleotidic linkage, Rp chiral internucleotidic linkage, Sp chiral internucleotidic linkage, etc. In some embodiments, A is followed by Sp. In some embodiments, A is followed by Rp. In some embodiments, A is followed by natural phosphate linkage (PO). In some embodiments, U is followed by Sp. In some embodiments, U is followed by Rp. In some embodiments, U is followed by natural phosphate linkage (PO). In some embodiments, C is followed by Sp. In some embodiments, C is followed by Rp. In some embodiments, C is followed by natural phosphate linkage (PO). In some embodiments, G is followed by Sp. In some embodiments, G is followed by Rp. In some embodiments, G is followed by natural phosphate linkage (PO). In some embodiments, C and U are followed by Sp. In some embodiments, C and U are followed by Rp. In some embodiments, C and U are followed by natural phosphate linkage (PO). In some embodiments, A and G are followed by Sp. In some embodiments, A and G are followed by Rp.

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, bhGNA, mGNA, TNA and h'GNA (Mod A-Mod K).

In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; and (viii) the dsRNA has a blunt end at 5'-end of the antisense strand, and wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hbGNA, mGNA, TNA and h'GNA (Mod A-Mod K).

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 3, 4 or 5 phosphorothioate internucleotide linkages; (v) the dsRNA comprises at least four 2'-fluoro modifications; (vi) the dsRNA comprises a duplex region of 12-40 nucleotide pairs in length; and (vii) the dsRNA has a blunt end at 5'-end of the antisense strand, wherein the destabilizing modification is selected from mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

In some embodiments, the dsRNA molecule of the invention comprises mismatch(es) with the target, within the duplex, or combinations thereof. The mismatch can occur in the overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In some embodiments, the dsRNA molecule of the invention comprises at least one of the first 1, 2, 3, 4, or 5 base pairs within the duplex regions from the 5'-end of the antisense strand can be chosen independently from the group of: A:U, G:U, I:C, and mismatched pairs, e.g., non-canonical or other than canonical pairings or pairings which include a universal base, to promote the dissociation of the antisense strand at the 5'-end of the duplex.

In some embodiments, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

The inventors found that introducing 4'-modified and/or 5'-modified nucleotide to the 3'-end of a phosphodiester (PO), phosphorothioate (PS), and/or phosphorodithioate (PS2) linkage of a dinucleotide at any position of single stranded or double stranded oligonucleotide can exert steric effect to the internucleotide linkage and, hence, protecting or stabilizing it against nucleases.

In some embodiments, 5'-modified nucleoside is introduced at the 3'-end of a dinucleotide at any position of single stranded or double stranded siRNA. For instance, a 5'-alkylated nucleoside may be introduced at the 3'-end of a dinucleotide at any position of single stranded or double stranded siRNA. The alkyl group at the 5' position of the ribose sugar can be racemic or chirally pure R or S isomer. An exemplary 5'-alkylated nucleoside is 5'-methyl nucleoside. The 5'-methyl can be either racemic or chirally pure R or S isomer.

In some embodiments, 4'-modified nucleoside is introduced at the 3'-end of a dinucleotide at any position of single stranded or double stranded siRNA. For instance, a 4'-alkylated nucleoside may be introduced at the 3'-end of a dinucleotide at any position of single stranded or double stranded siRNA. The alkyl group at the 4' position of the ribose sugar can be racemic or chirally pure R or S isomer. An exemplary 4'-alkylated nucleoside is 4'-methyl nucleoside. The 4'-methyl can be either racemic or chirally pure R or S isomer. Alternatively, a 4'-O-alkylated nucleoside may be introduced at the 3'-end of a dinucleotide at any position of single stranded or double stranded siRNA. The 4'-O-alkyl of the ribose sugar can be racemic or chirally pure R or S isomer. An exemplary 4'-O-alkylated nucleoside is 4'-O-methyl nucleoside. The 4'-O-methyl can be either racemic or chirally pure R or S isomer.

In some embodiments, 5'-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 5'-alkylated nucleoside is 5'-methyl nucleoside. The 5'-methyl can be either racemic or chirally pure R or S isomer.

In some embodiments, 4'-alkylated nucleoside is introduced at any position on the sense strand or antisense strand of a dsRNA, and such modification maintains or improves potency of the dsRNA. The 4'-alkyl can be either racemic or chirally pure R or S isomer. An exemplary 4'-alkylated nucleoside is 4'-methyl nucleoside. The 4'-methyl can be either racemic or chirally pure R or S isomer.

In some embodiments, 4'-O-alkylated nucleoside is introduced at any position on the sense strand or antisense strand of a dsRNA, and such modification maintains or improves potency of the dsRNA. The S'-alkyl can be either racemic or chirally pure R or S isomer. An exemplary 4'-O-alkylated nucleoside is 4'-O-methyl nucleoside. The 4'-O-methyl can be either racemic or chirally pure R or S isomer.

In some embodiments, the dsRNA molecule of the invention can comprise 2'-5' linkages (with 2'-H, 2'-OH and 2'-OMe and with P═O or P═S). For example, the 2'-5' linkages modifications can be used to promote nuclease resistance or to inhibit binding of the sense to the antisense strand, or can be used at the 5' end of the sense strand to avoid sense strand activation by RISC.

In another embodiment, the dsRNA molecule of the invention can comprise L sugars (e.g., L ribose, L-arabinose with 2'-H, 2'-OH and 2'-OMe). For example, these L sugars modifications can be used to promote nuclease resistance or to inhibit binding of the sense to the antisense strand, or can be used at the 5' end of the sense strand to avoid sense strand activation by RISC.

Various publications describe multimeric siRNA which can all be used with the dsRNA of the invention. Such publications include WO2007/091269, U.S. Pat. No. 7,858,769, WO2010/141511, WO2007/117686, WO2009/014887 and WO2011/031520 which are hereby incorporated by their entirely.

The dsRNA molecule that contains conjugations of one or more carbohydrate moieties to a dsRNA molecule can optimize one or more properties of the dsRNA molecule. In many cases, the carbohydrate moiety will be attached to a modified subunit of the dsRNA molecule. E.g., the ribose sugar of one or more ribonucleotide subunits of a dsRNA molecule can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

In one embodiment the dsRNA molecule of the invention is conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3] dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

The double-stranded RNA (dsRNA) agent of the invention may optionally be conjugated to one or more ligands. The ligand can be attached to the sense strand, antisense strand or both strands, at the 3'-end, 5'-end or both ends. For instance, the ligand may be conjugated to the sense strand, in particular, the 3'-end of the sense strand.

In some embodiments dsRNA molecules of the invention are 5' phosphorylated or include a phosphoryl analog at the 5' prime terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O—5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S) P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl-methyl, ethyl, isopropyl, propyl, etc., e.g. RP(OH)(O)—O-5'-, 5'-alkenylphosphonates (i.e. vinyl, substituted vinyl), (OH)$_2$(O)P-5'-CH$_2$—), 5'-alkyletherphosphonates (R=alkylether-methoxymethyl (MeOCH2-), ethoxymethyl, etc., e.g. RP(OH)(O)—O-5'-). In one example, the modification can in placed in the antisense strand of a dsRNA molecule.

Ligands

A wide variety of entities can be coupled to the oligonucleotides of the present invention. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, receptor e.g., a cellular or organ compartment, tissue, organ or region of the body, as, e.g., compared to a species absent such a ligand. Ligands providing enhanced affinity for a selected target are also termed targeting ligands.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In some embodiments, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., Biochemistry, 1987, 26:2964-2972, which is incorporated by reference in its entirety), the EALA peptide (Vogel et al., J. Am. Chem. Soc., 1996, 118:1581-1586, which is incorporated by reference in its entirety), and their derivatives (Turk et al., Biochem. Biophys. Acta, 2002, 1559:56-68, which is incorporated by reference in its entirety). In some embodiments, the endosomolytic component may contain a chemical group (e.g., an amino acid) which will undergo a change in charge or protonation in response to a change in pH. The endosomolytic component may be linear or branched.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly (L-lactide-co-glycolide) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyamino acids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases or a chelating agent (e.g. EDTA), lipophilic molecules, e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptide species, such as lipids, lectins, carbohydrates, vitamins, cofactors, multivalent lactose, multivalent galactose, N-acetyl-galactosamine, N-acetyl-glucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide into the cell by activating an inflammatory response, for example. Exemplary ligands that would have such an effect include tumor necrosis factor alpha (TNF-alpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include B vitamins, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or cross-linked peptide. In another alternative, the peptide moiety can include a hydrophobic membrane translocation sequence (MTS). An exemplary hydrophobic MTS-containing peptide is RFGF having the amino acid sequence AAVALLPAVL-LALLAP (SEQ ID NO: 3). An RFGF analogue (e.g., amino acid sequence AALLPVLLAAP (SEQ ID NO: 4)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 5)) and the Drosophila Antennapedia protein (RQIKIWFQNRRMKWKK (SEQ ID NO: 6)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-94, 1991, which is incorporated by reference in its entirety). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell (Zitzmann et al., Cancer Res., 62:5139-43, 2002, which is incorporated by reference in its entirety). An RGD peptide can facilitate targeting of an iRNA agent to tumors of a variety of other tissues, including the lung, kidney, spleen, or liver (Aoki et al., Cancer Gene Therapy 8:783-787, 2001, which is incorporated by reference in its entirety). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing αvβ3 (Haubner et al., Jour. Nucl. Med., 42:326-336, 2001, which is incorporated by reference in its entirety). Peptides that target markers enriched in proliferating cells can be used. E.g., RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogenesis. Preferred conjugates of this type ligands that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003, which is incorporated by reference in its entirety).

In some embodiments, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, omithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an aptamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycarboxylates, polycations, masked oligo or poly cations or anions, acetals, polyacetals, ketals/polyketals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Exemplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable to the present invention as ligands (e.g. as PK modulating ligands).

In addition, aptamers that bind serum components (e.g. serum proteins) are also amenable to the present invention as PK modulating ligands.

Other ligand conjugates amenable to the invention are described in U.S. patent application Ser. No. 10/916,185, filed Aug. 10, 2004; U.S. patent application Ser. No. 10/946, 873, filed Sep. 21, 2004; U.S. patent application Ser. No. 10/833,934, filed Aug. 3, 2007; U.S. patent application Ser. No. 11/115,989 filed Apr. 27, 2005 and U.S. patent application Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether, e.g. a carrier described herein. The ligand or tethered ligand may be present on a monomer when said monomer is incorporated into the growing strand. In some embodiments, the ligand may be incorporated via coupling to a "precursor" monomer after said "precursor" monomer has been incorporated into the growing strand. For example, a monomer having, e.g., an amino-terminated tether (i.e., having no associated ligand), e.g., TAP-$(CH_2)_n NH_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithioate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

In some embodiments, the ligand is conjugated to the sense strand. As described herein, the ligand can be conjugated at the 3'-end, 5'-end or at an internal position of the sense strand. In some embodiments, the ligand is conjugated to the 3'-end of the sense strand. Further, the ligand can be conjugated to a nucleobase, sugar moiety or internucleotide linkage of the sense strand.

Any suitable ligand in the field of RNA interference may be used, although the ligand is typically a carbohydrate e.g. monosaccharide (such as GalNAc), disaccharide, trisaccharide, tetrasaccharide, polysaccharide.

Linkers that conjugate the ligand to the nucleic acid include those discussed above. For example, the ligand can be one or more GalNAc (N-acetylgalactosamine) derivatives attached through a monovalent, bivalent or trivalent branched linker.

In some embodiments, the dsRNA of the invention is conjugated to a bivalent and trivalent branched linkers include the structures shown in any of formula (IV)-(VII):

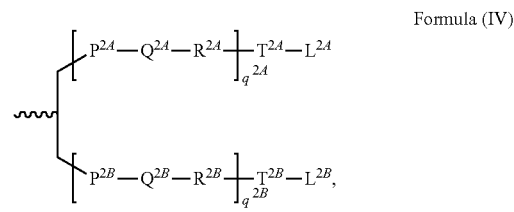

Formula (IV)

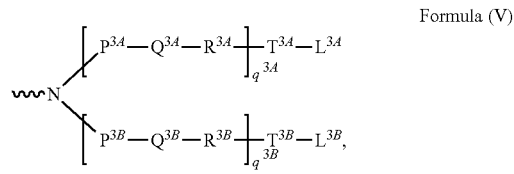

Formula (V)

-continued

Formula (VI)

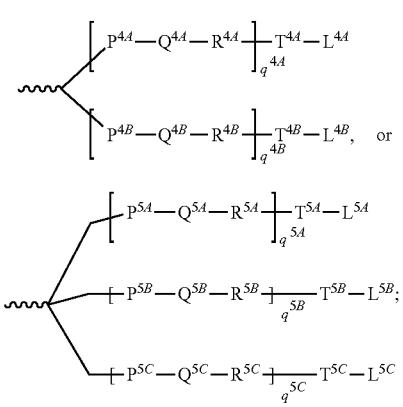

Formula (VII)

wherein:
$q^{2A}$, $q^{2B}$, $q^{3A}$, $q^{3B}$, $q^{4A}$, $q^{4B}$, $q^{5A}$, $q^{5B}$ and $q^{5C}$ represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{5A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, $C(R')=C(R'')$, $C\equiv C$ or $C(O)$;

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—CH$(R^a)$—NH—, CO, CH=N—O,

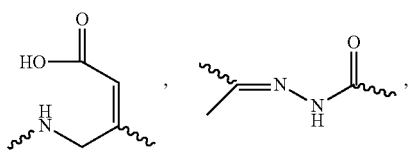

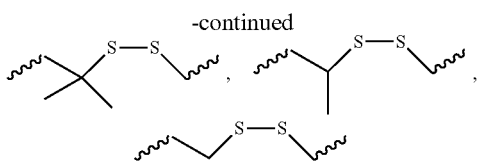

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain.

Trivalent conjugating GalNAc derivatives are particularly useful for use with RNAi agents for inhibiting the expression of a target gene, such as those of formula (VII):

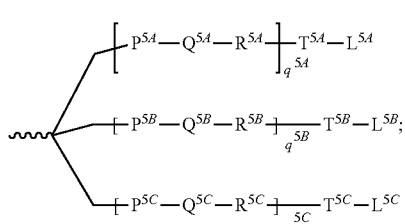

Formula (VII)

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the following compounds:

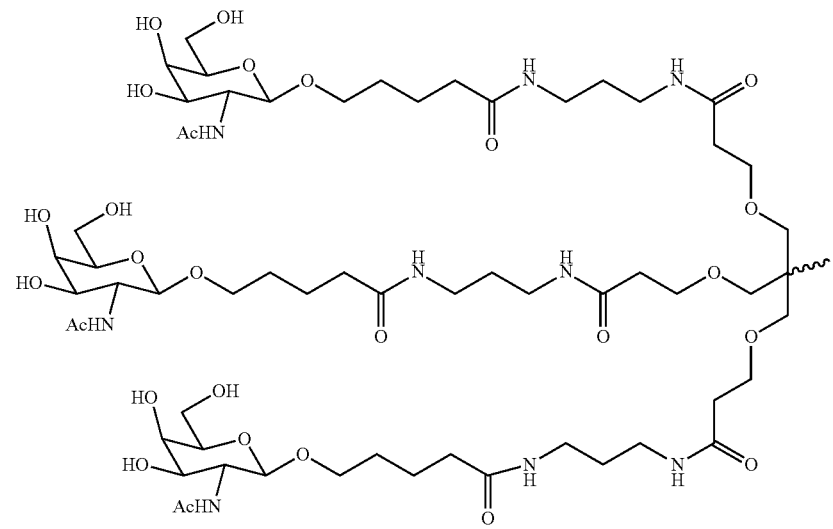

-continued
131
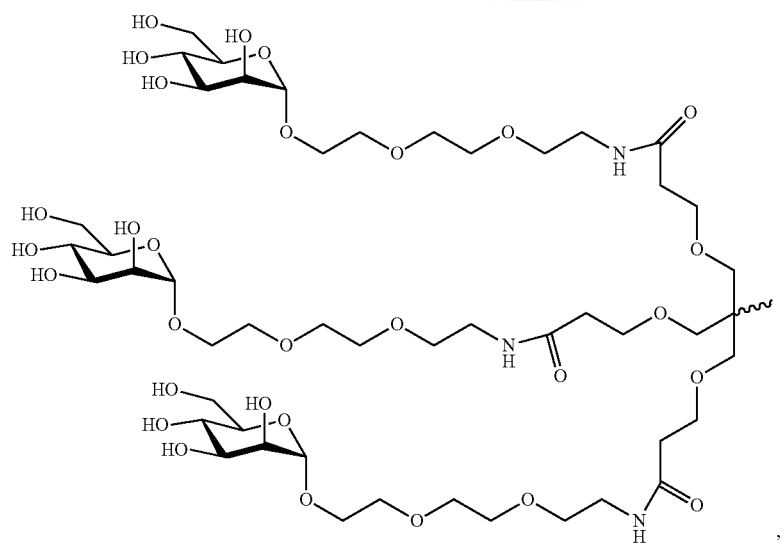
132
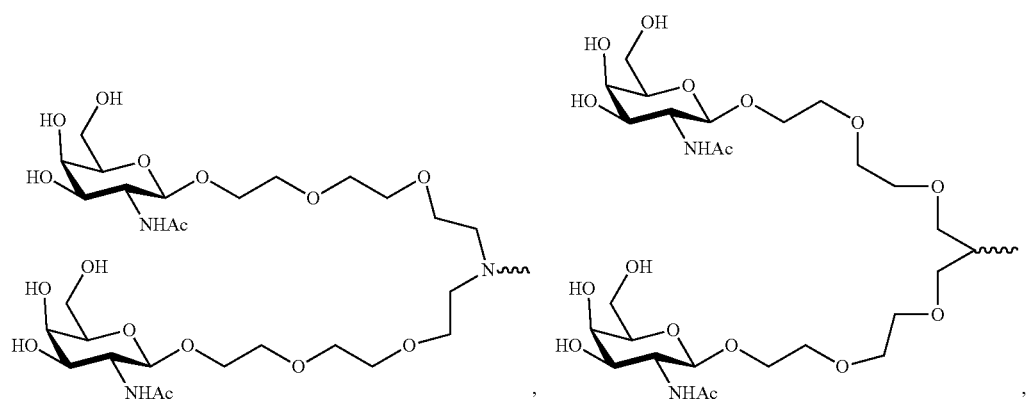
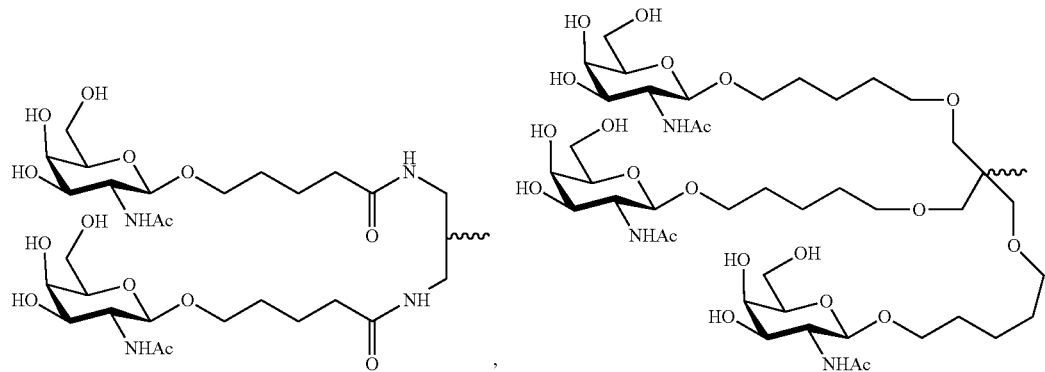

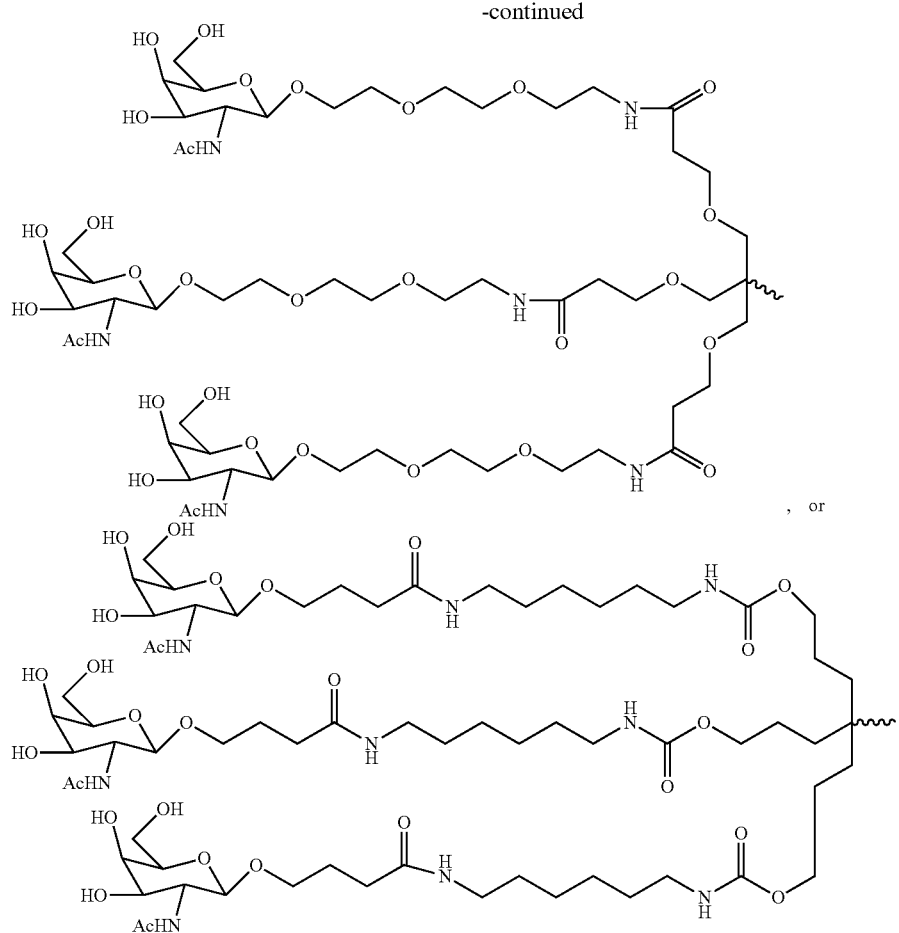

, or

Definitions

As used herein, the terms "dsRNA", "siRNA", and "iRNA agent" are used interchangeably to agents that can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an siRNA agent of 21 to 23 nucleotides.

As used herein, "specifically hybridizable" and "complementary" are terms which are used to indicate a sufficient degree of complementarity such that stable and specific binding occurs between a compound of the invention and a target RNA molecule. Specific binding requires a sufficient degree of complementarity to avoid non-specific binding of the oligomeric compound to non-target sequences under conditions in which specific binding is desired, i.e., under physiological conditions in the case of assays or therapeutic treatment, or in the case of in vitro assays, under conditions in which the assays are performed. The non-target sequences typically differ by at least 5 nucleotides.

In some embodiments, a dsRNA molecule of the invention is "sufficiently complementary" to a target RNA, e.g., a target mRNA, such that the dsRNA molecule silences production of protein encoded by the target mRNA. In another embodiment, the dsRNA molecule of the invention is "exactly complementary" to a target RNA, e.g., the target RNA and the dsRNA duplex agent anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in some embodiments, the dsRNA molecule of the invention specifically discriminates a single-nucleotide difference. In this case, the dsRNA molecule only mediates RNAi if exact complementary is found in the region (e.g., within 7 nucleotides of) the single-nucleotide difference.

As used herein, the term "oligonucleotide" refers to a nucleic acid molecule (RNA or DNA) for example of length less than 100, 200, 300, or 400 nucleotides.

The term 'BNA' refers to bridged nucleic acid, and is often referred as constrained or inaccessible RNA. BNA can contain a 5-, 6-membered, or even a 7-membered bridged structure with a "fixed" C3'-endo sugar puckering. The bridge is typically incorporated at the 2'-, 4'-position of the ribose to afford a 2',4'-BNA nucleotide (e.g., LNA, or ENA). Examples of BNA nucleotides include the following nucleosides:

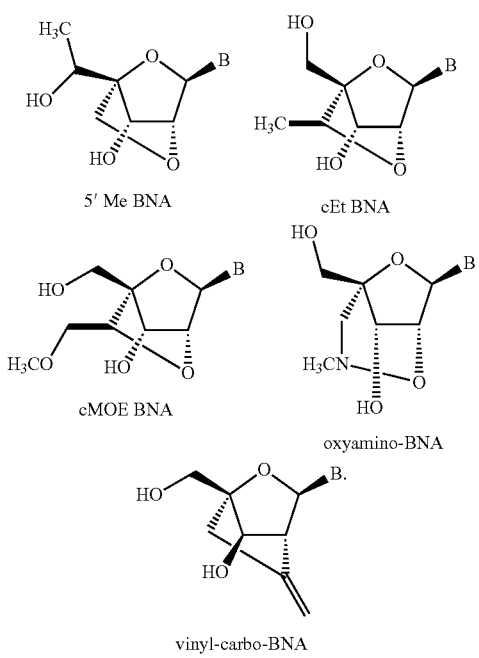

The term 'LNA' refers to locked nucleic acid, and is often referred as constrained or inaccessible RNA. LNA is a modified RNA nucleotide. The ribose moiety of an LNA nucleotide is modified with an extra bridge (e.g., a methylene bridge or an ethylene bridge) connecting the 2' hydroxyl to the 4' carbon of the same ribose sugar. For instance, the bridge can "lock" the ribose in the 3'-endo North) conformation:

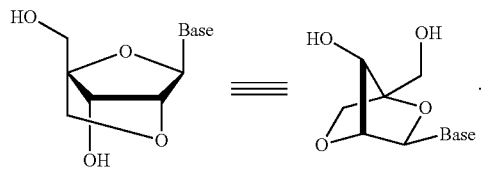

The term 'ENA' refers to ethylene-bridged nucleic acid, and is often referred as constrained or inaccessible RNA.

The "cleavage site" herein means the backbone linkage in the target gene or the sense strand that is cleaved by the RISC mechanism by utilizing the iRNA agent. And the target cleavage site region comprises at least one or at least two nucleotides on both side of the cleavage site. For the sense strand, the cleavage site is the backbone linkage in the sense strand that would get cleaved if the sense strand itself was the target to be cleaved by the RNAi mechanism. The cleavage site can be determined using methods known in the art, for example the 5'-RACE assay as detailed in Soutschek et al., Nature (2004) 432, 173-178, which is incorporated by reference in its entirety. As is well understood in the art, the cleavage site region for a conical double stranded RNAi agent comprising two 21-nucleotides long strands (wherein the strands form a double stranded region of 19 consecutive base pairs having 2-nucleotide single stranded overhangs at the 3'-ends), the cleavage site region corresponds to positions 9-12 from the 5'-end of the sense strand.

Cleavable Linking Groups

A cleavable linking group is one which is sufficiently stable outside the cell, but which upon entry into a target cell is cleaved to release the two parts the linker is holding together. In a preferred embodiment of the dsRNA molecule according to the present invention, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups is redox cleavable linking groups, which may be used in the dsRNA molecule according to the present invention that are cleaved upon reduction or oxidation. An example of reductively cleavable linking group is a disulfide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups, which may be used in the dsRN A molecule according to the present invention, are cleaved by agents that degrade or hydrolyze the phosphate group. An example of an agent that cleaves phosphate groups in cells are enzymes such as phosphatases in cells. Examples of phosphate—based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—. —O—P(S)(Rk)S—. Preferred embodiments are O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(I)—O—, —S—P(S)(H)—O—, —S—P(O)(H)—S—, —O—P(S)(II)—S—. A preferred embodiment is —O—P(O)(OH)—O—. These candidates can be evaluated using methods analogous to those described above.

Acid Cleavable Linking Groups

Acid cleavable linking groups, which may be used in the dsRNA molecule according to the present invention, are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups, which may be used in the dsRNA molecule according to the present invention, are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups, which may be used in the dsRNA molecule according to the present invention, are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynylene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCIR$^A$C(O)NHCHR$^B$C(O)—, where R$^A$ and R$^B$ are the R groups of the two adjacent amino acids. These candidates can be evaluated using methods analogous to those described above. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$).

The present invention further relates to a use of a dsRNA molecule as defined herein for inhibiting expression of a target gene. In some embodiments, the present invention further relates to a use of a dsRNA molecule for inhibiting expression of a target gene in vitro.

The present invention further relates to a dsRNA molecule as defined herein for use in inhibiting expression of a target gene in a subject. The subject may be any animal, such as a mammal, e.g., a mouse, a rat, a sheep, a cattle, a dog, a cat, or a human In some embodiments, the dsRNA molecule of the invention is administered in buffer.

In some embodiments, siRNA compounds described herein can be formulated for administration to a subject. A formulated siRNA composition can assume a variety of states. In some examples, the composition is at least partially crystalline, uniformly crystalline, and/or anhydrous (e.g., less than 80, 50, 30, 20, or 10% water). In another example, the siRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the siRNA composition is formulated in a manner that is compatible with the intended method of administration, as described herein. For example, in particular embodiments the composition is prepared by at least one of the following methods: spray drying, lyophilization, vacuum drying, evaporation, fluid bed drying, or a combination of these techniques; or sonication with a lipid, freeze-drying, condensation and other self-assembly.

A siRNA preparation can be formulated in combination with another agent, e.g., another therapeutic agent or an agent that stabilizes a siRNA, e.g., a protein that complexes with siRNA to form an iRNP. Still other agents include chelating agents, e.g., EDTA (e.g., to remove divalent cations such as $Mg^{2+}$), salts, RNAse inhibitors (e.g., a broad specificity RNAse inhibitor such as RNAsin) and so forth.

In some embodiments, the siRNA preparation includes another siRNA compound, e.g., a second siRNA that can mediate RNAi with respect to a second gene, or with respect to the same gene. Still other preparation can include at least 3, 5, ten, twenty, fifty, or a hundred or more different siRNA species. Such siRNAs can mediate RNAi with respect to a similar number of different genes.

In some embodiments, the siRNA preparation includes at least a second therapeutic agent (e.g., an agent other than a RNA or a DNA). For example, a siRNA composition for the treatment of a viral disease, e.g., HIV, might include a known antiviral agent (e.g., a protease inhibitor or reverse transcriptase inhibitor). In another example, a siRNA composition for the treatment of a cancer might further comprise a chemotherapeutic agent.

Exemplary formulations which can be used for administering the dsRNA molecule according to the present invention are discussed below.

Liposomes. For ease of exposition the formulations, compositions and methods in this section are discussed largely with regard to unmodified siRNA compounds. It may be understood, however, that these formulations, compositions and methods can be practiced with other siRNA compounds, e.g., modified siRNAs, and such practice is within the invention, An siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparation can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the siRNA composition. The lipophilic material isolates the aqueous interior from an aqueous exterior, which typically does not include the siRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the siRNA are delivered into the cell where the siRNA can specifically bind to a target RNA and can mediate RNAL In some cases the liposomes are also specifically targeted, e.g., to direct the siRNA to particular cell types.

A liposome containing a siRNA can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The siRNA preparation is then added to the micelles that include the lipid component. The cationic groups on the lipid interact with the siRNA and condense around the siRNA to form a liposome. After condensation, the detergent is removed, e.g., by dialysis, to yield a liposomal preparation of siRNA.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favor condensation.

Further description of methods for producing stable polynucleotide delivery vehicles, which incorporate a polynucleotide/cationic lipid complex as structural components of the delivery vehicle, are described in, e.g., WO 96/37194. Liposome formation can also include one or more aspects of exemplary methods described in Feigner, P. L. et al., *Proc. Natl. Acad. Sci., USA* 8:7413-7417, 1987; U.S. Pat. Nos. 4,897,355; 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984, which are incorporated by reference in their entirety. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986, which is incorporated by reference in its entirety). Microfluidization can be used when consistently small (50 to 200 nm) and relatively uniform aggregates are desired (Mayhew, et al. *Biochim. Biophys. Acta* 775:169, 1984, which is incorporated by reference in its entirety). These methods are readily adapted to packaging siRNA preparations into liposomes.

Liposomes that are pH-sensitive or negatively-charged entrap nucleic acid molecules rather than complex with them. Since both the nucleic acid molecules and the lipid are similarly charged, repulsion rather than complex formation occurs. Nevertheless, some nucleic acid molecules are entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 19, (1992) 269-274, which is incorporated by reference in its entirety).

One major type of liposomal composition includes phospholipids other than naturally-derived phosphatidyleholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and include U.S. Pat. Nos. 5,283,185; 5,171,678; WO 94/00569; WO 93/24640; WO 91/16024; Feigner, J. Biol. Chem. 269:2550, 1994; Nabel, Proc. Natl. Acad. Sci. 90:11307, 1993; Nabel, Human Gene Ther. 3:649, 1992; Gershon, Biochem. 32:7143, 1993; and Strauss EMBO J. 11:417, 1992.

In some embodiments, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver siRNAs to macrophages.

Further advantages of liposomes include: liposomes obtained from natural phospholipids are biocompatible and biodegradable; liposomes can incorporate a wide range of water and lipid soluble drugs; liposomes can protect encapsulated siRNAs in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of siRNA (see, e.g., Feigner, P. L. et al., Proc. Nat. Acad. Sci., USA 8:7413-7417, 1987 and U.S. Pat. No. 4,897,355 for a description of DOTMA and its use with DNA, which are incorporated by reference in their entirety).

A DOTMA analogue, 1,2-bis(oleoyloxy)-3-(trimethylammonia)propane (DOT AP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Indiana) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioetaoleoylamide ("DOGS") (Transfectam™, Promega, Madison, Wisconsin) and dipalmitoylphosphatidylethanolamine 5-carboxyspermylamide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991, which is incorporated by reference in its entirety). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, California) and Lipofectamine (DOSPA) (Life Technology, Inc., Gaithersburg, Maryland). Other cationic lipids suitable for the delivery of oligonucleotides are described in WO 98/39359 and WO 96/37194.

Liposomal formulations are particularly suited for topical administration. Liposomes present several advantages over other formulations. Such advantages include reduced side effects related to high systemic absorption of the administered drug, increased accumulation of the administered drug at the desired target, and the ability to administer siRNA, into the skin. In some implementations, liposomes are used for delivering siRNA to epidermal cells and also to enhance the penetration of siRNA into dermal tissues, e.g., into skin. For example, the liposomes can be applied topically. Topical delivery of drugs formulated as liposomes to the skin has been documented (see, e.g., Weiner et al., Journal of Drug Targeting, 1992, vol. 2, 405-410 and du Plessis et al., Antiviral Research, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987, which are incorporated by reference in their entirety).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with siRNA are useful for treating a dermatological disorder.

Liposomes that include siRNA can be made highly deformable. Such deformability can enable the liposomes to penetrate through pore that are smaller than the average radius of the liposome. For example, transfersomes are a type of deformable liposomes. Transfersomes can be made by adding surface edge activators, usually surfactants, to a standard liposomal composition. Transfersomes that include siRNA can be delivered, for example, subcutaneously by infection in order to deliver siRNA to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transfersomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. No. 61/018,616, filed Jan. 2, 2008; 61/018,611, filed Jan. 2, 2008;

61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Surfactants. For ease of exposition the formulations, compositions and methods in this section are discussed largely with regard to unmodified siRNA compounds. It may be understood, however, that these formulations, compositions and methods can be practiced with other siRNA compounds, e.g., modified siRNA compounds, and such practice is within the scope of the invention. Surfactants find wide application in formulations such as emulsions (including microemulsions) and liposomes (see above). siRNA (or a precursor, e.g., a larger dsiRNA which can be processed into a siRNA, or a DNA which encodes a siRNA or precursor) compositions can include a surfactant. In some embodiments, the siRNA is formulated as an emulsion that includes a surfactant. The most common way of classifying and ranking the properties of the many different types of surfactants, both natural and synthetic, is by the use of the hydrophile/lipophile balance (HLB). The nature of the hydrophilic group provides the most useful means for categorizing the different surfactants used in formulations (Rieger, in "Pharmaceutical Dosage Forms," Marcel Dekker, Inc., New York, NY, 1988, p. 285).

If the surfactant molecule is not ionized, it is classified as a nonionic surfactant. Nonionic surfactants find wide application in pharmaceutical products and are usable over a wide range of pH values. In general, their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms," Marcel Dekker, Inc., New York, NY, 1988, p. 285).

Micelles and other Membranous Formulations. For ease of exposition the micelles and other formulations, compositions and methods in this section are discussed largely with regard to unmodified siRNA compounds. It may be understood, however, that these micelles and other formulations, compositions and methods can be practiced with other siRNA compounds, e.g., modified siRNA compounds, and such practice is within the invention. The siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof)) composition can be provided as a micellar formulation. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin. hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

Particles. For ease of exposition the particles, formulations, compositions and methods in this section are discussed largely with regard to modified siRNA compounds. It may be understood, however, that these particles, formulations, compositions and methods can be practiced with other siRNA compounds, e.g., unmodified siRNA compounds, and such practice is within the invention. In another embodiment, an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparations may be incorporated into a particle, e.g., a microparticle. Microparticles can be produced by spray-drying, but may also be produced by other methods including lyophilization, evaporation, fluid bed drying, vacuum drying, or a combination of these techniques.

Pharmaceutical Compositions

The iRNA agents of the invention may be formulated for pharmaceutical use. The present invention further relates to a pharmaceutical composition comprising the dsRNA molecule as defined herein. Pharmaceutically acceptable compositions comprise a therapeutically-effective amount of one or more of the dsRNA molecules in any of the preceding embodiments, taken alone or formulated together with one or more pharmaceutically acceptable carriers (additives), excipient and/or diluents.

The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. Delivery using subcutaneous or intravenous methods can be particularly advantageous.

The phrase "therapeutically-effective amount" as used herein means that amount of a compound, material, or composition comprising a compound of the invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, IDL and LDL; and (22) other non-toxic compatible substances employed in pharmaceutical formulations.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

iRNA agent preparation can be formulated in combination with another agent, e.g., another therapeutic agent or an agent that stabilizes a iRNA, e.g., a protein that complexes with iRNA to form an iRNP. Still other agents include chelating agents, e.g., EDTA (e.g., to remove divalent cations such as $Mg^{2+}$), salts, RNAse inhibitors (e.g., a broad specificity RNAse inhibitor such as RNAsin) and so forth.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The compounds according to the invention may be formulated for administration in any convenient way for use in human or veterinary medicine, by analogy with other pharmaceuticals.

The term "treatment" is intended to encompass also prophylaxis, therapy and cure. The patient receiving this treatment is any animal in need, including primates, in particular humans, and other mammals such as equines, cattle, swine and sheep; and poultry and pets in general.

Double-stranded RNAi agents are produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328,470, which is incorporated by reference in its entirety), or by stereotactic injection (see, e.g., Chen et al. (1994) Proc. Natl. Acad. Sci. USA 91:3054-3057, which is incorporated by reference in its entirety). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of a dsRNA molecule and one that produces a transcript that includes the bottom strand of a dsRNA molecule. When the templates are transcribed, the dsRNA. molecule is produced, and processed into siRNA agent fragments that mediate gene silencing.

Routes of Delivery

The dsRNA molecule as defined herein or a pharmaceutical composition comprising a dsRNA molecule as defined herein can be administered to a subject using different routes of delivery. A composition that includes an iRNA can be delivered to a subject by a variety of routes. Exemplary routes include: intravenous, subcutaneous, topical, rectal, anal, vaginal, nasal, pulmonary, ocular.

The iRNA molecules and/or the dsRNA molecule of the invention can be incorporated into pharmaceutical compositions suitable for administration. Such compositions typically include one or more species of iRNA and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the iRNA in aerosol form. The vascular endothelial cells could be targeted by coating a balloon catheter with the iRNA and mechanically introducing the DNA.

Dosage

In one aspect, the invention features a method of administering a dsRNA molecule, e.g., a siRNA agent, to a subject (e.g., a human subject). In another aspect, the present invention relates to a dsRNA molecule as defined herein for use in inhibiting expression of a target gene in a subject. The method or the medical use includes administering a unit dose of the dsRNA molecule, e.g., a siRNA agent, e.g., double stranded siRNA agent that (a) the double-stranded part is 14-40 nucleotides (nt) long, for example, 21-23 nt, (b) is complementary to a target RNA (e.g., an endogenous or pathogen target RNA), and, optionally, (c) includes at least one 3' overhang 1-5 nucleotide long. In some embodiments, the unit dose is less than 10 mg per kg of bodyweight, or less than 10, 5, 2, 1, 0.5, 0.1, 0.005, 0.01, 0.005, 0.001, 0.0005, 0.0001, 0.00005 or 0.00001 mg per kg of bodyweight, and less than 200 nmole of NA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight.

The defined amount can be an amount effective to treat or prevent a disease or disorder, e.g., a disease or disorder associated with the target RNA. The unit dose, for example, can be administered by injection (e.g., intravenous, subcutaneous or intramuscular), an inhaled dose, or a topical application. In some embodiments dosages may be less than 10, 5, 2, 1, or 0.1 mg/kg of body weight.

In some embodiments, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In some embodiments, the effective dose is administered with other traditional therapeutic modalities. In some embodiments, the subject has a viral infection and the modality is an antiviral agent other than a dsRNA molecule, e.g., other than a siRNA agent. In another embodiment, the subject has atherosclerosis and the effective dose of a dsRNA molecule, e.g., a siRNA agent, is administered in combination with, e.g., after surgical intervention, e.g., angioplasty.

In some embodiments, a subject is administered an initial dose and one or more maintenance doses of a dsRNA molecule, e.g., a siRNA agent, (e.g., a precursor, e.g., a larger dsRNA molecule which can be processed into a siRNA agent, or a DNA which encodes a dsRNA molecule, e.g., a siRNA agent, or precursor thereof). The maintenance dose or doses can be the same or lower than the initial dose, e.g., one-half less of the initial dose. A maintenance regimen can include treating the subject with a dose or doses ranging from 0.01 µg to 15 mg/kg of body weight per day, e.g., 10, 1, 0.1, 0.01, 0.001, or 0.00001 mg per kg of bodyweight per day. The maintenance doses are, for example, administered no more than once every 2, 5, 10, or 30 days. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In some embodiments, the composition includes a plurality of dsRNA molecule species. In another embodiment, the dsRNA molecule species has sequences that are non-overlapping and non-adjacent to another species with respect to a naturally occurring target sequence. In another embodiment, the plurality of dsRNA molecule species is specific for different naturally occurring target genes. In another embodiment, the dsRNA molecule is allele specific.

The dsRNA molecules of the invention described herein can be administered to mammals, particularly large mammals such as nonhuman primates or humans in a number of ways.

In some embodiments, the administration of the dsRNA molecule, e.g., a siRNA agent, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The medication can be provided in measured doses or in a dispenser which delivers a metered dose. Selected modes of delivery are discussed in more detail below.

The invention provides methods, compositions, and kits, for rectal administration or delivery of dsRNA molecules described herein In particular embodiments, the present invention relates to the dsRNA molecules of the present invention for use in the methods described above.

Methods of Inhibiting Expression of the Target Gene

Embodiments of the invention also relate to methods for inhibiting the expression of a target gene. The method comprises the step of administering the dsRNA molecules in any of the preceding embodiments, in an amount sufficient to inhibit expression of the target gene. The present invention further relates to a use of a dsRNA molecule as defined herein for inhibiting expression of a target gene in a target cell. In a preferred embodiment, the present invention further relates to a use of a dsRNA molecule for inhibiting expression of a target gene in a target cell in vitro.

Another aspect the invention relates to a method of modulating the expression of a target gene in a cell, comprising providing to said cell a dsRNA molecule of this invention. In some embodiments, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, hepcidin, Activated Protein C, Cyclin D gene, VEGF gene, EGFR gene, Cyclin A gene, Cyclin E gene, WNT-1 gene, beta-catenin gene, C-MET gene, PKC gene, NFKB gene, STAT3 gene, survivin gene, Her2/Neu gene, topoisomerase I gene, topoisomerase II alpha gene, mutations in the p73 gene, mutations in the p21(WAF1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

In particular embodiments, the present invention relates to the dsRNA molecules of the present invention for use in the methods described above.

In some other aspects the invention relates to a method for preparing oligonucleotides conjugated with a ligand or a second oligonucleotide. The method comprises copper free "click" conjugation. A generic version of the method is shown in Scheme 1.

Scheme 1

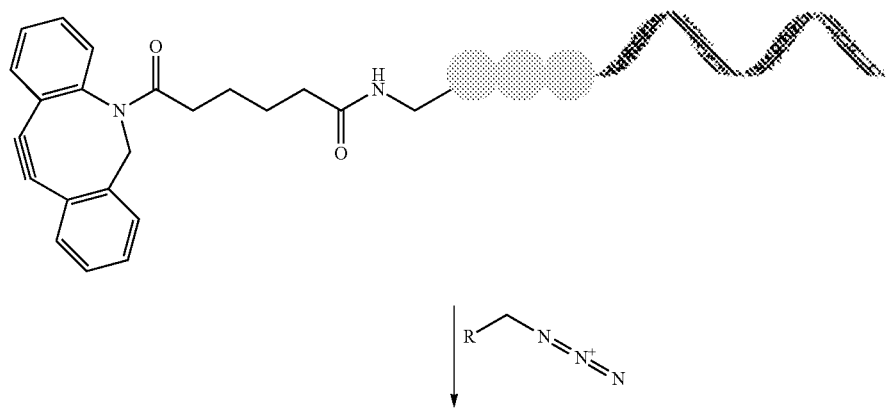

-continued

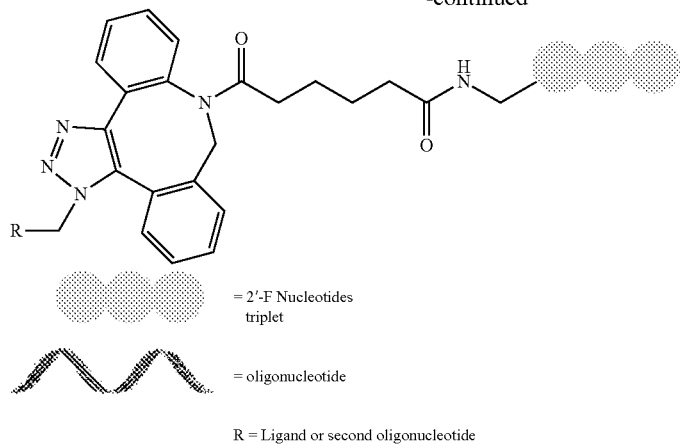

= 2'-F Nucleotides triplet

= oligonucleotide

R = Ligand or second oligonucleotide

As shown, a first oligonucleotide comprising dibenzylcyclooctyne (DBCO) moiety is reacted with a ligand or a second oligonucleotide, wherein the ligand and the second oligonucleotide comprises an azide functional group. To prepare the conjugate, the DBCO moiety can be attached to the oligonucleotide on either the 3' end or the 5' end. In some embodiments the oligonucleotide comprises 3 consecutive 2'-F-nucleotides (e.g., a 2'-F nucleotide triplet) at either the 3' or 5' end, and the DBCO moiety is conjugated to the terminal 2'-F nucleotide. The three 2'-F nucleotides can all be the same or they can all be different. Alternatively, two of the three 2'-F can be the same and can be arranged in any linear order with respect to each other and the nucleotice and DBCO moiety. The method can be useful in preparing longmer strands for Bis-RNAi synthesis. Accordingly, the DBCO moiety can be placed anywhere at the the 3' or 5' end of the sense or antisense strand for preparing Bis-RNAi.

The invention is further illustrated by the following examples, which should not be construed as further limiting. The contents of all references, pending patent applications and published patents, cited throughout this application are hereby expressly incorporated by reference.

EXAMPLES

Example 1: Design and Synthesis of Novel Modified Unlocked Nucleic Acid (mUNA) and Glycol Nucleic Acid (GNA) Building Blocks Synthetic approaches for novel mUNA and GNA derivatives are shown below. Briefly, nucleoside derivatives with substituted furanose ring and/or modified bases can be oxidatively cleaved at their 2'- and 3'-carbon-carbon bond by $NaIO_4$ followed by $NaBH_4$ reduction to give novel acyclic nucleoside derivatives. These nucleosides, nucleoside prodrugs with 5'-phosphate derivatives, and 3'-phosphoramidites can be applicable to oligonucleotide therapeutics and as an antiviral agent.

General synthetic approach for modified UNA building blocks is shown in Scheme 2.

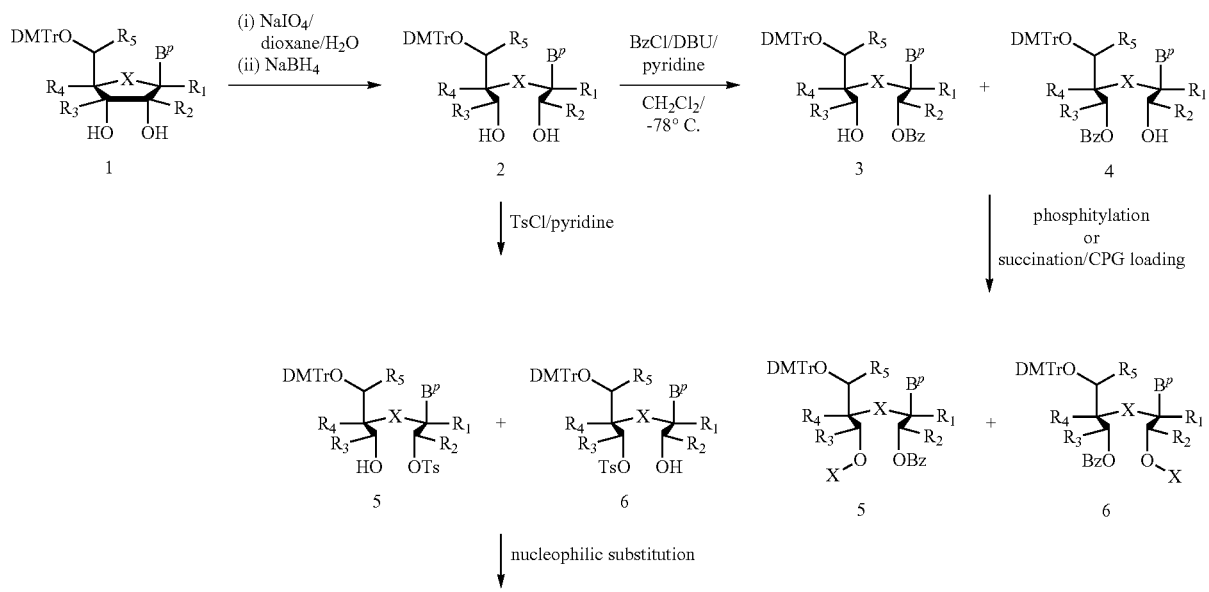

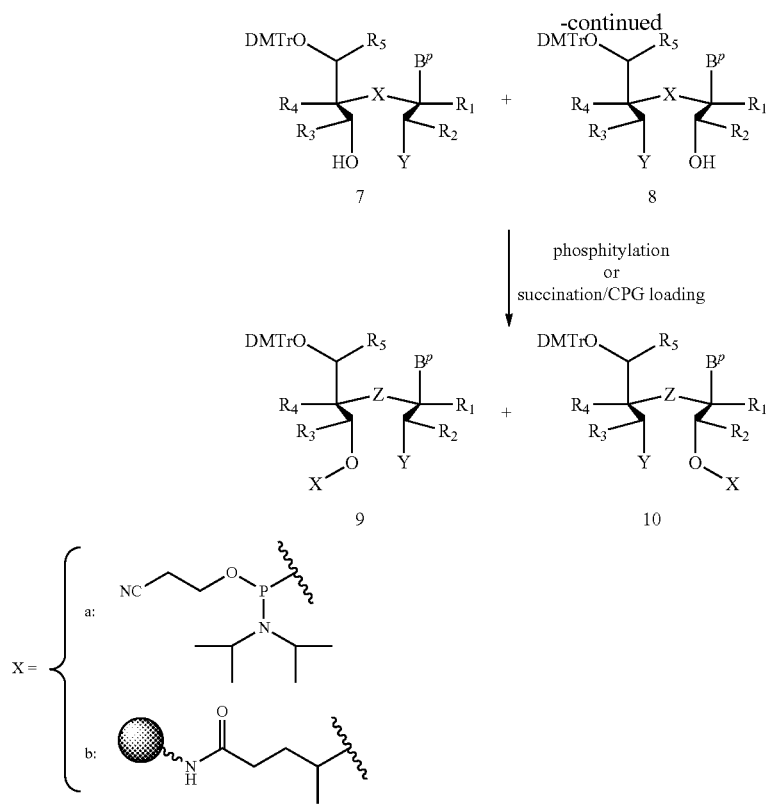

R1/R2/R3/R4/Y = H, Me, Et, IPr, OTBS, CN, F, Cl, Br, I, O-alkyl, OCH3, OCH2CH2OCH3, OCH2CONHCH3, O(CH2)$_n$CH3, O-aryl, OPh, O-alkylamine, (CH2)$_n$NH2, COOH, (CH2)2COOH, CH2F, CH2Cl, CH2Br, CH2I, O-allyl, O-propargyl, SME, NMe2, NPhth B$^p$ (protected nucleobase) = U/T/5-Me-C$^{Bz}$/C$^{Bz}$/A$^{Bz}$/G$^{IBu}$/inosine/pseudouracil/isoC/isoG/2,6-diamninopurine/pseudocytosine/2-aminopurine/xanthosine/N6-alkyl-A/O6-alkyl-G/2-thiouridine; 4-thiouridine; C5-modified pyrimidines; C2-modified purines; N8-modified purines; 7-deazapurines, phenoxazine; G-clamp; non-canonical mono, bi and tricyclic heterocycles Z = O, S, CH2, NHCOCF3, N-alkyl, Se Exemplary mUNA Building Blocks Example of mUNA Building Block for Oligonucleotide Synthesis

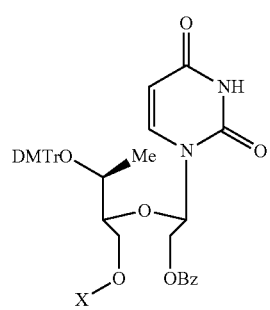

11

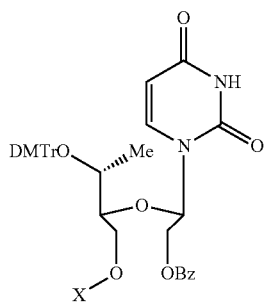

12

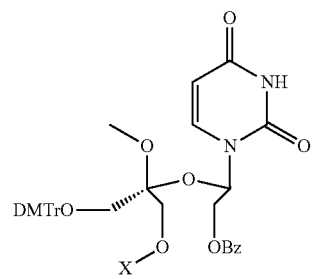

13

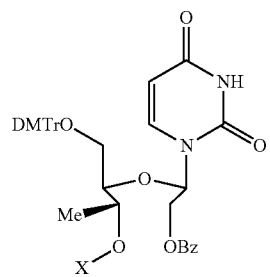
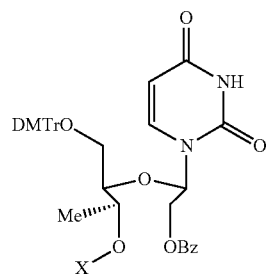
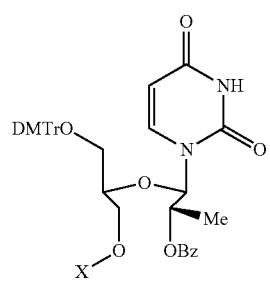
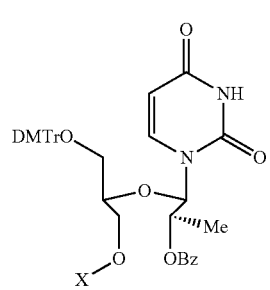
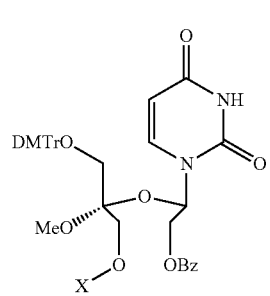
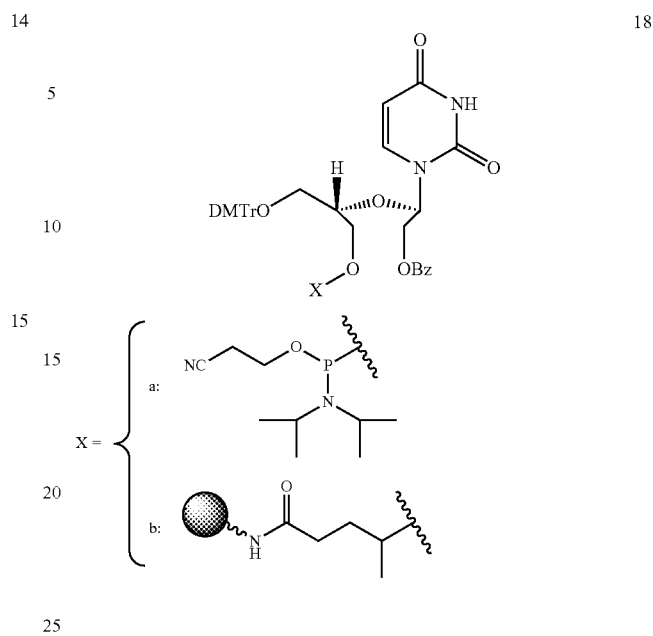
4'-Modified mUNA Building Blocks (1)
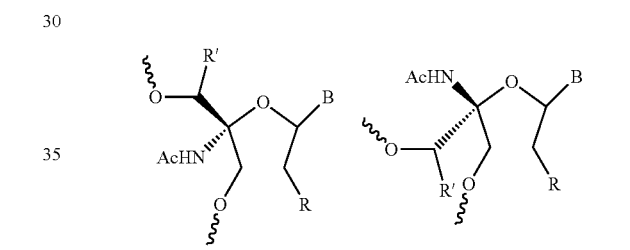
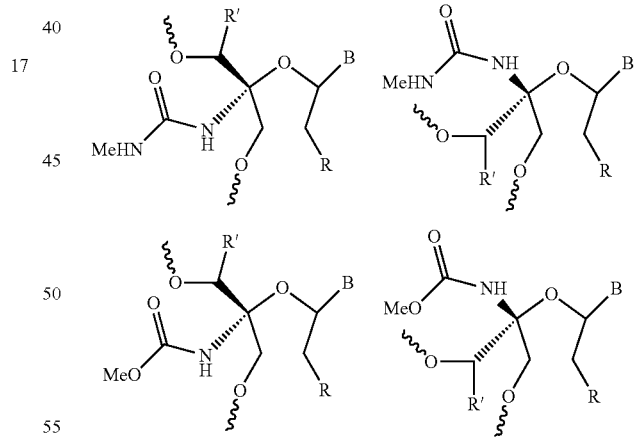
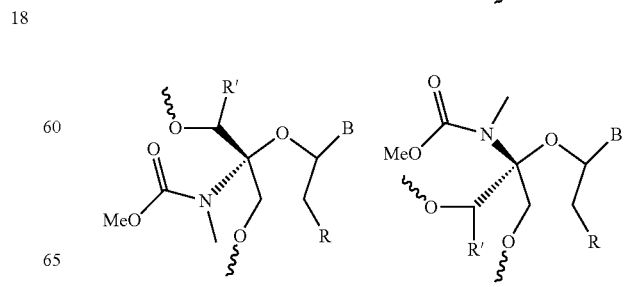

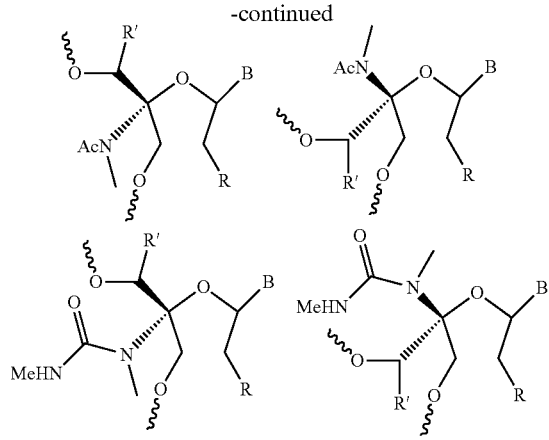

Wherein:

R is H, OH; OMe; Cl, F; OH; O—(CH$_2$)$_2$OMe; SMe, NMe$_2$; NH$_2$; Me; CCH (alkyne), O-nPr; O-alkyl; or O-alkylamino;

R' is H or Me;

B is A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; O6-alkyl-O; 2-thiouridine; 4-thiouridine; C5-modified pyrimidines; C2-modified purines; N8-modified purines; 7-deazapurines, phenoxazine; G-clamp; or non-canonical mono, bi and tricyclic heterocycles; and Stereochemistry is R or S and combination of R and S for the unspecified chiral centers.

4'-Modified mUNA Building Blocks (2)

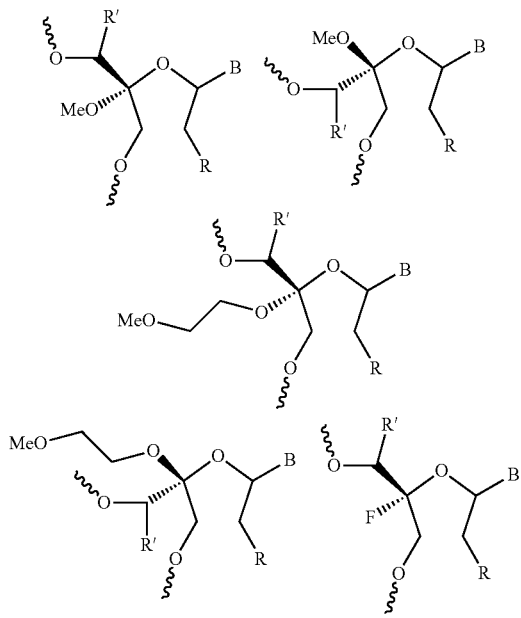

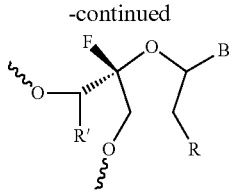

Wherein:

R is H, OH; OMe; Cl, F; OH; O—(CH$_2$)$_2$OMe; SMe, NMe$_2$; NH$_2$; Me; CCH (alkyne), O-nPr; O-alkyl; or O-alkylamino;

R' is H or Me;

B is A; C; 5-Me-C; G; I; U; T; Y; 2-thiouridine; 4-thiouridine; C5-modified pyrimidines; C2-modified purines; N8-modified purines; phenoxazine; 0-clamp; non-canonical mono, bi and tricyclic heterocycles; pseudouracil; isoC; isoG; 2,6-diamninopurine; pseudocytosine; 2-aminopurine; xanthosine; N6-alkyl-A; O6-alkyl-G; 2-thiouridine; 4-thiouridine; C5-modified pyrimidines; C2-modified purines; N8-modified purines; 7-deazapurines, phenoxazine; 0-clamp; ornon-canonical mono, bi and tricyclic heterocycles; and Stereochemistry is R or Sand combination of R and S for the unspecified chiral centers.

4'-Modified mUNA Building Blocks (3)

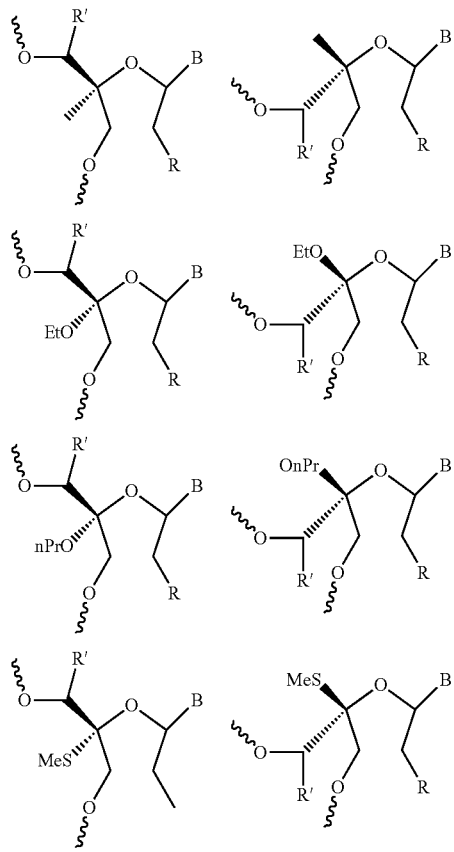

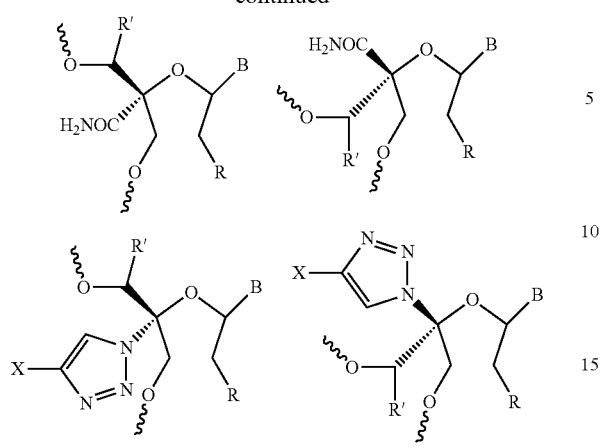

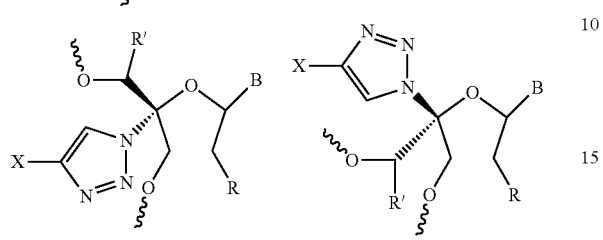

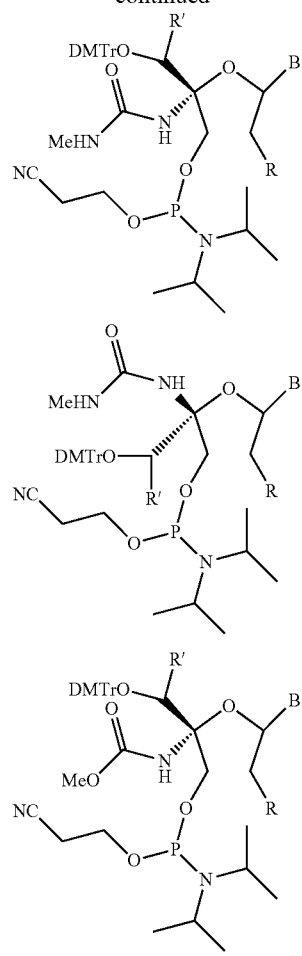

Wherein:

R is H, OMe; F; OH; O—(CH$_2$)$_2$OMe; SMe, NMe$_2$; NH$_2$; Me; O-nPr; O-alkyl; or O-alkylamino;

R' is H or Me;

B is A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; O6-alkyl-G; or 7-deazapurines; and Stereochemistry is R or S and combination of R and S for the unspecified chiral centers.

4'-Modified mUNA Building Blocks (4)

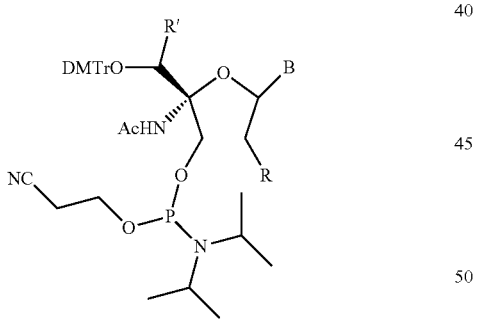

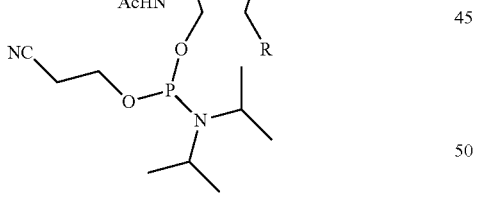

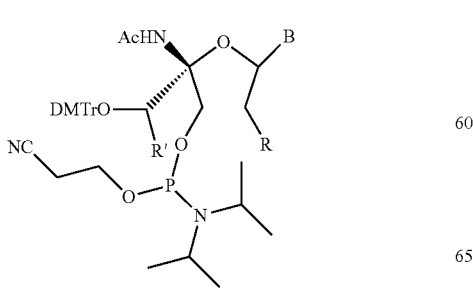

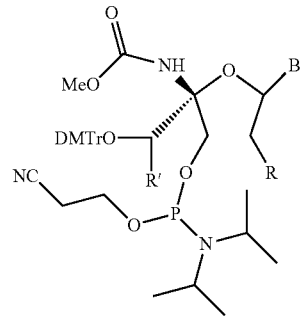

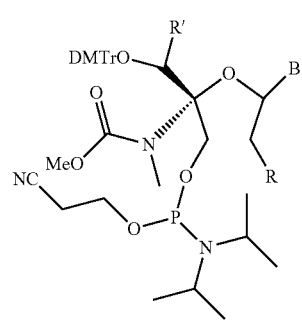

161
-continued

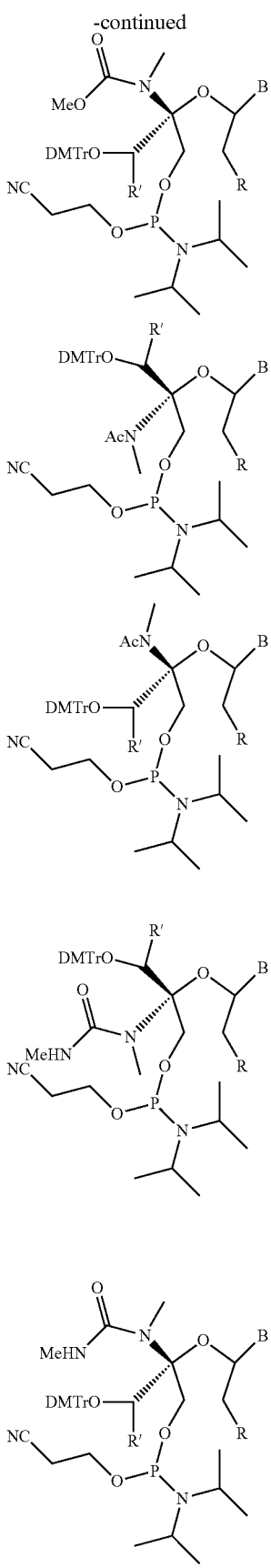

162

Wherein:
R is H; OMe; OEt, F; OTBDMS; O—(CH$_2$)$_2$OMe; SMe, NMe$_2$; NPhth; Me; O-nPr; O-alkyl; or O-alkylamino;

R' is H or Me;

B$^p$ is A$^{Bz}$; C$^{Ac}$; 5-Me-C$^{Bz}$; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil isoC; isoG; 2,6-diamninopurine; pseudocytosine; 2-aminopurine; xanthosine; N6-alkyl-A; O6-atkyl-G; or 7-deazapurines; and Stereochemistry is R or S and combination of R and S for the unspecified chiral centers.

4'-Modified mUNA Building Blocks (5)

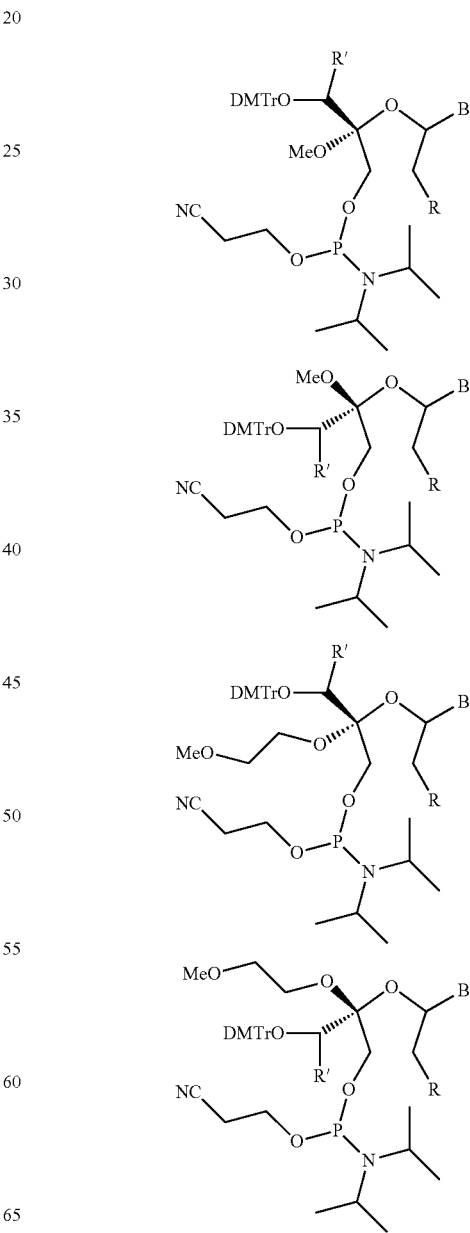

-continued

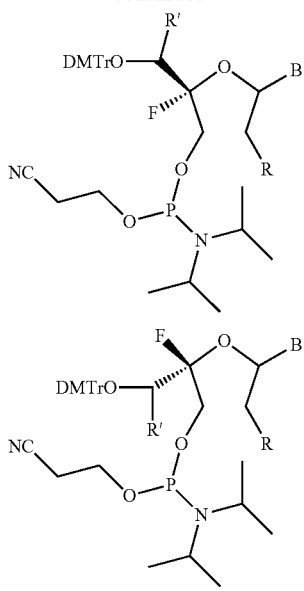

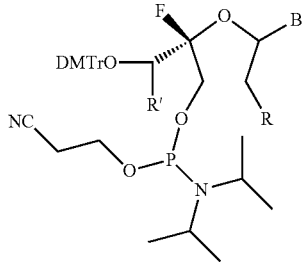

Wherein:

R is OMe; OEt, F; OTBDMS; O—(CH$_2$)$_2$OMe; SMe, NMe$_2$; NPhth; Me; O-nPr; O-alkyl; or O-alkylamino;

R' is H or Me;

B$^p$ is A$^{Bz}$; C$^{Ac}$; 5-Me-C$^{Bz}$; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil isoC; isoG; 2,6-diamninopurine; pseudo-cytosine; 2-aminopurine; xanthosine; N6-alkyl-A; O6-alkyl-G; or 7-deazapurines; and Stereochemistry is R or S and combination of R and S for the unspecified chiral centers 4'-Modified mUNA Building Blocks

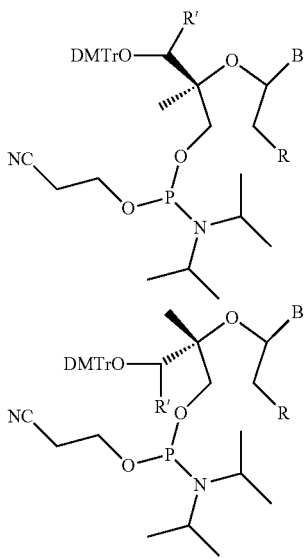

-continued

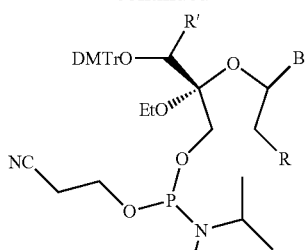

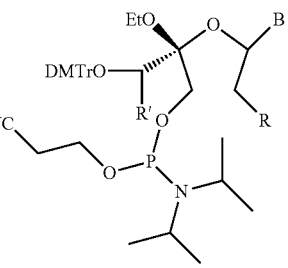

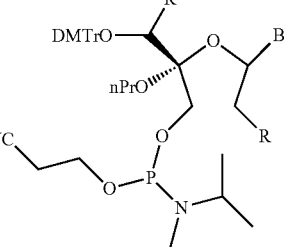

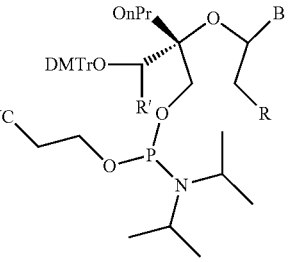

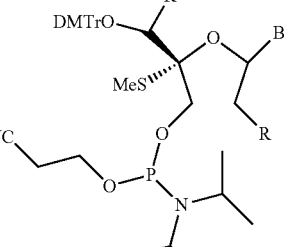

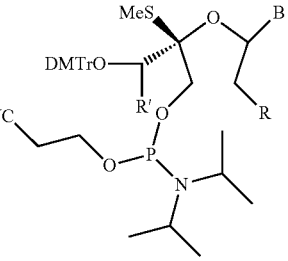

165

-continued

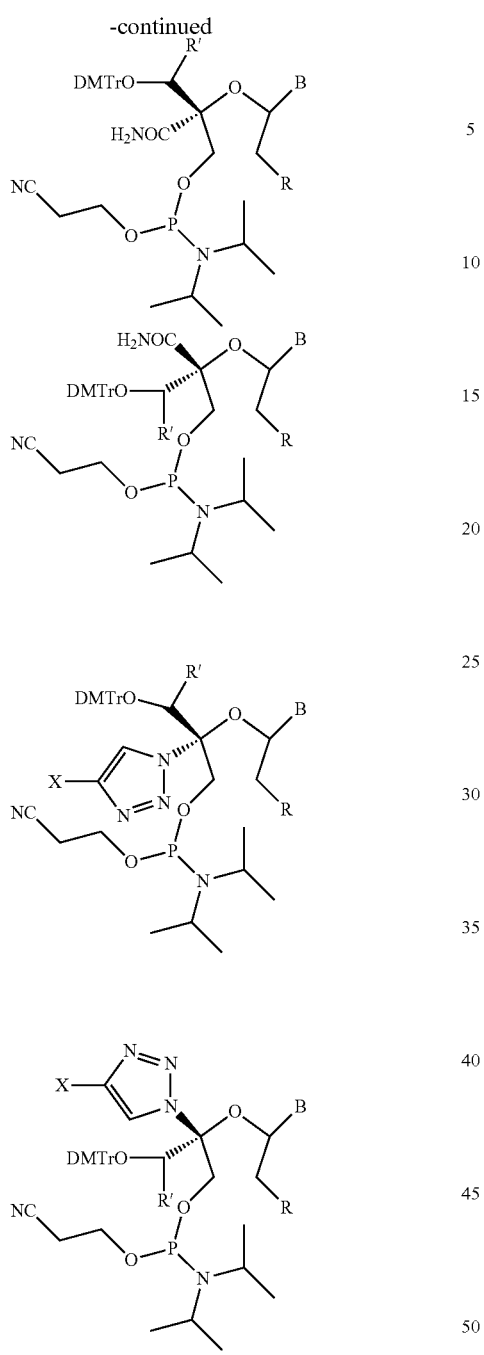

166

Other mUNA Building Blocks with 3'-Phosphoramidite Group

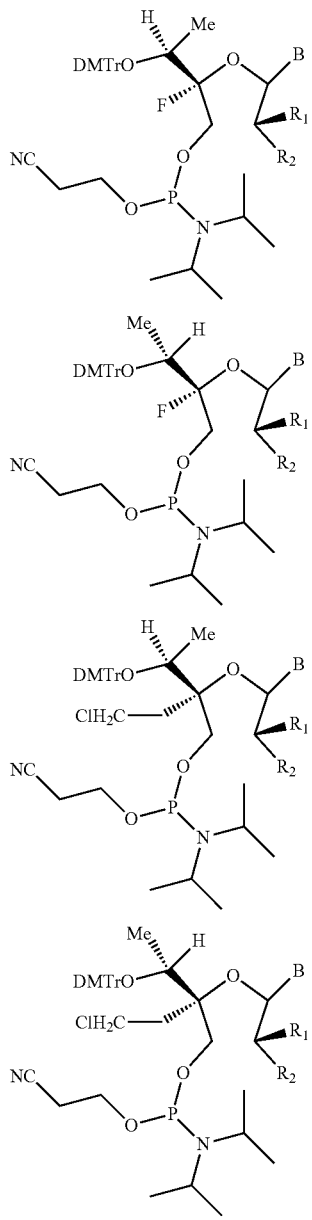

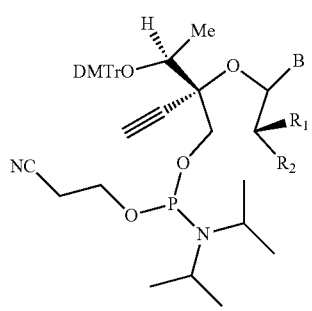

Wherein:

R is H, OMe; OEt, F; OTBDMS; O—(CH$_2$)$_2$OMe; SMe, NMe$_2$; NPhth; Me; O-nPr; O-alkyl; or O-alkylamino;

R' is H or Me

B$^p$ is A$^{Bz}$; C$^{Ac}$; 5-Me-C$^{Bz}$; G; I; U; T; Y; 2-thiouridine; 4-thiouridine; C5-modified pyrimidines; C2-modified purines; N8-modified purines; phenoxazine; G-clamp; non-canonical mono, hi and tricyclic heterocycles; pseudouracil isoC; isoG; 2,6-diamninopurine; pseudocytosine; 2-aminopurine; xanthosine; N6-alkyl-A; O6-alkyl-G; or 7-deazapurines; and Stereochemistry is R or S and combination of R and S for the unspecified chiral centers -continued
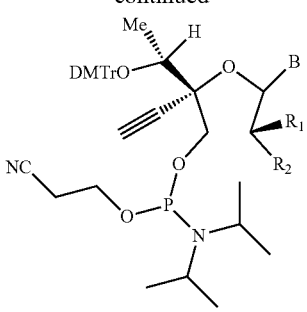
R$_1$, R$_2$ = OTBS; F, H, Me, Cl
B = A$^{Bz}$; C$^{Bz}$; 5-Me—C$^{Bz}$; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil isoC; isoG; 2,6-diamninopurine; pseudocytosine; 2-aminopurine; xanthosine; N6-alkyl-A; O6-alkyl-G; 7-deazapurines
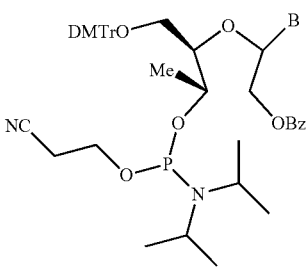
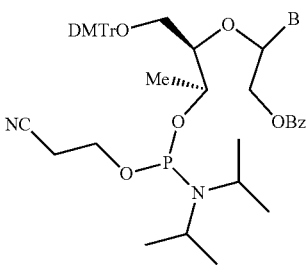
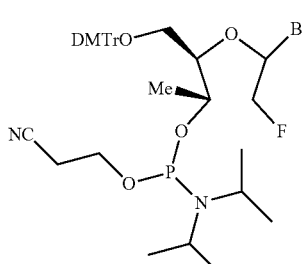
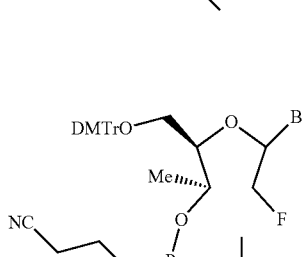
-continued
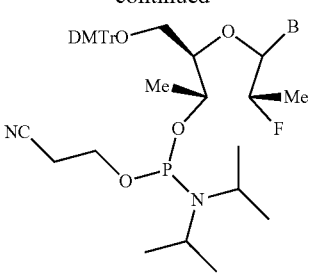
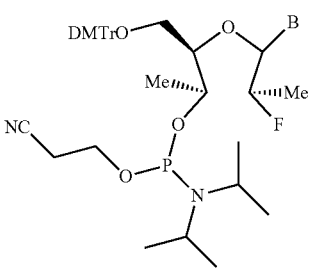
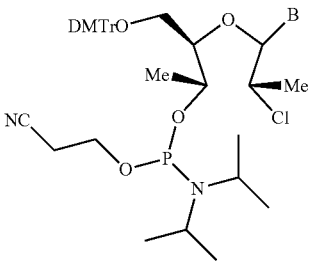
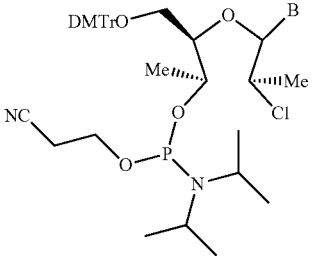
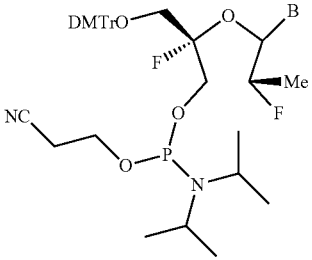
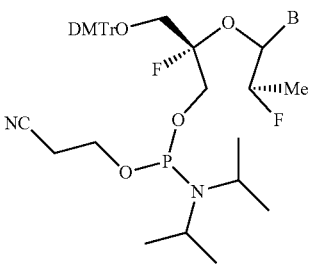

169
-continued
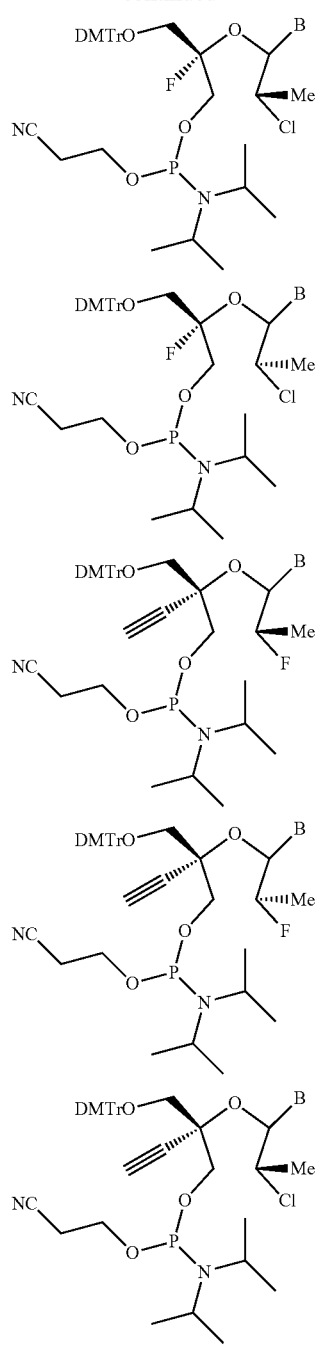
170
-continued
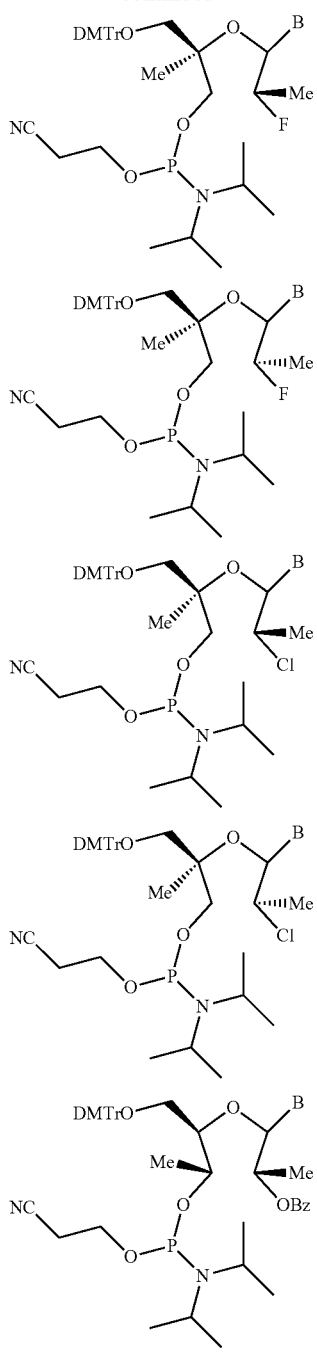
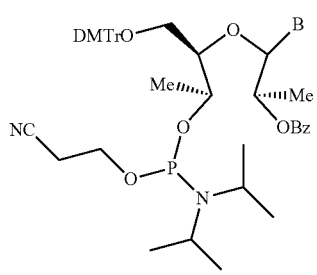

171
-continued
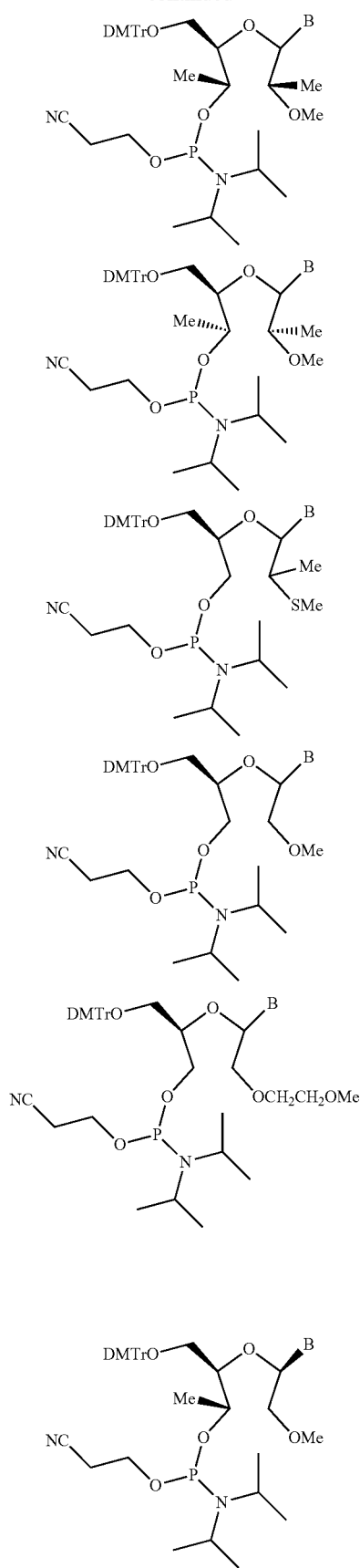
172
-continued
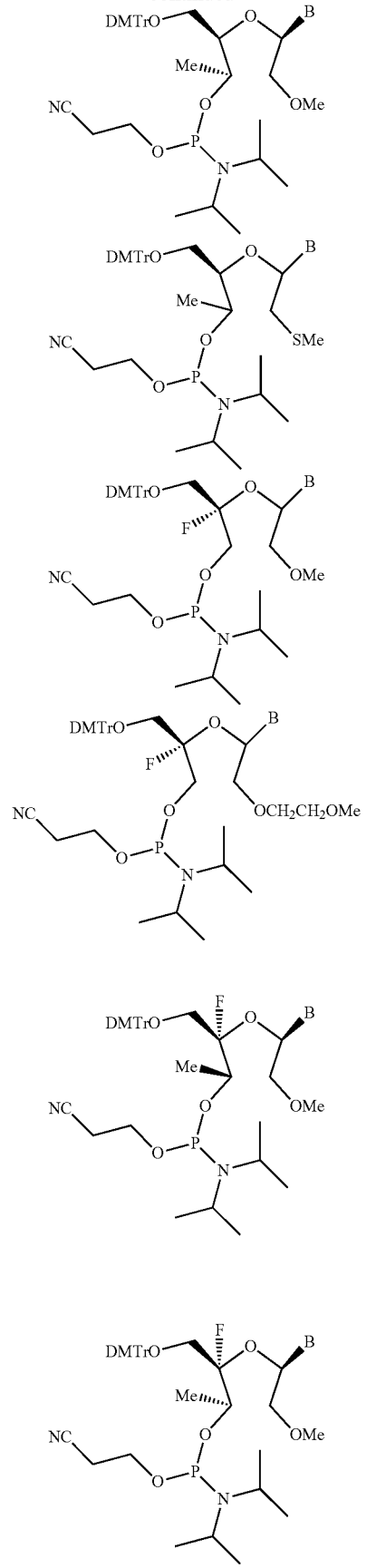

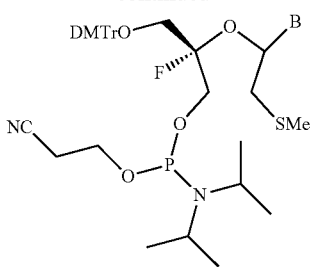

Other mUNA Building Blocks with 2'-Phosphoramidite Group

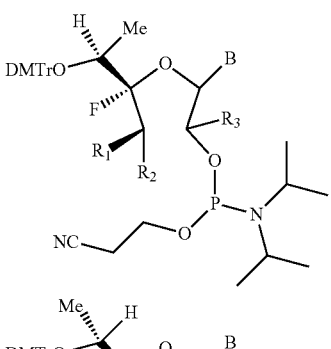

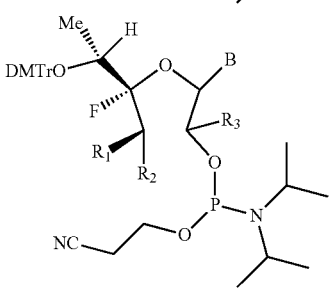

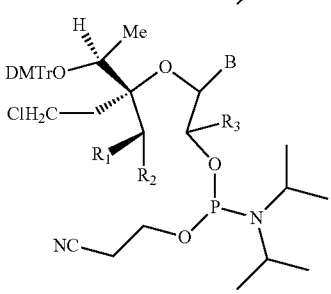

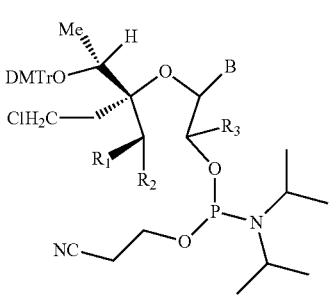

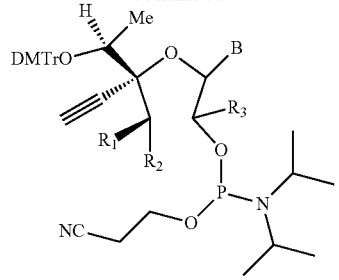

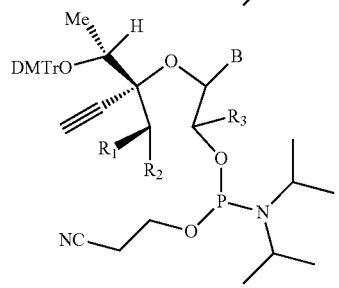

$R_1, R_2$ = OTBS; F, H, Me, Cl
$R_3$ = H, Me
B = $A^{Bz}$; $C^{Bz}$; 5-Me—$C^{Bz}$; G; I; U; T; Y; 2-thiouridine; 4-thiouridine; C5-modified pyrimidines; N8-modified purines; C2-modified purines; G-clamp; non-canonical mono, bi and tricyclic heterocycles; phenoxazine; pseudouracil isoC; isoG; 2,6-diamninopurine; pseudocytosine; 2-aminopurine; xanthosine; N6-alkyl-A; O6-alkyl-G; 7-deazapurines

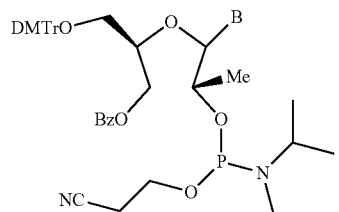

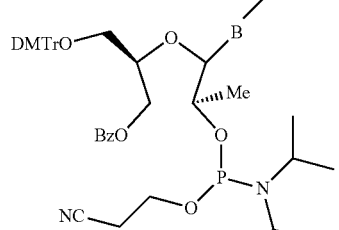

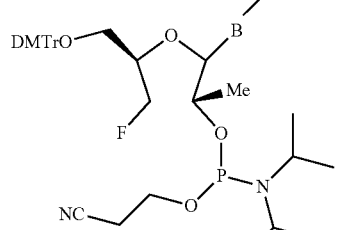

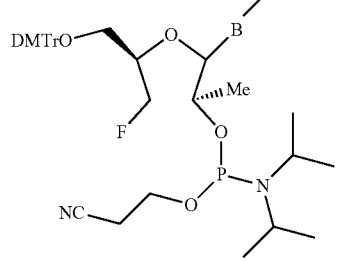

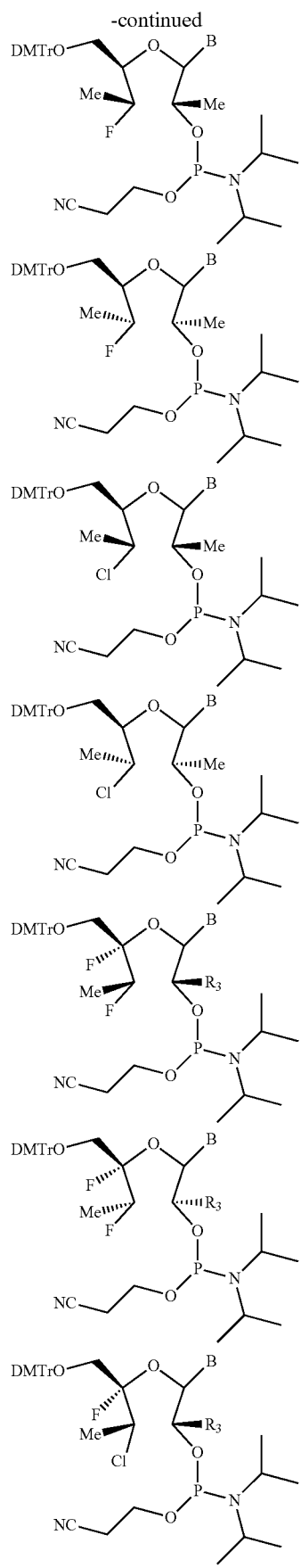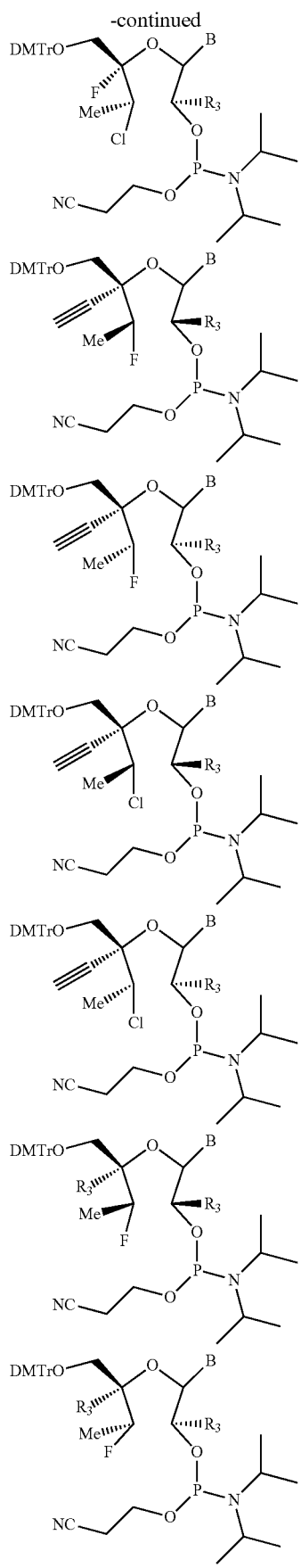

177
-continued
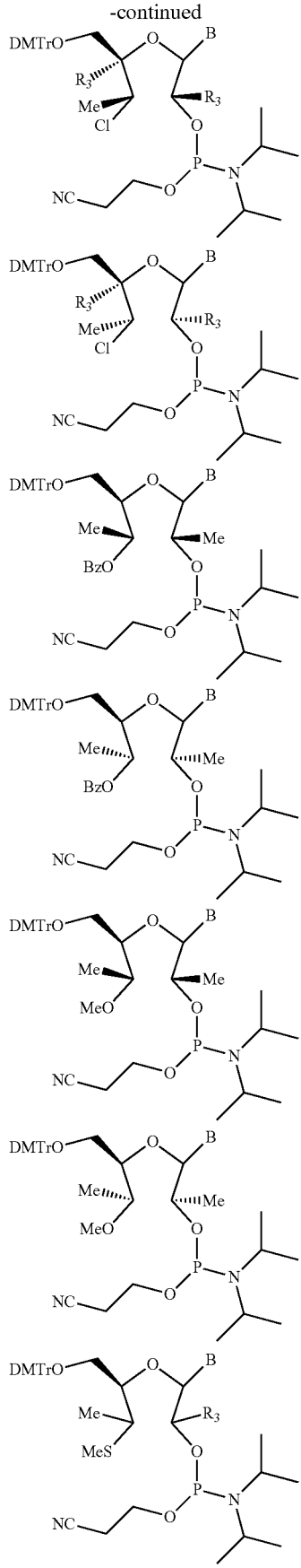
178
-continued
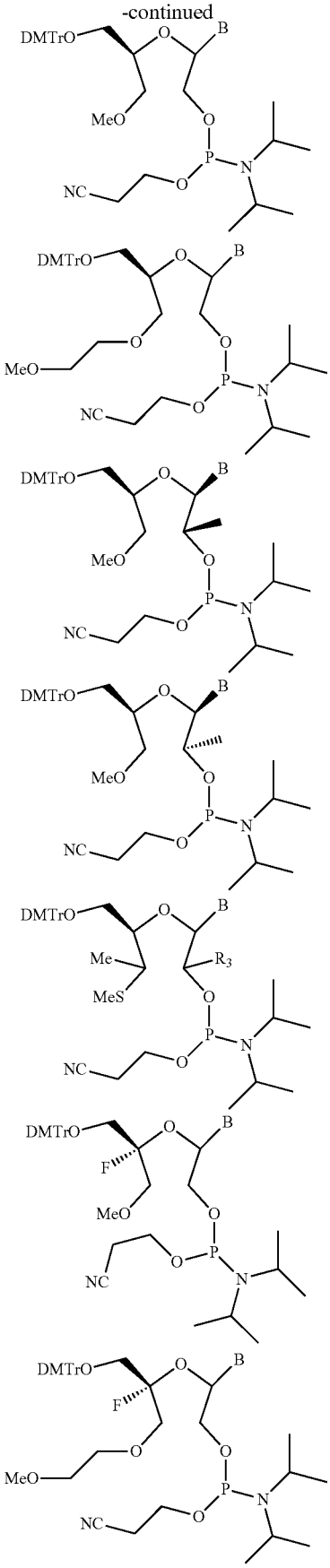

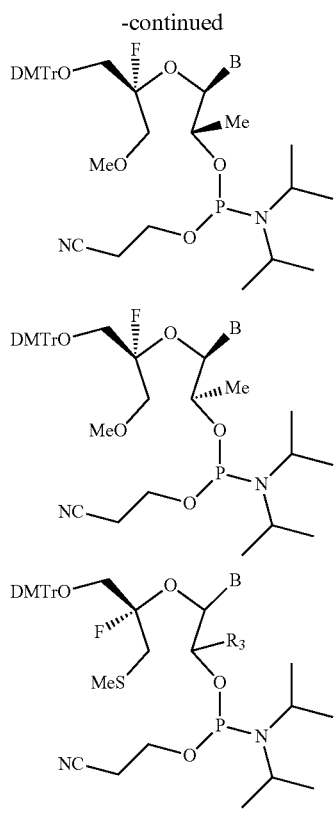

Modified UNA Nucleoside (1)

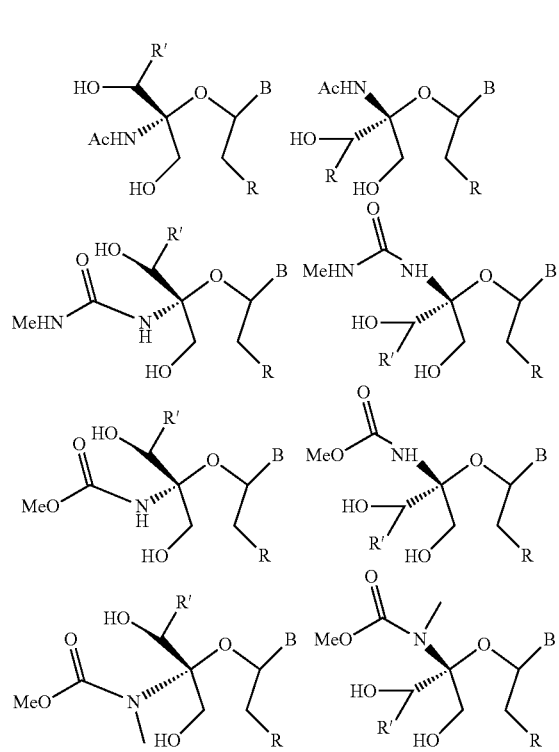

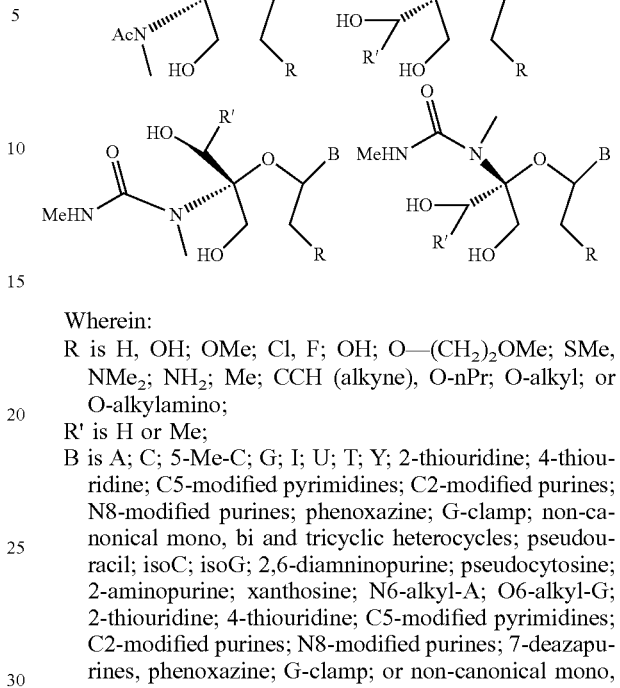

Wherein:
R is H, OH; OMe; Cl, F; OH; O—(CH$_2$)$_2$OMe; SMe, NMe$_2$; NH$_2$; Me; CCH (alkyne), O-nPr; O-alkyl; or O-alkylamino;
R' is H or Me;
B is A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; O6-alkyl-G; 2-thiouridine; 4-thiouridine; C5-modified pyrimidines; C2-modified purines; N8-modified purines; 7-deazapurines, phenoxazine; G-clamp; or non-canonical mono, hi and tricyclic heterocycles; and
Stereochemistry is R or S and combination of R and S for the unspecified chiral centers Modified UNA Nucleosides (32)

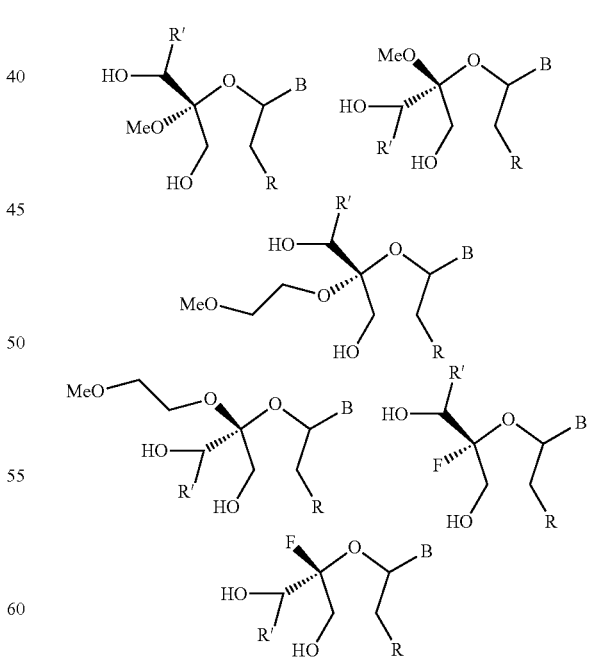

Wherein:
R is H, OH; OMe; Cl, F; OH; O—(CH$_2$)$_2$OMe; SMe, NMe$_2$; NH$_2$; Me; CCH (alkyne), O-nPr; O-alkyl; O-alkylamino;

R' is H or Me;

B is A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; O6-alkyl-G; 2-thiouridine; 4-thiouridine; C5-modified pyrimidines; C2-modified purines; N8-modified purines; 7-deazapurines, phenoxazine; G-clamp; or non-canonical mono, bi and tricyclic heterocycles; and Stereochemistry is R or S and combination of R and S for the unspecified chiral centers Modified UNA Nucleosides (3)

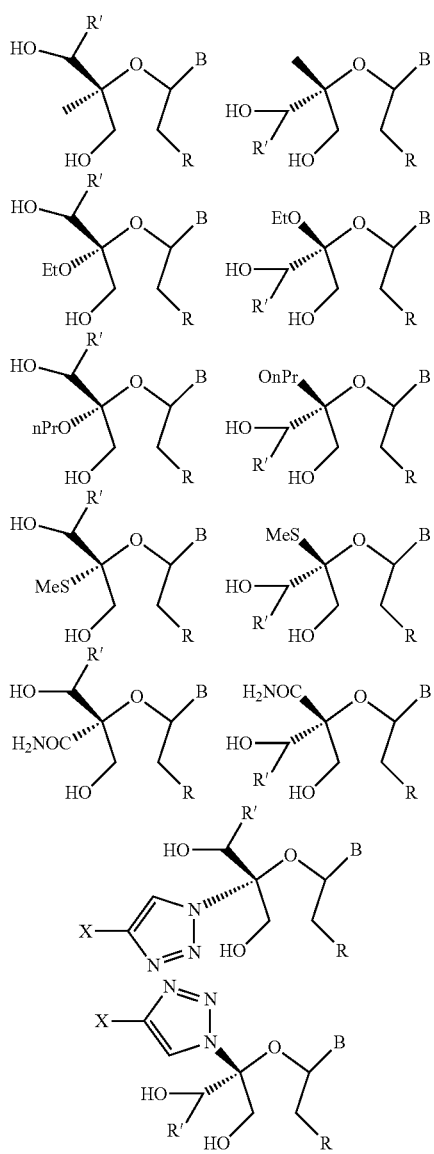

Wherein:

R is H, OMe; F; OH; O—(CH$_2$)$_2$OMe; SMe, NMe$_2$; NH$_2$; Me; O-nPr; O-alkyl; or O-alkylamino;

R' is H or Me;

B is A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; O6-alkyl-G; or 7-deazapurines; and Stereochemistry is R or S and combination of R and S for the unspecified chiral centers Modified UNA Free Nucleosides with 5'-Phosphate Analogs

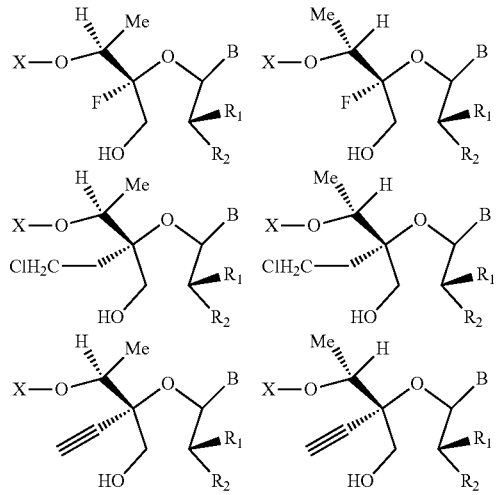

R$_1$, R$_2$ = OTBS; F, H, Me, Cl

B = A$^{Bz}$; C$^{Bz}$; 5-Me—C$^{Bz}$; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil isoC; isoG; 2,6-diamninopurine; pseudocytosine; 2-aminopurine; xanthosine; N6-alkyl-A; O6-alkyl-G; 7-deazapurines X = DMTr,

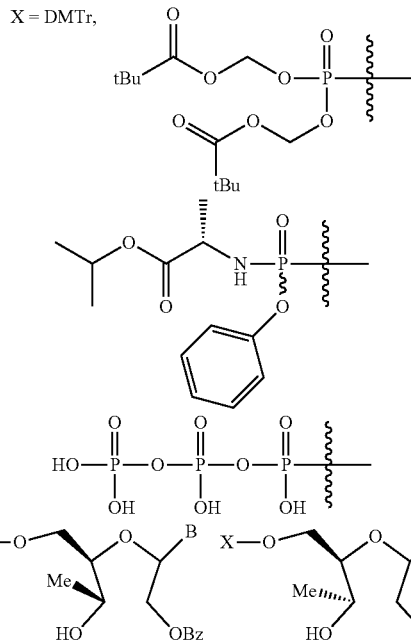

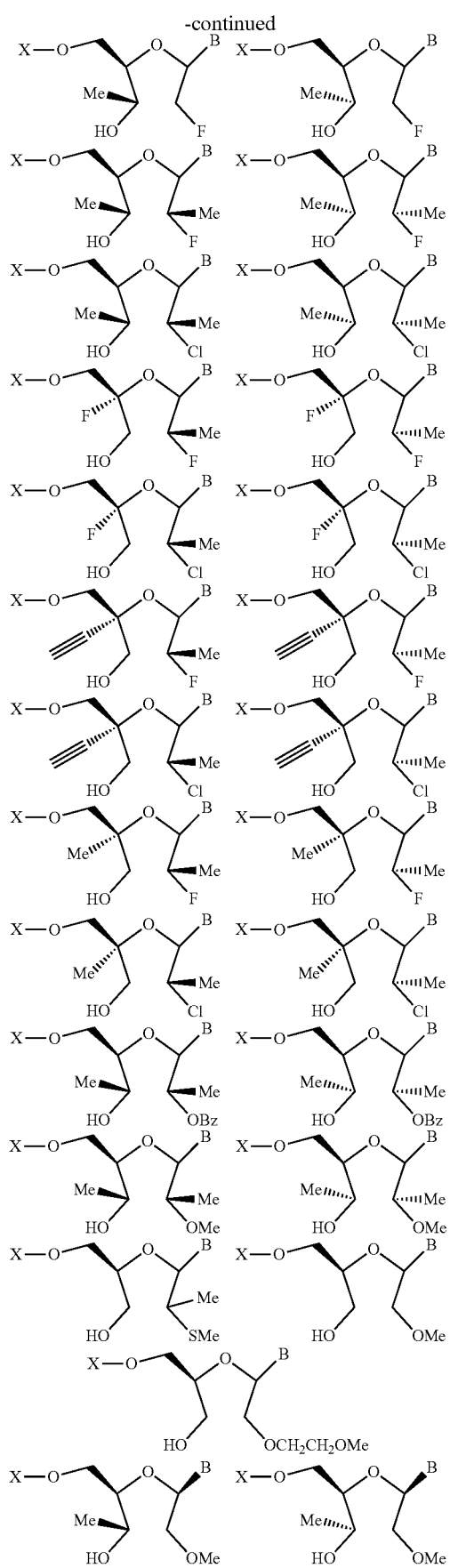
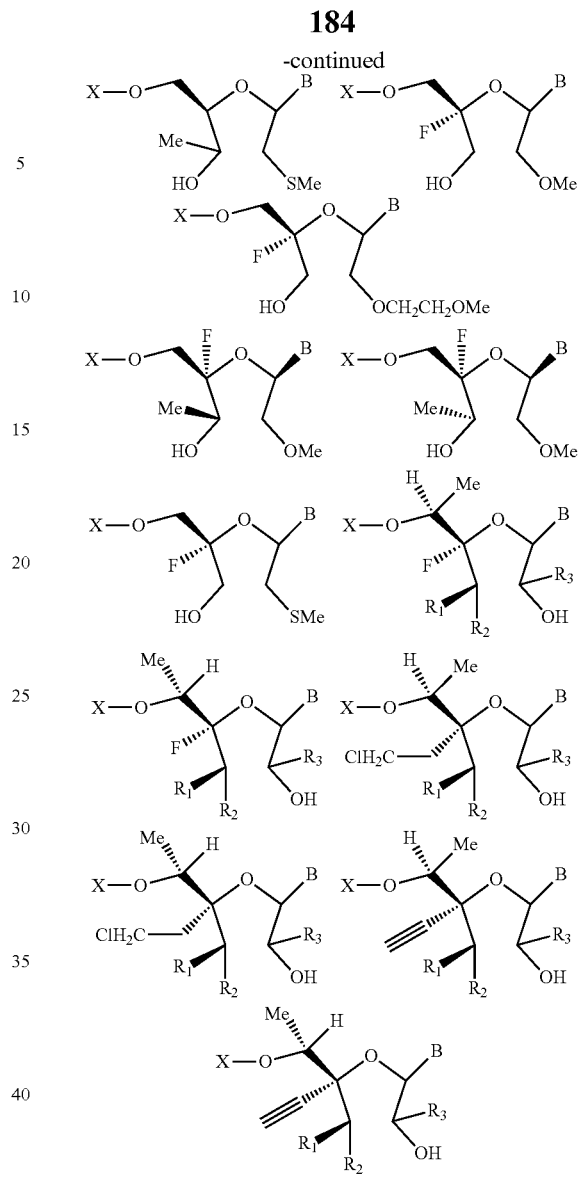
R₁, R₂ = OTBS; F, H, Me, Cl
R₃ = H, Me
B = $A^{Bz}$; $C^{Bz}$; 5-Me—$C^{Bz}$; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil isoC; isoG; 2,6-diamninopurine; pseudocytosine; 2-aminopurine; xanthosine; N6-alkyl-A; O6-alkyl-G; 7-deazapurines
X = DMTr,
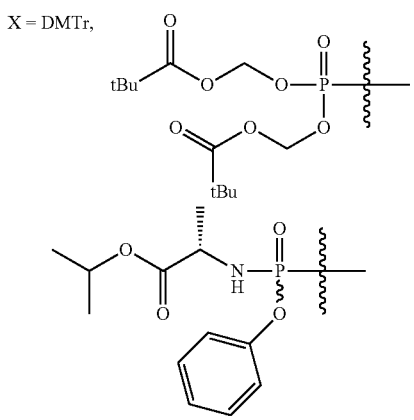

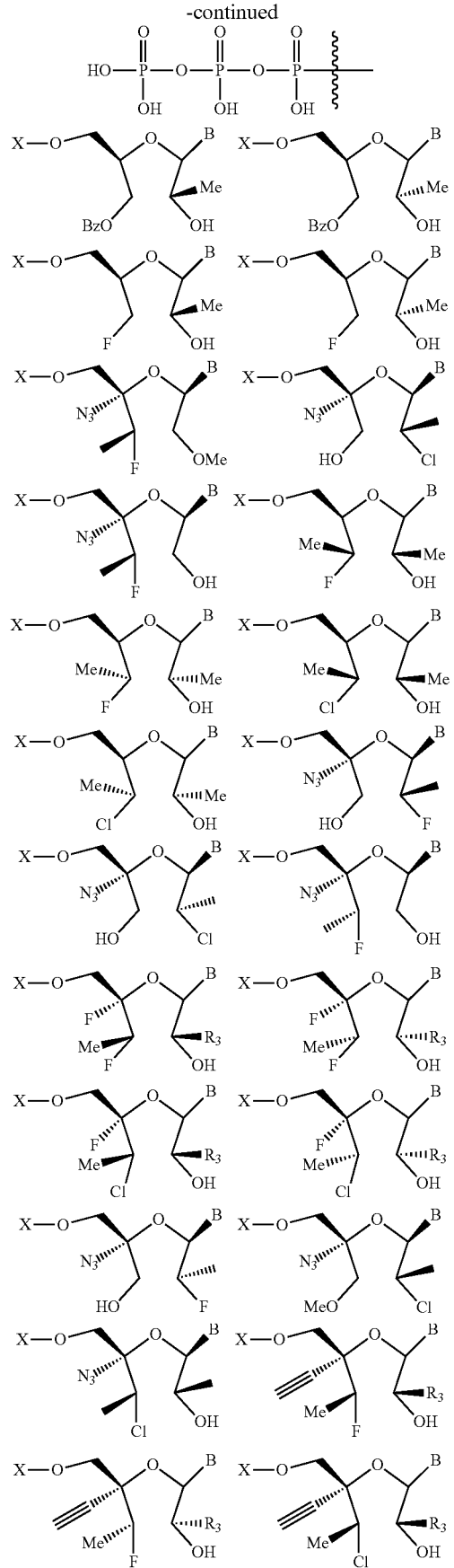
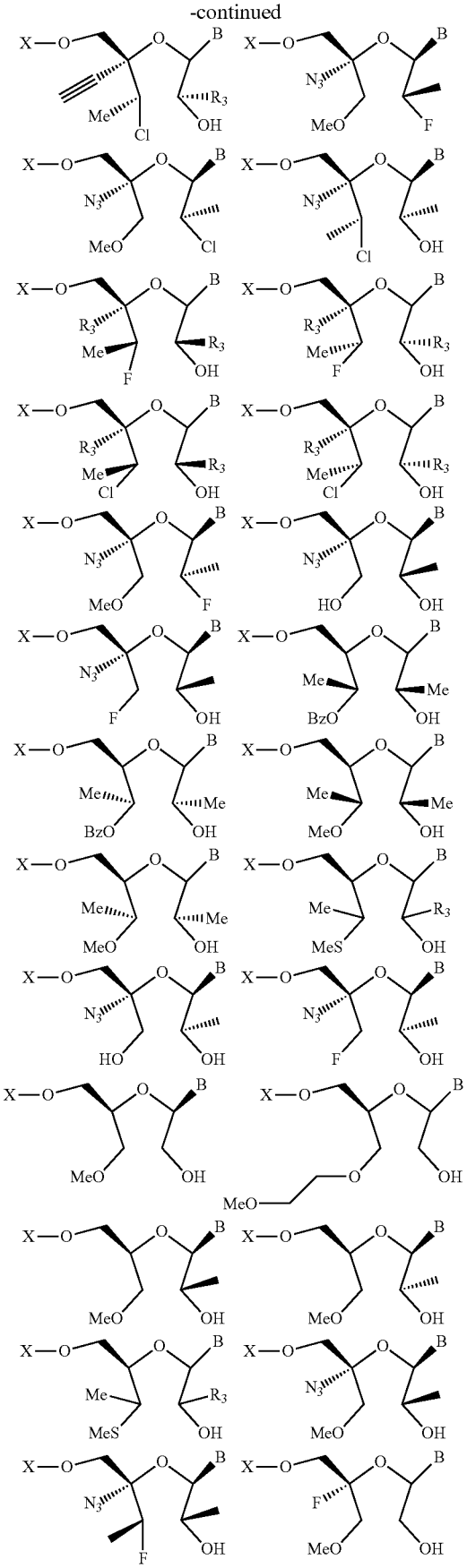

187
-continued
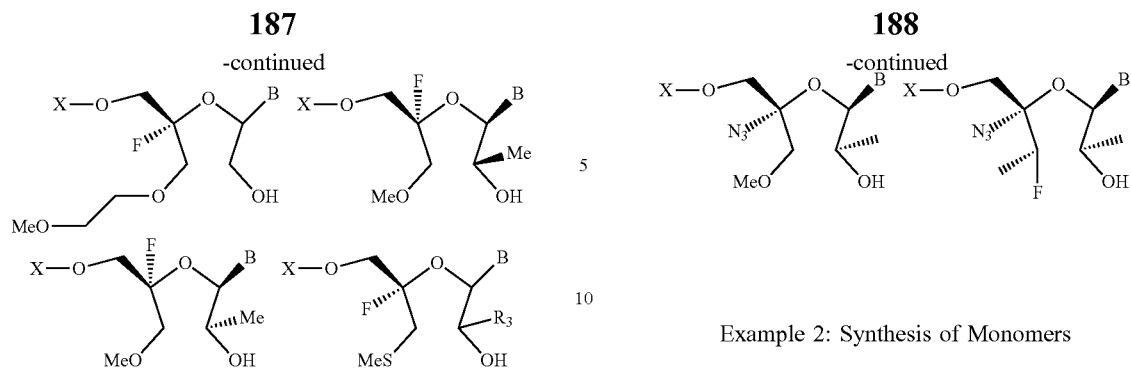
188
-continued
Example 2: Synthesis of Monomers
Synthesis of 5'-(S)-Methyl-U-UNA Building Blocks
Scheme 3
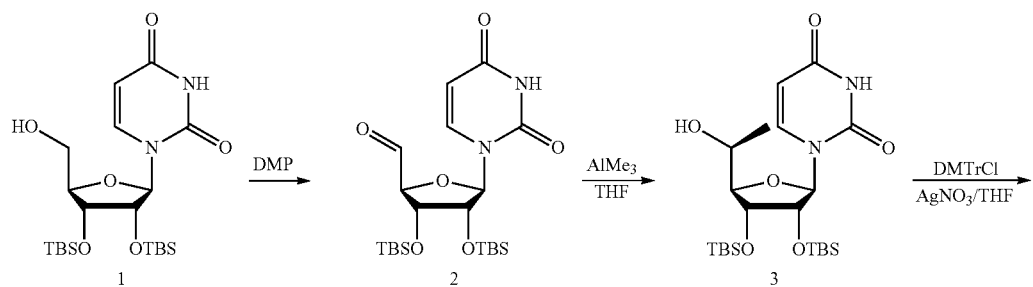
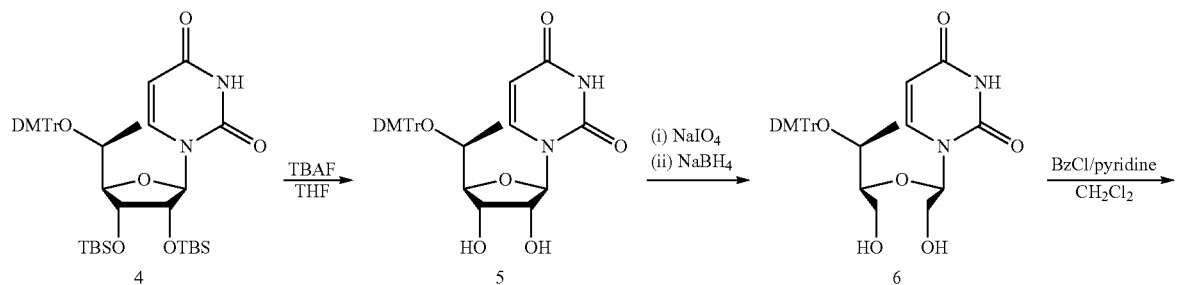
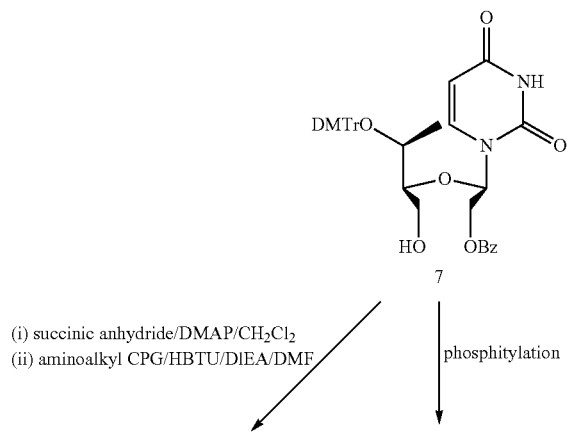
(i) succinic anhydride/DMAP/CH$_2$Cl$_2$
(ii) aminoalkyl CPG/HBTU/DIEA/DMF
phosphitylation -continued

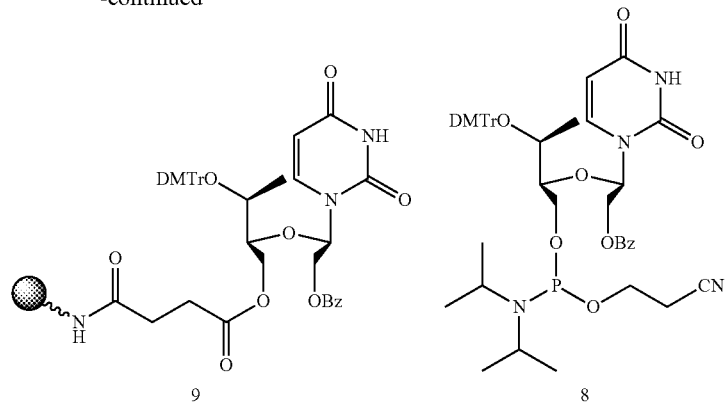

Synthesis of compound 3: To a solution of Compound 1 (20.0 g, 42.3 mmol) in anhydrous dichloromethane (500 mL) cooled to 0° C., Dess-Martin periodinane (21.5 g, 50.8 mmol, 1.2 eq) was added. The reaction was stirred at 0° C. for 1 hour, warmed to room temperature, and stirred for additional 1.5 hours. The reaction was then quenched by slowly adding to a vigorously stirred mixture of 10% aq. $Na_2S_2O_3$ (300 mL) and saturated aq. $NaHCO_3$ (300 mL) at 0° C. and stirred for 1 hour. After quenching, the organic layer was extracted 3 times with DCM, dried over anhydrous $Na_2SO_4$, filtered, and concentrated under reduced pressure. Upon drying on high vacuum, product yielded as flakey white solid. The dried crude material was resuspended in anhydrous THF (300 mL) and the solution was added via cannula to a stirring solution of $Me_3Al$ (2M in toluene, 63.5 mL, 126.9 nmmol, 3 eq) in TUF (300 mL) at 0° C. The crude material flask was rinsed with additional TIH and added to the reaction via cannula. After stirring at 0° C. for 1 hour, the reaction was warmed to room temperature and allowed to stir overnight. The reaction brought to 0° C. and was quenched by gradually adding 20 mL of 1:1 solution of aq. $H_3PO_4$(10%) and saturated aq. $NH_4Cl$. After the solvent was removed under reduced pressure, the crude residue was extracted with DCM and sat. $NaHCO_3$. The organic layer was separated, washed with brine, dried and filtered over anhydrous $Na_2SO_4$, and concentrated under reduced pressure. The crude material was purified by flash silica gel column chromatography (0-30% EtOAc in hexanes, 2% triethylamine) to obtain compound 3 as a white foam (5.85 g, 12.02 mmol, 25%; $R_f$=0.48, developed with 50% EtOAc in Hexanes). $^1$H NMR (400 MHZ, DMSO-$d_6$) δ 11.35 (s, 1H), 8.07 (d, J=8.1 Hz, 1H), 5.83 (d, J=6.0 Hz, 1H), 5.71 (d, J=8.1 Hz, 1H), 5.27 (d, J=4.2 Hz, 1H), 4.26 (dd, J=6.1, 4.4 Hz, 1H), 4.12 (dd, J=4.5, 2.5 Hz, 1H), 3.88-3.78 (m, 1H), 3.72 (t, J=2.2 Hz, 1H), 1.14 (d, J=6.4 Hz, 3H), 0.89 (s, 9H), 0.83 (s, 9H), 0.08 (d, J=3.6 Hz, 6H), −0.04 (s, 3H). $^{13}$C NMR (101 MHz, DMSO-$d_6$) δ 162.94, 150.74, 140.17, 102.05, 88.54, 86.43, 74.75, 72.90, 65.04, 25.70, 25.59, 19.98, 17.74, 17.60, 4.63, −4.77, −4.84, −5.07.

Synthesis of compound 4: To a solution of compound 3 (5.85 g, 12.02 mmol) in anhydrous THF (50 mL) and anhydrous pyridine (10 mL), DMTrCl (12.2 g, 36.1 mmol, 3 eq) and $AgNO_3$ (4.08 g, 24.0 mmol, 2 eq) were added, and the mixture was stirred overnight at ambient temperature. After 24 hours, additional DMTrCl (6.11 g, 18.0 mmol, 1.5 eq) and $AgNO_3$ (2.04 g, 12.0 mmol, 1.0 eq) was added to the reaction. The mixture was stirred at ambient temperature overnight. The mixture was filtered over celite, and the filter cake was washed with DCM. The filtrate was concentrated under reduced pressure, and the residue was extracted with DCM and saturated aq. $NaHCO_3$. The organic layer was washed with brine, dried and filtered over anhydrous $Na_2SO_4$, and concentrated. The crude residue was purified by flash column chromatography (0-25% EtOAc in Hexanes, 2% triethylamine) to obtain compound 4 as yellow foam (8.05 g, 10.2 mmol, 85%, $R_f$=0.35, developed with 33% EtOAc in hexanes).

Synthesis of compound 5: To a solution of compound 4 (8.05 g, 10.2 mmol) in THF (51 mL), TBAF (1M in THF, 25.5 mL, 25.5 mmol, 2 eq) was added. After stirring at room temperature overnight, the solvent was removed under reduced pressure. The crude residue was purified by flash column chromatography (0-100% EtOAc in hexane then 2.5% MeOH in EtOAC, 2% triethylamine) to obtain compound 5 as yellow-white foam (5.84 g, quant.; $R_f$=0.50, developed with 5% MeOH in EtOAc), 1H NMR (500 MHZ, DMSO-$d_6$) δ 11.41-11.34 (m, 1H), 7.57 (d, J=8.1 Hz, 1H), 7.46-7.40 (m, 2H), 7.30 (t, J=7.9 Hz, 6H), 7.21 (t, J=7.3 Hz, 1H), 6.88 (dd, J=8.8, 6.7 Hz, 4H), 5.68 (d, J=5.1 Hz, 1H), 5.58 (dd, J=8.0, 1.6 Hz, 1H), 5.39 (d, J=5.2 Hz, 1H), 5.03 (d, J=5.1 Hz, 1H), 4.01 (h, J=5.8 Hz, 2H), 3.74 (s, 3H), 3.72 (s, 4H), 3.61-3.51 (m, 1H), 0.67 (d, J=6.2 Hz, 3H). $^{13}$C NMR (126 MHz, DMSO-$d_6$) δ 162.93, 158.06, 150.67, 146.11, 140.47, 136.40, 136.30, 130.16, 130.08, 127.95, 127.61, 126.61, 112.99, 101.93, 87.25, 86.43, 85.81, 72.56, 69.24, 68.89, 55.00, 54.99, 17.09.

Synthesis of compound 6: To a solution of compound 5 (5.84 g, 10.42 mmol) in dioxane (135 mL) and $H_2O$ (25 mL), $NaIO_4$ (2.45 g, 11.46 mmol, 1.1 eq) dissolved in $H_2O$ (25 mL) was added. The bi-layer reaction mixture was vigorously stirred at ambient temperature for 4 hours. The reaction mixture was filtered through a sintered funnel, and the filter cake was washed with additional dioxane. To the filtrate was added $NaBH_4$ (0.434 g, 11.46 mmol, 1.1 eq). After stirring at ambient temperature for 2 hours, the mixture was cooled to 0° C. then quenched with 1:1 v/v AcOH: Pyridine buffer. After the solvent was removed under reduced pressure, the crude residue was extracted with EtOAc and saturated aq. $NaHCO_3$. The organic layer was separated, dried over anhydrous $Na_2SO_4$, filtered, and concentrated under reduced pressure. The crude material was purified by flash column chromatography (0-5% MeOH in DCM, 2% triethylamine), to obtain compound 6 as a white foam (5.01 g, 8.90 mmol, 85%; $R_f$=0.13 developed with 5% MeOH in DCM). $^1$H NMR (400 MHZ, DMSO-$d_6$) δ 11.14 (d, J=2.2 Hz, 1H), 7.35 (dd, J=8.0, 1.8 Hz, 3H), 7.30-7.15

(m, 7H), 6.90-6.78 (m, 4H), 5.64 (dd, J=6.4, 4.7 Hz, 1H), 5.47 (dd, J=8.0, 2.2 Hz, 1H), 5.01 (t, J=6.0 Hz, 1H), 4.68 (t, J=5.4 Hz, 1H), 3.82 (dd, J=11.7, 5.7, 2.2 Hz, 1H), 3.60-3.51 (m, 2H), 3.50-3.39 (m, 2H), 3.24-3.17 (m, 1H), 3.12-3.01 (m, 1H), 2.07 (s, 2H), 1.19 (t, J=7.3 Hz, 2H), 0.56 (d, J=6.3 Hz, 3H). $^{13}$C NMR (126 MHZ, DMSO-$d_6$) δ 163.08, 158.09, 158.03, 150.80, 145.64, 140.57, 136.49, 136.11, 129.75, 129.60, 127.65, 127.62, 126.68, 113.02, 101.18, 85.80, 84.73, 81.69, 68.82, 61.24, 60.36, 54.98, 45.48, 39.24, 15.38, 8.49, 1.12.

Synthesis of compound 7: To a solution of compound 6 (5.01 g, 8.90 mmol) in anhydrous DCM (245 mL) and pyridine (7 mL), cooled to −78° C., benzoyl chloride (1.14 mL, 9.79 mmol, 1.1 eq) was slowly added. After stirring at −78° C. for 1 hour, reaction mixture was brought to 0° C., and quenched with EtOH (5 mL). The mixture was extracted with DCM and saturated aq. NaHCO$_3$. The organic layer was washed with brine, separated, dried over anhydrous Na$_2$SO$_4$, filtered, and concentrated. The crude residue was purified by flash column chromatography (0-75% EtOAC in hexanes) to yield compound 7 as a white foam (1.31 g, 1.96 mmol, 22%; R=0.32, developed with 50% EtOAc in hexanes). $^1$H NMR (400 MHz, DMSO-$d_6$) δ 11.29-11.25 (m, 1H), 7.87 (dd, J=8.4, 1.4 Hz, 2H), 7.69-7.61 (m, 1H), 7.55-7.46 (m, 3H), 7.39-7.32 (m, 2H), 7.27 (d, J=1.0 Hz, 1H), 7.25 (d, J=1.7 Hz, 2H), 7.23 (d, J=2.7 Hz, 3H), 7.22 (d, J=2.1 Hz, 1H), 7.20 (t, J=1.4 Hz, 1H), 6.03 (dd, J=6.8, 5.0 Hz, 1H), 5.57-5.52 (m, 1H), 4.78 (t, J=5.3 Hz, 1H), 4.50 (dd, J=11.5, 5.0 Hz, 1H), 4.33 (dd, J=11.5, 6.8 Hz, 1H), 3.84 (ddd, J=11.6, 5.1, 2.2 Hz, 1H), 3.72 (s, 7H), 3.59 (ddd, J=11.6, 8.4, 5.5 Hz, 1H), 3.54-3.47 (m, 1H), 3.12 (ddd, J=8.5, 4.6, 2.2 Hz, 1H), 0.69 (d, J=6.3 Hz, 3H). $^{13}$C NMR (101 MHZ, DMSO-$d_6$) δ 164.93, 162.94, 158.12, 158.06, 150.58, 145.59, 139.93, 136.40, 136.10, 133.55, 129.74, 129.62, 129.12, 129.01, 128.77, 127.68, 127.64, 126.71, 113.03, 101.88, 85.88, 81.76, 81.60, 68.74, 63.36, 60.42, 54.98, 39.40, 39.18, 38.97, 15.50.

Synthesis of compound 8: To a solution of compound 7 (1.21 g, 1.81 mmol) in DCM (10 ml) and DIPEA (0.66 ml, 5.4 mmol) 1) was added 2-cyanoethyl N,N-diisopropylchlorophosphoramidite (0.695 ml, 2.2 mmol) at 0° C. The mixture was stirred at 0° C. for 2 h. The reaction mixture was diluted with CH$_2$Cl$_2$ (100 mL) then washed with saturated NaHCO$_3$ aqueous solution (100 mL). The organic layer was separated, dried over anhydrous Na$_2$SO$_4$, filtered and concentrated. The amidite 8 was precipitated out from hexane (1.33 g, 1.5 mmol, 85%). 31P NMR (202 MHz, CD$_3$CN) δ 148.81, 148.58.

Synthesis of compound 9: Standard succination of compound 7 using succinic anhydride and DMAP in CH$_2$Cl$_2$ followed by CPG loading using HBTU and DIPEA in DMF gives compound 9.

Synthesis of 5'-(R)-methyl-U-UNA Building Blocks

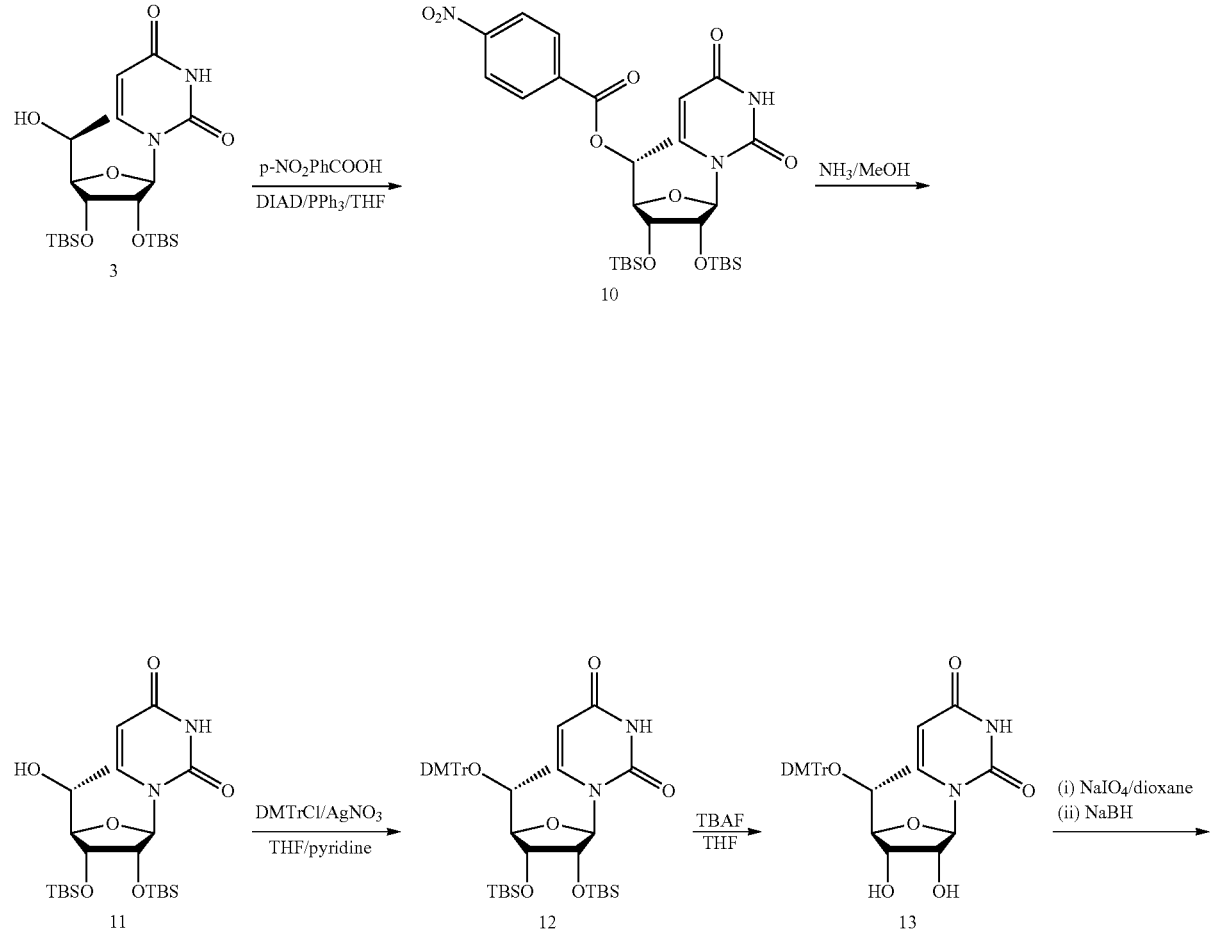

Scheme 4

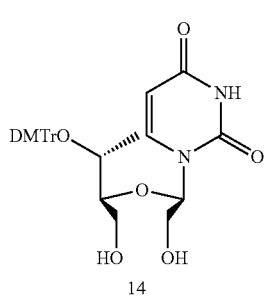

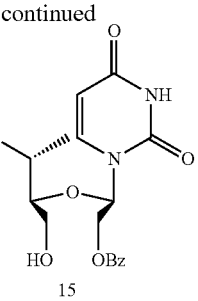

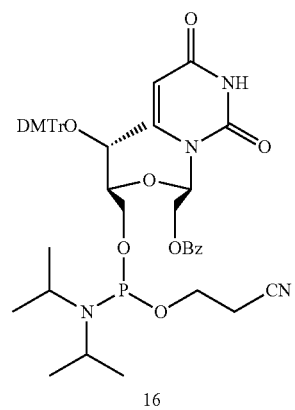

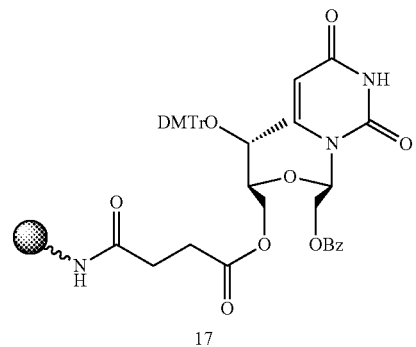

Synthesis of Compound 11: To a solution of compound 3 (2.36 g, 4.85 mmol) in anhydrous THF (48.5 mL), p-nitrobenzoic acid (4.05 g, 24.25 mmol, 5.0 eq), triphenylphosphine (6.36 g, 24.25 mmol, 5.0 eq) and DIAD (4.69 mL, 24.25 mmol, 5.0 eq) were added at 0° C. The reaction was allowed to stir at ambient temperature overnight. The solvent was removed under reduced pressure. The crude material was purified by flash column chromatography (0-25% EtOAc in hexanes) to obtain compound 10 as yellow-white foam (2.86 g, 4.50 mmol, $R_f$=0.37 developed in 33% EtOAc in hexanes). This material was resuspended in 7N ammonia in methanol solution (100 mL) and stirred at room temperature overnight. The solvent was removed and the crude material was purified by flash column chromatography (0-30% EtOAc in hexanes) to yield compound 11 as a white foam (1.47 g, 3.01 mmol, 62%, 2 step; $R_f$=0.27, developed with 33% EtOAc in hexanes). $^1$H NMR (400 MHz, DMSO-$d_6$) δ 11.37 (s, 1H), 7.85 (d, J=8.1 Hz, 1H), 5.89 (d, J=7.8 Hz, 1H), 5.71 (d, J=8.0 Hz, 1H), 5.19 (d, J=4.9 Hz, 1H), 4.30 (dd, J=7.8, 4.5 Hz, 1H), 4.21 (d, J=4.4 Hz, 1H), 3.82-3.73 (m, 1H), 3.62 (d, J=4.7 Hz, 1H), 1.11 (d, J=6.5 Hz, 3H), 0.89 (s, 9H), 0.81 (s, 9H), 0.10 (d, J=2.9 Hz, 6H), 0.00 (s, 3H), −0.09 (s, 3H). $^{13}$C NMR (101 MHz, DMSO-$d_6$) δ 162.78, 150.87, 140.66, 102.41, 90.00, 85.75, 73.90, 71.64, 66.39, 39.18, 25.69, 25.56, 20.08, 17.71, 17.57, −4.57, −4.63, −4.70, −5.22.

Synthesis of Compound 12: To a solution of compound 11 (1.40 g, 2.88 mmol) in anhydrous THF (11.5 mL) and anhydrous pyridine (2.2 mL), DMTrCl (2.92 g, 8.63 mmol, 3 eq) and AgNO$_3$ (0.97 g, 5.75 mmol, 2 eq) were added, and the mixture was stirred overnight at ambient temperature. The mixture was filtered over celite, and the filter cake was washed with DCM. The filtrate was concentrated under reduced pressure, and the residue was extracted with DCM and saturated aq. NaHCO$_3$. The organic layer was washed with brine, dried and filtered over anhydrous Na$_2$SO$_4$, and concentrated. The crude residue was purified by flash column chromatography (0-25% EtOAc in hexanes, 2% triethylamine) to obtain compound 12 as bright yellow foam (2.03 g, 2.57 mmol, 89%, $R_f$=0.27; developed with 33% EtOAc in hexanes). $^1$H NMR (400 MHz, DMSO-$d_6$) δ 11.38 (s, 1H), 7.46-7.38 (m, 2H), 7.30 (td, J=8.1, 7.7, 5.7 Hz, 7H), 7.26-7.17 (m, 1H), 6.94-6.84 (m, 4H), 5.66 (d, J=5.8 Hz, 1H), 5.31 (d, J=8.0 Hz, 1H), 4.11 (dd, J=4.6, 3.2 Hz, 1H), 4.06-4.02 (m, 1H), 3.86 (dd, J=4.6, 3.2 Hz, 1H), 3.74 (s, 6H), 3.49-3.41 (m, 1H), 0.85 (s, 9H), 0.82 (s, 8H), 0.79 (d, J=6.2 Hz, 3H), 0.06 (d, J=3.2 Hz, 5H), 0.01 (s, 3H), −0.08 (s, 3H). $^{13}$C NMR (101 MHZ, DMSO-$d_6$) δ 158.13, 158.09, 150.42, 141.13, 135.84, 130.07, 130.03, 127.75, 127.65, 126.66, 113.09, 113.04, 101.86, 88.28, 87.24, 86.16, 73.32, 71.44, 69.53, 55.00, 25.64, 25.54, 17.62, 17.54, 17.09, −4.45, −4.64, −4.86, −5.07.

Synthesis of Compound 13: To a solution of compound 12 (2.03 g, 2.57 mmol) in THF (12.9 mL), TBAF (5.14 g, 5.14 mmol, 2 eq) was added. After stirring at room temperature overnight, the solvent was removed under reduced pressure. The crude reside was pre-absorbed to silica gel (pretreated with 2% triethylamine) then purified via flash column chromatography (0-100% EtOAc in hexane then 2.5% MeOH in EtOAC, 2% triethylamine) to obtain compound 13 as a white foam (1.00 g, 1.78 mmol, 69%; $R_f$=0.45, developed with 5% MeOH in EtOAc). 1H NMR (400 MHZ, DMSO-$d_6$) δ 11.35 (d, J=2.1 Hz, 1H), 7.47-7.40 (m, 2H), 7.31 (ddd, J=10.1, 7.7, 3.8 Hz, 7H), 7.25-7.18 (m, 1H), 6.95-6.84 (m, 4H), 5.68 (d, J=5.9 Hz, 1H), 5.37 (d, J=5.8 Hz, 1H), 5.18 (dd, J=8.1, 2.0 Hz, 1H), 5.09 (d, J=5.5 Hz, 1H), 4.18 (q, J=5.3 Hz, 1H), 3.97 (q, J=5.9 Hz, 1H), 3.74 (s, 6H), 3.68 (dd, J=4.3, 3.1 Hz, 1H), 3.48-3.39 (m, 1H), 0.76 (d, J=6.4 Hz, 3H). $^{13}$C NMR (101 MHz, DMSO-$d_6$) δ 162.83, 158.10, 158.08, 150.61, 146.33, 140.77, 136.26, 136.16, 130.13, 130.09, 127.84, 127.69, 126.58, 113.10, 113.06, 101.65, 87.36, 86.92, 85.98, 72.53, 69.67, 68.96, 55.05, 55.03, 17.08.

Synthesis of Compound 14: To a solution of compound 13 (1.00 g, 1.78 mmol) in Dioxane (24 mL) and H$_2$O (3 mL), NaIO$_4$ (0.42 g, 1.96 mmol, 1.1 eq) dissolved in H$_2$O (3 mL) was added. The bi-layer reaction mixture was vigorously stirred at ambient temperature for 4 hours. The reaction mixture was filtered and the filter cake was washed with additional dioxane. To the filtrates was added NaBH$_4$ (0.074 g, 1.96 mmol, 1.1 eq). After stirring at ambient temperature for 2 hours, the mixture was cooled to 0° C. then quenched with 1:1 v/v AcOH:pyridine buffer. After the solvent was removed under reduced pressure, the crude residue was extracted with EtOAc and saturated aq. NaHCO$_3$. The organic layer was separated, dried over anhydrous Na$_2$SO$_4$, filtered, and concentrated under reduced pressure. The crude material was purified by flash column chromatography (0-5% MeOH in DCM, 2% triethylamine), to obtain compound 14 as a white foam (250 mg, 0.44 mmol, 25%; R$_f$=0.28 developed with 5% MeOH in DCM). $^1$H NMR (400 MHZ, DMSO-d$_6$) δ 11.22 (d, J=2.3 Hz, 1H), 7.65 (d, J=8.1 Hz, 1H), 7.37-7.30 (m, 2H), 7.29-7.14 (m, 8H), 6.90-6.77 (m, 4H), 5.65 (t, J=5.8 Hz, 1H), 5.53 (dd, J=8.0, 2.2 Hz, 1H), 5.10 (t, J=5.9 Hz, 1H), 4.64 (t, J=5.3 Hz, 1H), 3.73 (s, 7H), 3.63-3.43 (m, 3H), 3.30-3.14 (m, 2H), 3.04-2.95 (m, 1H), 1.23 (t, J=7.3 Hz, 1H), 0.77 (d, J=6.3 Hz, 3H). $^{13}$C NMR (101 MHZ, DMSO-d$_6$) δ 163.30, 157.97, 151.06, 145.81, 141.30, 136.45, 136.36, 129.91, 129.86, 127.90, 127.55, 126.48, 112.98, 112.96, 101.48, 85.79, 84.25, 83.07, 69.00, 61.65, 61.03, 54.98, 15.80, 1.12.

Synthesis of Compound 15: To a solution of compound 14 (4.63 g, 7.75 mmol) in anhydrous DCM (215 mL) and pyridine (1.5 mL), cooled to −78° C., benzoyl chloride (1.0 mL, 8.53 mmol) was added dropwise. After stirring at −78° C. for 1 hour, reaction mixture was brought to 0° C., and quenched with EtOH (5 mL). The mixture was extracted with DCM and saturated aq. NaHCO$_3$. The organic layer was washed with brine, separated, dried over anhydrous Na$_2$SO$_4$, filtered, and concentrated. The crude residue was purified by flash column chromatography (0-75% EtOAC in hexanes) to yield compound 15 as a white foam (2.30 g, 3.45 mmol, 45%; R$_f$=0.54, developed in 50% EtOAc in hexanes). $^1$H NMR (400 MHz, DMSO-d$_6$) δ 11.32 (d, J=2.2 Hz, 1H), 7.88 (dd, J=8.4, 1.4 Hz, 2H), 7.79 (d, J=8.0 Hz, 1H), 7.70-7.63 (m, 1H), 7.53 (t, J=7.8 Hz, 2H), 7.37-7.31 (m, 2H), 7.29-7.15 (m, 7H), 6.87-6.78 (m, 4H), 6.03 (dd, J=6.7, 5.0 Hz, 1H), 5.53 (dd, J=8.0, 2.1 Hz, 1H), 4.73 (t, J=5.1 Hz, 1H), 4.55 (dd, J=11.4, 5.0 Hz, 1H), 4.40 (dd, J=11.4, 6.8 Hz, 1H), 3.73 (s, 6H), 3.57 (qd, J=6.4, 1.8 Hz, 1H), 3.35-3.25 (m, 2H), 3.20 (dt, J=11.4, 5.0 Hz, 1H), 2.97-2.91 (m, 1H), 0.85 (d, J=6.3 Hz, 3H). $^{13}$C NMR (101 MHZ, DMSO-d$_6$) δ 164.96, 163.08, 158.02, 150.86, 145.75, 140.73, 136.37, 136.24, 133.60, 129.92, 129.85, 129.10, 129.05, 128.83, 127.88, 127.59, 126.54, 113.04, 113.00, 102.08, 85.92, 83.05, 81.25, 68.92, 63.63, 61.13, 55.00, 39.99, 15.74.

Synthesis of Compound 16: To a solution of compound 15 (2.30 g, 3.45 mmol) in DCM (30 ml) and DIPEA (2.30 ml, 18.9 mmol) was added 2-cyanoethyl N,N-diisopropylchlorophosphoramidite (2.41 ml, 7.57 mmol) at 0° C. The mixture was stirred at 0° C. for 2 h. The reaction mixture was diluted with CH$_2$Cl$_2$ (100 mL) then washed with saturated NaHCO$_3$ aqueous solution (100 mL). The organic layer was separated, dried over anhydrous Na$_2$SO$_4$, filtered and concentrated. The crude material was purified by flash column chromatography (0-33% ethyl acetate in hexane) to give phosphoramidite 16 (2.31 g, 2.66 mmol, 77%, R$_f$=0.41; developed with 50% ethyl acetate in hexanes). 31P NMR (202 MHz, CD$_3$CN) δ 148.78, 148.74.

Synthesis of compound 17: Standard succination of compound 15 using succinic anhydride and DMAP in CH$_2$Cl$_2$ followed by CPG loading using HBTU and DIPEA in DMF gives compound 17.

Synthesis of 4'-C-(β)-methoxy-U-UNA Building Blocks

Scheme 5

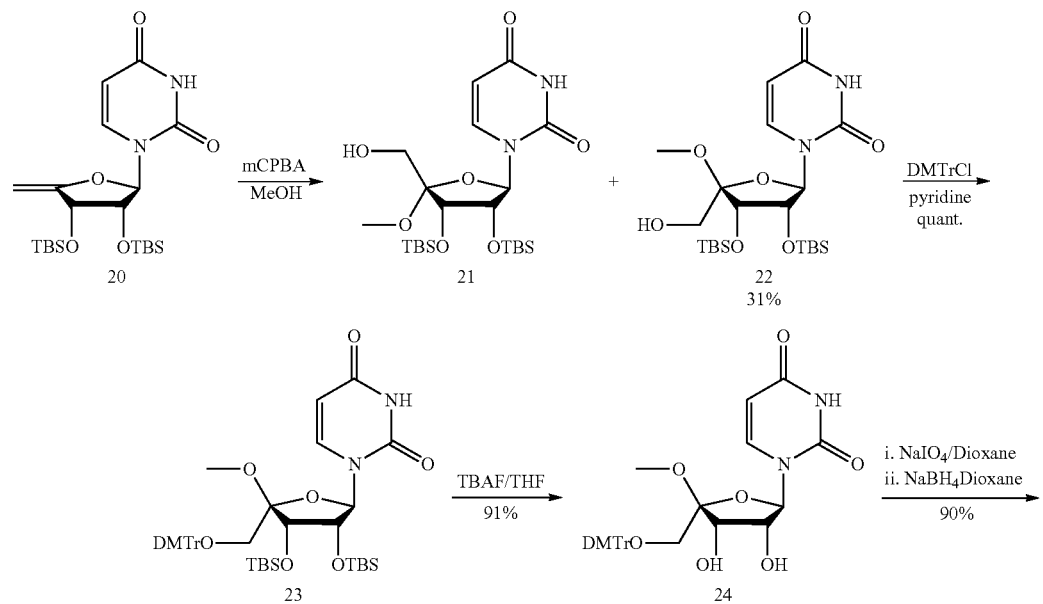

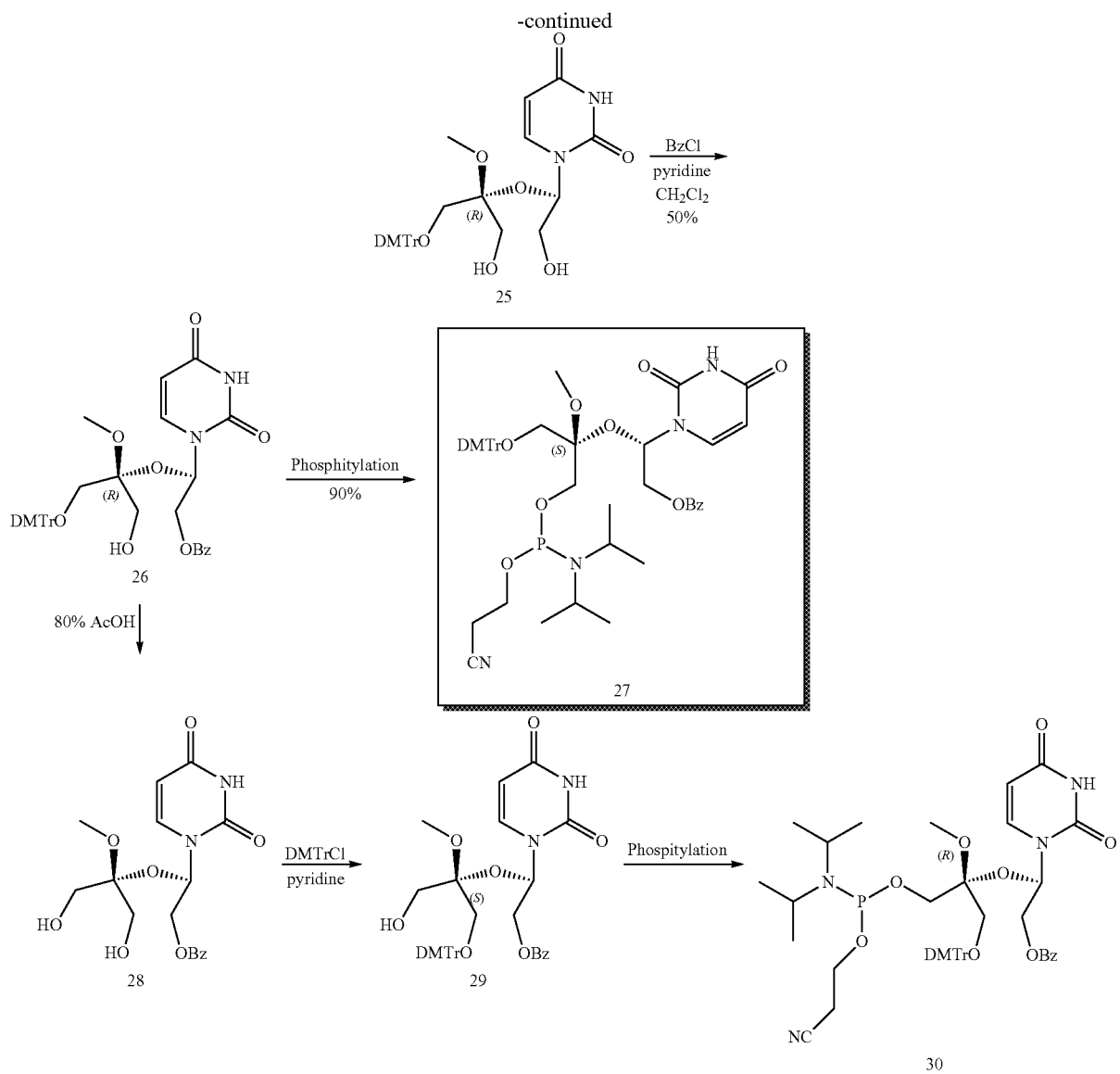

Synthesis of compound 21 and 22: mCPBA (19.9 g, 116 mmol) was added to a cooled solution of compound 1 (25.0 g, 55.9 mmol) in methanol (275 ml) and the mixture was stirred overnight at room temperature. About 100 ml each of 10% aqueous $Na_2S_2O_3$ (aq) and saturated aqueous $NaHCO_3$ was added to the solution and stirred for 15 minutes. The reaction mixture was then extracted with DCM (3× with 150 ml). The organic layers were combined, dried over sodium sulfate, filtered and concentrated. The crude material was purified by flash column chromatography (1.7% MeOH in DCM) to give compound 22 (8.8 g, 17.5 mmol, 31%, $R_f$=0.42; developed with 5% MeOH in DCM) and 21 (1.0 g, 1.9 mmol, 3.6%, $R_f$=0.48; developed with 5% MeOH in DCM). Compound 22: $^1H$ NMR (400 MHZ, DMSO-$d_6$) δ 11.44 (d, J=2.1 Hz, 1H), 7.42 (d, J=8.2 Hz, 1H), 6.01 (d, J=7.4 Hz, 1H), 5.81 (dd, J=8.1, 2.0 Hz, 1H), 4.74 (t, J=4.9 Hz, 1H), 4.56 (dd, J=7.4, 3.7 Hz, 1H), 4.00 (d, J=3.6 Hz, 1H), 3.55 (t, J=4.3 Hz, 2H), 3.31 (s, 1H), 3.29 (s, 3H), 0.86 (d, J=40.3 Hz, 18H), 0.12 (d, J=8.3 Hz, 6H), −0.01 (s, 3H), −0.09 (s 3H). $^{13}C$ NMR (126 MHZ, DMSO-$d_6$) δ 162.60, 150.98, 140.16, 109.53, 103.49, 86.14, 75.18, 74.91, 55.45, 48.85, 25.82, 25.77, 17.99, 17.77, 4.33, −4.39, −4.97, −5.10. Compound 21: 1H NMR (400 MHZ, DMSO-$d_6$) δ 11.41 (d, J=2.2 Hz, 1H), 7.76 (d, J=8.1 Hz, 1H), 5.99 (d, J=7.2 Hz, 1H), 5.73 (dd, J=8.4, 2.4 Hz, 1H), 5.34 (t, J=5.6 Hz, 1H), 4.32 (dd, J=7.2, 5.2 Hz, 1H), 4.22 (d, J=5.2 Hz, 1H), 3.54-3.41 (m, 2H), 3.30 (s, 3H), 0.90 (s, 9H), 0.80 (s, 9H), 0.07 (d, J=6.2 Hz, 6H), −0.01 (s, 3H), −0.10 (s, 3H). $^{13}C$ NMR (126 MHz, DMSO-$d_6$) δ 162.60, 150.98, 140.16, 109.53, 103.49, 86.14, 75.18, 74.91, 55.45, 48.85, 25.82, 25.77, 17.99, 17.77, −4.33, −4.39, −4.97, −5.10.

Synthesis of compound 23: To a solution of compound 22 (8.8 g, 17.5 mmol) in anhydrous pyridine (60 ml) was added DMTrCl (8.89 g, 26.3 mmol) and the mixture was stirred at room temperature overnight. After removing the solvent, the residue was extracted with DCM and saturated aq. $NaHCO_3$. The organic layer was dried over sodium sulfate, filtered and concentrated. The crude material was purified by flash column chromatography to give compound 23 (14.1 g. 17.9 mmol, 99%, $R_f$=0.77; developed in 50% EtOAC in Hexanes). $^1H$ NMR (400 MHz, DMSO-$d_6$) δ 11.46 (s, 1H), 7.61 (d, J=8.1 Hz, 1H), 7.46-7.37 (m, 2H), 7.33-7.23 (m, 6H), 7.22-7.15 (m, 1H), 6.86 (dd, J=9.0, 3.1 Hz, 4H), 6.01 (d, J=4.9 Hz, 1H), 5.80 (d, J=8.1 Hz, 1H), 4.43 (t, J=4.7 Hz, 1H), 4.03 (d, J=4.4 Hz, 1H), 3.71 (s, 6H), 3.65 (d, J=10.7 Hz, 1H), 3.45 (s, 3H), 2.88 (d, J=10.7 Hz, 1H), 0.71 (s, 8H), 0.63 (s, 8H), −0.03 (s, 3H), −0.04 (d, J=3.6 Hz, 6H), −0.19 (s, 3H). $^{13}$C NMR (126 MHz, DMSO-$d_6$) δ 158.07, 150.80, 144.86, 140.29, 135.71, 129.59, 129.57, 127.77, 127.55, 126.57, 113.20, 113.12, 108.03, 102.81, 88.51, 75.64, 74.36, 64.56, 54.97, 52.32, 25.63, 25.50, 17.51, 17.44, −4.33, −4.81, −4.86, −5.18.

Synthesis of compound 24: To a solution of compound 23 (12.1 g, 15.0 mmol) in THF (100 ml) was added 30 ml (30 mmol) of 1 M TBAF in THF. The reaction was stirred overnight under argon atmosphere and the next day the solvent was evaporated under vacuum. The crude material was purified with column chromatography in 2% MeOH in EtOAc to yield compound 24 (8.31 g, 14.4 mmol, 96%, $R_f$=0.48; developed with 10% MeOH in DCM). $^1$H NMR (400 MHZ, DMSO-$d_6$) δ 11.35 (s, 1H), 7.48-7.42 (m, 2H), 7.39 (d, J=8.2 Hz, 1H), 7.34-7.17 (m, 8H), 6.87 (d, J=8.9 Hz, 3H), 5.98 (d, J=7.4 Hz, 1H), 5.71 (d, J=5.1 Hz, 2H), 5.52 (d, J=6.7 Hz, 1H), 4.44 (td, J=7.2, 4.2 Hz, 1H), 4.05 (t, J=4.4 Hz, 1H), 3.72 (d, J=1.3 Hz, 7H), 3.44 (d, J=9.8 Hz, 1H), 3.31 (s, 3H), 2.83 (s, 4H), 2.80 (d, J=3.5 Hz, 1H), 1.98 (s, 1H).

Synthesis of compound 25: Compound 24 (7.28 g, 12.6 mmol) was dissolved in dioxane (85 ml) and water (15 ml). NaIO$_4$ (3.24 g, 15.2 mmol) was added slowly to this solution while stirring at room temperature. The reaction mixture was stirred at room temperature overnight then filtered and the precipitate was washed using 100 ml of additional dioxane. To the filtrate, NaBH$_4$ (0.500 g, 19.0 mmol) was added and the reaction mixture was again stirred at room temperature for 3 hours. The reaction was quenched with 20 ml of 1:1 mixture of pyridine and acetic acid. After removing the solvents, the residue was extracted with DCM and saturated aq. NaHCO$_3$. The organic layer was dried over sodium sulfate, filtered and concentrated. The crude material was purified by flash column chromatography (0-3% MeOH in DCM) to give compound 25 (5.40 g, 9.33 mol, 74%, $R_f$=0.26; developed with 5% MeOH in DCM). $^1$H NMR (400 MHZ, DMSO-$d_6$) δ 11.12 (s, 1H), 7.47 (d, J=8.0 Hz, 1H), 7.42-7.12 (m, 9H), 6.95-6.82 (m, 4H), 5.84 (t, J=5.8 Hz, 1H), 5.50 (d, J=8.0 Hz, 1H), 5.08 (s, 1H), 4.85 (t, J=3.9 Hz, 1H), 3.73 (s, 6H), 3.44 (dd, J=7.1, 3.9 Hz, 3H), 3.26 (d, J=9.7 Hz, 1H), 2.90 (s, 3H), 2.87 (d, J=9.6 Hz, 1H). $^{13}$C NMR (126 MHZ, DMSO-$d_6$) δ 163.40, 158.04, 150.41, 144.66, 141.80, 135.46, 135.09, 129.75, 129.70, 127.78, 127.66, 126.64, 113.15, 113.11, 102.82, 100.91, 75.32, 61.95, 59.63, 58.85, 54.99, 48.13, 45.55, 10.23.

Synthesis of compound 26: To a solution of compound 25 (4.7 g, 8.12 mmol) in DCM (175 ml) and pyridine (7 mL) at −78° C. was added a solution of BzCl (1.04 ml, 8.9 mmol) in DCM (50 mL) over a period of 30 min. The reaction mixture was then stirred for 1 hour at −78° C. and then allowed to room temperature, at which point 5 ml of ethanol was added to quench the reaction. The mixture was washed with 250 ml of NaHCO$_3$ and extracted 3 times with 100 ml of DCM. The organic layers were combined, dried over sodium sulfate and concentrated. Purification by column chromatography (0-3% MeOH in DCM) yielded compound 26 (2.73 g, 4.0 mmol, 49%, R$=0.30; developed with 5% MeOH in DCM). $^1$H NMR (400 MHZ, DMSO-$d_6$) δ 11.24 (s, 1H), 7.85-7.77 (m, 2H), 7.68 (d, J=8.1 Hz, 1H), 7.66-7.62 (m, 1H), 7.49 (t, J=7.8 Hz, 2H), 7.43-7.37 (m, 2H), 7.33-7.14 (m, 7H), 6.86 (d, J=8.9 Hz, 3H), 6.22 (t, J=6.2 Hz, 1H), 5.59 (d, J=8.1 Hz, 1H), 4.99 (t, J=4.2 Hz, 1H), 4.38 (d, J=6.1 Hz, 2H), 3.73 (dd, J=11.5, 4.1 Hz, 1H), 3.70 (s, 6H), 3.47 (dd, J=11.5, 4.1 Hz, 1H), 3.26 (d, J=9.9 Hz, 1H), 2.98 (d, J=10.2 Hz, 1H), 2.96 (s, 3H). $^{13}$C NMR (126 MHz, DMSO-$d_6$) δ 164.86, 163.13, 158.07, 150.30, 144.52, 141.08, 135.23, 135.01, 133.62, 129.72, 129.70, 129.07, 128.89, 128.79, 127.81, 127.63, 126.68, 113.16, 113.13, 103.38, 101.72, 85.40, 72.77, 63.73, 59.64, 59.36, 54.96, 48.56.

Synthesis of compound 27: To a solution of compound 26 (2.58 g, 3.77 mmol) in DCM (20 ml) was added DIPEA (1.38 ml, 11.31 mmol) and 2-cyanoethyl N,N-diisopropylchlorophosphoramidite (1.32 ml, 4.15 mmol) at 0° C. The reaction mixture was allowed to room temperature and stirred for 3 h. The reaction mixture was diluted with CH$_2$Cl$_2$ (100 mL) then washed with saturated NaHCO$_3$ aqueous solution (100 mL). The organic layer was separated, dried over anhydrous Na$_2$SO$_4$, filtered and concentrated. Pure compound 27 (3.89 g, 4.4 mmol, quant) was obtained by precipitating the crude mixture, dissolved in minimal DCM in 1 L of hexane. Solids were collected by dissolving in DCM and then concentrated to white foam. 31P NMR (202 MHz, CD$_3$CN) δ 148.70, 148.68.

Synthesis of compound 28: Compound 27 (2.43 g, 3.56 mmol) was treated with 80% AcOH (80 mL). After removing the solvent, the residue was purified by flash column chromatography (1.1 g, 2.89 mmol, 81%).

Synthesis of compound 29: Compound 29 is synthesized using standard conditions with DMTrCl and pyridine, as described for compound 23.

Synthesis of compound 30: Compound 30 is synthesized using standard conditions for phosphitylation, as described for compound 27.

Synthesis of 2'-methyl-U-UNA Building Blocks

Scheme 5

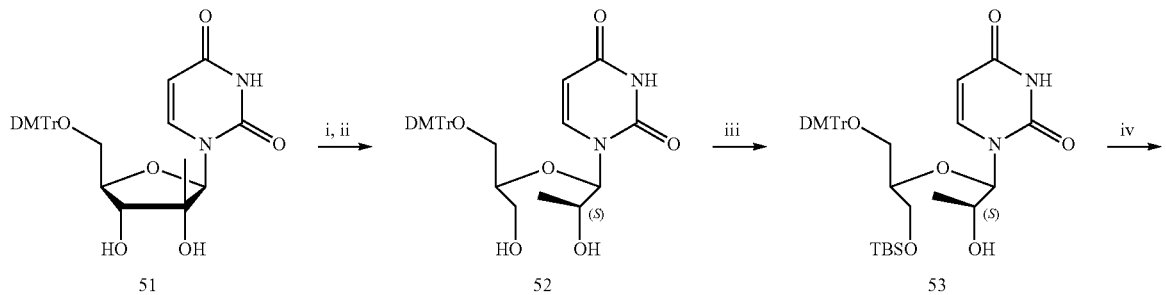

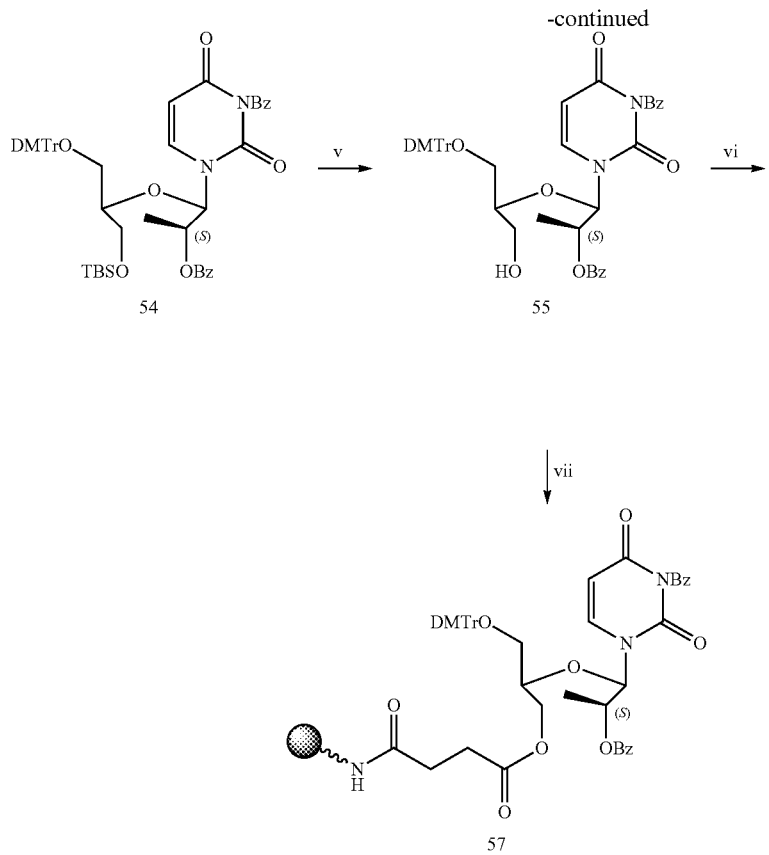

Reagents and conditions: (i) NaIO₄/H₂O/DCM, rt, 4 h; (ii) RuCl(p-cymene)[(S,S)-Ts-DPEN]/HCOONa/H₂O/AcOEt, rt, 12 h, 80% over 2 steps; (iii) TBSCl/Pyridine, rt, 3 h, 64%; (iv) BzCl/Et₃N/DCM, rt, 4 h, 90%; (v) NEt₃•HF/THF, rt, 8 h, 96%; (vi) 2-cyanoethyl N,N-diisopropylchlorophosphoramidite/DIEA/DCM, 1 h, 87%; (vii) (a) succinic anhydride/DMAP/CH₂Cl₂ (b) aminoalkyl CPG/HBTU/DIEA/DM.

Synthesis of compound 52: To a solution of compound 51 (500 mg, 0.893 mmol) in DCM (10 mL) was added NaIO₄ (287 mg, 1.34 mmol) in H₂O (10 mL). The resulting mixture was vigorously stirred for 4 h, the reaction completion was checked by TLC. The organic layer was separated and evaporated in vacuo. The resulting keto-aldehyde colorless foam was used for next step without further purification. A round-bottom flask was charged with η6-(p-cymene)-(S,S)—N-toluenesulfonyl-1,2-diphenylethylenediamine (1-)ruthenium (II) chloride (15 mg, 0.024 mmol, 2.5 mol %) and the keto-aldehyde (500 mg, 0.893 mmol), and the system was flushed with Ar 3 times. A solution of sodium formate (2.27 g, 33.3 mmol) in water (13 mL) was added, followed by ethyl acetate (3 mL). The resulting two-phase mixture was vigorously stirred for 24 h at room temperature. The organic phase was separated, and the aqueous phase was extracted with another 10 mL of ethyl acetate. The solvent was removed from the combined organic layers at reduced pressure on a rotary evaporator. The crude residue was purified by flash column chromatography on silica gel to afford compound 52 as a colorless foam (401 mg, 80% over 2 steps). $^1$H NMR (400 MHz, DMSO-$d_6$): δ 11.34 (s, 1H), 7.60 (d, J=8.0 Hz, 1H), 7.37-7.08 (m, 9H), 6.85 (d, J=8.4 Hz, 4H), 5.48 (dd, J=15.5, 6.5 Hz, 2H), 5.08 (d, J=5.3 Hz, 1H), 4.72 (s, 1H), 3.72 (s, 7H), 3.55 (s, 3H), 3.10 (s, 2H), 1.03 (d, J=6.4 Hz, 3H). $^{13}$C NMR (126 MHZ, DMSO-$d_6$) δ 163.21, 157.99, 151.08, 144.81, 141.57, 135.61, 135.51, 129.61, 129.57, 127.75, 127.63, 126.59, 113.12, 113.09, 101.20, 86.46, 85.50, 79.54, 67.11, 63.64, 60.44, 59.75, 54.99, 39.23, 18.38, 14.09. HRMS; [M+Na]⁺ calc. for $C_{31}H_3N_2O_8Na$, 585.2213; found: 585.2224.

Synthesis of compound 53: To a solution of compound 52 (520 mg, 0.925 mmol) in dry pyridine (10 mL) was added TBSCI (154 mg, 1.02 mmol) and DMAP (11 mg, 0.09 mmol). The reaction mixture was stirred for 3 h at room temperature and then the resulting mixture was diluted with DCM. The reaction was quenched with saturated aq. NaHCO₃. The organic layer was separated, washed with brine and concentrated in vacuo. The crude residue was purified by flash column chromatography on silica gel to afford compound 53 as a colorless foam (400 mg, 64%). 1H NMR (400 MHZ, DMSO-$d_6$) δ 11.34 (d, J=2.0 Hz, 1H), 7.62 (d, J=8.0 Hz, 1H), 7.45-7.06 (m, 9H), 7.00-6.69 (m, 4H), 5.62-5.31 (m, 2H), 4.98 (d, J=5.9 Hz, 1H), 3.73 (ddd, J=41.8, 11.1, 5.2 Hz, 8H), 3.60-3.38 (m, 2H), 3.05 (d, J=5.1 Hz, 2H), 1.05 (d, J=6.3 Hz, 3H), 0.74 (s, 9H), −0.07 (d, J=6.9 Hz, 6H). $^{13}$C NMR (126 MHz, DMSO-$d_6$) δ 163.21, 158.01, 151.07, 144.76, 141.61, 135.59, 135.41, 129.56, 129.54, 127.71, 127.57, 126.57, 113.09, 113.06, 101.02, 85.92, 85.61, 78.31, 66.87, 63.36, 61.41, 54.96, 25.58, 18.56, 17.70, −5.65, −5.69. HRMS; [M+Na]⁺ calc. for $C_{37}H_{48}N_2O_8SiNa$, 699.3078; found: 699.3067.

Synthesis of compound 54: To a solution of compound 53 (6.6 g, 9.76 mmol) in dry DCM (100 mL) were added Et₃N (13.5 mL, 97.6 mmol) and BzCl (5.6 mL, 48.8 mmol). The reaction mixture was stirred for 4 h at room temperature and then the resulting mixture was diluted with DCM. The reaction was quenched with saturated aq. NaHCO$_3$. The organic layer was separated, washed with brine and concentrated in vacuo. The crude residue was purified by flash column chromatography on silica gel to afford compound 54 as a colorless foam (7.8 g, 90%). 1H NMR (400 MHZ, DMSO-de) δ 8.07-7.11 (m, 20H), 6.98-6.69 (m, 4H), 6.02 (d, J=4.6 Hz, 1H), 5.69-5.27 (m, 2H), 3.81-3.42 (m, 9H), 3.17 (qd, J=10.7, 4.4 Hz, 2H), 1.37 (d, J=6.5 Hz, 3H), 0.71 (s, 9H), −0.10 (d, J=12.1 Hz, 6H). $^{13}$C NMR (126 MHz, DMSO-d$_6$) δ 169.19, 165.01, 161.61, 158.08, 149.35, 144.66, 141.00, 135.57, 135.52, 135.30, 133.60, 130.92, 130.23, 129.62, 129.47, 129.23, 129.18, 128.73, 127.78, 127.63, 126.71, 113.14, 113.11, 101.19, 85.91, 84.66, 78.65, 69.99, 63.23, 61.81, 54.96, 25.54, 17.67, 14.99, −5.76. HRMS; [M+Na]$^+$ calc. for C$_{51}$H$_{56}$N$_2$O$_{10}$SiNa, 907.3602; found: 907.3611.

Synthesis of compound 55: To a solution of compound 54 (7.3 g, 8.25 mmol) in dry THF (83 mL) was added Et$_3$N·3HF (13.4 mL, 82.5 mmol) dropwisely. The reaction mixture was stirred for 8 h at room temperature then diluted with AcOEt and quenched with saturated aq. NaHCO$_3$. The organic layer was separated, washed with brine and concentrated in vacuo. The crude residue was purified by flash column chromatography on silica gel to afford compound 55 as a colorless foam (6.1 g, 96%). $^1$H NMR (400 MHZ, DMSO-d$_6$) δ 8.05-7.11 (m, 20H), 7.04-6.67 (m, 4H), 6.04 (d, J=3.9 Hz, 1H), 5.67-5.25 (m, 2H), 4.85 (t, J=5.1 Hz, 1H), 3.72-3.70 (m, 7H), 3.60-3.38 (m, 2H), 3.18 (qd, J=10.7, 5.1 Hz, 2H), 1.39 (d, J=6.5 Hz, 3H). $^{13}$C NMR (126 MHz, DMSO-d$_6$) δ 169.19, 165.10, 161.60, 158.05, 149.26, 144.64, 141.00, 135.56, 135.50, 135.37, 133.56, 130.95, 130.19, 129.65, 129.47, 129.21, 129.17, 128.73, 127.78, 127.70, 126.72, 113.14, 113.12, 100.84, 85.83, 84.54, 79.12, 70.06, 63.63, 60.48, 54.97, 14.94. HRMS; [M+Na]$^+$ calc. for C$_{45}$H$_{42}$N$_2$O$_{10}$Na, 793.2737; found: 793.2724.

Synthesis of compound 56: To a solution of compound 55 (568 mg. 0.737 mmol) in dry DCM 8 mL were added DIPEA (385 μL, 2.21 mmol) and 2-cyanoethylchloro-N,N-diisopropylphosphoramidite (181 μL, 0.811 mmol) dropwisely. The reaction mixture was stirred for 1 h at room temperature, then diluted with DCM and quenched the reaction with saturated aq. NaHCO$_3$. The organic layer was separated, washed with brine and concentrated in vacuo. The crude residue was purified by flash column chromatography on silica gel to afford compound 56 as a colorless foam (623 mg, 87%). $^1$H NMR (500 MHZ, Acetonitrile-d$_3$) δ 8.09-7.89 (m, 4H), 7.86-7.13 (m, 16H), 6.95-6.74 (m, 4H), 6.01 (dd, J=8.7, 3.7 Hz, 1H), 5.45 (dtt, J=21.1, 8.2, 4.1 Hz, 2H), 3.90-3.60 (m, 11H), 3.51 (ddq, J=13.5, 10.3, 6.7 Hz, 2H), 3.44-3.10 (m, 2H), 2.54 (dt, J=8.8, 5.9 Hz, 2H), 1.44 (t, J=6.2 Hz, 3H), 1.32-0.93 (m, 12H). $^{13}$C NMR (101 MHz, Acetonitrile-d$_3$) δ 169.12, 165.27, 161.69, 158.37, 149.44, 144.58, 140.43, 135.10, 133.09, 131.14, 129.94, 129.69, 129.67, 129.39, 129.11, 128.33, 127.69, 127.54, 126.57, 118.12, 116.96, 112.76, 112.75, 100.82, 84.61, 69.86, 54.58, 42.58, 42.46, 23.67, 23.62, 23.55, 23.48, 19.68, 19.62. $^{31}$P NMR (202 MHZ, Acetonitrile-d$_3$) δ 149.67; 149.29.HRMS; [M+H]$^+$ calc. for C$_{54}$H$_{60}$N$_4$O$_{11}$P, 971.3996; found: 971.3989.

Synthesis of compound 57: Standard succination of compound 55 using succinic anhydride and DMAP in CH$_2$Cl$_2$ followed by CPG loading using HBTU and DIPEA in DMF gives compound 57.

Synthesis of 2'-(R)-methyl-U-UNA Building Blocks

Scheme 7

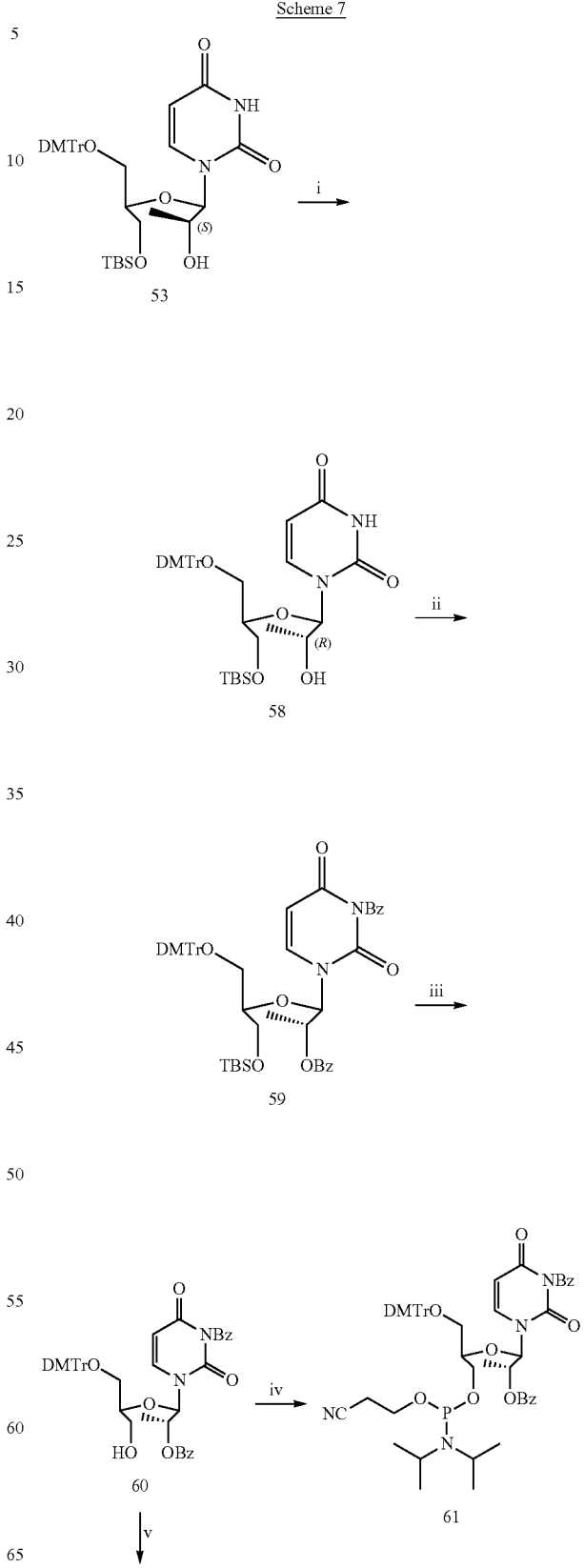

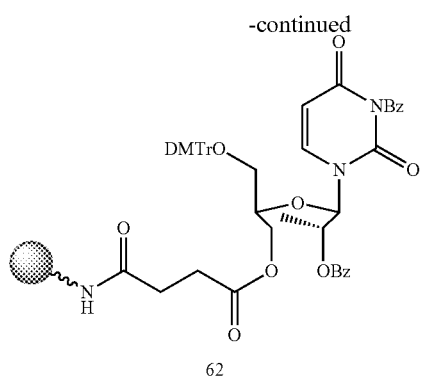

62

Reagents and conditions:
(i) BzOH, DIAD, PPh₃, THF, rt, 3 h; NaOH aq., rt, 3 h, 80%;
(ii) BzCl, Et₃N, DCM, rt, 4 h, 92%;
(iii) NEt₃•HF, THF, rt, 8 h, 97%;
(iv) 2-cyanoethyl N,N-diisopropylchlorophosphoramidite, DIEA, DCM, 1 h, 80%;
(v) (a) succinic anhydride/DMAP/CH₂Cl₂
  (b) aminoalkyl CPG/HBTU/DIEA/DMF.

Synthesis of compound 58: To a solution of compound 53 (2.2 g, 3.25 mmol) in dry THE 100 mL were added PPh3 (4.26 g, 16.3 mmol), BzOH (1.98 g, 16.3 mmol) and DIAD (3.15 mL, 16.3 mmol) dropwisely. The reaction mixture was stirred for 3 h at room temperature, the reaction completion was checked by TLC. The solvent was removed in vacuo. The crude residue was purified by flash column chromatography on silica gel to afford a mixture of 2,2'-anhydronucleoside and DIAD byproducts. This mixture was dissolved in THF (50 mL). To the solution of mixture was added IN aq. NaOH (10 mL) dropwisely. Resulting mixture was stirred for 3 h. The solvent was removed in vacuo. The crude residue was purified by flash column chromatography on silica gel to afford compound 58 as a colorless foam (1.8 g, 80%). $^{1}$H NMR (400 MHZ, DMSO-$d_6$) δ 11.30 (d, J=2.1 Hz, 1H), 7.62 (d, J=8.1 Hz, 1H), 7.43-7.04 (m, 9H), 6.96-6.65 (m, 4H), 5.60-5.40 (m, 2H), 5.07 (d, J=5.4 Hz, 1H), 3.96-3.44 (m, 10H), 3.11-2.77 (m, 2H), 1.14 (d, J=6.2 Hz, 3H), 0.75 (s, 9H), −0.05 (s, 6H). $^{13}$C NMR (126 MHz, DMSO-$d_6$) δ 163.22, 158.00, 157.99, 151.78, 144.75, 141.42, 135.58, 135.38, 129.51, 129.46, 127.70, 127.53, 126.56, 113.10, 113.06, 101.70, 86.25, 85.44, 77.71, 66.11, 63.07, 61.51, 54.96, 25.59, 19.72, 17.73, −5.66, −5.68. HRMS; [M+Na]$^+$ calc. for $C_{37}H_{48}N_2O_8SiNa$, 699.3078; found: 699.3099.

Synthesis of compound 59: To a solution of compound 58 (3.3 g, 4.88 mmol) in dry DCM (50 mL) were added Et₃N (6.8 mL, 48.8 mmol) and BzCl (2.8 mL, 24.4 mmol). The reaction mixture was stirred for 4 h at room temperature and then the resulting mixture was diluted with DCM. The reaction was quenched with saturated aq. NaHCO₃. The organic layer was separated, washed with brine and concentrated in vacuo. The crude residue was purified by flash column chromatography on silica gel to afford compound 59 as a colorless foam (4.0 g, 92%). $^{1}$H NMR (400 MHz, DMSO-$d_6$) δ 8.11-7.76 (m, 3H), 7.76-7.56 (m, 4H), 7.48 (t, J=7.7 Hz, 2H), 7.39-7.02 (m, 11H), 7.08-6.69 (m, 4H), 6.03 (d, J=7.1 Hz, 1H), 5.83 (d, J=8.2 Hz, 1H), 5.40 (p, J=6.4 Hz, 1H), 3.70 (s, 9H), 3.19-2.93 (m, 2H), 1.41 (d, J=6. Hz, 3H), 0.75 (s, 9H), −0.06 (d, J=1.4 Hz, 6H). $^{13}$C NMR (101 MHZ, DMSO-$d_6$) δ 164.48, 161.58, 158.07, 158.05, 149.77, 141.63, 135.50, 135.42, 135.31, 133.72, 130.77, 129.81, 129.61, 129.55, 129.34, 129.21, 128.99, 128.87, 127.77, 127.58, 126.66, 113.16, 113.12, 102.04, 85.74, 78.75, 70.38, 62.97, 61.91, 54.96, 39.97, 25.59, 17.71, 16.19, −5.67, −5.71. HRMS; [M+Na]$^+$ calc. for $C_{51}H_{56}N_2O_{10}SiNa$, 907.3602; found: 907.3616.

Synthesis of compound 60: To a solution of compound 60 (3.8 g, 4.30 mmol) in dry THF (43 mL) was added Et₃N·3HF (6.98 mL, 43.0 mmol) dropwisely. The reaction mixture was stirred for 8 h at room temperature and then the resulting mixture was diluted with DCM. The reaction was quenched with saturated aq. NaHCO₃. The organic layer was separated, washed with brine and concentrated in vacuo. The crude residue was purified by flash column chromatography on silica gel to afford compound 60 as a colorless foam (3.2 g, 97%). $^{1}$H NMR (400 MHZ, DMSO-$d_6$) δ 7.96 (dd, J=8.2, 1.4 Hz, 1H), 7.90 (dt, J=8.3, 1.4 Hz, 2H), 7.74-7.61 (m, 4H), 7.48 (t, J=7.7 Hz, 2H), 7.40-7.16 (m, 11H), 6.86 (d, J=8.4 Hz, 4H), 6.03 (dd, J=7.1, 2.0 Hz, 1H), 5.84 (d, J=8.1 Hz, 1H), 5.46-5.34 (m, 1H), 4.86 (td, J=5.1, 1.7 Hz, 1H), 3.66-3.62 (m, 7H), 3.52 (s, 2H), 3.21-3.01 (m, 2H), 1.48-1.37 (m, 3H). $^{13}$C NMR (101 MHZ, DMSO-$d_6$) δ 169.14, 164.53, 161.60, 158.03, 158.01, 149.76, 144.74, 141.66, 135.50, 135.43, 133.70, 130.82, 129.80, 129.65, 129.57, 129.35, 129.22, 129.02, 128.87, 127.78, 127.64, 126.65, 113.15, 113.13, 101.94, 85.62, 84.94, 79.38, 70.53, 63.44, 60.51, 54.96, 16.33, 14.07. HRMS; [M+Na]$^+$ calc. for $C_{45}H_{42}N_2O_{16}Na$, 793.2737; found: 793.2742.

Synthesis of compound 61: To a solution of compound 60 (543 mg, 0.705 mmol) in dry DCM (7 mL) were added DIPEA (368 μL, 2.12 mmol) and 2-cyanoethylchloro-N,N-diisopropylphosphoramidite (173 μL, 0.776 mmol) dropwisely. The reaction mixture was stirred for 1 h at room temperature and then the resulting mixture was diluted with DCM. The reaction was quenched with saturated aq. NaHCO₃. The organic layer was separated, washed with brine and concentrated in vacuo. The crude residue was purified by flash column chromatography on silica gel to afford compound 61 as a colorless foam (549 mg, 80%). $^{1}$H NMR (500 MHz, Acetonitrile-$d_3$) δ 7.95 (ddd, J=8.4, 2.7, 1.4 Hz, 2H), 7.81-7.56 (m, 5H), 7.52-7.35 (m, 4H), 7.35-7.16 (m, 9H), 6.90-6.77 (m, 4H), 6.04 (dd, J=8.7, 6.8 Hz, 1H), 5.39 (dt, J=11.2, 6.5 Hz, 1H), 3.86-3.61 (m, 11H), 3.62-3.40 (m, 2H), 3.33-3.11 (m, 2H), 2.56 (q, J=5.9 Hz, 2H), 1.45 (dd, J=6.4, 3.9 Hz, 3H), 1.30-0.97 (m, 12H). $^{13}$C NMR (101 MHz, Acetonitrile-$d_3$) δ 166.05, 163.01, 159.76, 151.29, 146.07, 142.03, 142.00, 136.94, 136.84, 136.31, 134.59, 132.37, 131.05, 131.01, 130.97, 130.67, 130.56, 130.44, 129.82, 129.04, 128.91, 127.92, 119.52, 118.35, 114.16, 114.14, 103.32, 87.38, 86.03, 71.83, 71.78, 64.57, 55.98, 44.01, 43.90, 43.88, 25.11, 25.09, 25.02, 24.99, 24.96, 24.89, 21.10, 21.03, 17.08, 17.04, 2.01, 1.80, 1.67. $^{31}$P NMR (202 MHz, Acetonitrile-$d_3$) δ 149.61, 149.29. HRMS; [M+H]$^+$ calc. for $C_{54}H_{60}NO_{11}P$, 971.3996; found: 971.3967.

Synthesis of compound 62: Standard succination of compound 60 using succinic anhydride and DMAP in CH₂Cl₂ followed by CPG loading using HBTU and DIPEA in DMF gives compound 62.

Synthesis of 2'-methyl-U-UNA Mosher Esters

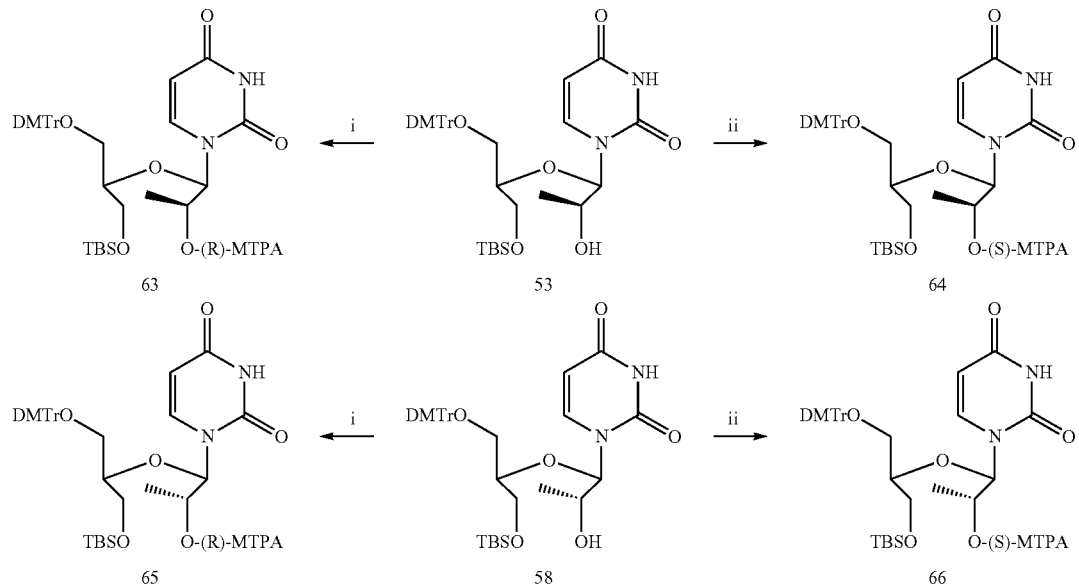

Reagents and conditions: (i) (S)-MTPACl/DMAP/ET₃N/MeCN, rt, 5 h, 52-77%; (ii) (R)-MTPACl/DMAP/Et₃N/MeCN, rt, 5 h, 54-78%.

Synthesis of compound 63: To a solution of compound 53 (100 mg, 0.148 mmol), DMAP (1.8 mg, 0.02 mmol), Et₃N (103μ, 0.740 mmol) in dry MeCN (2 mL) was added(S)-(+)-MTPACl (33.2 μL, 0.178 mmol) dropwisely. The reaction mixture was stirred for 5 h at room temperature and then the resulting mixture was diluted with AcOEt. The reaction was quenched with saturated aq. NaHCO₃. The organic layer was separated, washed with brine and concentrated in vacuo. The crude residue was purified by flash column chromatography on silica gel to afford compound 63 as a colorless foam (68 mg, 52%). ¹H NMR (400 MHZ, DMSO-d₆) δ 11.44 (s, 1H), 7.60-7.08 (m, 15H), 6.84 (dd, J=8.9, 3.5 Hz, 4H), 5.86 (d, J=5.9 Hz, 1H), 5.48-5.19 (m, 2H), 3.72 (s, 6H), 3.51-3.34 (m, 5H), 2.93 (t, J=4.4 Hz, 3H), 1.31 (d, J=6.4 Hz, 3H), 0.69 (s, 9H), −0.15 (d, J=9.4 Hz, 6H). ¹³C NMR (126 MHZ, DMSO-d₆) δ 165.03, 162.83, 158.02, 150.90, 144.65, 139.94, 135.42, 135.24, 131.20, 129.81, 129.56, 128.41, 127.68, 127.52, 126.85, 126.59, 113.06, 113.03, 102.06, 85.63, 82.96, 77.67, 72.79, 63.22, 61.07, 55.35, 54.95, 39.23, 25.48, 17.59, 15.09, −5.78, −5.84. HRMS; [M+Na]⁺ calc. for $C_{47}H_{55}F_3N_2O_{10}SiNa$, 915.3476; found: 915.3485.

Synthesis of compound 64: To a solution of compound 53 (100 mg, 0.148 mmol), DMAP (1.8 mg, 0.02 mmol), Et₃N (103 μL, 0.740 mmol) in dry MeCN (2 mL) was added (R)-(−)-MTPACl (33.2 μL, 0.178 mmol) dropwisely. The reaction mixture was stirred for 5 h at room temperature and then the resulting mixture was diluted with AcOEt. The reaction was quenched with saturated aq. NaHCO₃. The organic layer was separated, washed with brine and concentrated in vacuo. The crude residue was purified by flash column chromatography on silica gel to afford compound 64 as a colorless foam (70 mg, 54%). ¹H NMR (400 MHZ, DMSO-d₆) δ 11.48 (s, 1H); 7.65 (d, J=8.1 Hz, 2H), 7.53-7.02 (m, 13H), 6.94-6.65 (m, 4H), 5.88 (d, J=6.0 Hz, 1H), 5.56-5.27 (m, 2H), 3.87-3.44 (m, 9H), 3.31 (s, 3H), 3.04 (t, J=4.0 Hz, 2H), 1.20 (d, J=6.4 Hz, 3H), 0.68 (s, 9H), −0.15 (d, J=7.4 Hz, 6H). ¹³C NMR (126 MHz, DMSO-d₆) δ 158.04, 150.98, 144.67, 135.45, 135.25, 129.94, 129.58, 128.53, 127.71, 127.54, 127.16, 126.61, 113.09, 113.06, 102.30, 77.77, 72.94, 63.27, 61.25, 55.19, 54.97, 39.06, 25.50, 17.62, 14.76, −5.83, −5.86. HRMS; [M+Na]⁺ calc. for $C_{47}H_{55}F_3N_2O_{10}SiNa$, 915.3476; found: 915.3484.

Synthesis of compound 65: To a solution of compound 58 (100 mg. 0.148 mmol), DMAP (1.8 mg, 0.02 mmol), Et₃N (103 μL, 0.740 mmol) in dry MeCN (2 mL) was added(S)-(+)-MTPACl (33.2 μL, 0.178 mmol) dropwisely. The reaction mixture was stirred for 5 h at room temperature and then the resulting mixture was diluted with AcOEt. The reaction was quenched with saturated aq. NaHCO₃. The organic layer was separated, washed with brine and concentrated in vacuo. The crude residue was purified by flash column chromatography on silica gel to afford compound 65 as a colorless foam (101 mg, 77%). ¹H NMR (400 MHz, DMSO-d₆) δ 11.47 (d, J=2.0 Hz, 1H), 7.67 (d, J=8.1 Hz, 1H), 7.56-7.04 (m, 14H), 6.94-6.71 (m, 4H), 5.98 (d, J=7.1 Hz, 1H), 5.62-5.23 (m, 2H), 3.71 (s, 6H); 3.68-3.44 (m, 2H), 3.36 (s, 3H), 3.01 (t, J=5.4 Hz, 2H), 1.30 (d, J=6.2 Hz, 3H), 0.74 (s, 9H), −0.06 (d, J=2.7 Hz, 6H). ¹³C NMR (126 MHz, DMSO-d₆) δ 164.68, 162.88, 158.01, 151.25, 144.68, 140.54, 135.48, 135.29, 131.12, 129.96, 129.51, 129.45, 128.61, 127.72, 127.49, 126.86, 126.60, 113.11, 113.07, 102.47, 78.80, 72.30, 62.90, 61.80, 55.01, 54.96, 25.56, 17.68, 15.69, −5.71. HRMS; [M+Na]⁺ calc. for $C_{47}H_{55}F_3N_2O_{10}SiNa$, 915.3476; found: 915.3460.

Synthesis of compound 66: To a solution of compound 58 (100 mg. 0.148 mmol), DMAP (1.8 mg, 0.02 mmol), Et₃N (103 μL, 0.740 mmol) in dry MeCN (2 mL) was added (R)-(−)-MTPACl (33.2 μL, 0.178 mmol) dropwisely. The reaction mixture was stirred for 5 h at room temperature and then the resulting mixture was diluted with AcOEt. The reaction was quenched with saturated aq. NaHCO$_3$. The organic layer was separated, washed with brine and concentrated in vacuo. The crude residue was purified by flash column chromatography on silica gel to afford compound 66 as a colorless foam (102 mg, 78%). $^1$H NMR (400 MHz, DMSO-d$_6$) δ 11.28 (d, J=2.0 Hz, 1H), 7.56-7.02 (m, 15H), 6.98-6.71 (m, 4H), 5.89 (d. J=7.3 Hz, 1H), 5.54-5.29 (m, 2H), 3.72 (d, J=1.3 Hz, 6H), 3.67-3.44 (m, 3H), 3.40 (s, 3H); 3.11-2.85 (m, 2H), 1.39 (d, J=6.2 Hz, 3H), 0.75 (s, 9H), −0.06 (d, J=1.9 Hz, 6H). $^{13}$C NMR (126 MHZ, DMSO-d$_6$) δ 164.54, 162.83, 158.02, 158.00, 151.10, 144.68, 135.50, 135.31, 131.00, 129.90, 129.49, 129.43, 128.57, 127.71, 127.49, 126.71, 126.58, 113.12, 113.07, 102.39, 85.54, 78.70, 71.71, 62.82, 61.77, 55.17, 54.97, 39.25, 25.57, 17.70, 16.08, −5.70, −5.72. HRMS; [M+Na]$^+$ calc. for C$_{47}$H$_{55}$F$_3$N$_2$O$_{10}$SiNa, 915.3476; found: 915.3466.

Synthesis of 3'-(S)-methyl-U-UNA Building Blocks

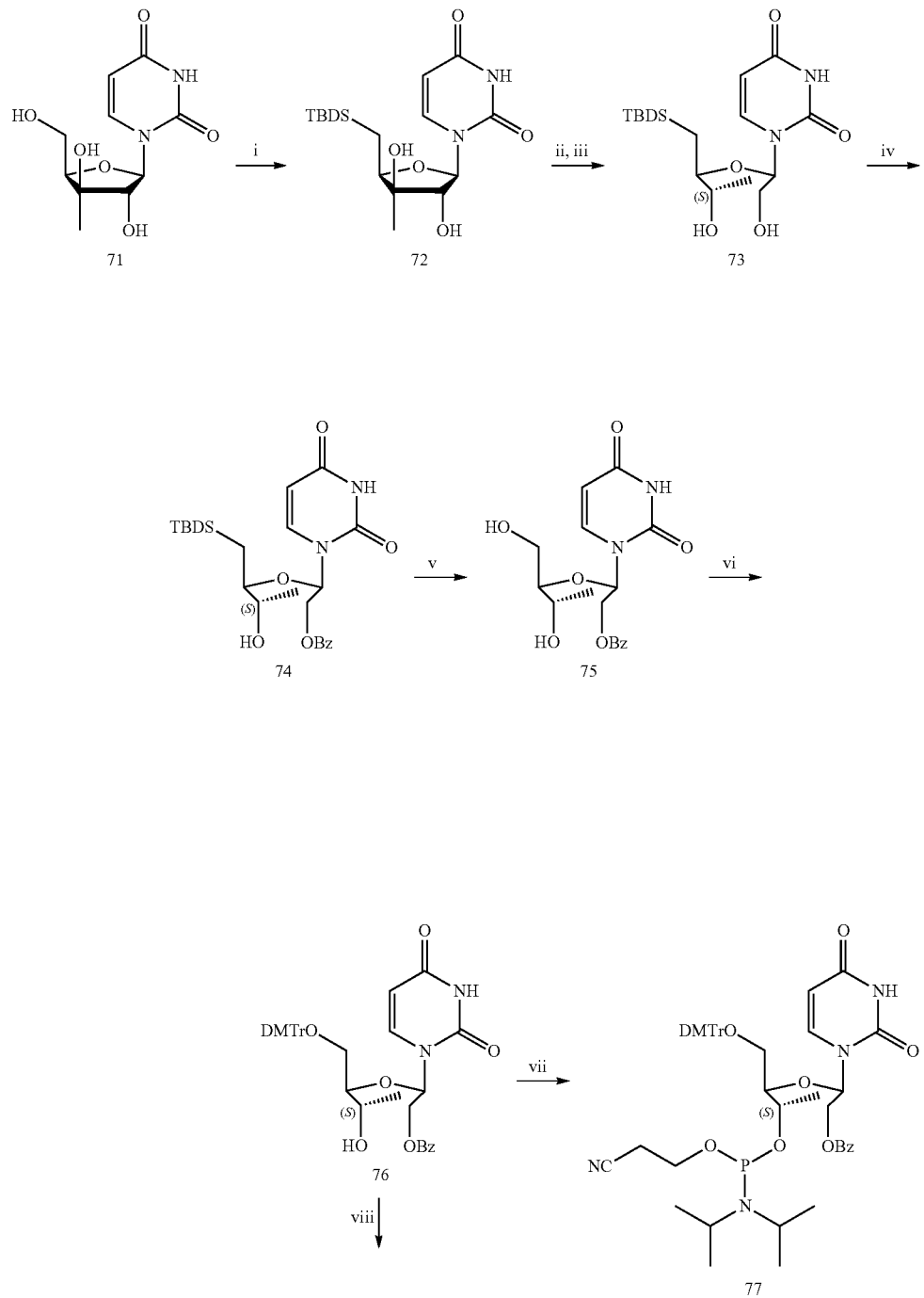

Scheme 9

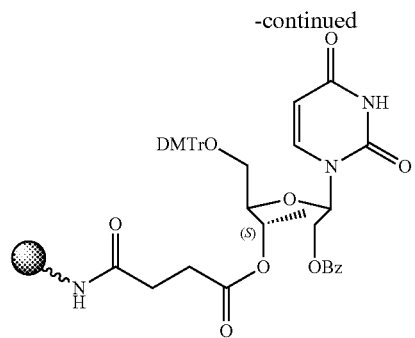

78

Reagents and conditions: (i) TBDPSCl, DMAP, Pyridine, rt, 12 h, 92%; (ii) Pb(AcO)$_4$, DCM, rt, 1 h; (iii) RuCl(p-cymene)[(R,R)-Ts-DPEN], HCOONa, H$_2$O/AcOEt, rt, 24 h, 76% over 2 steps; (iv) Bz$_2$O, DMAP, Pyridine, rt, 5 h, 85%; (v) TBAF, THF, rt, 1 h, 95%; (vi) DMTrCl, Pyridine, rt, 5 h, 98%; (vii) 2-cyanoethyl N,N-diisopropylchlorophosphoramidite, DIEA, DCM, rt, 1-2 h, 81-86%; (viii) (a) succinic anhydride/DMAP/CH$_2$Cl$_2$ (b) aminoalkyl CPG/HBTU/DIEA/DMF Synthesis of compound 72: To a solution of compound 71 (9 g, 34.9 mmol) in pyridine (350 mL) were added DMAP (426 mg, 3.49 mmol) and TBDPSCl (13.6 mL, 52.4 mmol) dropwisely. The resulting mixture was stirred for 12 h, and then diluted with DCM. The reaction was quenched with saturated aq. NaHCO$_3$. The organic layer was separated, washed with brine and removed in vacuo. The crude residue was purified by flash column chromatography on silica gel to afford compound 72 as a colorless foam (16 g, 92%). $^1$H NMR (400 MHZ, DMSO-d$_6$) δ 11.27 (d, J=2.2 Hz, 1H), 7.84-7.27 (m, 11H), 5.89 (d, J=5.6 Hz, 1H), 5.62 (s, 1H), 5.49 (dd, J=8.2, 2.2 Hz, 1H), 5.04 (s, 1H), 4.02-3.60 (m, 4H), 1.11 (s, 3H), 0.99 (s, 9H). $^{13}$C NMR (101 MHz, DMSO-d$_6$) δ 163.23, 150.43, 141.24, 135.13, 135.08, 132.86, 132.65, 129.89, 127.90, 127.85, 100.27, 91.35, 86.74, 82.40, 77.33, 62.57, 26.57, 18.91, 18.70. HRMS; [M+H]+ calc. for C26H33N2O6Si, 497.2108; found: 497.2108.

Synthesis of compound 73: To a solution of compound 72 (12 g, 24.2 mmol) in DCM (240 mL) was added Pb (AcO)$_4$ (21.5 g, 48.4 mmol). The resulting mixture was vigorously stirred for 1 h, the reaction completion was checked by TLC. The reaction was quenched with brine. The resulting mixture was diluted with excess amount of Et$_2$O, and then the insoluble materials were filtered off through a celite pad. The organic layer was washed with brine, dried over Na$_2$SO$_4$ and evaporated in vacuo. The resulting keto-aldehyde colorless form was used for next step without further purification. A round-bottom flask was charged with η6-(p-cymene)-(S,S)—N-toluenesulfonyl-1,2-diphenylethylenediamine (1-) ruthenium (II) chloride (360 mg, 0.576 mmol, 2.5 mol %) and keto-aldehyde (12 g, 24.2 mmol), and the system was flushed with Argon 3 times. A solution of sodium formate (54.5 g, 800 mmol) in water (300 mL) was added, followed by ethyl acetate (75 mL). The resulting two-phase mixture was vigorously stirred for 24 h at room temperature. The organic phase was separated, and the aqueous phase was extracted with another 100 mL of ethyl acetate. The solvent was removed from the combined organic layers at reduced pressure on a rotary evaporator. The crude residue was purified by flash column chromatography on silica gel to afford compound 73 as a colorless foam (9.2 g, 76% over 2 steps). $^1$H NMR (400 MHz, DMSO-d$_6$) δ 11.25 (s, 1H), 7.66-7.33 (m, 11H), 7.29-7.06 (m, 1H), 5.88 (dd, J=6.5, 4.9 Hz, 1H), 5.40 (d, J=8.0 Hz, 1H), 5.19-5.00 (m, 1H), 4.77 (d, J=4.8 Hz, 1H), 3.91-3.80 (m, 1H); 3.73-3.64 (m, 1H), 360-3.49 (m, 3H); 1.01 (d, J=6.3 Hz, 3H); 0.93 (s, 9H). 13C NMR (101 MHZ, DMSO-d$_6$) δ 163.14, 151.28, 140.87, 134.96, 134.91, 132.73, 132.64, 129.83, 128.85, 128.15, 127.83, 125.26, 101.53, 84.06, 83.20, 65.48, 63.18, 61.16, 26.53, 18.63, 18.05. HRMS; [M+Na]+ calc. for C$_{26}$H$_3$N$_2$O$_6$SiNa, 521.2084; found: 521.2076.

Synthesis of compound 74: To a solution of compound 73 (3.6 g, 7.23 mmol) in dry pyridine (72 mL) were added DMAP (88 mg, 0.72 mmol) and Bz20) (1.7 mg, 7.59 mmol). The reaction mixture was stirred for 5 h at room temperature and then the resulting mixture was diluted with DCM. The reaction was quenched with saturated aq. NaHCO$_3$. The organic layer was separated, washed with brine and removed in vacuo. The crude residue was purified by flash column chromatography on silica gel to afford compound 74 as a colorless form (3.7 g, 85%). $^1$H NMR (400 MHZ, DMSO-d$_6$) δ 11.37 (d, J=1.9 Hz, 1H), 8.03-7.82 (m, 2H), 7.82-7.29 (m, 14H), 6.31 (t, J=5.6 Hz, 1H), 5.43 (dd, J=8.1, 1.8 Hz, 1H), 4.89 (d, J=4.6 Hz, 1H), 4.63 (dd, J=11.6, 5.1 Hz, 1H), 4.46 (dd, J=11.5, 6.2 Hz, 1H), 3.89 (s, 1H), 3.77-3.42 (m, 3H), 1.03 (d, J=6.5 Hz, 3H), 0.94 (s, 9H). $^{13}$C NMR (126 MHz, DMSO-d$_6$) δ 165.00, 162.97, 150.90, 149.56, 140.29, 135.03, 134.96, 134.92, 133.57, 132.65, 132.57, 129.86, 129.14, 129.11, 128.98, 128.76, 127.85, 127.82, 101.96, 83.37, 81.29, 65.52, 63.47, 63.11, 39.24, 26.53, 18.63, 17.85.

Synthesis of compound 75: To a solution of compound 74 (3.8 g, 6.31 mmol) in dry THF (50 mL) was added 1 M TBAF in THE solution (12.6 mL, 12.6 mmol). The reaction mixture was stirred for 1 h at room temperature and then the resulting mixture was diluted with AcOEt. The reaction was poured into saturated aq. NH$_4$Cl. The organic layer was separated, washed with brine and removed in vacuo. The crude residue was purified by flash column chromatography on silica gel to afford compound 75 as a colorless foam (2.2 g, 95%). $^1$H NMR (400 MHz, DMSO-d$_6$) δ 11.28 (s, 1H), 7.98-7.84 (m, 2H), 7.84-7.44 (m, 4H), 6.25 (t, J=5.8 Hz, 1H), 5.61 (d, J=8.0 Hz, 1H), 4.88-4.70 (m, 1H), 4.58 (dt, J=9.5, 5.4 Hz, 2H), 4.40 (dd, J=11.5, 6.3 Hz, 1H), 3.76 (ddd, J=9.0, 6.5, 4.4 Hz, 1H), 3.55-3.21 (m, 3H), 1.07 (d, J=6.4 Hz, 3H). $^{13}$C NMR (126 MHZ, DMSO-d$_6$) δ 165.04, 163.26, 151.03, 140.96, 133.59, 129.33-128.63 (m), 101.46, 84.39, 81.57, 65.83, 63.63, 60.70, 17.95.

Synthesis of compound 76: To a solution of compound 75 (3.1 g, 8.52 mmol) in dry pyridine (85 mL) was added DMTrCl (3.17 g, 9.37 mmol). The reaction mixture was stirred for 5 h at room temperature and then diluted with DCM. The reaction was quenched with saturated aq. NaHCO$_3$. The organic layer was separated, washed with brine and removed in vacuo. The crude residue was purified by flash column chromatography on silica gel to afford compound 76 as a colorless foam (5.2 g, 98%). $^1$H NMR (400 MHZ, DMSO-d$_6$) δ 11.41 (s, 1H), 7.96-7.82 (m, 2H), 7.82-7.43 (m, 4H), 7.41-7.04 (m, 9H), 7.02-6.73 (m, 4H), 6.32-6.12 (m, 1H), 5.51 (d, J=8.1 Hz, 1H), 4.84 (d, J=4.5 Hz, 1H), 4.65 (dd, J=11.6, 5.2 Hz, 1H), 4.49 (dd, J=11.5, 6.8 Hz, 1H), 3.79-3.61 (m, 8H), 3.17-2.74 (m, 2H), 0.90 (d, J=6.4 Hz, 3H). $^{13}$C NMR (126 MHz, DMSO-d$_6$) δ 164.99, 163.04, 157.97, 157.94, 151.05, 144.70, 140.63, 135.53, 135.44, 133.60, 129.54, 129.45, 129.12, 128.99, 128.80, 127.73, 127.65, 127.57, 126.57, 113.10, 113.08, 102.08, 85.57, 82.77, 81.62, 66.04, 63.31, 62.91, 59.71, 54.96, 39.05, 17.87, 14.05.

Synthesis of compound 77: To a solution of compound 76 (2.5 g, 3.75 mmol) in dry DCM (38 mL) were added DIPEA (2 mL, 11.3 mmol) and 2-cyanoethylchloro-N,N-diisopropylphosphoramidite (921 µL, 14.13 mmol) dropwisely. The reaction mixture was stirred for 1 h at room temperature, then diluted with DCM and quenched the reaction with saturated aq. NaHCO$_3$. The organic layer was separated, washed with brine and concentrated in vacuo. The crude residue was purified by flash column chromatography on silica gel to afford compound 77 as a colorless foam (2.8 g, 86%). $^1$H NMR (500 MHZ, Acetonitrile-d$_3$) δ 9.03 (s, 1H); 7.96 (ddt, J=8.4, 3.1, 1.7 Hz, 2H), 7.73-7.12 (m, 13H), 6.83 (ddd, J=8.9, 4.1, 2.1 Hz, 4H), 6.30 (dt, J=8.8, 5.3 Hz, 1H), 4.61-4.35 (m, 2H), 4.19-3.98 (m, 1H), 3.82-3.40 (m, 12H), 3.28-2.99 (m, 2H), 2.65-2.53 (m, 2H), 1.26-0.89 (m, 15H). $^{13}$C NMR (126 MHz, Acetonitrile-d$_3$) δ 159.70, 136.91, 134.49, 131.01, 130.99, 130.94, 130.54, 129.70, 128.98, 128.89, 127.87, 118.36, 114.12, 103.11, 64.81, 64.15, 55.97, 43.97, 43.87, 25.02, 24.95, 24.87, 1.89, 1.33, 1.22, 1.06. $^{31}$P NMR (202 MHz, Acetonitrile-d$_3$) δ 148.99, 148.80.

Synthesis of compound 78: Standard succination of compound 76 using succinic anhydride and DMAP in CH$_2$Cl$_2$ followed by CPG loading using HBTU and DIPEA in DMF gives compound 78.

Synthesis of 3'-(R)-methyl-U-UNA Building Blocks

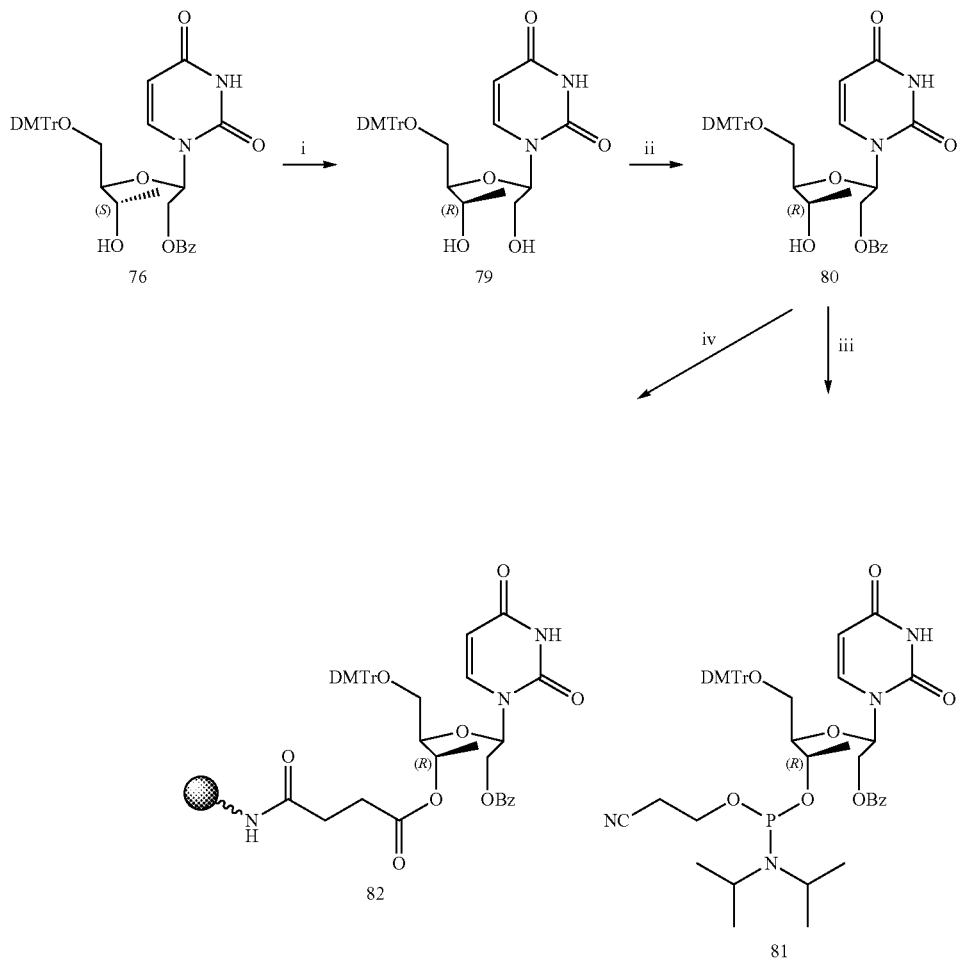

Scheme 10

Reagents and conditions: (i) BzOH, DIAD, PPh$_3$, THF, rt, 5 h; NaOH aq., rt, 12 h, 77%; (ii) Bz$_2$O, DMAP, Pyridine, rt, 5 h, 84%; (iii) 2-cyanoethyl N,N-diisopropylchlorophosphoramidite, DIEA, DCM, rt, 1-2 h, 81%; (iv) (a) succinic anhydride/DMAP/CH$_2$Cl$_2$ (b) aminoalkyl CPG/HBTU/DIEA/DMF Synthesis of compound 79: To a solution of compound 76 (3.37 g, 5.06 mmol) in dry THF (50 mL) were added PPh$_3$ (2.70 g, 15.2 mmol), BzOH (1.85 g, 15.2 mmol) and DIAD (2.99 mL, 15.2 mmol) dropwisely. The reaction mixture was stirred for 5 h at room temperature, the reaction completion was checked by TLC. The solvent was removed in vacuo. The crude residue was purified by flash column chromatography on silica gel to afford a di-benzoylated nucleoside. This compound was dissolved in THF (50 mL). To the solution of the mixture was added 1N aq. NaOH (10 mL) dropwisely. Resulting mixture was stirred for 12 h then the solvent was removed in vacuo. The crude residue was purified by flash column chromatography on silica gel to afford compound 79 as a colorless foam (2.2 g, 77% in 2 steps). $^1$H NMR (500 MHZ, DMSO-d$_6$) δ 11.48-11.15 (m, 1H), 7.62 (d, J=8.0 Hz, 1H), 7.39-7.04 (m, 8H), 6.97-6.67 (m, 4H), 5.81 (t, J=5.9 Hz, 1H), 5.49 (dd, J=8.0, 1.5 Hz, 1H), 5.17 (t, J=5.9 Hz, 1H), 4.74 (d, J=4.8 Hz, 1H), 3.95-3.40 (m, 10H), 3.11-2.79 (m, 2H), 0.86 (d, J=6.4 Hz, 3H). $^{13}$C NMR (126 MHZ, DMSO-d$_6$) δ 163.21, 157.94, 151.39, 144.76, 141.16, 135.55, 135.54, 129.57, 129.48, 127.71, 127.60, 126.53, 113.08, 113.06, 101.67, 85.29, 84.77, 82.99, 65.87, 62.86, 61.15, 54.97, 39.25, 39.08, 18.53.

Synthesis of compound 80: To a solution of compound 79 (2 g, 3.56 mmol) in dry pyridine (36 mL) were added DMAP (44 mg, 0.356 mmol) and Bz$_2$O (845 mg, 3.74 mmol). The reaction mixture was stirred for 5 h at room temperature and then the resulting mixture was diluted with DCM. The reaction was quenched with saturated aq. NaHCO$_3$. The organic layer was separated, washed with brine and removed in vacuo. The crude residue was purified by flash column chromatography on silica gel to afford compound 80 as a colorless foam (2.0 g, 84%). $^1$H NMR (400 MHZ, DMSO-d$_6$) δ 11.45 (d, J=2.2 Hz, 1H), 7.99-7.41 (m, 6H), 7.41-7.03 (m, 9H), 6.95-6.58 (m, 4H), 6.20 (t, J=6.0 Hz, 1H), 5.54 (dd, J=8.0, 2.1 Hz, 1H), 4.86 (d, J=4.9 Hz, 1H), 4.70 (dd, J=11.6, 5.5 Hz, 1H), 4.51 (dd, J=11.5, 6.6 Hz, 1H), 3.71 (s, 8H), 3.17-2.80 (m, 2H), 0.84 (d, J=6.4 Hz, 3H). $^{13}$C NMR (101 MHZ, DMSO-d$_6$) δ 165.01, 163.07, 157.97, 157.94, 151.08, 144.73, 140.73, 135.51, 135.48, 133.66, 129.59, 129.50, 129.10, 128.99, 128.85, 127.74, 127.61, 126.57, 113.09, 102.18, 85.39, 83.15, 81.89, 65.73, 63.38, 62.73, 59.74, 54.98, 38.97, 18.48, 14.07.

Synthesis of compound 81: To a solution of compound 80 (2.00 g, 3.00 mmol) in dry DCM (30 mL) were added DIPEA (1.57 mL, 9.00 mmol) and 2-cyanoethylchloro-N, N-diisopropylphosphoramidite (737 µL, 3.30 mmol) dropwisely. The reaction mixture was stirred for 2 h at room temperature, then diluted with DCM and quenched the reaction with saturated aq. NaHCO$_3$. The organic layer was separated, washed with brine and concentrated in vacuo. The crude residue was purified by flash column chromatography on silica gel to afford compound 81 as a colorless foam (2.1 g, 81%). $^1$H NMR (500 MHz, Acetonitrile-d$_3$) δ 7.95 (ddd, J=8.4, 2.7, 1.4 Hz, 2H), 7.81-7.56 (m, 5H), 7.52-7.35 (m, 4H), 7.35-7.16 (m, 9H), 6.90-6.77 (m, 4H), 6.04 (dd, J=8.7, 6.8 Hz, 1H), 5.39 (dt, J=11.2, 6.5 Hz, 1H), 3.86-3.61 (m, 11H), 3.62-3.40 (m, 2H), 3.33-3.11 (m, 2H), 2.56 (q, J=5.9 Hz, 2H), 1.45 (dd, J=6.4, 3.9 Hz, 3H), 1.30-0.97 (m, 12H). 1H NMR (500 MHz, Acetonitrile-d$_3$) δ 9.09 (s, 1H), 7.97 (dt, J=8.5, 1.6 Hz, 2H), 7.73-7.11 (m, 17H), 6.96-6.75 (m, 5H), 6.23 (td, J=5.5, 3.3 Hz, 1H), 5.50 (dd, J=8.1, 6.7 Hz, 1H), 4.67-4.38 (m, 3H), 4.28-3.99 (m, 2H), 3.86-3.40 (m, 15H), 3.25 (ddd, J=12.7, 10.5, 2.5 Hz, 1H), 3.18-3.02 (m, 1H), 1.29-0.92 (m, 23H). $^{13}$C NMR (101 MHZ, CD$_3$CN) δ 166.53, 163.82, 159.67, 159.67, 151.98, 146.01, 141.42, 136.92, 134.55, 131.04, 131.04, 130.98, 130.48, 130.48, 129.75, 129.75, 128.86, 128.86, 127.83, 118.37, 114.07, 114.07, 103.32, 87.24, 83.13, 82.91, 70.44, 70.28, 64.81, 64.00, 61.03, 59.35, 55.95, 55.95, 46.01, 44.07, 24.94, 23.15, 21.01, 20.94, 17.81, 14.58, 2.01, 1.81, 1.60, 1.39, 1.19, 0.98, 0.77. $^{31}$P NMR (202 MHZ, Acetonitrile-d$_3$) δ 149.12, 148.42.

Synthesis of compound 82: Standard succination of compound 80 using succinic anhydride and DMAP in CH$_2$Cl$_2$ followed by CPG loading using HBTU and DIPEA in DMF gives compound 82.

Synthesis of 3'-methyl-U-UNA Mosher Esters

Scheme 11

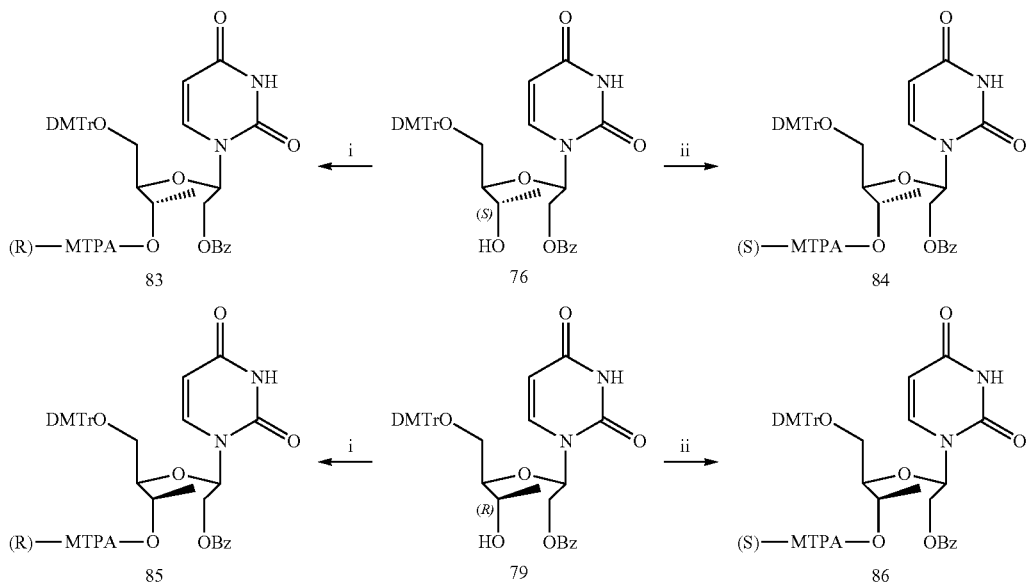

Reagents and conditions: (i) (S)-MTPACl, DMAP, Et$_3$N, MeCN, 3 h, 76-81%; (ii) (R)-MTPACl, DMAP, Et$_3$N, MeCN, rt, 3-5 h, 67-70%.

Synthesis of compound 83: To a solution of compound 76 (150 mg, 0.225 mmol), DMAP (3 mg, 0.023 mmol), Et$_3$N (157 µL, 1.13 mmol) in dry MeCN (3 mL) was added(S)-(+)-MTPACl (50.5 µL, 0.27 mmol) dropwisely. The reaction mixture was stirred for 3 h at room temperature and then diluted with AcOEt. The reaction was quenched with saturated aq. NaHCO$_3$. The organic layer was separated, washed with brine and removed in vacuo. The crude residue was purified by flash column chromatography on silica gel to afford compound 83 as a colorless foam (161 mg, 81%). $^1$H NMR (400 MHZ, DMSO-d$_6$) δ 11.47 (d, J=2.0 Hz, 1H), 7.99-7.74 (m, 2H), 7.74-7.58 (m, 2H), 7.58-7.00 (m, 16H), 7.00-6.63 (m, 4H), 6.05 (t, J=5.8 Hz, 1H), 5.62-5.34 (m, 2H), 3.72 (s, 7H), 3.37 (s, 3H), 2.97 (t, J=5.6 Hz, 2H), 1.13 (dd, J=15.8, 6.9 Hz, 3H). $^{13}$C NMR (126 MHz, DMSO-d$_6$) δ 164.93, 164.86, 162.93, 158.04, 151.01, 144.42, 140.43, 135.27, 135.11, 133.64, 131.35, 129.69, 129.43, 129.38, 129.12, 128.82, 128.76, 128.53, 128.41, 127.77, 127.46, 126.93, 126.67, 124.22, 113.14, 113.11, 102.27, 85.96, 83.81, 81.17, 79.91, 72.52, 63.05, 61.94, 55.15, 54.97, 14.72.

Synthesis of compound 84: To a solution of compound 76 (150 mg, 0.225 mmol), DMAP (3 mg, 0.023 mmol), Et$_3$N (157 µL, 1.13 mmol) in dry MeCN (3 mL) was added (R)-(−)-MTPACl (50.5 µL, 0.27 mmol) dropwisely. The reaction mixture was stirred for 3 h at room temperature and then diluted with AcOEt. The reaction was quenched with saturated aq. NaHCO$_3$. The organic layer was separated, washed with brine and removed in vacuo. The crude residue was purified by flash column chromatography on silica gel to afford compound 84 as a colorless foam (139 mg, 70%). $^1$H NMR (400 MHZ, DMSO-d6) δ 11.49 (s, 1H), 7.94-6.98 (m, 20H), 6.96-6.61 (m, 4H), 6.16 (t, J=5.8 Hz, 1H), 5.55 (d, J=8.0 Hz, 1H), 5.38 (qd, J=6.4, 2.1 Hz, 1H), 4.40 (ddd, J=40.1, 11.5, 5.7 Hz, 2H), 3.87 (ddd, J=6.8, 3.8, 1.9 Hz, 1H), 3.38 (s, 3H), 3.19-2.85 (m, 2H), 1.03 (d, J=6.6 Hz, 3H). $^{13}$C NMR (126 MHz, DMSO-d$_6$) δ 164.91, 164.83, 162.98, 158.04, 158.02, 151.07, 144.39, 140.53, 135.23, 135.13, 133.60, 131.46, 129.72, 129.47, 129.41, 129.06, 128.79, 128.75, 128.45, 127.76, 127.51, 126.79, 126.67, 113.13, 113.11, 102.35, 85.96, 81.12, 79.65, 72.78, 63.15, 61.95, 55.27, 54.96, 14.37.

Synthesis of compound 85: To a solution of compound 79 (100 mg, 0.150 mmol), DMAP (2 mg, 0.02 mmol), Et$_3$N (104 µL, 0.750 mmol) in dry MeCN (3 mL) was added(S)-(+)-MTPACl (33.6 µL, 0.180 mmol) dropwisely. The reaction mixture was stirred for 5 h at room temperature and then diluted with AcOEt. The reaction was quenched with saturated aq. NaHCO$_3$. The organic layer was separated, washed with brine and removed in vacuo. The crude residue was purified by flash column chromatography on silica gel to afford compound 85 as a colorless foam (101 mg, 76%). $^1$H NMR (400 MHZ, DMSO-d$_6$) δ 11.46 (d, J=2.2 Hz, 1H), 8.03-7.74 (m, 2H), 7.80-7.02 (m, 18H), 6.82 (dd, J=8.9, 2.7 Hz, 4H), 6.16 (t, J=5.9 Hz, 1H), 5.47 (ddd, J=54.4, 7.4, 3.0 Hz, 2H), 4.53 (ddd, J=48.6, 11.6, 5.9 Hz, 2H), 4.09-3.95 (m, 2H), 3.71 (d, J=1.7 Hz, 6H), 3.22 (s, 3H), 3.02 (ddd, J=35.9, 10.3, 5.6 Hz, 2H), 1.15-1.06 (m, 3H). $^{13}$C NMR (126 MHz, DMSO-d$_6$) δ 165.10, 164.92, 162.88, 158.07, 150.86, 144.32, 140.26, 135.11, 135.04, 133.66, 131.08, 129.85, 129.44, 129.39, 129.08, 128.84, 128.80, 128.54, 127.78, 127.46, 127.02, 126.71, 113.14, 113.11, 102.37, 85.81, 82.15, 79.51, 72.05, 63.29, 62.03, 59.72, 55.05, 54.97, 39.24, 20.71, 14.54, 14.04.

Synthesis of compound 86: To a solution of compound 79 (100 mg, 0.150 mmol), DMAP (2 mg, 0.02 mmol), Et$_3$N (104 µL, 0.750 mmol) in dry MeCN (3 mL) was added (R)-(−)-MTPACl (33.6 µL, 0.180 mmol) dropwisely. The reaction mixture was stirred for 3 h at room temperature and then diluted with AcOEt. The reaction was quenched with saturated aq. NaHCO$_3$. The organic layer was separated, washed with brine and removed in vacuo. The crude residue was purified by flash column chromatography on silica gel to afford compound 86 as a colorless foam (89 mg, 67%). $^1$H NMR (400 MHZ, DMSO-d$_6$) δ 11.45 (s, 1H), 7.96-7.80 (m, 2H), 7.72-6.96 (m, 18H), 6.92-6.69 (m, 4H), 6.11 (t, J=5.9 Hz, 1H), 5.67-5.21 (m, 2H), 4.55-4.31 (m, 2H), 3.97-3.85 (m, 1H), 3.71 (d, J=1.4 Hz, 6H), 3.29 (s, 3H), 2.92 (ddd, J=50.1, 10.2, 5.5 Hz, 2H), 1.24 (d, J=6.5 Hz, 3H). $^{13}$C NMR (126 MHz, DMSO-d$_6$) δ 165.05, 164.89, 162.85, 158.04, 150.83, 144.35, 140.12, 135.10, 135.06, 133.69, 131.14, 129.84, 129.45, 129.36, 129.09, 128.87, 128.82, 128.52, 127.74, 127.43, 126.94, 126.80, 126.67, 124.14, 121.85, 113.09, 113.06, 102.37, 85.70, 81.90, 79.45, 72.34, 63.17, 62.10, 59.72, 55.11, 54.97, 39.24, 20.72, 14.88, 14.04.

Synthesis of isoC-GNA Building Blocks

Scheme 12

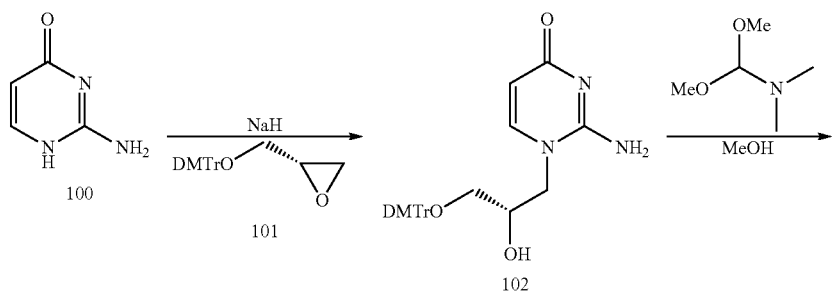

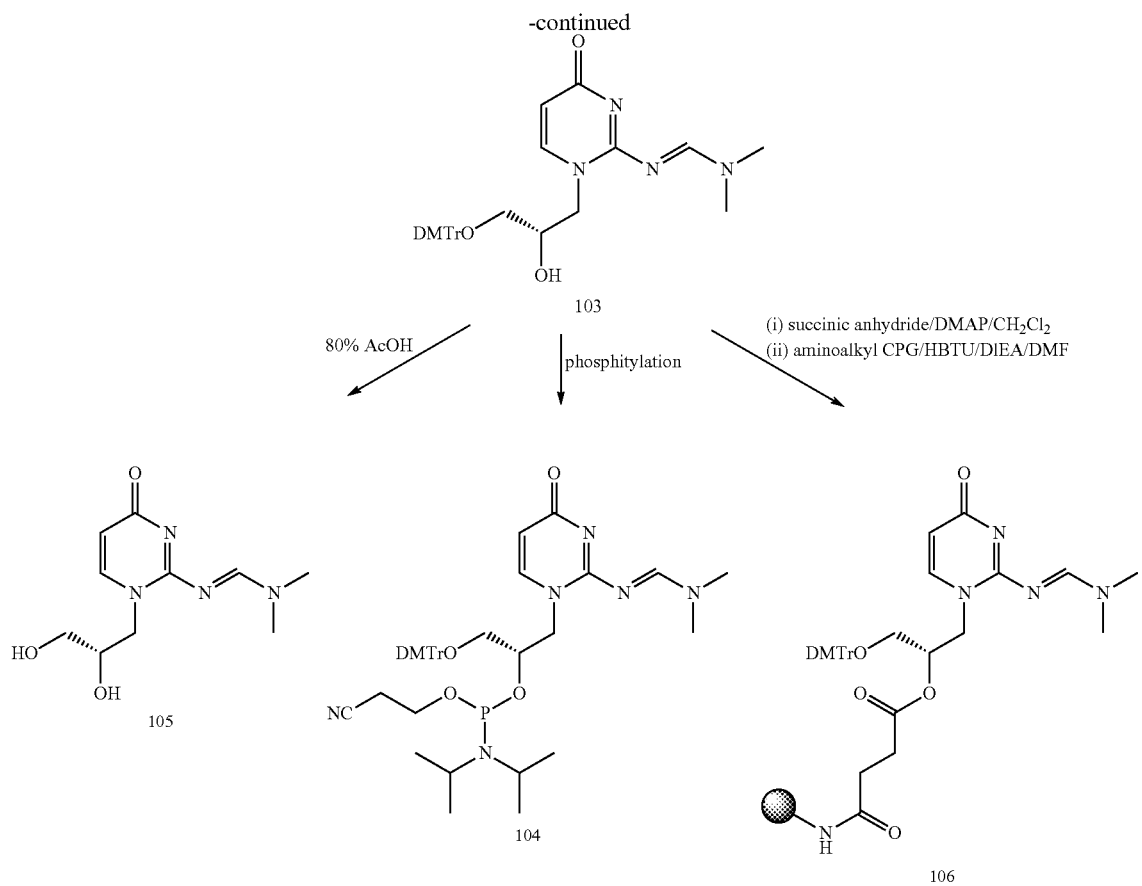

Synthesis of compound 102: To a solution of compound 100 (1.90 g, 5.85 mmol) in anhydrous DMF (34 mL) was added NaH (60% in mineral oil; 137 mg, 3.42 mmol, 0.2 eq.). The reaction mixture was stirred at room temperature for 1 h then a solution of compound 101 (5.85 g, 15.5 mmol) was added. The mixture was heated at 110° C. for 18 h. After removing the solvent under reduced pressure, the residue was extracted with EtOAc and H$_2$O. The organic layer was separated, dried over anhydrous Na$_2$SO$_4$, filtered and concentrated. The crude material was purified by flash column chromatography on silica gel (0-10% MeOH in CH$_2$Cl$_2$) to obtain compound 102 as a slightly yellow foam (3.27 g, 6.71 mmol, 43%, R$_f$=0.44; developed with 8% MeOH in CH$_2$Cl$_2$). $^1$H NMR (400 MHZ, DMSO-d$_6$) δ 7.44 (d, J=7.3 Hz, 2H), 7.36-7.11 (m, 8H), 6.97-6.83 (m, 4H), 6.73 (s, 2H), 5.47 (dt, J=14.4, 7.3 Hz, 2H), 3.93 (brs, 1H), 3.85 (d, J=3.3 Hz, 1H), 3.74 (s, 6H), 3.70-3.58 (m, 1H), 2.96 (ddd, J=28.5, 9.4, 5.0 Hz, 2H).

Synthesis of compound 103: To a solution of compound 102 (3.25 g, 6.67 mmol) in MeOH (40 mL) was added N,N-dimethylformamide dimethyl acetal (1.77 mL, 13.3 mmol). The reaction mixture was stirred at room temperature overnight. After removing the solvent under reduced pressure, the residue was purified by flash column chromatography on silica gel (0-8% MeOH in CH$_2$Cl$_2$) to obtain compound 103 as a slightly yellow foam (3.47 g, 6.39 mmol, 96%, R$_f$=0.41; developed with 8% MeOH in CH$_2$Cl$_2$). $^1$H NMR (400 MHz, DMSO-d$_6$) δ 8.59 (s, 1H), 7.40 (d, J=7.3 Hz, 2H), 7.37-7.19 (m, 8H), 6.94-6.82 (m, 4H), 5.59 (d, J=7.5 Hz, 1H). 5.17 (d, J=5.9 Hz, 1H), 4.43 (dd, J=13.4, 3.5 Hz, 1H), 3.97 (s, 1H), 3.74 (s, 6H), 3.51 (dd, J=13.4, 8.6 Hz, 1H), 3.17 (s, 3H), 3.00-2.96 (m, 4H), 2.92-2.82 (m, 1H).

Synthesis of compound 104: To a solution of compound 103 (2.00 g, 3.69 mmol) in CH$_2$Cl$_2$ (20 mL) and N,N-diisopropylethylamine (1.29 mL, 7.38 mmol) was added 2-cyanoethyl N,N-diisopropylchlorophosphoramidite (1.32 mL, 5.90 mmol). The reaction mixture was stirred at room temperature overnight under argon atmosphere. The reaction mixture was diluted with CH$_2$Cl$_2$ (200 mL) then washed with saturated NaHCO$_3$ aqueous solution (100 mL). The organic layer was separated, dried over anhydrous Na$_2$SO$_4$, filtered and concentrated. The crude material was purified by flash column chromatography on silica gel (33-100% EtOAc in hexane then CH$_2$Cl$_2$:acetone:Et$_3$N=50:50:1) to obtain compound 104 (880 mg, 1.18 mmol, 32%, R$_f$=0.41 developed with 8% MeOH in CH$_2$Cl$_2$) as a slightly yellow foam. $^{31}$P NMR (202 MHz, CD$_3$CN): δ 150.28, 149.99.

Synthesis of compound 105: Compound 103 (250 mg, 0.461 mmol) was treated with 80% AcOH (10 mL) overnight. After removing the solvent, the crude was purified by flash column chromatography on silica gel (0-20% MeOH in CH$_2$Cl$_2$) to obtain compound 105 (83 mg, 0.345 mmol, 75%, R$_f$=0.26; developed with 15% MeOH in CH$_2$Cl$_2$). $^1$H NMR (400 MHZ, DMSO-d$_6$) δ 8.58 (s, 1H). 7.41 (d. J=7.5 Hz, 1H), 5.64 (d, J=7.4 Hz, 1H), 4.96 (d, J=5.7 Hz, 1H), 4.72 (t, J=5.6 Hz, 1H), 4.31 (dd, J=13.4, 3.4 Hz, 1H), 3.74 (ddd, J=9.0, 5.8, 3.4 Hz, 1H), 3.49 (dd, J=13.4, 8.4 Hz, 1H), 3.42-3.24 (m, 1H), 3.17 (s, 3H), 3.03 (s, 3H).

Synthesis of compound 106: Standard succination of compound 103 using succinic anhydride and DMAP in CH$_2$Cl followed by CPG loading using HBTU and DIPEA in DMF gives compound 106.

Synthesis of isoG-GNA Building Blocks
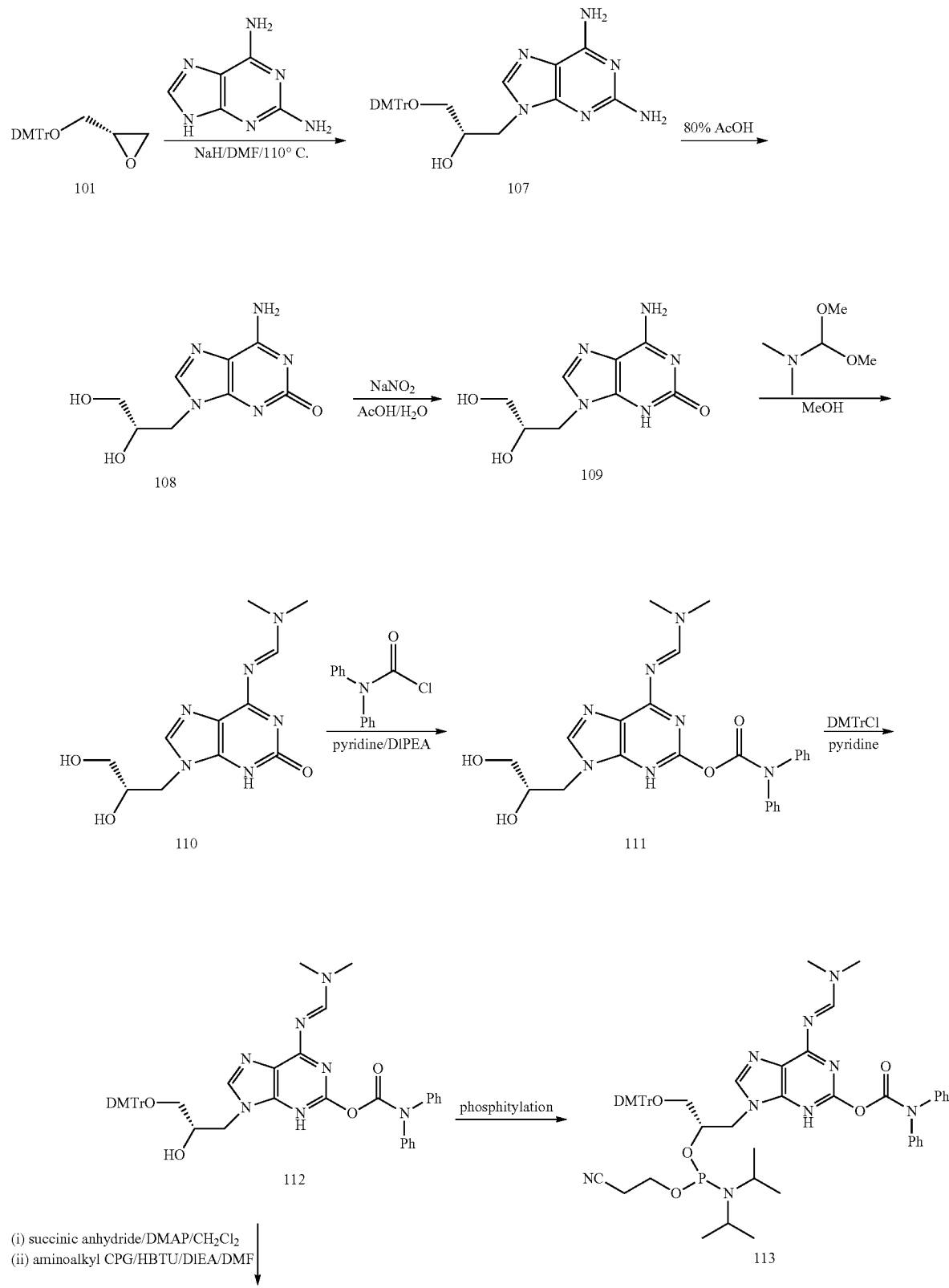

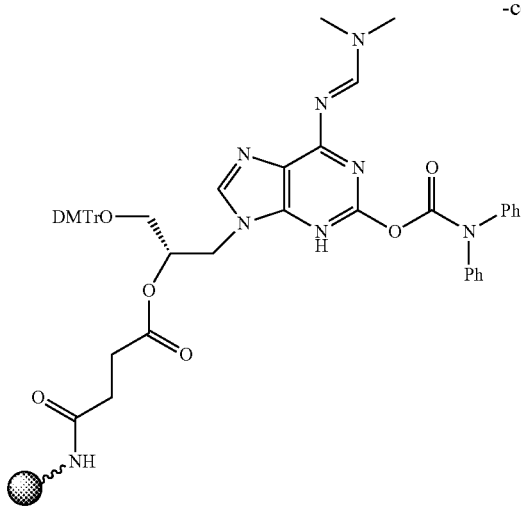

114

Synthesis of compound 107: To a suspension of 2,6-diaminopurine (9.38 g, 62.5 mmol) in anhydrous DMF (125 mL) was added NaH (60% in mineral oil; 500 mg, 12.5 mmol, 0.2 eq.). The reaction mixture was stirred at room temperature for 1 h then a solution of compound 101 (22.4 g, 59.5 mmol) in DMF (100 mL) was added. The mixture was heated at 110° C. for 21 h. After removing the solvent under reduced pressure, the crude material was purified by flash column chromatography on silica gel (0-10% MeOH in $CH_2Cl_2$) to obtain compound 107 as a slightly yellow foam (19.3 g, 36.6 mmol, 61%, $R_f$=0.33; developed with 8% MeOH in $CH_2Cl_2$). $^1$H NMR (400 MHZ, DMSO-$d_6$) δ 7.57 (s, 1H), 7.46-7.36 (m, 2H), 7.36-7.12 (m, 8H), 6.87 (dd, J=8.9, 3.3 Hz, 4H), 6.61 (s, 2H), 5.71 (s, 2H), 5.43 (d, J=5.3 Hz, 1H), 4.16-3.88 (m, 3H), 3.74 (s, 6H), 2.96-2.86 (m, 2H).

Synthesis of compound 108: Compound 107 (19.0 g, 36.1 mmol) was treated with 80% AcOH (500 mL) overnight. After removing the solvent, the residue was dissolved in toluene (200 mL) and $CH_2Cl_2$ (100 mL). White precipitation was formed and filtered. The solid was washed with $CH_2Cl_2$ to give compound 108 as an off-white powder (8.68 g, 30.5 mmol, 84% as acetate salt, $R_f$=0.18; developed with 20% MeOH in $CH_2Cl$), 1H NMR (400 MHZ, DMSO-$d_6$) δ 7.61 (s, 1H), 6.65 (s, 2H), 5.79 (s, 2H), 4.09 (dd, J=13.8, 3.6 Hz, 1H), 3.94-3.66 (m, 2H), 3.51-3.06 (m, 2H), 1.91 (s, 3H).

Synthesis of compound 109: To a suspension of compound 108 (7.88 g, 27.7 mmol) in $H_2O$ (250 mL) was added a solution of $NaNO_2$ (7.41 g, 107.4 mmol) in $H_2O$ (47 mL) at 50° C. Then AcOH (11.1 mL, 193.9 mmol) was added dropwise. The mixture was heated at 50° C. for 10 min then cooled to room temperature and diluted with $H_2O$ (250 mL). Conc. $NH_4OH$ was added to the solution to adjust the pH 8. The solution was evaporated and the residue was re-suspended in $H_2O$ (250 mL). The resulting precipitation was filtered and the case was dried in vacuo. The material was transferred to flask then co-evaporated with toluene then dried in vacuo overnight to give compound 109 as a pale purple solid (7.61 g, 96%). $^1$H NMR (500 MHz, DMSO-$d_6$) δ 7.62 (s, 1H), 4.02 (dd, J=13.9, 3.6 Hz, 1H), 3.81 (dd, J=14.0, 7.1 Hz, 1H), 3.77-3.68 (m, 1H), 3.34 (dd, J=11.2, 5.1 Hz, 1H), 3.21 (dd, J=11.2, 6.4 Hz, 1H), 1.83 (s, 3H).

Synthesis of compound 110: To a suspension of compound 109 (3.03 g, 13.5 mmol) in MeOH (54 mL) was added N,N-dimethylformamide dimethyl acetal (3.57 mL, 26.9 mmol). The reaction mixture was stirred for 15 h at room temperature. Additional N,N-dimethylformamide dimethyl acetal (1.8 mL) and MeOH (20 mL) were added then heated at 55° C. for 3 h. The mixture was evaporated and the residue was dried in vacuo to give compound 110 as a grey powder (3.68 g, 13.1 mmol, 97%). $^1$H NMR (400 MHZ, DMSO-$d_6$) δ 10.97 (s, 1H), 9.20 (s, 1H), 7.77 (s, 1H), 5.14 (d, J=4.9 Hz, 1H), 4.95 (t, J=5.9 Hz, 1H), 4.16-3.94 (m, 1H), 3.92-3.66 (m, 2H), 3.39-3.20 (m, 2H), 3.20 (s, 3H), 3.10 (s, 3H).

Synthesis of compound 111: To a suspension of compound 110 (3.66 g, 13.1 mmol) in anhydrous pyridine (180 mL) and N,N-diisopropylethylamine (2.97 mL, 17.0 mmol) was added diphenylcarbamoyl chloride (3.04 g, 13.1 mmol). The reaction mixture was stirred at room temperature for 2 h then quenched with saturated aq. $NaHCO_3$ (50 mL). The mixture was extracted with $CH_2Cl_2$ (300 mL) and the organic layer was separated, dried over anhydrous $Na_2SO_4$, filtered and concentrated. The crude material was purified by flash column chromatography on silica gel (0-8% MeOH in $CH_2Cl_2$) to obtain 111 (2.82 g, 5.93 mmol, 45%, $R_f$=0.24 developed with 8% MeOH in $CH_2Cl_2$) as a brown foam. $^1$H NMR (400 MHZ, DMSO-$d_6$) δ 8.93 (s, 1H), 8.14 (s, 1H), 7.44-7.28 (m, 10H), 5.09 (d, J=5.4 Hz, 1H), 4.82 (t, J=5.6 Hz, 1H), 4.28 (dd, J=13.9, 3.5 Hz, 1H), 3.99 (dd, J=13.9, 8.5 Hz, 1H), 3.84-3.80 (m, 1H), 3.44-3.33 (m, 2H), 3.21 (s, 3H), 3.13 (s, 3H).

Synthesis of compound 112: To a solution of compound 111 (385 mg, 0.810 mmol) in pyridine (4 mL) was added DMTrCl (274 mg, 0.810 mmol) and the mixture was stirred overnight. After removing the solvent, the residue was purified by flash column chromatography on silica gel (0-8% MeOH in $CH_2Cl_2$) to give compound 112 (392 mg, 0.504 mmol, 62%, $R_f$=0.34 developed with 5% MeOH in $CH_2Cl_2$) as a pale yellow foam. $^1$H NMR (400 MHZ, DMSO-$d_6$) δ 8.91 (s, 1H), 8.09 (s, 1H), 7.47-7.11 (m, 21H), 6.83 (dd, J=9.0, 3.2 Hz, 4H), 5.33 (d, J=5.4 Hz, 1H), 4.32 (dd, J=13.6, 3.6 Hz, 1H), 4.17-3.95 (m, 2H), 3.70 (s, 6H), 3.22 (s, 3H), 3.13 (s, 3H), 3.00 (dd, J=9.3, 5.0 Hz, 1H), 2.86 (dd, J=9.4, 6.0 Hz, 1H).

Synthesis of compound 113: Standard phosphitylation of compound 112 using 2-cyanoethyl N,N-diisopropyl-chlorophosphoramidite and DIPEA in CH$_2$Cl$_2$ gives compound 113 in 80% yield. $^{31}$P NMR (202 MHZ, CD$_3$CN) δ 150.65, 149.98.
Synthesis of compound 114: Standard succination of compound 112 using succinic anhydride and DMAP in CH$_2$Cl$_2$ followed by CPG loading using HBTU and DIPEA in DMF gives compound 114. Loading of 114:79 μmol/g.
Synthesis of 3'-C—(R)-methyl-4'-(S)-U-UNA Building Blocks
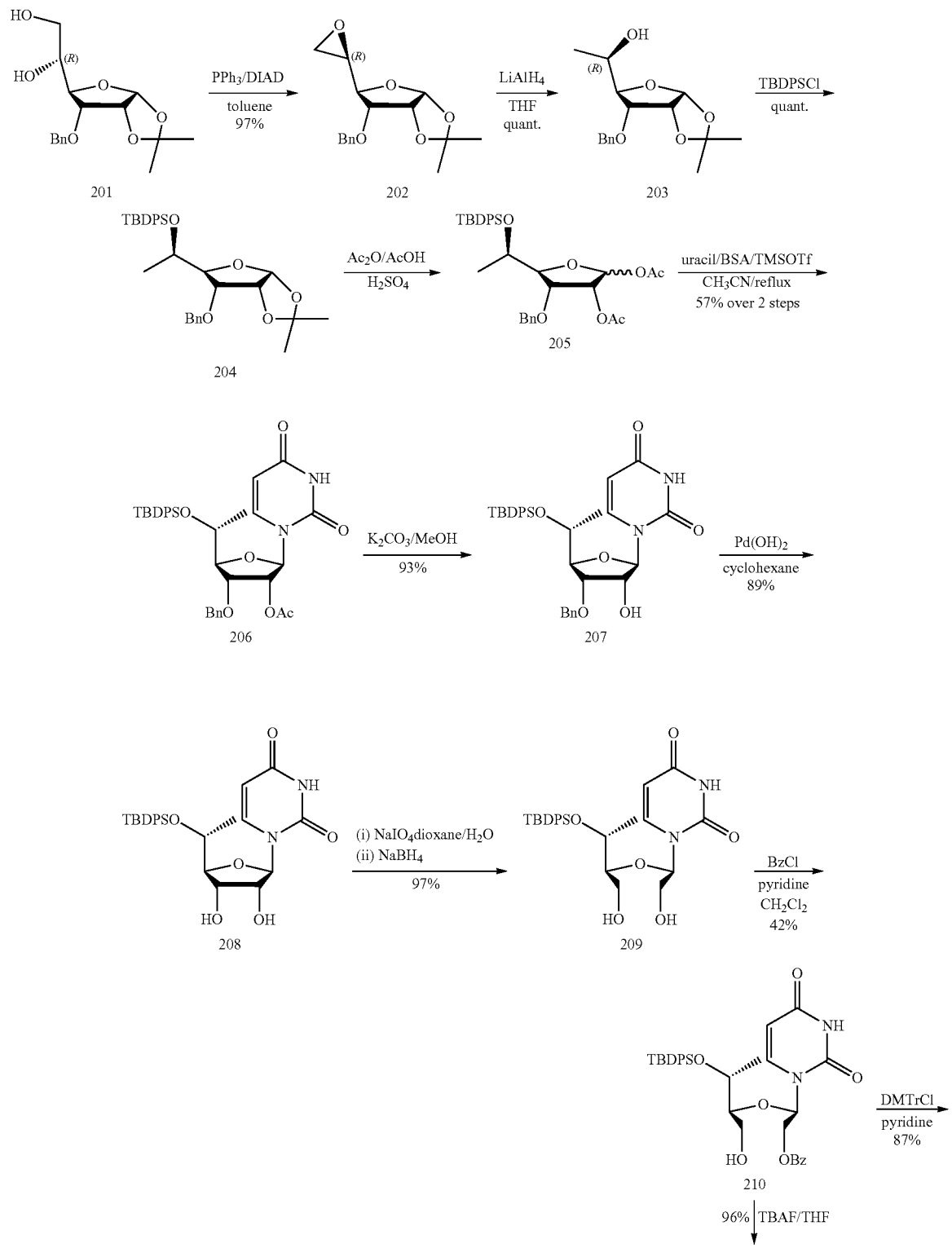
Scheme 14

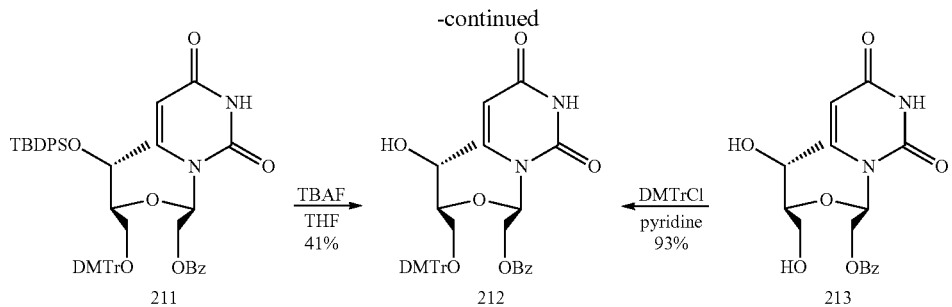

Synthesis of compound 202: To a suspension of compound 201 (2.00 g, 6.44 mmol) in anhydrous toluene (45 mL) were added PPh₃ (2.03 g, 7.73 mmol) and DIAD (1.50 mL, 7.73 mmol). The reaction mixture was stirred at 110° C. for 22 h. After removing the solvent under reduced pressure, the residue was extracted with EtOAc and saturated NaHCO₃ aqueous solution. The organic layer was separated, dried over anhydrous Na₂SO₄, filtered and concentrated. The crude material was purified by flash column chromatography on silica gel (0-33% EtOAc in hexane) to obtain compound 202 (1.83 g, 6.26 mmol, 97%, $R_f$=0.33; developed with 20% EtOAc in hexanes). $^1$H NMR (400 MHZ, DMSO-$d_6$): δ 7.44-7.24 (m, 5H), 5.75 (d, J=3.7 Hz, 1H), 4.76 (t, J=4.1 Hz, 1H), 4.63 (d, J=11.7 Hz, 1H), 4.50 (d, J=11.6 Hz, 1H), 3.97 (dd, J=8.9, 3.4 Hz, 1H), 3.67 (dd, J=8.9, 4.4 Hz, 1H), 3.18-3.12 (m, 1H), 2.74 (dd, J=5.3, 4.3 Hz, 1H), 2.61 (dd, J=5.3, 2.7 Hz, 1H), 1.45 (s, 3H), 1.29 (s, 3H) $^{13}$C NMR (126 MHz, DMSO-$d_6$): δ 137.67, 128.26, 127.75, 127.67, 111.90, 103.66, 77.63, 77.08, 76.79, 70.83, 50.23, 43.47, 26.64, 26.52.

Synthesis of compound 203: To a solution of compound 202 (1.82 g, 6.23 mmol) in THF (40 mL) was added 2M LiAlH₄ in THF (2.50 mL, 4.98 mmol) at −10° C. The reaction mixture was stirred at −10° C. for 30 min then at room temperature for 2 h. After removing the solvent under reduced pressure, the residue was purified by flash column chromatography on silica gel (0-50% EtOAc in hexane) to obtain compound 203 (1.83 g, 6.22 mmol, quant., $R_f$=0.42; developed with 50% EtOAc in hexanes). $^1$H NMR (400 MHZ, DMSO-$d_6$): δ 7.43-7.23 (m, 5H), 5.71 (d, J=3.8 Hz, 1H), 4.72 (t. J=3.8 Hz, 1H), 4.68-4.60 (m, 2H), 4.50 (d, J=11.7 Hz, 1H), 3.88-3.74 (m, 3H), 1.45 (s, 3H), 1.30 (s, 3H), 1.03 (d, J=6.5 Hz, 3H). $^{13}$C NMR (126 MHz, DMSO-$d_6$): δ 138.10, 128.18, 127.56, 127.49, 111.60, 103.76, 81.96, 77.26, 77.24, 70.82, 65.15, 26.76, 26.71, 18.26.

Synthesis of compound 204: To a solution of compound 203 (2.07 g, 7.03 mmol) in DMF (20 mL) were added TBDPSCl (2.73 mL, 10.5 mmol) and imidazole (1.44 g, 21.1 mmol), and the mixture was stirred at room temperature overnight. After removing the solvent under reduced pressure, the residue was extracted with CH₂Cl₂ and saturated NaHCO₃ aqueous solution. The organic layer was separated, dried over anhydrous Na₂SO₄, filtered and concentrated. The crude material was purified by flash column chromatography on silica gel (0-10% EtOAc in hexane) to obtain compound 204 (4.85 g, quant, $R_f$=0.41; developed with 10% EtOAc in hexane). $^1$H NMR (400 MHZ, DMSO-$d_6$): δ 7.70-7.55 (m, 7H), 7.51-7.22 (m, 15H), 5.63 (d, J=3.7 Hz, 1H), 4.79 (t, J=4.1 Hz, 1H), 4.67 (d, J=12.1 Hz, 1H), 4.46 (d, J=12.1 Hz, 1H), 4.10-3.92 (m, 3H), 3.88 (dd, J=8.8, 1.6 Hz, 1H), 1.42 (s, 3H), 1.30 (s, 3H), 0.953-0.947 (m, 12H).

Synthesis of compound 206: o a solution of compound 204 (3.00 g, 5.63 mmol) in AcOH (15 mL) and Ac₂O (3 mL) was added H₂SO₄ (10 drops) at 0° C. The reaction mixture was stirred at room temperature for 14 h. The solvent was removed under reduced pressure, and the residue was extracted with EtOAc and H₂O. The organic layer was separated, dried over anhydrous Na₂SO₄, filtered and concentrated. The crude material was co-evaporated with CH₃CN then used next step. To a solution of the crude material in CH₃CN (35 mL) were added uracil (1.88 g, 16.8 mmol) and N,O-bis(trimethylsilyl)acetamide (6.85 mL, 28.0 mmol). The mixture was stirred at 40° C. for 15 min the TMSOTf (1.52 mL, 8.40 mmol) was added at 0° C. The mixture was stirred at 80° C. for 2 h. Standard work-up and purification by flash column chromatography on silica gel (0-50% EtOAc in hexane) gave compound 206 (2.01 g, 3.20 mmol, 57%, $R_f$=0.32; developed with 50% EtOAc in hexane). $^1$H NMR (400 MHZ, DMSO-$d_6$): δ 11.43 (s, 1H), 7.66-7.59 (m, 4H), 7.55 (d, J=8.1 Hz, 1H), 7.51-7.22 (m, 12H), 5.84 (d, J=4.9 Hz, 1H), 5.51 (dd, J=8.1, 1.4 Hz, 1H), 5.41 (t, J=5.4 Hz, 1H), 4.58-4.43 (m, 2H), 4.40 (t, J=5.9 Hz, 1H), 4.14 (dd, J=6.4, 3.5 Hz, 1H), 3.87 (dd, J=5.8, 3.5 Hz, 1H), 2.06 (s, 3H), 1.07-0.95 (m, 9H), 0.90 (d, J=6.4 Hz, 3H).

$^{13}$C NMR (126 MHz, DMSO-d$_6$): & 169.69, 162.90, 150.26, 141.73, 137.60, 135.40, 135.26, 133.52, 133.27, 129.88, 129.87, 128.27, 127.76, 127.72, 127.70, 102.08, 87.52, 84.90, 74.88, 72.51, 71.92, 68.44, 26.82, 20.53, 18.79, 18.60.

Synthesis of compound 207: To a solution of compound 206 (1.94 g, 3.09 mmol) in MeOH (30 mL) was added K$_2$CO$_3$ (854 mg, 6.18 mmol) at 0° C. The reaction mixture was stirred for 3 h at 0° C. by addition of MeOH (0.2 mL). EtOAc (100 mL) and H$_2$O (20 mL) were added then extracted. The organic layer was separated, dried over anhydrous Na$_2$SO$_4$, filtered and concentrated. The crude material was purified by flash column chromatography on silica gel (0-75% EtOAc in hexane) to obtain compound 207 (1.68 g, 2.86 mmol, 93%, R$_f$=0.28; developed with 67% EtOAc in hexane). $^1$H NMR (400 MHz, DMSO-d$_6$): δ 11.40 (d, J=2.2 Hz, 1H), 7.67-7.57 (m, 4H), 7.53-7.24 (m, 12H), 5.77 (d, J=6.6 Hz, 1H), 5.59 (d, J=6.3 Hz, 1H), 5.48 (dd, J=8.0, 2.1 Hz, 1H), 4.73 (d, J=12.0 Hz, 1H), 4.53 (d, J=12.0 Hz, 1H), 4.22 (q, J=6.2 Hz, 1H), 4.13-3.98 (m, 2H), 3.84 (t, J=4.2 Hz, 1H), 0.99 (s, 9H), 0.91 (d, J=6.3 Hz, 3H). $^{13}$C NMR (126 MHz, DMSO-d$_6$): δ 162.85, 150.73, 140.84, 138.27, 135.40, 135.22, 133.53, 133.38, 129.88, 128.15, 127.79, 127.74, 127.46, 127.41, 102.01, 87.51, 85.56, 76.32, 71.50, 71.29, 69.02, 26.82, 19.12, 18.82.

Synthesis of compound 208: To a solution of compound 207 (3.70 g, 6.31 mmol) in EtOH (150 mL) were added cyclohexene (32.1 mL, 0.317 mol, 50 eq.) and palladium hydroxide on carbon (20 wt. % loading; 2.23 g). The mixture was heated at 80° C. for 3 h. The reaction mixture was filtered through Celite then concentrated. The crude material was purified by flash column chromatography on silica gel (0-5% MeOH in CH$_2$Cl) to obtain compound 208 (2.80 g. 5.64 mmol, 89%, R$_f$=0.16; developed with 5% MeOH in CH$_2$Cl$_2$). $^1$H NMR (400 MHZ, DMSO-d$_6$): δ 11.37 (d, J=2.2 Hz, 1H), 7.65-7.62 (m, 4H), 7.56-7.26 (m, 7H), 5.72 (d, J=6.4 Hz, 1H), 5.54-5.30 (m, 2H), 5.11 (d, J=5.4 Hz, 1H), 4.23-4.04 (m, 2H), 3.97 (q, J=6.1 Hz, 1H), 3.67 (t, J=4.2 Hz, 1H), 1.02 (s, 9H), 0.96 (d, J=6.4 Hz, 3H). $^{13}$C NMR (126 MHz, DMSO-d$_6$): δ 162.85, 150.72, 140.85, 135.41, 135.24, 133.71, 133.50, 129.85, 129.83, 127.77, 127.73, 101.97, 87.42, 87.15, 71.88, 69.15, 68.91, 26.84, 19.20, 18.88.

Synthesis of compound 209: To a solution of compound 208 (2.80 g, 5.64 mmol) in dioxane (70 mL) was added a solution of NaIO$_4$ (1.33 g, 6.20 mmol) H$_2$O (12 mL) was added. The reaction mixture was vigorously stirred at ambient temperature for 2 hours. The reaction mixture was filtered through a sintered funnel, and the filter cake was washed with additional dioxane. To the filtrate was added NaBH$_4$ (320 mg, 8.46 mmol). After stirring at ambient temperature for 2 hours, the solvent was removed under reduced pressure. The crude material was purified by flash column chromatography (0-5% MeOH in DCM) to obtain compound 209 as a white foam (2.73 g, 5.47 mmol, 97%; R$_f$=0.20 developed with 5% MeOH in DCM). $^1$H NMR (400 MHZ, DMSO-d$_6$): δ 11.23 (d, J=2.1 Hz, 1H), 7.63-7.53 (m, 4H), 7.51-7.35 (m, 8H), 5.86 (dd, J=6.7, 5.0 Hz, 1H), 5.45 (dd, J=8.0, 2.1 Hz, 1H), 5.10 (t, J=5.9 Hz, 1H), 4.77 (t, J=5.3 Hz, 1H), 3.81 (dd, J=6.4, 3.5 Hz, 1H), 3.71-3.59 (m, 1H), 3.58-3.44 (m, 4H), 0.95 (s, 9H), 0.87 (d, J=6.3 Hz, 3H). $^{13}$C NMR (126 MHz, DMSO-d$_6$): δ 163.15, 151.33, 140.93, 135.38, 135.31, 133.73, 133.00, 129.81, 129.71, 127.72, 127.61, 101.56, 83.67, 83.58, 68.94, 61.31, 60.21, 26.75, 18.74, 18.54.

Synthesis of compound 210: To a solution of compound 209 (720 mg, 1.44 mmol) in anhydrous DCM (40 mL) and pyridine (1.17 mL, 14.4 mmol), cooled to −78° C., benzoyl chloride (0.184 mL, 1.58 mmol) was slowly added. After stirring at −78° C. for 2 hours, reaction mixture was brought to 0° C., and quenched with EtOH (1 mL). The mixture was diluted with DCM (40 mL) then washed with saturated aq. NaHCO$_3$ (20 mL). The organic layer was washed with brine, separated, dried over anhydrous Na$_2$SO$_4$, filtered, and concentrated. The crude residue was purified by flash column chromatography (0-80% EtOAC in hexanes) to give compound 210 as a white foam (361 mg, 0.599 mmol, 42%; R$_f$=0.64, developed with 80% EtOAc in hexanes). $^1$H NMR (400 MHZ, DMSO-d$_6$): δ 11.34 (s, 1H), 8.02-7.82 (m, 2H), 7.71-7.63 (m, 1H), 7.61-7.50 (m, 7H), 7.49-7.36 (m, 6H), 6.27 (dd, J=6.6, 5.1 Hz, 1H), 5.45 (d, J=8.0 Hz, 1H), 4.89 (t, J=5.0 Hz, 1H), 4.58 (dd, J=11.5, 5.1 Hz, 1H), 4.43 (dd, J=11.5, 6.6 Hz, 1H), 3.85 (dd, J=6.4, 2.8 Hz, 1H), 3.61-3.55 (m, 3H), 0.95 (s, 9H), 0.93 (d, J=6.4 Hz, 3H). $^{13}$C NMR (126 MHz, DMSO-d$_6$): δ 164.98, 162.97, 150.99, 140.24, 135.38, 135.31, 133.69, 133.62, 132.95, 129.85, 129.75, 129.11, 129.03, 128.82, 127.74, 127.63, 102.03, 83.76, 80.95, 69.13, 63.51, 60.35, 26.75, 18.75, 18.45.

Synthesis of compound 211: To a solution of compound 210 (585 mg, 0.971 mmol) in anhydrous pyridine (5 mL) was added DMTrCl (495 mg, 1.46 mmol). The reaction mixture was stirred at room temperature for 16 h. After removing the solvent, the residue was extracted with CH$_2$Cl$_2$ (100 mL) and saturated NaHCO$_3$ aqueous solution (50 mL). The organic layer was separated, dried over anhydrous Na$_2$SO$_4$, filtered and concentrated. The crude material was purified by flash column chromatography on silica gel (0-33% EtOAc in hexanes) to give compound 211 (764 mg, 0.844 mmol, 87%, R$_f$=0.22 developed with 33% EtOAc in hexanes) as a white foam. 1H NMR (400 MHZ, DMSO-d$_6$): δ 11.42 (s, 1H), 7.86-7.73 (m, 2H), 7.73-7.59 (m, 1H), 7.52-7.40 (m, 9H), 7.34 (tt, J=7.3, 4.0 Hz, 6H), 7.29-7.14 (m, 7H), 6.80 (dd, J=8.9, 3.1 Hz, 4H), 6.44 (t, J=5.9 Hz, 1H), 5.47 (d, J=8.0 Hz, 1H), 4.47 (dd, J=11.5, 5.5 Hz, 1H), 4.37 (dd, J=11.5, 6.4 Hz, 1H), 3.81 (dt, J=7.9, 4.2 Hz, 1H), 3.69 (d, J=5.9 Hz, 7H), 3.26 (dd, J=10.2, 4.5 Hz, 1H), 3.13 (dd, J=10.2, 7.1 Hz, 1H), 0.83 (s, 9H), 0.78 (d, J=6.3 Hz, 3H). $^{13}$C NMR (126 MHZ, DMSO-d$_6$): δ 164.79, 162.97, 158.05, 158.01, 151.12, 144.60, 140.14, 135.51, 135.35, 135.30, 133.61, 133.43, 132.73, 129.84, 129.77, 129.58, 129.49, 129.08, 128.90, 128.74, 127.80, 127.68, 127.60, 127.54, 126.64, 113.11, 102.22, 86.15, 81.65, 81.21, 69.53, 63.42, 63.36, 54.97, 54.95, 26.63, 18.74, 18.63.

Synthesis of compound 212: Compound 211 (740 mg, 0.818 mmol) in THF (8 mL) was treated with 1 M n-TBAF in THF (1.06 mmol, 1.06 mL) overnight. After removing the solvent, the residue was purified by flash column chromatography on silica gel (0-66% EtOAc in hexane) to give compound 212 (226 mg, 0.339 mmol, 41%, R$_f$=0.25 developed with 66% EtOAc in hexane) as a white solid. This compound was also synthesized from compound 213 by standard dimethoxytritylation in 93% yield. 1H NMR (400 MHZ, DMSO-d$_6$): δ 11.38 (s, 1H), 7.88-7.76 (m, 3H), 7.72-7.61 (m, 1H), 7.49 (t, J=7.8 Hz, 2H), 7.44-7.37 (m, 2H), 7.32-7.24 (m, 6H), 7.24-7.16 (m, 1H), 6.84 (dd, J=8.7, 5.8 Hz, 4H), 6.45 (dd, J=7.1, 5.1 Hz, 1H), 5.67 (d, J=8.0 Hz, 1H), 4.64 (d, J=5.2 Hz, 1H), 4.55 (dd, J=11.6, 5.1 Hz, 1H), 4.48 (dd, J=11.5, 7.1 Hz, 1H), 3.69 (d, J=4.9 Hz, 6H), 3.66-3.57 (m, 1H), 3.51 (q, J=5.8 Hz, 1H), 3.27 (dd, J=10.3, 3.2 Hz, 1H), 3.08 (dd, J=10.2, 7.2 Hz, 1H), 0.89 (d, J=6.3 Hz, 3H). $^{13}$C NMR (126 MHZ, DMSO-d$_6$): δ 164.85, 163.16, 158.02, 157.99, 151.32, 144.74, 141.09, 135.67, 135.54, 133.63, 129.65, 129.59, 129.11, 128.93, 128.79, 127.81, 127.68, 126.64, 113.15, 113.12, 101.91, 85.91, 82.29, 81.26, 65.61, 63.89, 63.28, 54.97, 54.95, 19.18.

Synthesis of compound 213: Compound 210 (361 mg, 0.599 mmol) in THF (5 mL) was treated with 1 M n-TBAF in THF (0.719 mmol, 0.719 mL) for 2 h After removing the solvent, the residue was purified by flash column chromatography on silica gel (0-100% EtOAc in hexane then 5% MeOH in EtOAc) to give compound 213 (209 mg, 0.574 mmol, 96%, $R_f$=0.29 developed with 5% MeOH in EtOAc) as a white solid. 1H NMR (400 MHZ, DMSO-$d_6$): δ 11.31 (s, 1H), 7.95-7.85 (m, 2H), 7.79 (d, J=8.1 Hz, 1H), 7.74-7.61 (m, 1H), 7.53 (t, J=7.8 Hz, 2H), 6.26 (dd, J=7.0, 5.1 Hz, 1H), 5.65 (d, J=8.0 Hz, 1H), 4.77 (t, J=5.4 Hz, 1H), 4.69-4.55 (m, 2H), 4.45 (dd, J=11.5, 7.1 Hz, 1H), 3.61 (ddt, J=13.8, 6.4, 4.5 Hz, 2H), 3.50 (dt, J=11.8, 6.1 Hz, 1H), 3.38-3.30 (m, 2H), 0.99 (d, J=6.3 Hz, 3H). $^{13}$C NMR (126 MHZ, DMSO-$d_6$) δ 165.00, 163.18, 151.16, 141.11, 133.61, 129.13, 128.84, 101.64, 84.00, 65.12, 63.40, 60.77, 18.80.

Synthesis of compound 214: To a solution of compound 212 (1.25 g, 1.87 mmol) in DCM (15 ml) and DIPEA (0.651 ml, 3.74 mmol) were added 2-cyanoethyl N,N-diisopropylchlorophosphoramidite (0.544 mL, 2.44 mmol) and 1-methylimidazole (0.149 mL, 1.87 mmol) at 0° C. The mixture was stirred at room temperature for 2 h. The reaction mixture was diluted with $CH_2Cl_2$ (100 mL) then washed with saturated $NaHCO_3$ aqueous solution (50 mL). The organic layer was separated, dried over anhydrous $Na_2SO_4$, filtered and concentrated. The crude material was purified by flash column chromatography on silica gel (0-50% EtOAc in hexane) to give compound 214 (1.40 g, 1.61 mmol, 86%, $R_f$=0.20, 0.27 developed with 50% EtOAc in hexane) as a mixture of diastereomers. $^1$H NMR (500 MHZ, $CD_3CN$): δ 9.16 (s, 1H), 7.90-7.87 (m, 2H), 7.64-7.59 (m, 2H), 7.47-7.41 (m, 4H), 7.32-7.19 (m, 7H), 6.84-6.80 (m, 4H), 6.44 (q, J=5.7 Hz, 1H), 5.69 (dd, J=11.9, 8.1 Hz, 1H), 4.51 (ddd, J=23.0, 11.6, 5.3 Hz, 1H), 4.39 (ddd, J=20.8, 11.6, 6.0 Hz, 1H), 4.03-3.15 (m, 15H), 2.59 (t, J=6.0 Hz, 1H), 2.50 (t, J=6.0 Hz, 1H), 1.16-0.94 (m, 15H). $^{13}$C NMR (126 MHz, $CD_3CN$): δ 166.34, 163.98, 163.96, 159.66, 159.63, 152.04, 151.98, 146.00, 145.97, 141.59, 141.55, 136.93, 136.82, 136.74, 134.42, 134.39, 130.99, 130.93, 130.88, 130.44, 130.41, 130.39, 129.65, 129.63, 128.96, 128.88, 127.81, 118.29, 114.09, 114.08, 103.09, 103.04, 87.70, 87.66, 83.17, 83.14, 82.89, 82.76, 82.71, 71.45, 71.30, 70.72, 70.58, 64.72, 64.69, 64.67, 64.62, 59.41, 59.34, 59.27, 59.19, 55.87, 43.89, 43.79, 43.75, 43.66, 25.05, 24.99, 24.92, 24.86, 24.81, 24.69, 24.63, 20.99, 20.93, 20.91, 20.85, 18.29, 18.26, 17.65, 17.62. $^{31}$P NMR (202 MHz, $CD_3CN$): δ 149.38, 148.56.

Synthesis of compound 215: Standard succination of compound 212 using succinic anhydride and DMAP in $CH_2Cl_2$ followed by CPG loading using HBTU and DIPEA in DMF gives compound 215.

Example 3. Synthesis of Building Blocks Containing Guanine Derivatives with Acyclic Sugar Structures Synthesis of 5'-(R)-methyl-guanine-UNA Building Blocks Scheme 15

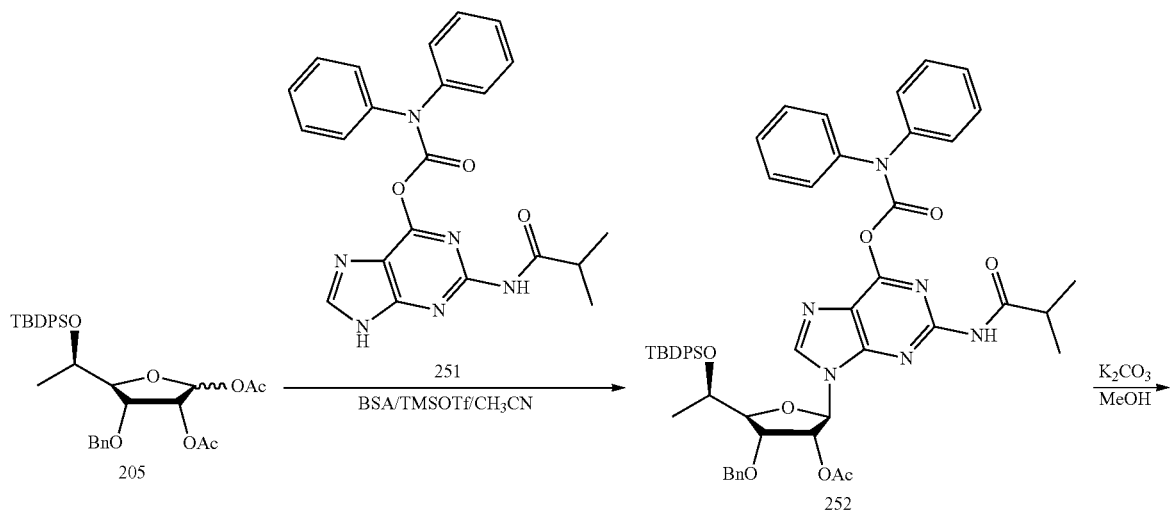

233  234
-continued
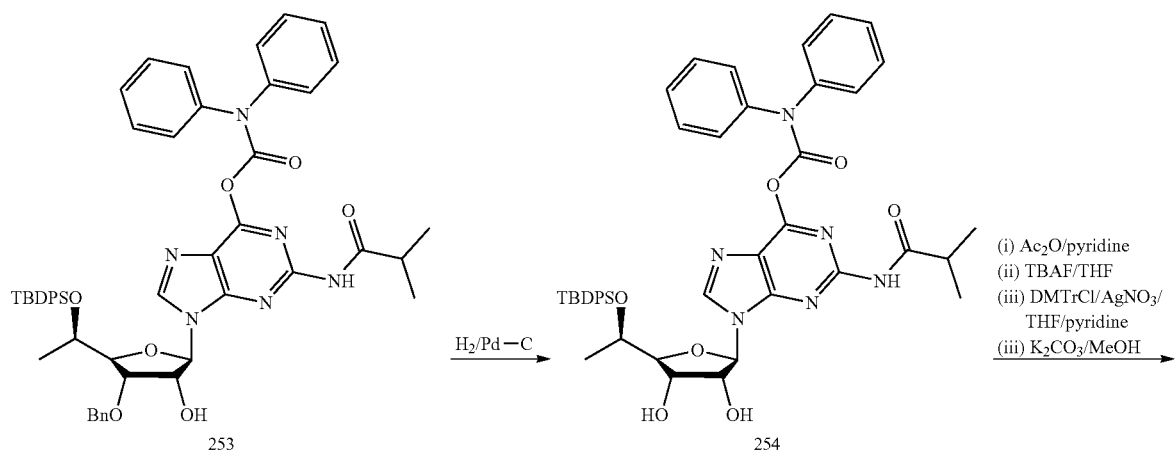
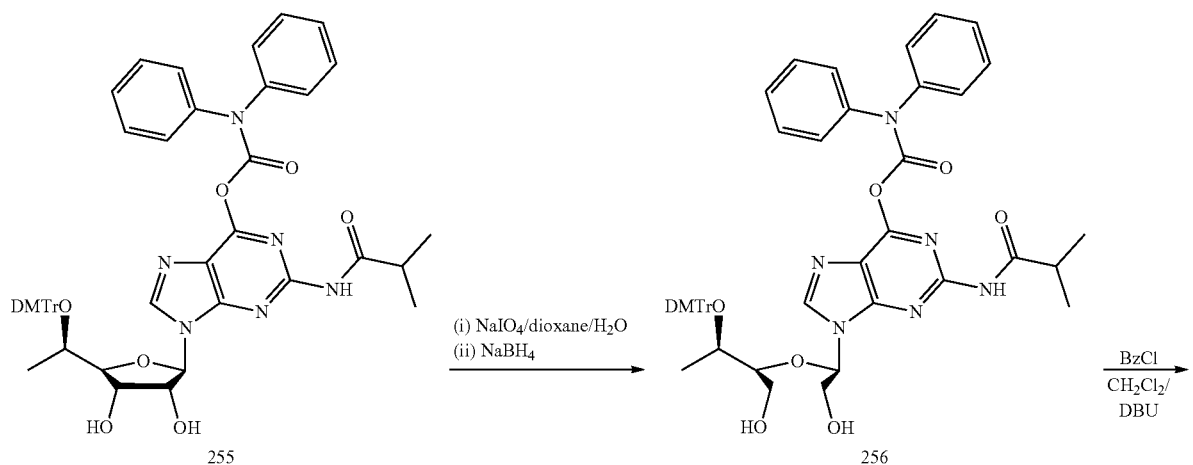

235 236

-continued

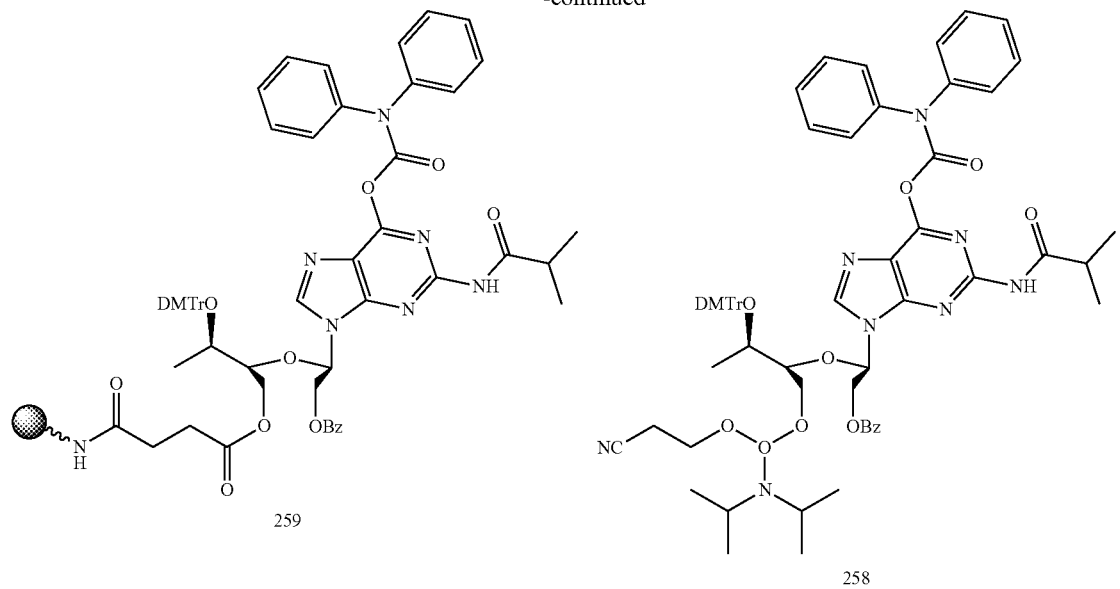

259

258

Protected guanine analog 251 is coupled with 205 to give 252. Removal of acetyl group and benzyl group gives 254. TBDPS group is changed to DMTr group to give 255 then oxidative cleavage followed by reduction gives 256. Selective benzoylation gives 257, which is converted to amidite 258 and loaded onto CPG to give 259 using standard conditions.

Synthesis of Inosine-UNA Building Blocks

Scheme 16

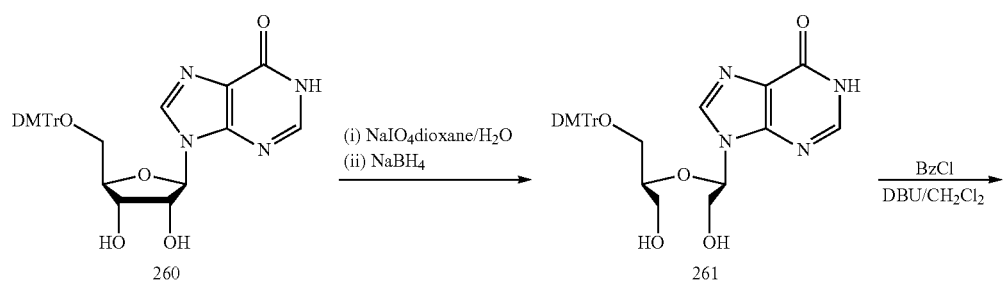

260 261

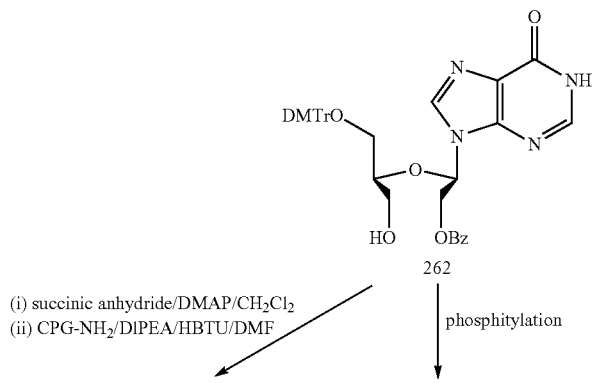

262

(i) succinic anhydride/DMAP/CH$_2$Cl$_2$
(ii) CPG-NH$_2$/DIPEA/HBTU/DMF phosphitylation

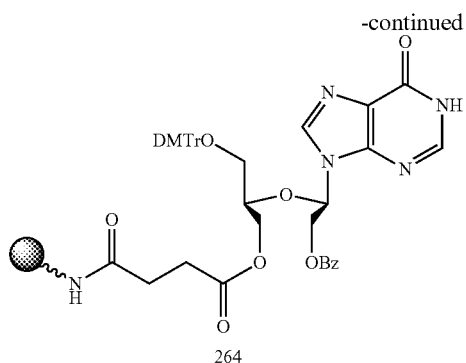
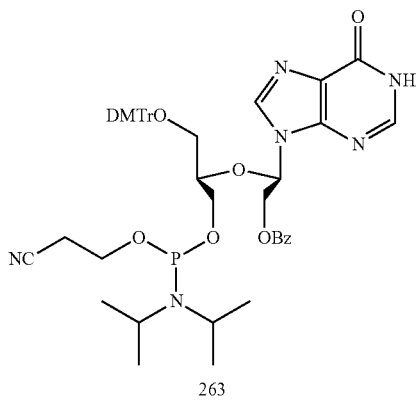
Building blocks 263 and 264 is synthesized from 5'-DMTr protected inosine ribonucleoside 260 using similar procedures described for the other UNA derivatives described above.
Synthesis of Inosine-GNA/SNA Building Blocks
Scheme 17
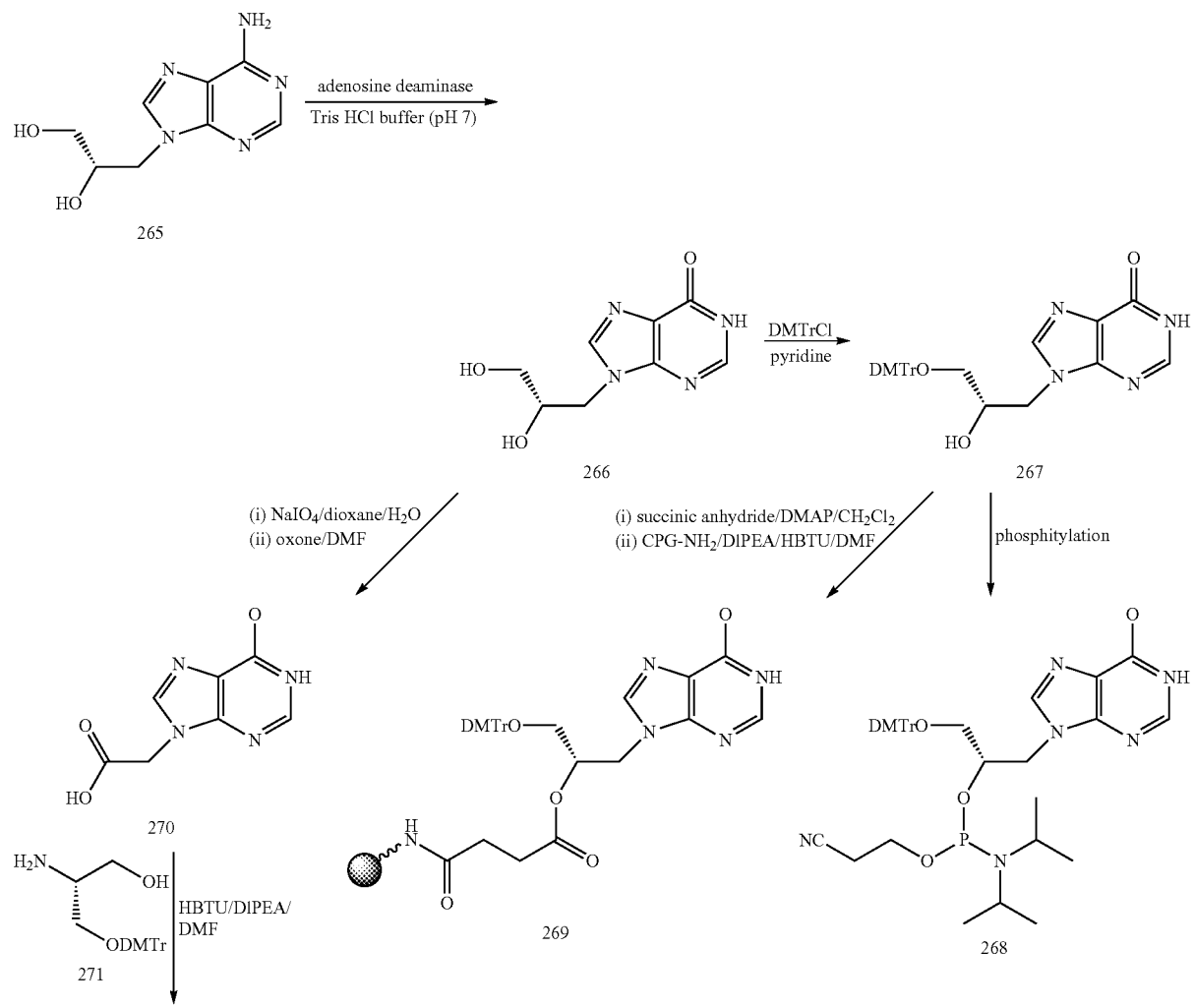

239

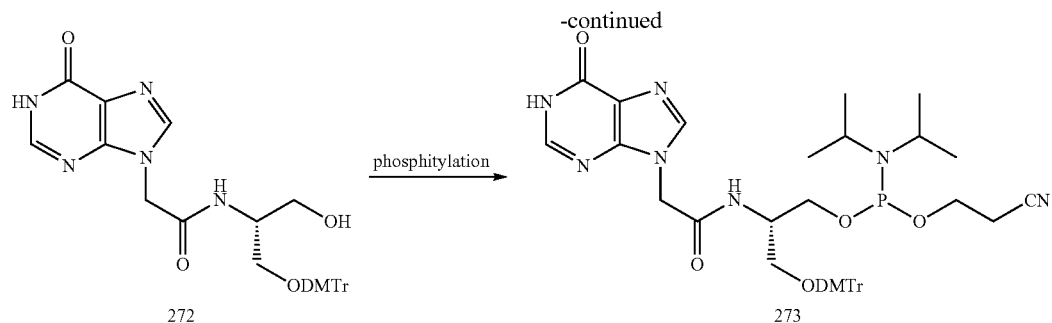

272 → 273

(i) succinic anhydride/DMAP/CH₂Cl₂
(ii) CPG-NH₂/DIPEA/HBTU/DMF

-continued

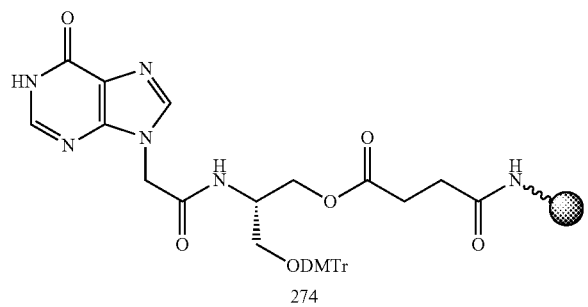

274

Compound 266, inosine-GNA is synthesized from A-GNA 265 by treatment with adenosine deaminase. Subsequent DMTr protection followed by phosphitylation and CPG loading gives 268 and 269. Oxidative cleavage of diol in 266 followed by mild oxidation gives 270, which is coupled with 271 to give inosine-SNA (serinol nucleic acid) precursor 272. 273 and 274 can be synthesized as described above.

Synthesis of isoG-UNA Building Blocks

Scheme 18

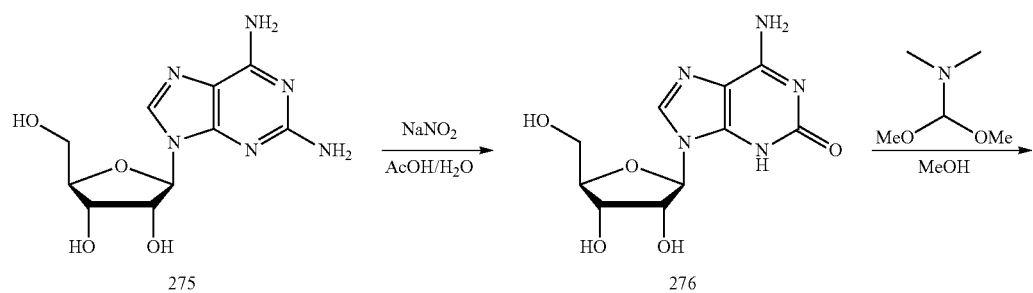

275 → 276

-continued
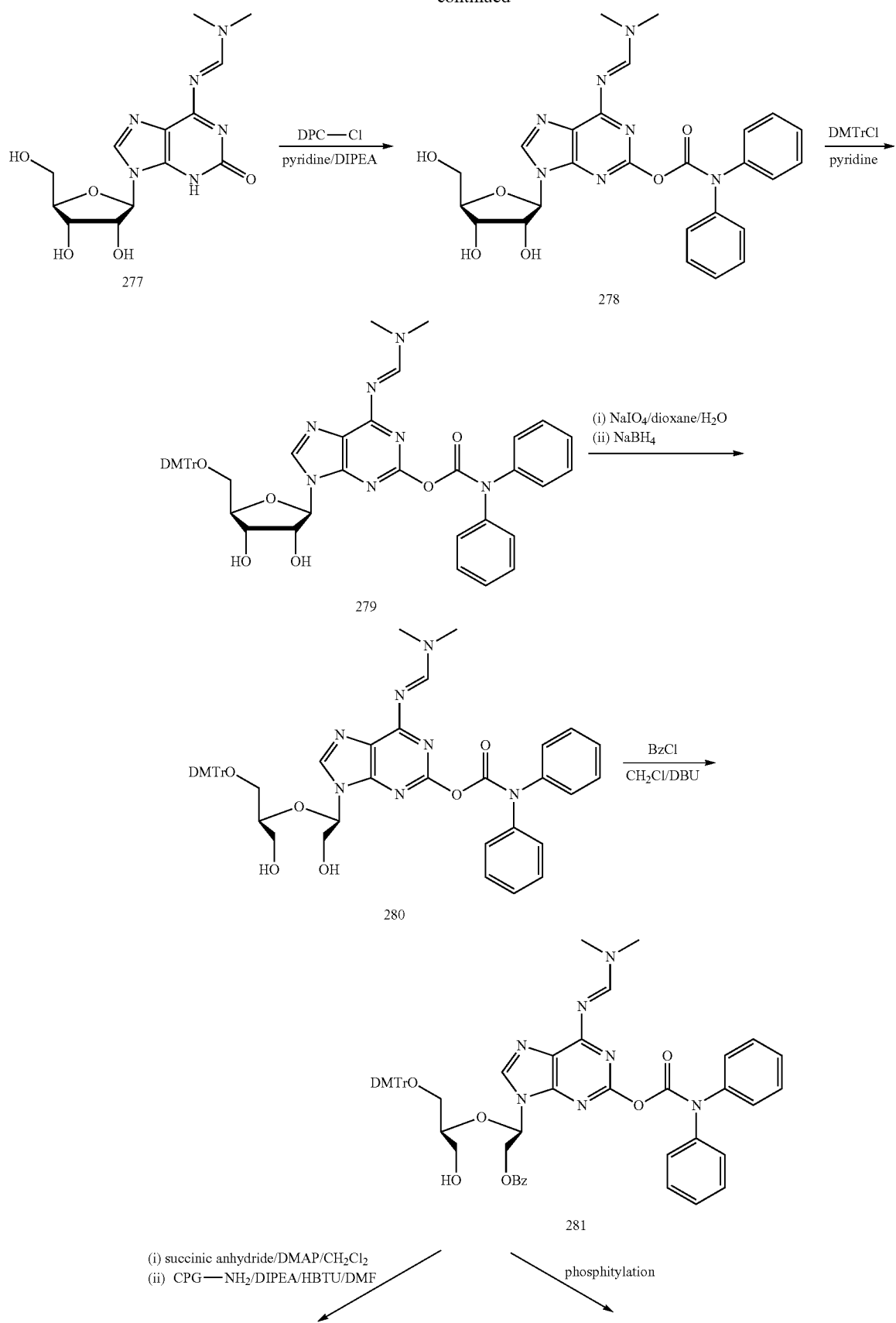

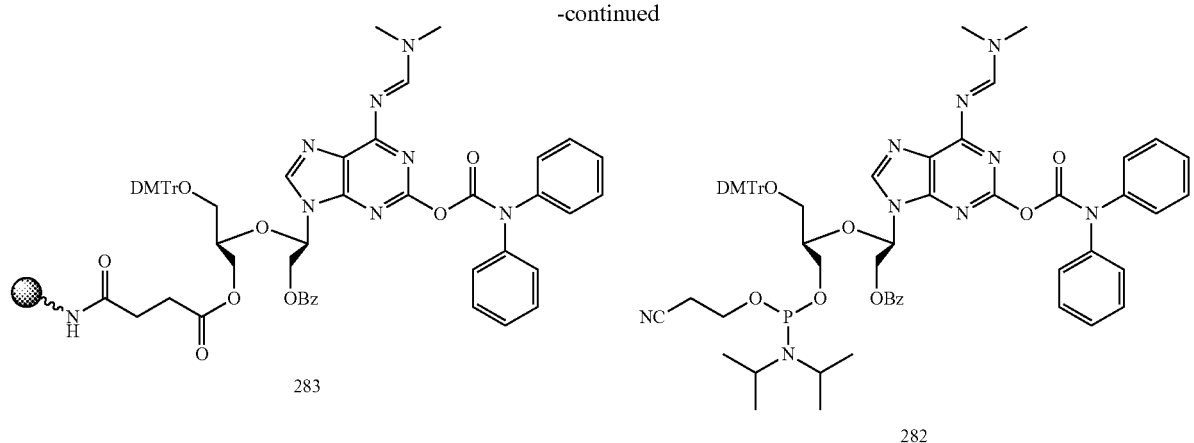
Starting from diaminoA ribonucleoside 275, similar procedures described for synthesis of isoG-ONA in scheme 11 gives 279. Standard producers for UNA analog synthesis described above can give imG-UNA building blocks 282 and 283.
Synthesis of isoG-SNA Building Blocks
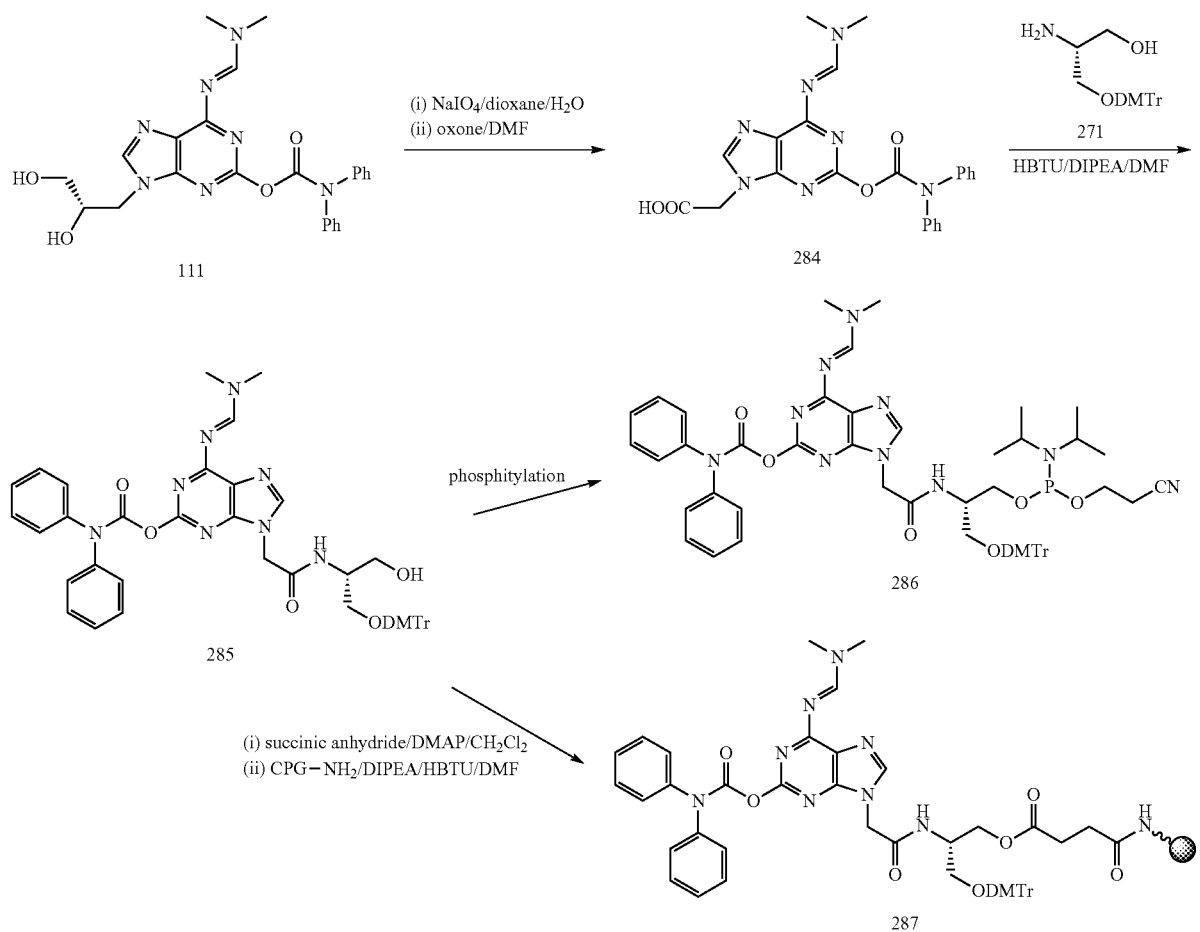

Oxidative cleavage of diol in 111 followed by mild oxidation gives 284, which is coupled with 271 to give isoG-SNA (serinol nucleic acid) precursor 285. 286 and 287 can be synthesized as described above.
Synthesis of 2-Aminopurine-UNA Building Blocks
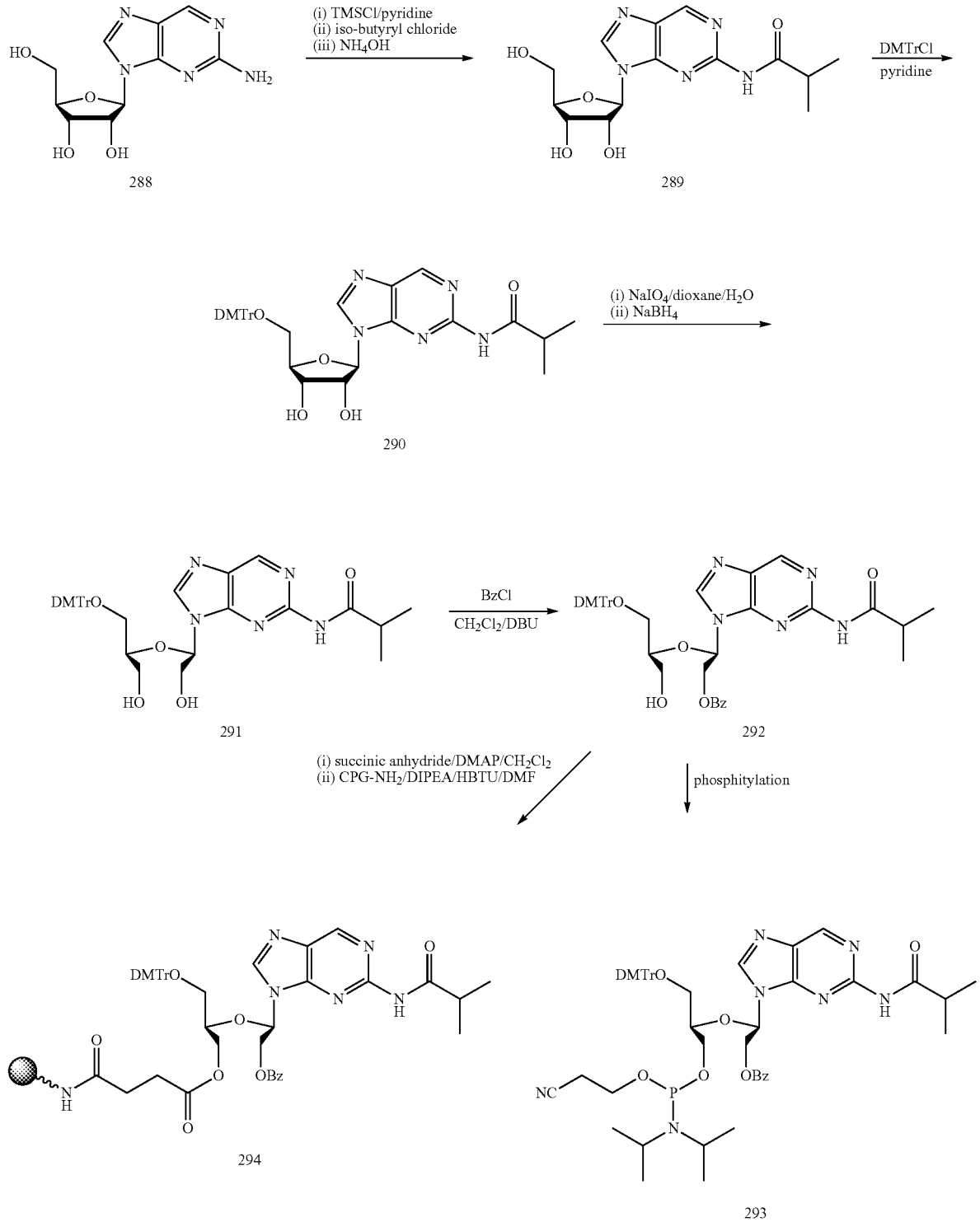

Starting from 2-aminopurine ribonucleoside 288, transient protection with TMS followed by exocyclic amino protection with iBuCl then alkali work-up gives 289. Standard producers for UNA analog synthesis described above can give 2-aminopurine-UNA building blocks 293 and 294.
Synthesis of 2-Aminopurine-GNA/SNA Building Blocks
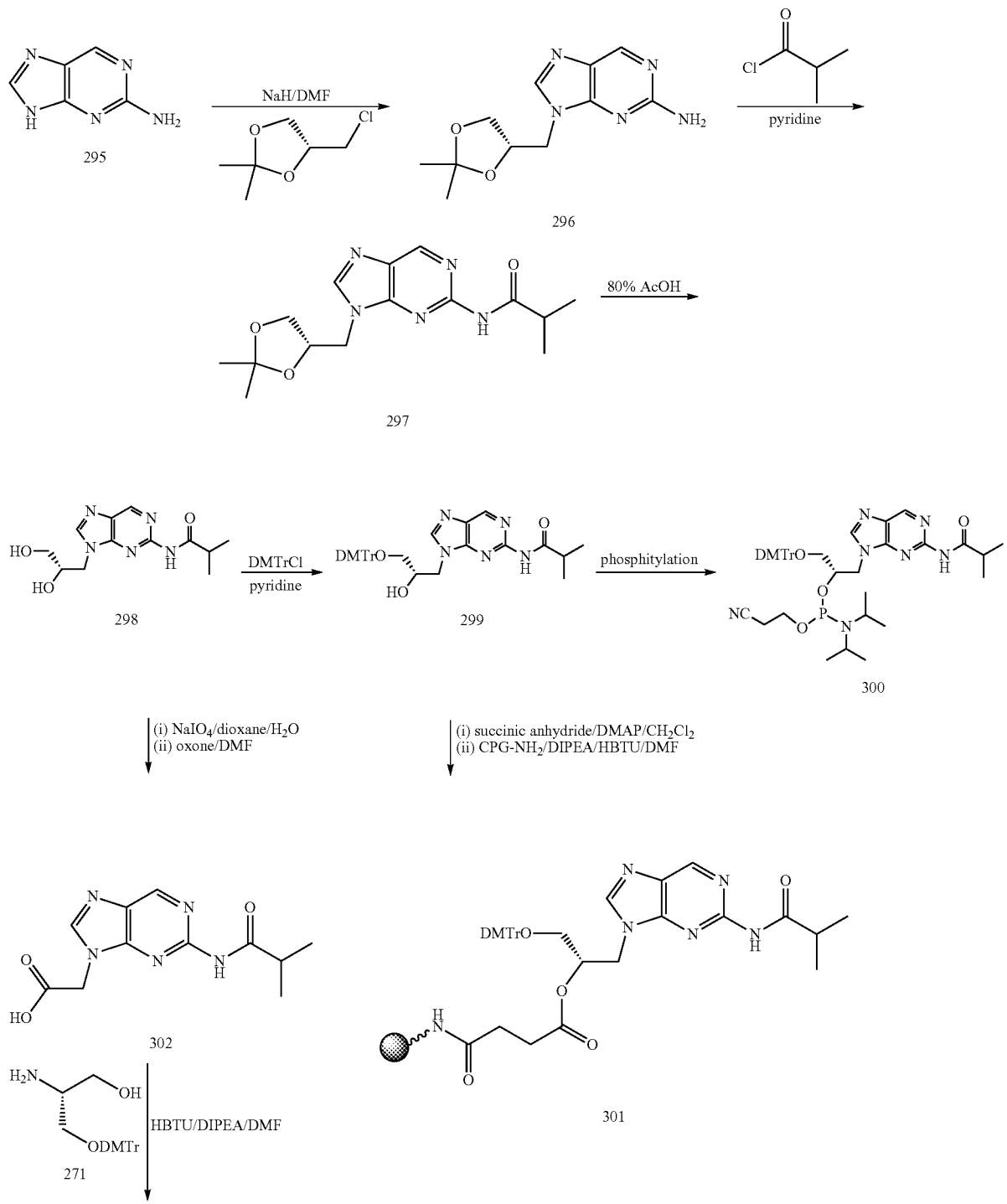

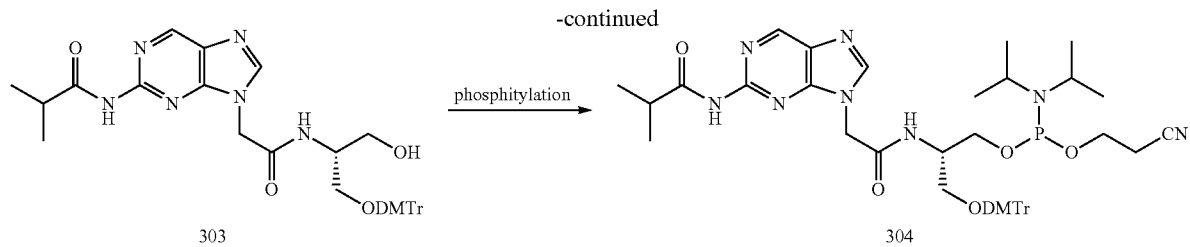

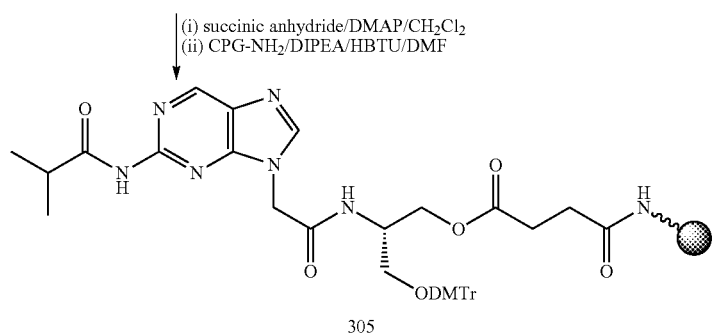

N-alkylation of 295 with actonide-protected chloro compound gives 296. Subsequent base protection, acid treatment, and DMTr protection give 299. 300 and 301 can be synthesized as described above. Oxidative cleavage of diol in 298 followed by mild oxidation gives acid 302, which is coupled with 271 to give 2-aminopurine-SNA (serinol nucleic acid) precursor 303. 304 and 305 can be synthesized as described above.

Synthesis of Xanthosine-UNA Building Blocks

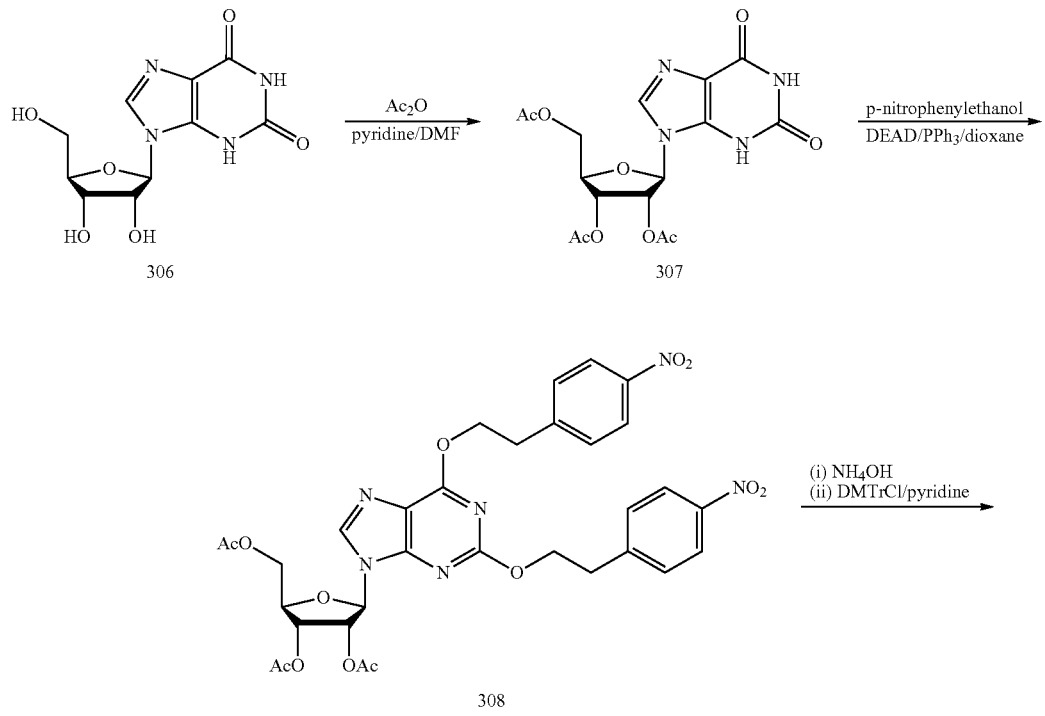

-continued
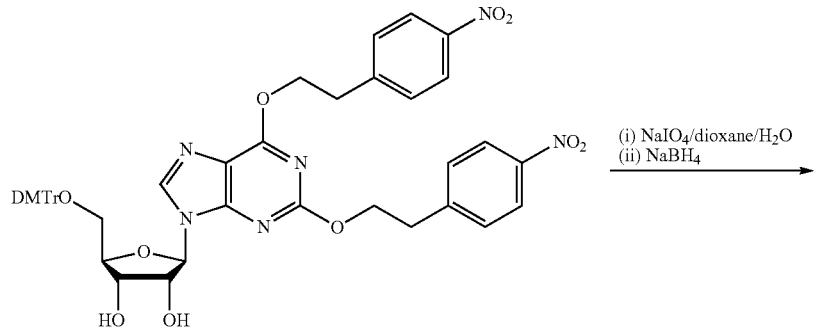
309
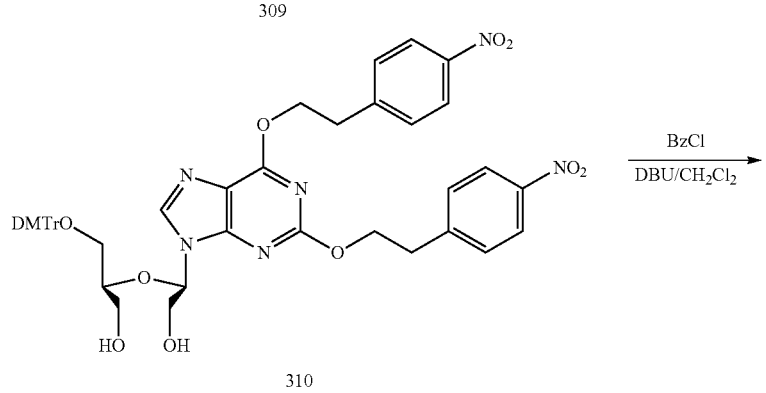
310
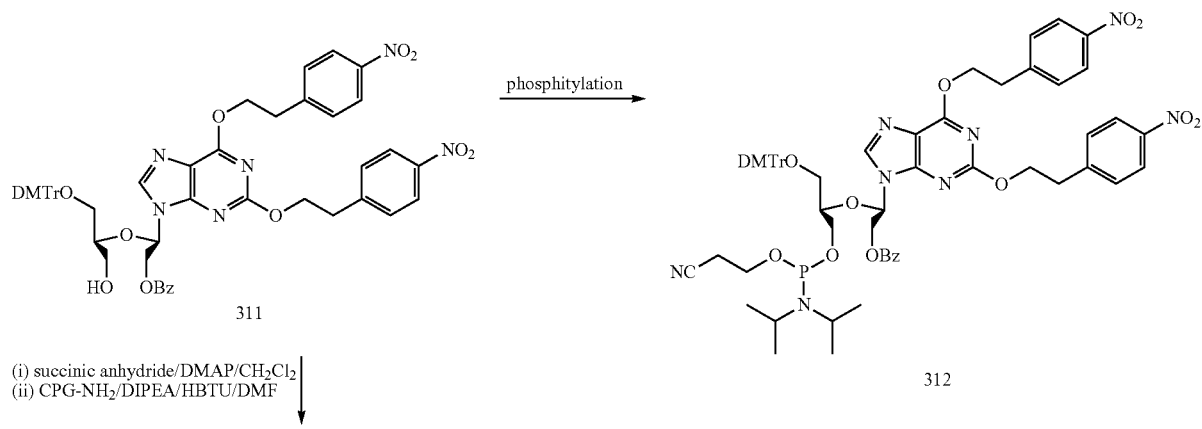
311 → 312
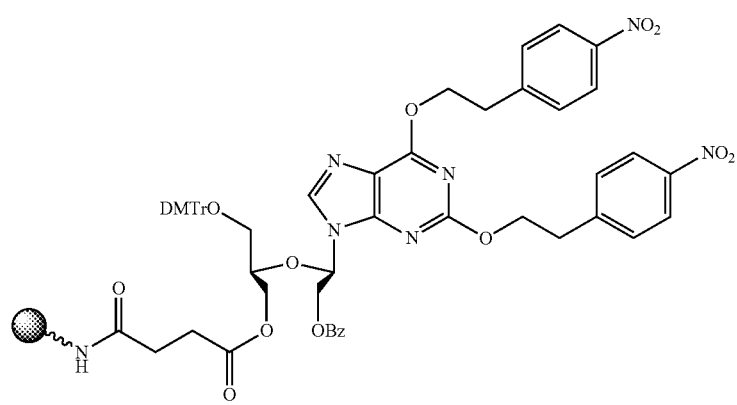
313

Xanthosine 306 is acetylated to give 367. Double Mitsunobu reactions followed by alkali treatment and DMTr protection give 389. Standard producers for UNA analog synthesis described above can give xanthosine-UNA building blocks 312 and 313.
Synthesis of Xanthosine-GNA Building Blocks
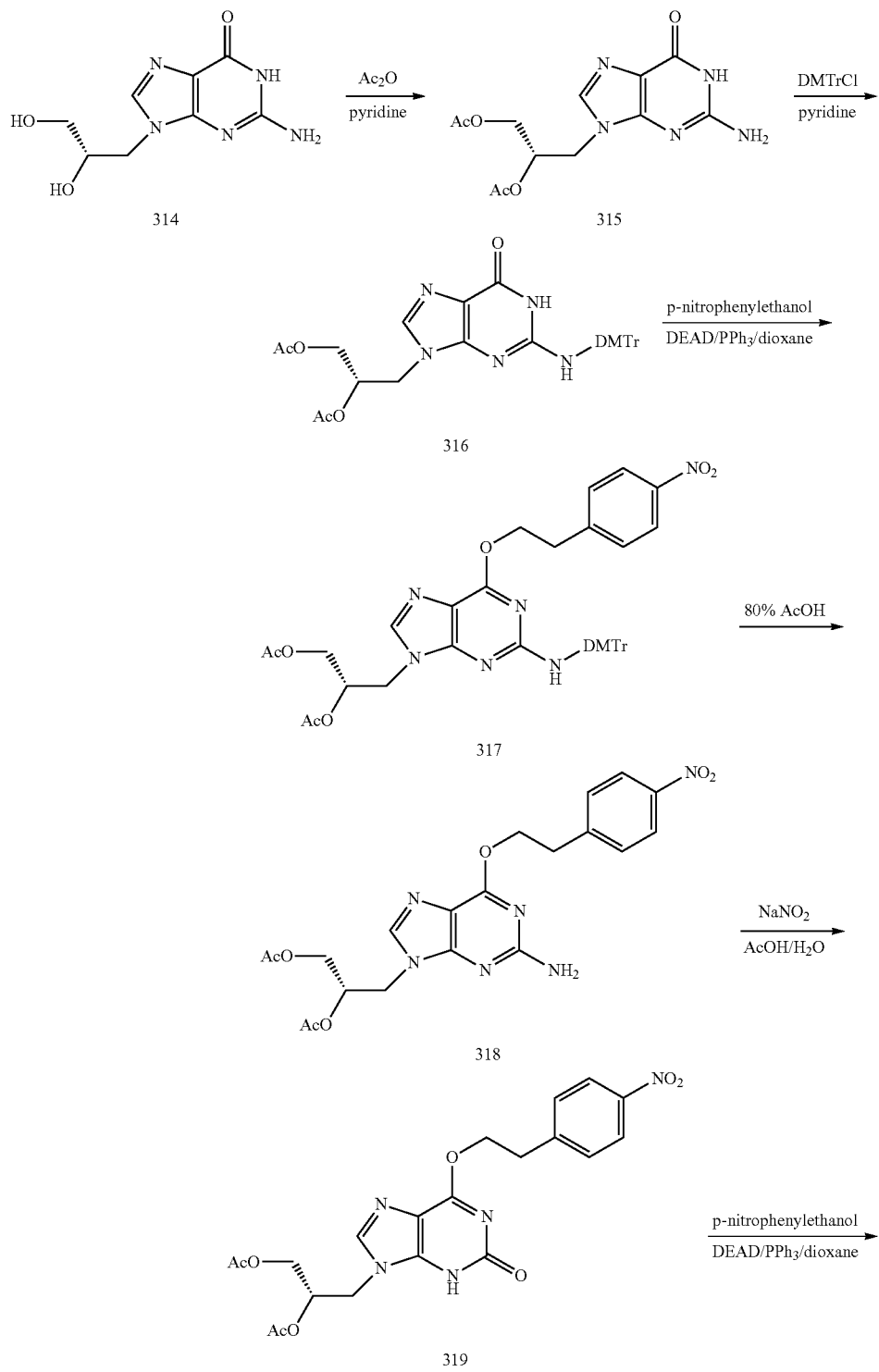

-continued
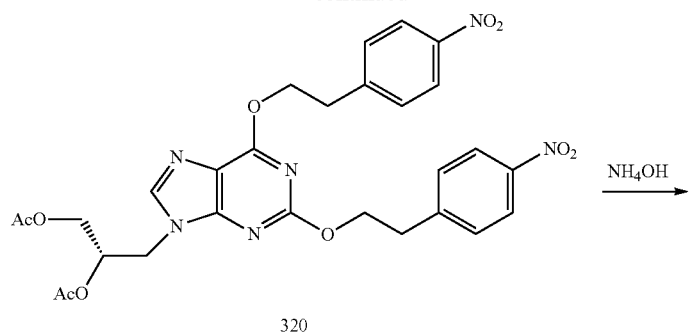
320
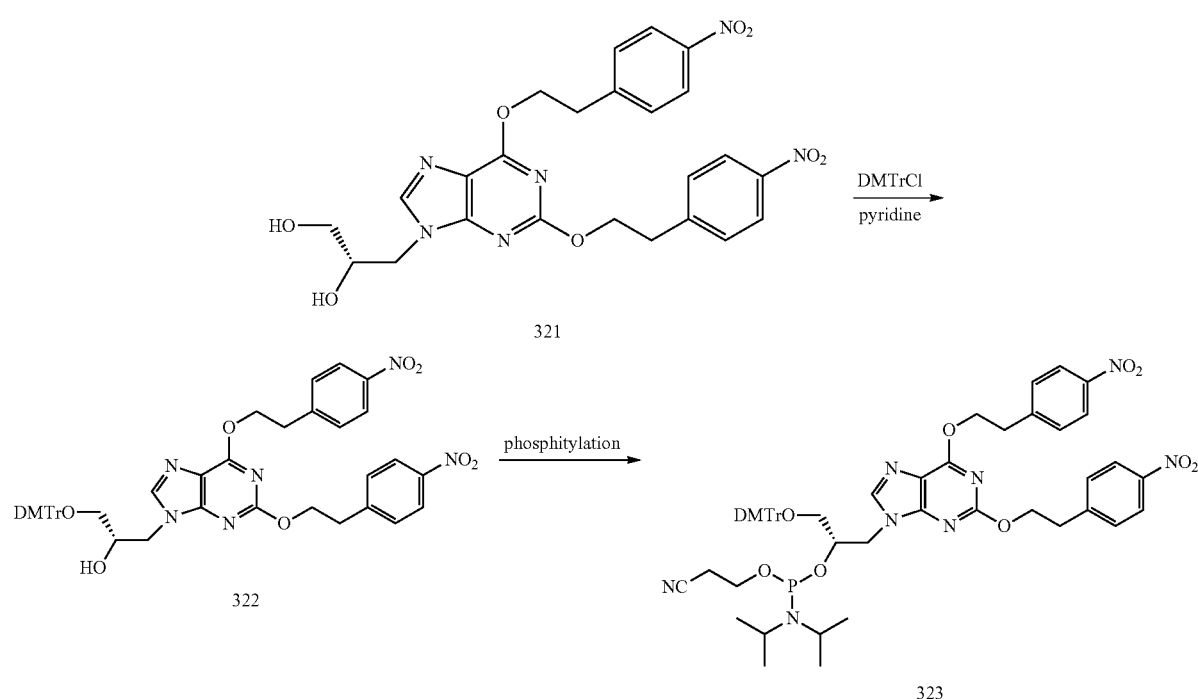
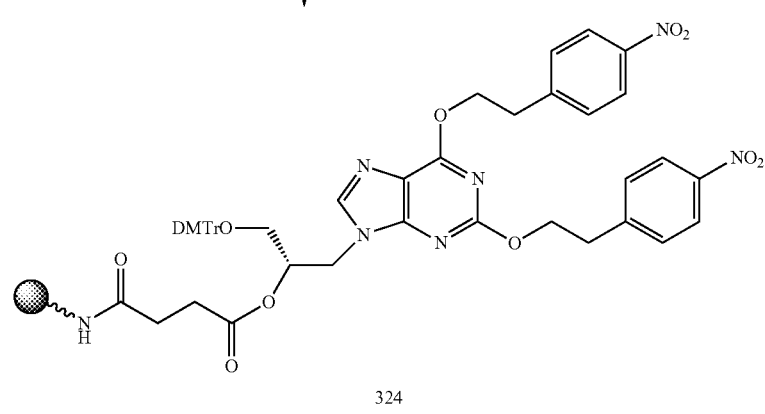
324

Acetylation of G-GNA gives 315 and following DMTr reaction for exocyclic amine gives 316. Mitsunobu reaction and acid treatment give 318. Treatment of 318 with sodium nitrite under acidic conditions gives 319. Mitsunobu reaction, removal of acetyl groups and DMTr protection give 322. 323 and 324 can be synthesized as described above.
Synthesis of Xanthosine-SNA Building Blocks
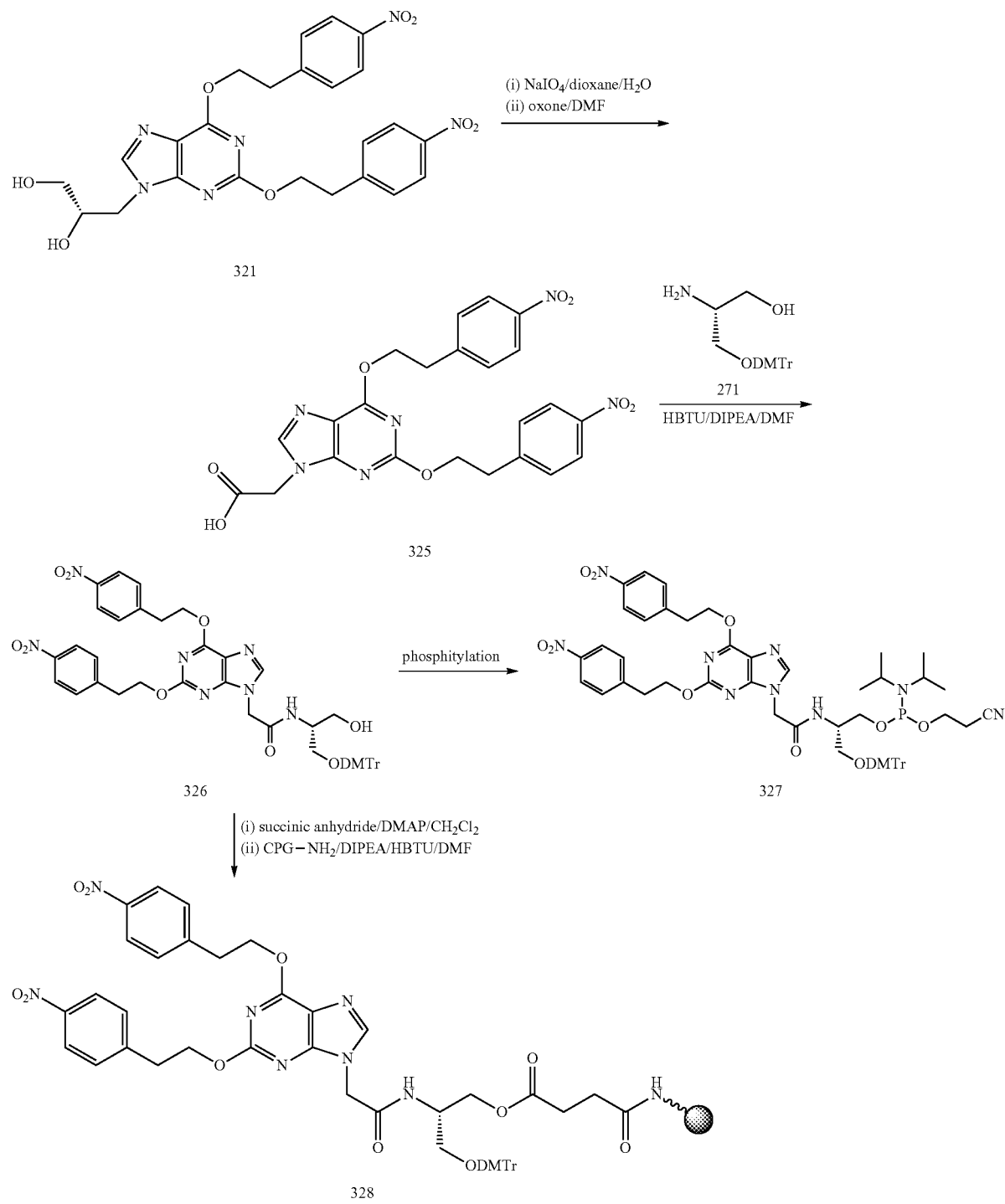
Scheme 24

Oxidative cleavage of diol in 321 followed by mild oxidation gives acid 325, which is coupled with 271 to give xanthosine-SNA (serinol nucleic acid) precursor 326. 327 and 328 can be synthesized as described above.
Synthesis of N1-methyl-G-UNA Building Blocks
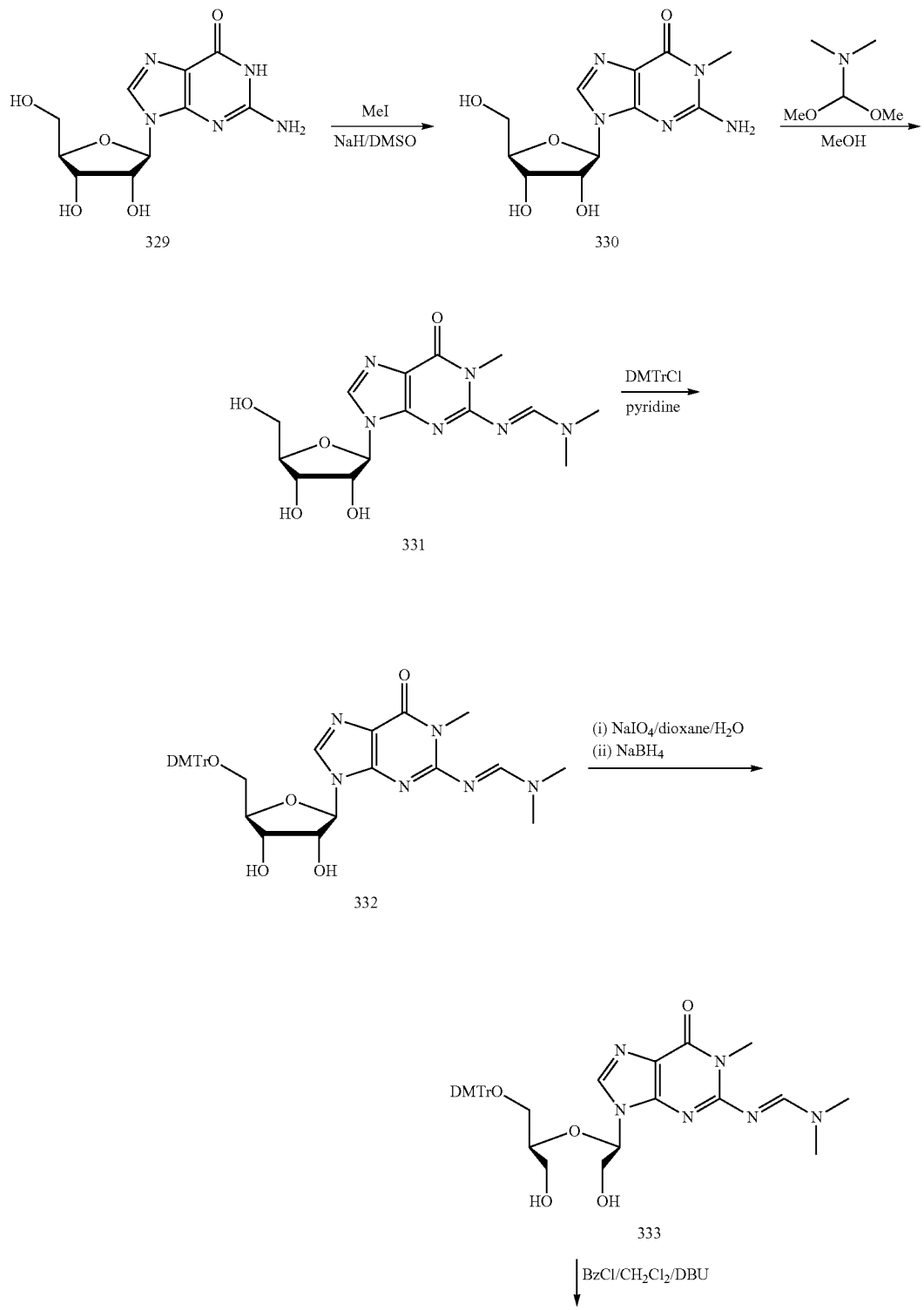

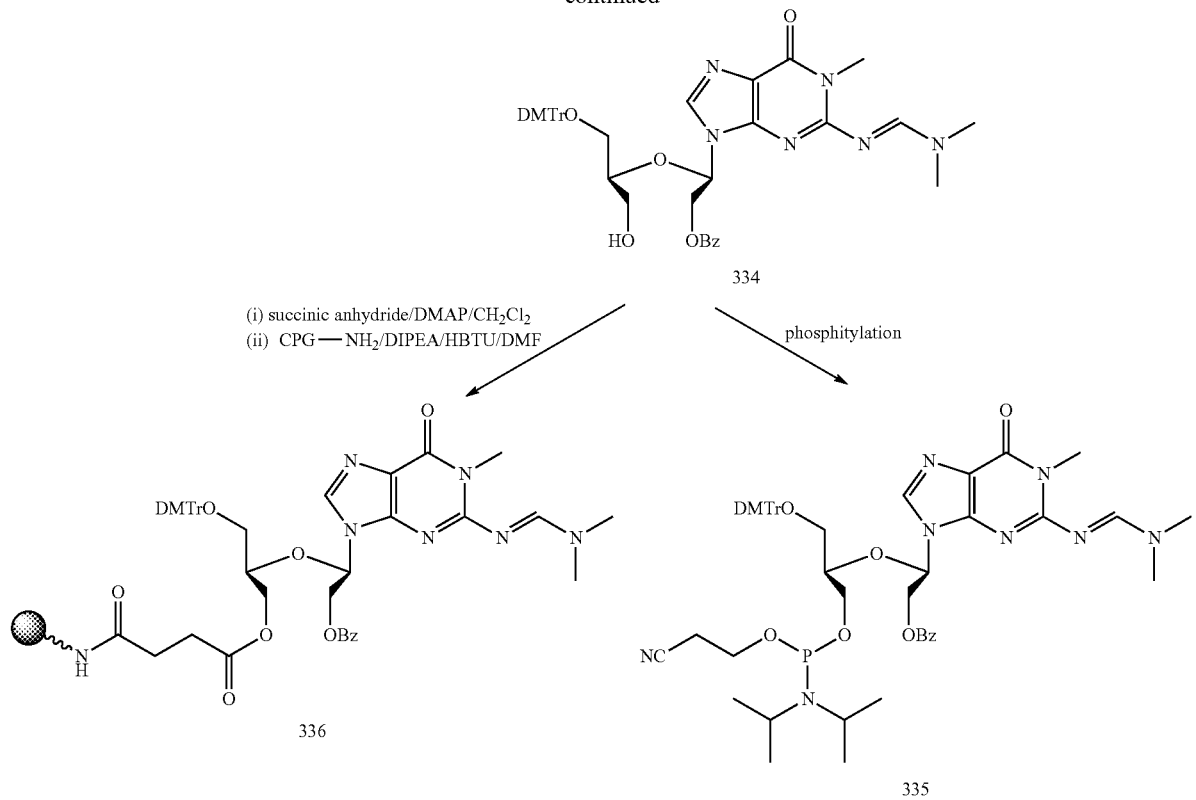
Guanosine 329 is treated with MeI in DMSO to give 330. Exocyclic amino protection followed by DMTr reaction gives 332. Standard producers for UNA analog synthesis described above can give N1-methylG-UNA building blocks 335 and 336.
Synthesis of N1-methyl-G-GNA Building Blocks
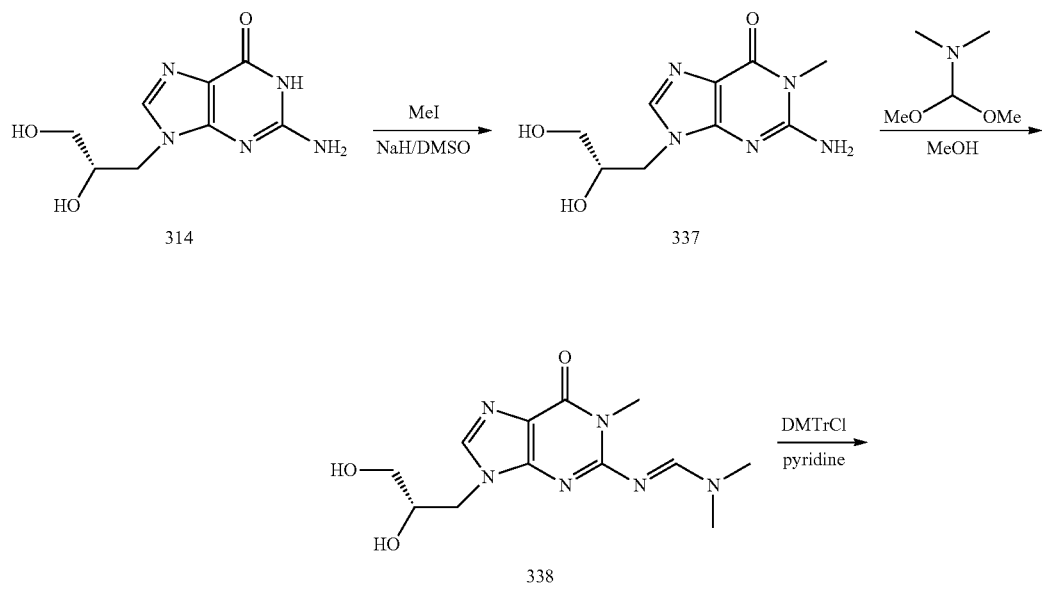

-continued
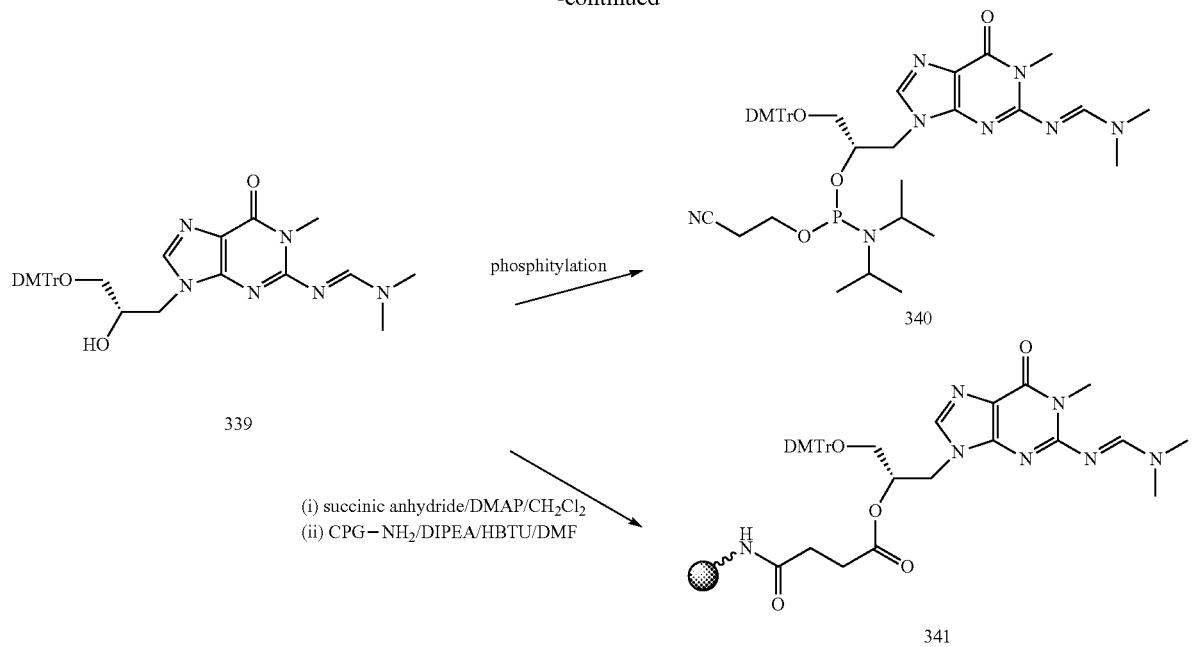
Methylation of G-GNA gives 314. Protection of exocyclic amino group and 5'-hydroxyl group gives 339. Standard phosphitylation and succination followed by CPG loading give 340 and 341, respectively.
Synthesis of N1-methyl-G-SNA Building Blocks
Scheme 27
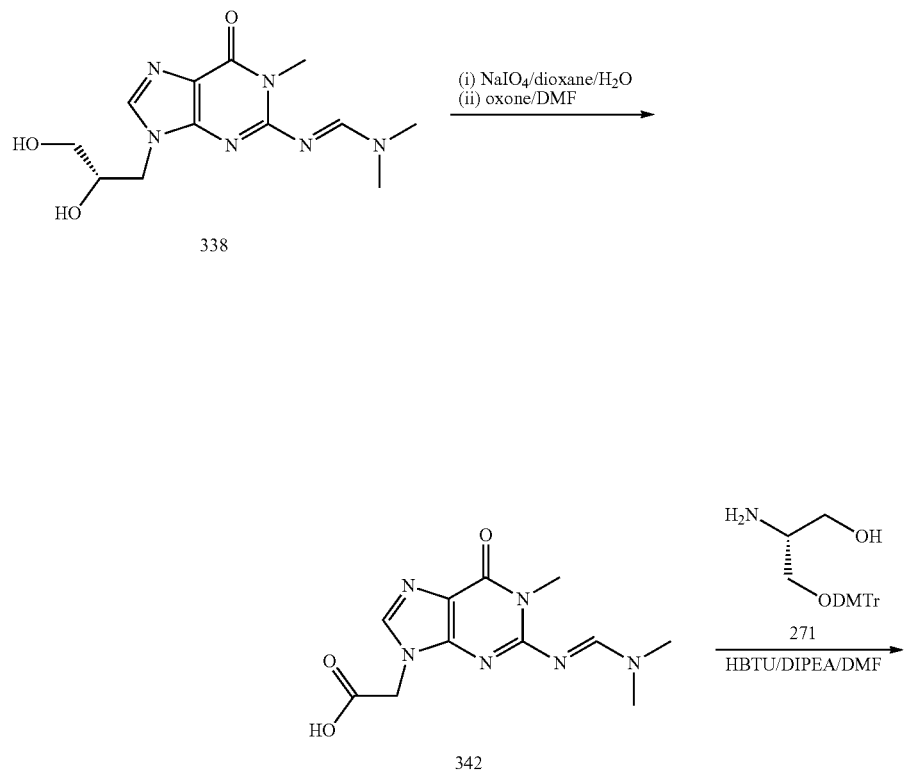

265 266

-continued

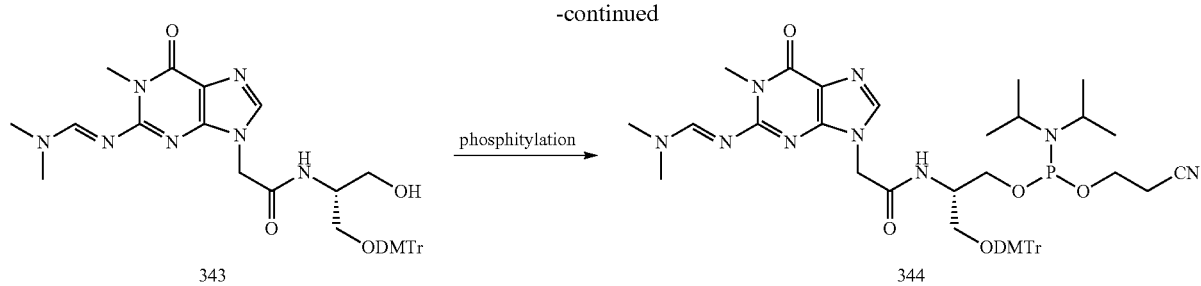

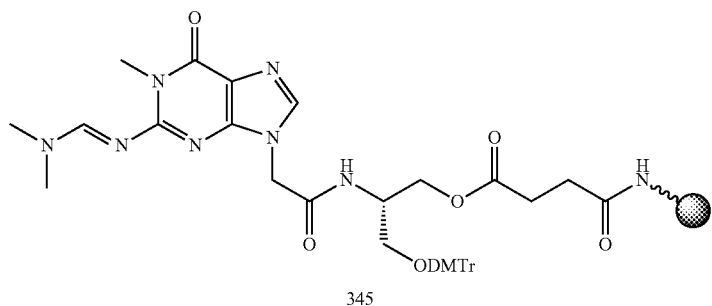

Oxidative cleavage of diol in 338 followed by mild oxidation gives acid 342, which is coupled with 271 to give N1-methylG-SNA (serinol nucleic acid) precursor 343. 344 and 345 can be synthesized as described above.

Synthesis of O6-alkyl-UNA Building Blocks

Scheme 28

Treatment of 346 with NaOMe followed by dmf protection gives 348. Subsequent DMTr reaction and following standard procedures for UNA analog synthesis described above can give O6-alkyl-G-UNA building blocks 352 and 353.

Synthesis of O6-alkyl-GNA/SNA building blocks

Scheme 29

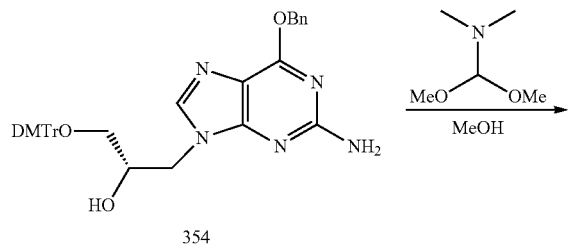

267 268
-continued
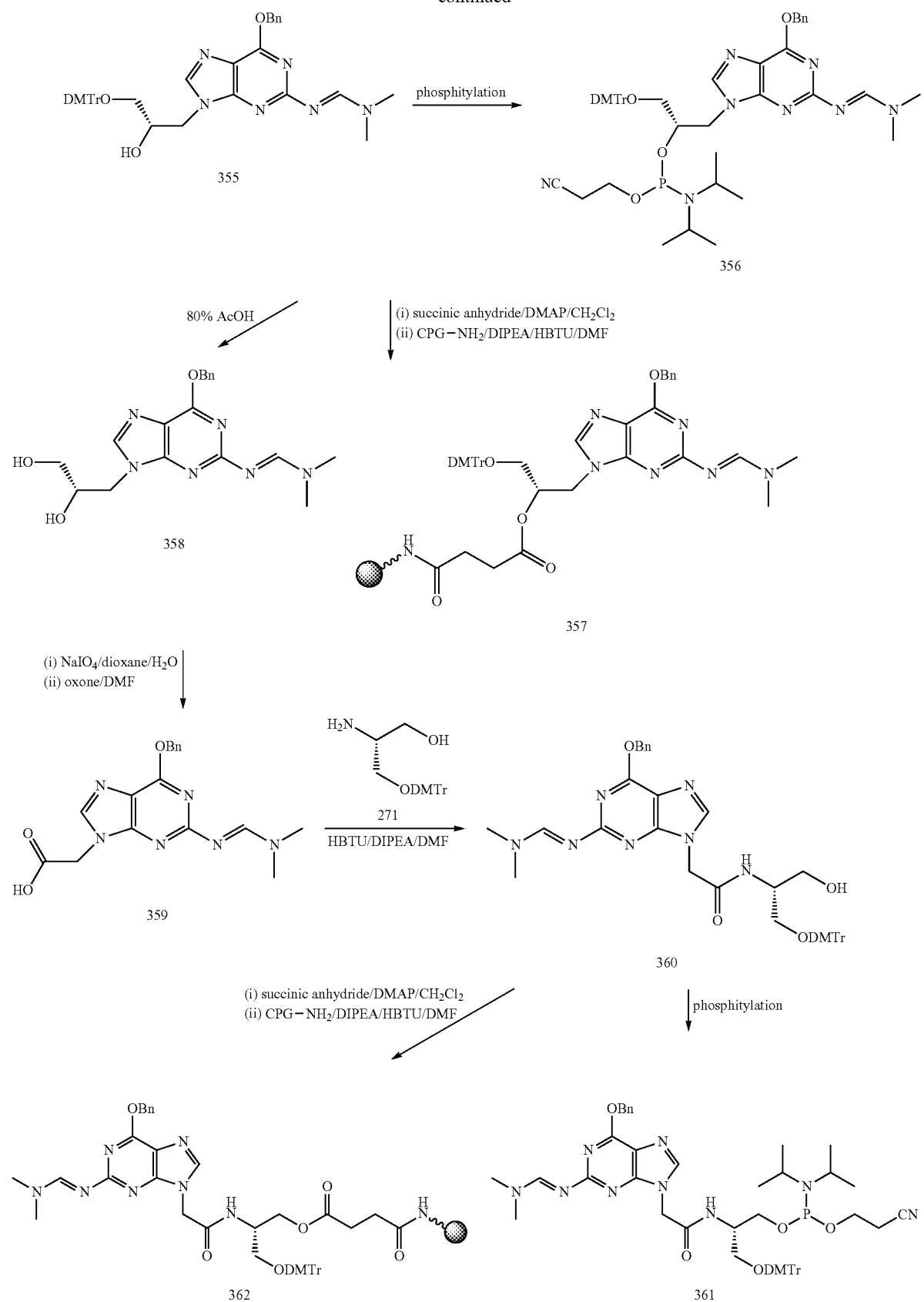

Protection of amino group in 354 gives 355. Standard phosphitylation and succination followed by CPG loading give 356 and 357, respectively. Acid treatment of 355 gives 358. Oxidative cleavage of diol in 358 followed by mild oxidation gives acid 359, which is coupled with 271 to give O6-alkylated G-SNA (serinol nucleic acid) precursor 360. 361 and 362 can be synthesized as described above.

Example 4: Synthesis Hydroxyprolinol Based Nucleoside Amidites

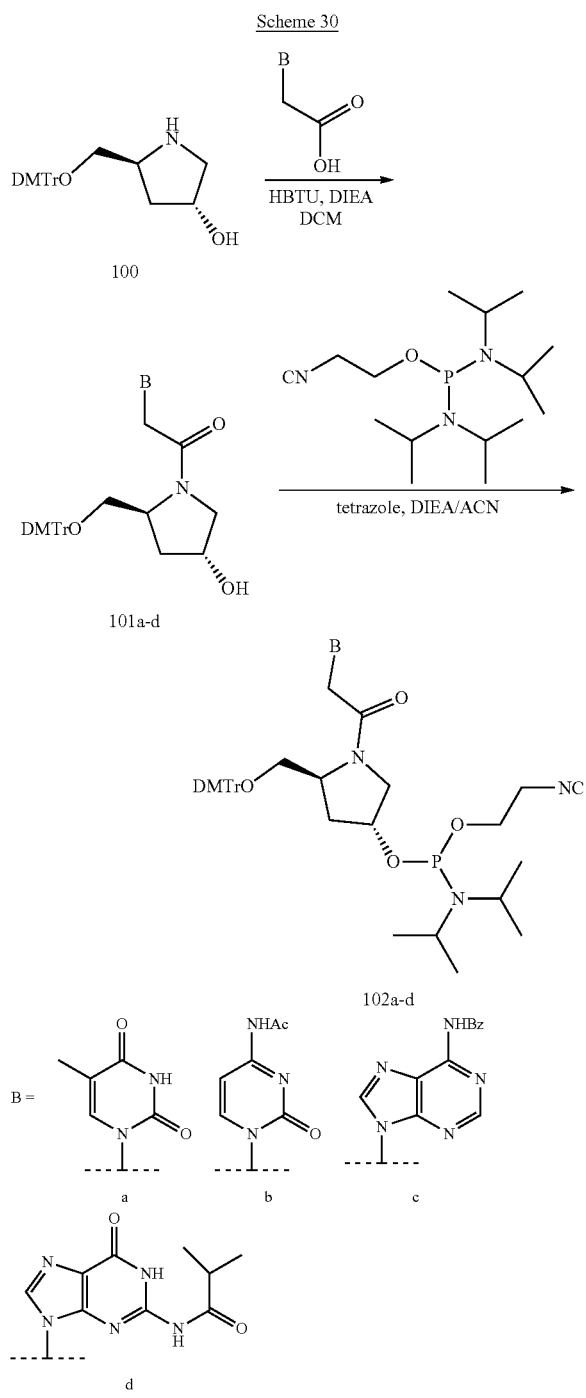

Compound (101a)-Carboxylic acid (5.00 g, 27.1 mmol) and HBTU (10.27 g, 27.1 mmol) were taken in DMF (100 mL), cooled the reaction mixture in ice-water mixture under argon. DIEA (14.1 mL, 3 eq.) was added and stirred the solution for 5 minutes. A solution of compound 100 (13.18 g, 27.1 mmol) in DMF (50 mL) was added to the above mixture and stirred for 2 hours. TLC checked and the mixture was poured in to ice water mixture, precipitated compound was filtered and dried under vacuum. It was purified by silica gel chromatography (DCM/MeOH) to get compound 101a as an off white solid (12.20, 76%). $^1$H NMR (400 MHZ, DMSO-$d_6$) δ 11.28 (d, J=17.8 Hz, 1H), 7.38-7.25 (m, 4H), 7.25-7.13 (m, 4H), 6.88 (dd, J=9.5, 2.6 Hz, 3H), 5.09 (d, J=4.1 Hz, 1H), 4.56 (d, J=16.7 Hz, 1H), 4.49-4.40 (m, 1H), 4.20-4.09 (m, 1H), 3.72 (d, J=2.6 Hz, 5H), 3.67 (dd, J=10.6, 5.3 Hz, 1H), 3.37 (dd, J=10.4, 4.0 Hz, 1H), 3.15 (dd, J=8.9, 5.3 Hz, 1H), 2.98 (dd, J=8.9, 3.2 Hz, 1H), 2.05-1.95 (m, 1H), 1.95-1.79 (m, 1H), 1.74 (d, J=1.1 Hz, 2H).

Compound (102a)—Compound 101a (4.0 g, 6.83 mmol) was added to a reaction flask, evacuated and purged with argon. The starting material was dissolved in acetonitrile, diisopropylamine (1.31 ml, 7.51 mmol), and 2-Cyanoethyl N,N,N',N'-tetraisopropylphosphordiamidite (3.38 ml, 10.25 mmol) were added via syringe. A solution of 1H-tetrazole (16.7 mL, 7.51 mmol, 0.45M) was added and stirred at room temperature for 1 hour. The reaction was checked by TLC (50% EtOAc/Hex) and the reaction was concentrated under reduced pressure. The residue was dissolved in dichloromethane, added to separation funnel and organic layer was washed with saturated sodium bicarbonate solution. The organic layer was separated and washed with brine. The organic layer was separated and dried with sodium sulfate. The solid was filtered off and the mother liquor was concentrated. The residue was purified by flash chromatography on silica gel (20% to 100% EtOAc/Hex) and the product fractions combined and concentrated on reduced pressure to yield (4.96 g, 93%) of 102a. $^1$H NMR (500 MHz, Acetonitrile-$d_3$) δ 9.06 (s, 1H), 7.44-7.35 (m, 3H), 7.34-7.24 (m, 8H), 7.24-7.18 (m, 1H), 7.03 (t, J=1.5 Hz, 1H), 6.91-6.82 (m, 5H), 4.75 (m, 1H), 4.55-4.32 (m, 3H), 4.24 (m, 1H), 4.18-3.99 (m, 1H), 3.87 (dd, J=10.6, 5.8 Hz, 1H), 3.84-3.78 (m, 1H), 3.76 (s, 10H), 3.61 (m, 4H), 3.54-3.44 (m, 1H), 3.41-3.28 (m, 2H), 3.02 (m, 1H), 2.75 (t, J=5.9 Hz, 1H), 2.64 (m, 3H), 2.22-2.15 (m, 1H), 2.12-1.99 (m, 1H), 1.82 (d, J=1.2 Hz, 3H), 1.76 (d, J=1.2 Hz, 1H), 1.23 (t, J=6.8 Hz, 3H), 1.21-1.09 (m, 17H). $^{31}$P NMR (202 MHZ, Acetonitrile-d3) δ 149.13, 148.63, 148.50, 148.30.

Compound (101b)—Carboxylic acid (5.00 g, 23.68 mmol) and HBTU (8.98 g, 23.68 mmol) were taken in DMF (100 mL), cooled the reaction mixture in ice-water mixture under argon. DIEA (12.36 mL, 3 eq.) was added and stirred the solution for 5 minutes. A solution of compound 100 (9.93 g, 23.68 mmol) in DMF (50 mL) was added to the above mixture and stirred for 2 hours. TLC checked and the mixture was poured in to ice water mixture, precipitated compound was filtered and dried under vacuum. It was purified by silica gel chromatography (DCM/MeOH) to get compound 101b as a pale yellow solid (13.1, 82%). $^1$H NMR (400 MHZ, DMSO-d6) δ 11.20 (s, 1H), 8.04-7.94 (m, 3H), 7.66-7.57 (m, 1H), 7.51 (t, J=7.6 Hz, 2H), 7.35-7.28 (m, 4H), 7.25 (d, J=8.8 Hz, 1H), 7.23-7.14 (m, 4H), 6.89 (m, 4H), 5.12 (d, J=4.1 Hz, 1H), 4.85-4.58 (m, 2H), 4.47 (m, 1H), 4.16 (m, 1H), 3.72 (d, J=2.6 Hz, 7H), 3.42 (dd, J=10.5, 3.9 Hz, 1H), 3.17 (dd, J=8.9, 5.3 Hz, 1H), 3.00 (dd, J=8.9, 3.1 Hz, 1H), 2.07-1.94 (m, 1H), 1.87 (m, 1H).

Compound (102b)—Compound 101b (2.0 g, 2.97 mmol) was added to a reaction flask, evacuated and purged with argon. The starting material was dissolved in acetonitrile, diisopropylamine (0.574 ml, 3.3 mmol), and 2-Cyanoethyl N,N,N',N'-tetraisopropylphosphordiamidite (1.47 ml, 4.46 mmol) were added via syringe. A solution of 1H-tetrazole (7.33 mL, 3.3 mmol, 0.45M) was added and stirred at room temperature for 1 hour. The reaction was checked by TLC (70% EtOAc/Hex) and the reaction was concentrated under reduced pressure. The residue was dissolved in dichloromethane, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated. The residue was purified by flash chromatography on silica gel (20% to 100% EtOAc/Hex) and the product fractions combined and concentrated on reduced pressure to yield (2.36 g, 91%) of 102b. 1H NMR (500 MHz, Acetonitrile-d3) δ 9.10 (s, 1H), 7.96 (d, J=7.7 Hz, 1H), 7.73-7.66 (m, 1H), 7.67-7.60 (m, 1H), 7.56-7.48 (m, 2H), 7.43 (m, 1H), 7.41-7.37 (m, 1H), 7.35-7.30 (m, 2H), 7.30-7.25 (m, 3H), 7.25-7.18 (m, 1H), 6.87 (m, 3H), 4.85-4.69 (m, 1H), 4.68-4.50 (m, 1H), 4.24 (m, 1H), 3.90-3.79 (m, 1H), 3.76 (s, 5H), 3.71-3.53 (m, 2H), 3.53-3.41 (m, 1H), 3.40-3.28 (m, 1H), 3.03 (m, 1H), 2.65 (m, 1H), 2.23-2.15 (m, 1H), 2.08 (m, 1H), 1.23 (t, J=6.8 Hz, 3H), 1.21-1.14 (m, 8H). 31P NMR (202 MHz, Acetonitrile-d3) δ 149.13, 148.60, 148.50, 148.30.

Compound (101c)—Carboxylic acid (5.00 g, 16.82 mmol) and HBTU (6.37 g, 16.82 mmol) were taken in DMF (100 mL), cooled the reaction mixture in ice-water mixture under argon. DIEA (8.80 mL, 3 eq.) was added and stirred the solution for 5 minutes. A solution of compound 100 (7.05 g, 27.1 mmol) in DMF (50 mL) was added to the above mixture and stirred for 2 hours. TLC checked and the mixture was poured in to ice water mixture, precipitated compound was filtered and dried under vacuum. It was purified by silica gel chromatography (DCM/MeOH) to get compound 101c as a pale brown solid (9.30, 79%). ¹H NMR (400 MHZ, DMSO-d6) δ 11.16 (s, 1H), 8.68 (s, 1H), 8.34 (s, 1H), 8.09-8.01 (m, 2H), 7.69-7.59 (m, 1H), 7.55 (dd, J=8.3, 6.9 Hz, 2H), 7.29 (m, 4H), 7.24-7.13 (m, 4H), 6.92-6.79 (m, 4H), 5.33-5.12 (m, 2H), 4.50 (t, J=4.8 Hz, 1H), 4.18 (q, J=4.0 Hz, 1H), 3.81 (dd, J=10.6, 5.2 Hz, 1H), 3.70 (dd, J=6.5, 1.7 Hz, 6H), 3.53 (m, 2H), 3.32 (m, 1H), 3.17 (m, 1H), 3.00 (dd, J=9.0, 3.2 Hz, 1H), 2.04 (m, 1H), 1.90 (m, 1H), 1.31-1.20 (m, 1H), 0.83 (m, 1H).

Compound (102c)—Compound 101c (2.0 g, 2.86 mmol) was added to a reaction flask, evacuated and purged with argon. The starting material was dissolved in acetonitrile, diisopropylamine (0.549 ml, 3.15 mmol), and 2-Cyanoethyl N,N,N',N'-tetraisopropylphosphordiamidite (1.41 ml, 4.29 mmol) were added via syringe. A solution of 1H-tetrazole (7.0 mL, 3.15 mmol, 0.45M) was added and stirred at room temperature for 1 hour. The reaction was checked by TLC (100% EtOAc) and the reaction was concentrated under reduced pressure. The residue was dissolved in dichloromethane, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated. The residue was purified by flash chromatography on silica gel (20% to 100% EtOAc/Hex) and the product fractions combined and concentrated on reduced pressure to yield (2.25 g, 90%) of 102c. 1H NMR (500 MHz, Acetonitrile-d3) δ 9.74 (s, 1H), 8.60 (d, J=32.4 Hz, 1H), 8.11 (d, J=3.4 Hz, 1H), 8.03 (d, J=7.6 Hz, 2H), 7.64 (t, J=7.5 Hz, 1H), 7.54 (t, J=7.6 Hz, 2H), 7.47-7.41 (m, 1H), 7.38 (m, 2H), 7.33 (m, 1H), 7.30-7.17 (m, 6H), 6.89-6.77 (m, 4H), 5.15-5.09 (m, 1H), 4.79 (m, 1H), 4.25 (dd, J=8.5, 4.6 Hz, 1H), 4.16-4.07 (m, 1H), 4.03 (m, 1H), 3.93 (dd, J=10.9, 5.1 Hz, 1H), 3.90-3.83 (m, 1H), 3.83-3.76 (m, 2H), 3.73 (dd, J=5.5, 2.0 Hz, 7H), 3.63 (m, 3H), 3.57-3.40 (m, 2H), 3.32 (s, 1H), 3.03 (m, 1H), 2.76 (t, J=5.9 Hz, 1H), 2.70 (t, J=5.9 Hz, 1H), 2.65 (m, 1H), 2.37 (dd, J=3.6, 1.8 Hz, 14H), 2.20 (m, 1H), 2.17-2.04 (m, 1H), 1.25-1.13 (m, 19H), 1.10 (d, J=6.7 Hz, 1H). 31P NMR (202 MHz, Acetonitrile-d3) δ 149.52, 149.14, 148.76, 148.67, 148.31.

Compound (101d)—Carboxylic acid (5.00 g, 17.91 mmol) and HBTU (6.79 g, 17.91 mmol) were taken in DMF (100 mL), cooled the reaction mixture in ice-water mixture under argon. DIEA (9.34 mL, 3 eq.) was added and stirred the solution for 5 minutes. A solution of compound 100 (7.51 g, 17.91 mmol) in DMF (50 mL) was added to the above mixture and stirred for 2 hours. TLC checked and the mixture was poured in to ice water mixture, precipitated compound was filtered and dried under vacuum. It was purified by silica gel chromatography (DCM/MeOH) to get compound 101d as an off white solid (8.10, 66%). ¹H NMR (400 MHZ, DMSO-d6) δ 12.05 (s, 1H), 11.65 (s, 1H), 7.83 (s, 1H), 7.34-7.26 (m, 4H), 7.26-7.20 (m, 1H), 7.20-7.14 (m, 4H), 6.85 (m, 4H), 5.18 (d, J=3.8 Hz, 1H), 5.05-4.96 (m, 1H), 4.91 (d, J=17.1 Hz, 1H), 4.44 (m, 1H), 4.14 (m, 1H), 3.70 (d, J=1.3 Hz, 5H), 3.68 (s, 1H), 3.63 (dd, J=10.7, 4.9 Hz, 1H), 3.44 (dd, J=10.6, 3.3 Hz, 1H), 3.20-3.09 (m, 1H), 3.03 (dd, J=8.8, 6.0 Hz, 1H), 2.79-2.64 (m, 1H), 2.04 (m, 1H), 1.93 (m, 1H), 1.09 (m, 6H).

Compound (102d)—Compound 101d (1.4 g, 2.06 mmol) was added to a reaction flask, evacuated and purged with argon. The starting material was dissolved in dichloromethane, diisopropylamine (0.4 ml, 2.3 mmol), and 2-Cyanoethyl N,N,N',N'-tetraisopropylphosphordiamidite (1.02 ml, 3.09 mmol) were added via syringe. A solution of 1H-tetrazole (5.11 mL, 2.3 mmol, 0.45M) was added and the reaction stirred at room temperature for 1 hour. The reaction was checked by TLC (70% EtOAc/Hex) and the reaction was concentrated under reduced pressure. The residue was dissolved in dichloromethane, added to separation funnel and organic layer was washed with saturated sodium bicarbonate solution. The organic layer was separated and washed with a brine solution. The organic layer was separated and dried with sodium sulfate. The solid was filtered off and the mother liquor was concentrated. The residue was purified by flash chromatography on silica gel (40% to 100% EtOAc/Hex) and the product fractions combined and concentrated on reduced pressure to yield (1.45 g, 80%) of 102d. 1H NMR (500 MHz, Acetonitrile-d3) δ 12.00 (s, 1H), 10.10 (s, 1H), 7.65 (d, J=1.5 Hz, 1H), 7.44 (dd, J=16.1, 6.9 Hz, 1H), 7.38 (dd, J=7.5, 1.8 Hz, 2H), 7.34-7.28 (m, 2H), 7.26 (m, 6H), 7.21 (m, 1H), 6.83 (m, 5H), 4.93-4.80 (m, 2H), 4.80-4.72 (m, 1H), 4.72-4.53 (m, 1H), 4.32-4.20 (m, 1H), 4.14-3.94 (m, 1H), 3.88 (m, 1H), 3.80 (m, 2H), 3.76-3.70 (m, 9H), 3.61 (m, 4H), 3.49 (d, J=18.4 Hz, 1H), 3.31 (m, 1H), 3.06 (m, 1H), 2.76 (t, J=5.9 Hz, 1H), 2.72-2.61 (m, 3H), 2.57-2.45 (m, 2H), 2.43-2.31 (m, 21H), 2.25-2.03 (m, 3H), 1.22 (t, J=6.8 Hz, 5H), 1.17 (m, 16H), 1.07 (dd, J=23.6, 6.8 Hz, 7H). 31P NMR (202 MHz, Acetonitrile-d3) δ 149.25, 149.01, 148.80, 148.22.

Example 5

Oligonucleotide Synthesis and Purification: All oligonucleotides were prepared on a MerMade 192 synthesizer on a 1 µmole scale using universal or custom supports. All phosphoramidites were used at a concentration 100 mM in 100% Acetonitrile or 9:1 Acetonitrile: DMF with a standard protocol for 2-cyanoethyl phosphoramidites, except that the coupling time was extended to 400 seconds. Oxidation of the newly formed linkages was achieved using a solution of 50 mM 12 in 9:1 Acetonitrile: Water to create phosphate linkages and 100 mM DDTT in 9:1 Pyridine: Acetonitrile to create phosphorothioate linkages. After the trityl-off synthesis, columns were incubated with 150 µL of 40% aqueous Methylamine for 45 minutes and the solution drained via vacuum into a 96-well plate. After repeating the incubation and draining with a fresh portion of aqueous Methylamine, the plate containing crude oligonucleotide solution was sealed and shaken at room temperature for an additional 60 minutes to completely remove all protecting groups. Precipitation of the crude oligonucleotides was accomplished via the addition of 1.2 mL of 9:1 Acetonitrile: EtOH to each well followed by incubation at −20° C. overnight. The plate was then centrifuged at 3000 RPM for 45 minutes, the supernatant removed from each well, and the pellets resuspended in 950 µL of 20 mM aqueous NaOAc. Each crude solution was finally desalted over a GE Hi-Trap Desalting Column (Sephadex G25 Superfine) using water to elute the final oligonucleotide products. All identities and purities were confirmed using ESI-MS and IEX HPLC, respectively.

Temperature-dependent UV Spectroscopy: The melting studies were performed at a duplex concentration of 1 µM (consisting of the modified antisense strand paired with the complementary modified sense strand) in 0.10×PBS (1.0 mM Na/K phosphate buffer, pH 7.4, with 13.7 mM NaCl and 0.3 mM KCl) in 1 cm path length quartz cells on a Cary 300 spectrophotometer equipped with a thermoprogrammer. Each cuvette contained 800 µL of sample solution covered by 200 µL of light mineral oil. Melting curves were monitored at 260 nm with a heating rate of 1° C./min from 15-90° C. Melting temperatures ($T_m$) were calculated from the first derivatives of the smoothed heating curves and the reported values are the result of at least two independent measurements.

In Vitro Activity Studies

Cell culture and transfections: Primary Mouse Hepatocytes (Thermo Fisher Scientific/Gibco) were transfected by adding 4.9 µL of Opti-MEM plus 0.1 µL of Lipofectamine RNAiMax per well (Invitrogen, cat #13778-150) to 5 µL of siRNA duplexes per well into a 384-well plate and incubated at room temperature for 15 minutes. 40 µL of Dulbecco's Modified Eagle Medium (Hep3b) or William's Medium (PMH) containing ~5×103 cells were then added to the siRNA mixture. Cells were incubated for 24 hours at 37° C. and then processed for RNA purification. Experiments were performed at 10 nM and 0.1 nM doses of siRNA.

Total RNA isolation using DYNABEADS mRNA Isolation Kit: RNA was isolated using an automated protocol on a BioTek-EL406 platform using DYNABEADs (Invitrogen, cat #61012). Briefly, 70 µL of Lysis/Binding Buffer and 10 µL of lysis buffer containing 3 µL of magnetic beads were added to each well. Plates were incubated on an electromagnetic shaker for 10 minutes at room temperature and then magnetic beads were captured and the supernatant was removed. Bead-bound RNA was then washed 2 times with 150 µl. Wash Buffer A and once with Wash Buffer B. Beads were then washed with 150 µL Elution Buffer, re-captured and supernatant removed.

cDNA synthesis using ABI High capacity cDNA reverse transcription kit (Applied Biosystems, cat #4368813): 12 µL of a master mix containing 1.2 µL 10× Buffer, 0.48 µL 25×dNTPs, 1.2 µL 10× Random primers, 0.6 µL Reverse Transcriptase, 0.6 µL RNase inhibitor and 7.92 µL of H2O per reaction was added to RNA isolated above. Plates were sealed, mixed, and incubated on an electromagnetic shaker for 10 minutes at room temperature, followed by 2 h 37° C.

Real time PCR: 2 µL of cDNA were added to a master mix containing 2 µL water, 0.5 µL of either an appropriate GAPDH TaqMan VIC Probe or the target probe and 5 µL Lightcycler 480 probe master mix (Roche, cat #04887301001) per well in a 384 well plate (Roche, cat #04887301001). Real time PCR was done in a LightCycler480 Real Time PCR system (Roche). Each duplex was tested in quadruplicate and data were normalized to cells transfected with a non-targeting control siRNA. To calculate relative fold change, real time data were analyzed using the AACt method and normalized to assays performed with cells transfected with a non-targeting control siRNA.

In Vitro Reporter Assays

Dual-Glo® Luciferase assay: Cos7 cells (ATCC, Manassas, VA) were grown to near confluence at 37° C. in an atmosphere of 5% CO2 in DMEM (ATCC) supplemented with 10% FBS, before being released from the plate by trypsinization. siRNA and psiCHCECK2 plasmid transfection was carried out by adding 5 µL of siRNA duplexes and 5 µL of psiCHECK2 plasmid per well along with 5 µL of Opti-MEM plus 0.1 µL of Lipofectamine 2000 per well (Invitrogen, Carlsbad CA. cat #13778-150) and then incubated at room temperature for 15 minutes. The mixture was then added to the cells which were re-suspended in 35 ul of fresh complete media. The transfected cells were incubated at 37° C. in an atmosphere of 5% CO2.

48 hours after the siRNAs and psiCHECK2 plasmid were transfected; Firefly (transfection control) and Renilla (fused to target sequence) luciferase were measured. First, media was removed from cells. Then Firefly luciferase activity was measured by adding 20 µL of Dual-Glo® Luciferase Reagent equal to the culture medium volume to each well and mix. The mixture was incubated at room temperature for 30 minutes before luminescence (500 nm) was measured on a Spectramax (Molecular Devices) to detect the Firefly luciferase signal. Renilla luciferase activity was measured by adding 20 µL of room temperature of Dual-Glo® Stop & Glo® Reagent was added to each well and the plates were incubated for 10-15 minutes before luminescence was again measured to determine the Renilla luciferase signal. The Dual-Glo® Stop & Glo® Reagent, quenches the firefly luciferase signal and sustained luminescence for the Renilla luciferase reaction. siRNA activity was determined by normalizing the Renilla signal to the Firefly (control) signal within each well. The magnitude of siRNA activity was then assessed relative to cells that were transfected with the same vector but were not treated with siRNA or were treated with a non-targeting siRNA. All transfections were done at n=2 or greater.

In Vivo Mouse and Rat Studies

All studies were conducted using protocols consistent with local, state and federal regulations as applicable and approved by the Institutional Animal Care and Use Committees (IACUCs) at Alnylam Pharmaceuticals.

In mouse pharmacodynamic studies, female C57BL/6 mice (Charles River Laboratories) were administered a single dose of a vehicle control (1×PBS or 0.9% sodium chloride) or siRNA subcutaneously in the upper back. Bleeds were collected by retro-orbital bleeding. Serum were separated by centrifuging at 13000 rpm at room temperature for 10 mins. Mouse livers were collected and immediately snap frozen in liquid nitrogen, and stored at −80° C. for mRNA and siRNA analysis.

mRNA and siRNA Quantitation

RNA was extracted with the miRNeasy Kit (Qiagen) according to manufacturer's instructions, converted to cDNA with the High-Capacity cDNA Reverse Transcription Kit (Thermo Fisher Scientific) according to manufacturer's instructions, and mRNA levels were assessed by quantitative polymerase chain reaction (qPCR) using gene-specific Taqman probes (Thermo Fisher Scientific) on Roche Light Cycler 480 II using LightCycler 480 Probes Master (Roche).

To quantitate exposure to siRNAs, cell pellets were resuspended in phosphate-buffer saline (PBS) containing 0.25% Triton X-100, heated at 95° C. for 10 min, centrifuged at 14,000 rpm at 4° C. for 10 min, and reverse transcription was performed on the supernatants using TaqMan MicroRNA Reverse Transcription Kit (Thermo Fisher Scientific) according to the manufacturer's instructions. qPCR was performed on Roche Light Cycler 480 II using LightCycler 480 Probes Master (Roche) according to the manufacturer's instructions.

Results

In Vitro Activity

In vitro activity: Results of in vitro activity assays are summarized in Table 1. As the data shows, glycolic nucleic acid (GNA) modifications using isoC or isoG in the seed region of the antisense strand preserves the on-target activity more effectively than GNA-C or GNA-G. Methyl UNA (mUNA) and 2'-5'-RNA modifications also preserve on-target activity relative to the parent when incorporated at various positions in the seed region from antisense 5-8.

TABLE 1

In vitro activity data for various thermally destabilizing modifications in primary mouse hepatocytes.

| | Position 5 | | | | | | | | Position 6 | | | | | | | |
|---|---|---|---|---|---|---|---|---|---|---|---|---|---|---|---|---|
| | Seq 1 | | Seq 2 | | Seq 3 | | Seq 4 | | Seq 1 | | Seq 2 | | Seq 3 | | Seq 4 | |
| Modification | On-target TX | On-target FU | On-target TX | On-target FU | On-target TX | On-target FU | On-target TX | On-target FU | On-target TX | On-target FU | On-target TX | On-target FU | On-target TX | On-target FU | On-target TX | On-target FU |
| Mod 1 (S) | 0.29 | 1.15 | | | | | | | | | | | | | | |
| Mod 2 (S) | −0.35 | 0.36 | | | | | | | | | | | | | | |
| Mod 3 (S) | | | | | | | | | | | −0.70 | −1.07 | | | | |
| Mod 4 (S) | | | | | | | | | | | −1.08 | −1.49 | | | | |
| Mod 5 (R) | | | | | 0.45 | −0.16 | | | | | | | | | | |
| Mod 5 (S) | | | | | −0.03 | −0.87 | | | | | | | | | | |
| Mod 6 (R) | | | | | −0.28 | −0.78 | | | | | | | | | | |
| Mod 6 (S) | | | | | 0.18 | −0.38 | | | | | | | | | | |
| Mod 7 (R) | | | | | 0.50 | 0.02 | | | | | | | | | | |
| Mod 7 (S) | | | | | 0.43 | −0.10 | | | | | | | | | | |
| Mod 8 | −0.15 | | −0.20 | | | | | | 0.54 | | −0.06 | | | | | |
| UNA | | | | | −0.21 | −1.14 | | | | | | | | | | |

| | Position 7 | | | | | | | | Position 8 | | | | | | | |
|---|---|---|---|---|---|---|---|---|---|---|---|---|---|---|---|---|
| | Seq 1 | | Seq 2 | | Seq 3 | | Seq 4 | | Seq 1 | | Seq 2 | | Seq 3 | | Seq 4 | |
| Modification | On-target TX | On-target FU | On-target TX | On-target FU | On-target TX | On-target FU | On-target TX | On-target FU | On-target TX | On-target FU | On-target TX | On-target FU | On-target TX | On-target FU | On-target TX | On-target FU |
| Mod 1 (S) | | | | | | | | | | | | | | | | |
| Mod 2 (S) | | | | | | | | | | | | | | | | |
| Mod 3 (S) | | | | | | | | | | | | | | | | |
| Mod 4 (S) | | | | | | | | | | | | | | | | |
| Mod 5 (R) | | | | | 0.50 | −0.03 | −1.26 | −0.33 | | | | | | | | |
| Mod 5 (S) | | | | | −0.04 | −1.20 | −0.97 | 0.22 | | | | | | | | |
| Mod 6 (R) | | | | | 0.67 | −0.32 | −0.98 | 0.36 | | | | | | | | |
| Mod 6 (S) | | | | | 0.06 | −0.53 | −0.31 | −0.09 | | | | | | | | |
| Mod 7 (R) | | | | | 0.15 | −0.35 | −0.99 | −0.24 | | | | | | | | |
| Mod 7 (S) | | | | | 0.72 | −0.02 | −0.79 | −0.14 | | | | | | | | |
| Mod 8 | −0.17 | | 0.34 | | | | | | 0.94 | | 0.71 | | | | | |
| UNA | | | | | 0.40 | −0.56 | −1.25 | −0.66 | | | | | | | | |

All values are log 2 transformed and relative to the parent; TX=as measured by transfection (10 no final duplex concentration), FU=as measured by free uptake (1 nM final duplex concentration). Modifications are as specified in Fig. x. Values for the parents are as follows (percent of target remaining): Seq 1 (GO1), On-target Tx 0.44±0.06%, On-target FU 22.39±5.76%; Seq 2 (TTR), On-target Tx 2.92±1.87%, On-target FU 25.19±7.65%; Seq 3 (TTR), On-target Tx 1.19±0.07%, On-target FU 25.89±3.32%.

In Vitro Reporter Assays

Results of off-target reporter assays are summarized in Table 2.

TABLE 2

In vitro reporter assays for antisense strand modified duplexes.

| | | On-Target mRNA remaining (%) | | Off-target IC$_{50}$ (nM) |
|---|---|---|---|---|
| | | 10 nM siRNA | 0.1 nM siRNA | |
| TTR (Seq 2) | Parent (AD-64958) | 2.3 | 25.5 | 0.05 |
| | 2'-5'-RNA @ AS5 | 2.0 | 24.6 | 0.47 |
| | 2'-5'-RNA @ AS6 | 2.2 | 30.5 | 0.02 |

TABLE 2-continued

In vitro reporter assays for antisense strand modified duplexes.

| | | On-Target mRNA remaining (%) | | Off-target IC$_{50}$ (nM) |
|---|---|---|---|---|
| | | 10 nM siRNA | 0.1 nM siRNA | |
| | 2'-5'-RNA @ AS7 | 2.9 | 31.1 | 11.08 |
| | 2'-5'-RNA @ AS8 | 3.7 | 31.5 | 0.21 |
| | (S)-isoG-GNA @ AS6 | 0.8 | 11.6 | 0.55 |
| HAO1 (Seq 1) | Parent (AD-65644) | 27.7 | 96.1 | 0.53 |
| | 2'-5'-RNA @ AS5 | 24.9 | 104.4 | 1.03 |
| | 2'-5'-RNA @ AS6 | 40.1 | 98.5 | 2.55 |
| | 2'-5'-RNA @ AS7 | 24.7 | 80.2 | >10 |
| | 2'-5'-RNA @ AS8 | 53.0 | 95.1 | 1.28 |
| | (S)-isoC-GNA @ AS5 | | | >50 |

On-target activity measured in primary mouse hepatocytes via transfection at the indicated concentrations. Off-target IC50s measured using luciferase reporter plasmids which were co-transfected with siRNAs into COS-7 cells.

Temperature-Dependent UV Spectroscopy

Results of temperature-dependent UV spectroscopy are summarized in Table 3.

TABLE 3

Thermal melting temperatures (Tm) of some exemplary modified dsRNAs.

| | Position 5 | | | | Position 6 | | | | Position 7 | | | |
|---|---|---|---|---|---|---|---|---|---|---|---|---|
| Modification | Seq 1 | Seq 2 | Seq 3 | Seq 4 | Seq 1 | Seq 2 | Seq 3 | Seq 4 | Seq 1 | Seq 2 | Seq 3 | Seq 4 |
| Mod 1 (S) | 61.8 | | | | | | | | | | | |
| Mod 2 (S) | 64.0 | | | | | | | | | | | |
| Mod 3 (S) | | | | | 59.0 | | | | | | | |
| Mod 4 (S) | | | | | 62.3 | | | | | | | |
| Mod 5 (R) | | | 84.2 | | | | | | | | 80.3 | 82.0 |
| Mod 5 (S) | | | 84.2 | | | | | | | | 80.3 | 82.0 |
| Mod 6 (R) | | | 84.1 | | | | | | | | 81.2 | 82.0 |
| Mod 6 (S) | | | 84.0 | | | | | | | | 81.1 | 82.0 |
| Mod 7 (R) | | | 84.0 | | | | | | | | 80.0 | 82.1 |
| Mod 7 (S) | | | 84.3 | | | | | | | | 80.0 | 83.0 |
| Mod 8 | 64.0 | 62.5 | | | 62.0 | 61.0 | | | 63.5 | 61.5 | | |
| UNA | | | 84.1 | | | | | | | | 80.1 | 82.0 |

Modifications are as specified in FIG. 1. Values for the parent duplexes are as follows: Seq 1 (GO1) 66.8° C.; Seq 2 (TTR) 66.3° C. (measured at 1 μM duplex concentration in 1×PBS); and Seq 3 (TTR) 87.3° C., Seq 4 (TTR) 89.0° C. (measured at 1 μM duplex concentration in 0.25×PBS)

More Pharmacodynamic Data

Results of in vivo studies are summarised in Table 4. GNA-isoC or mUNA modifications preserve potency in vivo.

TABLE 4

GNA-isoC and GNA-isoG preserve potency more effectively than GNA-C and GNA-G, respectively, in vivo. Methyl-UNA modifications also preserve activity relative to the parent at antisense position 7. Mice were administered a single dose of siRNAs at 1 mg/kg and liver mRNA or protein knockdown was assessed at Day 7.

| | Position 5 | | | | | | | | Position 6 | | | | | | | |
|---|---|---|---|---|---|---|---|---|---|---|---|---|---|---|---|---|
| | Seq 1 | | Seq 2 | | Seq 3 | | Seq 4 | | Seq 1 | | Seq 2 | | Seq 3 | | Seq 4 | |
| Modification | On-target | St. Dev. | On-target | St. Dev. | On-target | St. Dev. | On-target | St. Dev. | On-target | St. Dev. | On-target | St. Dev. | On-target | St. Dev. | On-target | St. Dev. |
| Mod 1 (S) | 0.58 | 0.14 | | | | | | | | | | | | | | |
| Mod 2 (S) | 0.24 | 0.02 | | | | | | | | | | | | | | |
| Mod 3 (S) | | | | | | | 0.25 | 0.08 | | | 0.42 | 0.25 | | | 0.47 | 0.13 |
| Mod 4 (S) | | | | | | | 0.25 | 0.03 | | | 0.24 | 0.04 | | | 0.47 | 0.05 |
| Mod 5 (R) | | | | | | | | | | | | | | | | |
| Mod 5 (S) | | | | | | | | | | | | | | | | |
| Mod 6 (R) | | | | | | | | | | | | | | | | |
| Mod 6 (S) | | | | | | | | | | | | | | | | |
| Mod 7 (R) | | | | | | | | | | | | | | | | |
| Mod 7 (S) | | | | | | | | | | | | | | | | |
| Mod 8 UNA | 0.21 | 0.07 | 0.28 | 0.04 | | | | | | | 0.25 | 0.02 | 0.27 | 0.06 | | |

| | Position 7 | | | | | | | | Position 8 | | | | | | | |
|---|---|---|---|---|---|---|---|---|---|---|---|---|---|---|---|---|
| | Seq 1 | | Seq 2 | | Seq 3 | | Seq 4 | | Seq 1 | | Seq 2 | | Seq 3 | | Seq 4 | |
| Modification | On-target | St. Dev. | On-target | St. Dev. | On-target | St. Dev. | On-target | St. Dev. | On-target | St. Dev. | On-target | St. Dev. | On-target | St. Dev. | On-target | St. Dev. |
| Mod 1 (S) | | | | | | | | | | | | | | | | |
| Mod 2 (S) | | | | | | | | | | | | | | | | |
| Mod 3 (S) | | | | | | | | | | | | | | | | |
| Mod 4 (S) | | | | | | | | | | | | | | | | |
| Mod 5 (R) | | | | | 0.17 | 0.02 | 0.16 | 0.03 | | | | | | | | |
| Mod 5 (S) | | | | | 0.17 | 0.03 | 0.16 | 0.03 | | | | | | | | |
| Mod 6 (R) | | | | | 0.20 | 0.07 | 0.29 | 0.02 | | | | | | | | |
| Mod 6 (S) | | | | | 0.20 | 0.03 | 0.23 | 0.03 | | | | | | | | |
| Mod 7 (R) | | | | | 0.18 | 0.05 | 0.14 | 0.02 | | | | | | | | |
| Mod 7 (S) | | | | | 0.15 | 0.04 | 0.20 | 0.02 | | | | | | | | |
| Mod 8 UNA | 0.17 | 0.06 | 0.20 | 0.02 | 0.14 | 0.03 | 0.22 | 0.05 | 0.43 | 0.10 | 0.24 | 0.06 | | | | |

Velses represent the level of mRNA (Seq 1, GO1) or protein (Seqs 2-3, TTR) remaining with respect to PBS control at day 7 post-dose in the liver or circulation, respectively. Parent knockdown at the specified dose was as follows: 0.129±0.028 for Seq 1 (GO1); 0.19±0.03 for Seq 2 (TTR); 0.123±0.036 for Seq 3 (TTR); 0.215±0.015 for Seq 4 (TTR). All values represent the results from a single experiment with an n 3 animals unless otherwise indicated. Modifications are as specified in FIG. 1.

TABLE 5

Sequences of exemplary siRNAs

| siRNA duplex | Passenger (5'-3') | Guide (5'-3') | target |
|---|---|---|---|
| AD-65644 (Seq 1) | g•a•auguGaaAGucaucgacaa(L) | u•U•gucGaUGacuuUcAcauuc•u•g | GO1 |
| AD-64958 (Seq 2) | a•a•caguGuUCUugcucuauaa(L) | u•U•auaGagcaagaAcAcuguu•u•u | TTR |

TABLE 5-continued

Sequences of exemplary siRNAs

| siRNA duplex | Passenger (5'-3') | Guide (5'-3') | target |
| --- | --- | --- | --- |
| AD-125762 (Seq 3) | a•g•uguuCuUGCucuauaaaca(L) | u•G•uuuauagagcaAgAacacu•g•u | TTR |
| AD-125773 (Seq 4) | u•u•cuugCuCUAuaaaccgugu(L) | a•C•acgguuuauagAgCaagaa•c•a | TTR |

Uppercase and lower-case letters represent 2'-F and 2'-OMe, respectively, to Adenosine, Cytosine, Guanosine, and Uridine.
(L) represents the tri-N-acetylgalactosamine ligand.
Phosphorothioate linkages are indicated by the "•" symbol.

TABLE 6

GNA-isoC and GNA-isoG improve or maintain potency in vivo relative to GNA-C and GNA-G, respectively.

| Sequence | siRNA Duplex | Parent KD (rel. to pre-bleed) | (S)-GNA KD (rel. to pre-bleed) | (S)-isoGNA KD (rel. to pre-bleed) |
| --- | --- | --- | --- | --- |
| 5 | a•g•gaucUuGCCaaagcaguaa(L)<br>u•U•acugcuuuggcAaGauccu•g•g | 0.49 ± 0.13 | 0.46 ± 0.13 | 0.38 ± 0.03 |
|   | a•g•gaucUuGCCaaagcaguaa(L)<br>u•U•acugcuuuggcAaGauccu•g•g |   | 0.33 ± 0.03 | 0.40 ± 0.18 |
| 6 | g•a•ccagGaUCUugccaaagca(L)<br>u•G•cuuuggcaagaUcCugguc•c•u | 0.53 ± 0.01 | 0.02 ± 0.01 | 0.08 ± 0.03 |
| 7 | u•g•cuuuGaGCCucagcuucua(L)<br>u•A•gaagcugaggcUcAaagca•c•u | 0.16 ± 0.03 | 0.43 ± 0.06 | 0.29 ± 0.03 |
| 8 | g•g•agccCaAGAaagugaaaga(L)<br>u•C•uuucacuuucuUgGgcucc•a•c | 0.71 ± 0.05 | 0.92 ± 0.11 | 0.78 ± 0.07 |

Uppercase and lower-case letters represent 2'-F and 2'-OMe, respectively, to Adenosine, Cytosine, Guanosine, and Uridine.
(L) represents the tri-N-acetylgalactosamine ligand.
Phosphorothioate linkages are indicated by the "•" symbol.
Bold and underlined letters represent the nucleotide which was replaced by (S)-GNA (Mod 1 or 3) or by (S)-isoGNA (Mod 2 or 4).
Mice were administered a single dose of siRNAs at 1 mg/kg (Seqs 5 and 7) or 3 mg/kg (Seqs 6 and 8) and liver protein knockdown was assessed at Day 7.

Example 6: Copper Free Click Linked Bis-RNAi

Figure 10:
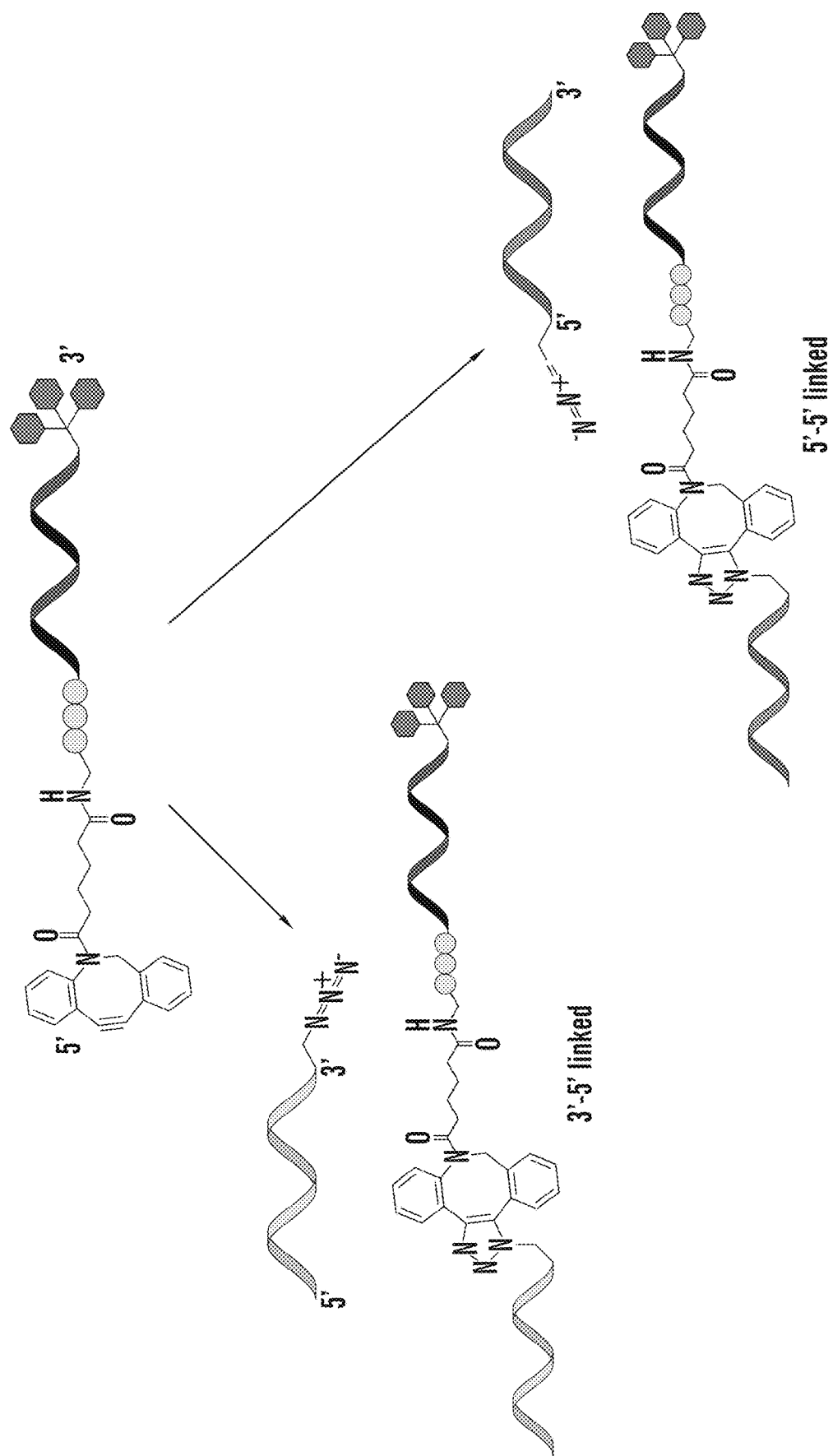
FIG. 10 is a scheme showing exemplary copper free "click" chemistry linked Bis-RNAi constructs.

An exemplary approach for preparing Bis-RNAi using a copper free "click" conjugation is shown with reference to FIG. 10. As shown, two individually synthesized strands having an azide functional group at a 3' or 5' end can be coupled to a strand functionalized with DBCO. In the approach nucleotide linker design (e.g., 2'-F triplet) can easily be incorporated. The method allows for 3'-5' linked or 5'-5' linked designs. This approach also allows preparation of each sense strand separately avoiding lower yields and difficult impurities encountered with longmer strands are made by conventional methods.

Longmer Conjugation Synthesis:

Three different linkers, Q327, Q328 and Q324 were constructed all using strain promoted azide-cyclooctyne additions. Schemes 31, 32 and 33 show the preparation of these linkers. In each case the 5' end of the F7 sense strand was functionalized with a dibenzylcyclooctyne moiety (DBCO) and either the 3' or 5' end of the TTR sense strand was functionalized with an azide. To "click" the strands together, equimolar amounts of each strand (0.45 M in water) and 30% 0.2 M phosphate buffer (pH 7.1) were mixed for 12 hrs at R.T. The crude ligand-conjugated and unconjugated oligonucleotides were purified by anion-exchange high-performance liquid chromatography (TEX-HPLC) with TSK-Gel Super Q-5 PW support (TOSOH Corp.) using a linear gradient of 30-62% buffer B over 130 min with 50 mL/min flow rate (Buffer A: 0.02 M Na2HPO4 in 10% CH3CN, pH 11 and buffer B: buffer A plus 1 M NaBr). The longmers were desalted by size exclusion chromatography on an AKTA Prime chromatography system using an AP-2 glass column (20×300 mm, Waters) custom-packed with Sephadex G25 (GE Healthcare), eluted with sterile nuclease-free water.

Table 7 lists some exemplary Bis-RNAi conjugates using the copper free "click" conjugation linkers Q327, Q328 and Q324. Table 8 summarizes some information regarding these conjugates.

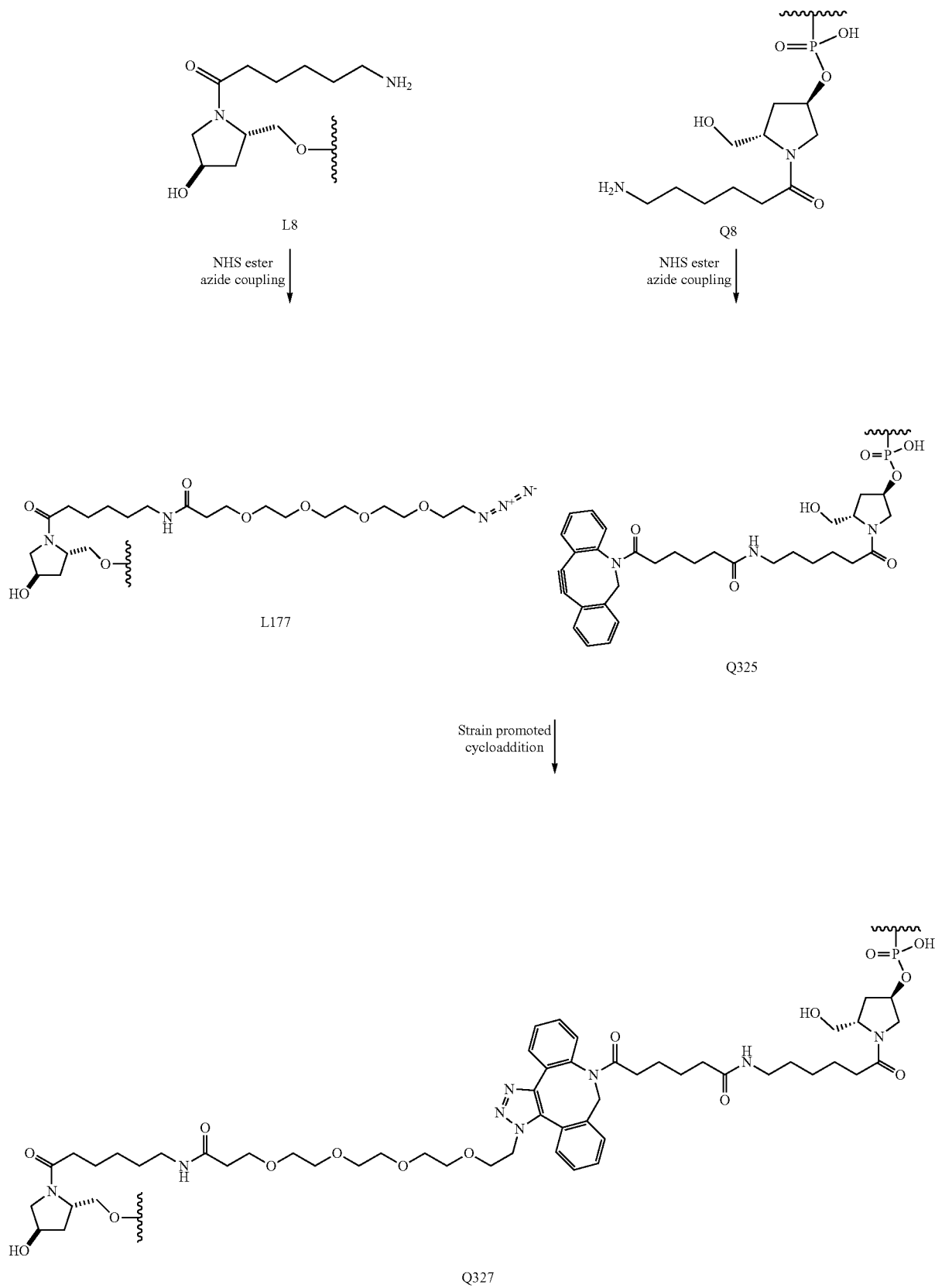
Scheme 31

Scheme 32
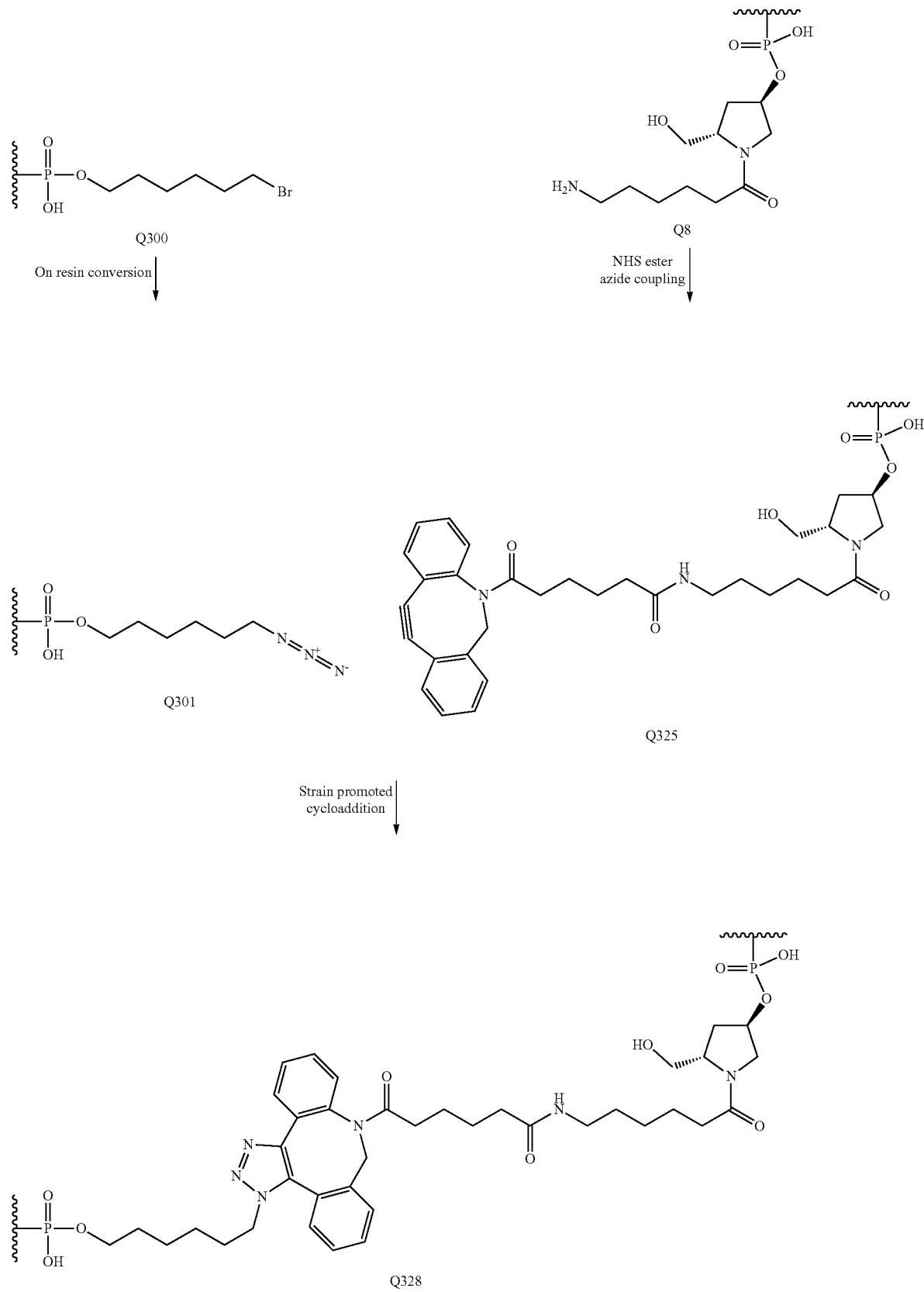

Scheme 33

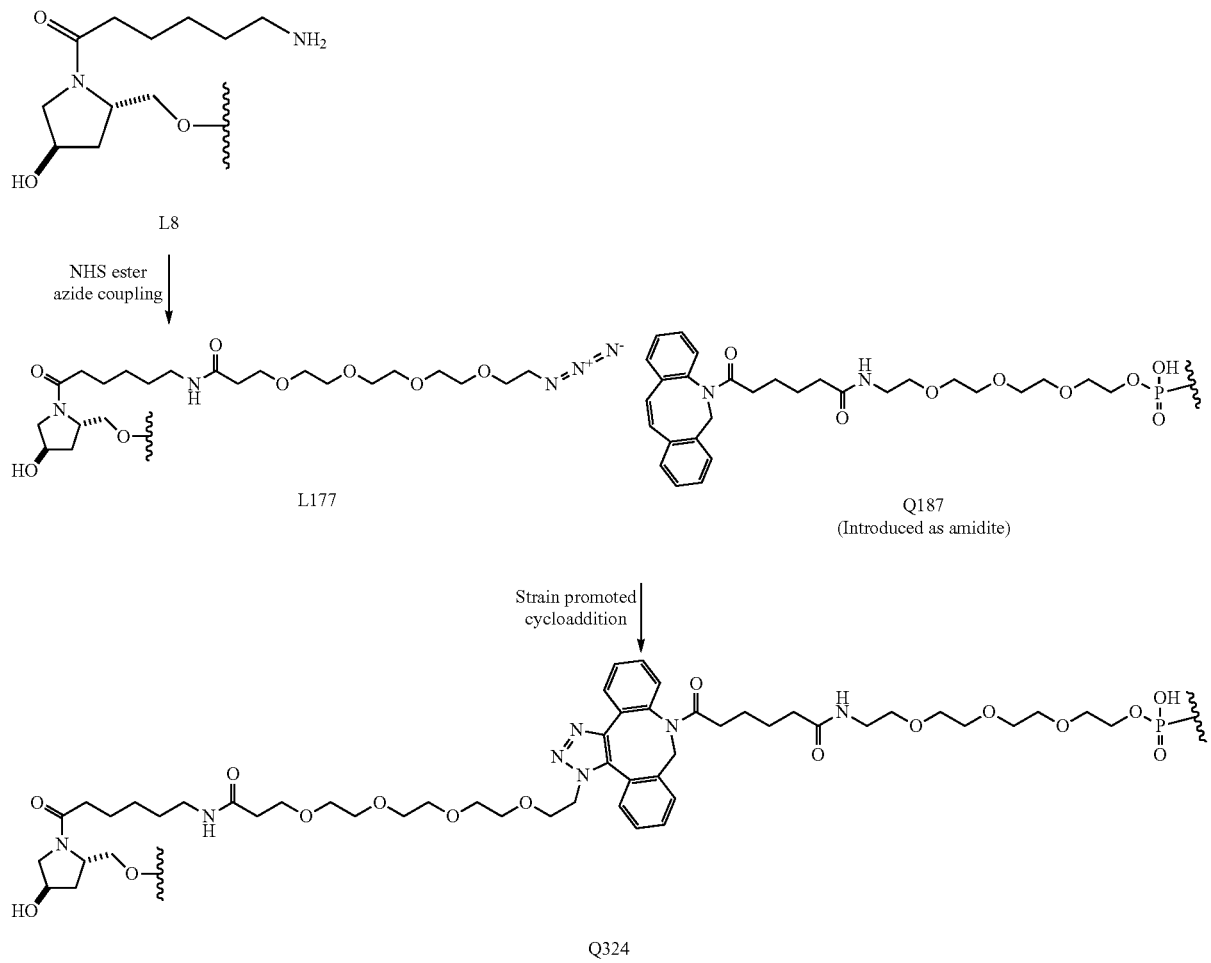

TABLE 8

Bis-RNAi conjugates

| Strand/ Multiplex ID | Linker | Connection Type | Calculated Mass | Observed Mass |
|---|---|---|---|---|
| AM-163 | Q327 | 5'-3' | 16416.85 | 16414.25 |
| AM-164 | Q328 | 5'-5' | 16088.45 | 16086.58 |
| AM-165 | Q327 | 5'-3' | 17765.76 | 17763.06 |
| AM-166 | Q324 | 5'-3' | 18037.04 | 18035.11 |

General Oligonucleotide Synthesis: FVII and mTTR siRNA sequences were synthesized at 1 µmol scale on an Applied Biosystems ABI 394 using the solid support mediated phosphoramidite chemistry. The solid support was controlled pore glass (500 Å) loaded with custom GalNAc ligand, custom L8 (amine group), or 2' OMe RNA functionalized support. Ancillary synthesis reagents, 2'-F and 2'-O-Methyl RNA and deoxy phosphoramidites were obtained from Thermo-Fisher (Milwaukee, WI) and Hongene (China). Custom Q8, Q300 bromohexyl (Glen Research), and Q187 DBCO-TEG (Glen Research) were introduced as the corresponding phosphoramidites. Synthesis of 3' GalNAc conjugated single strands were performed on a GalNAc modified CPG support. Custom CPG universal solid support was used for the synthesis of antisense single strands. Coupling time for all phosphoramidites (0.15 M in acetonitrile) was 10 min employing 5-Ethylthio-1H-tetrazole (ETT) as activator (0.25 M in acetonitrile). Phosphorothioate linkages were generated using a 0.09 M solution of 3-((Dimethylamino-methylidene) amino)-3H-1,2,4-dithiazole-3-thione (DDTT, (AM Chemicals, CA, USA) in pyridine. Oxidation time was 3 minutes. All sequences were synthesized with final removal of the DMT group ("DMT off").

Upon completion of the solid phase synthesis, oligoribonucleotides were cleaved from the solid support and deprotected in 5% diethylamine 95% aq. ammonia for 16 hrs at 35° C. The crude ligand-conjugated and unconjugated oligonucleotides were purified by anion-exchange high-performance liquid chromatography (IEX-HPLC) with TSK-Gel Super Q-5 PW support (TOSOH Corp.) using a linear gradient of 22-42% buffer B over 130 min with 50 mL/min flow rate (Buffer A: 0.02 M Na2HPO4 in 10% CH3CN, pH 8.5 and buffer B: buffer A plus 1 M NaBr). All single strands were purified to >85% HPLC (260 nm) purity and then desalted by size exclusion chromatography on an AKTA Prime chromatography system using an AP-2 glass column (20×300 mm, Waters) custom-packed with Sephadex G25 (GE Healthcare), eluted with sterile nuclease-free water.

The azides were installed via NHS ester post-synthetic conjugation (Click Chemistry Tools) or on-resin conversion from the 5' hexylbromo phosphoramidite. For the bromohexyl conversion, the support was washed with acetonitrile and dried under vacuum. The support was transferred to a tube and NaN$_3$ was added in DMF. The support was heated to 65° C. for 1.3 hr and washed three times with DMF and 3 times with DCM before cleaving under standard conditions. The non-amidite DBCO modifications were installed via NHS ester post-synthetic conjugation (Click chemistry tools). Both azide and DBCO NHS conjugations were performed in a 50/50 acetonitle 0.2 M phosphate buffer (pH 11) v/v solution for 3 hr.

Annealing: For the multiplex constructs composed of 3 and less single strands, annealing of FVII and mTTR single strands was performed by mixing equimolar mixture of sense and antisense single strands. After combining the complementary single strands, the mixture was lyophilized to dryness. The powder was then reconstituted in 1×PBS buffer. In all cases, non-denaturing IEX-HPLC methods showed the presence of a single chromatogram peak, corresponding to the single entity multiplex construct.

In vivo Studies: All animals were held in a pathogen-free environment, and all procedures involving animals were performed in accordance with local, state, and federal regulations as applicable and approved by the Institutional Animal Care and Use Committee (IACUC). Female C57BL/6 mice (7-8 weeks old) were obtained from Charles River Labs. The Bis-siRNA compounds (targeting FVII and TTR) were diluted to the appropriate concentrations in sterile PBS. Mice received either PBS or Bis-siRNA compounds via subcutaneous (s.c.) injection at a volume of 10 mL/kg on Day 0. Blood samples were collected from animals by retro-orbital bleed at various time points (Day 0 [pre-dose], 7, 14, 21, and 28) and processed to serum (Microtainer Serum Separator Tubes; Becton Dickinson, Franklin Lakes, NJ, USA). Serum levels of Factor VII protein were determined by using an activity-based chromogenic assay (Biophen FVII, Aniara Corporation, Mason, OH). Serum levels of TTR protein were determined using a mouse TTR ELISA. Table 9 summarizes the experiment design.

Mouse TTR Serum Protein Methods: TTR serum protein was quantified using a commercially available enzyme-linked immunosorbent assay, 41-ALBMS-E01 (ALPCO, Salem, NH), according to manufacturer's instructions. Briefly, serum samples were diluted 4000 fold in 1×ALPCO Kit Dilution Buffer. An 8-point mouse TTR standard curve was generated using 2.5× serial dilutions, ranging from 0 to 1000 ng/mL. Standards and samples (100 µL) were added to the plate and allowed to incubate for 30 minutes at room temperature. Plates were washed in 1×ALPCO Kit Wash Buffer and incubated for 20 minutes at room temperature with an affinity purified anti-Prealbumin antibody conjugated with horseradish peroxidase in a stabilizing buffer. After a wash in ALPCO Kit 1× Wash Buffer, plates were incubated for 10 minutes at room temperature in the dark with 3,3', 5,5'-tetramethybenzidine (TMB) and hydrogen peroxide in citric acid buffer at pH 3.3. Reactions were quenched with 100 µL of 0.3 mL sulfuric acid per well. Absorbance at 405 nm was read on a SpectraMax plate reader, and data were fit to a 4-parameter curve (y=(A−D)/(1+(x/C)^B)+D) as calculated in Softmax Pro Software to determine serum TTR protein levels expressed in ug/mL. Protein levels at each time point were normalized to the respective group average of vehicle control serum protein values.

Figure 11:
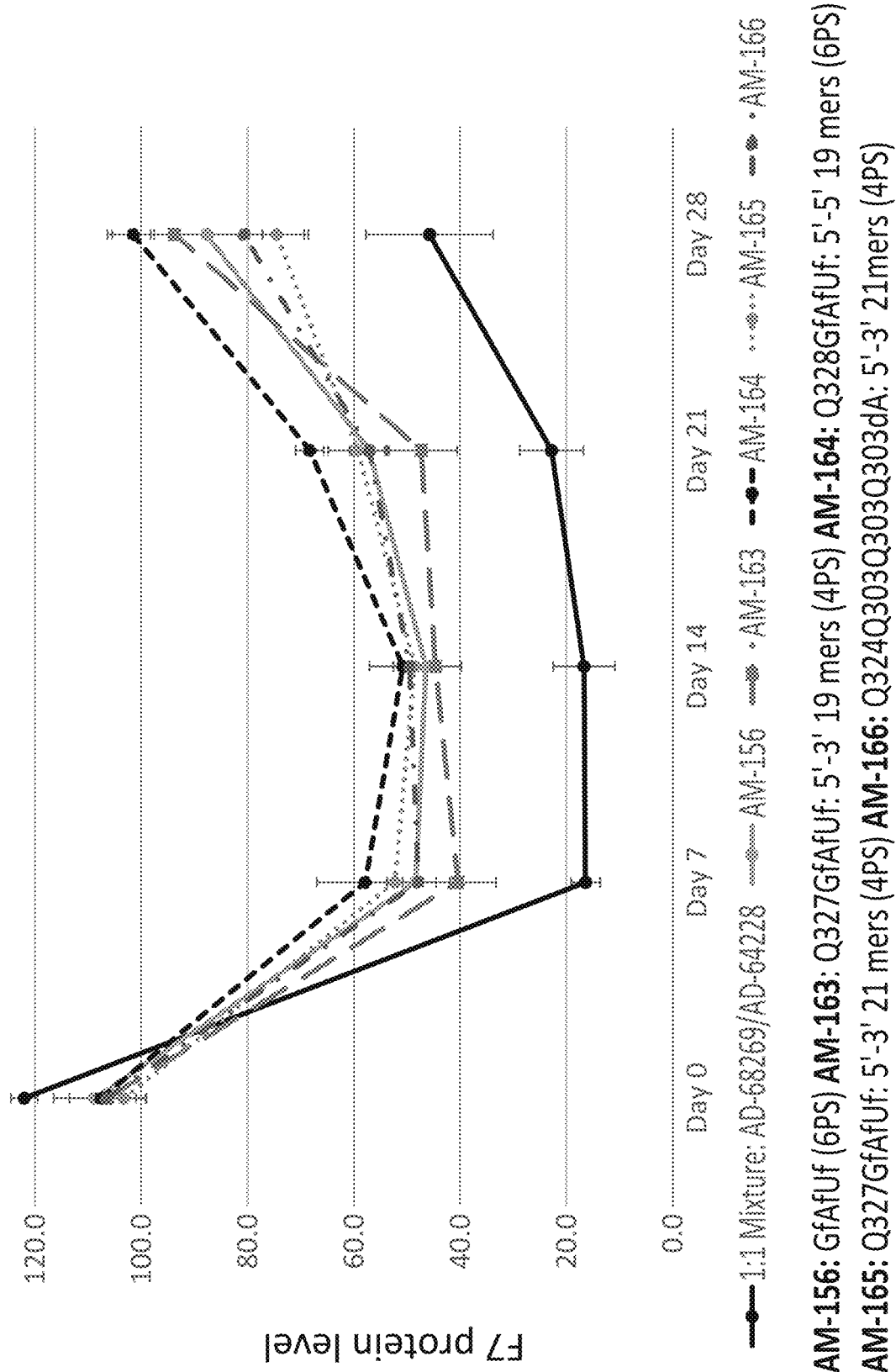
FIG. 11 is a graph showing F7 knockdown with "click" linkers.
Figure 12:
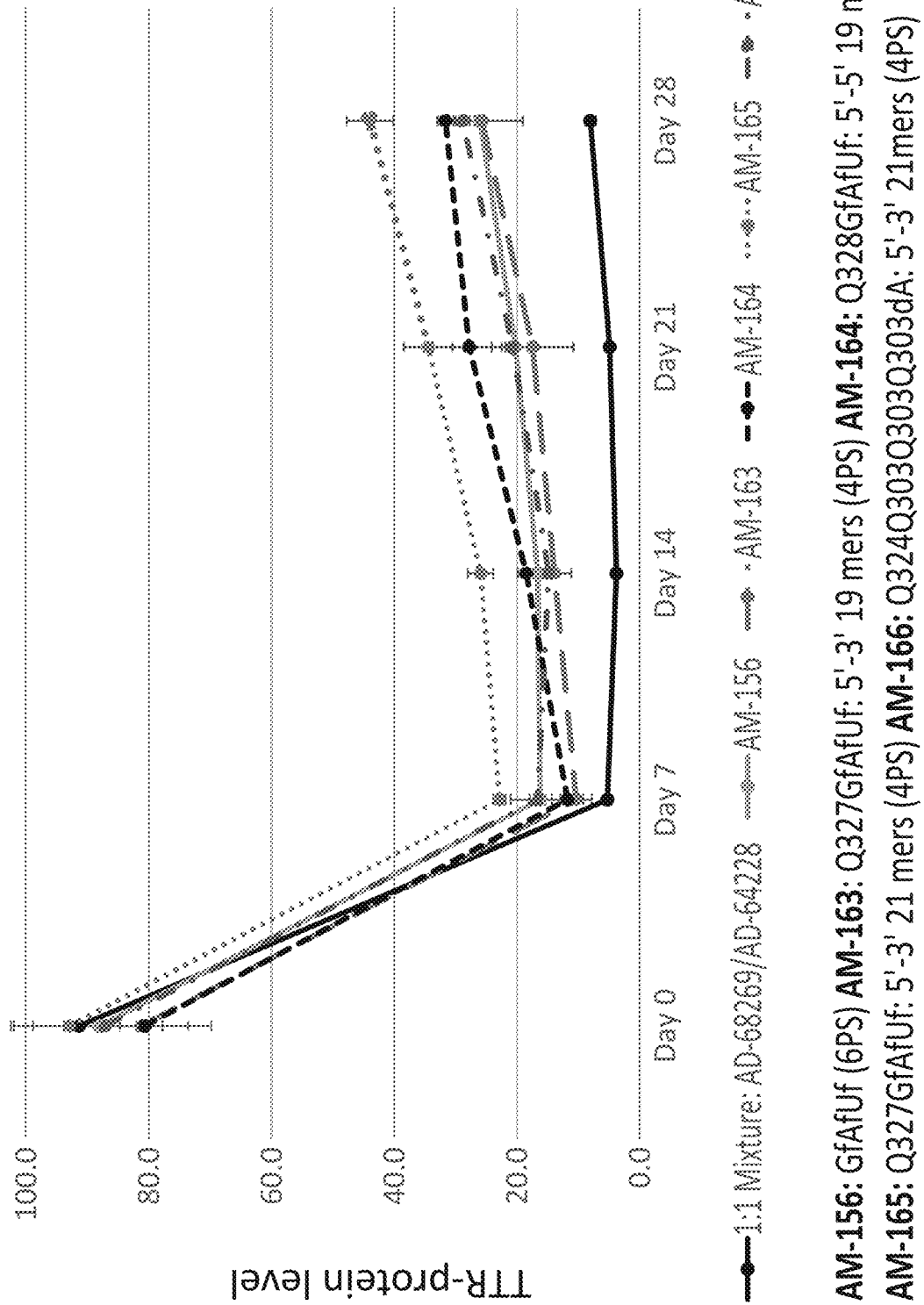
FIG. 12 is a graph showing TTR knockdown with "click" linkers.

Results of in vivo Studies: As described above, weekly timepoints were sampled until day 28. The samples were analyzed for TTF and F7 levels and compared to mixture. The results are shown in FIGS. 11 and 12. FIG. 11 show the F7 knockdown over time, while FIG. 12 shows the TTR knockdown over time.

Example 7: N,N-Diethylamine as an Additive Scavenger Agent for the Deprotection of 5-[O,O-bis(pivaloyloxymethyl)]-(E)-Vinyl Phosphonate Containing Oligonucleotides in Aqueous Ammonin 5'-(E)-Vinylphopshonate (VP) is an effective bioisostere of the natural 5'-monophosphate in small interfering RNAs (siRNAs). Solid-phase synthesis of VP-siRNAs requires use of appropriately protected VP-phosphoramidites in combination with optimal oligonucleotide deprotection conditions. Addition of 3% (v) neat diethylamine to the standard aqueous ammonia deprotection conditions allows clean and rapid one-step deprotection of 5'-[O,O-bis(pivaloyloxymethyl)] (POM)-protected VP oligonucleotides, minimizing side reactions and impurities and broadly enhancing the scope of VP oligonucleotide synthesis.

In recent years, oligonucleotide (ON)-based therapeutics, and RNA interference (RNAi)-based therapeutics in particular, have demonstrated clinical benefit for a variety of disease applications [(a) Selvam, C., Mutisya, D., Prakash, S., Ranganna, K. & Thilagavathi, R. Therapeutic potential of

TABLE 9

Mouse PD Study Design; sugars and "click" linkers

| Group # | Test Article | Linker | No. of animals | Time Points | Dose (mg/kg) |
|---|---|---|---|---|---|
| 1 | PBS | — | 3 | Day 0, 7, 14, 21, 28 | — |
| 2 | 1:1 Mixture | — | | | 1 + 1 mg/kg |
| 3 | AM-133 | 3X Q113: Galactose-C5 | | | 2 mg/kg |
| 4 | AM-137 | 3X Q115: Glucose-C5 | | | |
| 5 | AM-141 | 3X Q117: NAc Glucosamine-C5 | | | |
| 6 | AM-142 | 2X Q304: GalNAc-C5 | | | |
| 7 | AM-143 | 3X Q304: GalNAc-C5 | | | |
| 8 | AM-147 | 3X Q306: Manose-C5 | | | |
| 9* | AM-163 | Q327GfAfUf: 5'-3' 19 mers (4PS) | | | |
| 10* | AM-164 | Q328GfAfUf: 5'-5' 19 mers (6PS) | | | |
| 11* | AM-165 | Q327GfAfUf: 5'-3' 21 mers (4PS) | | | |
| 12* | AM-166 | Q324Q303Q303Q303dA: 5'-3' 21mers (4PS) | | | |
| 13 | AM-156 | GfAfUf (6PS) | | | |

*"click" multiplex designs chemically modified siRNA:Recent trends. Chem. Biol. Drug Des. 90, 665-678 (2017); (b) Stein, C. A. & Castanotto, D. FDA-Approved Oligonucleotide Therapies in 2017. Molecular Therapy 25, 1069-1075 (2017); (c) Titze-de-Almeida, R., David, C. & Titze-de-Almeida, S. S. The Race of 10 Synthetic RNAi-Based Drugs to the Pharmaceutical Market. Pharm. Res. 34, 1339-1363 (2017)]. Recently, the positive outcome of the APOLLO Phase 3 clinical trial of patisiran in patients with hereditary ATTR amyloidosis, has realized the promise of bringing RNAi-based therapeutics to patients [(a) Adams, D., Gonzalez-Duarte, A., O'Riordan, W., Yang, C. C., Yamashita, T., Kristen, A., Tournev, I., Schmidt, H., Coelho, T., Berk, J., Lin, K. P., Sweetser, M., Gandhi, P., Chen, J., Gollob, J. & Suhr, O. B. Patisiran, an investigational RNAi therapeutic for the treatment of hereditary ATTR. amyloidosis with polyneuropathy: results from the phase 3 APOLLO study. EU ATTR Meeting, Nov. 2, 2017, Paris, http://www.alnylam.com/wp-content/uploads/2017/2011/EU-ATTR 2017_APOLLOTRL_CAPELLA_FINAL_2012_Nov2017.pdf (2017); (b) Adams, D., Suhr, O. B., Dyck, P. J., Litchy, W. J., Leahy, R.G., Chen, J., Gollob, J. & Coelho, T. Trial design and rationale for APOLLO, a Phase 3, placebo-controlled study of patisiran in patients with hereditary ATTR amyloidosis with polyneuropathy. BMC Neurol 17, 181 (2017)]. Chemical modifications of siRNA are required for attributing drug-like properties by addressing metabolic instability, immune stimulation and overall unfavorable biodistribution and pharmacokinetics [(a) Manoharan, M. & Rajeev, K. G. Utilizing chemistry to harness RNA interference pathways for therapeutics: chemically modified siRNAs and antagomirs. (CRC Press LLC, 2008); (b) Shen, X. & Corey, D. R. Chemistry, mechanism and clinical status of antisense oligonucleotides and duplex RNAs. Nucleic Acids Research, 10.1093/nar/gkx1239 (2017)]. This was particularly impactful for the development of N-acetylgalactosamine (GalNAc)-siRNA conjugates [Nair, J. K., Willoughby, J. L. S., Chan, A., Charisse, K., Alam, M. R., Wang, Q., Hoekstra, M., Kandasamy, P., Kel'in, A. V., Milstein, S., Taneja, N., O'Shea, J., Shaikh, S., Zhang, L., van der Sluis, R. J., Jung, M. E., Akinc, A., Hutabarat, R., Kuchimanchi, S., Fitzgerald, K., Zimmermann, T., van Berkel, T. J. C., Maier, M. A., Rajeev, K. G. & Manoharan, M. Multivalent N-Acetylgalactosamine-Conjugated siRNA Localizes in Hepatocytes and Elicits Robust RNAi-Mediated Gene Silencing. J. Am. Chem. Soc. 136, 16958-16961 (2014).], allowing their rapid progress into clinical trials [(a) Fitzgerald, K., White, S., Borodovsky, A., Bettencourt, B. R., Strahs, A., Clausen, V., Wijngaard, P., Horton, J. D., Taubel, J., Brooks, A., Fernando, C., Kauffman, R. S., Kallend, D., Vaishnaw, A. & Simon, A. A highly durable RNAi therapeutic inhibitor of PCSK9. N. Engl. J. Med. 376, 41-51 (2017); (b) Pasi, K. J., Rangarajan, S., Georgiev, P., Mant, T., Creagh, M. D., Lissitchkov, T., Bevan, D., Austin, S., Hay, C. R., Hegemann, I., Kazmi, R., Chowdary, P., Gercheva-Kyuchukova, L., Mamonov, V., Timofeeva, M., Soh, C.-H., Garg, P., Vaishnaw, A., Akinc, A., Sorensen, B. & Ragni, M. V. Targeting of Antithrombin in Hemophilia A or B with RNAi Therapy. N Engl J Med 377, 819-828 (2017); (c) Zimmermann, T. S., Karsten, V., Chan, A., Chiesa, J., Boyce, M., Bettencourt, B. R., Hutabarat, R., Nochur, S., Vaishnaw, A. & Gollob, J. Clinical Proof of Concept for a Novel Hepatocyte-Targeting GalNAc-siRNA Conjugate. Mol. Ther. 25, 71-78 (2017)].

In GalNAc-siRNA conjugates, use of ribose modifications such as 2'-O-methyl (OMe) and 2'-deoxy-2'-fluoro (F) were vital to achieving high in vivo potency and duration of action [(a) Foster, D. J., Brown, C. R., Shaikh, S., Trapp, C., Schlegel, M. K., Qian, K., Sehgal, A., Rajeev, K. G., Jadhav, V., Manoharan, M., Kuchimanchi, S., Maier, M. A. & Milstein, S. Advanced siRNA Designs Further Improve in vivo Performance of GalNAc-siRNA Conjugates. Molecular Therapy, doi.org/10.1016/j.ymthe.2017.1012.1021 (2018); (b) Nair, J. K., Attarwala, H., Sehgal, A., Wang, Q., Aluri, K., Zhang, X., Gao, M., Liu, J., Indrakanti, R., Schofield, S., Kretschmer, P., Brown, C. R., Gupta, S., Willoughby, J. L. S., Boshar, J. A., Jadhav, V., Charisse, K., Zimmermann, T., Fitzgerald, K., Manoharan, M., Rajeev, K. G., Akinc, A., Hutabarat, R. & Maier, M. A. Impact of enhanced metabolic stability on pharmacokinetics and pharmacodynamics of GalNAc-siRNA conjugates. Nucleic Acids Res 45, 10969-10977 (2017)]. However, substantial chemical modifications can hamper endogenous 5'-monophosphorylation of the siRNA. Indeed, Clp1 kinase-mediated phosphorylation of the siRNA antisense strand is a critical step that leads to effective loading into the Argonaute (Ago2) protein of the RNA-induced silencing complex (RISC) to elicit gene silencing [(a) Weitzer, S. & Martinez, J. The human RNA kinase hClp1 is active on 3' transfer RNA exons and short interfering RNAs. Nature 447, 222-226 (2007); (b) Schirle, N. T., Kinberger, G. A., Murray, H. F., Lima, W. F., Prakash, T. P. & MacRae, I. J. Structural Analysis of Human Argonaute-2 Bound to a Modified siRNA Guide. J. Am. Chem. Soc. 138, 8694-8697 (2016); (c) Tolia, N. H. & Joshua-Tor, L. Slicer and the Argonautes. Nat. Chem. Biol. 3, 36-43 (2006)]. In addition, the chemical introduction of an unmodified 5'-monophosphate to the antisense strand does not circumvent this phosphorylation issue, as 5'-monophosphates are rapidly hydrolyzed by phosphatases in the lysosomal compartment [Lima, W. F., Prakash, T. P., Murray, H. M., Kinberger, G. A., Li, W., Chappell, A. E., Li, C. S., Murray, S. F., Gaus, H., Seth, P. P., Swayze, E. E. & Crooke, S. T. Single-Stranded siRNAs Activate RNAi in Animals. Cell 150, 883-894 (2012)]. Recently, several phosphatase-stable phosphate mimics for use in therapeutic siRNAs have been developed [(a) Haraszti, R. A., Roux, L., Coles, A. H., Turanov, A. A., Alterman, J. F., Echeverria, D., Godinho, B. M., Aronin, N. & Khvorova, A. 5'-Vinylphosphonate improves tissue accumulation and efficacy of conjugated siRNAs in vivo. Nucleic Acids Research (2017); (b) Parmar, R., Willoughby, J. L. S., Liu, J., Foster, D. J., Brigham, B., Theile, C. S., Charisse, K., Akinc, A., Guidry, E., Pei, Y., Strapps, W., Cancilla, M., Stanton, M. G., Rajeev, K. G., Sepp-Lorenzino, L., Manoharan, M., Meyers, R., Maier, M. A. & Jadhav, V. 5'-(E)-Vinylphosphonate: A Stable Phosphate Mimic Can Improve the RNAi Activity of siRNA-GalNAc Conjugates. ChemBioChem 17, 985-989 (2016); (c) Prakash, T. P., Lima, W. F., Murray, H. M., Li, W., Kinberger, G. A., Chappell, A. E., Gaus, H., Seth, P. P., Bhat, B., Crooke, S. T. & Swayze, E. E. Identification of metabolically stable 5'-phosphate analogs that support single-stranded siRNA activity. Nucleic Acids Res. 43, 2993-3011 (2015) (d) Zlatev, I., Foster, D. J., Liu, J., Charisse, K., Brigham, B., Parmar, R. G., Jadhav, V., Maier, M. A., Rajeev, K. G., Egli, M. & Manoharan, M. 5'-C-Malonyl RNA:Small Interfering RNAs Modified with 5'-Monophosphate Bioisostere Demonstrate Gene Silencing Activity. ACS Chemical Biology 11, 953-960 (2016)]. Among them, the (E)-vinylphosphonate (VP) has proved to be the most effective bioisostere of natural 5'-monophosphate [(a) Elkayam, E., Joshua-Tor, L., Parmar, R., Brown, C. R., Willoughby, J. L., Theile, C. S. & Manoharan, M. siRNA carrying an (E)-vinylphosphonate moiety at the 5 end of the guide strand augments gene silencing by enhanced binding to buman Argonaute-2. Nucleic Acids Res 45, 3528-3536 (2017); (b) Prakash, T. P., Kinberger, G. A., Murray, H. M., Chappell, A., Riney, S., Graham, M. J., Lima, W. F., Swayze, E. E. & Seth, P. P. Synergistic effect of phosphorothioate, 5'-vinylphosphonate and GalNAc modifications for enhancing activity of synthetic siRNA. Bioorg. Med. Chem. Lett. 26, 2817-2820 (2016)]. When added to the 5'-end of the antisense strand of siRNA, VP provided enhanced metabolic stability and enhanced potency in vivo.

Efficient solid-phase synthesis of VP-siRNA requires appropriately protected VP-phosphoramidites in combination with optimal ON deprotection conditions. The first iteration of VP-siRNA synthesis was the use of 5'-(O,O-diethyl) VP phosphoramidites during ON synthesis. Removal of the two VP ethyl groups, however, requires harsh deprotection conditions performed on the ON still attached to the solid support, using trimethyl silyl iodide and mercaptoethanol, leading to decomposition and/or side products, resulting in lower yields. Another VP protecting group, the 5'-[O,O-bis(pivaloyloxymethyl)] (POM) VP is more compatible with standard solid-phase synthesis, which could facilitate and enable large-scale synthesis of 5'-phosphonate-modified ONs [Parmar, R., Brown, C. R., Matsuda, S., Willoughby, J. L., Theile, C. S., Charisse, K., Foster, D. J., Zlatev, I., Jadhav, V., Maier, M. A., Egli, M., Manoharan, M. & Rajeev, K. G. Facile Synthesis, Geometry and 2'-Substituent-Dependent In Vivo Activity of 5'-(E)- and 5'-(Z)-Vinylphosphonate-Modified siRNA Conjugates. J. Med. Chem. DOI: 10.1021/acs.jmedchem.7b01147 (2018)].

Scheme 34

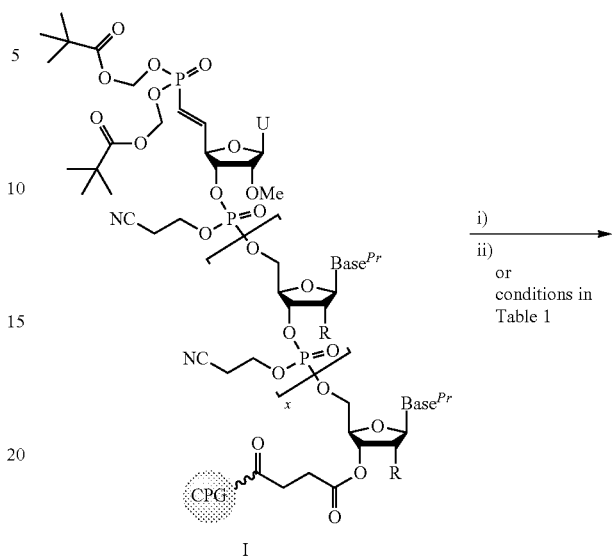

Results and Discussion

Herein is established optimal conditions of POM VP deprotection, providing for a clean and rapid one-step procedure, minimizing side reactions and impurities, and broadly enhancing the scope of VP ON synthesis. A standard two-step ON deprotection protocol was initially applied including: (i) treatment of the support-bound POM VP ON with a steady flow of a base solution (e.g. diethylamine or piperidine) in acetonitrile [Capaldi, D. C., Gaus, H., Krotz, A. H., Arnold, J., Carty, R. L., Moore, M. N., Scozzari, A. N., Lowery, K., Cole, D. L. & Ravikumar, V. T. Synthesis of High-Quality Antisense Drugs. Addition of Acrylonitrile to Phosphorothioate Oligonucleotides: Adduct Characterization and Avoidance. Organic Process Research & Development 7, 832-838 (2003)], followed by (ii) incubation of the solid support with saturated (28-30%-w/v) aqueous ammonia (ammonium hydroxide solution). It was found that the presence of the POM VP 5'-terminal nucleotide induced base-mediated strand cleavage: the 5'-terminal nucleotide was lost from the VP compound I, leaving the corresponding N-1 structure II, with a 5'-monophosphate attached to it, as the major impurity (−317 amu, ~20%) to the desired full-length VP compound III. Scheme 34 shows the deprotection scheme and compounds I, II and III. The deprotection can be by using the two step protocol, (i) and (ii) as described above, or conditions shown in 7 (below).

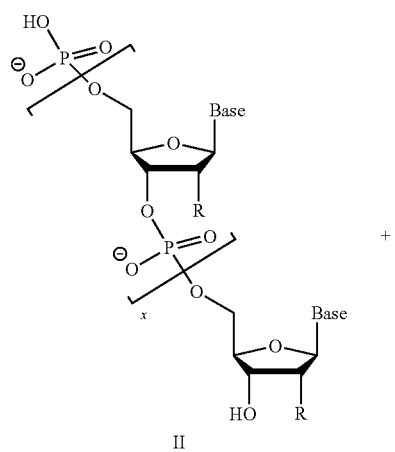

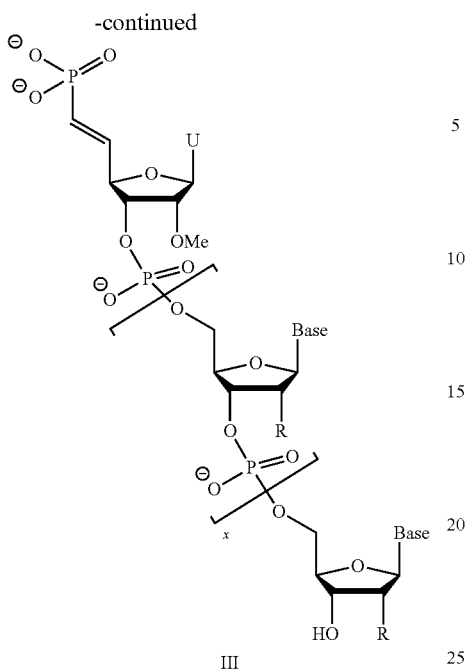

Base = A, C, G, U or T at a given position
Base$^{Pr}$: Exocyclic amine protected: A(Bz), C(Ac) or G(ibu), and T or U
R = H, F, OMe Without being bound by any specific theory, it is hypothesized that in presence of the POM VP phosphonotriester at the terminal 5'-nucleotide, its 4' proton is especially labile to base due to the possibility of delocalizing the resulting negative charge within the VP phosphonotriester moiety. This leads to a β-elimination reaction where the leaving group is the 3'-O-phosphate and the rest of the ON. On the other hand, when the on-support piperidine treatment was not performed (Scheme 34, step (ii) only), the N-1 compound II (−317 amu) was not observed. However, in absence of the on column base treatment, significant amount of acrylonitrile adduct (+53 amu) was detected, yielded by the addition of acrylonitrile released from the phosphate protecting cyanoethyl groups to the N$^r$ position of the uracil bases Structure A below.

A way to avoid these acrylonitrile adducts is to replace the single step ammonia treatment with a more nucleophilic base (e.g. methylamine), that would be an effective scavenger of acrylonitrile. However, the use of stronger nucleophile amines can generate another uracil base impurity, yielded by the nucleophilic addition of the amine to the C-6 position (Structure B), an intermediary in the depyrimidination decomposition cascade [(a) Dellinger, D. J., Timár, Z., Myerson, J., Sierzchala, A. B., Turner, J., Ferreira, F., Kupihár, Z., Dellinger, G., Hill, K. W., Powell, J. A., Sampson, J. R. & Caruthers, M. H. Streamlined Process for the Chemical Synthesis of RNA Using 2'-O-Thionocarbamate-Protected Nucleoside Phosphoramidites in the Solid Phase. Journal of the American Chemical Society 133, 11540-11556 (2011); (b) Shetlar, M. D., Hom, K. & Venditto, V. J. Photohydrate-Mediated Reactions of Uridine, 2'-Deoxyuridine and 2'-Deoxycytidine with Amines at Near Neutral pH. Photochemistry and Photobiology 89, 869-877 (2013)].

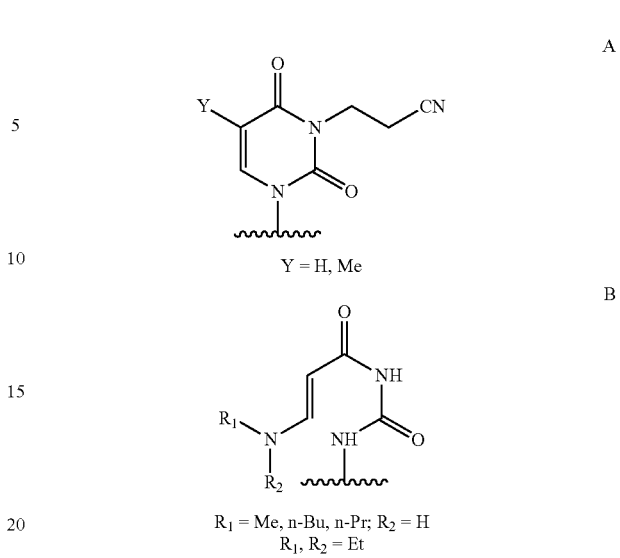

Thymine and uracil are reported to be the nucleobases that are most sensitive to generating A and B as impurities. Structure A is M-cyanocthyl adducts of uracil (Y=H) or thymine (Y=Me) and structure B is a C-6 amino adducts of uracil. A "worst-case scenario" ON-1, an alternating 2'-deoxythymidine-2'-fluorouridine 20-mer (Table 9) was selected for experimentation. 2'-Deoxythymidine is well known to be the most susceptible nucleotide for acrylonitrile addition [Umemoto, T. & Wada, T. Nitromethane as a scavenger of acrylonitrile in the deprotection of synthetic oligonucleotides. Tetrahedron Letters 46, 4251-4253 (2005)], while 2'-fluorouridine is easily degraded by strong amine bases, such as methylamine. ON-1 allowed experimentation focused on narrowly exploring the nucleobase impurities A and B, before translating the most optimal conditions to a POM VP ON.

Cleavage of ON-1 from the controlled pore glass (CPG) solid support was first performed using four commonly employed deprotection conditions (Table 9, Entries 1-4): Entry 1: direct incubation with 28-30% aqueous ammonia at 35° C. for 20 h; Entry 2: incubation with 40% w/v aqueous methylamine for 15 minutes at 60° C.; Entry 3: incubation with 1:1 (v/v) mixture of ammonia and methylamine (AMA) for 3 h at rt; Entry 4: incubation with aqueous ammonia at 35° C. for 20 h, after pre-treatment by washing the CPG with a flow of 5% piperidine in ACN, three times over 15 min. The single ammonia incubation sample, showed a large amount of +53 amu acrylonitrile adducts (Entry 1, Table 10). Meanwhile the quick treatment with methylamine, which was the current standard for deprotection of POM protected VP ONs, showed significant amounts of adducts of methylamine to the uracil (and thymine) bases (Entry 2, Table 10). Similar significant methylamine adducts (c.a. 20%) were also observed with the AMA treatment (Entry 3, Table 10). Albeit being incompatible with VP ON deprotection (Scheme 1), the piperidine pre-treated support condition (Entry 4, Table 10) showed no acrylonitrile nor amine adducts on ON-1, and was set as the benchmark to emulate in our search for the future most optimal deprotection conditions.

Following these benchmark studies, we set to replace the on-column piperidine treatment with direct addition of various amines to the ammonia deprotection solution in order to scavenge acrylonitrile. This treatment was designed to eliminate any VP-related N-1 impurities while also minimizing all nucleobase adduct impurities.

Methylamine, n-butylamine, n-propylamine, or diethylamine, all of which are readily available and inexpensive, were added as scavengers (3%, v/v) to the aqueous ammonia solution during cleavage of ON-1 at 35° C. for 20 h (Table 9). Other more hydrophobic amines were not included in these studies, since in our previous experience they tend to associate to the phosphate backbone and are difficult to separate during purification. In addition, a previously described acrylonitrile scavenger, nitromethane, showed good results but produced dark coloration of the media and made analysis and purification difficult (example in Supporting Information). The major by-products observed (A and B) were quantified by RP-HPLC/MS analysis. While the amine adduct peaks were easily quantifiable by LC/MS analysis, due to their distinct retention time shift, the acrylonitrile adducts tended to co-elute with the main product peak and only the relative abundance determined by LC/MS could be reported (Table 10)

and a reduced time of deprotection, if desired. Although overall most effective, the 3% DEA solution did not fully remove acrylonitrile adducts. Therefore, we tested whether an increased 5% DEA (v/v) solution would reduce such impurities with ON-1 at 35° C. and 60° C. (Table 10, Entries 10 and 11). However, we obtained nearly indistinguishable results as observed with the 3% DEA solution.

These same testing conditions were then applied to an oligonucleotide with 2'-F/OMe chemical modifications and the POM-protected VP (ON2, Table 10. Again, the previous standard of methylamine treatment for 15 minutes at 60° C. showed a large amount of methylamine adduct (Table 10, Entry 12), while the pretreatment with piperidine caused the N-1 product (Entry 13), and pure ammonia had a large amount of acrylonitrile adduct (Table 10, Entry 14). When the scavenger amines were tested as a 3% solution (methylamine and DEA), acrylonitrile adducts were largely absent and no N-1 plus phosphate was seen (Table 10, Entries 15-16). However, amine adducts were observed in the case

TABLE 10

Deprotection of solid support-bound poly-(2'-deoxythymidine-2'-fluorouridine) ON (ON-1) and POM VP ON (ON-2) in various conditions.

| Entry | ON[a,b] | Deprotection Conditions | Acrylonitrile Adducts A[c] | Amine Adducts B[c] |
|---|---|---|---|---|
| 1 | ON-1 | 28-30% (w/v) NH$_4$OH, 35° C., 20 h | 9.9% | n.d.[d] |
| 2 | ON-1 | 40% (w/v) Methylamine, 35° C., 20 h | n.d. | 19.2% |
| 3 | ON-1 | 40% (w/v) Methylamine/ NH$_4$OH - 1:1 (v/v, AMA), rt, 2 h | n.d. | 21.5% |
| 4 | ON-1 | Pre-treatment with 5% (v/v) piperidine, steady flow, 3 × 5 min, followed by NH$_4$OH, 35° C., 20 h | n.d. | n.d. |
| 5 | ON-1 | 3% (v/v) Methylamine in NH$_4$OH, 35° C., 20 h | 7.4% mixture | |
| 6 | ON-1 | 3% (v/v) n-Propylamine in NH$_4$OH, 35° C., 20 h | 2.0% | 7.7% |
| 7 | ON-1 | 3% (v/v) n-Butylamine in NH$_4$OH, 35° C., 20 h | 2.6% | 6.7% |
| 8 | ON-1 | 3% (v/v) Diethylamine in NH$_4$OH, 35° C., 20 h | 1.9% | 1.4% |
| 9 | ON-1 | 3% (v/v) Diethylamine in NH$_4$OH, 60° C., 5 h | 2.8% | n.d. |
| 10 | ON-1 | 5%(v/v) Diethylamine in NH$_4$OH, 35° C., 20 h | 1.6% | 1.4% |
| 11 | ON-1 | 5% (v/v) Diethylamine in NH$_4$OH, 60° C., 5 h | 2.1% | 2.3% |
| 12 | ON-2 | 40% (w/v) Methylamine, 60° C., 15 min | n.d. | 5.5% |
| 13 | ON-2 | Pre-treatment with 5% (v/v) piperidine, steady flow, 3 × 5 min, followed by NH$_4$OH, 35° C., 20 h | n.d.* | n.d.* |
| 14 | ON-2 | 28-30% (w/v) NH$_4$OH, 35° C., 20 h | 4.3% | n.d. |
| 15 | ON-2 | 3% (v/v) Methylamine in NH$_4$OH, 35° C., 20 h | n.d. | 3.8% |
| 16 | ON-2 | 3% (v/v) Diethylamine in NH$_4$OH, 35° C., 20 h | n.d. | n.d. |
| 17 | ON-2 | 3% (v/v) Diethylamine in NH$_4$OH, 60° C., 5 h | n.d. | n.d. |

[a,b]50 mg of CPG support (~80 μmol/g) with ON-1 or ON-2 were incubated with 1000 μL of deprotection solution according to Scheme 1 and the conditions in Table 1.
[a]Sequence of ON-1: 5'-UdTUdTUdTUdTUdTUdTUdTUdTUdTUdTu-3' where U is 2'-fluorouridine, dT is 2'-deoxythymidine and u is 2'-O-methyluridine.
[b]Sequence of ON-2: 5'-(VP)uUuCgAaUcAaucCaAcAgUagu-3' where lower case nucleotides are 2'-O-methy and upper case italicized nucleotides are 2'-fluoro.
[c]Percentage of impurities calculated by integrating peaks of the crude material on the UV-LC/MS spectrum at 260 nm. RP-LC/MS run on a C8 column.
[d]n.d.—not detected (<1.0%).
*Formation of 19.4% of N-1 product (−317.29 amu), as described in Scheme 34).

From these experiments it was determined that, compared to the other amines used, 3% diethylamine (DEA) provided excellent results in terms of product purity and yield, with minimal amounts of both nucleobase adducts generated (Table 10, Entries 5-8). Based on these results, propyl- and butylamines were not considered any further. Furthermore, incubation with the 3% DEA ammonia at 60° C. for 5 h (Table 10, Entry 9) provided results nearly identical to those of the incubation at 35° C. for 20 h, allowing for flexibility of methylamine, whereas in the DEA conditions, no detectable adduct was observed. As show in Table 11, the results of the 3% DEA in ammonia solution were repeated among several other 2'-F/OMe modified sequences with and without phosphorothioate modifications, showing a clean profile with no acrylonitrile or amine adducts forming. Likewise, a comparison of deprotections at 35° C. for 20 hours and 60° C. for 5 hours showed nearly identical results therefore allowing for more rapid deprotection when desired.

TABLE 11

Deprotection of solid support-bound POM VP ONs in various scales using the optimal 3% diethylamine scavenger in aqueous ammonia. Incubation at 35° C. for 20 h (ON-3-ON-6) or 60° C. for 5 h (ON-7).

| Scale[a] (µmol) | ON | Sequence[b] | Acrylonitrile Adducts A[c] | Amine Adducts B[c] |
|---|---|---|---|---|
| 10 | ON-3 | (VP) u•U•agaAaUAagugGuAgucac•u•u | n.d.[d] | n.d. |
| 10 | ON-4 | (VP) u•U•ucuGgCAuucuUcAuuugu•u•a | n.d. | n.d. |
| 100 | ON-5 | (VP) uAaagCacuuuauUgAguuuc•u•g | n.d. | n.d. |
| 100 | ON-6 | (VP) uCguuUucaaagcAcUuuauu•g•a | n.d. | n.d. |
| 320 | ON-7 | (VP) u•A•uugAcCCaaaaUuCaacaa•u•g | n.d. | n.d. |

[a]Based on the amount and the loading of the CPG support used.
[b]Lower case nucleotides are 2'-O-methy and upper case italicized nucleotides are 2'-fluoro.
• is phosphorothioate diester linkage between nucleotides.
[c]Percentage of impurities calculated by integrating peaks of the crude material on the UV-LC/MS spectrum at 260 nm. RP-LC/MS run on a C8 column.
[d]n.d.—not detected (<1.0%).

POM protected VP moiety is a stable phosphate mimic that can be readily deprotected using standard oligonucleotide deprotection reagents. Instead of pretreatment with a diethylamine or piperidine solution, which causes undesired byproducts, a 3% solution of DEA in aqueous ammonia as described herein can be used for cleavage at either 35° C. for 20 h or 60° C. for 5 h to yield a crude ON in good yield and purity for subsequent ion exchange or reverse phase purification. The conditions reported herein minimize the acrylonitrile and methylamine adducts observed during conventional deprotection, provide higher yields and may be used as a general deprotection of other oligonucleotides with or without the POM protected VP.

Figure 13:
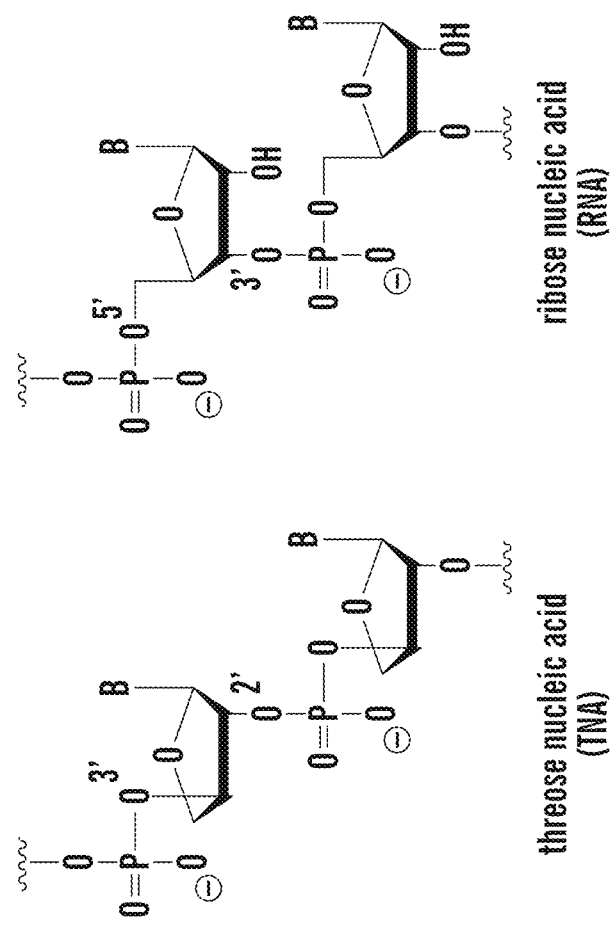
FIG. 13 shows the structure of threose nucleic acids (TNA) and ribose nucleic acids (RNA).

Example 8: Threofuranosyl Nucleic Acid (TNA) Gene Silencing Activity of siRNA α-(L)-threofuranosyl nucleic acid with a (3'-2') phosphodiester backbone (TNA), are nucleic acid alternatives [Schoning, K. U. et al. Science 2000, 290, 1347]. The sugar-phosphate backbone of TNA and, for comparison RNA, are shown in FIG. 13. TNA consists of unnatural four-carbon threose sugar and has a unique sugar-phosphate backbone that allows the formation of stable, antiparallel Watson-Crick duplex structures. TNA also shows efficient cross-pairing with complementary strands of DNA and RNA, and exhibits strong nuclease stability under biologically relevant conditions. Even though TNA has been well-studied in terms of its base pairing properties and structural features [(a) Wilds, C. J. et al. J. Am. Chem. Soc. 2002, 124, 13716. (b) Pallan, P. S. et al. Angew. Chem. Int. Ed. 2003, 42, 5893. (c) Anosova I. et al. ChemBioChem 2016, 17, 1705.

(d) Ebert, M. O. et al. J. Am. Chem. Soc. 2008, 130, 15105. (e) Schoning, K. U. et al. Helv. Chim. Acta 2002, 85, 399], little is known about its potential application in the context of short interfering RNAs (siRNAs).

Exemplary siRNA modifications are 5'-Methyl [Kel'in, A. V. et al. J. Org. Chem. 2016, 81, 2261], siRNA-GalNAc conjugate [(a) Nair, J. K. et al. J. Am. Chem. Soc. 2014, 136, 16958. (b) Matsuda, S. et al. ACS Chem. Biol., 2015, 10, 1181. (c) Rajeev, K. G. ChemBioChem 2015, 16, 903. (d) Nair, J. K. et al. Nucleic Acids Res. 2017, 45, 10969. (e) Meade, B. R. et al. Nature Biotechnol. 2014, 32, 1256], 4'-modification [(a) Liboska, R. et al. Org. Biomol. Chem. 2011, 9, 8261. (b) Martinez-Montero, S. et al. ACS Chem. Biol., 2015, 10, 2016. (c) Malek-Adamian, E. et al. J. Am. Chem. Soc. 2017, 139, 14542. (d) Malek-Adamian, E. et al. J. Org. Chem. 2018, doi: 10.1021/acs.joc.8b01329. (e) Harp, J. M. et al. Nucleic Acids Res. 2018, doi: 10.1093/nar/gky703], GNA [(a) Schlegel, M. K. et al. J. Am. Chem. Soc. 2017, 139, 8537. (b) Janas, M. M. et al. Nature Communications 2018, 9, 723] and Vinylphosphonate [(a) Parmar, R. et al. ChemBioChem 2016, 17, 985. (b) Elkayam, E. et al. Nucleic Acids Res. 2017, 45, 3528. (c) Parmar, R. G. et al. J. Med. Chem 2018, 61, 734. (d) Schirle, N. T. et al. J. Am. Chem. Soc. 2016, 138, 8694].

The TNA phosphoramidite building blocks can be synthesised and incorporated into siRNA using optimized synthesis conditions as depicted in Scheme 35 [Sau, S. P. et al. J. Org. Chem., 2016, 81, 2302]. The effects of TNA incorporation on the oligonucleotide metabolic stability, duplex thermal stability and in vitro gene silencing activity of siRNAs were evaluated.

Scheme 35

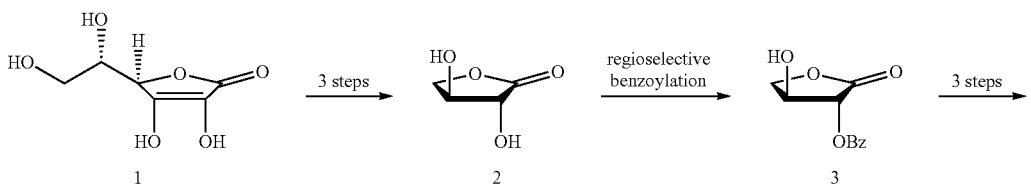

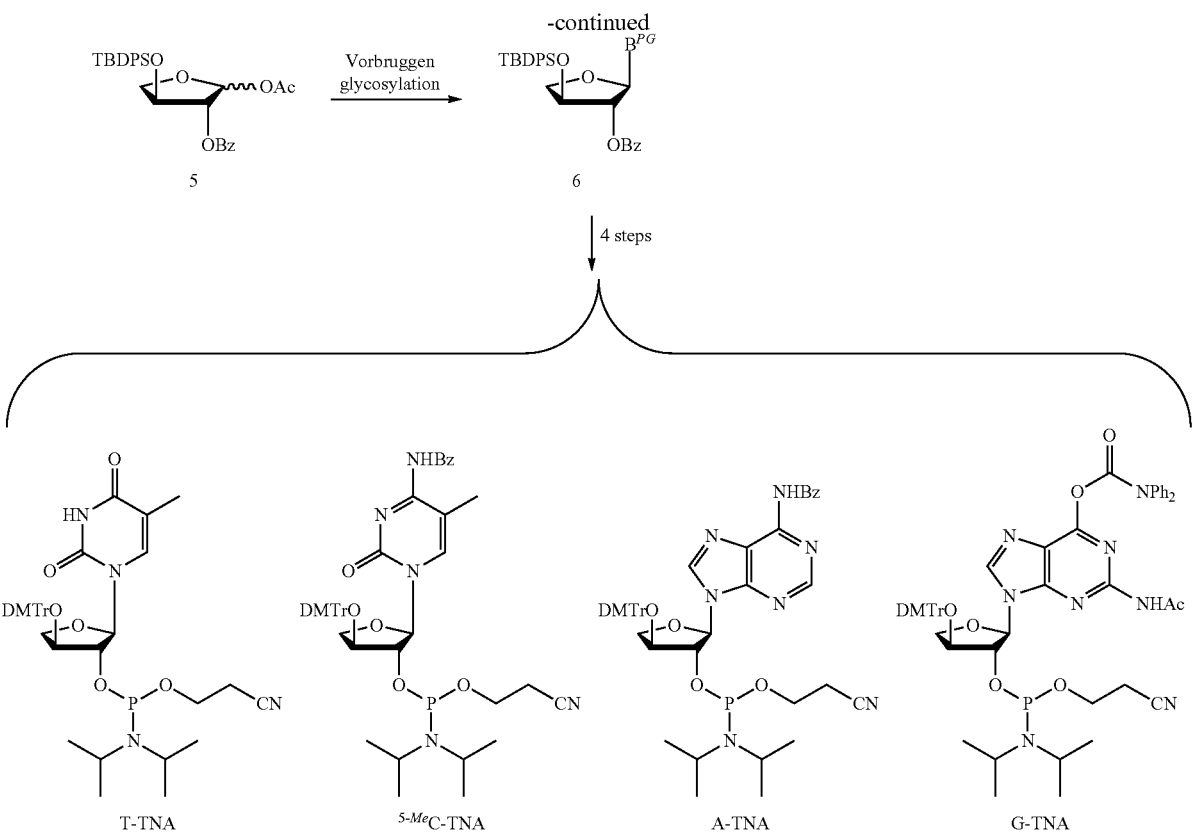

See Sau, S. P. et al. *J. Org. Chem.*, 2016, 81, 2302 for details.

Synthesis of $^{5\text{-}Me}$C-TNA (Compound 2): An example for the preparation of the TNA building block $^{5\text{-}Me}$C-TNA is shown by Scheme 36.

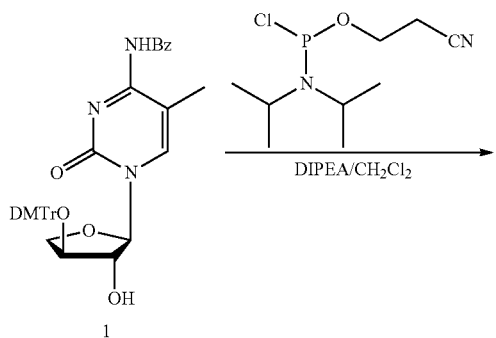

Scheme 36

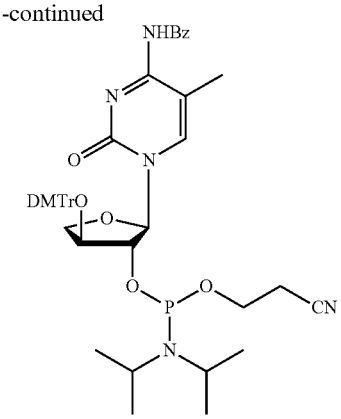

Synthesis of compound 2: To a solution of compound 1 (5.00 g, 7.89 mmol) in $CH_2Cl_2$ (40 ml) was added DIPEA (4.13 ml, 23.7 mmol) and 2-cyanoethyl N,N-diisopropylchlorophosphoramidite (2.11 ml, 9.47 mmol) at 0° C. The reaction mixture was allowed to room temperature and stirred for 3 h. The reaction mixture was diluted with $CH_2Cl_2$ (200 mL) then washed with saturated $NaHCO_3$ aqueous solution (100 mL). The organic layer was separated, dried over anhydrous $Na_2SO_4$, filtered and concentrated. The crude material was purified by flash silica gel column chromatography (0-33% EtOAc in hexanes) to give compound 2 (5.90 g, 7.07 mmol, 90%, Rf=0.36 developed with 33% EtOAc in hexanes) as a pale yellow foam. $^1$H NMR (400 MHZ, DMSO-$d_6$): δ 13.40 (s, 1H), 8.30 (d, J=7.5 Hz, 2H), 7.83-7.09 (m, 13H), 6.94-6.68 (m, 4H), 5.87-5.59 (m, 1H), 4.30-4.24 (m, 1H), 4.15-4.05 (m, 2H), 3.91-3.47 (m, 13H), 2.72-2.33 (m, 3H), 1.29-0.93 (m, 12H). $^{31}$P NMR (162 MHZ, CD$_3$CN): δ 152.98, 151.73. $^{13}$C NMR (126 MHz, CD$_3$CN): δ 180.24, 161.79, 159.88, 159.85, 148.60, 145.88, 140.44, 138.41, 136.81, 136.75, 136.72, 136.55, 133.35, 130.93, 130.85, 130.81, 130.54, 129.19, 129.17, 129.13, 128.80, 128.70, 127.99, 127.97, 119.58, 119.32, 118.27, 114.58, 114.51, 114.48, 110.44, 110.34, 93.13, 93.07, 92.88, 92.86, 89.09, 89.03, 81.98, 81.84, 81.72, 78.51, 78.46, 78.17, 78.15, 76.46, 76.34, 59.64, 59.48, 59.45, 59.30, 55.95, 55.93, 44.42, 44.31, 44.24, 44.14, 24.90, 24.87, 24.83, 24.82, 24.77, 24.73, 24.68, 20.87, 20.81, 20.72, 20.66, 13.80, 13.78.

Stability of modified oligonucleotides toward 3'- or 5'-specific exonucleases: Oligonucleotides were prepared in a final concentration of 0.1 mg/mL in either 50 mM Tris (pH 7.2), 10 mM MgCl$_2$ or 50 mM sodium acetate (pH 6.5), 10 mM MgCl$_2$ for assessing the stability towards 3'- or 5'-specific exonucleases, respectively. The exonuclease (150 mU/mL SVPDE for 3'-stability or 500 mU/mL phosphodiesterase II for 5'-stability) was added immediately prior to analysis via IEX HPLC (dionex DNAPac PA200, 4×250 mm) using a gradient of 37-52% mobile phase (1 M NaBr, 20 mM sodium phosphate, pH 11, 15% MeCN; stationary phase: 20 mM sodium phosphate, 15% MeCN, pH 11) over 7.5 min with a flow of 1 mL/min. Samples were analyzed at given time points for up to 24 h. The quantity of full length oligonucleotides was determined as the area under the curve at $A_{260}$. Percent full length oligonucleotides was calculated by dividing by the area under the curve at t=0 and multiplying by 100. Activity of enzyme was verified for each experiment by including a oligodeoxythymidylate with a terminal phosphorothioate linkage (5'-$T_{19}$.T (SEQ ID NO: 708) or 5'-T*$T_{19}$ (SEQ ID NO: 708) for 3'- or 5'-exonuclease activity, respectively). Each aliquot of enzyme was thawed just prior to the experiment. The half-life was determined by fitting to first order kinetics.

Figure 14:
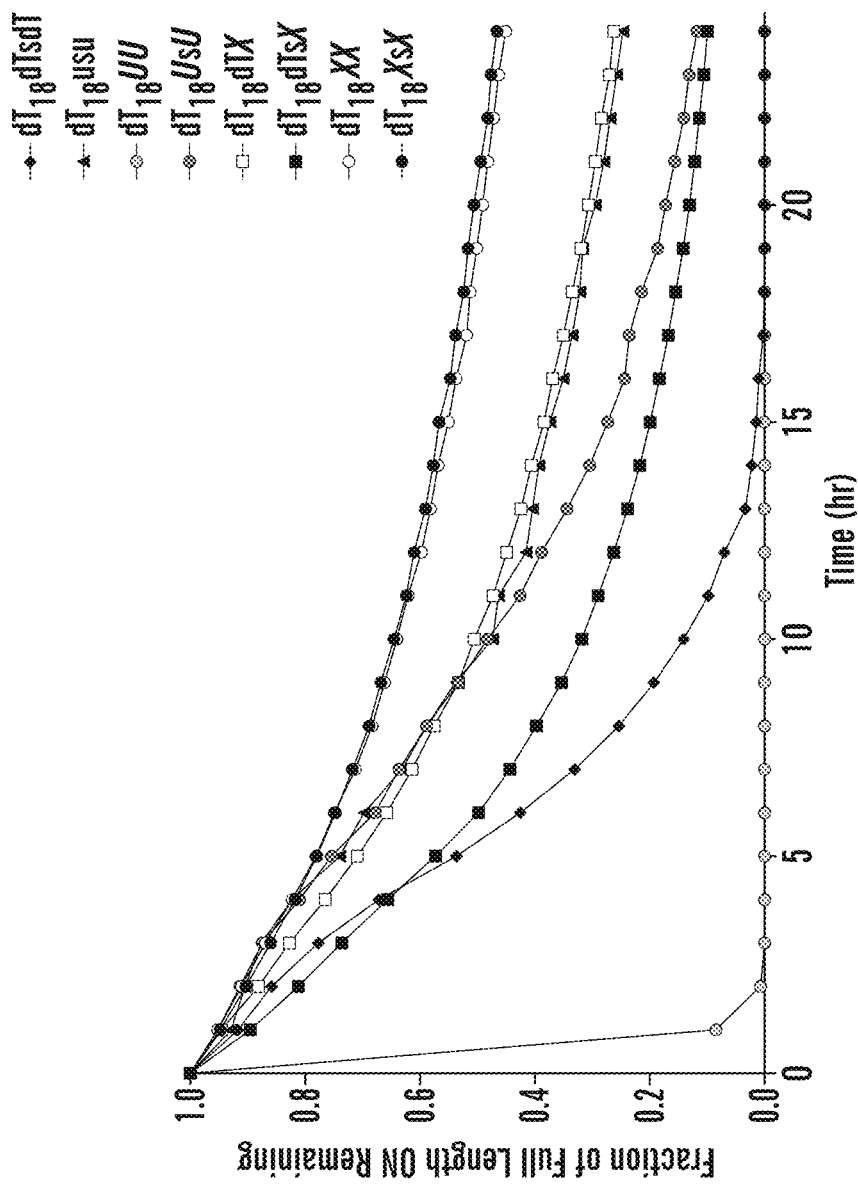
FIG. 14 is a graph showing the stability of TNA modified oligonucleotides against 3'-exonuclease.
Figure 14:
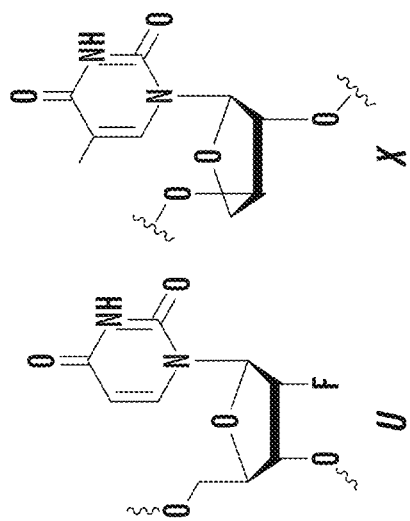

Results for the stability of TNA modified oligonucleotides against 3'-Exonuclease are shown in FIG. 14. Single incorporation of T-TNA (oligo 5) showed ~5-fold improvement of the stability when compared to a single PS bond 3'-dTsdT (oligo 1). Double incorporation of T-TNA (oligo 7) provided significant stabilization of a PO bond with >8-fold resistance against 3'-exo nuclease when compared to 3'-dTsdT. TNA-T showed remarkable stability when compared to 2'-F-U (oligo 7 vs 3).

Figure 15:
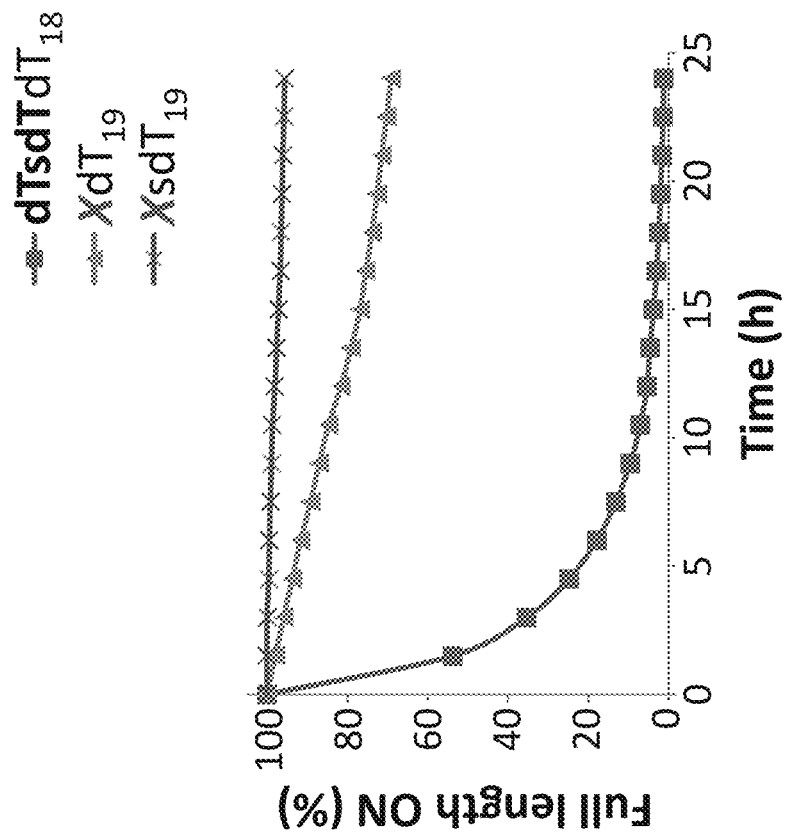
FIG. 15 is a graph showing the stability of TNA modified oligonucleotides against 5'-exonuclease.
Figure 15:
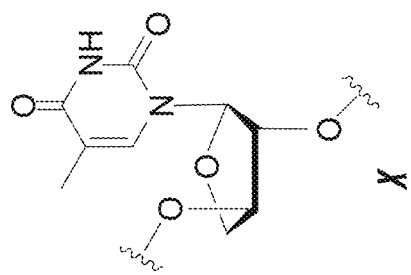

Results for the stability of TNA modified oligonucleotides against 5'-exonuclease are shown in FIG. 15. T-TNA provides significant stabilization of a PO bond (oligo 10) with >10 fold resistance to degradation by phosphodiesterase II compared to a single PS bond (5'-dTsdT). T-TNA in combination with a PS bond (oligo 11) is remarkably resistant to degradation under these conditions (~4% degradation in 24 h).

Determination of UV thermal melting temperatures: Thermal melting temperatures were measured with equimolar concentrations of both strands (2.5 μM) in 1×PBS ([NaCl]=137 mM, [KCl]=2.7 mM, [Na$_2$HPO$_{4}]_{=10}$ mM, [KH$_2$PO$_{4}]_{=1.8}$ mM, pH 7.4) by monitoring $A_{260}$ with increasing temperature (1° C./min). Values were reported as the maximum of the first derivative and are the average of at least two experiments. The results are shown in Tables 12 and 13. TNA showed minor destabilization in DNA and larger destabilization in RNA. The structures x and y are shown here:

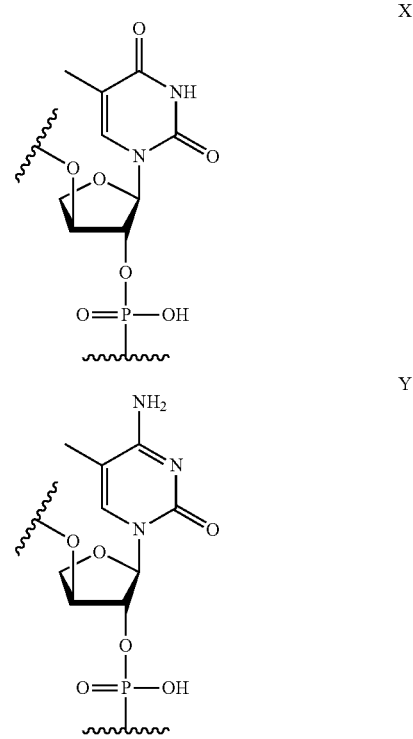

TABLE 12

Thermal Stability of TNA Modified Oligonucleotides. RNA (X) duplex.

| Duplex | Sequence | $T_m$ value | Δ $T_m$ |
|---|---|---|---|
| RNA-RNA control | 5'-UACAGUCUAUGU-3'<br>5'-ACAUAGACUGUA-3' | 52.6° C. | — |
| RNA (X) duplex | 5'-UACAGXCUAUGU-3'<br>5'-ACAUAGACUGUA-3' | 47.7° C. | -4.9° C. |
| DNA-DNA control | 5'-dTdAdCdAdGdTdCdTdAdTdGdT-3'<br>5'-dAdCdAdTdAdGdAdCdTdGdTdA-3' | 43.0° C. | — |
| DNA (X) duplex | 5'-dTdAdCdAdGdXdCdTdAdTdGdT-3'<br>5'-dAdCdAdTdAdGdAdCdTdGdTdA-3' | 40.8° C. | -2.2° C. |

TABLE 13

Thermal Stability of TNA Modified Oligonucleotides. RNA (Y)

| Duplex | Sequence | Tm value | ΔTm |
|---|---|---|---|
| RNA-RNA control | 5'-UACAGUCUAUGU-3'<br>5'-ACAUAGACUGUA-3' | 52.3° C. | — |
| RNA (Y) duplex | 5'-UACAGUYUAUGU-3'<br>5'-ACAUAGACUGUA-3' | 47.1° C. | -5.2° C. |
| DNA-DNA control | 5'-dTdAdCdAdGdCdCd<br>TdAdTdGdT-3'<br>5'-dAdCdAdTdAdGdGd<br>CdTdGdTdA-3' | 48.3° C. | — |
| DNA(Y) duplex | 5'-dTdAdCdAdGYdCd<br>TdAdTdGdT-3'<br>5'-dAdCdAdTdAdGdG<br>dCdTdGdTdA-3' | 47.8° C. | -0.50° C. |

RT qPCR for Ttr mRNA quantification: Primary mouse hepatocytes (PMH) were cultured in Williams E Medium with 10% fetal bovine serum. Transfection of cells using RNAiMAX reagent was done as per the manufacturer's recommended protocol. Thus, cells were thawed immediately prior to transfection and then plated onto 384-well plates with a seed density of ~5000 cells/well. Pre-incubated lipid/siRNA complex (0.1 µL RNAiMax, siRNA, in 5 µL Opti-MEM for 15 min) was added to a 384-well collagen-coated plate (BioCoat; Corning) and cells were incubated for 20 h at 37° C. in an atmosphere of 5% $CO_2$. Eight 6-fold serial dilutions ranging from 10 to 0.036 nM were used to perform dose response experiments. Media was removed before washing and lysing the cells. Using Dynabeads mRNA isolation kit according to manufacturer's protocol, RNA was extracted and subsequently reverse-transcribed with the ABI high capacity cDNA reverse transcription kit. Quantification was done by real-time PCR, whereby the cDNA (2 µL) was added to a master mix that contained 0.5 µL mouse Gapdh TaqMan Probe, 0.5 µL Ttr TaqMan probes, and 5 µL Lightcycler 480 probe master mix per well in a 384-well 50 plate. Real-time PCR was accomplished in an ABI 7900HT RT-PCR system using the ΔΔCt (RQ) assay. Each duplex and concentration was tested in four biological replicates. To calculate relative fold change, real time data were analyzed using the ΔΔCt method and normalized to assays performed with cells transfected with 10 nM non-specific siRNA. IC50 values were calculated using a 4-parameter fit model using XLFit.

Figure 16:
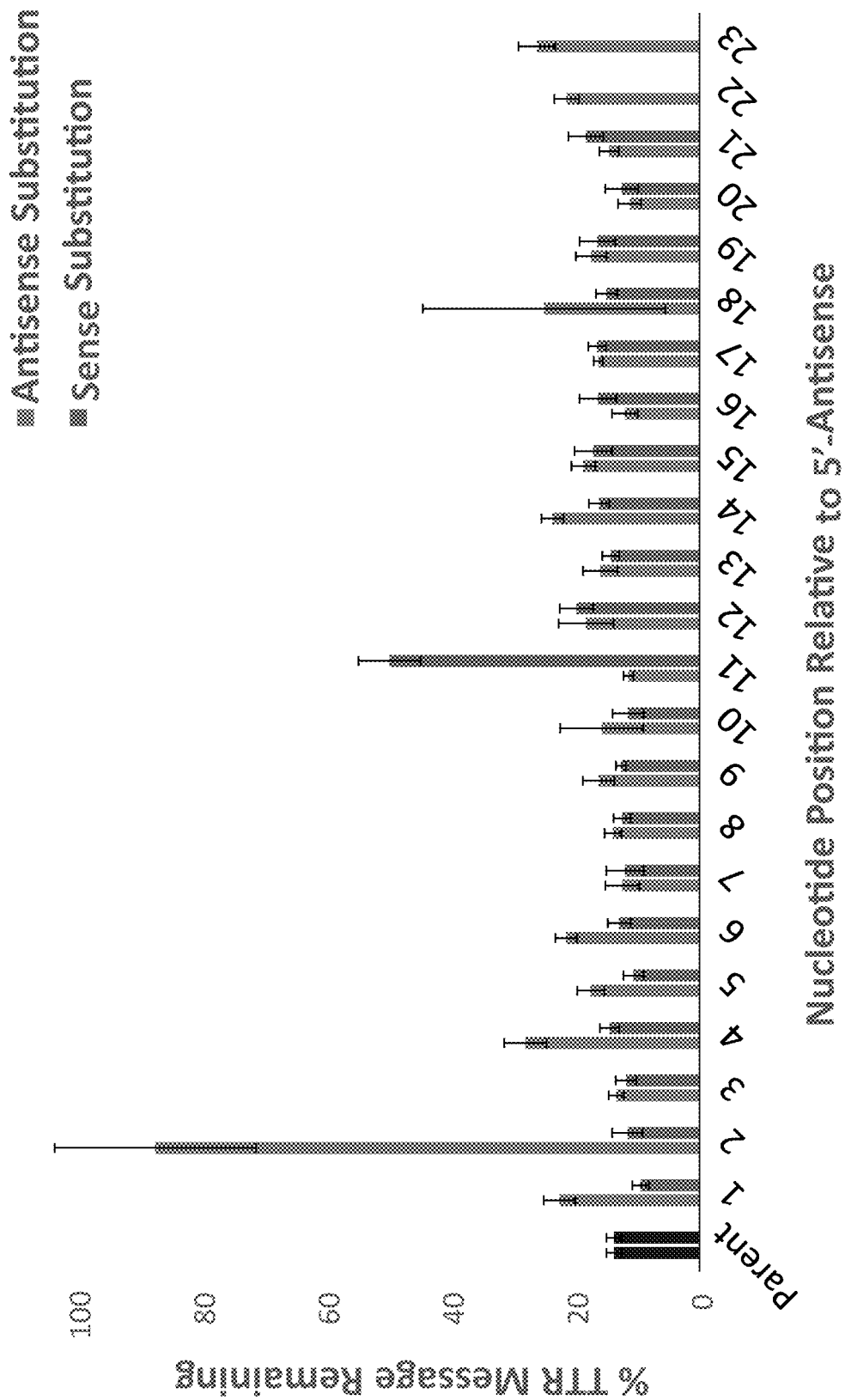
FIG. 16 is a graph showing the influence of single TNA Nucleotide incorporation on in vitro siRNA Activity.
Figure 17:
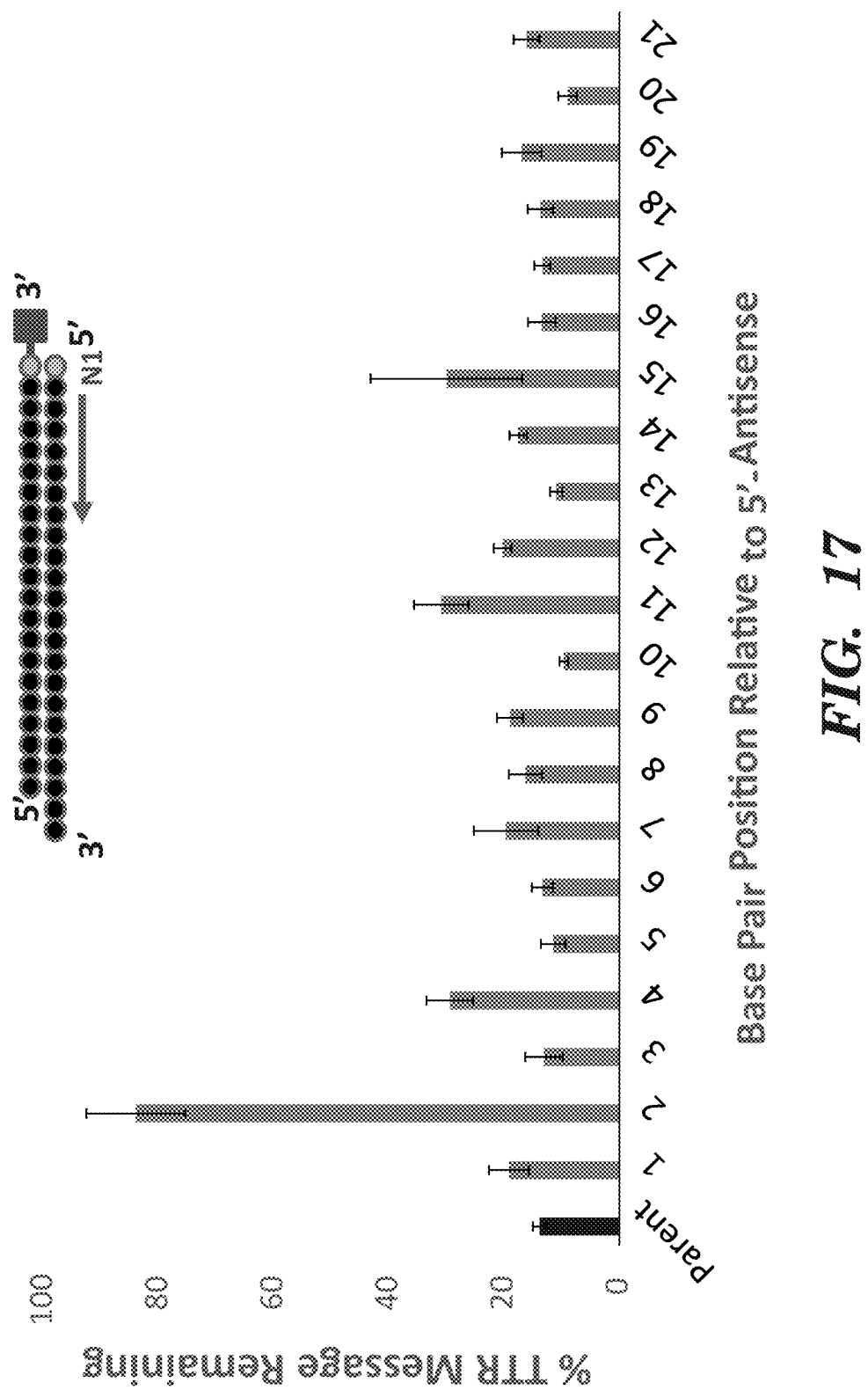
FIG. 17 is a graph showing the influence of single TNA Base Pair incorporation on in vitro siRNA Activity.
Figure 18:
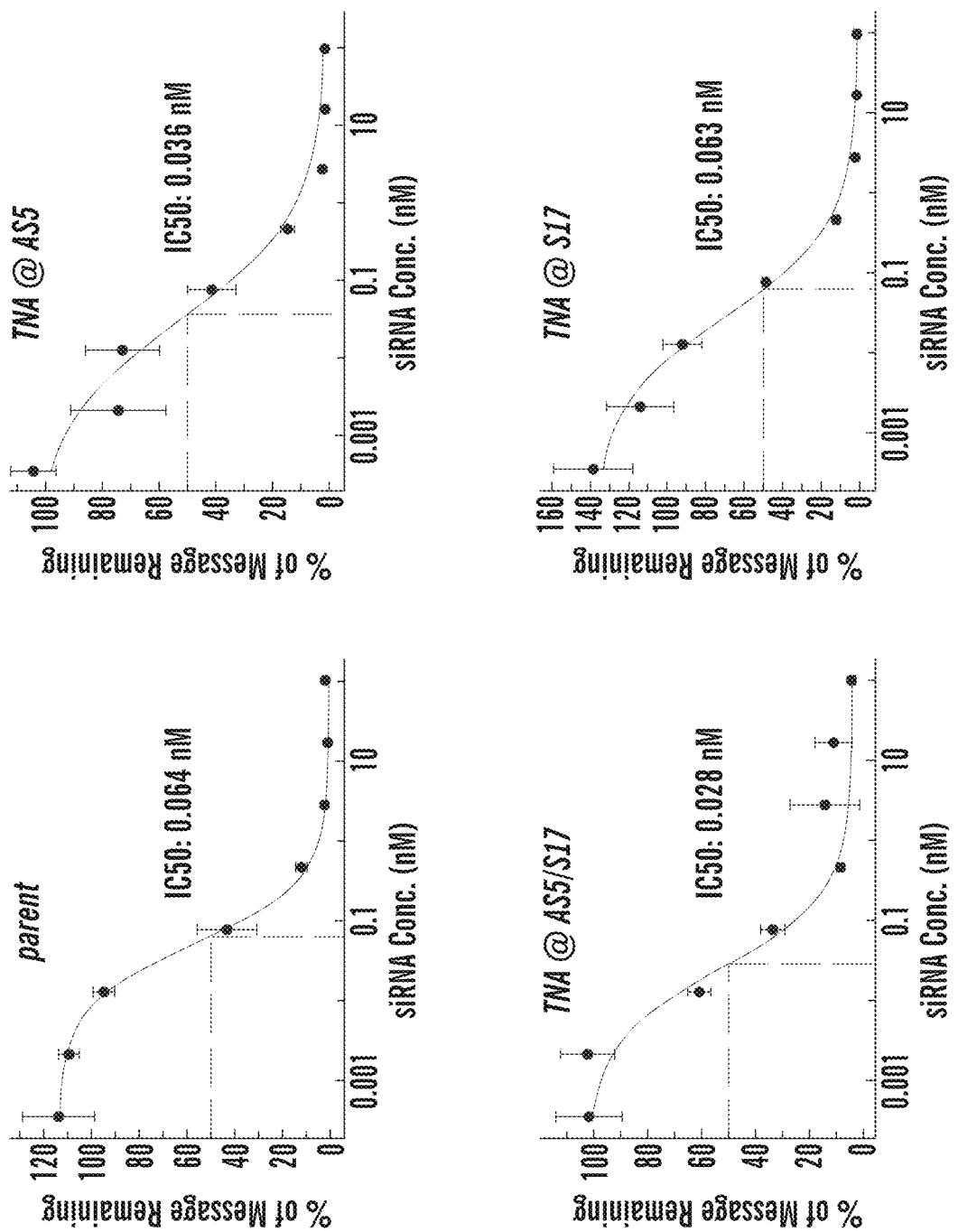
FIG. 18 are graphs showing dose response curves of an in vitro gene silencing assay.

FIG. 16 shows the influence of Single TNA Nucleotide incorporation on in vitro siRNA activity. FIG. 17 shows the influence of single TNA Base Pair Incorporation on in vitro siRNA activity. FIG. 18 shows dose response curves of in vitro Gene silencing assay.

In Vivo Screening: All studies were conducted using protocols consistent with local, state and federal regulations, as applicable, and approved by an Institutional Animal Care and Use Committee (IACUC). Animals received a single subscapular subcutaneous injection of 1 mg/kg siRNA, prepared as an injection volume of 10 µL/g in PBS. At the indicated time pre- or postdosing, animals were anesthetized with isofluorane and blood obtained via retroorbital bleed. TTR protein was quantified by ELISA from serum isolated from whole blood. ELISA was performed according to manufacturer protocol (ALPCO, 41-PALMS-E01) after a 3025-fold dilution of the serum samples. Data were normalized to pre-bleed TTR levels. All samples were assayed in duplicate and each data point is the average of all the mice within each cohort (n=3). Data were analyzed using a two-way ANOVA with a Tukey posthoc test for multiple comparison in GraphPad Prism.

Figure 19:
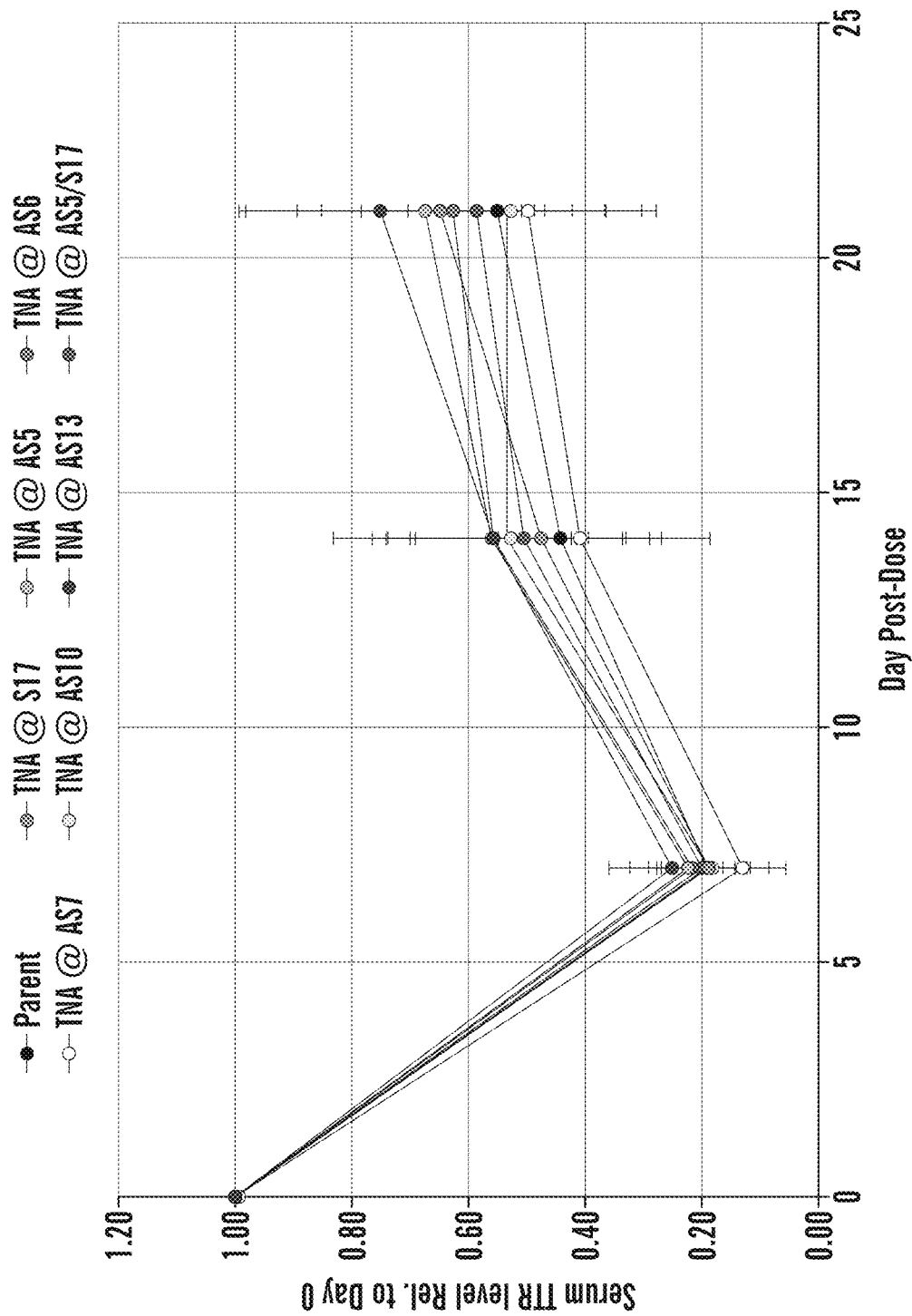
FIG. 19 and FIG. 20, are graphs showing the effet of in vivo gene silencing in mice using TNA-Modified siRNA duplexes on serum TTR Levels.
Figure 20:
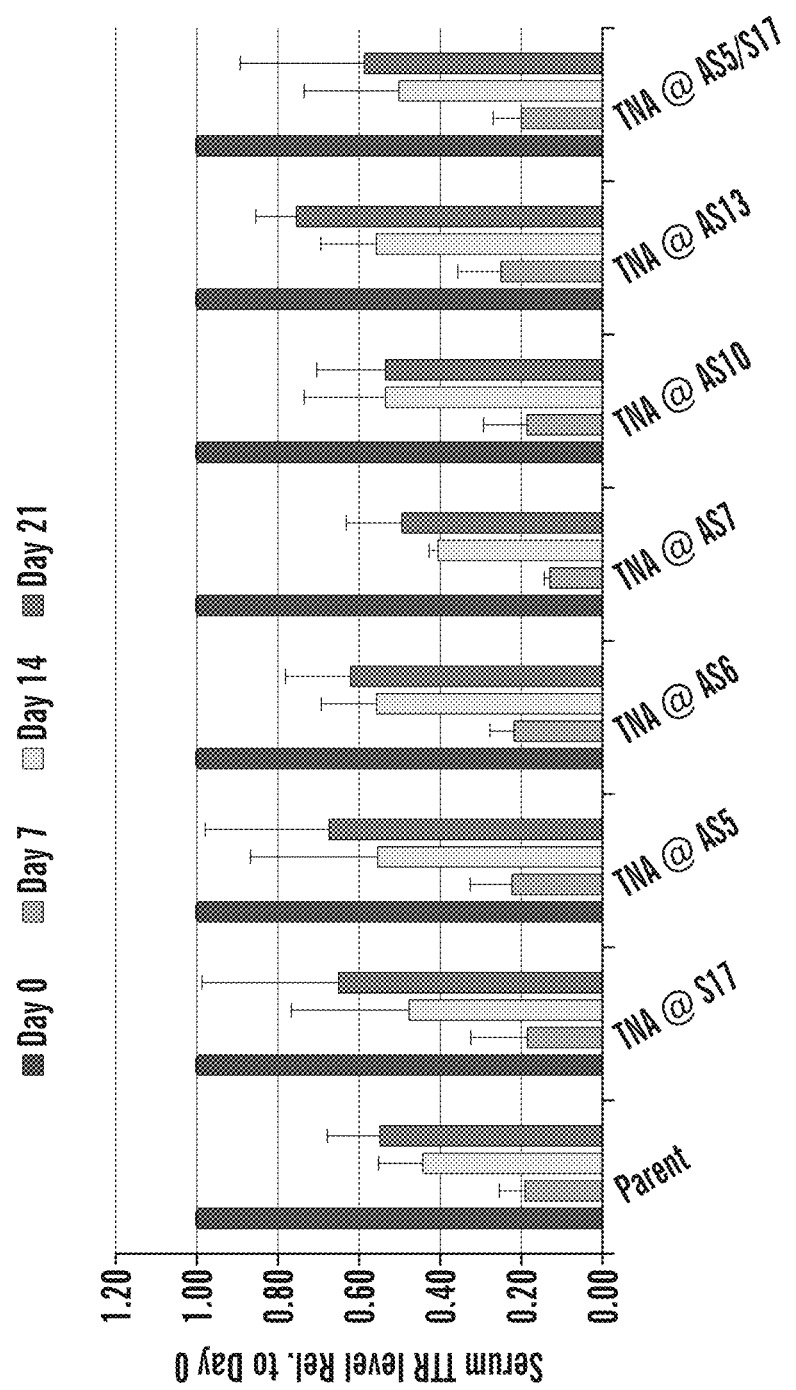

The results of in vivo screening are shown by FIGS. 19 and 20, showing the effet of in vivo gene silencing in mice Using TNA-Modified siRNA duplexes on serum TTR Levels. FIG. 19 is a line graph showing the results while FIG. 20 is a bar graph showing the results.

Figure 21:
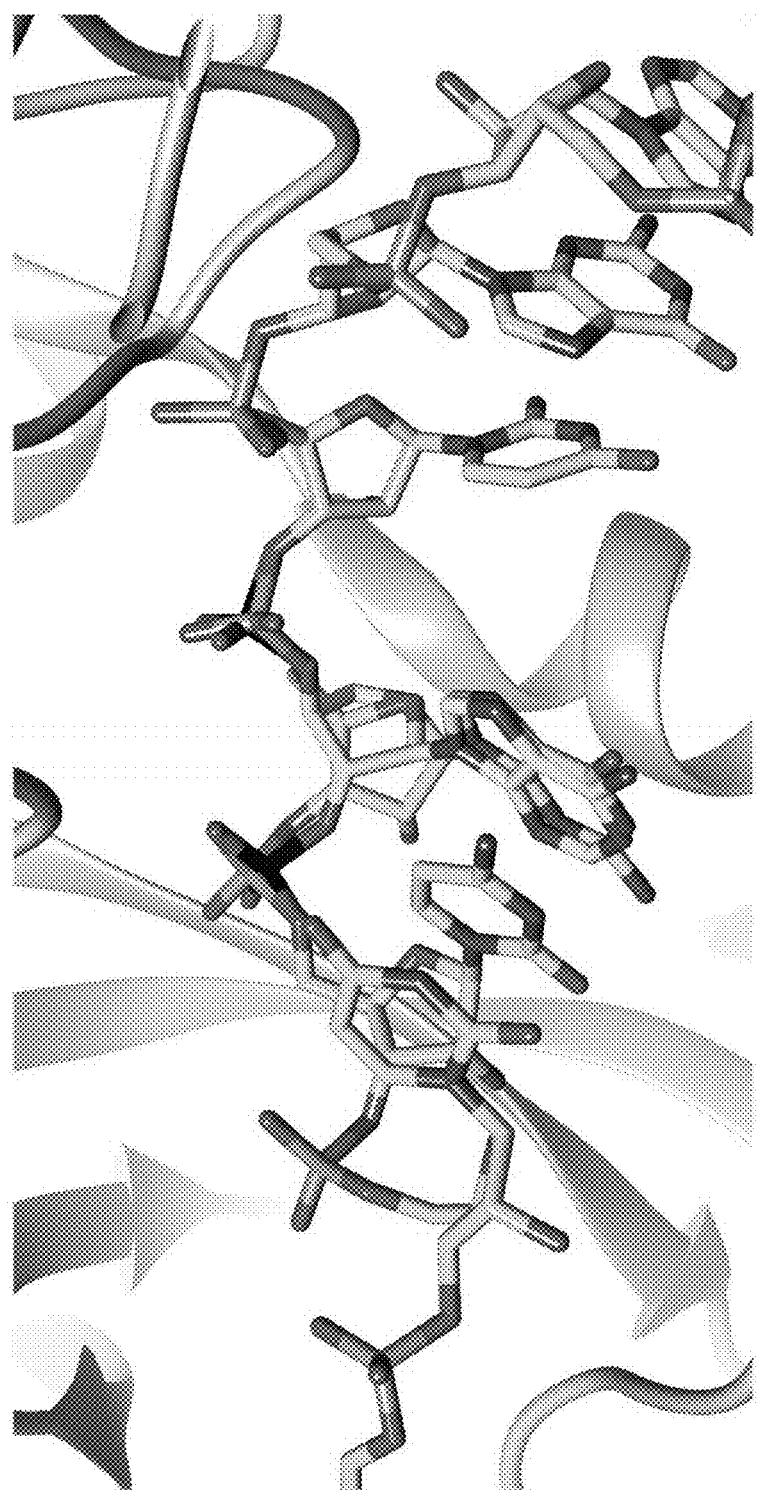
FIG. 21 shows a structural model of TNA Bound to human Argonaute-2 protein (hAgo2).

Single incorporation of T-TNA provides significant stabilization of a PO bond both at 3' and 5' ends, with ~5 fold and 10 fold improvements, respectively, when compared to a single PS bond. Tm studies using model sequences showed TNA showed minor destabilization in DNA and larger destabilization in RNA. The incorporation of single TNA nucleotides into the seed region of siRNA duplexes resulted in similar levels of knockdown of TTR mRNA in vitro. In addition, siRNA containing TNA base-pairs within the seed region demonstrated comparable knockdown in vitro to the corresponding parent siRNA. In vivo gene silencing correlated well with the in vitro results for duplexes containing a single TNA substitution and the structural model suggests that TNA is well accommodated in the duplex bound to Ago2. A structural model of TNA Bound to hAgo2 is shown by FIG. 21.

Figure 22:
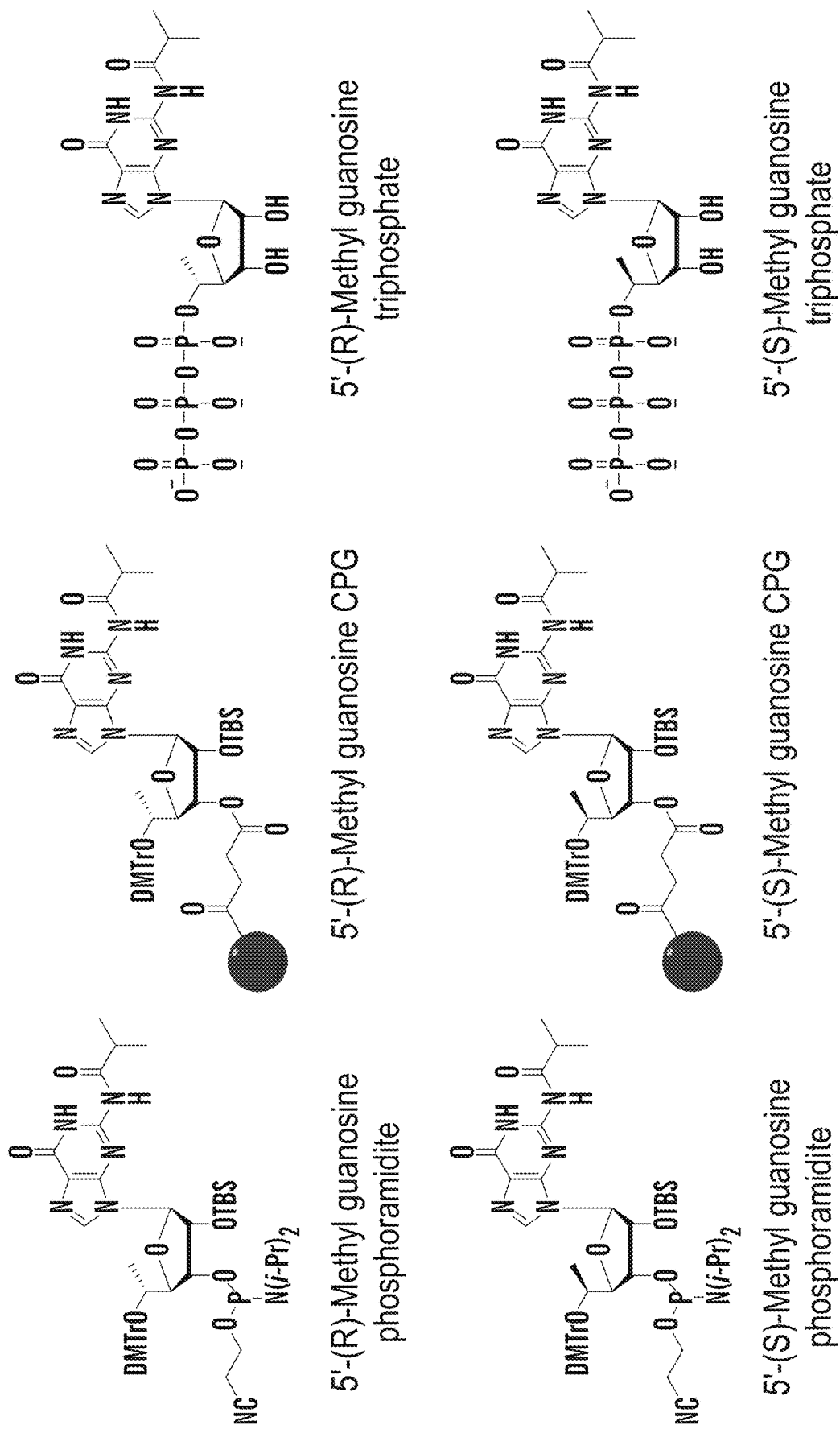
FIG. 22 shows the structure of various 5'-(R) and (S)-methyl guanosine building blocks.

Example 9: Oligonucleotide Building Blocks Containing 5'-(R) and (S)-Methyl Guanosine Chemical modification of the nucleoside monomers that constitute siRNA strands can modulate the potency, thermodynamic stability and can enhance biostability of these nucleic acid-based drugs. They can also potentially reduce the off-target effects of siRNAs. Stereoisomerically pure 5'-C-methyl 2'-deoxy and 2'-O-methyl and 2'-fluoro modified nucleosides were synthesized and these monomers were incorporated into siRNAs. The 5'-C-methyl pyrimidine nucleosides were prepared from the corresponding appropriately protected 2'-modified or 2'-deoxy nucleoside precursors [Kel'in, Alexander et al., *J. Org. Chem.* 2016, 81, 2261-2279]. The 2'-modified 5'-C-methyl pyrimidine-containing siRNAs had better exonuclease stability than the siRNAs with 5'-C-methyl deoxy residues. Herein is also reported the synthesis of 5'-(R)- and (S)-methyl guanosine building blocks. The 5'-C-methyl guanosine has been synthesized in the past by Beigelman et al. starting from L-rhamnose [Beigelman, Karpeisky, and Usman, *Nucleosides Nucleotides* 1995, 14, 901] as shown in scheme 37. In contrast to that approach, we started from guanosine, which was appropriately 3'-protected, oxidized, and methylated at the 5' position as shown in scheme 38. Pure (R) and (S) isomers were isolated and used to make the corresponding phosphoramidites, controlled-pore glass (CPG), and triphosphates. Various 5'-(R)- and (S)-methyl guanosine building blocks were synthesized by these methods as shown in FIG. 22. Chemical modification of the nucleoside monomers that constitute siRNA strands can modulate the potency.

Scheme 37

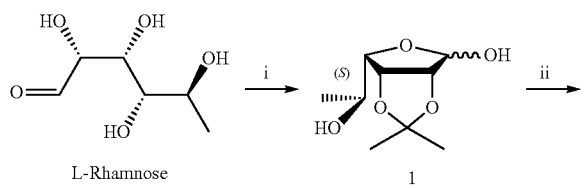

L-Rhamnose   1

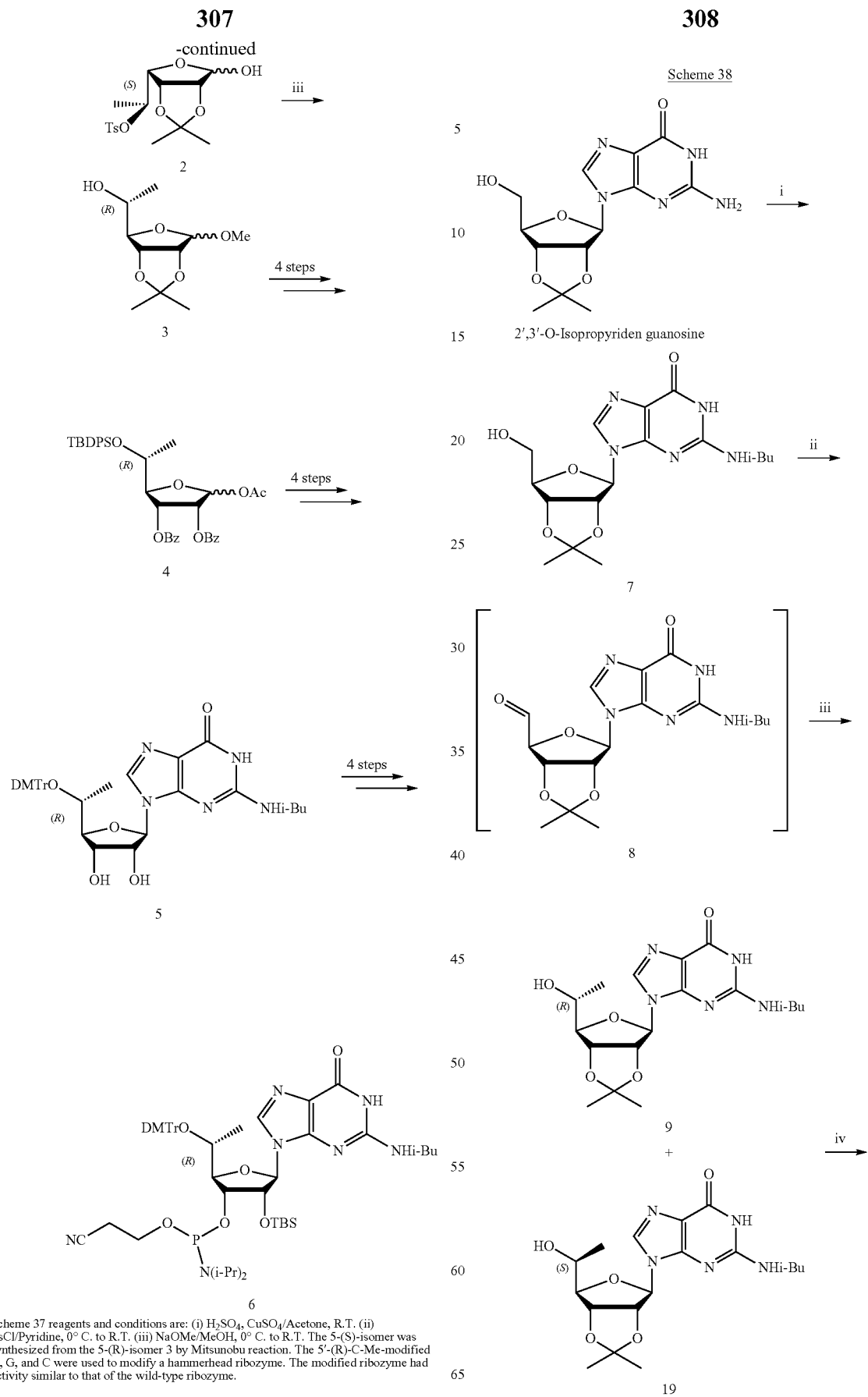

Scheme 38

2',3'-O-Isopropyriden guanosine

Scheme 37 reagents and conditions are: (i) H$_2$SO$_4$, CuSO$_4$/Acetone, R.T. (ii) TsCl/Pyridine, 0° C. to R.T. (iii) NaOMe/MeOH, 0° C. to R.T. The 5-(S)-isomer was synthesized from the 5-(R)-isomer 3 by Mitsunobu reaction. The 5'-(R)-C-Me-modified A, G, and C were used to modify a hammerhead ribozyme. The modified ribozyme had activity similar to that of the wild-type ribozyme.

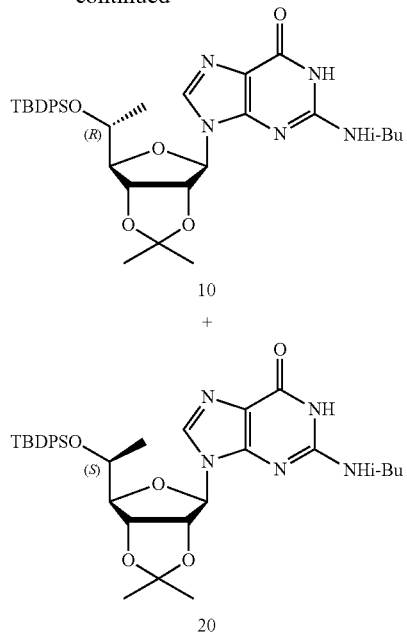

10

+

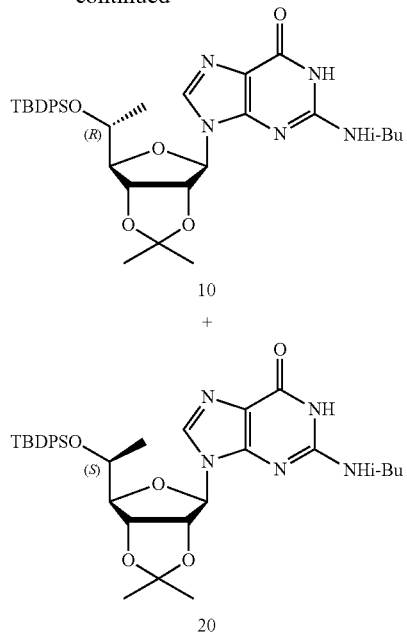

20

The reagenst and conditions used for Scheme 38 are: (i) 1) TMSCl/Pyridine, 0° C. to R.T., 1 h. 2) i-BuCl/Pyridine, 0° C. to R.T., overnight; 93%. (ii) Dess-Martin periodinane/DCM, 0° C. to R.T., 2 h. (iii) MeMgBr/DCM, 0° C., 30 min; 2 steps 33% as a mixture of 9 and 19. 9 and 19 are inseparable. (iv) TBDPSCl, Imidiazole/DMF, R.T., overnight; 17% for 10 and 23% for 20.

Figure 23:
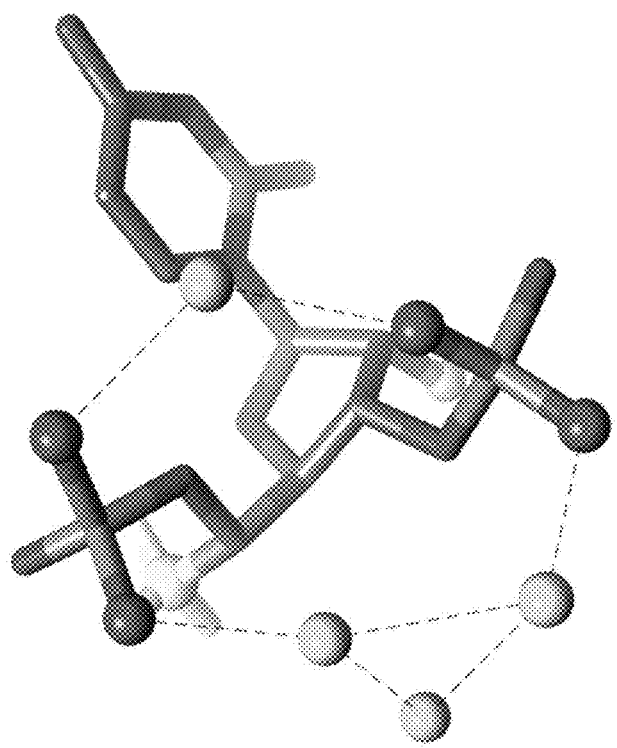
FIG. 23 shows structures of 5'-C-methyl-nucleoside within oligonucleotides.
Figure 23:
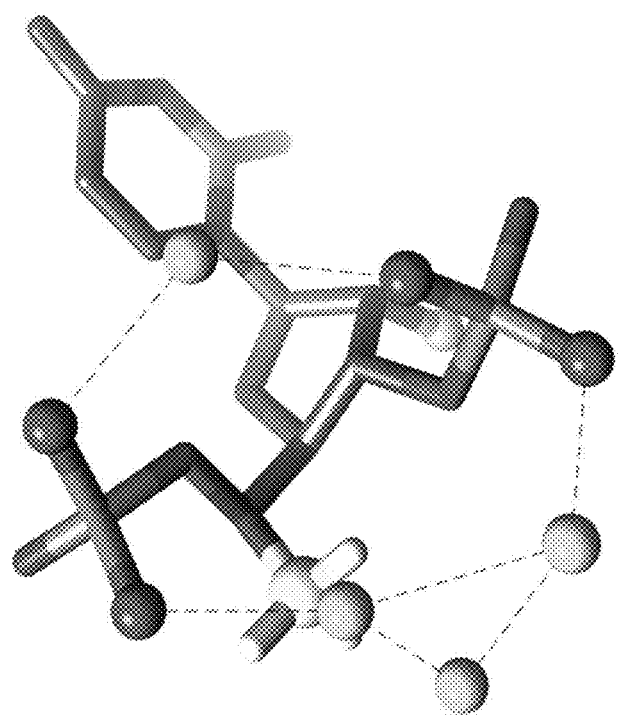

The structural result from molecular modeling of 5'-C-methyl-nucleoside within oligonucleotides is shown by FIG. 23. As shown in FIG. 23, The (R)-isomer juts into a polar region of negative electrostatic polarization that is heavily hydrated (cyan spheres) and interferes (flash) with phosphate hydration and engages in steric clash with the phosphate backbone (arrows). Perturbation due to the steric effect of the methyl group is more significant in the (R)-isomer than the (S)-isomer.

Example 10: Effect of the 5'-C-Methyl Guanosine Modification on S'-Nuclease and 3'-Nuclease Stability 5'-Nuclease Stability: To evaluate the 5'-exonuclease stability of enantiomerically pure (R)- and (S)-5'-C-methyl (C5'-Me) Guanosine substituted nucleosides a dT20 template sequence ("dT20" disclosed as SEQ ID NO: 1) was modified at the 5'-end with one modified nucleotide via PO or PS linkages (Table 14). The structures of the compounds are shown below with guanosine for comparison.

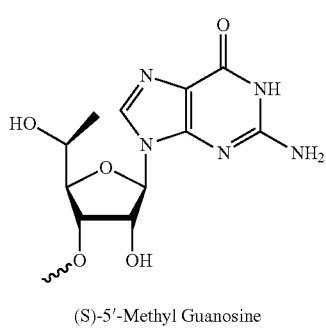

(S)-5'-Methyl Guanosine

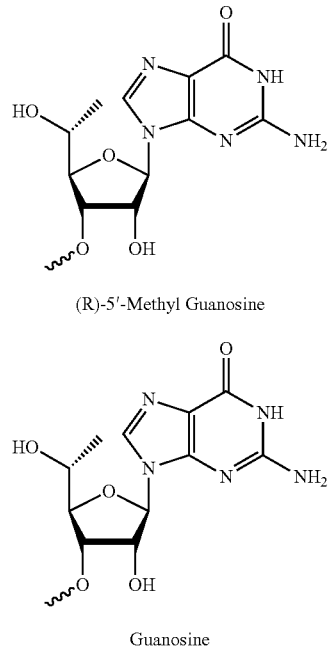

(R)-5'-Methyl Guanosine

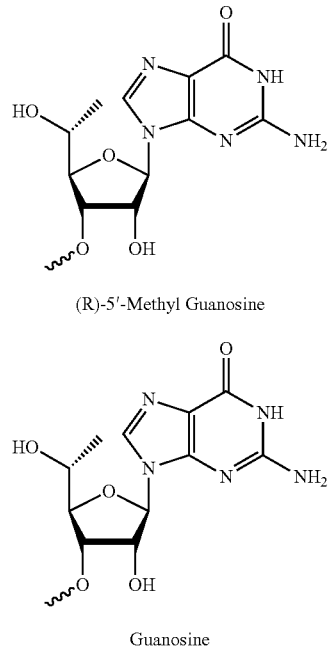

Guanosine

Figure 24A:
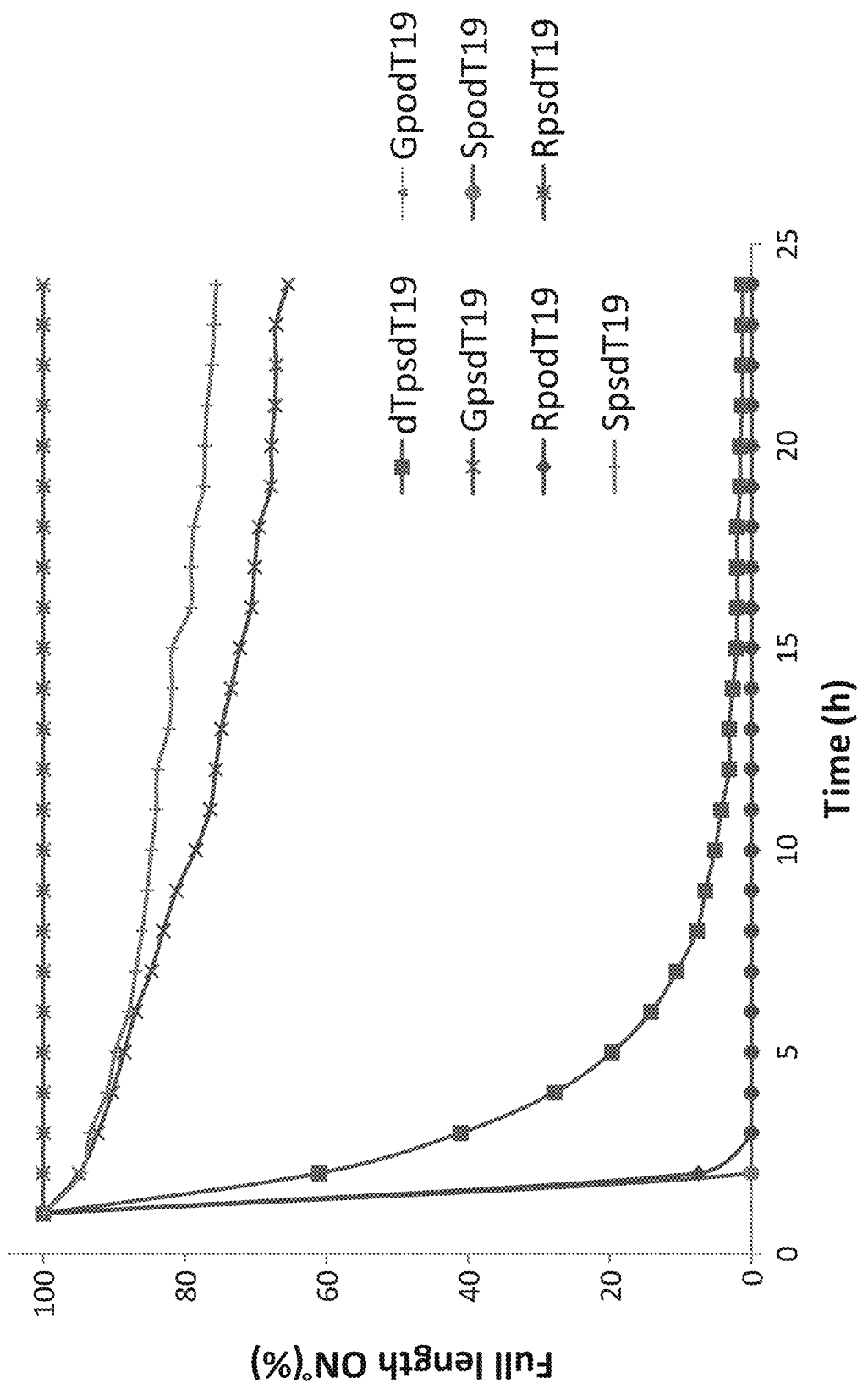
FIG. 24A and FIG. 24B are decay curves of dT20 modified ("dT20" disclosed as SEQ ID NO: 1) at the 5' end with Guanosine and (R) or (S)-5'-C-methyl Guanosine (C5'-MeG) with PO or PS linkages upon incubation with 5' exonucleases-phosphodiesterase-II as a function of time.
Figure 24B:
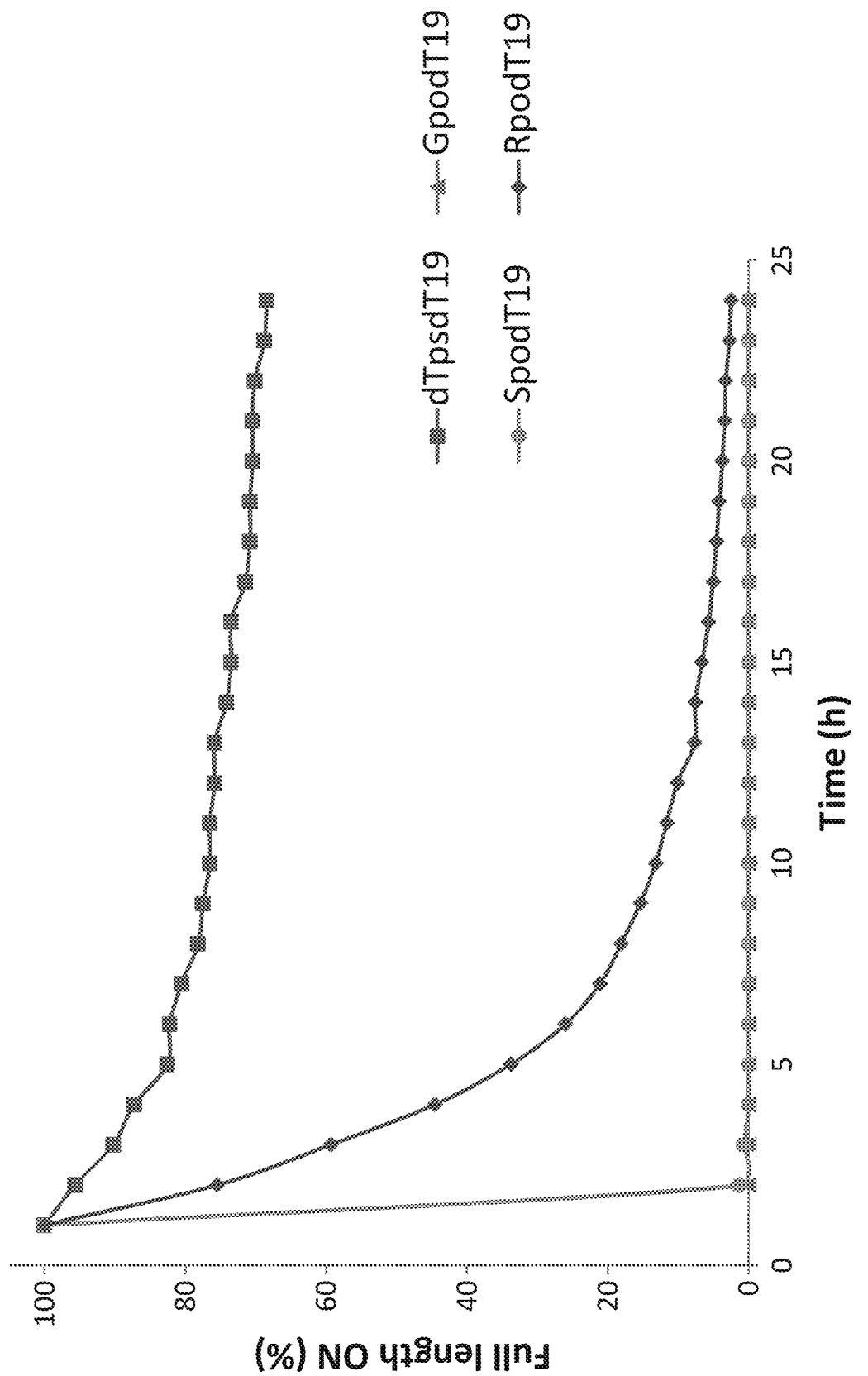

A dT20 template ("dT20" disclosed as SEQ ID NO: 1) having 5'end dT with PS linkages and 5'end Guanosine (G) with either PO or PS linkages were used as the control. ONs were incubated with Phosphodiesterase-II (500 mU/mL), and the half-life (T1/2) of each modified ON was determined by HPLC-based quantification of the full-length ON as a function of time. The results are summarized in Table 14 and HPLC stability profiles are depicted in FIGS. 24A and 24B showing decay curve of dT20 (SEQ ID NO: 1) modified at the 5' end with Guanosine and (R) or (S)-5'-C-methyl Guanosine (C5'-MeG) with PO or PS linkages upon incubation with 5' exonucleases-phosphodiesterase-II as a function of time. FIG. 24A is for the following conditions: a) enzyme conc. 500 mU/mL, Oligo Conc. 0.1 mg/mL, 50 mM NaOAc (pH-6.5): 10 Mm $MgCl_2$. FIG. 24B is for the following conditions: enzyme conc. 100 mU/mL, Oligo Conc. 0.1 mg/mL, 50 mM NaOAc (pH-6.5):10 mMMgCl2. The percentage full length ON is calculated by dividing the area under the peak corresponding to full length ON at a given time point by the full length at t=0 and multiplied by 100.

All the ONs attached via PO linkage to the 5'-end of dT19 (SEQ ID NO: 9) are found to be less stable compare to dT residue with PS linkages and were degraded by the first time point upon incubation with PE-II. All the ONs with Guanine at 5'end was more stable compare to dTpsdT19. ONs modified with a single (R)-5'Me-G linked by a PS does not showed any degradation till 24 h while(S)-5'-C-methyl-G were more stable compare to control G, with T1/2 values of 72 and 41 h, respectively. To find out the stability difference between the (R) and (S)-5'-C-methyl isomers linked through PO bond we carried out the similar experiment with reduced concentration of PE-II (100 mU/mL). The results are summarized in Table 14 and HPLC stability profiles are depicted in FIG. 24B. A similar trend was observed for (R)- and (S)-5'-C-Me-Guanosine and control G. The G and (S)-5'-C-methyl-G isomers were degraded by the first time point upon incubation with reduced conc of PE-II while the (R)-5'-C- methyl-G isomer was stable with T1/2 value 4.3 hr. The dTpsdT19 is most stable oligo at this reduced concentration with T1/2 value 53h.

TABLE 14

Half-lives ($T_{1/2}$) of 5'-End-Modified dT18-mer ("dT18" disclosed as SEQ ID NO: 2) in the Presence of Phosphodiesterase-H

| .Sr.No | Code | Sequence | $t_{1/2}$ (h) | $t_{1/2}$ (h) |
|---|---|---|---|---|
| 1 | dTpsdT19 | dTsdTdTdTd TdTdTdTdTd TdTdTdTdTd TdTdTdTdTd T | 4.0 | 52 |
| 2 | GpodT19 | GdTdTdTdTd TdTdTdTdTd TdTdTdTdTd TdTdTdTdT | <1 | <1 |
| 3 | SpodT19 | (G5m)dTdTd TdTdTdTdTd TdTdTdTdTd TdTdTdTdTd TdT | <1 | <1 |
| 4 | RpodT19 | (G5mR)dTdT dTdTdTdTdT dTdTdTdTdT dTdTdTdTdT dTdT | <1 | 4.3 |
| 6 | GpsdT19 | GsdTdTdTdT dTdTdTdTdT dTdTdTdTdT dTdTdTdTdT | 41 | |
| 7 | RpsdT19 | (G5mRs)dTd TdTdTdTdTd TdTdTdTdTd TdTdTdTdTd TdTdT | No degradation | |
| 8 | SpsdT19 | (G5ms)dTdT dTdTdTdTdT dTdTdTdTdT dTdTdTdTdT dTdT | 66 | |

(Table 14 discloses SEQ ID NOS 65-71, repectively, in order of appearance)

Figure 25A:
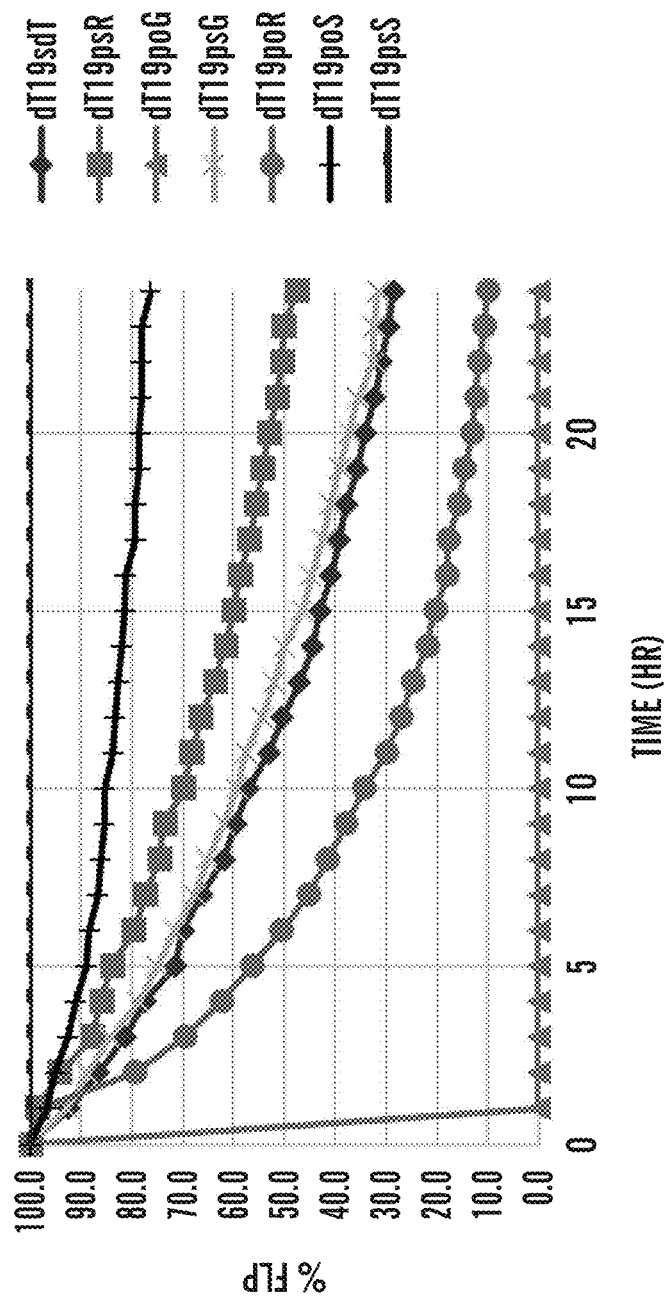
FIG. 25A and FIG. 25B show the decay cures of dT20 modified ("dT20" disclosed as SEQ ID NO: 1) at the 3' end with Guanosine and (R) or (S)-5'-C-methyl Guanosine (C5'-MeG) upon incubation with snake venom phosphodiesterase as a function of time.
Figure 25B:
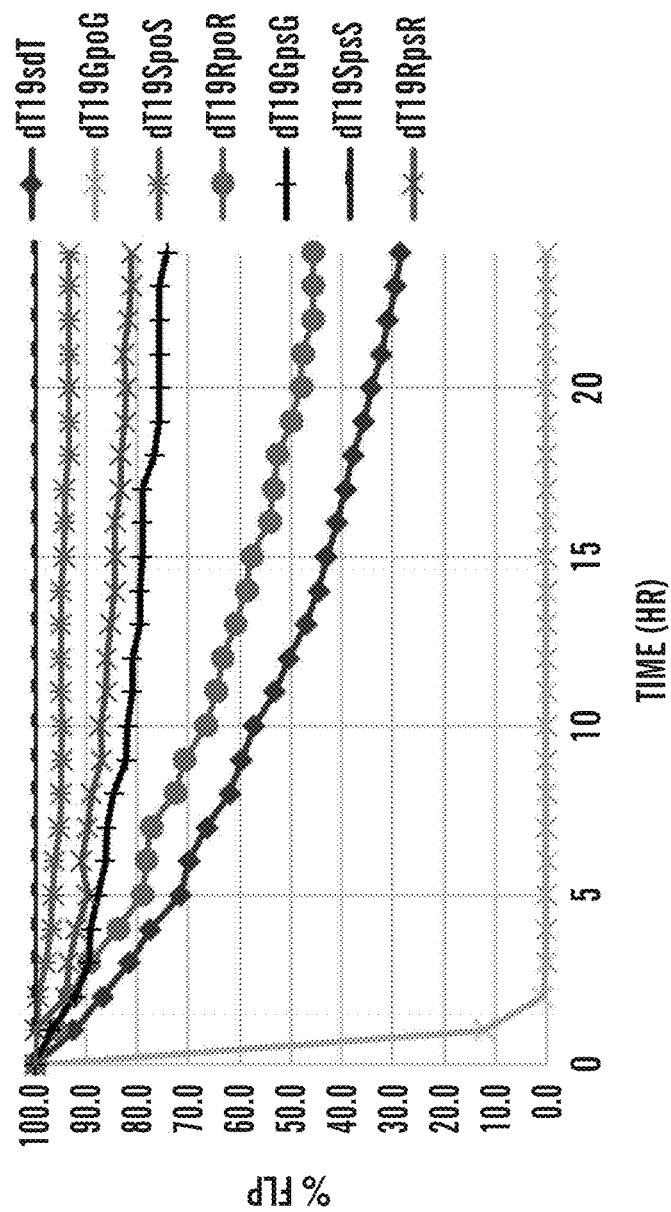

3'-Nuclease Stability: To evaluate the 3'-exonuclease stability of enantiomerically pure (R)- and (S)-5'-C-methyl (C5'-Me) Guanosine substituted nucleosides a dT20 template sequence ("dT20" disclosed as SEQ ID NO: 1) was modified at the 3'-end with either one or two modified nucleotides via PO or PS linkages (Table 14). A dT20 template ("dT20" disclosed as SEQ ID NO: 1) having 3'end dT with PS linkages and 3'end Guanosine (G) with either PO or PS linkages were used as the control. ONs were incubated with SVPD (Phosphodiesterase-I) (75 mU/mL) in presence of 50 mM Tris-HCl (pH-7.2): 10 mM $MgCl_2$, and the half-life (T1/2) of each modified ON was determined by HPLC-based quantification of the full-length ON as a function of time. The results are summarized in Table 14 and HPLC stability profiles are depicted in FIGS. 25A and 25B. FIGS. 25A and 25B show the HPLC stability profiles of dT20 modified ("dT20" disclosed as SEQ ID NO: 1) at the 3' end with Guanosine and (R) or (S)-5'-C-methyl Guanosine (C5'-MeG) upon incubation with snake venom phosphodiesterase as a function of time. FIG. 25A if for a single incorporation with PO or PS linkage between dT and modified nucleosides and FIG. 25B is for a double incorporation with PO and PS linkages between the two modified nucleosides.

Figure 26:
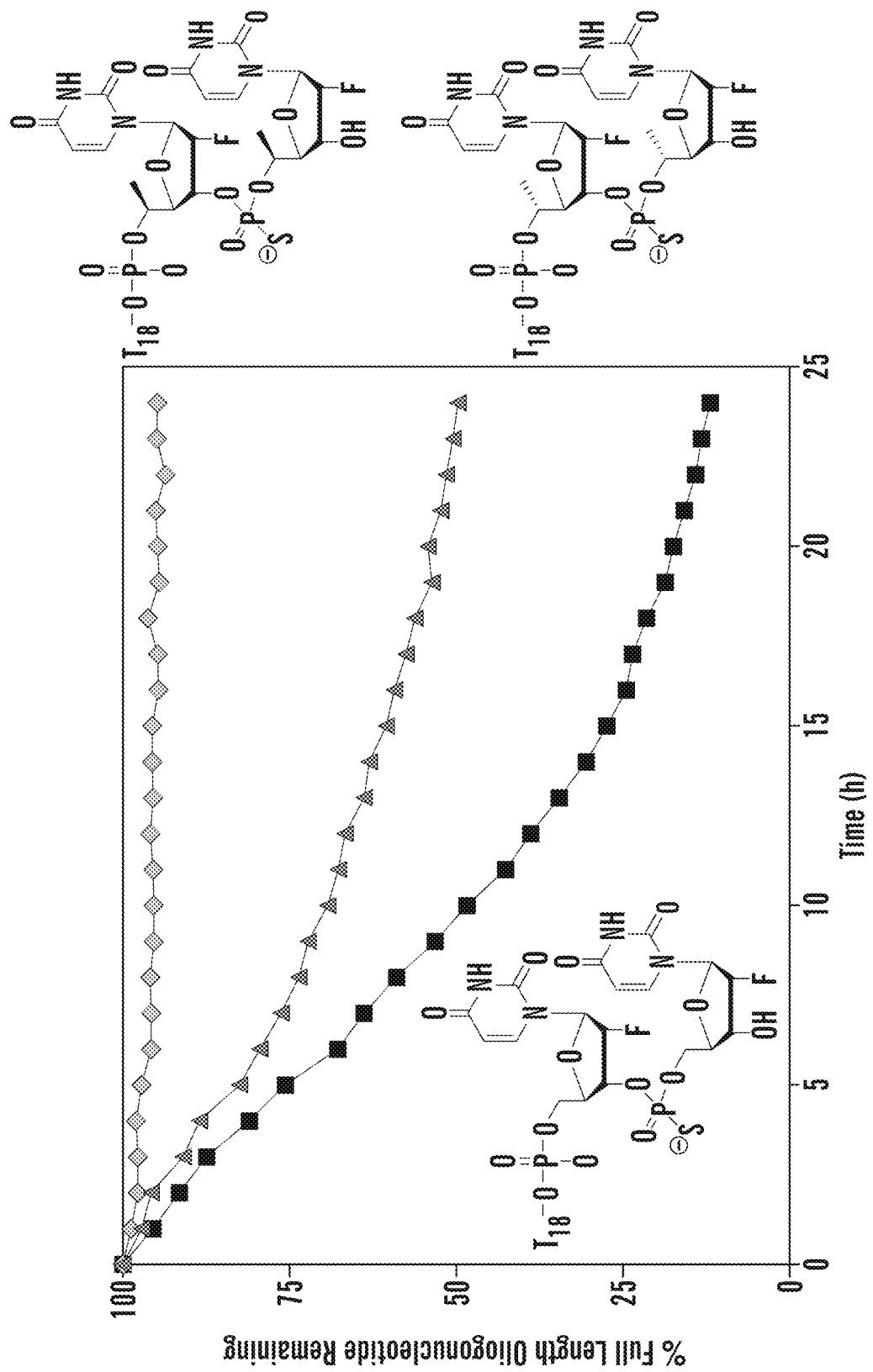
FIG. 26 is a plot showing the relative exonuclease stability of dT18 modified ("dTis" disclosed as SEQ ID NO: 2) at the 3' end with two 5'-(R)-C-Me-2'-F-U or 5'-(S)-C-Me-2'-F-U nucleotides.

Compared to dT20 (SEQ ID NO: 1) modified at the 3' end with 2'-F-U-2'-F-U, 5'-(S)-C-Me-2'-F-U and 5'-(R)-C-Me-2'-F-U imparted more resistant to 3'-exonuclease. The(S) isomer was more resistant than the (R) isomer [Kel'in, A. V.; Zlatev, I.; Harp, J.; Jayaraman, M.; Bisbe, A.; O'Shea, J.; Taneja, N.; Manoharan, R. M.; Khan, S.; Charisse, K.; Maier, M. A.; Egli, M.; Rajeev, K. G.; Manoharan, M. *The Journal of Organic Chemistry* 2016, 81, 2261]. 5'-(S)-C-Me-G, and 5'-(R)-C-Me-G were reported by Beigelman et al. and modified ribozyme activity was evaluated [Beigelman, L.; Karpeisky, A.; Usman, N. *Nucleosides and Nucleotides* 1995, 14, 901]. The utility of this modification in siRNA using guanine as an example was evaluated. FIG. 26 show the HPLC analysis results of $dT_{18}$ modified ("$dT_{18}$" disclosed as SEQ ID NO: 2) at the 3' end with two 5'-(R)-C-Me-2'-F-U or 5'-(S)-C-Me-2'-F-U nucleotides (structures shown below) upon incubation with snake venom phosphodiesterase as a function of time. There was a phosphorothioate (PS) linkage between dT and the modified nucleotides.

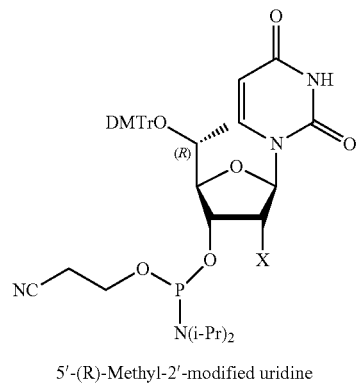

5'-(R)-Methyl-2'-modified uridine phorphoramidite

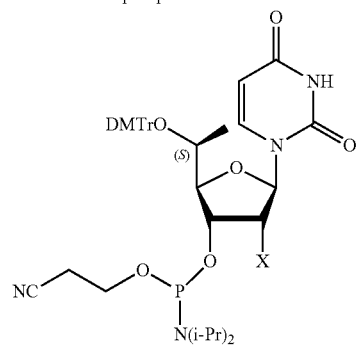

5'-(S)-Methyl-2'-modified uridine phorphoramidite

X = H, OMe, F

TABLE 15

| Sr.No | Code | Sequence | $t_{1/2}$ (h) |
|---|---|---|---|
| 1 | dT19psdT | dTdTdTdTdTdTd TdTdTdTdTdTdT dTdTdTdTsdT | 13.4 |

TABLE 15-continued

| Sr.No | Code | Sequence | t₁/₂ (h) |
|---|---|---|---|
| 2 | dT19poG | dTdTdTdTdTdTdTd TdTdTdTdTdTdTdT dTdTdTdTG | <1 |
| 3 | dT19poR | dTdTdTdTdTdTdTd TdTdTdTdTdTdTdT dTdTdTdT(G5mR) | 7.1 |
| 4 | dT19poS | dTdTdTdTdTdTdTd TdTdTdTdTdTdTdT dTdTdTdT(G5m) | 70.7 |
| 6 | dTpsG | dTdTdTdTdTdTdTd TdTdTdTdTdTdTdT dTdTdTdTsG | 14.4 |
| 7 | dT19psS | dTdTdTdTdTdTdTd TdTdTdTdTdTdTdT dTdTdTdTs(G5m) | No degradation |
| 8 | dT19PSR | dTdTdTdTdTdTdTd TdTdTdTdTdTdTdT dTdTdTdTs(G5mR) | 22.6 |
| 9 | dT19GpoG | dTdTdTdTdTdTdTd TdTdTdTdTdTdTdT dTdTdTGG | <1 |
| 10 | dT19RpoR | dTdTdTdTdTdTdTd TdTdTdTdTdTdTdT dTdTdT(G5mR)(G5 mR) | 20.8 |
| 11 | dT19SpoS | dTdTdTdTdTdTdTd TdTdTdTdTdTdTdT dTdTdT(G5m)(G5m) | 260 |
| 12 | dTGpsG | dTdTdTdTdTdTdTd TdTdTdTdTdTdTdT dTdTdTGsG | 65.5 |
| 13 | dT19SpsS | dTdTdTdTdTdTdTd TdTdTdTdTdTdTdT dTdTdT(G5mS) (G5m) | No degradation |
| 14 | dT19RPSR | dTdTdTdTdTdTdTd TdTdTdTdTdTdTdT dTdTdT(G5mRS)(G5 mR) | 89 |

(Table 15 discloses SEQ ID NOS 72-84, repectively, in order of appearance)

Building blocks derived from specific (R)-isomer and (S)-isomer intermediates: Scheme 39 shows Building blocks derived from (R)-isomer intermediate 10 and (S)-isomer intermediate 20. The reagents and conditions used in the scheme are: (i) 80% aq. TFA/DCM, 0° C. to R.T., overnight; 83% for 11, 70% for 21. (ii) Bz₂O, DMAP/Pyridine, R.T., overnight; 99% fro 12, 22. (iii) 1 M TBAF in THF/THF, R.T., overnight; 87% for 13, 94% for 23. (iv) DMTrCl, AgNO₃/Pyridine-THF, R.T., overnight; 98% for 14, 98% for 24. (v) 1 M NaOH in H₂O/THF-MeOH—H₂O, 0° C., 30 min; 96% for 15, 25. (vi) TBSCl, AgNO₃/THF-Pyridine, R.T., overnight; 50% for 16, 53% for 26. (vii) i-Pr₂NP(Cl) O(CH₂)₂CN, DIPEA, 1-Methylimidazole/DCM, R.T., 2 h; 88% for 17, 65% for 27. (viii) 1) Succinic anhydride, DMAP/DCM, R.T., overnight. 2) LCAA-CPG (pore size 500 Å NH₂, 171 µmol/g), HBTU, DIPEA/DMF, R.T., overnight. 3) Ac₂O/Pyridine, R.T., overnight; loading: 70 µmol/g for 18, 97 µmol/g for 28. Table 15 gives estimated percentages of C3'-endo conformers based on ¹H-NMR ³$J_{H-H}$ coupling constants calculated as 100-10×³$J_{H1'-H2'}$.

TABLE 16 estimated percentages of C3'-endo conformers.

| | ³$J_{H1'-H2'}$ (Hz) | % N (C3'-endo) |
|---|---|---|
| 11 | 6.60 | ~30 |
| 21 | 5.30 | ~50 |

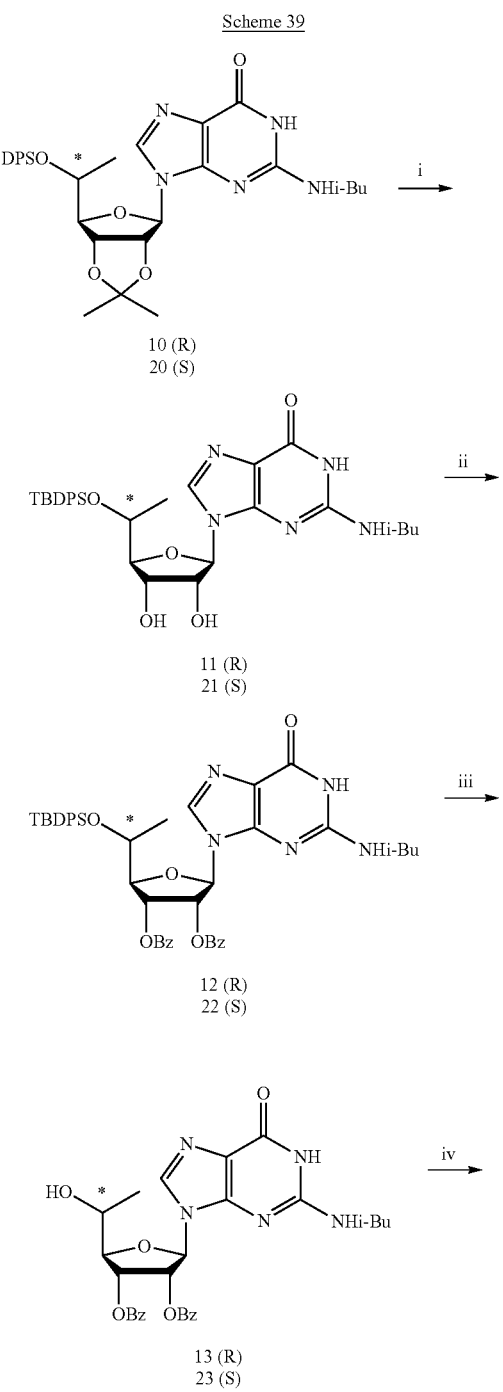

Scheme 39

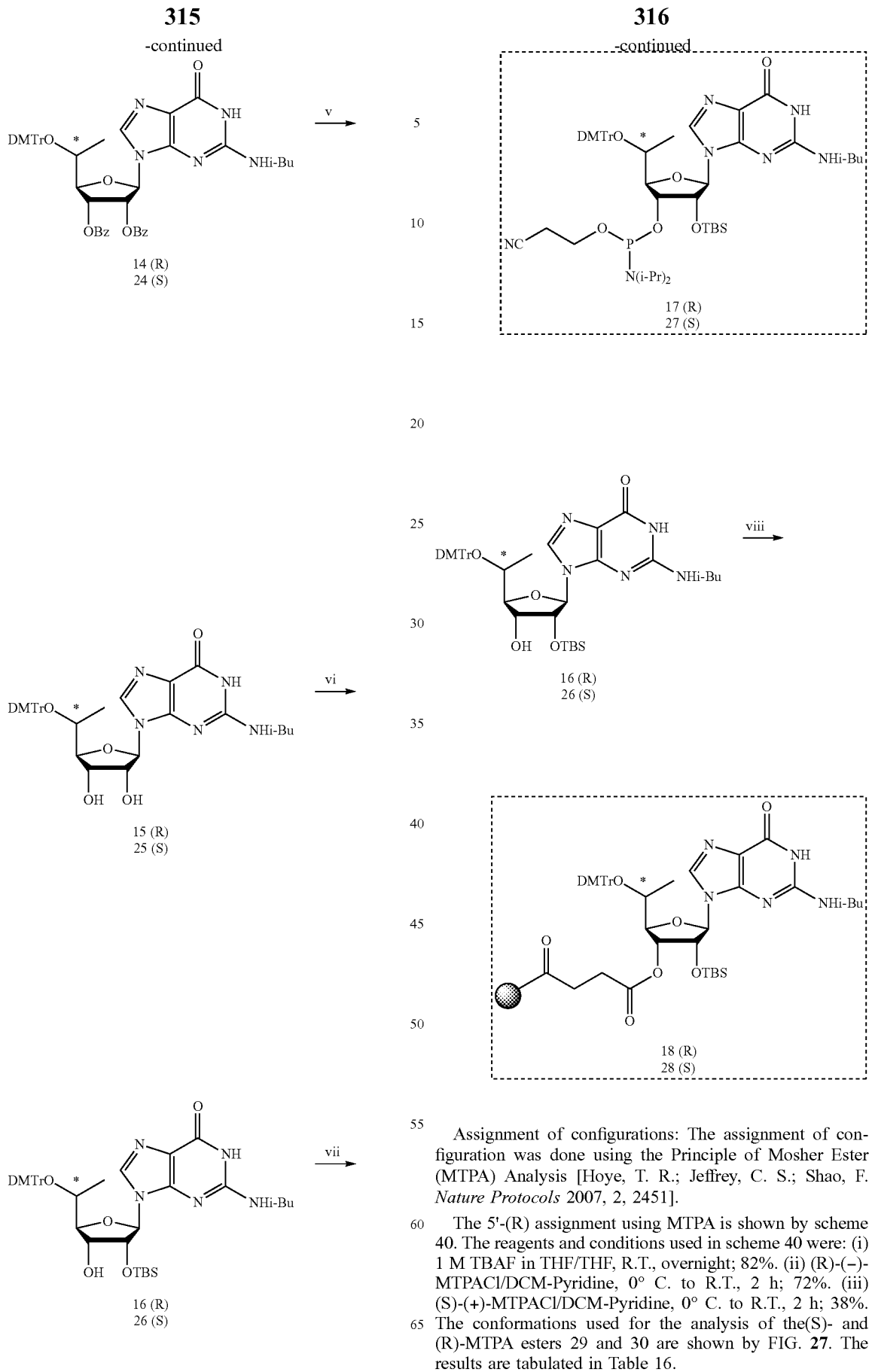

Assignment of configurations: The assignment of configuration was done using the Principle of Mosher Ester (MTPA) Analysis [Hoye, T. R.; Jeffrey, C. S.; Shao, F. *Nature Protocols* 2007, 2, 2451].

The 5'-(R) assignment using MTPA is shown by scheme 40. The reagents and conditions used in scheme 40 were: (i) 1 M TBAF in THF/THF, R.T., overnight; 82%. (ii) (R)-(−)-MTPACl/DCM-Pyridine, 0° C. to R.T., 2 h; 72%. (iii) (S)-(+)-MTPACl/DCM-Pyridine, 0° C. to R.T., 2 h; 38%. The conformations used for the analysis of the(S)- and (R)-MTPA esters 29 and 30 are shown by FIG. 27. The results are tabulated in Table 16.

Scheme 40
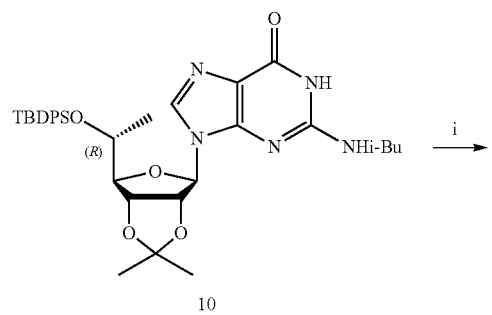
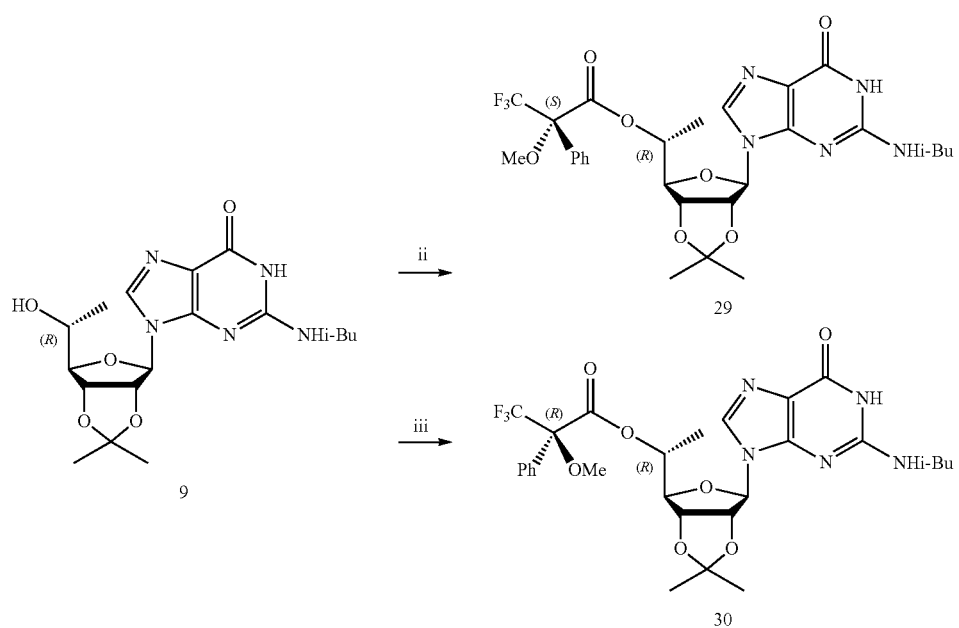
TABLE 17
Dd$^{SR}$ data for the (S)- and (R)-MTPA esters 29 and 30
| | 29 | 30 | Dd$^{SR}$ (=d$_S$ − d$_R$) | |
|---|---|---|---|---|
| | d (S)-Mosher ester | d (R)-Mosher ester | ppm | Hz (400 MHz) |
| 3'H | 4.98 | 5.12 | −0.14 | −56 |
| 4'H | 4.03 | 4.09 | −0.06 | −24 |
| 1'H | 6.02 | 6.07 | −0.05 | −20 |
| 2'H | 5.35 | 5.37 | −0.02 | −8 |
| 5'H | 5.24 | 5.24 | 0 | 0 |
| 5'Me | 1.23 | 1.13 | 0.1 | 40 |
The 5'-(S) assignment using MTPA is shown by scheme 41. The reagents and conditions used in scheme 41 were: (i)

1 M TBAF in THF/THF, R.T., overnight; 78%. (ii) (R)-(−)-MTPACl/DCM-Pyridine, 0° C. to R.T., 2 h; 31%. (iii) (S)-(+)-MTPACl/DCM-Pyridine, 0° C. to R.T., 2 h; 51%. The conformations used for the analysis of the(S)- and (R)-MTPA esters 31 and 32 are shown by FIG. 28. The results are tabulated in Table 17.

2013, 21, 722.]. The reagents and conditions for scheme 42 were: (i)-(iii) were performed on ABI-394 synthesizer following Table 19. (iv) 1) NH$_4$OH/EtOH, R.T., overnight. 2) 1 M TBAF/THF, R.T., overnight. 3) AMA/H$_2$O, R.T., overnight.; 28% for 34 and 39% for 38. Table 18 lists the estimated percentages of C3'-endo conformers based on $^1$H-NMR $^3J_{H-H}$ coupling constants calculated as $100-10\times^3J_{H1'-H2'}$. Table 19 lists ABI-394 protocol.

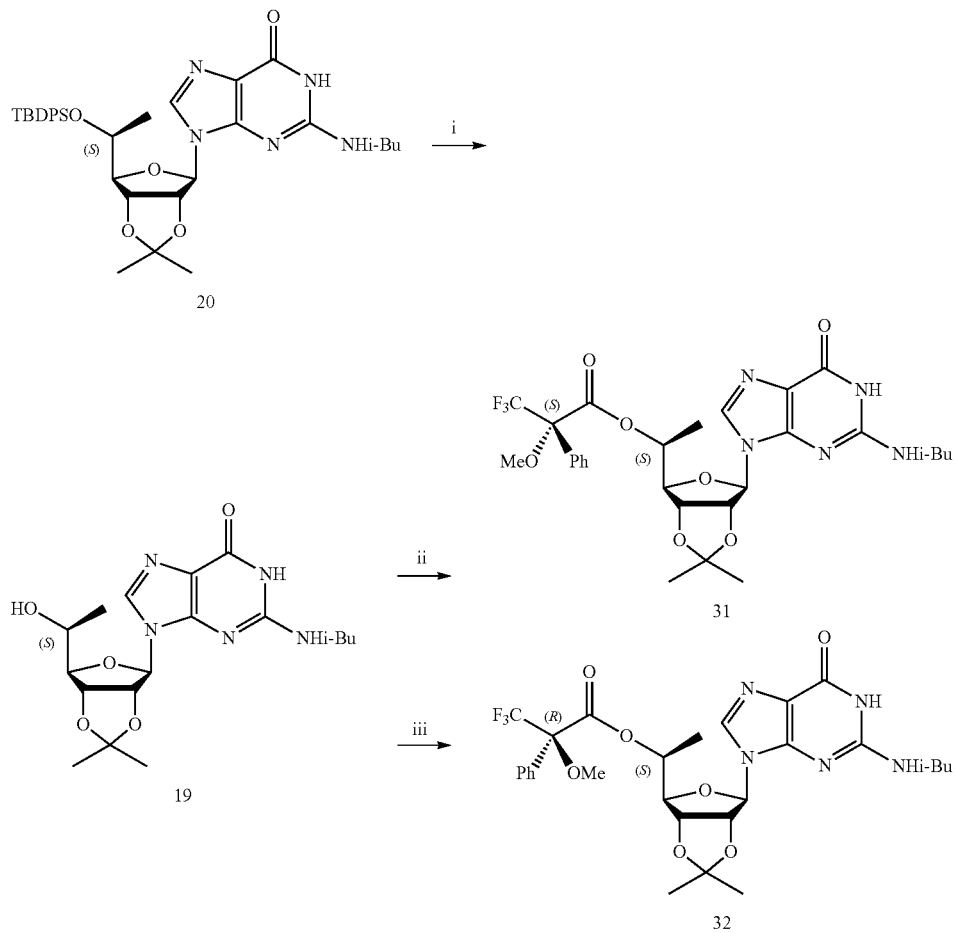

Scheme 41

TABLE 18

Dd$^{SR}$ data data for the (S)- and (R)-MTPA esters 31 and 32.

| | 31 | 32 | Dd$^{SR}$ (=d$_S$ − d$_R$) | |
|---|---|---|---|---|
| | d (S)-Mosher ester | d (R)-Mosher ester | ppm | Hz (400 MHz) |
| 3'H | 5.24 | 4.80 | 0.44 | 176 |
| 4'H | 4.10 | 4.13 | −0.03 | −12 |
| 1'H | 6.19 | 6.03 | 0.16 | 64 |
| 2'H | 5.33 | 5.08 | 0.25 | 100 |
| 5'H | 5.33 | 5.29 | 0.04 | 16 |
| 5'Me | 1.26 | 1.35 | −0.09 | −36 |

Example 11: Evaluation of (R)- and/or (S)-Isomers as RNA Polymerase Substrates

Triphosphate synthesis: Triphosphates were synthesized as shown by Scheme 42 [Zlatev, I.; Lackey, J. G.; Zhang, L.; Dell, A.; McRae, K.; Shaikh, S.; Duncan, R. G.; Rajeev, K. G.; Manoharan, M. *Bioorganic & Medicinal Chemistry*

TABLE 19

Estimated percentages of C3'-endo conformers

| | $^3J_{H1'-H2'}$ (Hz) | % N (C3'-endo) |
|---|---|---|
| 34 | 7.04 | ~30 |
| 38 | 6.08 | ~40 |

TABLE 20

ABI-394 protocol

| Reaction | Reagent | Delivery time (sec) | Wait time (sec) |
| --- | --- | --- | --- |
| i (1) | 1M Diphenyl phosphite/Pyridine | 30 + 10 × 2 | 150 × 2 + 300 |
| i (2) | 0.1M TEAB/$H_2O$—$CH_3CN$ | 30 + 10 × 5 | 60 × 2 + 450 × 4 |
| ii | 1M Imidazole, 1M BSA/$CBrCl_3$—$CH_3CN$—$NEt_3$ | 30 + 10 × 6 | 60 × 2 + 1800 × 5 |
| iii | 0.25M Tributylammonium pyrophosphate/DMF-ACN | 30 × 2 + 15 × 2 | 300 × 4 + 18000 |

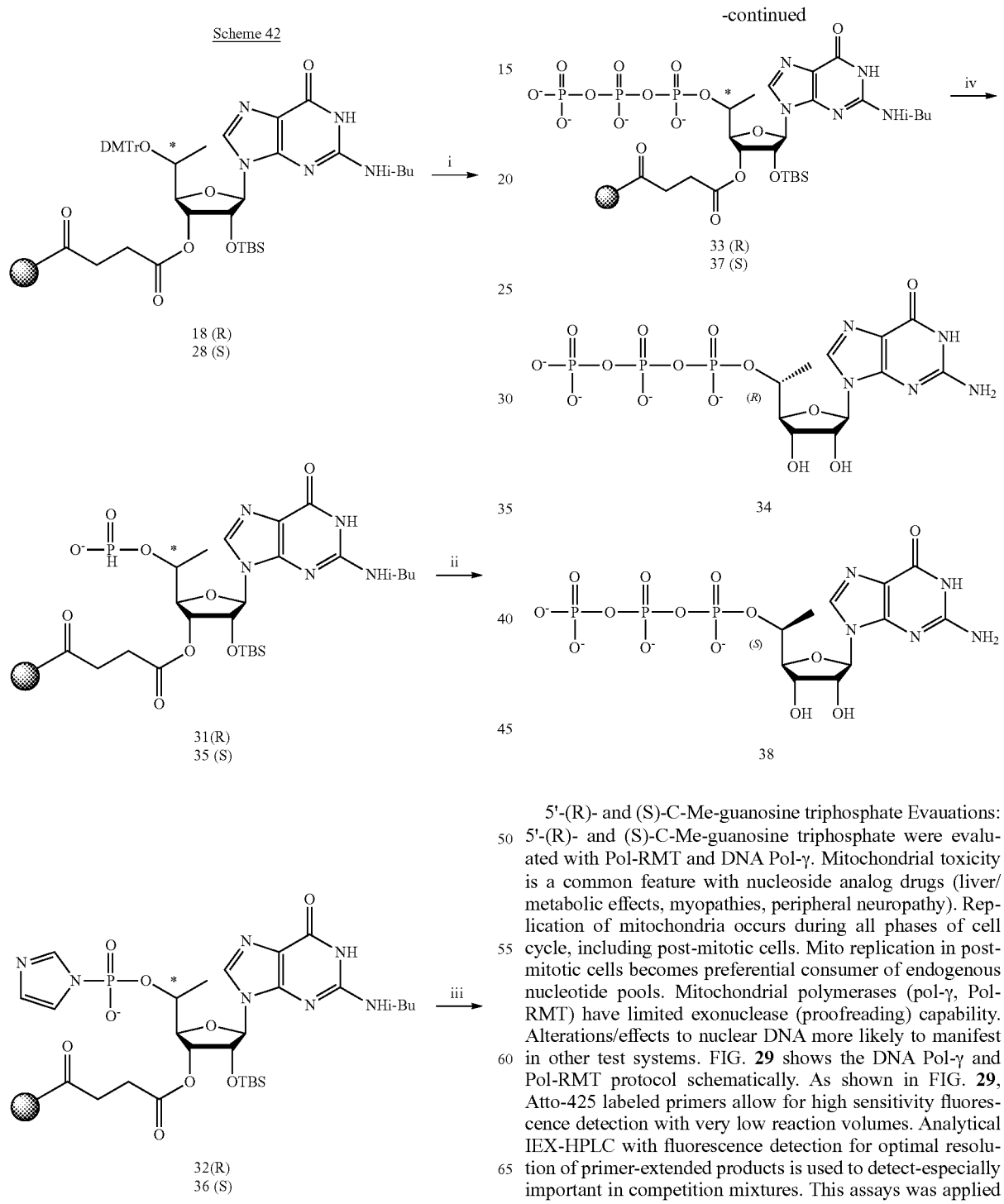

5'-(R)- and (S)-C-Me-guanosine triphosphate Evauations:

5'-(R)- and (S)-C-Me-guanosine triphosphate were evaluated with Pol-RMT and DNA Pol-γ. Mitochondrial toxicity is a common feature with nucleoside analog drugs (liver/metabolic effects, myopathies, peripheral neuropathy). Replication of mitochondria occurs during all phases of cell cycle, including post-mitotic cells. Mito replication in post-mitotic cells becomes preferential consumer of endogenous nucleotide pools. Mitochondrial polymerases (pol-γ, Pol-RMT) have limited exonuclease (proofreading) capability. Alterations/effects to nuclear DNA more likely to manifest in other test systems. FIG. 29 shows the DNA Pol-γ and Pol-RMT protocol schematically. As shown in FIG. 29, Atto-425 labeled primers allow for high sensitivity fluorescence detection with very low reaction volumes. Analytical IEX-HPLC with fluorescence detection for optimal resolution of primer-extended products is used to detect-especially important in competition mixtures. This assays was applied for the assessment of incorporation efficiencies.

Figure 30:
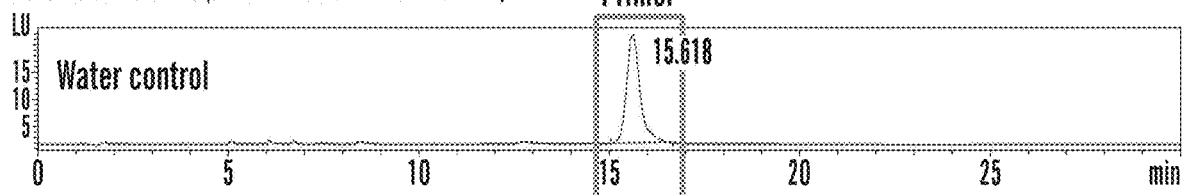
FIG. 30 shows the incorporation assay results by Pol-RMT.
Figure 30:
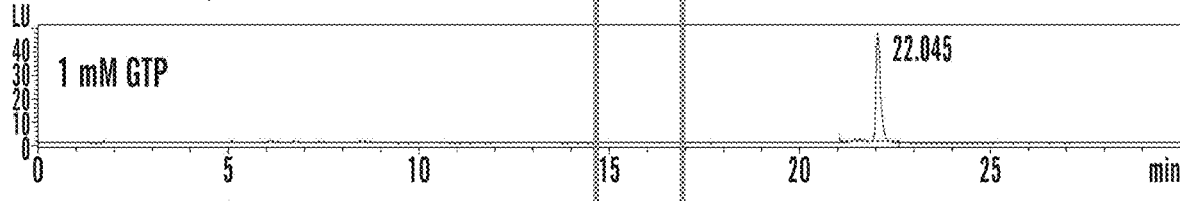
Figure 30:
Figure 30:
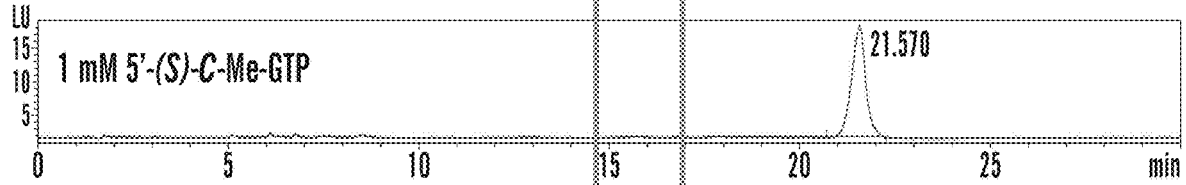
Figure 30:
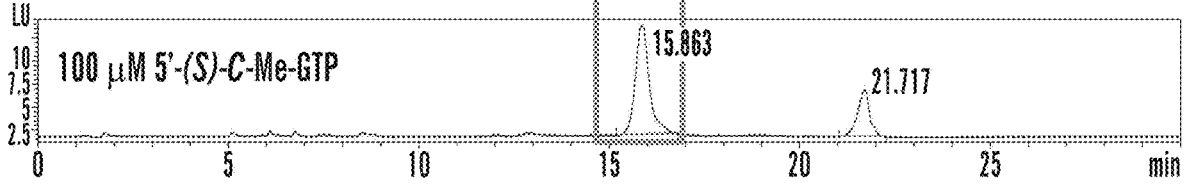
Figure 30:
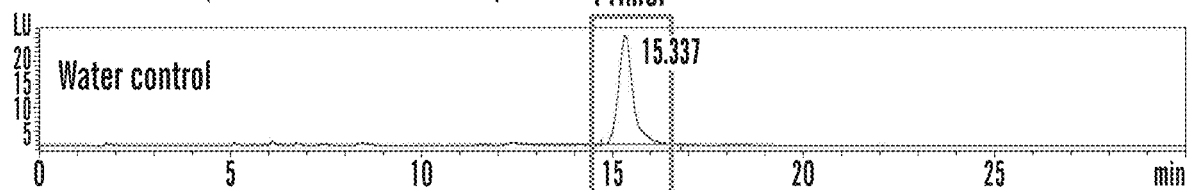
Figure 30:
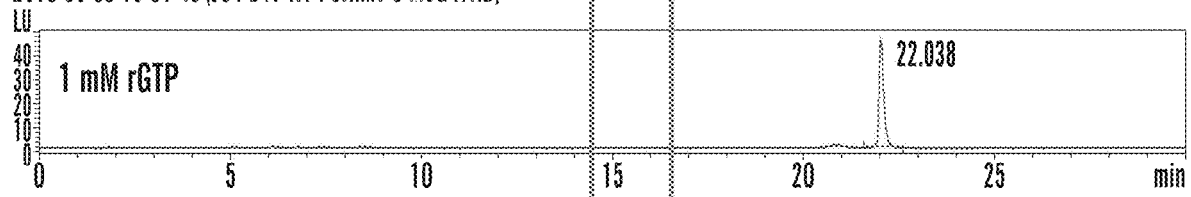
Figure 30:
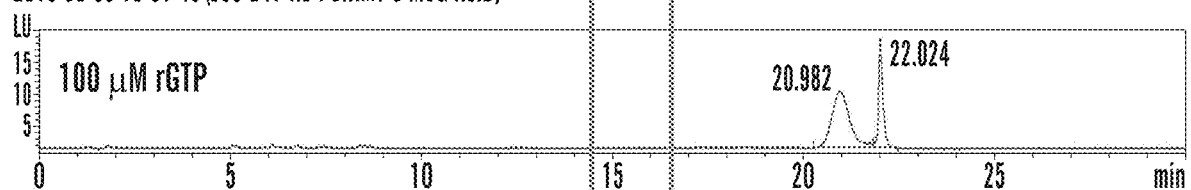
Figure 30:
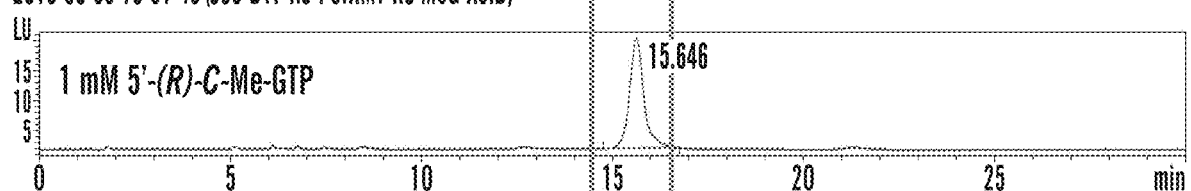
Figure 30:
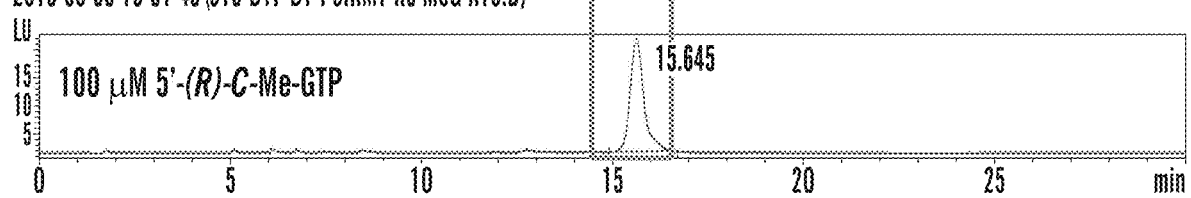

FIG. 30 shows the incorporation assay results by Pol-RMT. 5'-(S)-C-Me-G triphosphate (GTP) incorporates in Pol-RMT at high concentrations, while 5'-(R)-C-Me-GTP appears not incorporate in Pol-RMT. The rection conditions were; 200 nM template, 50 nM primer, 300 nM enzyme and 1 mM or 100 μM NTPs, 30 min, 35° C.

Figure 31:
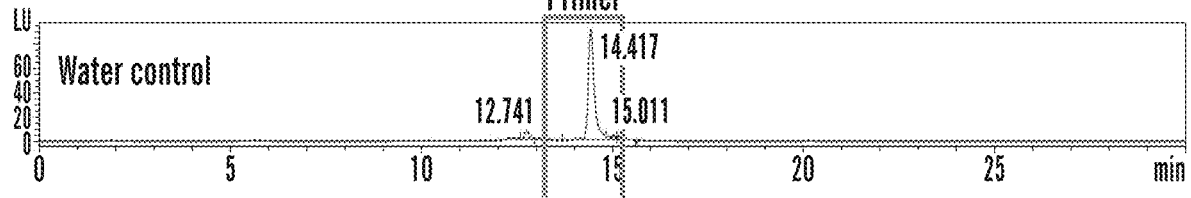
FIG. 31 shows the incorporation assay results by Pol-γ.
Figure 31:
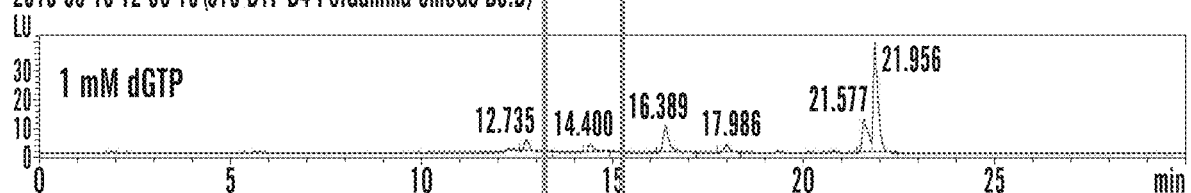
Figure 31:
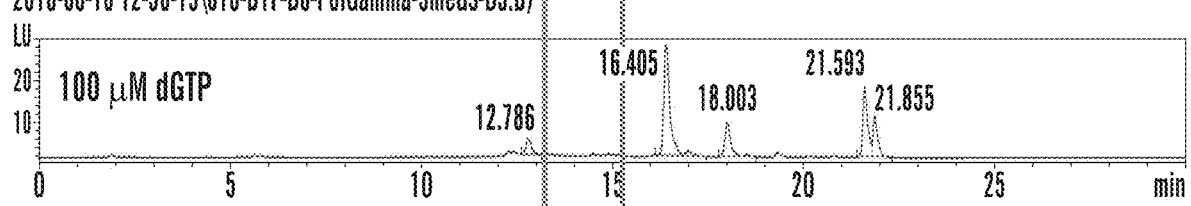
Figure 31:
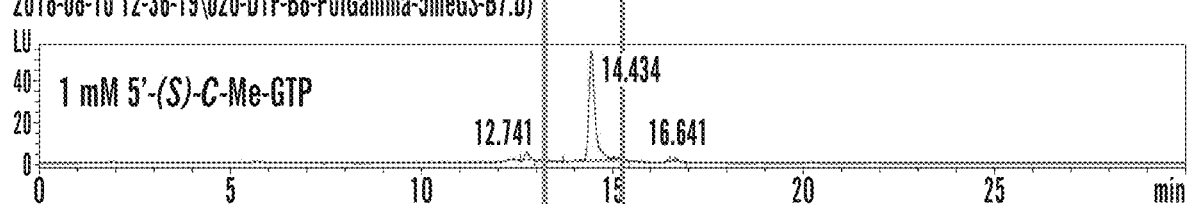
Figure 31:
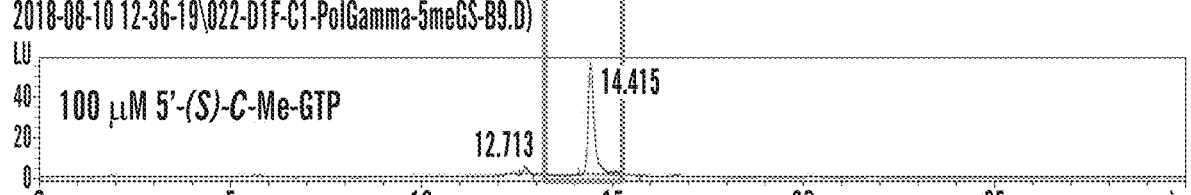
Figure 31:
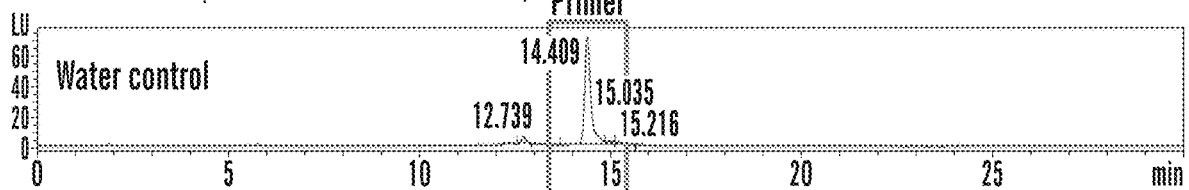
Figure 31:
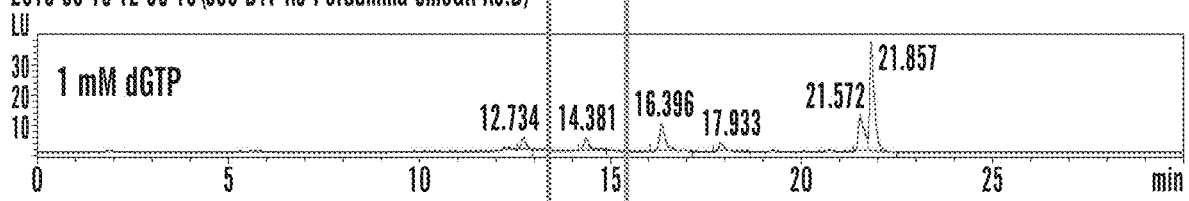
Figure 31:
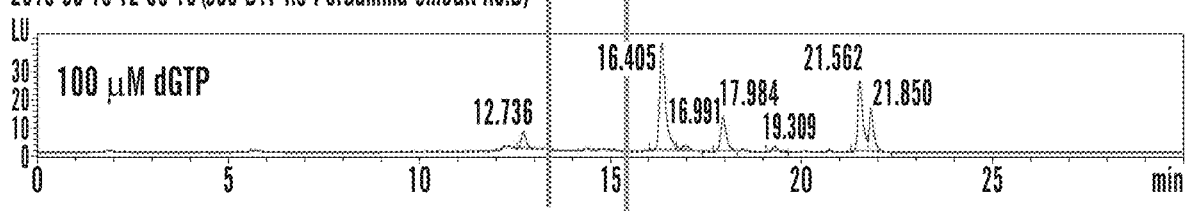
Figure 31:
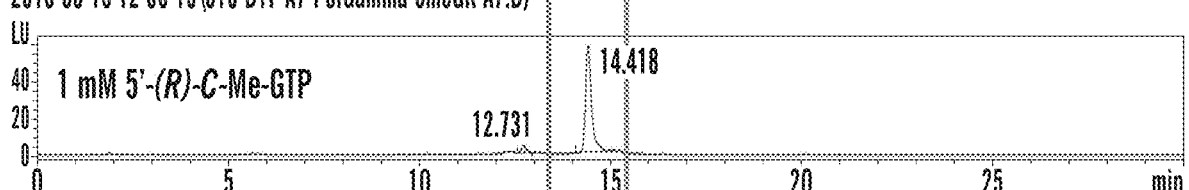
Figure 31:
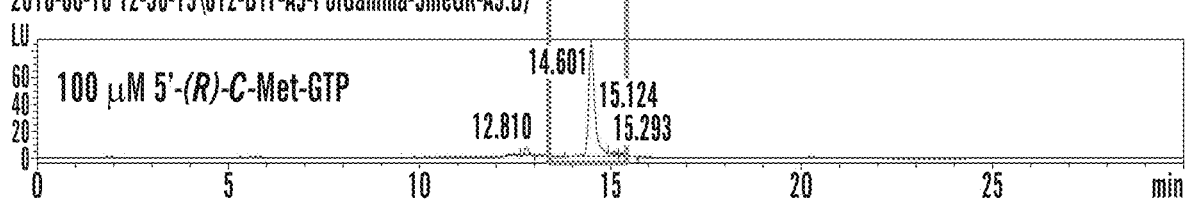

FIG. 31 shows the incorporation assay results by Pol-γ. Neither 5'-(S) nor (R)-C-Me-Gtp incorporate in Pol-γ at high concentrations. The reaction conditions were: Reaction: 100 nM template, 100 nM primer, 40 Units of enzyme and 1 mM or 100 μM dNTPs, 30 min, 37° C.; diluted to 5 nM primer and analyzed by FLD-IEX-HPLC (Ex: 437, Em: 483 nm).

Example 12

Figure 32:
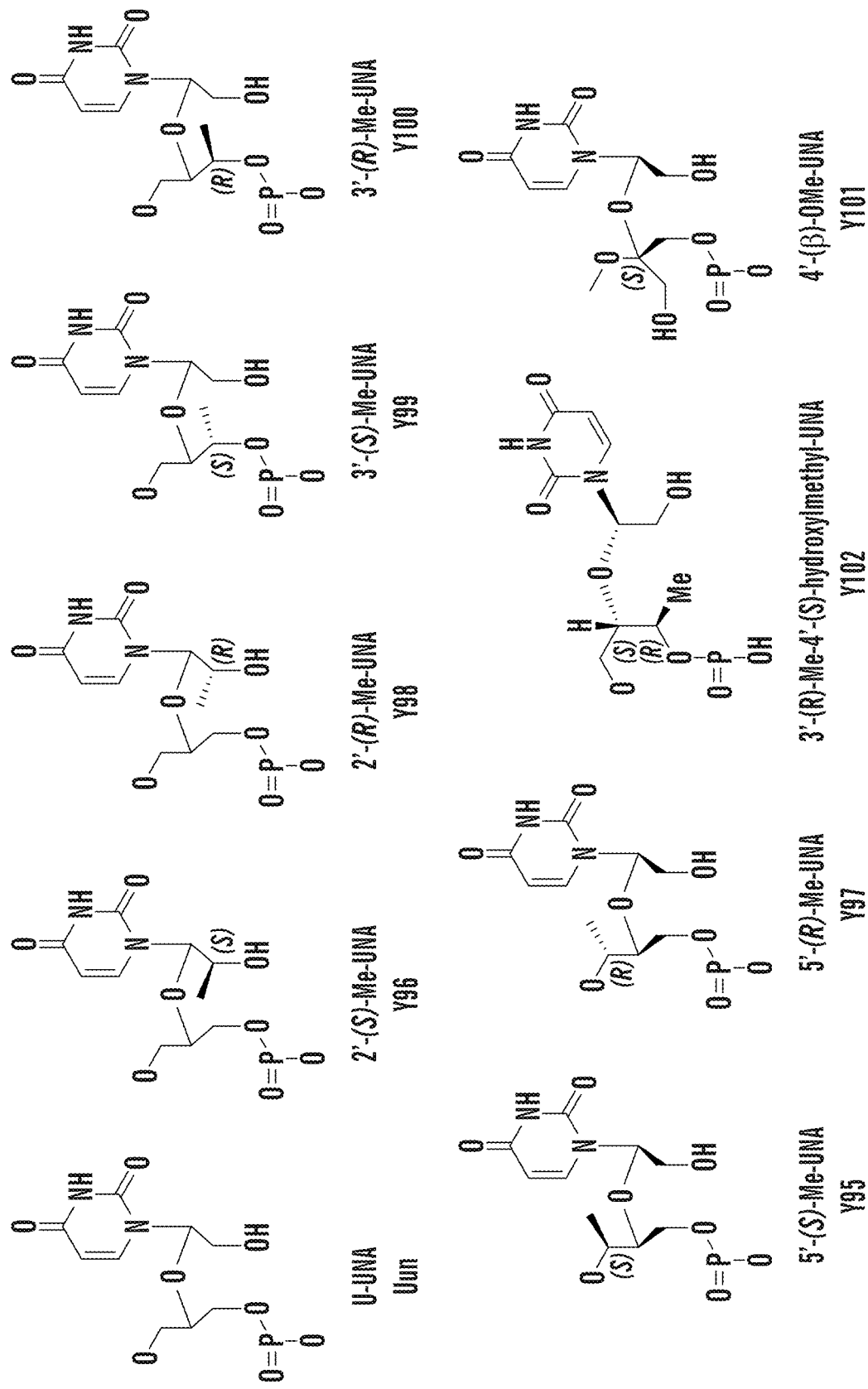
FIG. 32 shows mUNA monomer structures.

Oligo Synthesis and characterization of mUNA:RNA oligonucleotides bearing modified nucleosides described here can be synthesized on an ABI 394 DNA/RNA synthesizer using standard phosphoramidite chemistry with commercially available 5'-O-(4,4'-dimethoxytrityl)-3'-O-(2-cyanoethyl-N,N-diisopropyl) phosphoramidite monomers of uridine (U), 4-N-acetylcytidine ($C^{Ac}$), 6-N-benzoyladenosine ($A^{Bz}$) and 2-N-isobutyrylguanosine ($G^{iBu}$) with 2'-O-t-butyldimethylsilyl protected phosphoramidites, 2'-fluoro substituted phosphoramidites, 2'-O-methyl phosphoramidites and the modified nucleoside building blocks shown here. After synthesis, a small portion of the oligonucleotide-bound CPG is treated with 100 μL of methylamine solution (40 wt % in water, Aldrich) in a microtube (1 mL) at 65° C. for 10 min or concentrated ammonium hydroxide at 55° C. for 8 hours. The mixture is cooled on dry ice for 5 min and the solid suspension is spun down. The supernatant (80 μL) is decanted into another microtube and heated with 120 μL of TEA·3HF (Lancaster Synthesis, Inc.) at 65° C. for 12 min. The purity of crude oligonucleotide is analyzed by RP-HPLC or IEX-HPLC and the mass is confirmed by LC-MS experiments. FIG. 32 shows mUNA monomer structures.

TABLE 21

Oligo Synthesis and characterization of mUNA for Tm study

| Oligo ID | Oligo Sequence | Molecular Weight | Observed Mass |
|---|---|---|---|
| A-126502 | UACAGUCUAUGU | 3757.27 | 3755.5 |
| A-126504 | dTdAdCdAdGdTdCdTdAdTdGdT | 3635.402 | 3633.6 |
| A-235396 | dTdAdCdAdG(Uun)dCdTdAdTdGdT | 3639.391 | 3637.6 |
| A-235403 | UACAG(Uun)CUAUGU | 3759.286 | 3757.5 |
| A-637538 | UACAGY95CUAUGU | 3773.314 | 3771.5 |
| A-637539 | dTdAdCdAdGY95dCdTdAdTdGdT | 3653.419 | 3651.7 |
| A-637540 | UACAGY96CUAUGU | 3773.314 | 3771.5 |
| A-637541 | dTdAdCdAdGY96dCdTdAdTdGdT | 3653.419 | 3651.7 |
| A-637542 | UACAGY97CUAUGU | 3773.314 | 3771.5 |
| A-637543 | dTdAdCdAdGY97dCdTdAdTdGdT | 3653.419 | 3651.7 |

TABLE 21-continued

Oligo Synthesis and characterization of mUNA for Tm study

| Oligo ID | Oligo Sequence | Molecular Weight | Observed Mass |
|---|---|---|---|
| A-637544 | UACAGY98CUAUGU | 3773.314 | 3771.5 |
| A-637545 | dTdAdCdAdGY98dCdTdAdTdGdT | 3653.419 | 3651.7 |
| A-637546 | UACAGY99CUAUGU | 3773.314 | 3771.5 |
| A-637547 | dTdAdCdAdGY99dCdTdAdTdGdT | 3653.419 | 3651.7 |
| A-637548 | UACAGY100CUAUGU | 3773.314 | 3771.5 |
| A-637549 | dTdAdCdAdGY100dCdTdAdTdGdT | 3653.419 | 3651.7 |
| A-637550 | UACAGY101CUAUGU | 3789.314 | 3787.5 |
| A-637551 | dTdAdCdAdGY101dCdTdAdTdGdT | 3669.419 | 3667.6 |
| A-637552 | UACAGY102CUAUGU | 3773.314 | 3771.5 |
| A-637553 | dTdAdCdAdGY102dCdTdAdTdGdT | 3653.419 | 3651.7 |

(Table 21 discloses SEQ ID NOS 85-104, repectively, in order of appearance)

TABLE 22

Oligo Synthesis and characterization of mUNA for 5'-exo study

| Oligo ID | oligo Sequence | Molecular Weight | Observed Mass |
|---|---|---|---|
| A-637472 | Y95dTdTdTdTdTdTdTdTdTdTdTdTdTdTdTdTdTdTdT | 6039.917 | 6036.97 |
| A-637473 | Y95sdTdTdTdTdTdTdTdTdTdTdTdTdTdTdTdTdTdTdT | 6055.977 | 6052.94 |
| A-637480 | Y96dTdTdTdTdTdTdTdTdTdTdTdTdTdTdTdTdTdTdT | 6039.917 | 6036.98 |
| A-637481 | Y96sdTdTdTdTdTdTdTdTdTdTdTdTdTdTdTdTdTdTdT | 6055.977 | 6052.9 |
| A-637488 | Y97dTdTdTdTdTdTdTdTdTdTdTdTdTdTdTdTdTdTdT | 6039.917 | 6037.1 |
| A-637489 | Y97sdTdTdTdTdTdTdTdTdTdTdTdTdTdTdTdTdTdTdT | 6055.977 | 6052.9 |
| A-637496 | Y98dTdTdTdTdTdTdTdTdTdTdTdTdTdTdTdTdTdTdT | 6039.917 | 6036.97 |
| A-637497 | Y98sdTdTdTdTdTdTdTdTdTdTdTdTdTdTdTdTdTdTdT | 6055.977 | 6052.9 |

TABLE 22-continued

Oligo Synthesis and characterization of mUNA for 5'-exo study

| Oligo ID | oligo Sequence | Molecular Weight | Observed Mass |
|---|---|---|---|
| A-637504 | Y99dTdTdTdTdTdTdTdTdTdTdTdTdTdTdTdTdTdTdTdT | 6039.917 | 6036.9 |
| A-637505 | Y99sdTdTdTdTdTdTdTdTdTdTdTdTdTdTdTdTdTdTdT | 6055.977 | 6052.9 |
| A-637512 | Y100dTdTdTdTdTdTdTdTdTdTdTdTdTdTdTdTdTdTdT | 6039.917 | 6036.9 |
| A-637513 | Y100sdTdTdTdTdTdTdTdTdTdTdTdTdTdTdTdTdTdTdT | 6055.977 | 6052.9 |
| A-637520 | Y101dTdTdTdTdTdTdTdTdTdTdTdTdTdTdTdTdTdTdT | 6055.917 | 6052.97 |
| A-637521 | Y101sdTdTdTdTdTdTdTdTdTdTdTdTdTdTdTdTdTdTdT | 6071.977 | 6068.9 |
| A-637528 | Y102dTdTdTdTdTdTdTdTdTdTdTdTdTdTdTdTdTdTdT | 6039.917 | 6036.98 |
| A-637529 | Y102sdTdTdTdTdTdTdTdTdTdTdTdTdTdTdTdTdTdTdT | 6055.978 | 6052.95 |
| A-637536 | (Uun)dTdTdTdTdTdTdTdTdTdTdTdTdTdTdTdTdTdT | 6025.889 | 6022.96 |
| A-637537 | (Uuns)dTdTdTdTdTdTdTdTdTdTdTdTdTdTdTdTdTdT | 6041.954 | 6038.94 |

(Table 22 discloses SEQ ID NOS 105-122, repectively, in order of appearance)

TABLE 23

Oligo Synthesis and characterization of mUNA for 3'-exo study

| Oligo ID | Oligo Sequence | Molecular Weight | Observed Mass |
|---|---|---|---|
| A-637466 | dTdTdTdTdTdTdTdTdTdTdTdTdTdTdTdTdTdTY95 | 6039.917 | 6036.98 |
| A-637467 | dTdTdTdTdTdTdTdTdTdTdTdTdTdTdTdTdTdTsY95 | 6055.983 | 6052.96 |
| A-637468 | dTdTdTdTdTdTdTdTdTdTdTdTdTdTdTdTdTdTY95Y95 | 6057.934 | 6054.99 |
| A-637469 | dTdTdTdTdTdTdTdTdTdTdTdTdTdTdTdTdTdTY95sY95 | 6073.994 | 6070.96 |
| A-637470 | dTdTdTdTdTdTdTdTdTdTdTdTdTdTdTdTdTdTY95dT | 6039.917 | 6036.98 |
| A-637471 | dTdTdTdTdTdTdTdTdTdTdTdTdTdTdTdTdTdTY95sdT | 6055.977 | 6052.95 |
| A-637474 | dTdTdTdTdTdTdTdTdTdTdTdTdTdTdTdTdTdTdTY96 | 6039.917 | 6036.98 |
| A-637475 | dTdTdTdTdTdTdTdTdTdTdTdTdTdTdTdTdTdTdTsY96 | 6055.983 | 6052.96 |
| A-637476 | dTdTdTdTdTdTdTdTdTdTdTdTdTdTdTdTdTY96Y96 | 6057.934 | 6054.99 |
| A-637477 | dTdTdTdTdTdTdTdTdTdTdTdTdTdTdTdTdTY96sY96 | 6073.994 | 6070.96 |
| A-637478 | dTdTdTdTdTdTdTdTdTdTdTdTdTdTdTdTdTY96dT | 6039.917 | 6036.98 |
| A-637479 | dTdTdTdTdTdTdTdTdTdTdTdTdTdTdTdTdTY96sdT | 6055.977 | 6052.95 |
| A-637482 | dTdTdTdTdTdTdTdTdTdTdTdTdTdTdTdTdTdTdTY97 | 6039.917 | 6036.98 |
| A-637483 | dTdTdTdTdTdTdTdTdTdTdTdTdTdTdTdTdTdTdTsY97 | 6055.983 | 6052.96 |
| A-637484 | dTdTdTdTdTdTdTdTdTdTdTdTdTdTdTdTdTY97Y97 | 6057.934 | 6054.99 |
| A-637485 | dTdTdTdTdTdTdTdTdTdTdTdTdTdTdTdTdTY97sY97 | 6073.994 | 6070.96 |
| A-637486 | dTdTdTdTdTdTdTdTdTdTdTdTdTdTdTdTdTY97dT | 6039.917 | 6036.98 |
| A-637487 | dTdTdTdTdTdTdTdTdTdTdTdTdTdTdTdTdTY97sdT | 6055.977 | 6052.95 |
| A-637490 | dTdTdTdTdTdTdTdTdTdTdTdTdTdTdTdTdTdTdTY98 | 6039.917 | 6036.98 |
| A-637491 | dTdTdTdTdTdTdTdTdTdTdTdTdTdTdTdTdTdTdTsY98 | 6055.983 | 6052.96 |
| A-637492 | dTdTdTdTdTdTdTdTdTdTdTdTdTdTdTdTdTY98Y98 | 6057.934 | 6054.99 |
| A-637493 | dTdTdTdTdTdTdTdTdTdTdTdTdTdTdTdTdTY98sY98 | 6073.994 | 6070.96 |
| A-637494 | dTdTdTdTdTdTdTdTdTdTdTdTdTdTdTdTdTY98dT | 6039.917 | 6036.98 |

TABLE 23-continued

Oligo Synthesis and characterization of mUNA for 3'-exo study

| Oligo ID | Oligo Sequence | Molecular Weight | Observed Mass |
|---|---|---|---|
| A-637495 | dTdTdTdTdTdTdTdTdTdTdTdTdTdTdTdTdTdTY98sdT | 6055.977 | 6052.95 |
| A-637498 | dTdTdTdTdTdTdTdTdTdTdTdTdTdTdTdTdTdTdTY99 | 6039.917 | 6036.98 |
| A-637499 | dTdTdTdTdTdTdTdTdTdTdTdTdTdTdTdTdTdTdTsY99 | 6055.983 | 6052.96 |
| A-637500 | dTdTdTdTdTdTdTdTdTdTdTdTdTdTdTdTdTdTY99Y99 | 6057.934 | 6054.99 |
| A-637501 | dTdTdTdTdTdTdTdTdTdTdTdTdTdTdTdTdTdTY99sY99 | 6073.994 | 6070.96 |
| A-637502 | dTdTdTdTdTdTdTdTdTdTdTdTdTdTdTdTdTdTY99dT | 6039.917 | 6036.98 |
| A-637503 | dTdTdTdTdTdTdTdTdTdTdTdTdTdTdTdTdTdTY99sdT | 6055.977 | 6052.95 |
| A-637506 | dTdTdTdTdTdTdTdTdTdTdTdTdTdTdTdTdTdTdTY100 | 6039.917 | 6036.98 |
| A-637507 | dTdTdTdTdTdTdTdTdTdTdTdTdTdTdTdTdTdTdTsY100 | 6055.983 | 6052.96 |
| A-637508 | dTdTdTdTdTdTdTdTdTdTdTdTdTdTdTdTdTdTY100Y100 | 6057.934 | 6054.99 |
| A-637509 | dTdTdTdTdTdTdTdTdTdTdTdTdTdTdTdTdTdTY100sY100 | 6073.994 | 6070.96 |
| A-637510 | dTdTdTdTdTdTdTdTdTdTdTdTdTdTdTdTdTdTY100dT | 6039.917 | 6036.98 |
| A-637511 | dTdTdTdTdTdTdTdTdTdTdTdTdTdTdTdTdTdTY100sdT | 6055.977 | 6052.95 |
| A-637514 | dTdTdTdTdTdTdTdTdTdTdTdTdTdTdTdTdTdTdTY101 | 6055.917 | 6052.97 |
| A-637515 | dTdTdTdTdTdTdTdTdTdTdTdTdTdTdTdTdTdTdTsY101 | 6071.983 | 6068.95 |
| A-637516 | dTdTdTdTdTdTdTdTdTdTdTdTdTdTdTdTdTdTY101Y101 | 6089.934 | 6086.97 |
| A-637517 | dTdTdTdTdTdTdTdTdTdTdTdTdTdTdTdTdTdTY101sY101 | 6105.994 | 6102.95 |
| A-637518 | dTdTdTdTdTdTdTdTdTdTdTdTdTdTdTdTdTdTY101dT | 6055.917 | 6052.97 |
| A-637519 | dTdTdTdTdTdTdTdTdTdTdTdTdTdTdTdTdTdTY101sdT | 6071.977 | 6068.95 |
| A-637522 | dTdTdTdTdTdTdTdTdTdTdTdTdTdTdTdTdTdTdTY102 | 6039.917 | 6036.98 |
| A-637523 | dTdTdTdTdTdTdTdTdTdTdTdTdTdTdTdTdTdTdTsY102 | 6055.983 | 6052.95 |
| A-637524 | dTdTdTdTdTdTdTdTdTdTdTdTdTdTdTdTdTdTY102Y102 | 6057.934 | 6054.99 |
| A-637525 | dTdTdTdTdTdTdTdTdTdTdTdTdTdTdTdTdTdTY102sY102 | 6073.995 | 6070.96 |
| A-637526 | dTdTdTdTdTdTdTdTdTdTdTdTdTdTdTdTdTdTY102dT | 6039.917 | 6036.98 |
| A-637527 | dTdTdTdTdTdTdTdTdTdTdTdTdTdTdTdTdTdTY102sdT | 6055.978 | 6052.95 |
| A-637530 | dTdTdTdTdTdTdTdTdTdTdTdTdTdTdTdTdTdTdT(Uun) | 6025.889 | 6022.96 |
| A-637531 | dTdTdTdTdTdTdTdTdTdTdTdTdTdTdTdTdTdTs(Uun) | 6041.955 | 6038.94 |
| A-637532 | dTdTdTdTdTdTdTdTdTdTdTdTdTdTdTdTdTdT(Uun)(Uun) | 6029.878 | 6026.95 |
| A-637533 | dTdTdTdTdTdTdTdTdTdTdTdTdTdTdTdTdTdT(Uuns)(Uun) | 6045.943 | 6042.93 |
| A-637534 | dTdTdTdTdTdTdTdTdTdTdTdTdTdTdTdTdTdT(Uun)dT | 6025.889 | 6022.96 |
| A-637535 | dTdTdTdTdTdTdTdTdTdTdTdTdTdTdTdTdTdT(Uuns)dT | 6041.954 | 6038.94 |

(Table 23 discloses SEQ ID NOS 123-176, repectively, in order of appearance)

TABLE 24

Oligo Synthesis and characterization of mUNA for in vitro study

| oligo ID | oligo Sequence | Molecular Weight | Observed Mass |
|---|---|---|---|
| A-173611 | usGfsuu(Tgn)aua gagcaAfgAfacacu sgsu | 7649.155 | 7645.2 |
| A-173769 | usGfsuuua(Tgn)a gagcaAfgAfacacu sgsu | 7649.155 | 7645.2 |

TABLE 24-continued

Oligo Synthesis and characterization of mUNA for in vitro study

| oligo ID | oligo Sequence | Molecular Weight | Observed Mass |
| --- | --- | --- | --- |
| A-173780 | asCfsacgg(Tgn)uuauagAfgCfaagaascsa | 7694.25 | 7690.3 |
| A-265018 | usGfsuu(Uun)auagagcaAfgAfacacusgsu | 7695.181 | 7691.2 |
| A-265020 | usGfsuuua(Uun)agagcaAfgAfacacusgsu | 7695.181 | 7691.2 |
| A-265053 | asCfsacgg(Uun)uuauagAfgCfaagaascsa | 7740.276 | 7736.3 |
| A-432461 | asCfsacggY95uuauagAfgCfaagaascsa | 7754.304 | 7750.3 |
| A-432462 | asCfsacggY97uuauagAfgCfaagaascsa | 7754.304 | 7750.3 |
| A-432463 | asCfsacggY96uuauagAfgCfaagaascsa | 7754.304 | 7750.3 |
| A-432464 | asCfsacggY98uuauagAfgCfaagaascsa | 7754.304 | 7750.3 |
| A-432465 | asCfsacggY99uuauagAfgCfaagaascsa | 7754.304 | 7750.3 |
| A-432466 | asCfsacggY100uuauagAfgCfaagaascsa | 7754.304 | 7750.3 |
| A-432468 | usGfsuuY95auagagcaAfgAfacacusgsu | 7709.209 | 7705.2 |
| A-432469 | usGfsuuY97auagagcaAfgAfacacusgsu | 7709.209 | 7705.2 |
| A-432470 | usGfsuuY96auagagcaAfgAfacacusgsu | 7709.209 | 7705.2 |
| A-432471 | usGfsuuY98auagagcaAfgAfacacusgsu | 7709.209 | 7705.2 |
| A-432472 | usGfsuuY99auagagcaAfgAfacacusgsu | 7709.209 | 7705.2 |
| A-432473 | usGfsuuY100auagagcaAfgAfacacusgsu | 7709.209 | 7705.2 |
| A-432474 | usGfsuuY101auagagcaAfgAfacacusgsu | 7725.209 | 7721.2 |
| A-432475 | usGfsuuuaY95agagcaAfgAfacacusgsu | 7709.209 | 7705.2 |
| A-432476 | usGfsuuuaY97agagcaAfgAfacacusgsu | 7709.209 | 7705.2 |
| A-432477 | usGfsuuuaY96agagcaAfgAfacacusgsu | 7709.209 | 7705.2 |
| A-432478 | usGfsuuuaY98agagcaAfgAfacacusgsu | 7709.209 | 7705.2 |
| A-432479 | usGfsuuuaY99agagcaAfgAfacacusgsu | 7709.209 | 7705.2 |
| A-432480 | usGfsuuuaY100agagcaAfgAfacacusgsu | 7709.209 | 7705.2 |
| A-432481 | usGfsuuuaY101agagcaAfgAfacacusgsu | 7725.209 | 7721.2 |

(Table 24 discloses SEQ ID NOS 177-202, repectively, in order of appearance)

TABLE 25

Oligo Synthesis and characterization of TNA for Tm study

| Oligo ID | Oligo Sequence | Molecular Weight | Observed Mass |
| --- | --- | --- | --- |
| A-140220 | UACAG(Tth)CUAUGU | 3741.272 | 3739.5 |
| A-140221 | dTdAdCdAdG(Tth)dCdTdAdTdGdT | 3621.377 | 3619.6 |
| A-144735 | UACAGU(Cth)UAUGU | 3741.273 | 3739.5 |
| A-815960 | ACAUA(Gth)ACUGUA | 3773.322 | 3771.6 |
| A-815961 | ACAUAG(Ath)CUGUA | 3773.327 | 3771.6 |
| A-815962 | dAdCdAdTdA(Gth)dAdCdTdGdTdA | 3639.406 | 3637.7 |
| A-815963 | dAdCdAdTdAdG(Ath)dCdTdGdTdA | 3639.406 | 3637.7 |
| A-1036755 | dTdAdCdAdGdT(Cth)dTdAdTdGdT | 3635.404 | 3633.7 |

(Table 25 discloses SEQ ID NOS 203-210, respectively, in order of appearance)

TABLE 26

Oligo Synthesis and characterization of TNA for 5'/3'-exo study

| Oligo ID | Oligo Sequence | Molecular Weight | Observed Mass |
|---|---|---|---|
| A-140216 | dTdTdTdTdTdTdTdTdTdTdTdTdTdTdTdTdTdTdT(Tths)(Tth) | 6009.911 | 6006.9 |
| A-140217 | dTdTdTdTdTdTdTdTdTdTdTdTdTdTdTdTdTdTdT(Tth)(Tth) | 5993.85 | 5990.9 |
| A-140218 | dTdTdTdTdTdTdTdTdTdTdTdTdTdTdTdTdTdTdT(Tth) | 6007.875 | 6004.9 |
| A-140219 | dTdTdTdTdTdTdTdTdTdTdTdTdTdTdTdTdTdTdTs(Tth) | 6023.941 | 6020.9 |
| A-555740 | (Tth)dTdTdTdTdTdTdTdTdTdTdTdTdTdTdTdTdTdTdT | 6007.875 | 6004.9 |
| A-555741 | (Tths)dTdTdTdTdTdTdTdTdTdTdTdTdTdTdTdTdTdTdT | 6023.936 | 6020.9 |

(Table 26 discloses SEQ ID NOS 211-216, repectively, in order of appearance)

TABLE 27

Oligo Synthesis and characterization of TNA for in vitro study

| Oligo ID | Oligo Sequence | Molecular Weight | Observed Mass |
|---|---|---|---|
| A-250711 | (Aths)asCfaGfuGfuUfCfUfuGfcUfcUfaUfaAfL96 | 8558.15 | 8553.1 |
| A-250712 | Afs(Aths)CfaGfuGfuUfCfUfuGfcUfcUfaUfaAfL96 | 8546.115 | 8541.8 |
| A-250713 | Afsas(Cth)aGfuGfuUfCfUfuGfcUfcUfaUfaAfL96 | 8572.181 | 8567.2 |
| A-250714 | AfsasCf(Ath)GfuGfuUfCfUfuGfcUfcUfaUfaAfL96 | 8546.119 | 8541.5 |
| A-250715 | AfsasCfa(Gth)uGfuUfCfUfuGfcUfcUfaUfaAfL96 | 8558.155 | 8553.9 |
| A-250716 | AfsasCfaGf(Tth)GfuUfCfUfuGfcUfcUfaUfaAfL96 | 8560.144 | 8555.8 |
| A-250717 | AfsasCfaGfu(Gth)uUfCfUfuGfcUfcUfaUfaAfL96 | 8558.155 | 8553.2 |
| A-250718 | AfsasCfaGfuGf(Tth)UfCfUfuGfcUfcUfaUfaAfL96 | 8560.144 | 8555.3 |
| A-250719 | AfsasCfaGfuGfu(Tth)CfUfuGfcUfcUfaUfaAfL96 | 8572.18 | 8567.8 |
| A-250720 | AfsasCfaGfuGfuUf(Cth)UfuGfcUfcUfaUfaAfL96 | 8572.181 | 8567.2 |
| A-250721 | AfsasCfaGfuGfuUfCf(Tth)uGfcUfcUfaUfaAfL96 | 8572.18 | 8567.6 |
| A-250722 | AfsasCfaGfuGfuUfCfUf(Tth)GfcUfcUfaUfaAfL96 | 8560.144 | 8555.3 |
| A-250723 | AfsasCfaGfuGfuUfCfUfu(Gth)cUfcUfaUfaAfL96 | 8558.155 | 8553.5 |
| A-250724 | AfsasCfaGfuGfuUfCfUfuGf(Cth)UfcUfaUfaAfL96 | 8560.145 | 8555.7 |
| A-250725 | AfsasCfaGfuGfuUfCfUfuGfc(Tth)cUfaUfaAfL96 | 8572.18 | 8567.5 |
| A-250726 | AfsasCfaGfuGfuUfCfUfuGfcUf(Cth)UfaUfaAfL96 | 8560.145 | 8555.4 |
| A-250727 | AfsasCfaGfuGfuUfCfUfuGfcUfc(Tth)aUfaAfL96 | 8572.18 | 8567.8 |
| A-250728 | AfsasCfaGfuGfuUfCfUfuGfcUfcUf(Ath)UfaAfL96 | 8546.119 | 8541.9 |
| A-250729 | AfsasCfaGfuGfuUfCfUfuGfcUfcUfa(Tth)aAfL96 | 8572.18 | 8567.5 |
| A-250730 | AfsasCfaGfuGfuUfCfUfuGfcUfcUfaUf(Ath)AfL96 | 8546.119 | 8541.8 |
| A-250731 | AfsasCfaGfuGfuUfCfUfuGfcUfcUfaUfa(Ath)L96 | 8558.155 | 8553.8 |
| A-250732 | (Tths)UfsaUfaGfaGfcAfagaAfcAfcUfgUfususu | 7565.908 | 7562.1 |
| A-250733 | us(Tths)aUfaGfaGfcAfagaAfcAfcUfgUfususu | 7577.943 | 7574.1 |
| A-250734 | usUfs(Ath)UfaGfaGfcAfagaAfcAfcUfgUfususu | 7551.887 | 7548 |
| A-250735 | usUfsa(Tth)aGfaGfcAfagaAfcAfcUfgUfususu | 7577.948 | 7574.1 |
| A-250736 | usUfsaUf(Ath)GfaGfcAfagaAfcAfcUfgUfususu | 7551.887 | 7548 |
| A-250737 | usUfsaUfa(Gth)aGfcAfagaAfcAfcUfgUfususu | 7563.923 | 7560.1 |

TABLE 27-continued

Oligo Synthesis and characterization of TNA for in vitro study

| Oligo ID | Oligo Sequence | Molecular Weight | Observed Mass |
|---|---|---|---|
| A-250738 | usUfsaUfaGf(Ath)GfcAfagaAfcAfcUfgUfsusu | 7551.887 | 7548 |
| A-250739 | usUfsaUfaGfa(Gth)cAfagaAfcAfcUfgUfsusu | 7563.923 | 7560.1 |
| A-250740 | usUfsaUfaGfaGf(Cth)AfagaAfcAfcUfgUfsusu | 7565.913 | 7562.1 |
| A-250741 | usUfsaUfaGfaGfc(Ath)agaAfcAfcUfgUfsusu | 7563.923 | 7560 |
| A-250742 | usUfsaUfaGfaGfcAf(Ath)gaAfcAfcUfgUfsusu | 7551.887 | 7548 |
| A-250743 | usUfsaUfaGfaGfcAfa(Gth)aAfcAfcUfgUfsusu | 7551.887 | 7548 |
| A-250744 | usUfsaUfaGfaGfcAfag(Ath)AfcAfcUfgUfsusu | 7551.887 | 7548 |
| A-250745 | usUfsaUfaGfaGfcAfaga(Ath)cAfcUfgUfsusu | 7563.923 | 7560.1 |
| A-250746 | usUfsaUfaGfaGfcAfagaAf(Cth)AfcUfgUfsusu | 7565.913 | 7562.1 |
| A-250747 | usUfsaUfaGfaGfcAfagaAfc(Ath)cUfgUfsusu | 7563.923 | 7560.1 |
| A-250748 | usUfsaUfaGfaGfcAfagaAfcAf(Cth)UfgUfsusu | 7565.913 | 7562.1 |
| A-250749 | usUfsaUfaGfaGfcAfagaAfcAfc(Tth)gUfsusu | 7577.948 | 7574.1 |
| A-250750 | usUfsaUfaGfaGfcAfagaAfcAfcUf(Gth)Ufsusu | 7551.887 | 7548 |
| A-250751 | usUfsaUfaGfaGfcAfagaAfcAfcUfg(Tth)ususu | 7577.948 | 7574.1 |
| A-250752 | usUfsaUfaGfaGfcAfagaAfcAfcUfgUf(Tths)usu | 7565.908 | 7562.1 |
| A-250753 | usUfsaUfaGfaGfcAfagaAfcAfcUfgUfus(Tths)u | 7565.908 | 7562.1 |
| A-250754 | usUfsaUfaGfaGfcAfagaAfcAfcUfgUfusus(Tth) | 7565.912 | 7562.1 |

(Table 15 discloses SEQ ID NOS 217-260, repectively, in order of appearance)

TABLE 28

Oligo Synthesis and characterization of HYP-based modification

| Oligo ID | Oligo Sequence | Molecular Weight | Observed Mass |
|---|---|---|---|
| A-157540 | usUfsguQ198GfaUfGfacuuUfcAfcauucsusg | 7439.856 | 7436 |
| A-157541 | usUfsgucQ198aUfGfacuuUfcAfcauucsusg | 7411.868 | 7408.1 |
| A-157542 | usUfsgucGfQ198UfGfacuuUfcAfcauucsusg | 7415.831 | 7412 |
| A-157543 | usUfsgucGfaQ198GfacuuUfcAfcauucsusg | 7450.907 | 7447.1 |
| A-173412 | usUfsauQ198GfagcaagaAfcAfcuguususu | 7534.033 | 7530.2 |
| A-173413 | usUfsauaQ198agcaagaAfcAfcuguususu | 7530.07 | 7526.2 |
| A-173414 | usUfsauaGfQ198gcaagaAfcAfcuguususu | 7534.033 | 7530.1 |
| A-173415 | usUfsauaGfaQ198caagaAfcAfcuguususu | 7518.034 | 7514.2 |
| A-594465 | usUfs(Ahp)auaGfagcaagaAfcAfcuguususu | 8010.38 | 8006.3 |
| A-594466 | usUfsQ198uaGfagcaagaAfcAfcuguususu | 7534.033 | 7530.2 |
| A-594467 | usUfsa(Thp)aGfagcaagaAfcAfcuguususu | 7681.172 | 7677.2 |
| A-594468 | usUfsaQ198aGfagcaagaAfcAfcuguususu | 7557.073 | 7553.2 |
| A-594469 | usUfsau(Ahp)GfagcaagaAfcAfcuguususu | 7667.147 | 7663.9 |
| A-594470 | usUfsaua(Ghp)agcaagaAfcAfcuguususu | 7679.183 | 7675.2 |
| A-594471 | usUfsauaGf(Ahp)gcaagaAfcAfcuguususu | 7667.147 | 7663.2 |
| A-594472 | usUfsauaGfa(Ghp)caagaAfcAfcuguususu | 7667.147 | 7663.5 |
| A-594473 | usUfsauaGfag(Chp)aagaAfcAfcuguususu | 7667.146 | 7663.2 |
| A-594474 | usUfsauaGfagQ198aagaAfcAfcuguususu | 7558.058 | 7554.2 |

TABLE 28-continued

Oligo Synthesis and characterization of HYP-based modification

| Oligo ID | Oligo Sequence | Molecular Weight | Observed Mass |
|---|---|---|---|
| A-594475 | usUfs(Ghp)ucGfaUfGfacuuUfcAfcauucsusg | 7548.945 | 7545.1 |
| A-594476 | usUfsQ198ucGfaUfGfacuuUfcAfcauucsusg | 7399.832 | 7396 |
| A-594477 | usUfsg(Thp)cGfaUfGfacuuUfcAfcauucsusg | 7562.97 | 7559.1 |
| A-594478 | usUfsgQ198cGfaUfGfacuuUfcAfcauucsusg | 7438.871 | 7435.1 |
| A-594479 | usUfsgu(Chp)GfaUfGfacuuUfcAfcauucsusg | 7548.944 | 7545.1 |
| A-594480 | usUfsguc(Ghp)aUfGfacuuUfcAfcauucsusg | 7560.981 | 7557.6 |
| A-594481 | usUfsgucGf(Ahp)UfGfacuuUfcAfcauucsusg | 7548.945 | 7545.1 |
| A-594482 | usUfsgucGfa(Thp)GfacuuUfcAfcauucsusg | 7575.006 | 7571.1 |
| A-594483 | usUfsgucGfaUf(Ghp)acuuUfcAfcauucsusg | 7560.981 | 7557.8 |
| A-594484 | usUfsgucGfaUfQ198acuuUfcAfcauucsusg | 7411.868 | 7408.1 |

(Table 28 discloses SEQ ID NOS 261-288, repectively, in order of appearance)

Determination of UV thermal melting temperatures of mUNA 12-mer duplexes: Thermal melting temperatures were measured with equimolar concentrations of both strands (2.0 μM) in (a) 1×PBS ([NaCl]=137 mM, [KCl]=2.7 mM, [Na$_2$HPO$_4$]=8 mM, [KH$_2$PO$_4$]=2 mM, pH 7.4) or in (b) 8×PBS ([NaCl]=1.1 M, [KCl]=22 mM, [Na$_2$HPO$_4$]=64 mM, [KH$_2$PO$_4$]=16 mM, pH 7.4) by monitoring A$_{260}$ with increasing temperature (1° C./min). Values were reported as the maximum of the first derivative and are the average of at least two experiments.

TABLE 29

UV thermal melting temperatures mUNA 12-mer duplexes

| Well | Sample Name | Target | sOligo Name | sOligo Seq | asOligo Name | asOligo Seq | Tm (° C.)$^a$ | ΔTm (° C.) | ΔTm (° C.)$^b$ | Tm (° C.) |
|---|---|---|---|---|---|---|---|---|---|---|
| A1 | AD-64366.2 | N/A | A-126502.7 | UACAGUCUAUGU | A-126503.7 | ACAUAGACUGUA | 52.1 | 0.0 | 61.1 | 0.0 |
| B1 | AD-511219.1 | N/A | A-637538.2 | UACAGY95CUAUGU | A-126503.8 | ACAUAGACUGUA | 35.2 | -17.0 | 43.3 | -17.8 |
| C1 | AD-511220.1 | N/A | A-637540.2 | UACAGY96CUAUGU | A-126503.9 | ACAUAGACUGUA | 34.3 | -17.8 | 42.4 | -18.7 |
| D1 | AD-511221.1 | N/A | A-637542.2 | UACAGY97CUAUGU | A-126503.10 | ACAUAGACUGUA | 33.4 | -18.7 | 42.5 | -18.6 |
| E1 | AD-511222.1 | N/A | A-637544.2 | UACAGY98CUAUGU | A-126503.11 | ACAUAGACUGUA | 33.5 | -18.6 | 42.6 | -18.5 |
| F1 | AD-511223.1 | N/A | A-637546.2 | UACAGY99CUAUGU | A-126503.12 | ACAUAGACUGUA | 34.1 | -18.0 | 42.1 | -19.0 |
| G1 | AD-511224.1 | N/A | A-637548.2 | UACAGY100CUAUGU | A-126503.13 | ACAUAGACUGUA | 34.2 | -18.0 | 43.3 | -17.8 |
| H1 | AD-511225.1 | N/A | A-637550.2 | UACAGY101CUAUGU | A-126503.14 | ACAUAGACUGUA | 36.3 | -15.8 | 45.4 | -15.7 |
| A2 | AD-511226.1 | N/A | A-637552.2 | UACAGY102CUAUGU | A-126503.15 | ACAUAGACUGUA | 38.4 | -13.7 | 47.5 | -13.6 |
| B2 | AD-511227.1 | N/A | A-235403.3 | UACAG(Uun)CUAUGU | A-126503.16 | ACAUAGACUGUA | 35.5 | -16.6 | 43.6 | -17.5 |
| C2 | AD-64367.2 | N/A | A-126504.3 | dTdAdCdAdGdTdCdTdAdTdGdT | A-126505.3 | dAdCdAdTdAdGdAdCdTdGdTdA | 43.1 | | 49.1 | 0.0 |
| D2 | AD-511228.1 | N/A | A-637539.2 | dTdAdCdAdGY95dCdTdAdTdGdT | A-126505.4 | dAdCdAdTdAdGdAdCdTdGdTdA | <30 | | 22.3 | -26.8 |

TABLE 29-continued

UV thermal melting temperatures mUNA 12-mer duplexes

| Well | Sample Name | Target | sOligo Name | sOligo Seq | asOligo Name | asOligo Seq | Tm (° C.)$^a$ | ΔTm (° C.) | ΔTm (° C.)$^b$ | Tm (° C.) |
|---|---|---|---|---|---|---|---|---|---|---|
| E2 | AD-511229.1 | N/A | A-637541.2 | dTdAdCdAdGY96dCdTdAdTdGdT | A-126505.5 | dAdCdAdTdAdGdAdCdTdGdTdA | <30 | | 23.4 | −25.7 |
| F2 | AD-511230.1 | N/A | A-637543.2 | dTdAdCdAdGY97dCdTdAdTdGdT | A-126505.6 | dAdCdAdTdAdGdAdCdTdGdTdA | <30 | | 23.5 | −25.6 |
| G2 | AD-511231.1 | N/A | A-637545.2 | dTdAdCdAdGY98dCdTdAdTdGdT | A-126505.7 | dAdCdAdTdAdGdAdCdTdGdTdA | <30 | | 23.6 | −25.5 |
| H2 | AD-511232.1 | N/A | A-637547.2 | dTdAdCdAdGY99dCdTdAdTdGdT | A-126505.8 | dAdCdAdTdAdGdAdCdTdGdTdA | <30 | | 25.1 | −24.0 |
| A3 | AD-511233.1 | N/A | A-637549.2 | dTdAdCdAdGY100dCdTdAdTdGdT | A-126505.9 | dAdCdAdTdAdGdAdCdTdGdTdA | <30 | | 22.3 | −26.8 |
| B3 | AD-511234.1 | N/A | A-637551.2 | dTdAdCdAdGY101dCdTdAdTdGdT | A-126505.10 | dAdCdAdTdAdGdAdCdTdGdTdA | <30 | | 23.4 | −25.7 |
| C3 | AD-511235.1 | N/A | A-637553.2 | dTdAdCdAdGY102dCdTdAdTdGdT | A-126505.11 | dAdCdAdTdAdGdAdCdTdGdTdA | <30 | | 26.5 | −22.6 |
| D3 | AD-511236.1 | N/A | A-235396.3 | dTdAdCdAdG(Uun)dCdTdAdTdGdT | A-126505.12 | dAdCdAdTdAdGdAdCdTdGdTdA | <30 | | 23.6 | −25.5 |
| E3 | AD-511237.1 | N/A | A-126502.8 | UACAGUCUAUGU | A-126505.13 | dAdCdAdTdAdGdAdCdTdGdTdA | 39.1 | | 45.1 | 0.0 |
| F3 | AD-511238.1 | N/A | A-637538.3 | UACAGY95CUAUGU | A-126505.14 | dAdCdAdTdAdGdAdCdTdGdTdA | <30 | | 22.3 | −22.8 |
| G3 | AD-511239.1 | N/A | A-637540.3 | UACAGY96CUAUGU | A-126505.15 | dAdCdAdTdAdGdAdCdTdGdTdA | <30 | | 23.4 | −21.7 |
| H3 | AD-511240.1 | N/A | A-637542.3 | UACAGY97CUAUGU | A-126505.16 | dAdCdAdTdAdGdAdCdTdGdTdA | <30 | | 22.5 | −22.6 |
| A4 | AD-511241.1 | N/A | A-637544.3 | UACAGY98CUAUGU | A-126505.17 | dAdCdAdTdAdGdAdCdTdGdTdA | <30 | | 22.6 | −22.5 |
| B4 | AD-511242.1 | N/A | A-637546.3 | UACAGY99CUAUGU | A-126505.18 | dAdCdAdTdAdGdAdCdTdGdTdA | <30 | | 27.1 | −18.0 |
| C4 | AD-511243.1 | N/A | A-637548.3 | UACAGY100CUAUGU | A-126505.19 | dAdCdAdTdAdGdAdCdTdGdTdA | <30 | | 27.3 | −17.8 |
| D4 | AD-511244.1 | N/A | A-637550.3 | UACAGY101CUAUGU | A-126505.20 | dAdCdAdTdAdGdAdCdTdGdTdA | <30 | | 23.4 | −21.7 |
| E4 | AD-511245.1 | N/A | A-637552.3 | UACAGY102CUAUGU | A-126505.21 | dAdCdAdTdAdGdAdCdTdGdTdA | <30 | | 26.5 | −18.6 |
| F4 | AD-511246.1 | N/A | A-235403.4 | UACAG(Uun)CUAUGU | A-126505.22 | dAdCdAdTdAdGdAdCdTdGdTdA | <30 | | 24.6 | −20.5 |

TABLE 29-continued

UV thermal melting temperatures mUNA 12-mer duplexes

| Well | Sample Name | Target | sOligo Name | sOligo Seq | asOligo Name | asOligo Seq | Tm (° C.)[a] | ΔTm (° C.) | ΔTm (° C.)[b] | Tm (° C.) |
|---|---|---|---|---|---|---|---|---|---|---|
| G4 | AD-511247.1 | N/A | A-126504.4 | dTdAdCdAdGdTdCdTdAdTdGdT | A-126503.17 | ACAUAGACUGUA | 42.1 | | 49.1 | 0.0 |
| H4 | AD-511248.1 | N/A | A-637539.3 | dTdAdCdAdGY95dCdTdAdTdGdT | A-126503.18 | ACAUAGACUGUA | <30 | | 29.2 | -20.0 |
| A5 | AD-511249.1 | N/A | A-637541.3 | dTdAdCdAdGY96dCdTdAdTdGdT | A-126503.19 | ACAUAGACUGUA | <30 | | 28.3 | -20.9 |
| B5 | AD-511250.1 | N/A | A-637543.3 | dTdAdCdAdGY97dCdTdAdTdGdT | A-126503.20 | ACAUAGACUGUA | <30 | | 26.4 | -22.7 |
| C5 | AD-511251.1 | N/A | A-637545.3 | dTdAdCdAdGY98dCdTdAdTdGdT | A-126503.21 | ACAUAGACUGUA | <30 | | 28.6 | -20.6 |
| D5 | AD-511252.1 | N/A | A-637547.3 | dTdAdCdAdGY99dCdTdAdTdGdT | A-126503.22 | ACAUAGACUGUA | <30 | | 27.1 | -22.0 |
| E5 | AD-511253.1 | N/A | A-637549.3 | dTdAdCdAdGY100dCdTdAdTdGdT | A-126503.23 | ACAUAGACUGUA | <30 | | 27.2 | -22.0 |
| F5 | AD-511254.1 | N/A | A-637551.3 | dTdAdCdAdGY101dCdTdAdTdGdT | A-126503.24 | ACAUAGACUGUA | <30 | | 31.3 | -17.9 |
| G5 | AD-511255.1 | N/A | A-637553.3 | dTdAdCdAdGY102dCdTdAdTdGdT | A-126503.25 | ACAUAGACUGUA | <30 | | 36.4 | -12.7 |
| H5 | AD-511256.1 | N/A | A-235396.4 | dTdAdCdAdG(Uun)dCdTdAdTdGdT | A-126503.26 | ACAUAGACUGUA | <30 | | 28.6 | -20.6 |

(Table 29 discloses SEQ ID NOS 289-368, repectively, in order of columns)

Determination of UV thermal melting temperatures of mUNA 21-/23-mer duplexes: Thermal melting temperatures were measured with equimolar concentrations of both strands (1.0 μM) in (a) 0.25×PBS ([NaCl]=34 mM, [KCl]=0.68 mM, [Na$_2$HPO$_4$]=2 mM, [KH$_2$PO$_4$]=0.5 mM, pH 7.4) by monitoring A$_{260}$ with increasing temperature (1° C./min). Values were reported as the maximum of the first derivative and are the average of at least two experiments.

TABLE 30

UV thermal melting temperatures mUNA 21-/23-mer duplexes

| Duplex ID | Sense Strand | Antisense Strand | Tm (° C.) | ΔTm (° C.) | Modification |
|---|---|---|---|---|---|
| AD-125773.8 | ususcuugCfasCfsacggu | uCfUfAfuaauuauagAfgCaccguguL96faagaascsa | 89.02 | 0 | |
| AD-218916.1 | ususcuugCfasCfsacggY100 | uCfUfAfuaa100uuauagAaccguguL96fgCfaagaascsa | 81.17 | -7.85 | Y100 |
| AD-218921.1 | asgsuguuCfusGfsuuY98 | uUfGfCfucuauagagcaAfauaaacaL96gAfacacusgsu | 83.97 | -5.05 | Y98 |
| AD-218927.1 | asgsuguuCfusGfsuuuaY | uUfGfCfucu96agagcaAfauaaacaL96gAfacacusgsu | 83.02 | -6 | Y96 |
| AD-126010.4 | ususcuugCfasCfsacgg(uCfUfAfuaaTgn)uuauagaccguguL96AfgCfaagaascsa | | 88.12 | -0.9 | GNA-T |
| AD-218922.1 | asgsuguuCfusGfsuuY99 | uUfGfCfucuauagagcaAfauaaacaL96gAfacacusgsu | 84.02 | -5 | Y99 |

TABLE 30-continued

UV thermal melting temperatures mUNA 21-/23-mer duplexes

| Duplex ID | Sense Strand Antisense Strand | Tm (° C.) | ΔTm (° C.) | Modification |
|---|---|---|---|---|
| AD-218928.1 | asgsuguuCfusGfsuuuaY uUfGfCfucu98agagcaAf auaaacaL96gAfacacusg su | 82.12 | −6.9 | Y98 |
| AD-133768.2 | ususcuugCfasCfsacgg( uCfUfAfuaaUun)uuauag accguguL96AfgCfaagaa scsa | 80.12 | −8.9 | UNA-U |
| AD-125762.7 | asgsuguuCfusGfsuuuau uUfGfCfucuagagcaAfgA auaaacaL96facacusgsu | 87.27 | 0 | Y101 |
| AD-218923.1 | asgsuguuCfusGfsuuY10 uUfGfCfucu0auagagcaA auaaacaL96fgAfacacus gsu | 84.07 | −3.2 | Y100 |
| AD-218929.1 | asgsuguuCfusGfsuuuuaY uUfGfCfucu99agagcaAf auaaacaL96gAfacacusg su | 81.97 | −5.3 | Y99 |
| AD-218911.1 | ususcuugCfasCfsacggY uCfUfAfuaa95uuauagAf accguguL96gCfaagaasc sa | 80.27 | −7 | Y95 |
| AD-125841.3 | asgsuguuCfusGfsuu(Tg uUfGfCfucun)auagagca auaaacaL96AfgAfacacu sgsu | 84.02 | −3.25 | GNA-T |
| AD-218924.1 | asgsuguuCfusGfsuuY10 uUfGfCfucu1auagagcaA auaaacaL96fgAfacacus gsu | 85.17 | −2.1 | Y101 |
| AD-218930.1 | asgsuguuCfusGfsuuuuaY uUfGfCfucu100agagcaAf auaaacaL96fgAfacacus gsu | 81.97 | −5.3 | Y100 |
| AD-218912.1 | ususcuugCfasCfsacggY uCfUfAfuaa97uuauagAf accguguL96gCfaagaasc sa | 80.32 | −6.95 | Y97 |
| AD-133733.2 | asgsuguuCfusGfsuu(Uu uUfGfCfucun)auagagca auaaacaL96AfgAfacacu sgsu | 84.07 | −3.2 | UNA-U |
| AD-125999.4 | asgsuguuCfusGfsuuuua( uUfGfCfucuTgn)agagca auaaacaL96AfgAfacacu sgsu | 83.22 | −4.05 | GNA-T |
| AD-218931.1 | asgsuguuCfusGfsuuuuaY uUfGfCfucu101agagcaA auaaacaL96fgAfacacus gsu | 82.97 | −4.3 | Y101 |
| AD-218913.1 | ususcuugCfasCfsacggY uCfUfAfuaa96uuauagAf accguguL96gCfaagaasc sa | 80.02 | −7.25 | Y96 |
| AD-218918.1 | asgsuguuCfusGfsuuY95 uUfGfCfucuauagagcaAf auaaacaL96gAfacacusg su | 84.17 | −3.1 | Y95 |
| AD-133735.2 | asgsuguuCfusGfsuuuua( uUfGfCfucuUun)agagca auaaacaL96AfgAfacacu sgsu | 81.97 | −5.3 | UNA-U |
| AD-218914.1 | ususcuugCfasCfsacggY uCfUfAfuaa98uuauagAf accguguL96gCfaagaasc sa | 80.02 | −7.25 | Y98 |
| AD-218919.1 | asgsuguuCfusGfsuuY97 uUfGfCfucuauagagcaAf auaaacaL96gAfacacusg su | 84.22 | −3.05 | Y97 |
| AD-218925.1 | asgsuguuCfusGfsuuuuaY uUfGfCfucu95agagcaAf auaaacaL96gAfacacusg su | 81.97 | −5.3 | Y95 |
| AD-218915.1 | ususcuugCfasCfsacggY uCfUfAfuaa99uuauagAf accguguL96gCfaagaasc sa | 81.12 | −6.15 | Y99 |
| AD-218920.1 | asgsuguuCfusGfsuuY96 uUfGfCfucuauagagcaAf auaaacaL96gAfacacusg su | 84.27 | −3 | Y96 |
| AD-218926.1 | asgsuguuCfusGfsuuuuaY uUfGfCfucu97agagcaAf auaaacaL96gAfacacusg su | 82.02 | −5.25 | Y97 |

(Table 30 discloses SEQ ID NOS 369-424, repectively, in order of columns)

Figure 33:
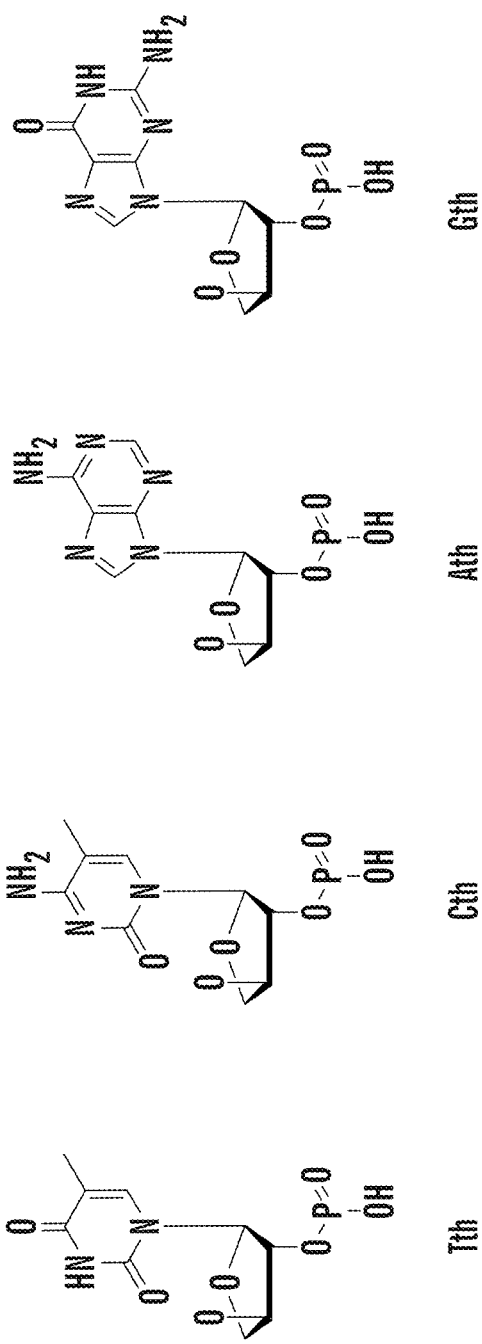
FIG. 33 shows TNA monomer structures.

Determination of UV thermal melting temperatures of TNA 12-mer duplexes: Thermal melting temperatures were measured with equimolar concentrations of both strands (2.0 µM) in 1× PBS ([NaCl]=137 mM, [KCl]=2.7 mM, [Na$_2$HPO$_4$]=8 mM, [KH$_2$PO$_4$]=2 mM, pH 7.4) by monitoring A$_{260}$ with increasing temperature (1° C./min). Values were reported as the maximum of the first derivative and are the average of at least two experiments. FIG. 33 shows TNA monomer structures.

TABLE 31

UV thermal melting temperatures of TNA 12-mer duplexes

| Duplex ID | sOligo ID | sOligo Sequence | asOligo ID | asOligo Sequence | Tm (° C.) | ΔTm (° C.) |
|---|---|---|---|---|---|---|
| AD-64366.3 | A-126502.9 | UACAGUCUAUGU | A-126503.27 | ACAUAGACUGUA | 52.57 | 0 |
| 649408A | A-126502.10 | UACAGUCUAUGU | A-815961.2 | ACAUAG(Ath)CUGUA | 48.07 | −4.5 |
| 72587.2 | A-144735.2 | UACAGU(Cth)UAUGU | A-126503.28 | ACAUAGACUGUA | 47.12 | −5.45 |
| 649409.1 | A-126502.11 | UACAGUCUAUGU | A-815960.2 | ACAUA(Gth)ACUGUA | 47.67 | −4.9 |
| 72585.2 | A-140220.2 | UACAG(Tth)CUAUGU | A-126503.29 | ACAUAGACUGUA | 47.745 | −4.825 |
| 649410.1 | A-140220.3 | UACAG(Tth)CUAUGU | A-815961.3 | ACAUAG(Ath)CUGUA | 43.07 | −9.5 |
| 6494111 | A-144735.3 | UACAGU(Cth)UAUGU | A-815960.3 | ACAUA(Gth)ACUGUA | 41.57 | −11 |
| 64366.4 | A-126502.12 | UACAGUCUAUGU | A-126503.30 | ACAUAGACUGUA | 52.62 | 0 |
| 649412.1 | A-126502.13 | UACAGUCUAUGU | A-163716.4 | ACAUAGAfCUGUA | 53.17 | 0.55 |
| 649413.1 | A-319061.4 | UACAGUCfUAUGU | A-126503.31 | ACAUAGACUGUA | 54.245 | 1.625 |
| 649414.1 | A-126502.14 | UACAGUCUAUGU | A-818179.3 | ACAUAGfACUGUA | 53.07 | 0.45 |
| 64980.2 | A-129612.3 | UACAGUfCUAUGU | A-126503.32 | ACAUAGACUGUA | 53.14 | 0.52 |
| 649415.1 | A-129612.4 | UACAGUfCUAUGU | A-163716.5 | ACAUAGAfCUGUA | 54.22 | 16 |
| 649416.1 | A-319061.5 | UACAGUCfUAUGU | A-818179.4 | ACAUAGfACUGUA | 55.32 | 2.7 |
| 64367.3 | A-126504.5 | dTdAdCdAdGdTdCdTdAdTdGdT | A-126505.23 | dAdCdAdTdAdGdAdCdTdGdTdA | 42.42 | 0 |
| 649417.1 | A-126504.6 | dTdAdCdAdGdTdCdTdAdTdGdT | A-815963.2 | dAdCdAdTdAdG(Ath)dCdTdGdTdA | 43.07 | 0.65 |
| 649418.1 | A-1036755.2 | dTdAdCdAdGdT(Cth)dTdAdTdGdT | A-126505.24 | dAdCdAdTdAdGdAdCdTdGdTdA | 40.64 | −1.78 |
| 649419.1 | A-126504.7 | dTdAdCdAdGdTdCdTdAdTdGdT | A-815962.2 | dAdCdAdTdA(Gth)dAdCdTdGdTdA | 44.22 | 18 |
| 72586.2 | A-140221.2 | dTdAdCdAdG(Tth)dCdTdAdTdGdT | A-126505.25 | dAdCdAdTdAdGdAdCdTdGdTdA | 40.32 | −2.1 |
| 649420.1 | A-140221.3 | dTdAdCdAdG(Tth)dCdTdAdTdGdT | A-815963.3 | dAdCdAdTdAdG(Ath)dCdTdGdTdA | 39.92 | −2.5 |
| 6494211 | A-1036755.3 | dTdAdCdAdGdT(Cth)dTdAdTdGdT | A-815962.3 | dAdCdAdTdA(Gth)dAdCdTdGdTdA | 40.055 | −2.365 |
| 64367.4 | A-126504.8 | dTdAdCdAdGdTdCdTdAdTdGdT | A-126505.26 | dAdCdAdTdAdGdAdCdTdGdTdA | 42.67 | 0 |
| 649422.1 | A-126504.9 | dTdAdCdAdGdTdCdTdAdTdGdT | A-163712.3 | dAdCdAdTdAdGAfdCdTdGdTdA | 42.27 | −0.4 |
| 649423.1 | A-816165.2 | dTdAdCdAdGdTCfdTdAdTdGdT | A-126505.27 | dAdCdAdTdAdGdAdCdTdGdTdA | 42.345 | −0.325 |

TABLE 31-continued

UV thermal melting temperatures of TNA 12-mer duplexes

| Duplex ID | sOligo ID | sOligo Sequence | asOligo ID | asOligo Sequence | Tm (° C.) | ΔTm (° C.) |
|---|---|---|---|---|---|---|
| 649424.1 | A-126504.10 | dTdAdCdAdGdTdCdTdAdTdGdT | A-1036756.2 | dAdCdAdTdAGfdAdCdTdGdTdA | 42.945 | 0.275 |
| 64981.2 | A-129613.2 | dTdAdCdAdGUfdCdTdAdTdGdT | A-126505.28 | dAdCdAdTdAdGdAdCdTdGdTdA | 40.055 | -2.615 |
| 649425.1 | A-129613.3 | dTdAdCdAdGUfdCdTdAdTdGdT | A-163712.4 | dAdCdAdTdAdGAfdCdTdGdTdA | 40.17 | -2.5 |
| 649426.1 | A-816165.3 | dTdAdCdAdGdTCfdTdAdTdGdT | A-1036756.3 | dAdCdAdTdAGfdAdCdTdGdTdA | 42.77 | 0.1 |

(Table 31 discloses SEQ ID NOS 425-480, repectively, in order of columns)

Determination of UV thermal melting temperatures of TNA 21-/23-mer duplexes: Thermal melting temperatures were measured with equimolar concentrations of both strands (1.0 μM) in (a) 0.1×PBS ([NaCl]=14 mM, [KCl]=0.27 mM, [Na$_2$HPO$_4$]=0.8 mM, [KH$_2$PO$_4$]=0.2 mM, pH 7.4) by monitoring A$_{260}$ with increasing temperature (1° C./min). Values were reported as the maximum of the first derivative and are the average of at least two experiments.

TABLE 32

UV thermal melting temperatures of TNA 21-/23-mer duplexes

| Duplex ID | Sense Strand | Antisense Strand | Tm | Δ Tm |
|---|---|---|---|---|
| AD-57727.134 | AfsasCfaGfuGfuUfCfUfuGfcUfcUfaUfaAfL96 | usUfsaUfaGfaGfcAfagaAfcAfcUfgUfususu | 79.02 | 0 |
| AD-126259.1 | (Aths)asCfaGfuGfuUfCfUfuGfcUfcUfaUfaAfL96 | usUfsaUfaGfaGfcAfagaAfcAfcUfgUfususu | 79.12 | 0.1 |
| AD-126260.1 | Afs(Aths)CfaGfuGfuUfCfUfuGfcUfcUfaUfaAfL96 | usUfsaUfaGfaGfcAfagaAfcAfcUfgUfususu | 78.22 | -0.8 |
| AD-126261.1 | Afsas(Cth)aGfuGfuUfCfUfuGfcUfcUfaUfaAfL96 | usUfsaUfaGfaGfcAfagaAfcAfcUfgUfususu | 76.36 | -2.66 |
| AD-126262.1 | AfsasCf(Ath)GfuGfuUfCfUfuGfcUfcUfaUfaAfL96 | usUfsaUfaGfaGfcAfagaAfcAfcUfgUfususu | 76.57 | -2.45 |
| AD-126263.1 | AfsasCfa(Gth)uGfuUfCfUfuGfcUfcUfaUfaAfL96 | usUfsaUfaGfaGfcAfagaAfcAfcUfgUfususu | 75.02 | -4 |
| AD-126264.1 | AfsasCfaGf(Tth)GfuUfCUfuGfcUfcUfaUfaAfL96 | usUfsaUfaGfaGfcAfagaAfcAfcUfgUfususu | 77.02 | -2 |

TABLE 32-continued

UV thermal melting temperatures of TNA 21-/23-mer duplexes

| Duplex ID | Sense Strand | Antisense Strand | Tm | Δ Tm |
|---|---|---|---|---|
| AD-126265.1 | AfsasCfaGfu(Gth)uUfCfUfuGfcUfcUfaUfaAfL96 | usUfsaUfaGfaGfcAfagaAfcAfcUfgUfususu | 76.12 | -2.9 |
| AD-126266.1 | AfsasCfaGfuGf(Tth)UfCfUfuGfcUfcUfaUfaAfL96 | usUfsaUfaGfaGfcAfagaAfcAfcUfgUfususu | 73.22 | -5.8 |
| AD-126267.1 | AfsasCfaGfuGfu(Tth)CfUfuGfcUfcUfaUfaAfL96 | usUfsaUfaGfaGfcAfagaAfcAfcUfgUfususu | 74.36 | -4.66 |
| AD-126268.1 | AfsasCfaGfuGfuUf(Cth)UfuGfcUfcUfaUfaAfL96 | usUfsaUfaGfaGfcAfagaAfcAfcUfgUfususu | 75.02 | -4 |
| AD-126269.1 | AfsasCfaGfuGfuUfCf(Tth)uGfcUfcUfaUfaAfL96 | usUfsaUfaGfaGfcAfagaAfcAfcUfgUfususu | 76.12 | -2.9 |
| AD-126270.1 | AfsasCfaGfuGfuUfefUf(Tth)GfcUfcUfaUfaAfL96 | usUfsaUfaGfaGfcAfagaAfcAfcUfgUfususu | 76.27 | -2.75 |
| AD-126271.1 | AfsasCfaGfuGfuUfefUfu(Gth)cUfcUfaUfaAfL96 | usUfsaUfaGfaGfcAfagaAfcAfcUfgUfususu | 75.42 | -3.6 |
| AD-126272.1 | AfsasCfaGfuGfuUfCfUfuGf(Cth)UfcUfaUfaAfL96 | usUfsaUfaGfaGfcAfagaAfcAfcUfgUfususu | 77.57 | -1.45 |

TABLE 32-continued

UV thermal melting temperatures of TNA 21-/23-mer duplexes

| Duplex ID | Sense Strand | Antisense Strand | Tm | Δ Tm |
|---|---|---|---|---|
| AD-126273.1 | AfsasCfaGfuGfuUfCfUfuGfc(Tth)cUfaUfaAfL96 | usUfsaUfaGfaGfcAfagaAfcAfcUfgUfususu | 75.02 | -4 |
| AD-126274.1 | AfsasCfaGfuGfuUfCfUfuGfcUf(Cth)UfaUfaAfL96 | usUfsaUfaGfaGfcAfagaAfcAfcUfgUfususu | 76.02 | -3 |
| AD-126275.1 | AfsasCfaGfuGfuUfCfUfuGfcUfc(Tth)aUfaAfL96 | usUfsaUfaGfaGfcAfagaAfcAfcUfgUfususu | 76.12 | -2.9 |
| AD-126276.1 | AfsasCfaGfuGfuUfCfUfuGfcUfcUf(Ath)UfaAfL96 | usUfsaUfaGfaGfcAfagaAfcAfcUfgUfususu | 77.27 | -1.75 |
| AD-126277.1 | AfsasCfaGfuGfuUfCfUfuGfcUfcUfa(Tth)aAfL96 | usUfsaUfaGfaGfcAfagaAfcAfcUfgUfususu | 77.42 | -16 |
| AD-126278.1 | AfsasCfaGfuGfuUfCfUfuGfcUfcUfaUf(Ath)AfL96 | usUfsaUfaGfaGfcAfagaAfcAfcUfgUfususu | 79.02 | 0 |
| AD-126279.1 | AfsasCfaGfuGfuUfefUfuGfcUfcUfaUfa(Ath)L96 | usUfsaUfaGfaGfcAfagaAfcAfcUfgUfususu | 78.52 | -0.5 |
| AD-126280.1 | AfsasCfaGfuGfuUfCfUfuGfcUfcUfaUfaAfL96 | (Tths)UfsaUfaGfaGfcAfagaAfcAfcUfgUfususu | 76.87 | -2.15 |
| AD-126281.1 | AfsasCfaGfuGfuUfCfUfuGfcUfcUfaUfaAfL96 | us(Tths)aUfaGfaGfcAfagaAfcAfcUfgUfususu | 78.53 | -0.49 |
| AD-126282.1 | AfsasCfaGfuGfuUfCfUfuGfcUfcUfaUfaAfL96 | usUfs(Ath)UfaGfaGfcAfagaAfcAfcUfgUfususu | 78.27 | -0.75 |
| AD-126283.1 | AfsasCfaGfuGfuUfCfUfuGfcUfcUfaUfaAfL96 | usUfsa(Tth)aGfaGfcAfagaAfcAfcUfgUfususu | 77.87 | -1.15 |
| AD-126284.1 | AfsasCfaGfuGfuUfCfUfuGfcUfcUfaUfaAfL96 | usUfsaUf(Ath)GfaGfcAfagaAfcAfcUfgUfususu | 79.02 | 0 |
| AD-126285.1 | AfsasCfaGfuGfuUfCfUfuGfcUfcUfaUfaAfL96 | usUfsaUfa(Gth)aGfcAfagaAfcAfcUfgUfususu | 75.52 | -3.5 |
| AD-126286.1 | AfsasCfaGfuGfuUfCfUfuGfcUfcUfaUfaAfL96 | usUfsaUfaGf(Ath)GfcAfagaAfcAfcUfgUfususu | 75.87 | -3.15 |
| AD-126287.1 | AfsasCfaGfuGfuUfCfUfuGfcUfcUfaUfaAfL96 | usUfsaUfaGfa(Gth)cAfagaAfcAfcUfgUfususu | 74.53 | -4.49 |
| AD-126288.1 | AfsasCfaGfuGfuUfCfUfuGfcUfcUfaUfaAfL96 | usUfsaUfaGfaGf(Cth)AfagaAfcAfcUfgUfususu | 76.02 | -3 |
| AD-126289.1 | AfsasCfaGfuGfuUfCfUfuGfcUfcUfaUfaAfL96 | usUfsaUfaGfaGfc(Ath)agaAfcAfcUfgUfususu | 75.12 | -3.9 |
| AD-126290.1 | AfsasCfaGfuGfuUfCfUfuGfcUfcUfaUfaAfL96 | usUfsaUfaGfaGfcAf(Ath)gaAfcAfcUfgUfususu | 77.22 | -18 |
| AD-126291.1 | AfsasCfaGfuGfuUfCfUfuGfcUfcUfaUfaAfL96 | usUfsaUfaGfaGfcAfa(Gth)aAfcAfcUfgUfususu | 75.42 | -3.6 |
| AD-126292.1 | AfsasCfaGfuGfuUfCfUfuGfcUfcUfaUfaAfL96 | usUfsaUfaGfaGfcAfag(Ath)AfcAfcUfgUfususu | 75.57 | -3.45 |
| AD-126293.1 | AfsasCfaGfuGfuUfCfUfuGfcUfcUfaUfaAfL96 | usUfsaUfaGfaGfcAfaga(Ath)cAfcUfgUfususu | 76.02 | -3 |
| AD-126294.1 | AfsasCfaGfuGfuUfCfUfuGfcUfcUfaUfaAfL96 | usUfsaUfaGfaGfcAfagaAf(Cth)AfcUfgUfususu | 77.02 | -2 |
| AD-126295.1 | AfsasCfaGfuGfuUfCfUfuGfcUfcUfaUfaAfL96 | usUfsaUfaGfaGfcAfagaAfc(Ath)cUfgUfususu | 77.12 | -19 |
| AD-126296.1 | AfsasCfaGfuGfuUfCfUfuGfcUfcUfaUfaAfL96 | usUfsaUfaGfaGfcAfagaAfcAf(Cth)UfgUfususu | 77.22 | -18 |
| AD-126297.1 | AfsasCfaGfuGfuUfCfUfuGfcUfcUfaUfaAfL96 | usUfsaUfaGfaGfcAfagaAfcAfc(Tth)gUfususu | 73.42 | -5.6 |
| AD-126298.1 | AfsasCfaGfuGfuUfCfUfuGfcUfcUfaUfaAfL96 | usUfsaUfaGfaGfcAfagaAfcAfcUf(Gth)Ufususu | 77.02 | -2 |
| AD-126299.1 | AfsasCfaGfuGfuUfCfUfuGfcUfcUfaUfaAfL96 | usUfsaUfaGfaGfcAfagaAfcAfcUfg(Tth)ususu | 77.12 | -19 |
| AD-1263C0.1 | AfsasCfaGfuGfuUfCfUfuGfcUfcUfaUfaAfL96 | usUfsaUfaGfaGfcAfagaAfcAfcUfgUf(Tths)usu | 78.32 | -0.7 |

TABLE 32-continued

UV thermal melting temperatures of
TNA 21-/23-mer duplexes

| Duplex ID | Sense Strand | Antisense Strand | Tm | Δ Tm |
|---|---|---|---|---|
| AD-126301.1 | AfsasCfaGfuGfuUfCfUfuGfcUfcUfaUfaAfL96 | usUfsaUfaGfaGfcAfagaAfcAfcUfgUfus(Tths)u | 79.52 | 0.5 |
| AD-126302.1 | AfsasCfaGfuGfuUfCfUfuGfcUfcUfaUfaAfL96 | usUfsaUfaGfaGfcAfagaAfcAfcUfgUfusus(Tth) | 77.66 | -1.36 |
| AD-57727.135 | AfsasCfaGfuGfuUfCfUfuGfcUfcUfaUfaAfL96 | usUfsaUfaGfaGfcAfagaAfcAfcUfgUfususu | 75.02 | 0 |
| AD-134022.1 | (Aths)asCfaGfuGfuUfCfUfuGfcUfcUfaUfaAfL96 | usUfsaUfaGfaGfcAfagaAfcAfcUfgUf(Tths)usu | 78.02 | 3 |
| AD-134023.1 | Afs(Aths)CfaGfuGfuUfCfUfuGfcUfcUfaUfaAfL96 | usUfsaUfaGfaGfcAfagaAfcAfcUfg(Tth)ususu | 77.12 | 2.1 |
| AD-134024.1 | Afsas(Cth)aGfuGfuUfCfUfuGfcUfcUfaUfaAfL96 | usUfsaUfaGfaGfcAfagaAfcAfcUf(Gth)Ufususu | 75.32 | 0.3 |
| AD-134025.1 | AfsasCf(Ath)GfuGfuUfCfUfuGfcUfcUfaUfaAfL96 | usUfsaUfaGfaGfcAfagaAfcAfc(Tth)gUfususu | 74.52 | -0.5 |
| AD-134026.1 | AfsasCfa(Gth)uGfuUfCfUfuGfcUfcUfaUfaAfL96 | usUfsaUfaGfaGfcAfagaAfcAf(Cth)UfgUfususu | 73.02 | -2 |
| AD-134027.1 | AfsasCfaGf(Tth)GfuUfCfUfuGfcUfcUfaUfaAfL96 | usUfsaUfaGfaGfcAfagaAfc(Ath)cUfgUfususu | 74.12 | -0.9 |
| AD-134028.1 | AfsasCfaGfu(Gth)uUfCfUfuGfcUfcUfaUfaAfL96 | usUfsaUfaGfaGfcAfagaAf(Cth)AfcUfgUfususu | 73.32 | -17 |
| AD-134029.1 | AfsasCfaGfuGf(Tth)UfCfUfuGfcUfcUfaUfaAfL96 | usUfsaUfaGfaGfcAfaga(Ath)cAfcUfgUfususu | 73.52 | -15 |
| AD-134030.1 | AfsasCfaGfuGfu(Tth)CfUfuGfcUfcUfaUfaAfL96 | usUfsaUfaGfaGfcAfag(Ath)AfcAfcUfgUfususu | 71.66 | -3.36 |
| AD-134031.1 | AfsasCfaGfuGfuUf(Cth)UfuGfcUfcUfaUfaAfL96 | usUfsaUfaGfaGfcAfa(Gth)aAfcAfcUfgUfususu | 71.02 | -4 |
| AD-134032.1 | AfsasCfaGfuGfuUfCf(Tth)uGfcUfcUfaUfaAfL96 | usUfsaUfaGfaGfcAf(Ath)gaAfcAfcUfgUfususu | 74.02 | -1 |
| AD-134033.1 | AfsasCfaGfuGfuUfefUf(Tth)GfcUfcUfaUfaAfL96 | usUfsaUfaGfaGfc(Ath)agaAfcAfcUfgUfususu | 73.12 | -19 |
| AD-134034.1 | AfsasCfaGfuGfuUfefUfu(Gth)cUfcUfaUfaAfL96 | usUfsaUfaGfaGf(Cth)AfagaAfcAfcUfgUfususu | 73.52 | -15 |
| AD-134035.1 | AfsasCfaGfuGfuUfCfUfuGf(Tth)UfcUfaUfaAfL96 | usUfsaUfaGfa(Gth)cAfagaAfcAfcUfgUfususu | 71.02 | -4 |
| AD-134036.1 | AfsasCfaGfuGfuUfCfUfuGfc(Tth)cUfaUfaAfL96 | usUfsaUfaGf(Ath)GfcAfagaAfcAfcUfgUfususu | | |
| AD-134037.1 | AfsasCfaGfuGfuUfCfUfuGfcUf(Cth)UfaUfaAfL96 | usUfsaUfa(Gth)aGfcAfagaAfcAfcUfgUfususu | 72.12 | -2.9 |
| AD-134038.1 | AfsasCfaGfuGfuUfCfUfuGfcUfc(Tth)aUfaAfL96 | usUfsaUf(Ath)GfaGfcAfagaAfcAfcUfgUfususu | 73.32 | -17 |
| AD-134039.1 | AfsasCfaGfuGfuUfCfUfuGfcUfcUf(Ath)UfaAfL96 | usUfsa(Tth)aGfaGfcAfagaAfcAfcUfgUfususu | 74.52 | -0.5 |
| AD-134040.1 | AfsasCfaGfuGfuUfCfUfuGfcUfcUfa(Tth)aAfL96 | usUfs(Ath)UfaGfaGfcAfagaAfcAfcUfgUfususu | 76.66 | 1.64 |
| AD-134041.1 | AfsasCfaGfuGfuUfCfUfuGfcUfcUfaUf(Ath)AfL96 | us(Tths)aUfaGfaGfcAfagaAfcAfcUfgUfususu | 78.02 | 3 |
| AD-134042.1 | AfsasCfaGfuGfuUfefUfuGfcUfcUfaUfa(Ath)L96 | (Tths)UfsaUfaGfaGfcAfagaAfcAfcUfgUfususu | 78.02 | 3 |

(Table 32 discloses SEQ ID NOS 481-614, repectively, in order of columns)

Stability of modified oligonucleotides toward 3'- or 5'-specific exonucleases: Modified oligonucleotides were prepared in a final concentration of 0.1 mg/mL in either 300 mM Tris (pH 7.2), 60 mM MgCl$_2$ or 300 mM sodium acetate (pH 6.5), 60 mM MgCl$_2$ for assessing the stability towards 3'- or 5'-specific exonucleases, respectively. The exonuclease (15 mU/mL SVPDE for 3'-stability or 500 mU/mL phosphodiesterase II for 5'-stability) was added immediately prior to analysis via IEX HPLC (dionex DNAPac PA200, 4×250 mm) using a gradient of 31-52% mobile phase (1 M NaBr, 20 mM sodium phosphate, pH 11, 15% MeCN; stationary phase: 20 mM sodium phosphate, 15% MeCN, pH 11) over 16 min with a flow of 1 mL/min. Samples were analyzed at given time points for up to 24 h. The quantity of full length oligonucleotides was determined as the area under the curve at A$_{260}$. Percent full length oligonucleotides was calculated by dividing by the area under the curve at t=0 and multiplying by 100. Activity of enzyme was verified for each experiment by including a oligodeoxythymidylate with a terminal phosphorothioate linkage (5'-T$_{19}$·T (SEQ ID NO: 708) or 5'-T·T$_{19}$ (SEQ ID NO: 708) for 3'- or 5'-exonuclease activity, respectively). Each aliquot of enzyme was thawed just prior to the experiment. The half-life was determined by fitting to first order kinetics.

Figure 34:
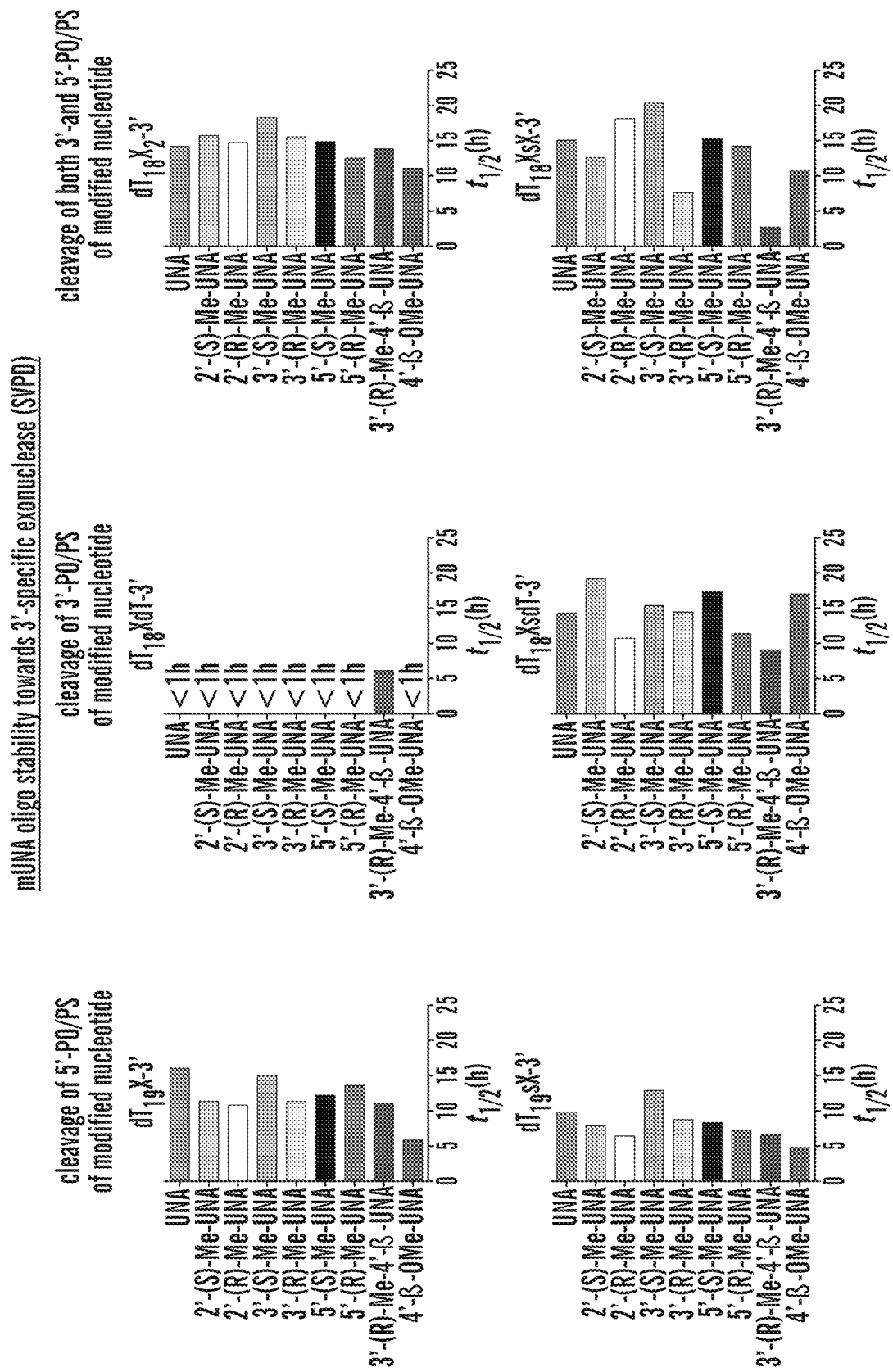
FIG. 34 shows plots of mUNA oligo stability towards 3'-specific exonuclease (SVPD).
Figure 35:
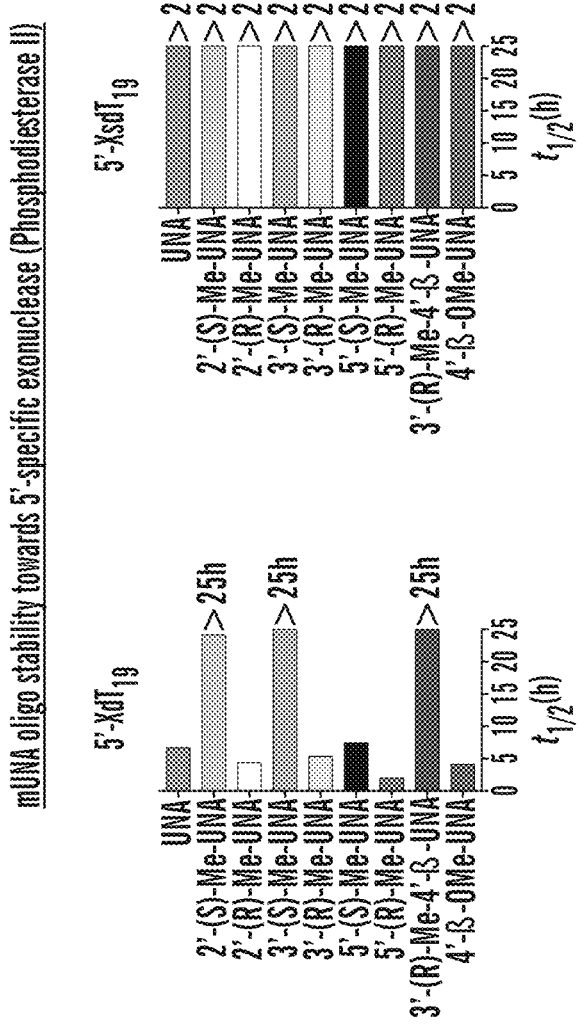
FIG. 35 shows plots of mUNA oligo stability towards 5'-specific exonuclease (Phosphodiesterase II).
Figure 36:
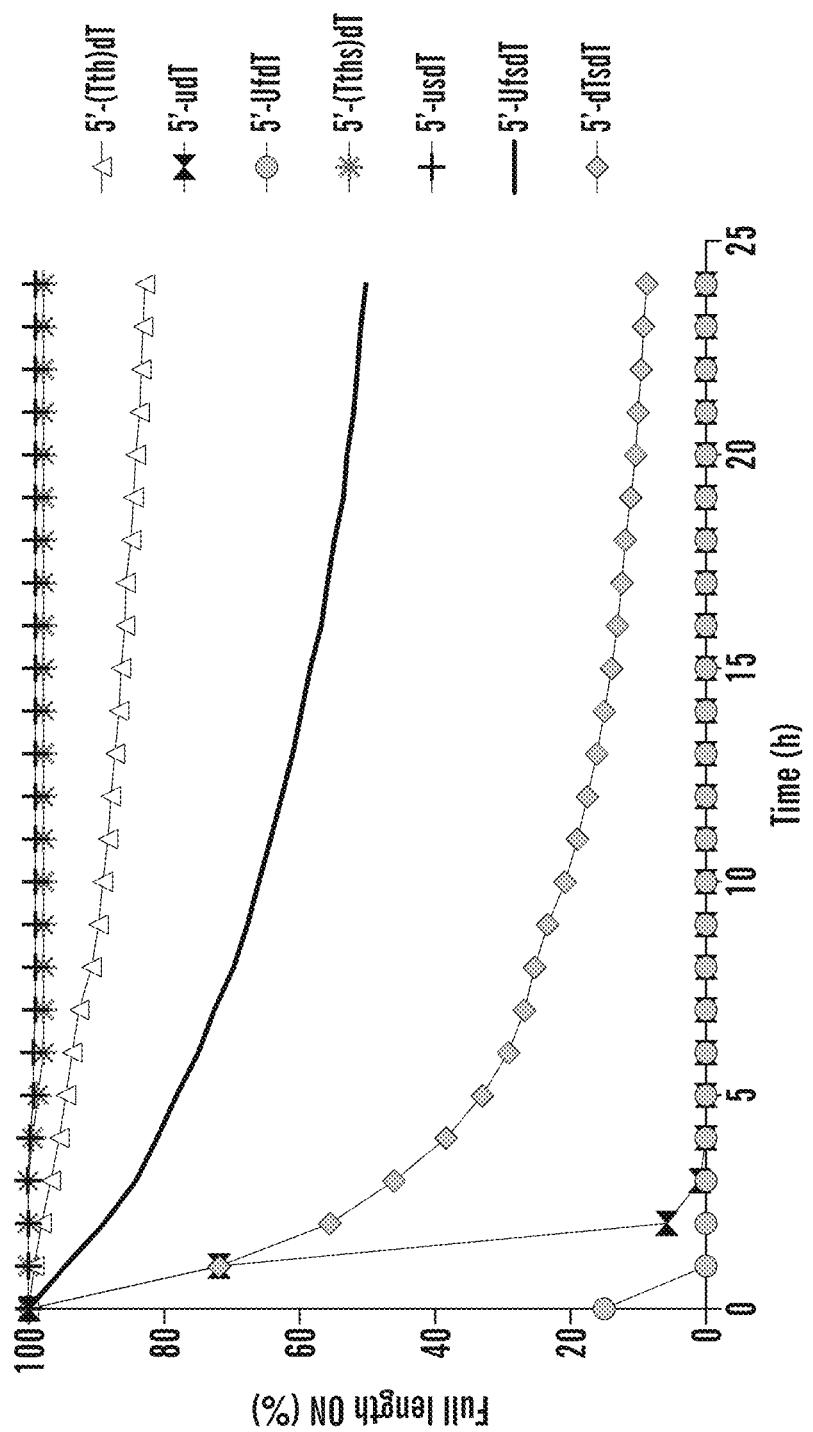
FIG. 36 shows a line graph of Stability of TNA-T against S'-exonuclease (phosphodiesterase II) degradation.

FIG. 34 shows plots of mUNA oligo stability towards 3'-specific exonuclease (SVPD). FIG. 35 shows plots of mUNA oligo stability towards 5'-specific exonuclease (Phosphodiesterase II). FIG. 36 shows a line graph of Stability of TNA-T against 5'-exonuclease (phosphodiesterase II) degradation.

TABLE 33

In vitro reporter assays for antisense strand modified duplexes (position 7).

| | | On-Target IC$_{50}$ (nM) | Off-Target IC$_{50}$ (nM) |
|---|---|---|---|
| TTR-4 | Parent (AD-125773) | 0.136 | 1.21 |
| | (S)-GNA | 0.176 | 10.8 |
| | 5'-(S)-mUNA Mod 5 (S): Y95 | 0.0421 | 8.73 |
| | 5'-(R)-mUNA Mod 5 (R): Y97 | 0.0898 | 8.13 |
| | 2'-(S)-mUNA Mod 7 (S): Y96 | 0.0486 | 1.35 |
| | 2'-(R)-mUNA Mod 7 (R): Y98 | 0.0277 | 1.61 |
| | 3'-(S)-mUNA Mod 6 (S): Y99 | 0.0239 | 3.65 |
| | 3'-(R)-mUNA Mod 6 (R): Y100 | 0.0358 | 2.86 |
| | UNA | 0.0463 | 1.80 |

On-target activity measured in primary mouse hepatocytes via transfection at the indicated concentrations. Off-target IC50s measured using luciferase reporter plasmids which were co-transfected with siRNAs into COS-7 cells.

TABLE 34

In vitro reporter assays for antisense strand modified duplexes (position 5).

| | | On-Target IC$_{50}$ (nM) | Off-Target IC$_{50}$ (nM) |
|---|---|---|---|
| TTR-3 | Parent (AD-125762) | 0.0502 | >50 |
| | (S)-GNA | 0.00298 | >50 |
| | 5'-(S)-mUNA Mod 5 (S): Y95 | 0.00110 | >50 |
| | 5'-(R)-mUNA Mod 5 (R): Y97 | 0.00147 | >50 |
| | 2'-(S)-mUNA Mod 7 (S): Y96 | 0.00254 | >50 |
| | 2'-(R)-mUNA Mod 7 (R): Y98 | 0.00064 | >50 |
| | 3'-(S)-mUNA Mod 6 (S): Y99 | 0.00316 | >50 |
| | 3'-(R)-mUNA Mod 6 (R): Y100 | 0.00157 | >50 |
| | 4'-OMe-mUNA: Y101 | 0.00488 | >50 |
| | UNA | 0.00064 | >50 |

On-target activity measured in primary mouse hepatocytes via transfection at the indicated concentrations. Off-target IC50s measured using luciferase reporter plasmids which were co-transfected with siRNAs into COS-7 cells.

TABLE 35

In vitro reporter assays for antisense strand modified duplexes (position 7).

| | | On-Target IC$_{50}$ (nM) | Off-Target IC$_{50}$ (nM) |
|---|---|---|---|
| TTR-3 | Parent (AD-125762) | 0.0502 | >50 |
| | (S)-GNA | 0.0160 | >50 |
| | 5'-(S)-mUNA Mod 5 (S): Y95 | 0.0150 | >50 |
| | 5'-(R)-mUNA Mod 5 (R): Y97 | 0.0138 | >50 |
| | 2'-(S)-mUNA Mod 7 (S): Y96 | 0.0235 | >50 |
| | 2'-(R)-mUNA Mod 7 (R): Y98 | 0.0186 | >50 |
| | 3'-(S)-mUNA Mod 6 (S): Y99 | 0.0322 | >50 |
| | 3'-(R)-mUNA Mod 6 (R): Y100 | 0.0348 | >50 |
| | 4'-OMe-mUNA: Y101 | 0.0391 | >50 |
| | UNA | 0.0115 | >50 |

On-target activity measured in primary mouse hepatocytes via transfection at the indicated concentrations. Off-target IC50s measured using luciferase reporter plasmids which were co-transfected with siRNAs into COS-7 cells.

Figure 37:
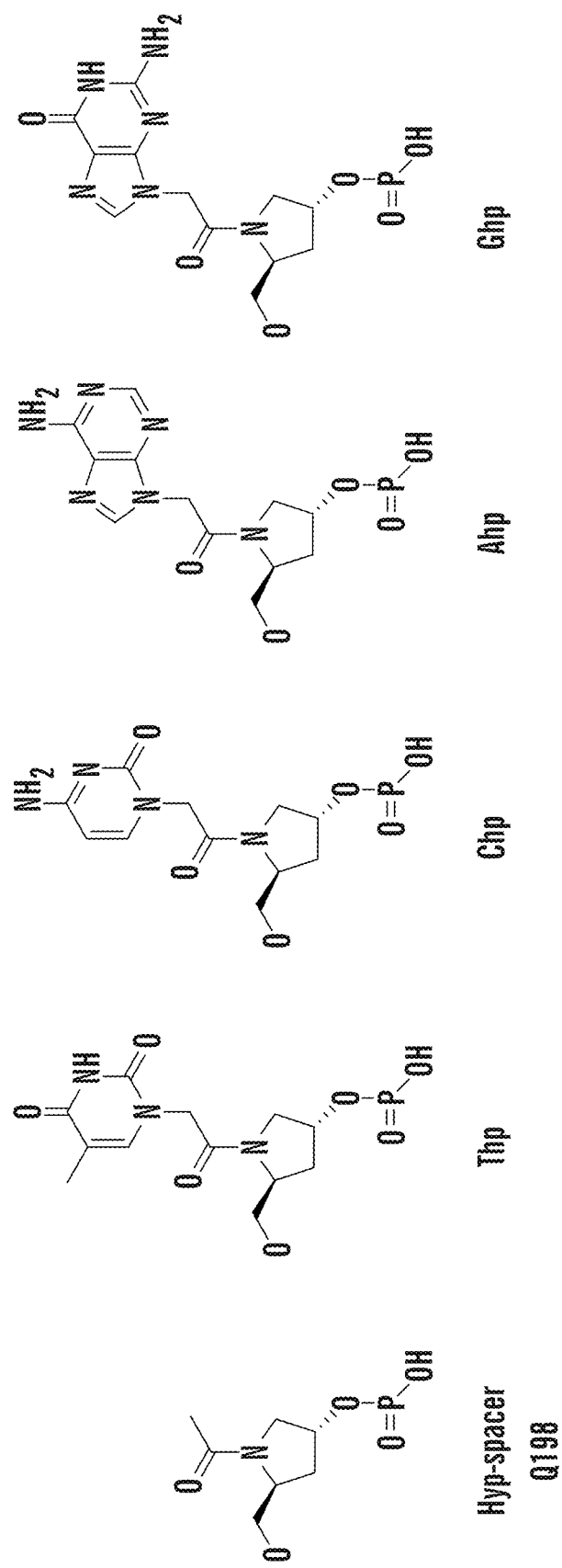
FIG. 37 shows the structure of Hyp monomers.

TTR in vitro gene silencing with Hyp-based Nucleosides was studied. Sequences used are shown in Table 35. FIG. 37 shows the structure of Hyp monomers.

TABLE 35

TTR in vitro gene silencing with Hyp-based Nucleosides (Table 35 discloses SEQ ID NOS 615-636, respectively, in order of columns)

| AD-64958.64 | TTR | A-128009.253 | asascaguGfuUfCfUfugcucuauaaL96 | A-126312.73 | usUfsauaGfagcaagaAfc Afcuguususu |
| AD-307612.2 | TTR | A-128009.257 | asascaguGfuUfCfUfugcucuauaaL96 | A-594468.1 | usUfsaQ198aGfagcaagaAfc Afcuguususu |
| AD-307611.2 | TTR | A-128009.256 | asascaguGfuUfCfUfugcucuauaaL96 | A-594467.1 | usUfsa(Thp)aGfagcaagaAfc Afcuguususu |
| AD-307614.2 | TTR | A-128009.259 | asascaguGfuUfCfUfugcucuauaaL96 | A-173412.2 | usUfsauQ198GfagcaagaAfc Afcuguususu |

TABLE 35-continued

TTR in vitro gene silencing with Hyp-based Nucleosides (Table 35 discloses SEQ ID NOS 615-636, respectively, in order of columns)

| | | | | | |
|---|---|---|---|---|---|
| AD-307613.2 | TTR | A-128009.258 | asascaguGfuUfCfUfugcucuauaaL96 | A-594469.1 | usUfsau(Ahp)GfagcaagaAfcAfcuguususu |
| AD-307616.2 | TTR | A-128009.261 | asascaguGfuUfCfUfugcucuauaaL96 | A-173413.2 | usUfsauaQ198agcaagaAfcAfcuguususu |
| AD-307615.2 | TTR | A-128009.260 | asascaguGfuUfCfUfugcucuauaaL96 | A-594470.1 | usUfsaua(Ghp)agcaagaAfcAfcuguususu |
| AD-133416.3 | TTR | A-128009.263 | asascaguGfuUfCfUfugcucuauaaL96 | A-173414.2 | usUfsauaGfQ198gcaagaAfcAfcuguususu |
| AD-307617.2 | TTR | A-128009.262 | asascaguGfuUfCfUfugcucuauaaL96 | A-594471.1 | usUfsauaGf(Ahp)gcaagaAfcAfcuguususu |
| AD-133417.3 | TTR | A-128009.265 | asascaguGfuUfCfUfugcucuauaaL96 | A-173415.2 | usUfsauaGfaQ198caagaAfcAfcuguususu |
| AD-307618.2 | TTR | A-128009.264 | asascaguGfuUfCfUfugcucuauaaL96 | A-594472.1 | usUfsauaGfa(Ghp)caagaAfcAfcuguususu |

Figure 38:
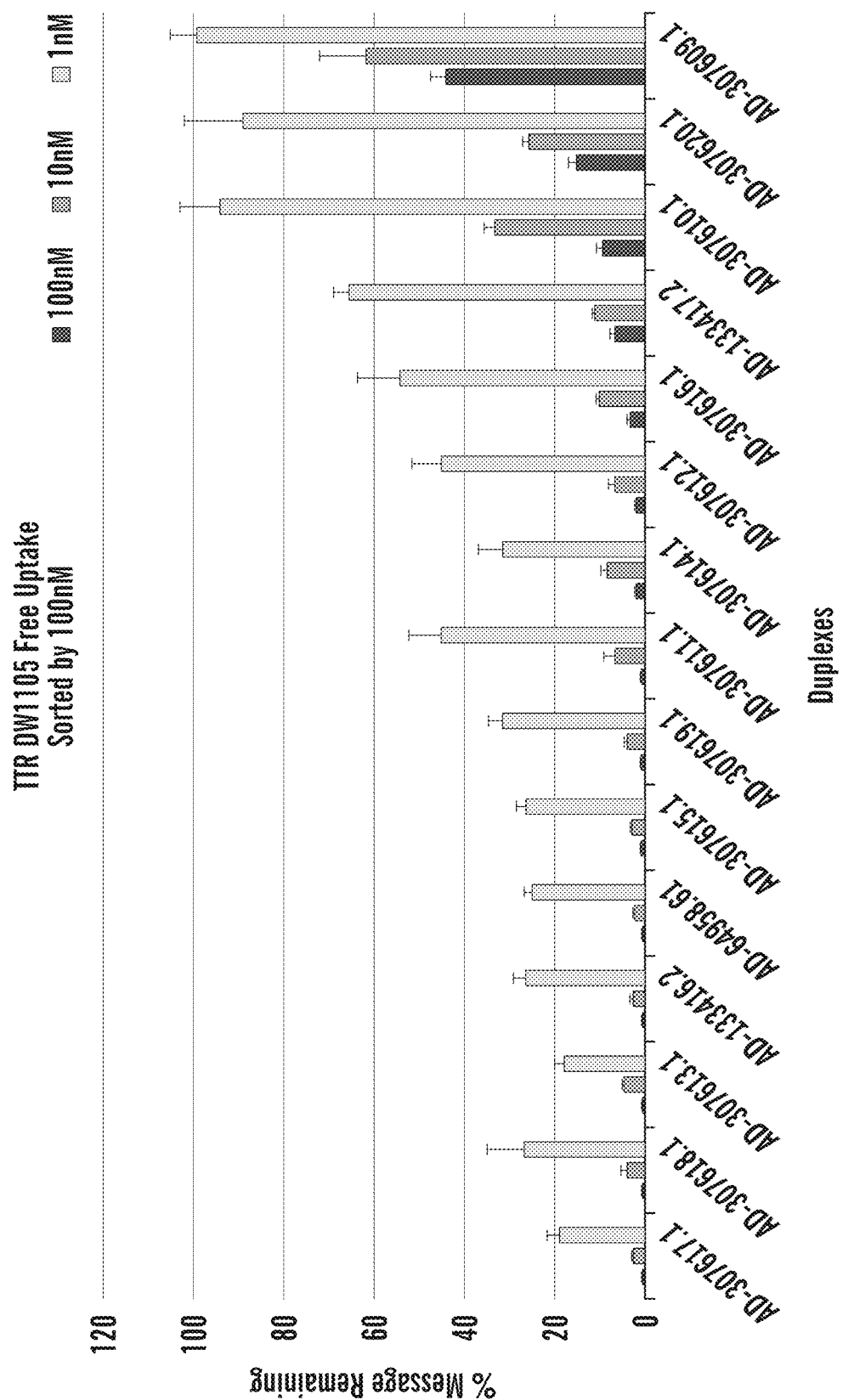
FIG. 38 shows a plot of TTR DW1105 Free Uptake Sorted by 100 nM.

FIG. 38 shows a plot of TTR DW1105 Free Uptake Sorted by 100 nM.

GO1 in vitro gene silencing with Hyp-based Nucleosides. Sequences used are shown in Table 36. Transfection results are summarized in Table 37.

Table 36: shows in vitro gene silencing with Hyp-based Nucleosides (Table 36 discloses SEQ ID NOS 637-666, respectively, in order of columns)

| Duplex Name | sense-Oligo | Sense oligoSeq | antis-Oligo | Antisense oligoSeq |
|---|---|---|---|---|
| AD-65644.56 | A-131560.208 | gsasauguGfaaAfGfucaucgacaaL96 | A-131569.40 | usUfsgucGfaUfGfacuuUfcAfcauucsusg |
| AD-307622.1 | A-131560.1 | gsasauguGfaaAfGfucaucgacaaL96 | A-S94476.1 | usUfsQ198ucGfaUfGfacuuUfcAfcauucsusg |
| AD-307621.1 | A-131560.1 | gsasauguGfaaAfGfucaucgacaaL96 | A-594475.1 | usUfs(Ghp)ucGfsUfGfacuuUfcAfcauucsusg |
| AD-307624.1 | A-131560.1 | gsasauguGfaaAfGfucaucgacaaL96 | A-594478.1 | usUfsgQ198cGfaUfGfacuuUfcAfcauucsusg |
| AD-307623.1 | A-131560.1 | gsasauguGfaaAfGfucaucgacaaL96 | A-594477.1 | usUfsg(Thp)cGfaUfGfacuUfcAfcauucsusg |
| AD-79731.3 | A-131560.214 | gsasauguGfaaAfGfucaucgacaaL96 | A-157540.2 | usUfsguQ198GfaUfGfacuuUfcAfcauucsusg |
| AD-307625.1 | A-131560.1 | gsasauguGfaaAfGfucaucgacaaL96 | A-594479.1 | usUfsgu(Chp)GfaUfGfacuuUfcAfcauucsusg |

-continued

| Duplex Name | sense-Oligo | Sense oligoSeq | antis-Oligo | Antisense oligoSeq |
|---|---|---|---|---|
| AD-79732.3 | A-131560.216 | gsasauguGf aaAfGfucau cgacaaL96 | A-157541.2 | usUfsgucQ1 98aUfGfacu uUfcAfcauu csusg |
| AD-307626.1 | A-131560.1 | gsasauguGf aaAfGfucau cgacaaL96 | A-594480.1 | usUfsguc(G hp)aUfGfac uuUfcAfcau ucsusg |
| AD-79733.3 | A-131560.218 | gsasauguGf aaAfGfucau cgacaaL96 | A-157542.2 | usUfsgucGf Q198UfGfac uuUfcAfcau ucsusg |
| AD-307627.1 | A-131560.1 | gsasauguGf aaAfGfucau cgacaaL96 | A-594481.1 | usUfsgucGf (Ahp)UfGac uuUfcAfcau ucsusg |
| AD-79734.2 | A-131560.220 | gsasauguGf aaAfGfucau cgacaaL96 | A-157543.2 | usUfsgucGf aq198Gfacu uUfcAfcauu csusg |
| AD-307628.1 | A-131560.1 | gsasauguGf aaAfGfucau cgacaaL96 | A-594432.1 | usUfsgucGf a(Thp)Gfac uuUfcAfcau ucsusg |
| AD-307630.1 | A-131560.1 | gsasauguGf aaAfGfucau cgacaaL96 | A-594484.1 | usUfsgucGf aUfQ198acu uUfcAfcauu csusg |
| AD-307629.1 | A-131560.1 | gsasauguGf aaAfGfucau cgacaaL96 | A-594483.1 | usUfsgucGf aUf(Ghp)ac uuUfcAfcau ucsusg |

TABLE 38

Summary of Transfection Data

| | Transfection Lipofecatamine RNAi Max | | | | Free Uptake | | | |
|---|---|---|---|---|---|---|---|---|
| DuplexID | 10 nM avg | stdev | 1 nM avg | stdev | 100 nM avg | stdev | 10 nM avg | stdev |
| AD-65644.56 | 29.31 | 4.57 | 69.13 | 11.95 | 50.83 | 5.89 | 75.69 | 15.45 |
| AD-307622.1 | 88.33 | 10.52 | 95.64 | 8.55 | 77.77 | 9.32 | 95.75 | 5.74 |
| AD-307621.1 | 77.53 | 6.67 | 99.29 | 21.13 | 71.37 | 12.67 | 85.72 | 12.97 |
| AD-307624.1 | 46.38 | 10.86 | 65.47 | 4.47 | 35.79 | 4.49 | 70.71 | 11.88 |
| AD-307623.1 | 44.82 | 11.32 | 58.87 | 9.56 | 42.79 | 12.66 | 69.34 | 8.79 |
| AD-79731.3 | 21.16 | 5.72 | 30.52 | 8.50 | 23.23 | 8.11 | 28.14 | 3.38 |
| AD-307625.1 | 13.33 | 4.62 | 48.54 | 6.89 | 14.25 | 3.10 | 29.87 | 4.60 |
| AD-79732.3 | 27.23 | 6.56 | 66.07 | 5.19 | 32.58 | 4.45 | 49.26 | 3.70 |
| AD-307626.1 | 25.27 | 4.22 | 67.26 | 11.98 | 29.18 | 1.39 | 45.34 | 9.25 |
| AD-79733.3 | 20.85 | 4.68 | 56.48 | 3.60 | 32.37 | 5.98 | 54.74 | 5.19 |
| AD-307627.1 | 13.48 | 1.86 | 61.15 | 14.49 | 26.84 | 8.42 | 61.67 | 3.77 |
| AD-79734.2 | 62.55 | 12.23 | 108.90 | 20.01 | 74.62 | 5.98 | 98.33 | 9.78 |
| AD-307628.1 | 31.92 | 2.64 | 86.18 | 14.10 | 45.23 | 4.75 | 72.39 | 8.91 |
| AD-307630.1 | 101.07 | 5.58 | 131.38 | 9.03 | 92.59 | 10.68 | 87.94 | 4.58 |
| AD-307629.1 | 38.85 | 10.20 | 87.79 | 14.73 | 55.91 | 16.56 | 70.17 | 5.57 |

Figure 39:
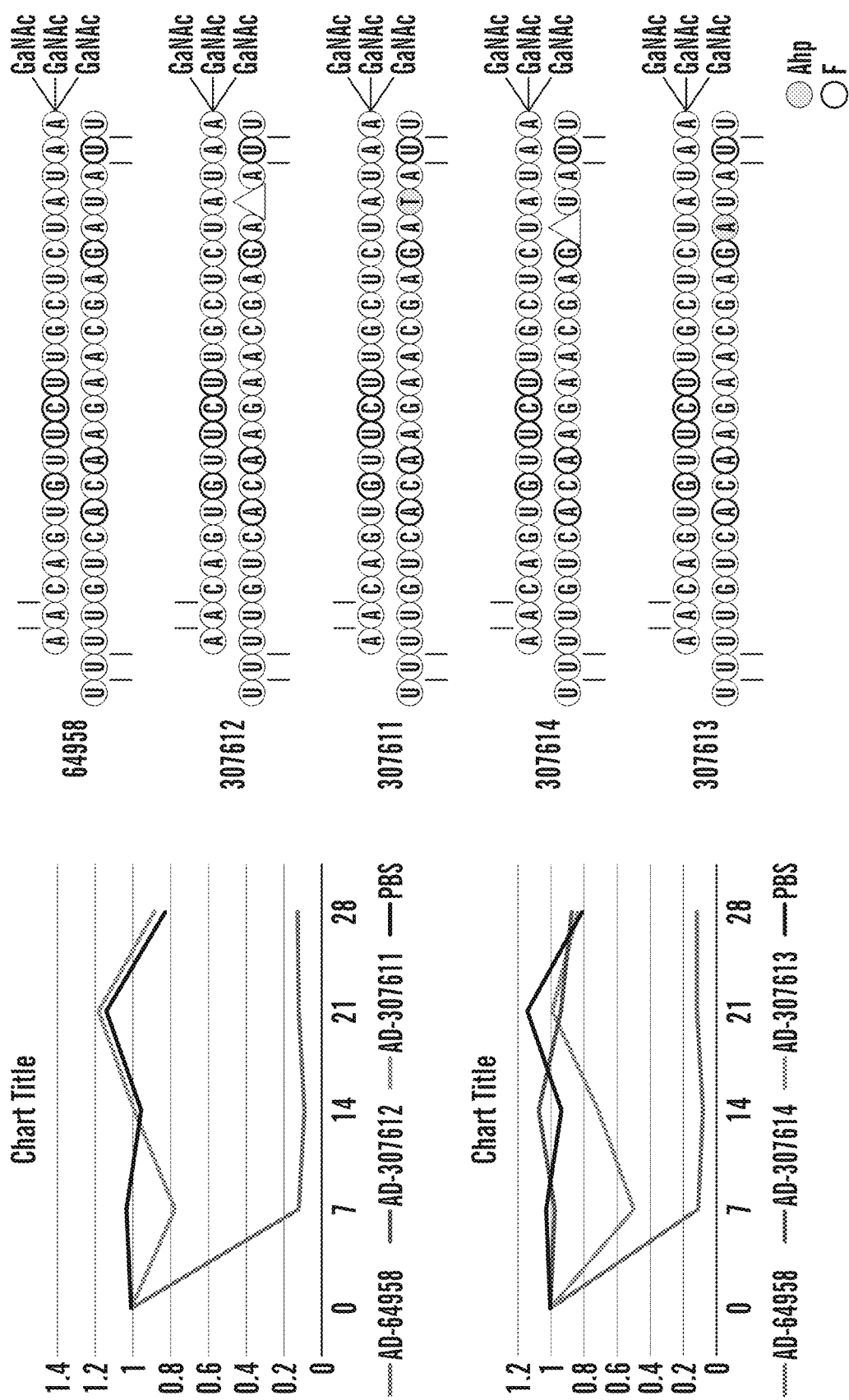
FIG. 39, FIG. 40 and FIG. 41 are line graphs showing in vivo gene silencing with Hyp-based Nucleosides.
Figure 40:
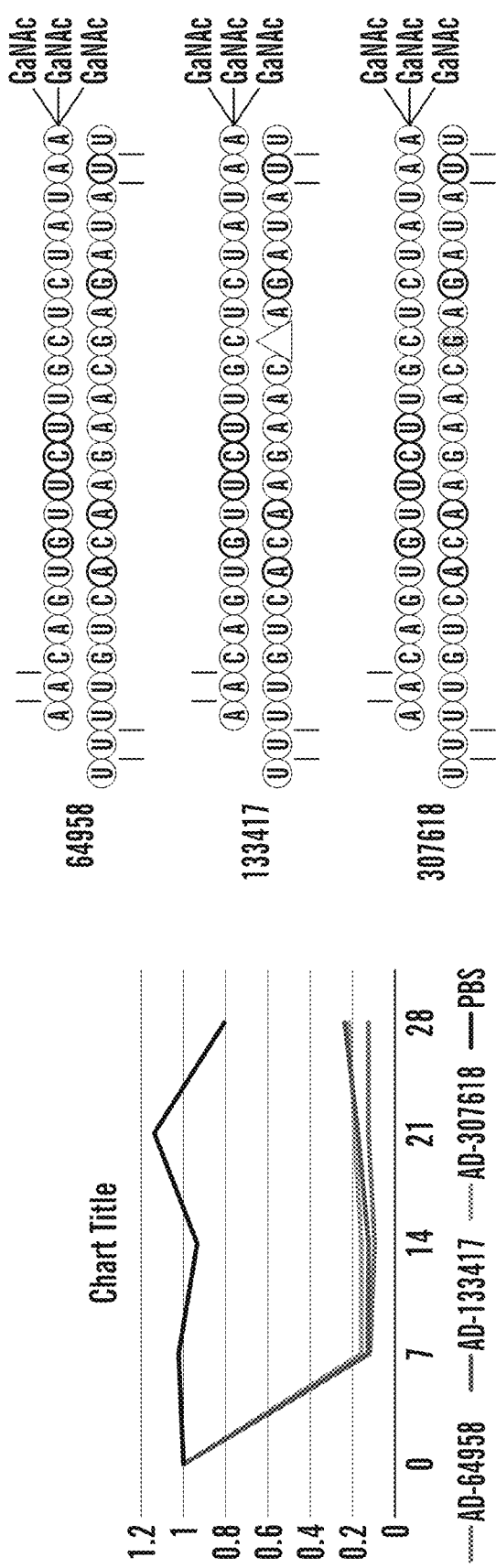
Figure 41:
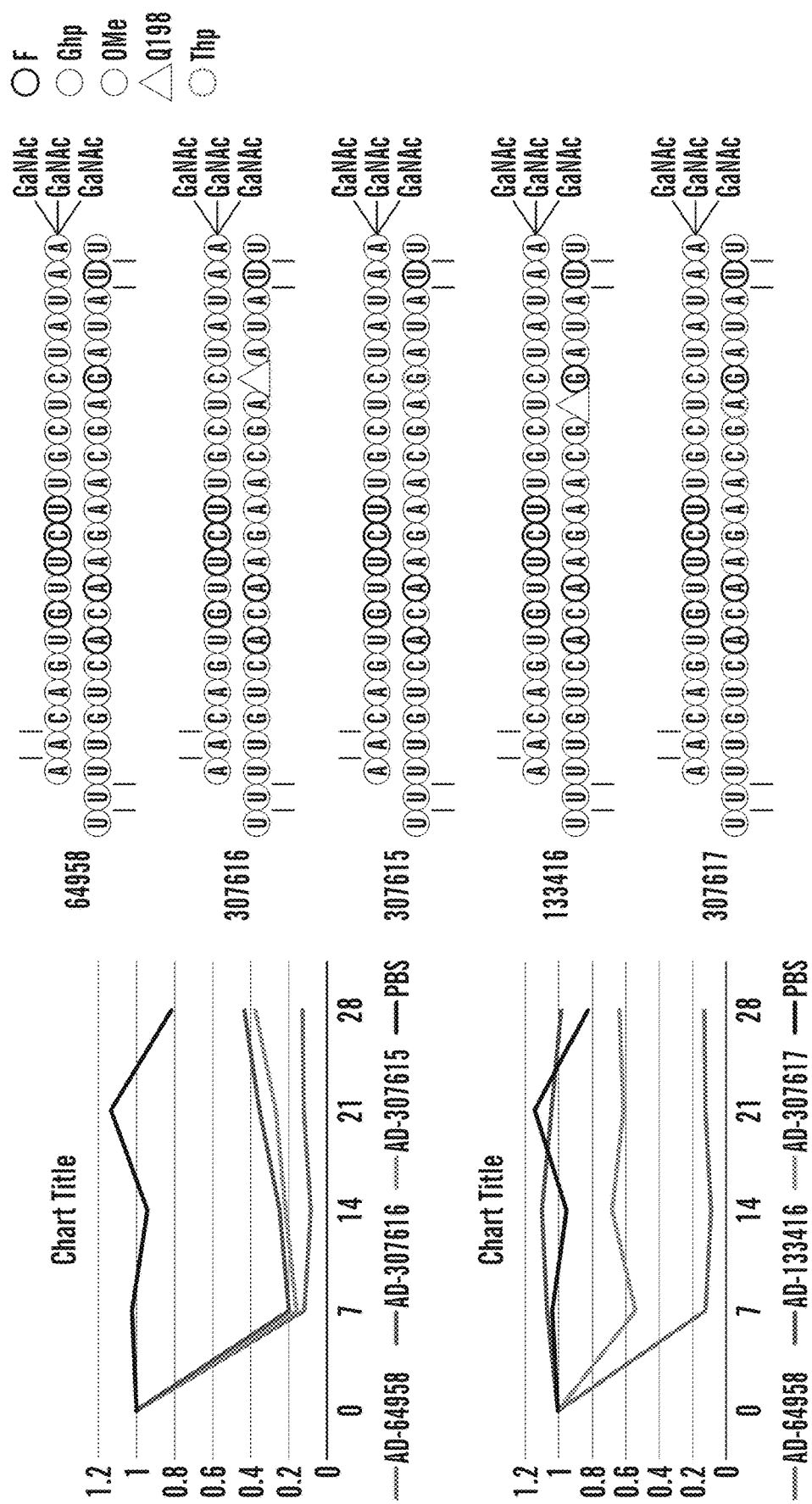
Figure 42:
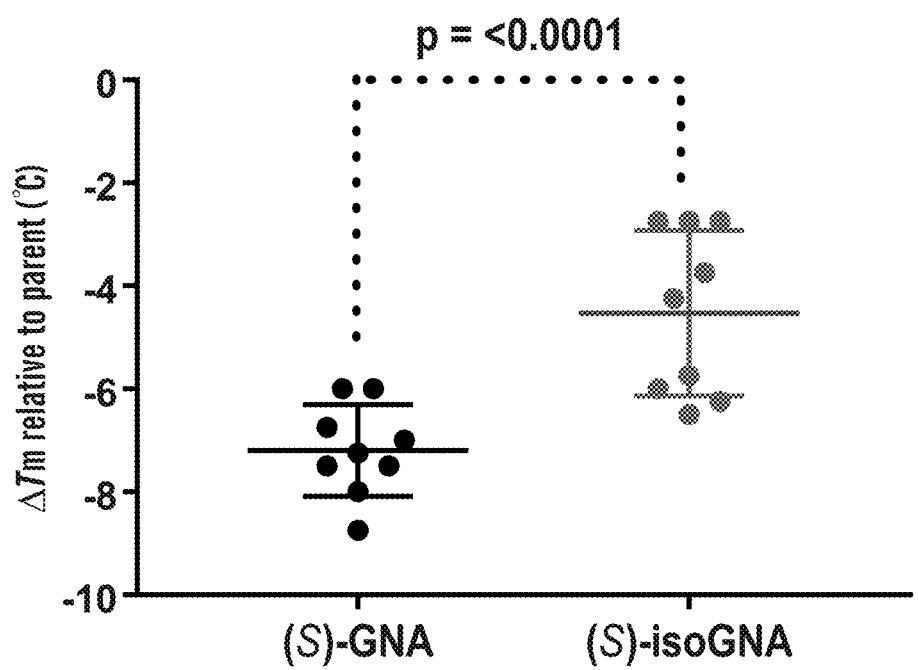
FIG. 42 is a probability plot showing Incorporation of (S)-isoGNA is significantly less thermally destabilizing than (S)-GNA.
Figure 43:
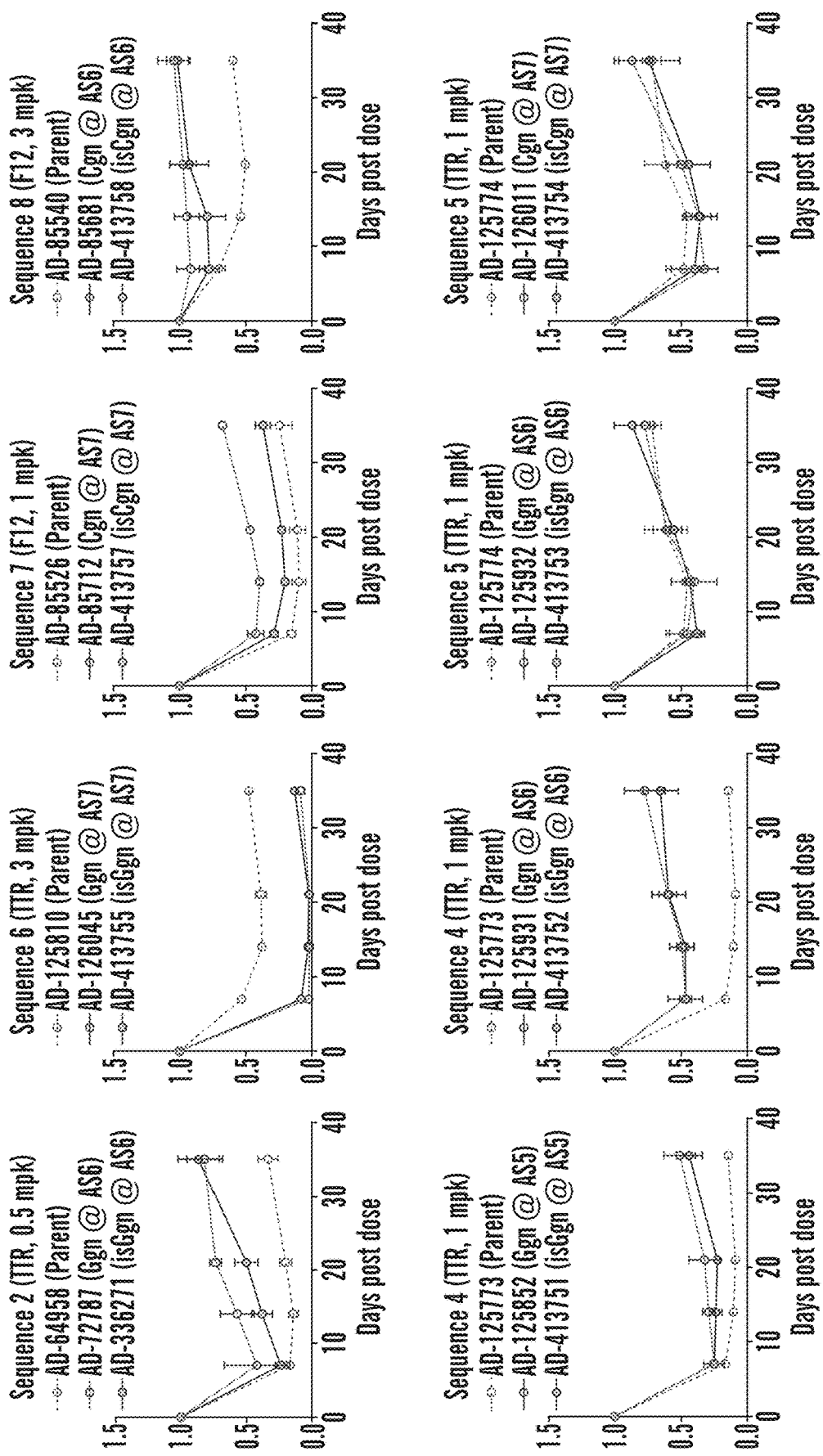
FIG. 43 are line graphs showing Incorporation of (S)-isoGNA generally improves in vivo activity over(S)-GNA.

Results of in vivo gene silencing with Hyp-based Nucleosides are shown in FIGS. 39-41. As shown in FIG. 42, incorporation of of (S)-isoGNA is significantly less thermally destabilizing than (S)-GNA. As seen from FIG. 43, incorporation of (S)-isoGNA generally improves in vivo activity over (S)-GNA.

Example 13: Incorporation of Mod 8 (2'-5' RNA) in Antisense Seed Region

Figure 44:
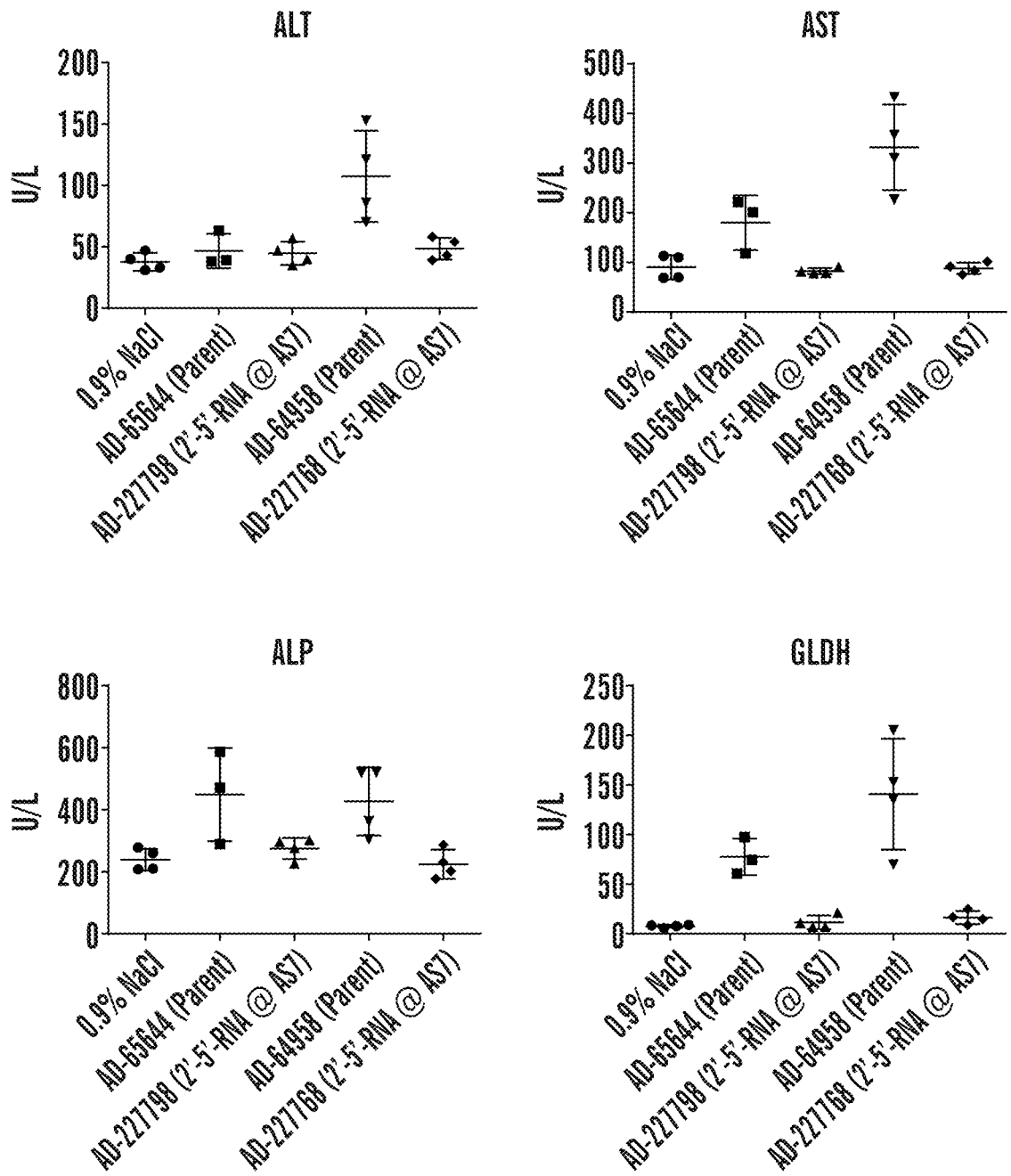
FIG. 44 are line graphs showing incorporation of Mod 8 (2'-S'-RNA) in antisense seed region improved clinical pathology measures in rat toxicity study.
Figure 45:
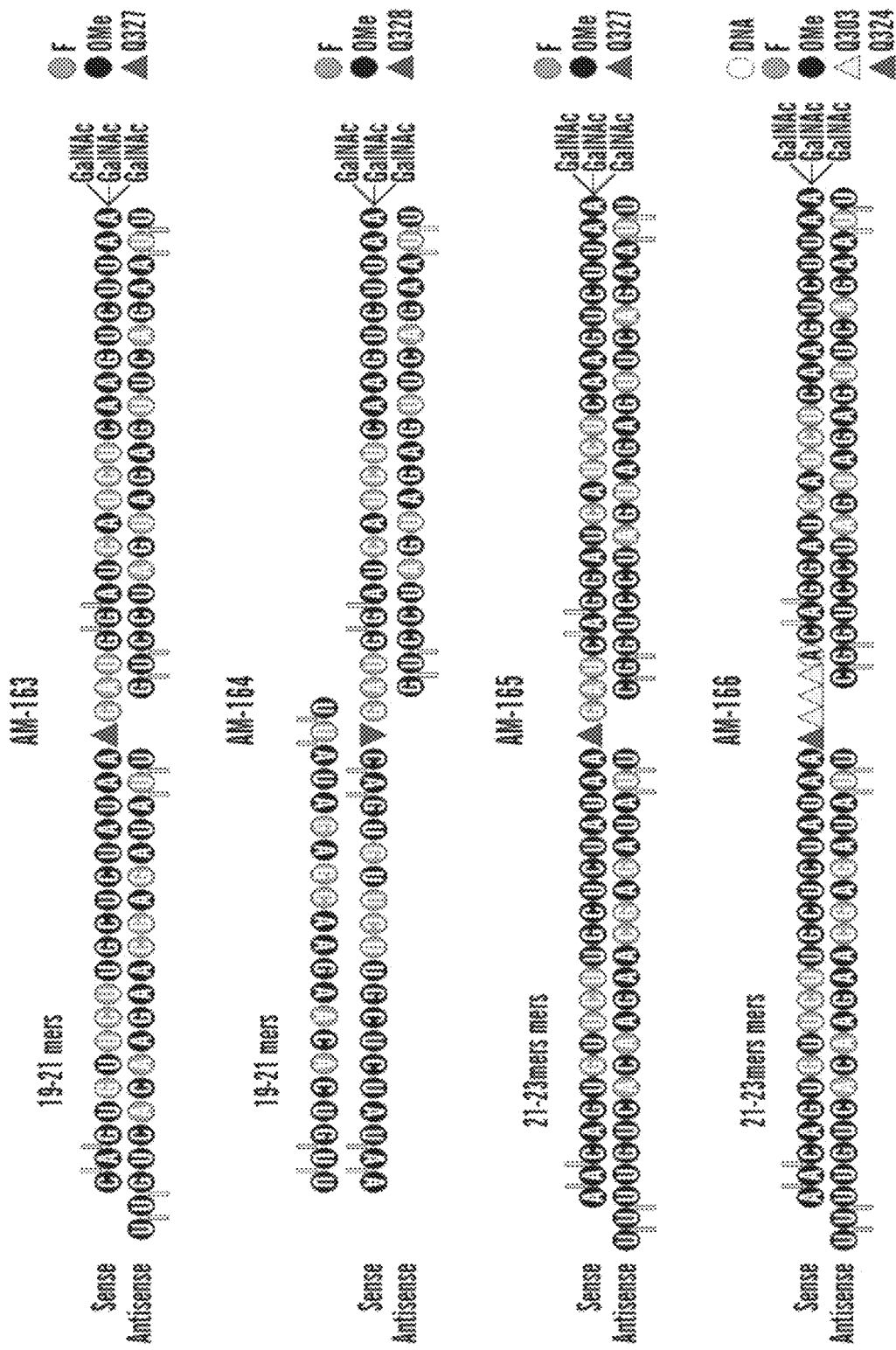

Mod 8 (2'-5' RNA) was incorporated in the antisense seed region and its effects studied. FIG. 44 shows that incorporation of Mod 8 (2'-5'-RNA) in antisense seed region improved clinical pathology measures in rat toxicity study. Clinical pathology parameters in rats after subcutaneous administration of a single dose (30 mg/kg) of a parent siRNA or siRNA containing a single Mod 8 (2'-5' RNA) are summarized in Table 38.

TABLE 39

Clinical pathology parameters in rats after subcutaneous administration of a single dose (30 mg/kg) of a parent siRNA or siRNA containing a single Mod 8 (2'-5' RNA linkage)

| | 0.9% NaCl | | Parent (AD-65644)* | | 2'-5'-RNA @ AS7 (AD-227798) | | Parent (AD-64958) | | 2'-5'-RNA @ AS7 (AD-227768) | |
|---|---|---|---|---|---|---|---|---|---|---|
| | Avg. | St. Dev. | Avg. | St. Dev. | Avg. | St. Dev. | Avg. | St. Dev. | Avg. | St. Dev. |
| ALT (U/L) | 38 | 7 | 47 | 14 | 45 | 10 | 108 | 37 | 49 | 9 |
| AST (U/L) | 91 | 24 | 180 | 55 | 83 | 6 | 332 | 86 | 88 | 12 |
| ALB (g/dL) | 3.1 | 0.1 | 3.0 | 0.1 | 3.1 | 0.1 | 2.9 | 0.1 | 3.0 | 0.1 |
| ALP (U/L) | 239 | 35 | 449 | 150 | 275 | 34 | 427 | 110 | 224 | 47 |
| BILI (mg/dL) | 0.12 | 0.03 | 0.52 | 0.40 | 0.11 | 0.01 | 0.48 | 0.33 | 0.12 | 0.01 |
| CA (mg/dL) | 10.0 | 0.3 | 10.3 | 0.2 | 9.9 | 0.2 | 9.9 | 0.2 | 10.2 | 0.2 |
| UREAN (mg/dL) | 14.3 | 1.5 | 16.8 | 3.6 | 14.6 | 1.2 | 18.6 | 2.6 | 16.5 | 4.1 |
| CHOL (mg/dL) | 58 | 10 | 74 | 18 | 50 | 11 | 43 | 10 | 34 | 10 |
| CL (mmol/L) | 100 | 2 | 100 | 3 | 102 | 2 | 102 | 2 | 103 | 2 |
| CREAT (mg/dL) | 0.22 | 0.03 | 0.23 | 0.03 | 0.22 | 0.02 | 0.21 | 0.02 | 0.23 | 0.03 |
| GLUC (mg/dL) | 118 | 18 | 113 | 12 | 148 | 6 | 124 | 5 | 121 | 7 |
| PHOS (mg/dL) | 8.5 | 0.4 | 8.8 | 0.5 | 8.2 | 0.4 | 9.0 | 1.2 | 8.8 | 0.6 |
| TRIG (mg/dL) | 65 | 33 | 138 | 88 | 120 | 31 | 51 | 5 | 52 | 7 |
| K (mmol/L) | 4.6 | 0.2 | 4.3 | 0.2 | 4.4 | 0.1 | 4.9 | 0.3 | 4.8 | 0.1 |
| NA (mmol/L) | 141 | 1 | 140 | 1 | 142 | 1 | 140 | 1 | 142 | 1 |
| GLDH (U/L) | 7.7 | 1.5 | 77.5 | 18.4 | 11.6 | 6.8 | 140.8 | 55.8 | 16.3 | 6.6 |
| PROT (g/dL) | 6 | 0.0 | 6 | 0.6 | 6 | 0.6 | 5 | 0.0 | 6 | 0.5 |
| GLOB (g/dL) | 2.65 | 0.10 | 2.63 | 0.12 | 2.43 | 0.17 | 2.27 | 0.12 | 2.63 | 0.22 |
| A/G | 1.1 | 0.0 | 1.1 | 0.1 | 1.3 | 0.1 | 1.3 | 0.1 | 1.2 | 0.1 |

All values represent the average across all four animals from each cohort.
*One animal from this group was euthanized early due to concerning clinical observations and this data was not included in this analysis.

Example 14: Alternate 3'-mUNA Synthesis

Scheme 43 shows synthesis of 3'-methl-UNA-uridine phosphoramidites.

Scheme 43

3'Me-(S)-UNA

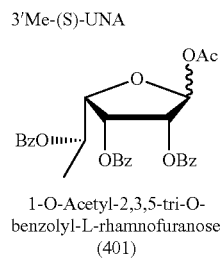

1-O-Acetyl-2,3,5-tri-O-benzolyl-L-rhamnofuranose (401)

-continued

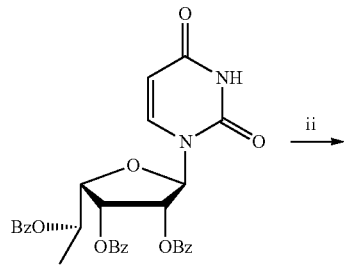

402

3'Me(R)-UNA
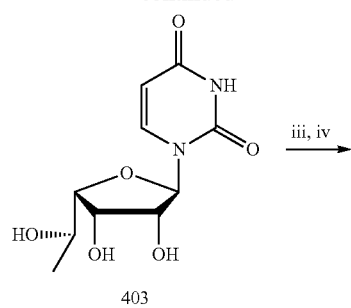
403
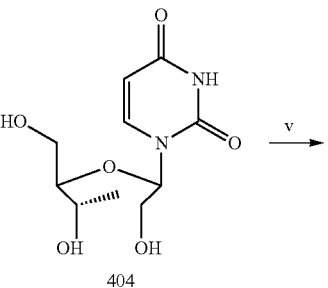
404
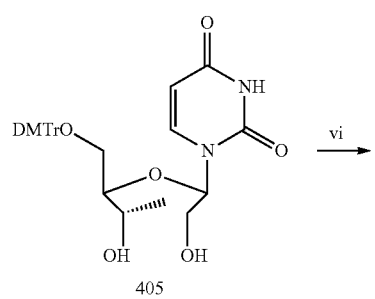
405
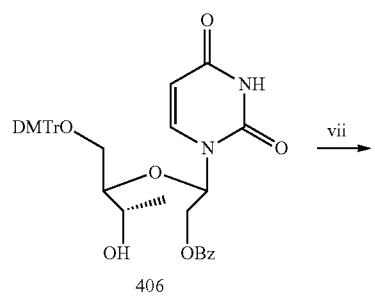
406
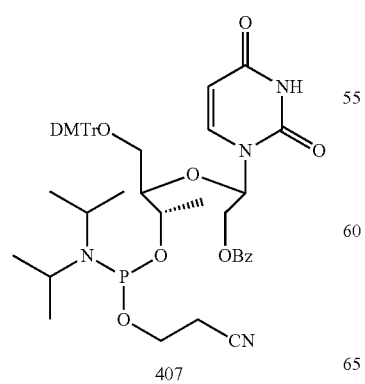
407
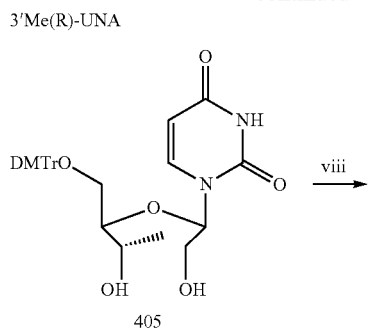
405
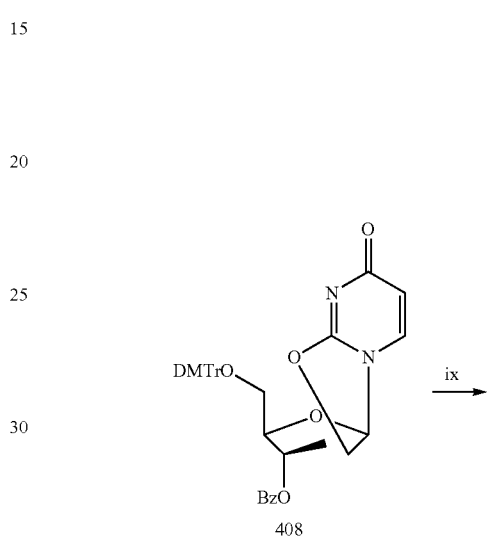
408
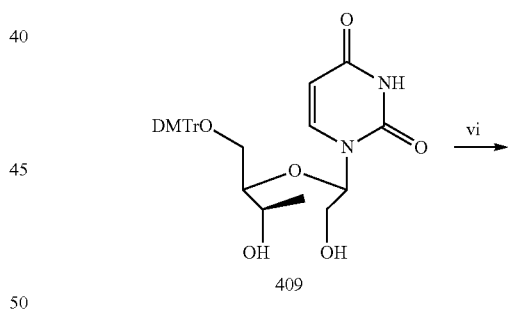
409
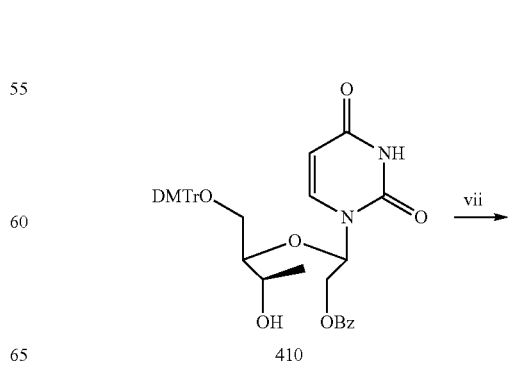
410

-continued

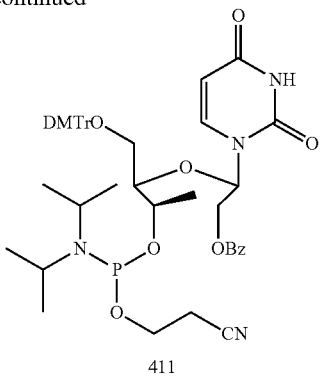

411

Reagents and conditions: (i) BSA, TMSOTf, uracil, MeCN, reflux, 1 h, 79%; (ii) NH$_3$, MeOH, rt, 3 d, 80%; (iii) NaIO$_4$, 1,4-dioxane, H$_2$O, rt, 1.5 h; (iv) NaBH$_4$, 85% over 2 steps; (v) DMTrCl, DMAP, Pyridine, rt, 12 h, 30%; (vi) Bz$_2$O, DMAP, Pyridine, rt, 5 h, 65-80%; (vii) 2-cyanoethyl N,N-diisopropylchlorophosphoramidite, DIEA, DCM, rt, 1-2 h, 81-86%; (viii) BzOH, DIAD, PPh$_3$, THF, rt, 5 h; (ix) NaOH aq., rt, 12 h, 77% over 2 steps.

Compound 402: To the solution of 1-O-acetyl-2,3,5-tri-O-benzoyl-L-thamnofuranose (401) (3.70 g, 7.14 mmol; Lemer, L. M. *J. Org. Chem.* 1976, 41, 306-310) and uracil (1.61 g, 14.3 mmol) in MeCN (80 mL), N,O-bis(trimethylsilyl)acetamide (10.6 mL, 42.9 mmol) was added. The mixture was refluxed for 1 h and Me$_3$SiOTf (1.55 mL, 8.57 mmol) was added dropwisely at room temperature. After refluxing again for 1 h, the mixture was quenched with saturated NaHCO$_3$ solution (100 mL), evaporated and extracted with CH$_2$Cl$_2$. The organic layer was dried over MgSO$_4$, concentrated and purified via column chromatography on silica gel (25% AcOEt in hexane) to afford compound 402 as white foam (3.22 g, 79%, R$_f$=0.15; developed with 25% AcOEt in hexane). $^1$H NMR (500 MHZ, DMSO-d$_6$) δ 11.46 (d, J=2.0 Hz, 1H), 7.95-7.30 (m, 16H), 6.26-6.19 (m, 2H), 6.10-6.07 (m, 1H), 5.73 (dd, J=8.5, 2.0 Hz, 1H), 5.41-5.34 (m, 1H), 5.05 (dd, J=8.5, 3.0 Hz, 1H), 1.43 (d, J=6.0 Hz, 3H). $^{13}$C NMR (126 MHz, DMSO-d$_6$) δ 164.59, 164.53, 164.41, 163.12, 150.61, 142.42, 133.90, 133.83, 133.42, 129.29, 129.22, 129.16, 129.10, 128.82, 128.65, 128.61, 128.59, 128.24, 102.34, 89.13, 81.75, 74.11, 71.96, 67.81, 17.22. HRMS; [M+H]$^+$ calc. for C$_{31}$H$_{27}$N$_2$O$_9$Na, 593.1536; found: 59.

Compound 403: Compound 402 (9.60 g, 16.8 mmol) was dissolved in 1N NH$_3$ MeOH solution (168 mL). The resulting mixture was stirred for 3 d at room temperature and then evaporated. The crude residue was purified via column chromatography on silica gel (10% MeOH in AcOEt) to afford compound 403 as white powder (3.41 g, 80%, R$_f$=0.23; developed with 10% MeOH in AcOEt). 1H NMR (400 MHZ, DMSO-d$_6$) δ 11.29 (brs, 1H), 7.75 (d, J=11.5 Hz, 1H), 5.77 (d, J=8.5 Hz, 1H), 5.64 (d, J=10.0 Hz, 1H), 5.33 (d, J=8.0 Hz, 1H), 5.03 (d, J=1.5 Hz, 1H), 4.56 (d, J=6.5 Hz, 1H), 4.39-4.31 (m, 1H), 4.06 (brs, 1H), 3.91 (dd, J=3.0, 10.5 Hz, 1H), 3.86-3.76 (m, 1H), 1.05 (d, J=7.5 Hz, 3H). $^{13}$C (126 MHz, DMSO-d$_6$) δ 163.11, 150.95, 141.90, 102.07, 88.24, 85.40, 74.32, 70.52, 63.45, 20.53. HRMS; [M+H]$^+$ calc. for C$_{10}$H$_{15}$N$_2$O$_6$, 259.0930; found: 259.0931.

Compound 404: To the solution of compound 403 (640 mg, 2.48 mmol) in a mixture of 1,4-dioxane (25 mL) and water (5 mL), NaIO$_4$ (591 mg, 2.72 mmol) was added. The reaction mixture was stirred for 1.5 h at room temperature and then diluted with 1,4-dioxane and filtered through a Celite pad. The solid residue was washed with 1,4-dioxane, and then sodium borohydrate (94.0 mg, 2.48 mmol) was added to the filtrate. the resulting mixture was stirred for 15 min. and the solvent was removed in vacuo. The crude residue was purified via column chromatography on silica gel (10-20% MeOH in AcOEt) to afford compound 404 as a colorless sticky glass (548 mg, 85%, R$_f$=0.34; developed with 15% MeOH in AcOEt). $^1$H NMR (400 MHZ, DMSO-d$_6$) δ 11.16 (brs, 1H), 7.60 (d, J=8.0 Hz, 1H), 5.83 (m, 1H), 5.55 (d, J=8.0 Hz, 1H), 5.06 (m, 1H), 4.68 (d, J=5.2 Hz, 1H), 4.49-4.41 (m, 1H), 3.76-3.67 (m, 1H), 3.65-3.46 (m, 1H), 3.38-3.21 (m, 3H), 1.05 (d, J=6.4 Hz, 1H). $^{13}$C NMR (101 MHZ, DMSO-d$_6$) δ 163.49, 151.39, 141.61, 101.00, 84.33, 83.90, 65.85, 61.46, 60.73, 18.25. HRMS; [M+H]$^+$ calc. for C$_{10}$H$_{16}$N$_2$O$_6$Na, 283.0906; found: 283.0916.

Compound 405: To the solution of compound 404 (2.04 g, 7.84 mmol) in dry pyridine 80 mL were added DMTrCl (2.89 g, 8.63 mmol) and 4-dimethylaminopyridine (95.8 mg, 0.784 mmol). The reaction mixture was stirred for 12 h at room temperature and then diluted with CH$_2$Cl$_2$. The reaction was quenched with saturated aq. NaHCO$_3$. Organic layer was separated and washed with brine. The solvent was removed in vacuo. The crude residue was purified via column chromatography on silica gel (AcOEt) to afford compound 405 as a white form (1.32 g, 30%, Rf=0.52; developed with AcOEt). $^1$H NMR (400 MHZ, DMSO-d$_6$) δ 11.31 (d, J=1.2 Hz, 1H), 7.58 (d, J=8.0 Hz, 1H), 7.35-7.10 (m, 9H), 6.88-6.81 (m, 4H), 5.89-5.80 (m, 1H), 5.46 (dd, J=1.2, 8.0 Hz, 1H), 5.13-5.06 (m, 1H), 4.72 (d, J=4.8 Hz, 1H), 3.78-3.52 (m, 10H), 3.04-2.78 (m, 2H), 0.87 (d, J=6.4 Hz, 3H). $^{13}$C NMR (101 MHz, DMSO-d$_6$) δ 163.28, 157.98, 157.96, 151.51, 144.82, 141.23, 135.66, 135.54, 129.58, 129.49, 127.77, 127.61, 126.58, 113.14, 113.11, 101.67, 85.45, 84.42, 82.56, 66.08, 63.02, 61.01, 55.03, 55.00, 18.09. HRMS; [M+Na]$^+$ calc. for C$_{31}$H$_{34}$N$_2$O$_8$Na, 585.2213; found: 585.2205.

Compound 406: To the solution of compound 405 (500 mg, 0.890 mmol) in dry pyridine 8.5 mL were added benzoic anhydride (211 mg, 0.979 mmol) and 4-dimethylaminopyridine (10.9 mg, 0.0890 mmol) at 0° C. The reaction mixture was stirred for 5 h at room temperature and then diluted with CH$_2$Cl$_2$. The reaction was quenched with saturated aq. NaHCO$_3$. Organic layer was separated and washed with brine. The solvent was removed in vacuo. The crude residue was purified via column chromatography on silica gel (50% AcOEt in hexane) to afford compound 406 as a white form (474 g, 80%, Rf=0.34; developed with 50% AcOEt in hexane). $^1$H NMR (400 MHZ, DMSO-d$_6$) δ 11.43 (d, J=2.0 Hz, 1H), 7.96-7.82 (m, 2H), 7.82-7.43 (m, 4H), 7.41-7.04 (m, 9H), 7.02-6.73 (m, 4H), 6.32-6.12 (m, 1H), 5.51 (d, J=8.1 Hz, 1H), 4.84 (d, J=4.5 Hz, 1H), 4.65 (dd, J=11.6, 5.2 Hz, 1H), 4.49 (dd, J=11.5, 6.8 Hz, 1H), 3.79-3.61 (m, 8H), 3.17-2.74 (m, 2H), 0.90 (d, J=6.4 Hz, 3H). $^{13}$C NMR (101 MHZ, DMSO-d$_6$) δ 165.02, 163.10, 157.99, 157.97, 151.10, 144.75, 140.70, 135.56, 135.46, 133.65, 129.58, 129.49, 129.16, 129.01, 128.84, 127.77, 127.60, 126.61, 113.13, 102.13, 85.58, 82.81, 81.64, 66.08, 63.34, 62.94, 55.01, 54.98, 17.91. HRMS; [M+Na]$^+$ calc. for C$_{38}$H$_{38}$N$_2$O$_9$Na, 689.2475; found: 689.2505.

Compound 407: To the solution of compound 406 (2.50 g, 3.75 mmol) in dry DCM 38 mL were added DIPEA (1.97 mL, 11.3 mmol) and 2-cyanoethylchloro-N,N-diisopropylphosphoramidite (921 μL, 14.1 mmol) dropwisely. The reaction mixture was stirred for 1 h at room temperature and then diluted with DCM. Quenched the reaction with saturated aq. NaHCO$_3$. Organic layer was separated and washed with brine. The solvent was removed in vacuo. The crude residue was purified via column chromatography on silica gel to afford a mixture of diastereomers 407 as a colorless form (2.79 g, 86%, $R_f$=0.23; developed with 40% AcOEt in hexane). $^1$H NMR (500 MHz, Acetonitrile-d$_3$) δ 9.20 (brs, 1H); 7.99-7.93 (m, 2H), 7.64-7.18 (m, 13H), 6.85-6.80 (m, 4H), 6.34-6.28 (m, 1H), 5.49 (d, J=8.0 Hz, 1H), 4.59-4.40 (m, 2H), 4.19-4.05 (m, 1H), 3.79-3.48 (m, 12H), 3.19-3.09 (m, 2H), 2.62-2.57 (m, 2H), 1.16-1.01 (m, 15H). $^{13}$C NMR (126 MHZ, Acetonitrile-d$_3$) δ 166.44, 163.94, 159.62, 159.59, 151.90, 151.82, 145.97, 145.95, 141.46, 141.41, 136.80, 136.77, 136.73, 134.38, 130.91, 130.89, 130.84, 130.80, 130.46, 130.44, 130.43, 129.60, 128.88, 128.82, 128.79, 127.77, 119.52, 114.03, 114.01, 103.05, 103.00, 87.48, 87.45, 83.30, 83.26, 83.08, 82.99, 82.89, 82.86, 71.64, 71.51, 71.35, 71.21, 64.76, 64.72, 64.09, 64.06, 59.52, 59.37, 59.14, 58.99, 55.87, 55.86, 43.88, 43.87, 43.79, 43.77, 25.05, 24.99, 24.93, 24.87, 24.81, 24.79, 24.73, 21.02, 20.98, 20.96, 20.92, 17.40, 17.39, 17.22, 17.19. $^{31}$P NMR (202 MHz, Acetonitrile-d$_3$) δ 148.94; 148.75. HRMS; [M+H]$^+$ calc. for C$_{47}$H$_{56}$N$_4$O$_{10}$P, 867.3734; found: 867.3742.

Compound 409: To the solution of compound 405 (500 g, 0.890 mmol) in dry THF 9 mL were added PPhs (622 mg, 2.67 mmol), benzoic acid (543 mg, 4.45 mmol) and DIAD (526 μL, 2.67 mmol) dropwisely. The reaction mixture was stirred for 5 h at room temperature, the reaction completion was checked by TLC. The solvent was removed in vacuo. The crude residue was purified via column chromatography on silica gel (5-10% MeOH in AcOEt) to afford a 2,2'-anhydro-nucleoside 408 (Rt=0.11; developed with AcOEt). $^1$H NMR (400 MHZ, DMSO-d$_6$) δ 7.93 (d, J=7.6 Hz, 1H), 7.88-7.84 (m, 2H), 7.70-7.64 (m, 1H), 7.53-7.48 (m, 2H) 7.36-7.16 (m, 9H), 6.85-6.76 (m, 4H), 6.13 (dd, J=5.6, 1.6 Hz, 1H), 5.76 (dt, J=7.6, 12.4 Hz, 1H), 4.67 (dd, J=10.0, 5.6 Hz, 1H), 4.51-4.41 (m, 2H), 3.70 (s, 3H), 3.69 (s, 3H), 3.26 (dd, J=10.0, 3.6 Hz, 1H), 2.96 (dd, J=10.4, 5.2 Hz, 1H), 1.15 (d, J=7.2 Hz, 3H). $^{13}$C NMR (101 MHz, DMSO-d$_6$) δ 171.00, 164.91, 160.23, 158.12, 158.05, 144.55, 136.77, 135.10, 135.05, 133.52, 129.62, 129.48, 129.16, 128.78, 127.86, 127.51, 126.75, 113.18, 108.72, 87.62, 85.63, 80.12, 73.40, 70.49, 62.56, 55.02, 54.98, 54.96, 15.37. HRMS; [M+H]$^+$ calc. for C$_{38}$H$_3$N$_2$O$_8$, 649.2550; found: 649.2546. Compound 408 was dissolved in THE 10 mL. To the solution of mixture was added IN aq. NaOH 3 mL dropwisely. Resulting mixture was stirred for 12 h. The solvent was removed in vacuo. The crude residue was purified via column chromatography on silica gel (0-5% MeOH in AcOEt) to afford compound 409 as a white form (452 g, 90% over 2 steps, $R_f$=0.32; developed with AcOEt). $^1$H NMR (500 MHz, DMSO-d$_6$) δ 11.39 (brs, 1H), 7.63 (d, J=8.0 Hz, 1H), 7.39-7.04 (m, 9H), 6.97-6.67 (m, 4H), 5.82 (t, J=5.9 Hz, 1H), 5.49 (d, J=8.0 Hz, 1H), 5.23-5.16 (m, 1H), 4.77 (d, J=4.8 Hz, 1H), 3.84-3.46 (m, 10H), 3.06-2.84 (m, 2H), 0.86 (d, J=6.4 Hz, 3H). $^{13}$C NMR (101 MHz, DMSO-d$_6$) δ 163.27, 157.97, 157.95, 151.44, 144.81, 141.22, 135.58, 135.56, 129.61, 129.52, 127.75, 127.63, 126.57, 113.10, 101.73, 85.31, 84.80, 83.02, 65.90, 62.88, 61.16, 55.00, 54.98, 18.55. HRMS; [M+Na]$^+$ calc. for C$_{31}$H$_{34}$N$_2$O$_8$Na, 585.2213; found: 585.2205.

Compound 410: To the solution of compound 409 (2.00 g, 3.56 mmol) in dry pyridine 36 mL were added DMAP (43.5 mg, 0.356 mmol) and Bz$_2$O (845 mg, 3.74 mmol). The reaction mixture was stirred for 5 h at room temperature and then the resulting mixture was diluted with DCM. The reaction was quenched with saturated aq. NaHCO$_3$. Organic layer was separated and washed with brine. The solvent was removed in vacuo. The crude residue was purified via column chromatography on silica gel (50% AcOEt in hexane) to afford compound 410 as a colorless form (1.99 g, 84%, $R_f$=0.34; developed with 50% AcOEt in hexane). $^1$H NMR (400 MHZ, DMSO-d$_6$) δ 11.45 (d, J=2.0 Hz, 1H), 7.99-7.41 (m, 6H), 7.41-7.03 (m, 9H), 6.95-6.58 (m, 4H), 6.20 (t, J=6.0 Hz, 1H), 5.54 (dd, J=7.6, 1.6 Hz, 1H), 4.86 (d, J=5.2 Hz, 1H), 4.70 (dd, J=12.0, 5.6 Hz, 1H), 4.51 (dd, J=12.0, 5.6 Hz, 1H), 3.86-3.52 (m, 8H), 3.10-2.91 (m, 2H), 0.84 (d, J=6.4 Hz, 3H). $^{13}$C NMR (101 MHz, DMSO-d$_6$) δ 165.03, 163.10, 157.98, 157.96, 151.11, 144.75, 140.76, 135.52, 135.49, 133.69, 129.61, 129.52, 129.12, 129.00, 128.87, 127.75, 127.62, 126.59, 113.10, 102.20, 85.40, 83.17, 81.90, 65.75, 63.40, 62.73, 55.00, 54.97, 18.49. HRMS; [M+Na]$^+$ calc. for C$_{38}$H$_{38}$N$_2$O$_9$Na, 689.2475; found: 689.2490.

Compound 411: To the solution of compound 410 (2.00 g, 3.00 mmol) in dry DCM 30 mL were added DIPEA (1.57 mL, 9.00 mmol) and 2-cyanoethylchloro-N,N-diisopropylphosphoramidite (737 μL, 3.30 mmol) dropwisely. The reaction mixture was stirred for 2 h at room temperature and then diluted with DCM. Quenched the reaction with saturated aq. NaHCO$_3$. Organic layer was separated and washed with brine. The solvent was removed in vacuo. The crude residue was purified via column chromatography on silica gel (50% AcOEt in hexane) to afford compound 411 as a colorless form (2.11 g, 81%, $R_f$=0.65; developed with 50% AcOEt in hexane). 1H NMR (500 MHz, Acetonitrile-d$_3$) δ 8.00-7.94 (m, 2H), 7.64-7.16 (m, 13H), 6.86-6.81 (m, 4H), 6.28-6.22 (m, 1H), 5.56-5.48 (m, 1H), 4.69-4.44 (m, 3H), 4.23-4.03 (m, 1H), 3.86-3.42 (m, 12H), 3.31-3.04 (m, 2H), 2.61-2.51 (m, 2H), 1.28-0.98 (m, 15H). $^{13}$C NMR (126 MHZ, Acetonitrile-d$_3$) δ 166.51, 164.07, 164.04, 159.66, 159.64, 151.98, 145.99, 141.49, 141.43, 136.89, 136.84, 136.83, 136.81, 134.54, 134.52, 131.03, 130.97, 130.47, 129.73, 129.02, 129.00, 128.85, 127.84, 127.82, 119.56, 114.11, 114.07, 103.34, 103.30, 87.26, 87.24, 83.19, 83.02, 82.99, 82.96, 82.87, 82.83, 70.43, 70.31, 64.84, 64.82, 64.01, 63.91, 59.32, 59.29, 59.17, 59.14, 58.19, 55.95, 44.06, 44.00, 43.96, 43.90, 25.09, 25.03, 24.99, 24.95, 24.94, 24.89, 24.82, 24.76, 22.03, 21.07, 21.02, 21.00, 20.95, 17.87, 17.84. $^{31}$P NMR (202 MHz, Acetonitrile-d$_3$) δ 149.10; 148.41. HRMS; [M+H]$^+$ calc. for C$_{47}$H$_{56}$N$_4$O$_{10}$P, 867.3734; found: 867.3760.

All of the U.S. patents, U.S. patent application publications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:
1. A double-stranded RNA (dsRNA) molecule comprising a sense strand and an antisense strand, each strand having 18 to 35 nucleotides, wherein
the dsRNA molecule has a duplex region of 17-30 nucleotide pairs in length;
the antisense strand has sufficient complementarity to a target sequence to mediate RNA interference;
the antisense strand comprises a thermally destabilizing modification at position 7 of the antisense strand, counting from the 5'-end of the antisense strand; and
the thermally destabilizing modification is of the formula,

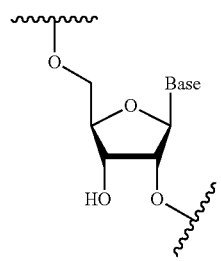

wherein Base is an optionally modified nucleobase;
the dsRNA molecule is optionally conjugated to a ligand.
2. The dsRNA molecule according to claim 1, wherein the duplex region is 19-23 base pairs in length.
3. The dsRNA molecule according to claim 1, comprising at least one ligand conjugated to the sense strand.
4. The dsRNA molecule according to claim 3, wherein at least one ligand is a targeting ligand.
5. The dsRNA molecule according to claim 4, wherein the targeting ligand is an ASGPR ligand that is conjugated to the 3'-end or 5'-end of the sense strand.
6. The dsRNA molecule according to claim 5, wherein the ASGPR ligand is one or more GalNAc derivatives attached through a bivalent or trivalent branched linker.
7. The dsRNA molecule of claim 6, wherein the ASGPR ligand is:

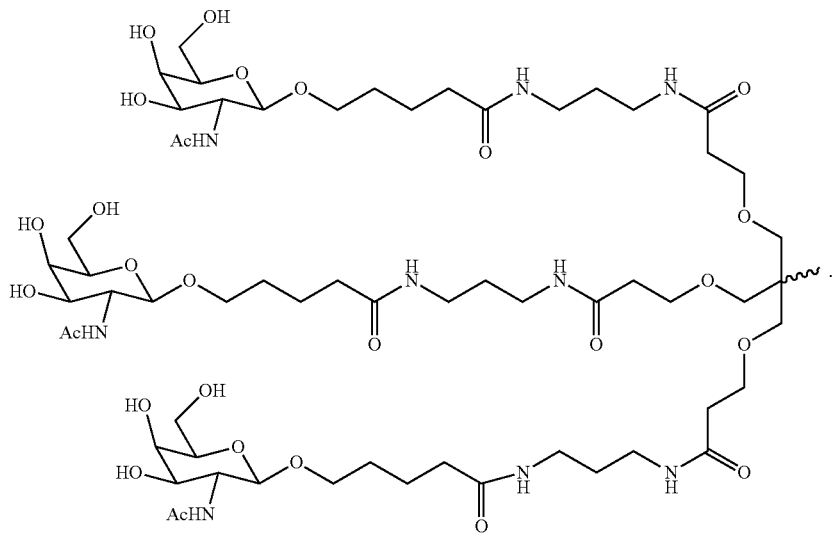 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

8. The dsRNA molecule according to claim 4, wherein the targeting ligand is a lipid.

9. The dsRNA molecule according to claim 4, wherein the targeting ligand is a cell targeting peptide.
10. The dsRNA molecule according to claim 3, wherein at least one ligand improves nuclease resistance of the dsRNA molecule.
11. The dsRNA molecule of claim 1, having a melting temperature of about 55° C. to about 67° C.
12. The dsRNA molecule of claim 1, having a blunt end at 5'-end of the antisense strand.
13. The dsRNA molecule of claim 12, having a blunt end at 3'-end of the antisense strand.
14. The dsRNA molecule of claim 12, having a single-stranded overhang of 1-10 nucleotides in length at the 3'-end of the antisense strand.
15. The dsRNA molecule of claim 1, wherein each strand is 19-25 nucleotides in length.
16. The dsRNA molecule of claim 1, wherein the sense strand has 21 nucleotides, and the antisense strand has 23 nucleotides.
17. The dsRNA molecule of claim 1, wherein the antisense strand comprises 2, 3, 4, 5, or 6 2'-fluoro modifications.
18. The dsRNA molecule according to claim 17, wherein there are no 2'-fluoro modifications at nucleotide positions 3-9 of the antisense strand, counting from the 5' end of the antisense strand.
19. The dsRNA molecule of claim 17, wherein the antisense strand has 2'-F modifications at positions 2, 14, and 16, counting from the 5' end of the antisense strand.
20. The dsRNA molecule of claim 17, wherein the antisense strand has 2'-F modifications at positions 2, 6, 14, and 16, counting from the 5' end of the antisense strand.
21. The dsRNA molecule of claim 17, wherein the antisense strand has 2'-F modifications at positions 2, 6, 8, 9, 14, and 16, counting from the 5' end of the antisense strand.
22. The dsRNA molecule of claim 1, wherein the sense strand comprises 2, 3, 4 or 5 2'-fluoro modifications.
23. The dsRNA molecule of claim 22, wherein the sense strand has 2'-F modifications at positions complimentary to positions 11, 12, and 15 of the antisense strand, counting from the 5'-end of the antisense strand.

24. The dsRNA molecule of claim 22, wherein the sense strand has 2'-F modifications at positions complimentary to positions 11, 12, 13, and 15 of the antisense strand, counting from the 5'-end of the antisense strand.

25. The dsRNA molecule of claim 1, wherein the antisense strand comprises 1, 2, 3, or 4 phosphorothioate internucleotide linkages.

26. The dsRNA molecule of claim 1, wherein at least the terminal two nucleotides at one end or both ends of the antisense strand are linked through phosphorothioate or methylphosphonate internucleotide linkages.

27. The dsRNA molecule of claim 1, wherein the terminal three nucleotides at one end or both ends of the antisense strand are linked through phosphorothioate internucleotide linkages.

28. The dsRNA molecule of claim 1, wherein the sense strand comprises 1, 2, 3, or 4 phosphorothioate internucleotide linkages.

29. The dsRNA molecule of claim 1, wherein at least the terminal two nucleotides at one end or both ends of the sense strand are linked through phosphorothioate or methylphosphonate internucleotide linkages.

30. The dsRNA molecule of claim 1, wherein the terminal three nucleotides at one end or both ends of the sense strand are linked through phosphorothioate internucleotide linkages.

31. The dsRNA molecule of claim 1, the first base pair within the duplex region from the 5'-end of the antisense strand is an AU base pair.

32. The dsRNA molecule of claim 1, wherein the antisense strand comprises a 5'-(E)-vinyl phopshonate (VP).

33. A pharmaceutical composition comprising the dsRNA agent according to claim 1, alone or in combination with a pharmaceutically acceptable carrier or excipient.

34. A method for silencing a target gene in a cell, the method comprising a step of introducing the dsRNA molecule of claim 1 into the cell.

35. The method of claim 34, wherein the dsRNA agent is administered through subcutaneous or intravenous administration.

36. A method for suppressing off-target effects caused by the antisense strand of a dsRNA molecule, the method comprising a step of introducing the dsRNA molecule claim 1 into a cell.

37. A method for delivering polynucleotide to a specific target in a subject by administering the dsRNA agent according to claim 1.

38. The method of claim 37, wherein said administering step is carried out by an administration means comprising intramuscular, intrabronchial, intrapleural, intraperitoneal, intraarterial, lymphatic, intravenous, subcutaneous, cerebrospinal, or combinations thereof.

* * * * *